(12) United States Patent
Aktoudianakis et al.

(10) Patent No.: US 12,377,100 B2
(45) Date of Patent: *Aug. 5, 2025

(54) TOLL LIKE RECEPTOR MODULATOR COMPOUNDS

(71) Applicant: GILEAD SCIENCES, INC., Foster City, CA (US)

(72) Inventors: Evangelos Aktoudianakis, Redwood City, CA (US); Gregory Chin, San Francisco, CA (US); Richard L. Mackman, Millbrae, CA (US); Samuel E. Metobo, Newark, CA (US); Michael R. Mish, Foster City, CA (US); Hyung-Jung Pyun, Fremont, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 17/540,563

(22) Filed: Dec. 2, 2021

(65) Prior Publication Data

US 2022/0218709 A1 Jul. 14, 2022

Related U.S. Application Data

(63) Continuation of application No. 16/254,333, filed on Jan. 22, 2019, now abandoned, which is a continuation of application No. 15/496,283, filed on Apr. 25, 2017, now Pat. No. 10,285,990, which is a continuation of application No. 15/059,070, filed on Mar. 2, 2016, now Pat. No. 9,670,205.

(60) Provisional application No. 62/250,403, filed on Nov. 3, 2015, provisional application No. 62/128,397, filed on Mar. 4, 2015.

(51) Int. Cl.
*C07D 471/04* (2006.01)
*A61K 31/517* (2006.01)
*C07D 239/84* (2006.01)
*C07D 401/04* (2006.01)

(52) U.S. Cl.
CPC .......... *A61K 31/517* (2013.01); *C07D 239/84* (2013.01); *C07D 401/04* (2013.01); *C07D 471/04* (2013.01)

(58) Field of Classification Search
CPC .................................................. C07D 471/04
See application file for complete search history.

(56) References Cited

U.S. PATENT DOCUMENTS

| | | |
|---|---|---|
| 2,512,572 A | 6/1950 | Smith, Jr. et al. |
| 2,581,889 A | 1/1952 | Millward |
| 2,665,275 A | 1/1954 | Robert et al. |
| 2,667,486 A | 1/1954 | Cain |
| 2,740,784 A | 4/1956 | Meyer et al. |
| 2,939,882 A | 6/1960 | Mecorney |
| 2,940,972 A | 6/1960 | Josef |
| 3,071,587 A | 1/1963 | Curran et al. |
| 3,081,230 A | 3/1963 | Joseph et al. |
| 3,122,546 A | 2/1964 | Osdene |
| 3,159,628 A | 12/1964 | Pachter et al. |
| 3,162,635 A | 12/1964 | Schroeder |
| 3,475,425 A | 10/1969 | Roch |
| 3,843,791 A | 10/1974 | Mcfarland |
| 3,859,287 A | 1/1975 | Parish et al. |
| 4,438,128 A | 3/1984 | Wiedemann et al. |
| 4,608,383 A | 8/1986 | Wiedemann et al. |
| 5,047,405 A | 9/1991 | Gennari |
| 5,064,833 A | 11/1991 | Ife et al. |
| 5,281,603 A | 1/1994 | Venkatesan et al. |
| 5,300,509 A | 4/1994 | Block et al. |
| 5,354,776 A | 10/1994 | Chandraratna |
| 5,380,724 A | 1/1995 | Zubovics et al. |
| 5,500,428 A | 3/1996 | Block et al. |
| 5,534,518 A | 7/1996 | Henrie et al. |
| 5,641,783 A | 6/1997 | Klein et al. |
| 5,665,772 A | 9/1997 | Cottens et al. |
| 5,707,998 A | 1/1998 | Takase et al. |
| 5,780,462 A | 7/1998 | Lee et al. |
| 5,843,943 A | 12/1998 | Carson et al. |
| 5,866,572 A | 2/1999 | Barker et al. |
| 5,929,046 A | 7/1999 | Mcmurry et al. |
| 5,955,464 A | 9/1999 | Barker |
| 5,992,713 A | 11/1999 | Manabat |
| 6,043,228 A | 3/2000 | Mcmurry et al. |
| 6,203,723 B1 | 3/2001 | Hsu |
| 6,331,547 B1 | 12/2001 | Zhu et al. |
| 6,440,991 B1 | 8/2002 | Zhu et al. |
| 6,559,149 B1 | 5/2003 | Matsuoka et al. |

(Continued)

FOREIGN PATENT DOCUMENTS

| | | |
|---|---|---|
| CH | 231852 A | 4/1944 |
| CN | 1583747 A | 2/2005 |
| DE | 1921308 A1 | 1/1971 |
| DE | 267495 A1 | 5/1989 |
| DE | 4009941 A1 | 10/1991 |
| EP | 0042593 A1 | 12/1981 |
| EP | 0108890 A2 | 5/1984 |
| EP | 0134922 A1 | 3/1985 |

(Continued)

OTHER PUBLICATIONS

American Chemical Society, 2022, Chemical Abstracts Service Registry Nos. 106941-25-7 and 142340-99-6, 1 page.

(Continued)

*Primary Examiner* — Timothy P Thomas
(74) *Attorney, Agent, or Firm* — Mintz, Levin, Cohn, Ferris, Glovsky and Popeo, P.C.

(57) ABSTRACT

The present disclosure relates generally to toll like receptor modulator compounds, such as diamino pyrido[3,2 D] pyrimidine compounds and pharmaceutical compositions which, among other things, modulate toll-like receptors (e.g. TLR-8), and methods of making and using them.

5 Claims, No Drawings

(56) References Cited

U.S. PATENT DOCUMENTS

| | | |
|---|---|---|
| 6,844,343 B1 | 1/2005 | Pfleiderer et al. |
| 6,946,465 B2 | 9/2005 | Waer et al. |
| 7,074,801 B1 | 7/2006 | Yoshida et al. |
| 7,276,506 B2 | 10/2007 | Waer et al. |
| 7,501,513 B2 | 3/2009 | Waer et al. |
| 7,928,111 B2 | 4/2011 | Tachdjian et al. |
| 8,143,394 B2 | 3/2012 | Watkins et al. |
| 8,232,278 B2 | 7/2012 | De et al. |
| 8,338,435 B2 | 12/2012 | Herdewijn et al. |
| 8,367,670 B2 | 2/2013 | Desai et al. |
| 8,536,187 B2 | 9/2013 | Zhang et al. |
| 8,541,421 B2 | 9/2013 | Tachdjian et al. |
| 8,633,186 B2 | 1/2014 | Tachdjian et al. |
| 8,637,531 B2 | 1/2014 | Bondy et al. |
| 8,673,929 B2 | 3/2014 | Gao et al. |
| 8,729,089 B2 | 5/2014 | Bondy et al. |
| 8,901,133 B2 | 12/2014 | Ren et al. |
| 8,916,575 B2 | 12/2014 | Mcgowan et al. |
| 8,969,363 B2 | 3/2015 | Castro et al. |
| 9,181,276 B2 | 11/2015 | Tachdjian et al. |
| 9,259,426 B2 | 2/2016 | Gao et al. |
| 9,603,848 B2 | 3/2017 | Servant et al. |
| 9,670,205 B2 | 6/2017 | Aktoudianakis et al. |
| 10,144,736 B2 | 12/2018 | Herdewijn et al. |
| 10,285,990 B2 | 5/2019 | Aktoudianakis et al. |
| 10,370,342 B2 | 8/2019 | Chin et al. |
| 10,640,499 B2 | 5/2020 | Chin et al. |
| 10,882,851 B2 | 1/2021 | Gao et al. |
| 11,124,487 B2 | 9/2021 | Chin et al. |
| 11,286,257 B2 | 3/2022 | Ambrosi |
| 11,396,509 B2 | 7/2022 | Asselin |
| 11,517,567 B2 | 12/2022 | Li |
| 11,583,531 B2 | 2/2023 | Asselin |
| 11,827,609 B2 | 11/2023 | Chin |
| 12,049,461 B2 | 7/2024 | Gao |
| 2003/0236255 A1 | 12/2003 | Waer et al. |
| 2004/0030156 A1 | 2/2004 | Maul et al. |
| 2004/0038856 A1 | 2/2004 | Chakravarty et al. |
| 2004/0102447 A1 | 5/2004 | Bonnert et al. |
| 2004/0167121 A1 | 8/2004 | Aronov et al. |
| 2004/0167198 A1 | 8/2004 | Wrasidlo et al. |
| 2005/0054626 A1 | 3/2005 | Cherney et al. |
| 2005/0054653 A1 | 3/2005 | Eisenbrand et al. |
| 2005/0191238 A1 | 9/2005 | Casebier et al. |
| 2005/0282814 A1 | 12/2005 | Wrasidlo et al. |
| 2006/0116371 A1 | 6/2006 | Martyres et al. |
| 2007/0004721 A1 | 1/2007 | Waer et al. |
| 2007/0043000 A1 | 2/2007 | Waer et al. |
| 2007/0054916 A1 | 3/2007 | Patel et al. |
| 2007/0287704 A1 | 12/2007 | Dollinger et al. |
| 2008/0004285 A1 | 1/2008 | De et al. |
| 2008/0027062 A1 | 1/2008 | Doblhofer et al. |
| 2008/0096883 A1 | 4/2008 | Caravatti et al. |
| 2008/0112884 A1 | 5/2008 | Casebier et al. |
| 2008/0182870 A1 | 7/2008 | Bondy et al. |
| 2008/0234251 A1 | 9/2008 | Doherty et al. |
| 2008/0306053 A1 | 12/2008 | Tachdjian et al. |
| 2008/0306093 A1 | 12/2008 | Servant et al. |
| 2008/0312227 A1 | 12/2008 | De et al. |
| 2009/0036430 A1 | 2/2009 | De et al. |
| 2009/0131414 A1 | 5/2009 | De et al. |
| 2009/0253696 A1 | 10/2009 | Herdewijn et al. |
| 2009/0318456 A1 | 12/2009 | Herdewijn et al. |
| 2009/0318471 A1 | 12/2009 | Sieger |
| 2010/0029585 A1 | 2/2010 | Howbert et al. |
| 2010/0143299 A1 | 6/2010 | Gao et al. |
| 2010/0143301 A1 | 6/2010 | Desai et al. |
| 2010/0305117 A1 | 12/2010 | Herdewijn et al. |
| 2011/0053997 A1 | 3/2011 | Beliaev |
| 2011/0098248 A1 | 4/2011 | Halcomb et al. |
| 2011/0224155 A1 | 9/2011 | Tachdjian et al. |
| 2011/0230502 A1 | 9/2011 | Tachdjian et al. |
| 2012/0122838 A1 | 5/2012 | Ren et al. |
| 2012/0238587 A1 | 9/2012 | Lee et al. |
| 2013/0029982 A1 | 1/2013 | Castro et al. |
| 2013/0109693 A1 | 5/2013 | Routier et al. |
| 2014/0235623 A1 | 8/2014 | Tachdjian et al. |
| 2016/0108045 A1 | 4/2016 | Brown |
| 2016/0289229 A1 | 10/2016 | Aktoudianakis et al. |
| 2017/0071944 A1 | 3/2017 | Geleziunas et al. |
| 2022/0073473 A1 | 3/2022 | Chin et al. |
| 2022/0274985 A1 | 9/2022 | Ambrosi |
| 2023/0364092 A1 | 11/2023 | Asselin |
| 2024/0254091 A1 | 8/2024 | Chin |
| 2024/0269142 A1 | 8/2024 | Cloutier |

FOREIGN PATENT DOCUMENTS

| | | |
|---|---|---|
| EP | 0185259 A2 | 6/1986 |
| EP | 0290819 A2 | 11/1988 |
| EP | 0322133 A1 | 6/1989 |
| EP | 0362645 A2 | 4/1990 |
| EP | 0404322 A1 | 12/1990 |
| EP | 0404355 A1 | 12/1990 |
| EP | 0544445 A2 | 6/1993 |
| EP | 0574906 A2 | 12/1993 |
| EP | 0837063 A1 | 4/1998 |
| EP | 0956855 A1 | 11/1999 |
| EP | 1144412 A1 | 10/2001 |
| EP | 1382603 A1 | 1/2004 |
| EP | 1479682 A1 | 11/2004 |
| EP | 1724268 A1 | 11/2006 |
| EP | 3097102 B1 | 10/2017 |
| EP | 2709989 B1 | 12/2017 |
| EP | 3321265 A1 | 5/2018 |
| GB | 677342 A | 8/1952 |
| GB | 763044 A | 12/1956 |
| GB | 785353 A | 10/1957 |
| GB | 1301319 A | 12/1972 |
| GB | 2143232 A | 2/1985 |
| GB | 2405793 A | 3/2005 |
| JP | H07138238 A | 5/1995 |
| JP | 2000038350 A | 2/2000 |
| JP | 2000053653 A | 2/2000 |
| JP | 2000053654 A | 2/2000 |
| WO | 9307124 A1 | 4/1993 |
| WO | 9325712 A1 | 12/1993 |
| WO | 9406431 A1 | 3/1994 |
| WO | 9411001 A1 | 5/1994 |
| WO | 9414065 A1 | 6/1994 |
| WO | 9422449 A1 | 10/1994 |
| WO | 9422855 A1 | 10/1994 |
| WO | 9427439 A1 | 12/1994 |
| WO | 9513075 A1 | 5/1995 |
| WO | 9531469 A1 | 11/1995 |
| WO | 9531987 A1 | 11/1995 |
| WO | 9532203 A2 | 11/1995 |
| WO | 9610568 A1 | 4/1996 |
| WO | 9616960 A1 | 6/1996 |
| WO | 9620710 A1 | 7/1996 |
| WO | 9723616 A1 | 7/1997 |
| WO | 9730034 A1 | 8/1997 |
| WO | 9731920 A1 | 9/1997 |
| WO | 9739358 A1 | 10/1997 |
| WO | 9804558 A1 | 2/1998 |
| WO | 9808516 A1 | 3/1998 |
| WO | 9852948 A1 | 11/1998 |
| WO | 9950264 A1 | 10/1999 |
| WO | 0039129 A1 | 7/2000 |
| WO | 0045800 A2 | 8/2000 |
| WO | 0119825 A1 | 3/2001 |
| WO | 0121619 A1 | 3/2001 |
| WO | 0232507 A1 | 4/2002 |
| WO | 03001887 A2 | 1/2003 |
| WO | 03031406 A2 | 4/2003 |
| WO | 03062240 A1 | 7/2003 |
| WO | 2004026307 A1 | 4/2004 |
| WO | 2004065392 A1 | 8/2004 |
| WO | 2004072033 A2 | 8/2004 |
| WO | 2004104005 A2 | 12/2004 |
| WO | 2005020899 A2 | 3/2005 |
| WO | 2005021003 A2 | 3/2005 |
| WO | 2005025574 A2 | 3/2005 |
| WO | 2005028444 A1 | 3/2005 |

(56) References Cited

FOREIGN PATENT DOCUMENTS

| | | |
|---|---|---|
| WO | 2005039587 A1 | 5/2005 |
| WO | 2005046698 A1 | 5/2005 |
| WO | 2005063752 A1 | 7/2005 |
| WO | 2005073204 A1 | 8/2005 |
| WO | 2005079391 A2 | 9/2005 |
| WO | 2005080377 A1 | 9/2005 |
| WO | 2005105761 A1 | 11/2005 |
| WO | 2006015859 A1 | 2/2006 |
| WO | 2006039718 A2 | 4/2006 |
| WO | 2006050843 A1 | 5/2006 |
| WO | 2006058867 A2 | 6/2006 |
| WO | 2006058869 A2 | 6/2006 |
| WO | 2006069805 A2 | 7/2006 |
| WO | 2006120251 A1 | 11/2006 |
| WO | 2006135993 A1 | 12/2006 |
| WO | 2007093901 A1 | 8/2007 |
| WO | 2007135026 A2 | 11/2007 |
| WO | 2007135027 A1 | 11/2007 |
| WO | 2008003149 A2 | 1/2008 |
| WO | 2008009076 A2 | 1/2008 |
| WO | 2008009077 A2 | 1/2008 |
| WO | 2008009078 A2 | 1/2008 |
| WO | 2008009079 A2 | 1/2008 |
| WO | 2008009706 A1 | 1/2008 |
| WO | 2008024977 A2 | 2/2008 |
| WO | 2008030455 A2 | 3/2008 |
| WO | 2008077649 A1 | 7/2008 |
| WO | 2008077651 A1 | 7/2008 |
| WO | 2008154221 A2 | 12/2008 |
| WO | 2009003669 A2 | 1/2009 |
| WO | 2010002877 A2 | 1/2010 |
| WO | 2010002998 A1 | 1/2010 |
| WO | 2010042489 A2 | 4/2010 |
| WO | 2010046639 A1 | 4/2010 |
| WO | 2010092340 A1 | 8/2010 |
| WO | 2011057148 A1 | 5/2011 |
| WO | 2011072275 A2 | 6/2011 |
| WO | 2011097607 A1 | 8/2011 |
| WO | 2011135259 A1 | 11/2011 |
| WO | 2012058601 A1 | 5/2012 |
| WO | 2012136834 A1 | 10/2012 |
| WO | 2012156498 A1 | 11/2012 |
| WO | 2013060881 A1 | 5/2013 |
| WO | 2013090840 A1 | 6/2013 |
| WO | 2013117615 A1 | 8/2013 |
| WO | 2013174947 A1 | 11/2013 |
| WO | 2014023813 A1 | 2/2014 |
| WO | 2014056953 A1 | 4/2014 |
| WO | 2014076221 A1 | 5/2014 |
| WO | 2014078778 A2 | 5/2014 |
| WO | 2014116755 A1 | 7/2014 |
| WO | 2014120995 A2 | 8/2014 |
| WO | 2014128189 A1 | 8/2014 |
| WO | 2015014815 A1 | 2/2015 |
| WO | 2015168269 A1 | 11/2015 |
| WO | 2015191752 A1 | 12/2015 |
| WO | 2016141092 A1 | 9/2016 |
| WO | 2017048727 A1 | 3/2017 |
| WO | 2018002319 A1 | 1/2018 |
| WO | 2018045144 A1 | 3/2018 |
| WO | 2018045150 A1 | 3/2018 |
| WO | 2020214652 A1 | 10/2020 |
| WO | 2020214663 A1 | 10/2020 |
| WO | 2022241134 | 11/2022 |

OTHER PUBLICATIONS

Balbach, "Pharmaceutical evaluation of early development candidates 'The 100 mg approach'", International J. Pharmaceutics, 2004, 275, 1-12.

Ramu et al, Circumvention of Adriamycin Resistance by Dipyridamole Analogues: A Structure-activity Relationship Study, Int. J. Cancer, 1989, pp. 487-491, vol. 43.

Abou-Hedeed et al. (1996) "Pteridines CVIII Reactions of 6, 7-Dichloro-1, 3-Dimethyllumazine with Sulfur-Nucleophiles", Pteridines, 7:113-122.

Anonymous, (Sep. 24, 2003) "FDA mulls drug to slow late-stage Alzheimer's", Retrieved from CNN.com, 2 pages.

Anonymous, (Jul. 27, 2007) "Ankylosing Spondylitis", Retrieved Online on from http://www.nlm.nih.gov/medicineplus/print/ankylosingspondylitis.html, 3 pages.

Armarego et al. (1967) "Quinazolines. Part IX. Covalent hydration in the neutral species of substituted quinazolines", Journal of the Chemical Society Biological Physical Organic, 449-454.

Baba et al. (1984) "Synergistic Antiviral Effects of Antiherpes Compounds and Human Leukocyte Interferon on Varicella-Zoster Virus in Vitro", Antimicrobial Agents and Chemotherapy, 25: 515-517.

Banker et al. (1996) "Modern Pharmaceutics", Third Edition, Revised and Expanded, 596 (3 pages).

Barl et al. (Jan. 2014) "The Halogen/Magnesium-Exhange using iPrMgCl.LiCl and related exchange reagents", Heterocycles, 88(2):827-844.

Beers et al., (1999) "The Merck Manual of Diagnosis and Therapy, Merck Research Laboratories", Whitehouse Station, N.J., Neurologic Disorders, Sec. 14, 1474-1476.

Beers et al. (1999) "The Merck Manual of Diagnosis and Therapy, Merck Research Laboratories", Whitehouse Station, N.J., Leukemias, Chapter 138, 953-954.

Bennett et al. (1996) "Cecil Textbook of Medicine", vol. 1, pp. 1004-1010.

Bennett et al. (1996) "Cecil Textbook of Medicine, 20th Ed.", 20th Edition, 2:1992-1996.

Bennett et al. (1996) "Cecil Textbook of Medicine, 20th Ed.", 20th Edition, 2:2050-2057.

Bigorgne et al. (2010) "TLRs in Hepatic Cellular Crosstalk, Gastroenterology Research and Practice", Article ID 618260, 2010:1-7.

Black et al. (1997) "Agents that Block TNF-a Synthesis or Activity", Annual Reports in Medicinal Chemistry, 32:241-250.

Boon, (1957) "Pteridines. Part IV. Derivatives of 2:4-Diaminopteridine and Related Compounds", Journal of the Chemical Society, 2146--2158.

Brown et al. (1961) "Pteridine Studies. Part XIV. Methylation of 2-Amino-4-hydroxypteridine and Related Compounds", Journal of the Chemical Society, 869:4413-4420.

Buitendijk et al. (Dec. 2013) "Toll-Like Receptor Agonists Are Potent Inhibitors of Human Immunodeficiency Virus-Type 1 Replication in Peripheral Blood Mononuclear Cells", AIDS Research and Human Retroviruses, 30(5):457-467.

Bundgaard Hans, (1985) "Design of Prodrugs: Bioreversible Derivatives for Various Functional Groups and Chemical Entities", Elsevier, 3 pages.

Buu-Hoi et al. (1968) "Phthalonimides (1,3,4-Trioxo-1,2,3,4-Tetrahydroisoquinolines) of Potential Biological Interest", Journal of Heterocyclic Chemistry, 5:545-546.

Cairo, (Sep. 30, 2003) "Immunology Lecture #20: Transplantation", Columbia University [online] Retrieved Jul. 12, 2005 from http://healthsciences.columbia.edu/dept/ps/2007/immuno/2006/IM20.pdf, 6 pages.

Cervantes et al. (2012) "TLR8: the forgotten relatuve revindicated", Cellular & Molecular Immunology, 9:434-438.

Chantry, (1999) "Tumor Necrosis Factor Antagonists", Expert Opinion on Emerging Drugs, 1:5-13.

Chapman et al. (1947) "Synthetic Antimalarials. Part XVI. 4-Dialkylaminoalkylaminoquinazolines; Variation of Substituents in the 6- and 7-Positions", Journal of the Chemical Society, 890-899 pages.

Cho, (Jul. 4, 1905) "Synthesis and antiviral activity of a series of 1'-substituted 4-aza-7,9-dideazaadenosince C-nucleosides", Bioorganic & Medicinal Chemistry Letters, pp. 2705-2707.

Chou et al. (1984) "Quantitative Analysis of Dose-Effect Relationships: The Combined Effects of Multiple Drugs or Enzyme Inhibitors", Advances in Enzyme Regulation, 22:27-55.

Cohen et al. (1999) "The Development and Therapeutic Potential of Protein Kinase Inhibitors", Current Opinion in Chemical Biology, 3:459-465.

(56) References Cited

OTHER PUBLICATIONS

Colonna et al. (2004) "Plasmacytoid dendritic cells in immunity", Nature Immunology, 5(12):1219-1226.
Cottam et al. (1996) "Substituted Xanthines, Pteridinediones and Related Compounds as Potential Anti-Inflammatory Agents. Synthesis and Biological Evaluation of Inhibitors of Tumor Necrosis Factor Alpha", Journal of Medicinal Chemistry, 39:2-9.
Database Beilstein, (Jan. 1, 1900) "Accession Nos. 1184281", XP002324247, 2 pages.
Database Beilstein, (Jan. 1, 1900) "Accession Nos. 7216143", 3 pages.
Database Beilstein, (Jan. 1, 1900) "Accession Nos. 7928670", XP002296938, 2 pages.
Database Beilstein, Accession Nos. 285496, 252276, and 250719, Beilstein Institute for Organic Chemistry, Angew. Chem. 73:695, 704, 1961; Ber. Bunsen-Ges. Phys. Chem. 69:458, 462, 465, 1965; Chem. Ber. 90:2631, 2633, 2635, 1957; Chem. Ber. 95:755, 762, 196, 22 pages.
Database Beilstein, (Jan. 1, 1900) "Accession Nos. 533693 and 540145", XP002296935, 4 pages.
Database Beilstein, (Jan. 1, 1900) "Accession Nos. 6337777 and 6373242", XP002296933, 6 pages.
Database Beilstein, (2003) "Accession Nos. 9571456 and 9570157", XP-002296936, 11 pages.
Database WPI, (Feb. 23, 2005) "Week 2005", Thompson Scientific, London, GB (XP002498175).
Dempcy et al. (1991) "Regioselective Synthesis of Imidazo[4,5-g]quinazoline Quinone Nucleosides and Quinazoline Amino Nucleosides. Studies of their Xanthine Oxidase and Purine Nucleoside Phosphorylase Substrate Activity", The Journal of Organic Chemistry, 56:776-785.
Dermer, (Mar. 12, 1994) "Another Anniversary for the War on Cancer", Bio/Technology, 12:320.
Deuis, (2017) "Pharmacological characterization of the highly Nav1.7 selective spider venom peptide Pn3a", Scientific Reports, 7:40883 (18 pages).
Dimauro et al. (2006), "Microwave-assisted preparation of fused bicyclic heteroaryl boronates: application in one-pot Suzuki couplings", The Journal of Organic Chemistry, 3959-3962.
Ding et al. (2005) "Parallel Synthesis of Pteridine Derivatives as Potent Inhibitors for Hepatitis C Virus NS5B RNA-Dependent RNA Polymerase", Bioorganic & Medicinal Chemistry Letters, 15:675-678.
Elion et al. (1954), "Antagonists of Nucleic Acid Derivatives. VIII. Synergism in Combinations of Biochemically Related Antimetabolites", Journal of Biological Chemistry, 477-488.
Elliott et al. (1975), "Synthesis of N-10-Methyl-4-Thiofolic Acid and Related Compounds", Journal of Medicinal Chemistry, 18:492-496.
Freshney, (1983) "Culture of Animal Cells", Alan R. Liss, Inc., 1-5.
Frohlich et al. (1999), "Inhibition of Neuronal Nitric Oxide Synthase by 4-Amino Pteridine Derivatives: Structure-Activity Relationship of Antagonists of (6R)-5, 6, 7, 8-Tetrahydrobiopterin Cofactor", Journal of Medicinal Chemistry, 42:4108-4121.
Ganellin, (2002), "Final Report on the Activities of the Medicinal Chemistry Section", Retrieved Jun. 2, 2004 from www.iupac.org/divisions/VII/VII.M/VIIM-ReportDec2001.pdf, 4 pages.
Gerlach et al. (1965) "Influence of Pyrimidopyrimidine and Pteridine Derivatives on Phosphate and Adenosine Permeability in Human Erythrocytes", Arzneimittelforschung (English Abstract), 15:558-563.
Giori, (1986) "Reactivity of 3H-Pyrimido[5, 4-c] [1, 2, 5] Oxadiazin-3-One Towards Carbanions: Synthesis of Pteridine-2, 4-Diones", Journal of Heterocyclic Chemistry, 23:1661-1665.
Golub et al. (1999) "Molecular Classification of Cancer: Class Discovery and Class Prediction by Gene Expression Monitoring", Science, 286(5439): 531-537.
Gonzalez-Rodriguez et al. (2017) "Synergistic combinations of the dual enkephalinase inhibitor PL265 given orally with various analgesic compounds acting on different targets, in a murine model of cancer-induced bone pain", Scandinavian Journal of Pain, 14(14):25-38.
Guillermo et al. (Apr. 1, 2007) "Targeting cell cycle kinases for cancer therapy", Current Medicinal Chemistry, 14:969-985.
Hayakawa et al. (2006) "Synthesis and Biological Evaluation of 4-Morpholino-2-Phenylquinazolines and Related Derivatives as Novel PI3 Kinase p110alpha Inhibitors", Bioorganic & Medicinal Chemistry, 14:6847-6858.
Hayden, (2001) "Antimicrobial Agents (Continued) Antiviral Agents (Nonretroviral)", Goodman and Gilman's The Pharmacological Basis for Therapeutics, 10th Edition, Chapter 50, 1313-1315.
Higuchi et al. (1976) "A Disproportionation of 6-Amino-5-Benzylideneamino-1,3-dimethyluracils in Formamide. Formation of 6,7-Diaryl-1,3-dimethyllumazines and Theophylline", Heterocycles, 4:977-980.
Horner et al. (1968) "Analogs of 3 Amino-7-chloro-1,2,4-benzotriazine 1-Oxide as Antimalarial Agents", Journal of Medicinal Chemistry, 11:946-949.
Illei et al. (2000) "Novel, Non-Antigen-Specific Therapeutic Approaches to Autoimmune/Inflammatory Diseases", Current Opinion in Immunology, 12:712-718.
Isensee, (2017) "Synergistic regulation of serotonin and opioid signaling contribute to pain insensitivity in Nav1.7 knockout mice", Neuroscience, Science Signaling, 11 pages.
Israel et al. (1965) "Pyrimidine Derivatives. VII. Some Condensed Derivatives of 2, 4, 5-Triamino-6-Methylthiopyrimidine", Journal of Pharmaceutical Sciences, 54:1626-1632.
Iwagaki et al. (1995) "Decreased Serum Tryptophan In Patients With Cancer Cachexia Correlates With Increased Serum Neopterin", Immunological Investigations, 24:467-478.
Jackson et al. (1996) "6, 7-Disubstituted 2, 4-Diaminoteridines: Novel Inhibitors of Pneumocystis carinii and Toxoplasma gondii Dihydrofolate Reductase", Antimicrobial Agents and Chemotherapy, 40:1371-1375.
Jo et al. (Jun. 1, 2014) "Toll Like Receptor 8 Agonist and Bacteria Trigger Potent Activation of Innate Immune Cells in Human Liver", PLOS Pathogens, 13 pages.
Kaczanowska et al., (Jul. 5, 1905) "TLR agonists: our best frenemy in cancer immunotherapy", Journal of Leukocyte Biology, 93(6):847-863.
Kaldrikyan et al. (1976) "Pteridine Derivatives. I. Synthesis of Some Substituted 6,7-Diarylpteridines", Armyanskii Khimicheskii Zhumat, (8 pages including English translation on pp. 6-8), 29:337-341.
Kandror et al. (1982) "Radical Arylation of N-Substituted Carboxylic Acid Thioamides and Cyclic Thioamides", Russian Chemical Bulletin (Abstract only), 31:1873-1876.
Kikelj, (2004) "From 2-Aminobenzonitriles and Carbon Dioxide, Carbon Monoxide, Carbon Disulfide, or Potassium 0-Ethyl Dithiocarbonate", Science of Synthesis, 573-749.
Kujime et al. (2007) "Regioselective Preparation of Pterin 6-Triflate and Its Application to 6-Substituted Pterin Synthesis", Heterocycles, 57:1841-1850.
Landauer et al. (1953) "A Convenient Synthesis of Some 4-Substituted 5-Aminopyrimidines", Journal of the Chemical Society, 3721-3722.
Landry et al. (2003) "Pharmacologie Des Cibles Vers L'Indication Therapeutique", Cours et Exercices, 177.
Leguen, (2003) "Pain management by a new series of dual inhibitors of enkephalin degrading enzymes: long lasting antinociceptive properties and potentiation by CCK2 antagonist or methadone", Pain, 104:139-148.
Lensink Cornelis, (Jun. 20, 1905) "Synthesis and Structure of Sulfonamido Cyclopentadiene Titanium Complexes: X-ray Structure of Ti(η5:σ-C5H4CH2CH2NSO2C6H4CH3)CI2", Journal of Organometallic Chemistry, 553:387-392.
Lin et al. (1997) "Use of the Methylxanthine Derivative A802715 in Transplantation Immunology, I. Strong in Vitro Inhibitory Effects on CD28-Costimulated T Cell", Transplantation, 63:1813-1818.
Lin et al. (1997) "Use of the Methylxanthine Derivative A802715 in Transplantation Immunology, II. In Vivo Experiments", Transplantation, 63:1734-1738.

(56) References Cited

OTHER PUBLICATIONS

Magnus et al. (2005) "Neural Stem Cells in Inflammatory CNS Diseases: Mechanisms and Therapy", Journal of Cellular and Molecular Medicine, 9:303-319.
Matter et al. (2002) "Structural Requirements for Inhibition of the Neuronal Nitric Oxide Synthase (NOS-I): 3D-QSAR Analysis of 4-Oxo- and 4-Amino-Pteridine-Based Inhibitors", Journal of Medicinal Chemistry, 45:2923-2941.
Merz et al. (1996) "Synthesis of 7-Benzylamino-6-chloro-2-piperazino-4-pyrrolidinopteridine and Novel Derivatives Free of Positional Isomers. Potent Inhibitors of CAMP-Specific Phosphodiesterase and of Malignant Tumor Cell Growth", Journal of Medicinal Chemistry, 41:4733-4743.
Minett, (2015) "Endogenous opioids contribute to insensitivity to pain in humans and mice lacking sodium channel Nav1.7", Nature Communciations, 8 pages.
Mohr et al. (1992) "Pteridines. Part XCVII. Synthesis and Properties of 6-thioxanthopterine and 7-thioisoxanthopterin", Helvetica Chimica Acta, 75:2317-2326.
Moody et al. (Mar. 15, 2014) "Toll-Like Receptor 7/8 (TLR7/8) and TLR9 Agonists Cooperate to Enhance HIV-1 Envelope Antibody Responses in Rhesus Macaques", Journal of Virology, 88(6):3329-3339.
Moreb et al. (1992) "The Therapeutic Potential of Interleukin-1 and Tumor Necrosis Factor on Hematopoietic Stem Cells", Leukemia & Lymphoma, 8:267-275.(Abstract Only).
Murata et al. (2000) "A Facile Method for Regioselective 6,7-Disubstitution of Pleridine,", Heterocycles, 53 (6):1259-1262.
Neilsen et al. (1987) "Unequivocal Syntheses of 6-Methykl- and 6-Phenylisoxanthoterin", Journal of Heterocyclic Chemistry, 24:1621-1628.
Nicolaus, (1983) "Symbiotic Approach to Drug Design", Decision Making in Drug Research, Gross (Ed.) Raven Press: New York, 173-186.
Novis et al. (2013) "Reactivation of latent HIV-1 in central memory CD4+ T cells through TLR-1/2 stimulation", Retrovirology, 10(119):15 pages.
Obach, (2003) "Drug-drug Interactions: An Important Negative Attribute in Drugs", Drugs Today, 39:301-338.
Ochoa et al. (1997) "Application of Neural Networks to the Study of Structure-Activity Relationships of 6.7-Diarylpteridines as Nematocides", Medicinal Chemistry Research, 7:530-545.
Ohto et al. (2014) "Structure and function of toll-like receptor 8", Microbes and Infection, 16:273-282.
O'Neill et al. (2013), "The history of Toll-like receptors—redefining innate immunity", Nature Reviews/immunology, 13:453-460.
Patani et al. (1996), "Bioisosterism: A Rational Approach in Drug Design", Chemical Reviews, 96(8):3147-3176.
Peng et al. (Aug. 26, 2005) "Toll-Like Receptor 8-Mediated Reversal of CD4+ Regulatory T Cell Function", Science, 1380-1384.
Pfleiderer et al. (1961) "Pteridine, XII: Synthese von 2-Amino-4-Alkoxy-Pteridinen", Chemische Berichte, 94:12-18.
Ping et al. (2012) "Synthesis of 2,4-Diaminoquinazolines and Tricyclic Quinazolines by Cascade Reductive Cyclization of Methyl N-Cyano-2-nitrobenzimidates", the journal of organic chemistry, 77(6):2649-2658.
Rodrigues et al. (2004) "Co/SiO2 Catalysts for Selective Hydrogenation of Crotonaldehyde III. Promoting Effect of Zinc", Applied Catalysis A: General, 257:201-211.
Roethle et al. (2013) "Identification and Optimization of Pteridinone Toll-Like Receptor 7 (TLR7) Agonists for the Oral Treatment of Viral Hepatitis", Journal of Medicinal Chemistry, 7324-7333.
Rosowsky et al. (1995) "Structure-activity and structure-selectivity studies on Diaminoquinozolines and other inhibitors of Pneumocystis carnii and Toxoplasma gondii Dihydrofolate Reductase", Antimicrobial Agents and Chemotherapy, 39(1):78-86.
Sasse Klaus, (1978) "A Simple New Method For Preparation of 2-Substituted Quinazolines", Synthesis, 379-382.
Sato et al. (Jun. 22, 1905) "Studies on Pyrazines. Part 37. Synthesis of 6-Propionylpteridine-2.4 (1 H,3H)-dione and its 1- and/or 3-Methyl Derivatives from Marine Natural Products", Journal of the Chemical Society, 1:89-95.
Schlaepfer et al. (2011) "TLR8 Activates HIV from Latently Infected Cells of Myeloid-monocytic Origin Directly via the MAPK Pathway and from Latently Infected CD4+ T Cells Indirectly via TNF-α", Journal of Immunology, 186(7):4314-4324.
Sielecki et al. (2001) "Quinazolines as Cyclin Dependent Kinase Inhibitors", Bioorganic & Medicinal Chemistry Letters, 9:1157-1160.
Spickett et al. (1954) "The Synthesis of Compounds With Potential Anti-Folic Acid Activity. Part I 7-Amino- And 7-Hydroxy-Pteridines", Journal of the Chemical Society, 2887-2895.
Sugimoto et al. (1997) "Regioselective Arylation of 1,3-Dimethyllumazine and Its 5-Oxide by Diazonium Salts", Pteridines, 8:188-194.
Sun, (2014) "Inhibitors of voltage-gated sodium channel Nav1.7: patent applications since 2010", Pharmaceutical Patent Analyst, 3(5): 509-521.
Taghavi-Moghadam, (1997) "A New, General, and Regioselective Method for the Synthesis of 2, 6-Disubstituted 4-Aminopteridines", Tetrahedron Letters, 38:6835-6836.
Taylor et al. (2013) "Opioid antagonists for pain", Expert Opinion on Investigational Drugs, 517-525.
Ulrich, (2002) "Kirk-Othmer Encyclopedia of Chemical Technology", Wiley, Chapter 4: Crystallization, 7 pages.
Urakov et al. (1995), "Multiple Reactivity and Tautomerism of Substituted Pyrimidines. IV. Multiple Reactivity of 2-Acetamido-4-Quinazolinones", Uzbek Chemical Journal, 5-6:37-41.
Vema et al. (2003), "Design of EGFR Kinase Inhibitors: A Ligand-Based Approach and its Confirmation with Structure-Based Studies", Bioorganic & Medicinal Chemistry, 11:4643-4653.
Vinot Nicolep, (1973) "N° 505.—EtudeEtudeEtude de Pteridiones-2,4 III Orientation de la Reaction de Condensation D'a-dicetones Avec le Diamino-4,5 Dimethyl-1,3 Uracile", Bulletin de la Societe Chimique de France, 9-10: 2752-2755.
Vippagunta et al. (2001) "Crystalline Solids", Advanced Drug Delivery Reviews, 48:3-26.
Wang et al. (2004) "Use of Polymer-supported Pd Reagents for Rapid and Efficient Suzuki Reactions Using Microwave Heating", Organic Letters, 6:2793-2796.
Warren et al. (Mar. 2, 2016) "Therapeutic Efficacy of the Small Molecule GS-5734 Against Ebola Virus in Rhesus Monkeys", Nature, 531(7594):381-385.
Watashi et al. (Nov. 1, 2013) "Interleukin-1 and Tumor Necrosis Factor Triggeer Restriction of Hepatitis B Virus Infection Via a Cytidine Deaminase Activation-induced Cytidine Deaminase (AID)", The Journal of Biological Chemistry, 288(44):31715-31727.
Weinstock et al. (1968), "Pteridines. XII. Structure-Activity Relationships of Some Pteridine Diuretics", Journal of Medicinal Chemistry, 11:573-579.
West, (Jun. 10, 1905) "Solid State Chemistry and its Applications", Wiley, 3 pages.
Wille-Reece et al. (May 15, 2006) "Toll-like receptor agonists influence the magnitude and quality of memory T cell responses after prime-boost immunization in nonhuman primates", The Journal of Experimental Medicine, 203(5):1249-1258.
Wikipedia, (Dec. 28, 2006) "Wikipedia entries for Anti histamine, Autoimmunity, List of Autoimmune Diseases, Lupus Erythematosus, and Sjogren's Syndrome", retrieved Dec. 28, 2006 from http://en.wikipedia.org, 23 pages.
Wolff, (1995) "Burger's Medicinal Chemistry and Drug Discovery: Fifth Edition", Principles and Practice, 1:783-802.
Wolff, (1995) "Some Considerations for Prodrug Design", Burger's Medicinal Chemistry and Drug Discovery: Fifth Edition, Principles and Practice, 1:975-977.
Xagorari, (2008) "Toll-Like Receptors and Viruses: Induction of Innate Antiviral Immune Responses", The Open Microbiology Journal, 2:49-59.
Yao et al. (2003) "Protection of Pteridines", Helvetica Chimica Acta., 86:1-12.

(56) References Cited

OTHER PUBLICATIONS

Yin et al. (2012) "Synthesis of 2,4-Diaminoquinazolines and Tricyclic Quinazolines by Cascade Reductive Cyclization of Methyl N-Cyano-2-nitrobenzimidates", The Journal of Organic Chemistry, 77(6):2649-2658.
Yu et al. (2013) "Dual Character of Toll-like Receptor Signaling: Pro-tumorigenic Effects and Anti-Tumor Functions", Biochimica et Biophysica Acta, 1835(2):144-154.
Zhao et al. (Jul. 2014) "Toll-like Receptors and prostate cancer", Frontiers in Immunology, Article 352, 5:6 Pages.
Australian Patent Office, Examination Report No. 1 for Australian Patent No. 2016216673, mailed on Sep. 5, 2016, 7 pages.
Australian Patent Office, Examination Report No. 1 for Australian Patent Application No. 2016322763, dated Nov. 28, 2018, 5 pages.
Australian Patent Office, Examination Report No. 2 for Australian Patent Application No. 2016216673, mailed on Nov. 14, 2016, 3 pages.
Chilean Patent Office, Official Action for CL Application No. 201702225, mailed on Nov. 9, 2018, 11 pages.
Dominican Patent Office, Office Action for DO Application No. P2017-0203, dated Oct. 8, 2020, 4 pages.
European Patent Office, Examination Report for EP Patent Application No. 16711723.3, mailed on Nov. 29, 2016.
European Patent Office, International Preliminary Report on Patentability and Written Opinion for International Application No. PCT/BE2007/000091, mailed on Jan. 20, 2009, 4 pages.
European Patent Office, International Preliminary Report on Patentability for International application No. PCT/BE2007/000092, dated Apr. 7, 2009, 13 pages.
European Patent Office, International Preliminary Report on Patentability received for PCT Application No. PCT/US2016/020499, mailed on Sep. 14, 2017, 12 pages.
European Patent Office, International Search Report and Written Opinion received for PCT Application No. PCT/US2016/051545, mailed on Dec. 8, 2016, 13 pages.
European Patent Office, International Search Report and Written Opinion for International Application No. PCT/US2017/049562, mailed on Nov. 14, 2017, 11 pages.
European Patent Office, International Search Report and Written Opinion for International Application No. PCT/US2017/049573, mailed on Oct. 25, 2017, 12 pages.
European Patent Office, International Search Report received for PCT Patent Application No. PCT/US2020/028237, mailed on Jun. 30, 2020, 8 pages.
European Patent Office, International Search Report received for PCT Patent Application No. PCT/US2020/028257, mailed on Jun. 26, 2020, 8 pages.
Gulf Cooperation Council Patent Office, Examination Report for GC application No. GC 2016-30932, dated Jul. 6, 2020, 4 pages.
Israel Patent Office, Office Action for IL Application No. 254164, dated Sep. 21, 2020, 2 pages.
Korean Patent Office, Notice of Preliminary Rejection for Korean Patent Application No. 10-2016-7023289, mailed on Oct. 14, 2016, 9 pages.
Korean Patent Office, Search Report for Korean Patent Application 10-2016-7023289, mailed on Aug. 25, 2016, 14 pages.
Mexico Patent Office, Notice of Allowance for MX application No. MX/a/2017011307, dated Oct. 14, 2020, 2 pages.
Ukraine Patent Office, Notice of Allowance for UA Application No. a210708923, dated Nov. 5, 2020, 17 pages.
Office Action for U.S. Appl. No. 15/264,401, mailed on Dec. 27, 2016, 11 pages.
Office Action for U.S. Appl. No. 12/374,242, mailed on April 9. 2012, 20 pages.
"Selgantolimod C14H20FN5O", PubChem CID 122585078, retrieved from web on Mar. 14, 2022, 15 pages.
(2018) "International Nonproprietary Names for Pharmaceutical Substances (INN)", Who Drug Information, 32(4):559-690 (132 pages).
"Selgantolimod (GS-9688)", MedChemExpress, retrieved from web on Mar. 14, 2022, 3 pages.
Database Registry, Chemical Abstracts Services, CAS Registry No. 2144926-17-8 (Entered STN: Nov. 22, 2017).
Hickey et al., Investigating the role of ligand electronics on stabilizing electrocatalytically relevant low-valent Co (I) intermediates. Journal of the American Chemical Society, 2019, 141(3), 1382-1392.

TOLL LIKE RECEPTOR MODULATOR COMPOUNDS

CROSS REFERENCE TO RELATED APPLICATIONS

This application is a Continuation of U.S. application Ser. No. 16/254,333, filed on Jan. 22, 2019, which is a Continuation of U.S. application Ser. No. 15/496,283, filed on Apr. 25, 2017, now U.S. Pat. No. 10,285,990, issued on May 14, 2019, which is a Continuation of U.S. application Ser. No. 15/059,070, filed on Mar. 2, 2016, now U.S. Pat. No. 9,670,205, issued on Jun. 6, 2017, which claims priority to U.S. Provisional Application Nos. 62/128,397, filed Mar. 4, 2015, and 62/250,403, filed Nov. 3, 2015, all of which are incorporated herein in their entireties for all purposes.

FIELD

This application relates generally to toll like receptor modulator compounds, including diamino pyrido[3,2 D] pyrimidine compounds, and pharmaceutical compositions which, among other things, modulate toll-like receptors (e.g. TLR-8), and methods of making and using them.

BACKGROUND

The toll-like receptor (TLR) family plays a fundamental role in pathogen recognition and activation of innate immunity. Toll-like receptor 8 (TLR-8) is predominantly expressed by myeloid immune cells and activation of this receptor stimulates a broad immunological response. Agonists of TLR-8 activate myeloid dendritic cells, monocytes, monocyte-derived dendridic cells and Kupffer cells leading to the production of proinflammatory cytokines and chemokines, such as interleukin-18 (IL-18), interleukin-12 (IL-12), tumor necrosis factor-alpha (TNF-α), and interferon-gamma (IFN-γ). Such agonists also promote the increased expression of co-stimulatory molecules such as CD8+ cells, major histocompatibility complex molecules (MAIT, NK cells), and chemokine receptors.

Collectively, activation of these innate and adaptive immune responses induces an immune response and provides a therapeutic benefit in various conditions involving autoimmunity, inflammation, allergy, asthma, graft rejection, graft versus host disease (GvHD), infection, cancer, and immunodeficiency. For example, with respect to hepatitis B, activation of TLR8 on professional antigen presenting cells (pAPCs) and other intrahepatic immune cells is associated with induction of IL-12 and proinflammatory cytokines, which is expected to augment HBV-specific T cell responses, activate intrahepatic NK cells and drive reconstitution of antiviral immunity. See e.g. Wille-Reece, U. et al. *J Exp Med* 203, 1249-1258 (2006); Peng, G. et al., *Science* 309, 1380-1384 (2005); Jo, J. et al., *PLoS Pathogens* 10, e1004210 (2014) and Watashi, K. et al., *J Biol Chem* 288, 31715-31727 (2013).

Given the potential to treat a wide array of diseases, there remains a need for novel modulators of toll like receptors, for example TLR-8. Potent and selective modulators of TLR-8 that have reduced potential for off target liabilities are particularly desireable.

SUMMARY

The present disclosure provides a compound of Formula (J):

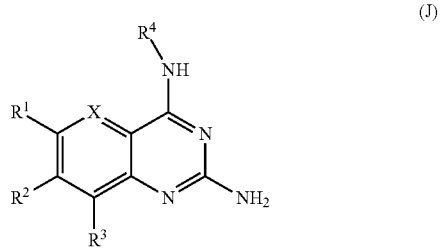

or a pharmaceutically acceptable salt thereof, wherein:
X is N or $CR^{10}$;
$R^1$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups;
$R^2$ is selected from the group consisting of hydrogen, halogen, $C_{1-6}$alkyl, CN, $-NR^aR^b$, $-S(O)_{1-2}R^a$ and $OR^a$, wherein $C_{1-6}$alkyl is optionally substituted with 1 to 5 $R^{20}$ groups;
$R^3$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups;
$R^4$ is $C_{1-12}$ alkyl which is optionally substituted with 1 to 5 substituents independently selected from halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-6}$ haloalkyl, $C_{3-6}$cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;
wherein each $C_{3-6}$cycloalkyl, 3 to 6 membered heterocyclyl, $C_{6-10}$ aryl, and 5 to 10 membered heteroaryl is optionally substituted with 1 to 5 $R^{21}$ groups;
$R^{10}$ is selected from hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups
each $R^{20}$ is independently selected from the group consisting of halogen, $C_{1-6}$ haloalkyl, CN, $-NR^aR^b$, $S(O)_{1-2}R^a$, and $OR^a$;
each $R^{21}$ is independently selected from the group consisting of halogen, $C_{1-6}$ alkyl, $C_{1-6}$haloalkyl, CN, $-NR^aR^b$, $S(O)_{1-2}R^a$, and $OR^a$; and
each $R^a$ and $R^b$ are independently selected from the group consisting of hydrogen and $C_{1-6}$alkyl; wherein each $C_{1-6}$alkyl is optionally substituted with 1 to 5 substituents independently selected from halogen, hydroxyl, amino, 5 to 10 membered heteroaryl wherein the 5 to 10 membered heteroaryl has 1 to 3 heteroatoms selected from oxygen, nitrogen, and sulfur, and $C_{1-6}$haloalkyl;
provided that when X is N, $R^1$ is Cl, $R^2$ is H and $R^3$ is H then $R^4$ is not $CH_2CH_2OMe$ or $CH_2CH_2SO_2Me$.

The present disclosure provides a compound of Formula (I):

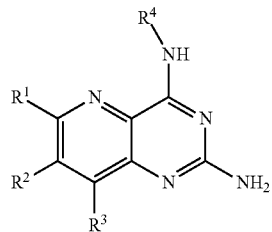

(I)

or a pharmaceutically acceptable salt thereof, wherein:

$R^1$ is selected from the group consisting of hydrogen, halogen, $C_{1-6}$alkyl, CN, —$NR^aR^b$, —$S(O)_{1-2}R^a$, and $OR^a$, wherein $C_{1-6}$alkyl is optionally substituted with 1 to 5 $R^{20}$ groups;

$R^2$ is selected from the group consisting of hydrogen, halogen, $C_{1-6}$alkyl, CN, —$NR^aR^b$, —$S(O)_{1-2}R^a$ and $OR^a$, wherein $C_{1-6}$alkyl is optionally substituted with 1 to 5 $R^{20}$ groups;

$R^3$ is selected from the group consisting of hydrogen, halogen, $C_{1-6}$alkyl, CN, —$NR^aR^b$, —$S(O)_{1-2}R^a$, and $OR^a$, wherein $C_{1-6}$alkyl is optionally substituted with 1 to 5 $R^{20}$ groups;

$R^4$ is $C_{1-12}$ alkyl which is optionally substituted with 1 to 5 substituents independently selected from halogen, —$OR^a$, —$NR^aR^b$, CN, —$C(O)R^a$, —$C(O)OR^a$, —$C(O)NR^aR^b$, —$OC(O)NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-6}$ haloalkyl, $C_{3-6}$cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

wherein each $C_{3-6}$cycloalkyl, 3 to 6 membered heterocyclyl, $C_{6-10}$ aryl, and 5 to 10 membered heteroaryl is optionally substituted with 1 to 5 $R^{21}$ groups;

each $R^{20}$ is independently selected from the group consisting of halogen, $C_{1-6}$ haloalkyl, CN, —$NR^aR^b$, $S(O)_{1-2}R^a$, and $OR^a$;

each $R^{21}$ is independently selected from the group consisting of halogen, $C_{1-6}$alkyl, $C_{1-6}$haloalkyl, CN, —$NR^aR^b$, $S(O)_{1-2}R^a$, and $OR^a$; and each $R^a$ and $R^b$ are independently selected from the group consisting of hydrogen and $C_{1-6}$alkyl; wherein each $C_{1-6}$alkyl is optionally substituted with 1 to 5 substituents independently selected from halogen, hydroxyl, amino, 5 to 10 membered heteroaryl wherein the 5 to 10 membered heteroaryl has 1 to 3 heteroatoms selected from oxygen, nitrogen, and sulfur, and $C_{1-6}$haloalkyl;

provided that when $R^1$ is Cl, $R^2$ is H and $R^3$ is H then $R^4$ is not $CH_2CH_2OMe$ or $CH_2CH_2SO_2Me$.

The present disclosure provides a compound of Formula (IV):

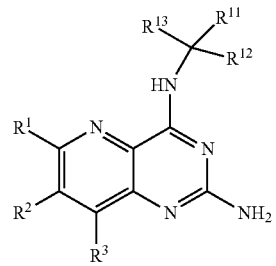

Formula (IV)

wherein:

$R^1$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups;

$R^2$ is selected from the group consisting of hydrogen, halogen, $C_{1-6}$ alkyl, CN, and $OR^a$, wherein $C_{1-6}$ alkyl optionally substituted with 1 to 5 $R^{20}$ groups;

$R^3$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups;

$R^{11}$ is selected from the group consisting of $C_{1-2}$ alkyl, $C_{3-6}$ cycloalkyl, and $C_{1-3}$ haloalkyl;

$R^{12}$ is selected from $C_{1-3}$ alkyl, halogen, —$OR^a$, —$NR^aR^b$, CN, —$C(O)R^a$, —$C(O)OR^a$, —$C(O)NR^aR^b$, —$OC(O)NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-3}$ alkyl group is optionally substituted with 1 or 2 substituents independently selected from halogen, —$OR^a$, —$NR^aR^b$, CN, —$C(O)R^a$, —$C(O)OR^a$, —$C(O)NR^aR^b$, —$OC(O)NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

$R^{13}$ is selected from $C_{1-6}$ alkyl, halogen, —$OR^a$, —$NR^aR^b$, CN, —$C(O)R^a$, —$C(O)OR^a$, —$C(O)NR^aR^b$, —$OC(O)NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-6}$ alkyl is optionally substituted with 1 to 2 substituents independently selected from halogen, —$OR^a$, —$NR^aR^b$, CN, —$C(O)R^a$, —$C(O)OR^a$, —$C(O)NR^aR^b$, —$OC(O)NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

each $R^{20}$ is independently selected from the group consisting of halogen, CN, —$NR^{a}R^{b}$, and $OR^{a}$; and each $R^{a}$ and $R^{b}$ is independently selected from the group consisting of hydrogen and $C_{1-3}$ alkyl, wherein each $C_{1-3}$ alkyl is optionally substituted with 1 to 3 substituents independently selected from halogen, —OH, and $NH_{2}$.

In certain embodiments, the present disclosure provides a pharmaceutical composition comprising a compound of the present disclosure, or a pharmaceutically acceptable salt thereof, and a pharmaceutically acceptable excipient. In certain embodiments, the pharmaceutical composition comprises one or more additional therapeutic agents.

In certain embodiments, a method of modulating TLR-8 is provided, comprising administering a compound of the present disclosure, or a pharmaceutically acceptable salt thereof, to an individual (e.g. a human).

In certain embodiments, a method of treating or preventing a disease or condition responsive to the modulation of TLR-8 is provided, comprising administering to an individual (e.g. a human) in need thereof a therapeutically effective amount of a compound of the present disclosure, or a pharmaceutically acceptable salt thereof. In certain embodiments, the method of treating or preventing a disease or condition responsive to the modulation of TLR-8, comprises administering one or more additional therapeutic agents.

In certain embodiments, a method of treating or preventing a viral infection is provided, comprising administering to an individual (e.g. a human) in need thereof a therapeutically effective amount a compound of the present disclosure, or a pharmaceutically acceptable salt thereof.

In certain embodiments, a method of treating or preventing a hepatitis B viral infection is provided, comprising administering to an individual (e.g. a human) in need thereof a therapeutically effective amount of a compound of the present disclosure, or a pharmaceutically acceptable salt thereof. In certain embodiments, the method of treating or preventing a hepatitis B viral infection comprises administering one or more additional therapeutic agents. In certain embodiments, the individual is a human infected with hepatitis B.

In certain embodiments, a method of treating or preventing a HIV infection is provided, comprising administering to an individual (e.g. a human) in thereof a therapeutically effective amount a compound of the present disclosure, or a pharmaceutically acceptable salt thereof. In certain embodiments, the method of treating or preventing a HIV infection comprises administering one or more additional therapeutic agents. In certain embodiments, the individual is a human infected with HIV (e.g. HIV-1).

In certain embodiments, a method of treating a hyperproliferative disease (e.g. cancer) is provided, comprising administering to an individual (e.g. a human) in thereof a therapeutically effective amount a compound of the present disclosure, or a pharmaceutically acceptable salt thereof. In certain embodiments, the method of treating a hyperproliferative disease (e.g. cancer) comprises administering one or more additional therapeutic agents. In certain embodiments, the individual is a human.

In certain embodiments, a compound of the present disclosure, or a pharmaceutically acceptable salt thereof, for use in medical therapy is provided.

In certain embodiments, a compound of the present disclosure, or a pharmaceutically acceptable salt thereof, for use in treating or preventing a disease or condition responsive to the modulation of TLR-8, is provided. In certain embodiments, the disease or condition is a viral infection.

In certain embodiments, a compound of the present disclosure, or a pharmaceutically acceptable salt thereof, for use in treating or preventing hepatitis B, is provided In certain embodiments, the use of a compound of the present disclosure, or a pharmaceutically acceptable salt thereof, for the manufacture of a medicament for treating or preventing a disease or condition responsive to the modulation of TLR-8, is provided.

In certain embodiments, the use of a compound of the present disclosure, or a pharmaceutically acceptable salt thereof, for the manufacture of a medicament for treating or preventing hepatitis B, is provided.

Kits comprising the compounds, or pharmaceutically acceptable salts thereof, or pharmaceutical compositions of the foregoing are also provided. Articles of manufacture comprising a unit dose of the compounds, or pharmaceutically acceptable salts thereof, of the foregoing are also provided. Methods of preparing compounds of the present disclosure are also provided.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

I. DEFINITIONS

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or $(C_{u}-C_{v})$ indicates that the following group has from u to v carbon atoms, where u and v are integers. For example, "$C_{1-6}$alkyl" indicates that the alkyl group has from 1 to 6 carbon atoms.

"Alkyl" is a linear or branched saturated monovalent hydrocarbon. For example, an alkyl group can have 1 to 10 carbon atoms (i.e., $(C_{1-10})$alkyl) or 1 to 8 carbon atoms (i.e., $(C_{1-8})$alkyl) or 1 to 6 carbon atoms (i.e., $(C_{1-6}$ alkyl) or 1 to 4 carbon atoms (i.e., $(C_{1-4})$alkyl). Examples of alkyl groups include, but are not limited to, methyl (Me, —$CH_{3}$), ethyl (Et, —$CH_{2}CH_{3}$), 1-propyl (n-Pr, n-propyl, —$CH_{2}CH_{2}CH_{3}$), 2-propyl (i-Pr, i-propyl, —$CH(CH_{3})_{2}$), 1-butyl (n-Bu, n-butyl, —$CH_{2}CH_{2}CH_{2}CH_{3}$), 2-methyl-1-propyl (i-Bu, i-butyl, —$CH_{2}CH(CH_{3})_{2}$), 2-butyl (s-Bu, s-butyl, —$CH(CH_{3})CH_{2}CH_{3}$), 2-methyl-2-propyl (t-Bu, t-butyl, —$C(CH_{3})_{3}$), 1-pentyl (n-pentyl, —$CH_{2}CH_{2}CH_{2}CH_{2}CH_{3}$), 2-pentyl (—$CH(CH_{3})CH_{2}CH_{2}CH_{3}$), 3-pentyl (—$CH(CH_{2}CH_{3})_{2}$), 2-methyl-2-butyl (—$C(CH_{3})_{2}CH_{2}CH_{3}$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkenyl" is a linear or branched monovalent hydrocarbon radical with at least one carbon-carbon double bond. For example, an alkenyl group can have 2 to 8 carbon atoms (i.e., C$_{2-8}$ alkenyl), or 2 to 6 carbon atoms (i.e., C$_{2-6}$ alkenyl) or 2 to 4 carbon atoms (i.e., C$_{2-4}$ alkenyl). Examples of suitable alkenyl groups include, but are not limited to, ethylene or vinyl (—CH═CH$_2$), allyl (—CH$_2$CH═CH$_2$), 5-hexenyl (—CH$_2$CH$_2$CH$_2$CH$_2$CH═CH$_2$), and 3-hexenyl (—CH$_2$CH$_2$CH═CHCH$_2$CH$_2$).

"Alkynyl" is a linear or branched monovalent hydrocarbon radical with at least one carbon-carbon triple bond. For example, an alkynyl group can have 2 to 8 carbon atoms (i.e., C$_{2-8}$ alkyne) or 2 to 6 carbon atoms (i.e., C$_{2-6}$ alkynyl) or 2 to 4 carbon atoms (i.e., C$_{2-4}$ alkynyl). Examples of alkynyl groups include, but are not limited to, acetylenyl (—C≡CH), propargyl (—CH$_2$C≡CH), and —CH$_2$—C≡C—CH$_3$.

The term "halo" or "halogen" as used herein refers to fluoro (—F), chloro (—Cl), bromo (—Br) and iodo (—I).

The term "haloalkyl" as used herein refers to an alkyl as defined herein, wherein one or more hydrogen atoms of the alkyl are independently replaced by a halo substituent, which may be the same or different. For example, C$_{1-8}$haloalkyl is a C$_{1-8}$alkyl wherein one or more of the hydrogen atoms of the C$_{1-8}$alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

The term "heteroalkyl" as used herein refers to an alkyl as defined herein, wherein one or more of the carbon atoms of the alkyl are replaced by an O, S, or NR$^q$, wherein each R$^q$ is independently H or C$_{1-6}$alkyl. For example, C$_{1-8}$heteroalkyl intends a heteroalkyl of one to eight carbons wherein one or more carbon atoms is replaced by a heteroatom (e.g., O, S, NR$^q$, OH, SH or N(R$^q$)$_2$), which may be the same or different. Examples of heteroalkyls include but are not limited to methoxymethyl, ethoxymethyl, methoxy, 2-hydroxyethyl and N,N'-dimethylpropylamine. A heteroatom of a heteroalkyl may optionally be oxidized or alkylated. A heteroatom may be placed at any interior position of the heteroalkyl group or at a position at which the group is attached to the remainder of the molecule. Examples include, but are not limited to, —CH$_2$OCH$_3$, —CH$_2$CH$_2$NHCH$_3$, —CH$_2$CH$_2$N(CH$_3$)—CH$_3$, —CH$_2$SCH$_2$CH$_3$, —S(O)CH$_3$, —CH$_2$CH$_2$S(O)$_2$CH$_3$, —CHCHOCH$_3$, —CH$_2$CHNOCH$_3$, —CHCHN(CH$_3$)CH$_3$, —CH$_2$NHOCH$_3$ and —CH$_2$OS(CH$_3$)$_3$ The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1, 2, 3, 4-tetrahydronaphthyl. Non-limiting examples of aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7- tetrahydro-1H-indazole and 3b,4,4a,5-tetrahydro-1H-cyclopropa[3,4]cyclopenta[1,2-c]pyrazole.

The term "cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 5 to about 20 annular atoms, for example from 3 to 12 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring system can be connected to each other via fused, spiro and bridged bonds when allowed by valency requirements. Heterocycles include, but are not limited to, azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like.

The term "oxo" as used herein refers to =O.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

A "compound of the present disclosure" includes compounds disclosed herein, for example a compound of the present disclosure includes compounds of Formula (J), (I), (Ia), (Ib), (II), (IIa), (IIb), (III), (IIIa), (IIIb), and the compounds listed in Table 1. A compound of the present disclosure also includes compounds of Formula (J), (I), (Ia), (Ib), (II), (IIa), (IIb), (III), (IIIa), (IIIb), (VI), (IVa), (IVb), (IVc), (IVd), the compounds of Examples 1-113, and the compounds listed in Tables 1 and 3. A compound of the present disclosure also includes the compounds of Examples 1-118

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming an individual's $HIV^+$ status and assessing the individual's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in individuals with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus. Thus, in certain embodiments, the term "preventing HIV infection" refers to administering to a subject who does not have a detectable HIV infection an anti-HIV therapeutic substance. It is understood that the subject for anti-HIV preventative therapy may be an individual at risk of contracting the HIV virus.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present disclosure, will be apparent to one of ordinary skill in the art.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals As used herein, modulation of a receptor includes agonism, partial agonism, antagonism, partial antagonism, or inverse agonism of a receptor.

The nomenclature used herein to name the subject compounds is illustrated in the Examples and elsewhere herein.

As used herein, "co-administration" includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21st Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds.

A "solvate" is formed by the interaction of a solvent and a compound. Solvates of salts of the compounds described herein are also provided. Hydrates of the compounds described herein are also provided.

A "prodrug" includes any compound that becomes a compound described herein when administered to a subject, e.g., upon metabolic processing of the prodrug.

The terms "combination antiretroviral therapy" ("cART") refers to combinations or "cocktails" of antiretroviral medications used to treat human viral infections, including HIV infections. As used herein, the terms "combination antiretroviral therapy" and "cART include combinations and regimens often referred to as Highly Active Antiretroviral Therapy (HAART). HAART and cART combinations and regimens commonly include multiple, often two or more, drugs such as nucleoside reverse transcriptase inhibitors (NRTIs), non-nucleoside reverse transcriptase inhibitors (NNRTIs), protease inhibitors (PIs), fusion inhibitors, CCR5 agonists, and/or integrase inhibitors.

The terms "latent HIV reservoir", "HIV latent reservoir", "HIV reservoir", "latent reservoir", and "latent HIV infection" refer to a condition in which resting CD4+ T lymphocytes or other cells are infected with HIV but are not actively producing HIV. The presently inactive HIV infected cells are referred to as "latently infected cells". Antiretroviral therapy (ART) can reduce the level of HIV in the blood to an undetectable level, while latent reservoirs of HIV continue to survive. When a latently infected cell is reactivated, the cell begins to produce HIV (HIV replication).

II. COMPOUNDS

The present disclosure provides a compound of Formula (J):

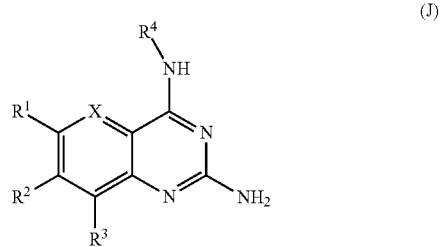

or a pharmaceutically acceptable salt thereof, wherein:
X is N or $CR^{10}$;
$R^1$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups;
$R^2$ is selected from the group consisting of hydrogen, halogen, $C_{1-6}$alkyl, CN, $-NR^aR^b$, $-S(O)_{1-2}R^a$ and $OR^a$, wherein $C_{1-6}$alkyl is optionally substituted with 1 to 5 $R^{20}$ groups;
$R^3$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups;

R⁴ is C$_{1-12}$ alkyl which is optionally substituted with 1 to 5 substituents independently selected from halogen, —OR$^a$, —NR$^a$R$^b$, CN, —C(O)R$^a$, —C(O)OR$^a$, —C(O)NR$^a$R$^b$, —OC(O)NR$^a$R$^b$, —NR$^a$C(O)R$^b$, —NR$^a$C(O)NR$^b$, —NR$^a$C(O)OR$^b$, —SR$^a$, —S(O)$_{1-2}$R$^a$, —S(O)$_2$NR$^a$R$^b$, —NR$^a$S(O)$_2$R$^b$, C$_{1-6}$haloalkyl, C$_{3-6}$cycloalkyl, 3 to 6 membered heterocyclyl wherein the 3 to 6 membered heterocyclyl has 1 to 3 heteroatoms selected from oxygen, nitrogen, and sulfur, C$_{6-10}$ aryl, and 5 to 10 membered heteroaryl wherein the 5 to 10 membered heteroaryl has 1 to 3 heteroatoms selected from oxygen, nitrogen, and sulfur;

wherein each C$_{3-6}$cycloalkyl, 3 to 6 membered heterocyclyl, C$_{6-10}$ aryl, and 5 to 10 membered heteroaryl is optionally substituted with 1 to 5 R$^{21}$ groups;

R$^{10}$ is selected from hydrogen, halogen, C$_{1-6}$alkyl, CN, —NR$^a$R$^b$, —S(O)$_{1-2}$R$^a$, and OR$^a$, wherein C$_{1-6}$alkyl is optionally substituted with 1 to 5 R$^{20}$ groups each R$^{20}$ is independently selected from the group consisting of halogen, C$_{1-6}$ haloalkyl, CN, —NR$^a$R$^b$, S(O)$_{1-2}$R$^a$, and OR$^a$;

each R$^{21}$ is independently selected from the group consisting of halogen, C$_{1-6}$ alkyl, C$_{1-6}$haloalkyl, CN, —NR$^a$R$^b$, S(O)$_{1-2}$R$^a$, and OR$^a$; and each R$^a$ and R$^b$ are independently selected from the group consisting of hydrogen and C$_{1-6}$alkyl; wherein each C$_{1-6}$alkyl is optionally substituted with 1 to 5 substituents independently selected from halogen, hydroxyl, amino, 5 to 10 membered heteroaryl wherein the 5 to 10 membered heteroaryl has 1 to 3 heteroatoms selected from oxygen, nitrogen, and sulfur, and C$_{1-6}$haloalkyl;

provided that when X is N, R$^1$ is Cl, R$^2$ is H and R$^3$ is H then R$^4$ is not CH$_2$CH$_2$OMe or CH$_2$CH$_2$SO$_2$Me.

In certain embodiments of Formula (J), X is CR$^{10}$. In certain embodiments of Formula (J), X is N.

The present disclosure provides a compound of Formula (I):

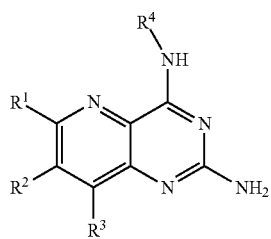

or a pharmaceutically acceptable salt thereof, wherein:

R$^1$ is selected from the group consisting of hydrogen, halogen, C$_{1-6}$alkyl, CN, —NR$^a$R$^b$, —S(O)$_{1-2}$R$^a$, and OR$^a$, wherein C$_{1-6}$alkyl is optionally substituted with 1 to 5 R$^{20}$ groups;

R$^2$ is selected from the group consisting of hydrogen, halogen, C$_{1-6}$alkyl, CN, —NR$^a$R$^b$, —S(O)$_{1-2}$R$^a$ and OR$^a$, wherein C$_{1-6}$alkyl is optionally substituted with 1 to 5 R$^{20}$ groups;

R$^3$ is selected from the group consisting of hydrogen, halogen, C$_{1-6}$alkyl, CN, —NR$^a$R$^b$, —S(O)$_{1-2}$R$^a$, and OR$^a$, wherein C$_{1-6}$alkyl is optionally substituted with 1 to 5 R$^{20}$ groups;

R$^4$ is C$_{1-12}$ alkyl which is optionally substituted with 1 to 5 substituents independently selected from halogen, —OR$^a$, —NR$^a$R$^b$, CN, —C(O)R$^a$, —C(O)OR$^a$, —C(O)NR$^a$R$^b$, —OC(O)NR$^a$R$^b$, —NR$^a$C(O)R$^b$, —NR$^a$C(O)NR$^b$, —NR$^a$C(O)OR$^b$, —SR$^a$, —S(O)$_{1-2}$R$^a$, —S(O)$_2$NR$^a$R$^b$, —NR$^a$S(O)$_2$R$^b$, C$_{1-6}$haloalkyl, C$_{3-6}$cycloalkyl, 3 to 6 membered heterocyclyl wherein the 3 to 6 membered heterocyclyl has 1 to 3 heteroatoms selected from oxygen, nitrogen, and sulfur, C$_{6-10}$ aryl, and 5 to 10 membered heteroaryl wherein the 5 to 10 membered heteroaryl has 1 to 3 heteroatoms selected from oxygen, nitrogen, and sulfur;

wherein each C$_{3-6}$cycloalkyl, 3 to 6 membered heterocyclyl, C$_{6-10}$ aryl, and 5 to 10 membered heteroaryl is optionally substituted with 1 to 5 R$^{21}$ groups;

each R$^{20}$ is independently selected from the group consisting of halogen, C$_{1-6}$ haloalkyl, CN, —NR$^a$R$^b$, S(O)$_{1-2}$R$^a$, and OR$^a$;

each R$^{21}$ is independently selected from the group consisting of halogen, C$_{1-6}$alkyl, C$_{1-6}$haloalkyl, CN, —NR$^a$R$^b$, S(O)$_{1-2}$R$^a$, and OR$^a$; and each R$^a$ and R$^b$ are independently selected from the group consisting of H and C$_{1-6}$ alkyl; wherein each C$_{1-6}$alkyl is optionally substituted with 1 to 5 substituents independently selected from halogen, hydroxyl, amino, 5 to 10 membered heteroaryl wherein the 5 to 10 membered heteroaryl has 1 to 3 heteroatoms selected from oxygen, nitrogen, and sulfur, and C$_{1-6}$haloalkyl;

provided that when R$^1$ is Cl, R$^2$ is H and R$^3$ is H then R$^4$ is not CH$_2$CH$_2$OMe or CH$_2$CH$_2$SO$_2$Me.

In certain embodiments of a compound of Formula (J) or (I), R$^4$ is C$_{1-8}$ alkyl which is optionally substituted with 1 to 5 substituents independently selected from the group consisting of halogen, —OR$^a$, —NR$^a$R$^b$, CN, —C(O)R$^a$, —C(O)OR$^a$, —C(O)NR$^a$R$^b$, —OC(O)NR$^a$R$^b$, —NR$^a$C(O)R$^b$, —NR$^a$C(O)NR$^b$, —NR$^a$C(O)OR$^b$, —SR$^a$, —S(O)$_{1-2}$R$^a$, —S(O)$_2$NR$^a$R$^b$, —NR$^a$S(O)$_2$R$^b$, C$_{1-6}$haloalkyl, C$_{3-6}$cycloalkyl, 3 to 6 membered heterocyclyl wherein the 3 to 6 membered heterocyclyl has 1 to 3 heteroatoms selected from oxygen, nitrogen, and sulfur, C$_{6-10}$ aryl, and 5 to 10 membered heteroaryl wherein the 5 to 10 membered heteroaryl has 1 to 3 heteroatoms selected from oxygen, nitrogen, and sulfur; and wherein each C$_{3-6}$cycloalkyl, 3 to 6 membered heterocyclyl, C$_{6-10}$ aryl, and 5 to 10 membered heteroaryl is optionally substituted with 1 to 5 R$^{21}$ groups.

In certain embodiments of a compound of Formula (J) or (I), R$^4$ is C$_{1-6}$ alkyl optionally substituted with 1 to 5 substituents independently selected from the group consisting of halogen, —OR$^a$, —C(O)OR$^a$, —C(O)NR$^a$R$^b$, —SR$^a$, C$_{1-6}$haloalkyl, C$_{3-6}$cycloalkyl, 3 to 6 membered heterocyclyl, and C$_{6-10}$ aryl; wherein each C$_{3-6}$cycloalkyl, 3 to 6 membered heterocyclyl, and C$_{6-10}$ aryl is optionally substituted with 1 to 5 R$^{21}$ groups. In certain embodiments of a compound of Formula (J) or (I), R$^4$ is C$_{3-8}$ alkyl optionally substituted with 1 to 5 substituents independently selected from the group consisting of halogen, —OR$^a$, —C(O)OR$^a$, —NR$^a$C(O)R$^b$, —SR$^a$, C$_{1-6}$haloalkyl, C$_{3-6}$ cycloalkyl, 3 to 6 membered heterocyclyl, and C$_{6-10}$ aryl; wherein each C$_{3-6}$cycloalkyl, 3 to 6 membered heterocyclyl, and C$_{6-10}$ aryl is optionally substituted with 1 to 5 R$^{21}$ groups.

In certain embodiments of a compound of Formula (J) or (I), R$^4$ is C$_{1-6}$ alkyl optionally substituted with 1 to 3 substituents independently selected from the group consisting of halogen, —OR$^a$, —C(O)OR$^a$, —C(O)NR$^a$R$^b$, —SR$^a$, —C$_{1-3}$haloalkyl, C$_{3-6}$ cycloalkyl, 3 to 6 membered heterocyclyl and C$_{6-10}$ aryl; wherein each C$_{3-6}$cycloalkyl and C$_{6-10}$ aryl is optionally substituted with 1 to 3 R$^{21}$ groups. In certain embodiments of a compound of Formula (J) or (I), R$^4$ is C$_{3-6}$ alkyl optionally substituted with 1 to 3 substituents independently selected from the group consisting of halogen, —OR$^a$, —C(O)OR$^a$, —NR$^a$C(O)R$^b$, —SR$^a$, —C$_{1-3}$haloalkyl, C$_{3-6}$cycloalkyl, 3 to 6 membered heterocyclyl and C$_{6-10}$ aryl; wherein each C$_{3-6}$cycloalkyl and C$_{6-10}$ aryl is optionally substituted with 1 to 3 R$^{21}$ groups.

In certain embodiments of a compound of Formula (J) or (I), R$^4$ is C$_{1-6}$ alkyl optionally substituted with 1 or 2 substituents independently selected halogen, —OR$^a$, —C(O)OR$^a$, —C(O)NR$^a$R$^b$, —SR$^a$, C$_{1-3}$haloalkyl, C$_{3-6}$cycloalkyl, 3 to 6 membered heterocyclyl and C$_{6-10}$ aryl; wherein each C$_{3-6}$cycloalkyl and C$_{6-10}$ aryl is optionally substituted with 1 to 3 R$^{21}$ groups and wherein R$^a$ and R$^b$ are each independently hydrogen or C$_{1-4}$alkyl, wherein the C$_{1-4}$ alkyl is optionally substituted with —NH$_2$, OH, or pyridyl. In certain embodiments of a compound of Formula (J) or (I), R$^4$ is C$_{3-8}$ alkyl which is optionally substituted with 1 or 2 substituents independently selected from the group consisting of halogen, —OR$^a$, —C(O)OR$^a$, —NR$^a$C(O)R$^b$, —SR$^a$, C$_{1-3}$haloalkyl, C$_{3-6}$ cycloalkyl, 3 to 6 membered heterocyclyl and C$_{6-10}$ aryl; wherein each C$_{3-6}$cycloalkyl and C$_{6-10}$ aryl is optionally substituted with 1 to 3 R$^{20}$ groups and wherein R$^a$ and R$^b$ are each independently hydrogen or C$_{1-4}$alkyl, wherein each C$_{1-4}$ alkyl is optionally substituted with —NH$_2$, OH, or pyridyl.

In certain embodiments of a compound of Formula (J) or (I), R$^4$ is C$_{1-6}$ alkyl optionally substituted with 1 or 2 substituents independently selected from the group consisting of OH, CF$_3$, —C(O)OH, —C(O)OCH$_3$, —C(O)NH$_2$, SCH$_3$, —C(O)NHCH$_3$, —C(O)NHCH$_2$CH$_2$NH$_2$, —C(O)NHCH$_2$CH$_2$OH, —C(O)NHCH$_2$-pyridyl, phenyl, tetrahydrofuranyl, and cyclopropyl. In certain embodiments of a compound of Formula (J) or (I), R$^4$ is C$_{3-8}$ alkyl which is optionally substituted with 1 or 2 substituents independently selected from OH, CF$_3$, —C(O)OH, —C(O)OCH$_3$, SCH$_3$, —NHC(O)CH$_3$, —NHC(O)CH$_2$CH$_2$NH$_2$, —NHC(O)CH$_2$CH$_2$OH, —NHC(O)CH$_2$-pyridyl, phenyl, tetrahydrofuranyl, and cyclopropyl.

In certain embodiments of a compound of Formula (J) or (I), R$^4$ is C$_{3-6}$ alkyl optionally substituted with 1 or 2 substituents independently selected from the group consisting of OH, CF$_3$, —C(O)OH, —C(O)OCH$_3$, —C(O)NH$_2$, SCH$_3$, —C(O)NHCH$_3$, —C(O)NHCH$_2$CH$_2$NH$_2$, —C(O)NHCH$_2$CH$_2$OH, and —C(O)NHCH$_2$-pyridyl. In certain embodiments of a compound of Formula (J) or (I), R$^4$ is C$_{3-6}$ alkyl which is optionally substituted with 1 or 2 substituents independently selected from OH, CF$_3$, —C(O)OH, —C(O)OCH$_3$, SCH$_3$, —NHC(O)CH$_3$, —NHC(O)CH$_2$CH$_2$NH$_2$, —NHC(O)CH$_2$CH$_2$OH, —NHC(O)CH$_2$-pyridyl, phenyl, tetrahydrofuranyl, and cyclopropyl.

In certain embodiments of a compound of Formula (J) or (I), R$^4$ is C$_{1-6}$ alkyl which is optionally substituted with OH. In certain embodiments of a compound of Formula (J) or (I), R$^4$ is C$_{3-8}$ alkyl which is optionally substituted with OH. In certain embodiments of a compound of Formula (J) or (I), R$^4$ is C$_{3-8}$ alkyl which is substituted with —NHC(O)CH$_3$.

In certain embodiments of a compound of Formula (J) or (I), R$^4$ is C$_{3-6}$ alkyl which is optionally substituted with OH. In certain embodiments of a compound of Formula (J) or (I), R$^4$ is C$_{3-6}$ alkyl which is substituted with —NHC(O)CH$_3$.

In certain embodiments of a compound of Formula (J) or (I), R$^4$ has at least one chiral center. In certain embodiments, the at least one chiral center is in the S configuration. In certain embodiments, the at least one chiral center is in the R configuration.

In certain embodiments of a compound of Formula (J) or (I), R$^4$ is selected from the group consisting of:

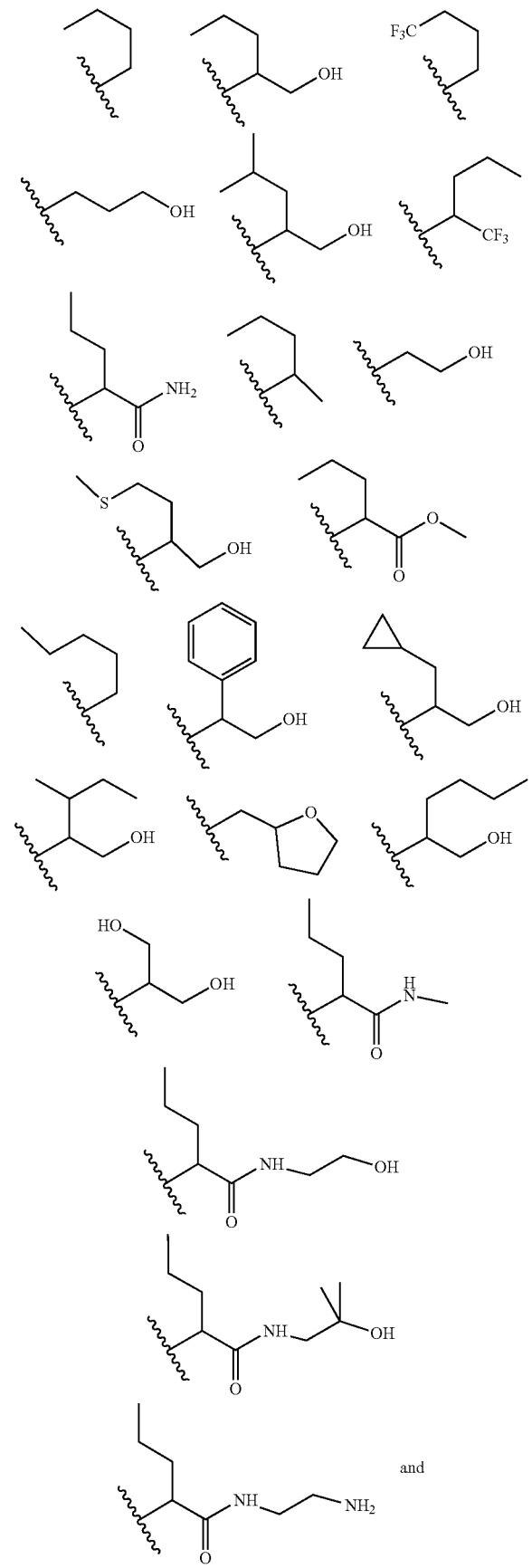

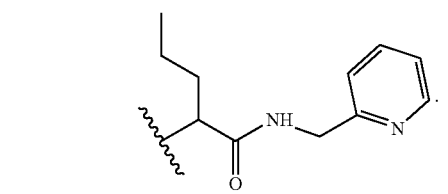
In certain embodiments of a compound of Formula (J) or (I), R⁴ is selected from the group consisting of:
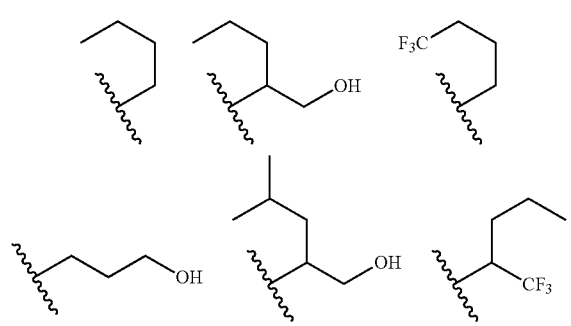
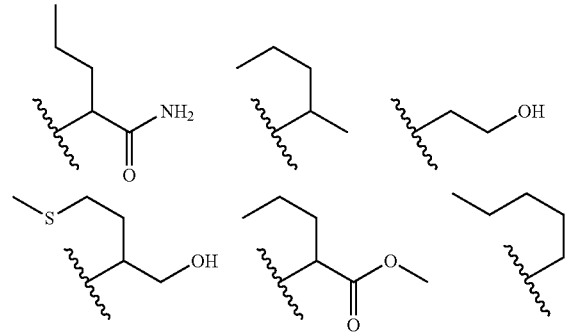
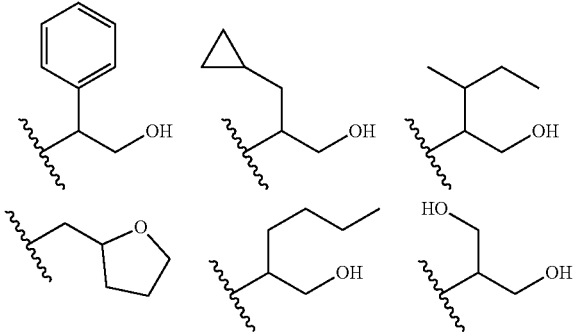
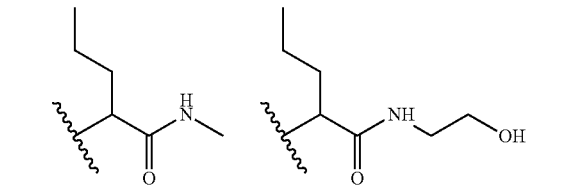
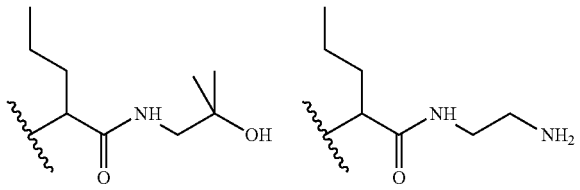
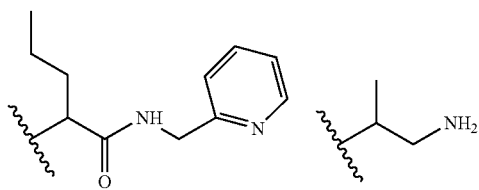
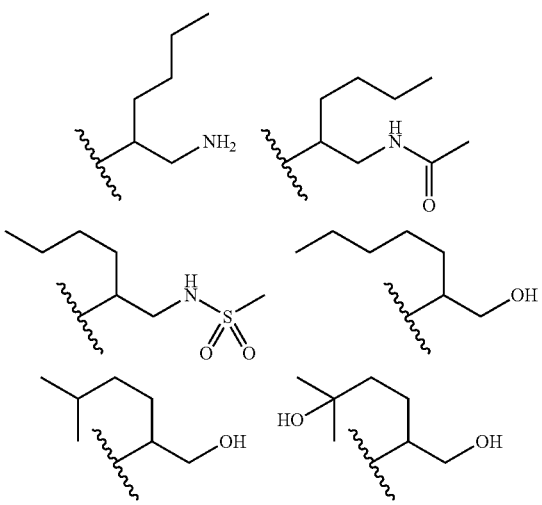
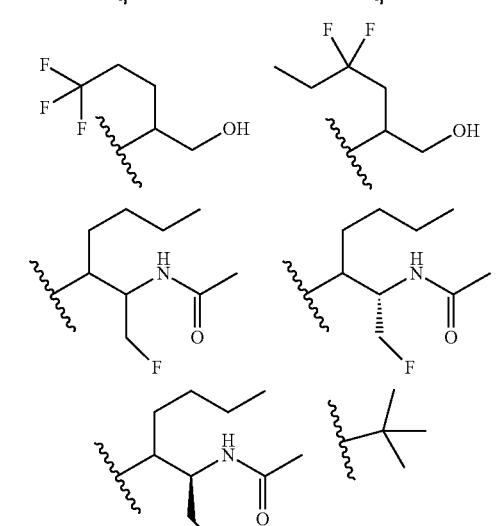
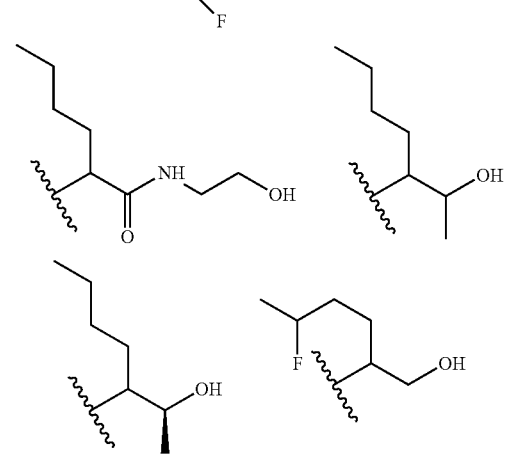

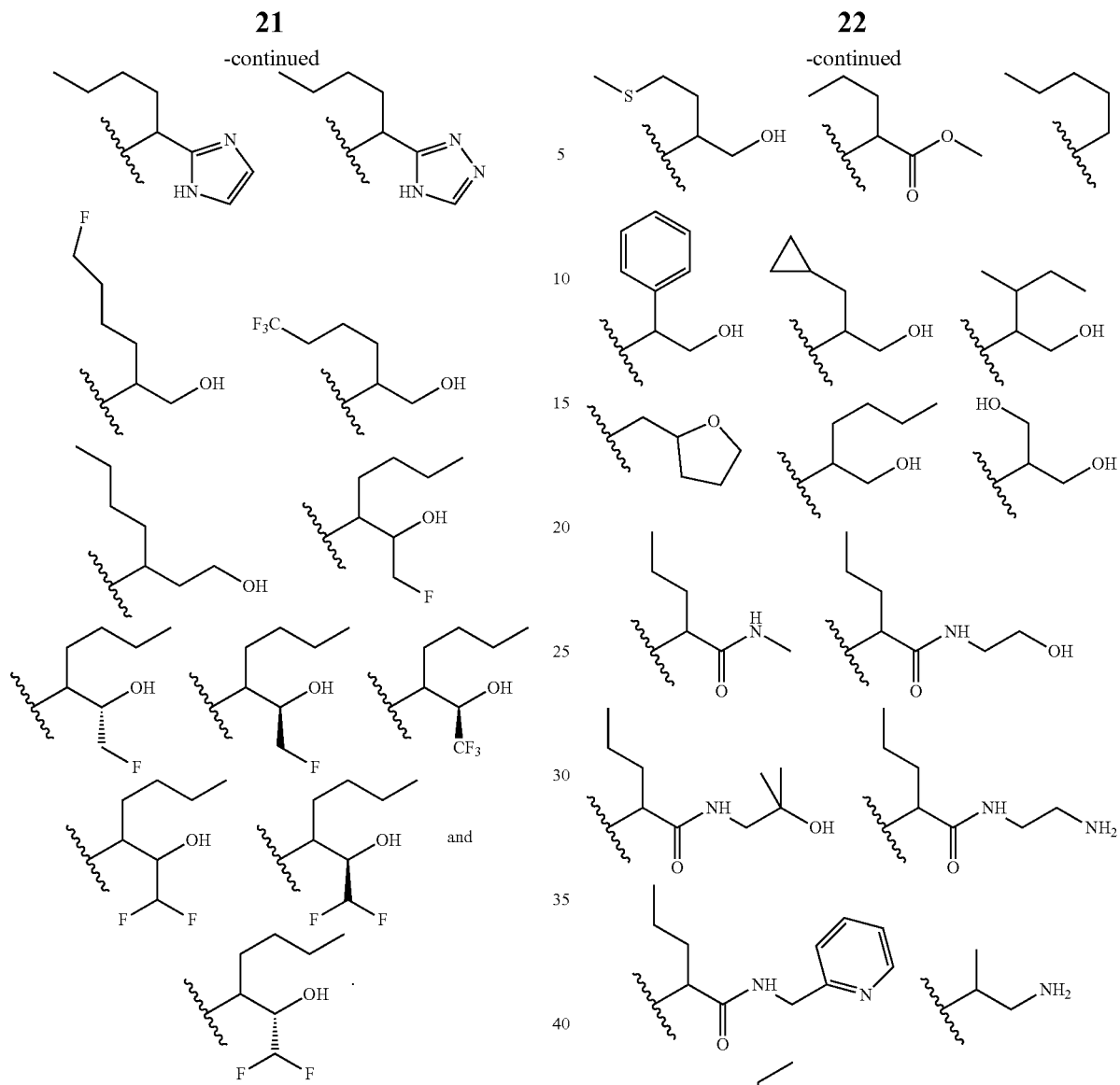
In certain embodiments of a compound of Formula (J) or (I), $R^4$ is selected from the group consisting of:
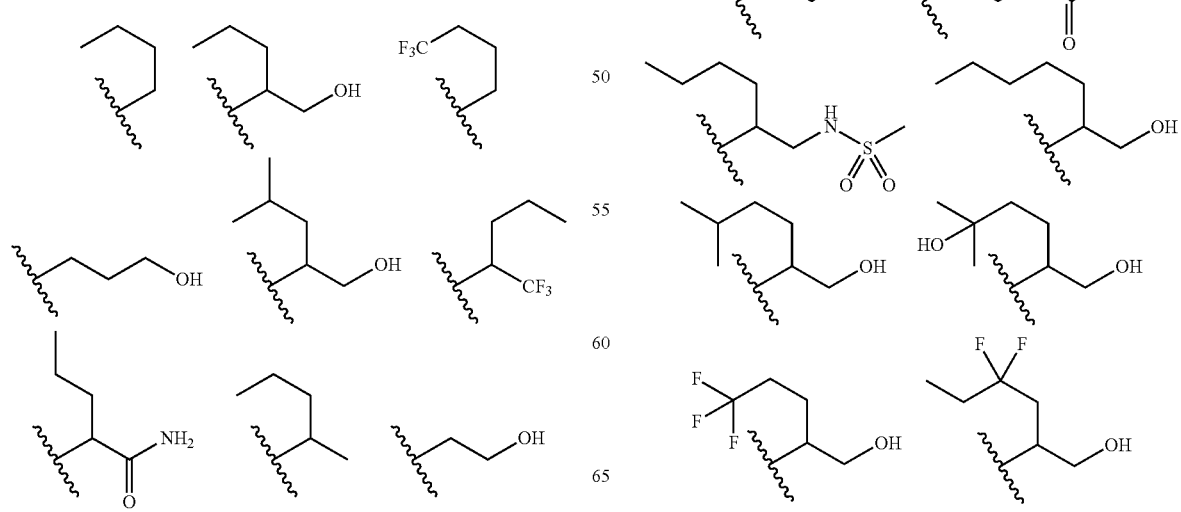

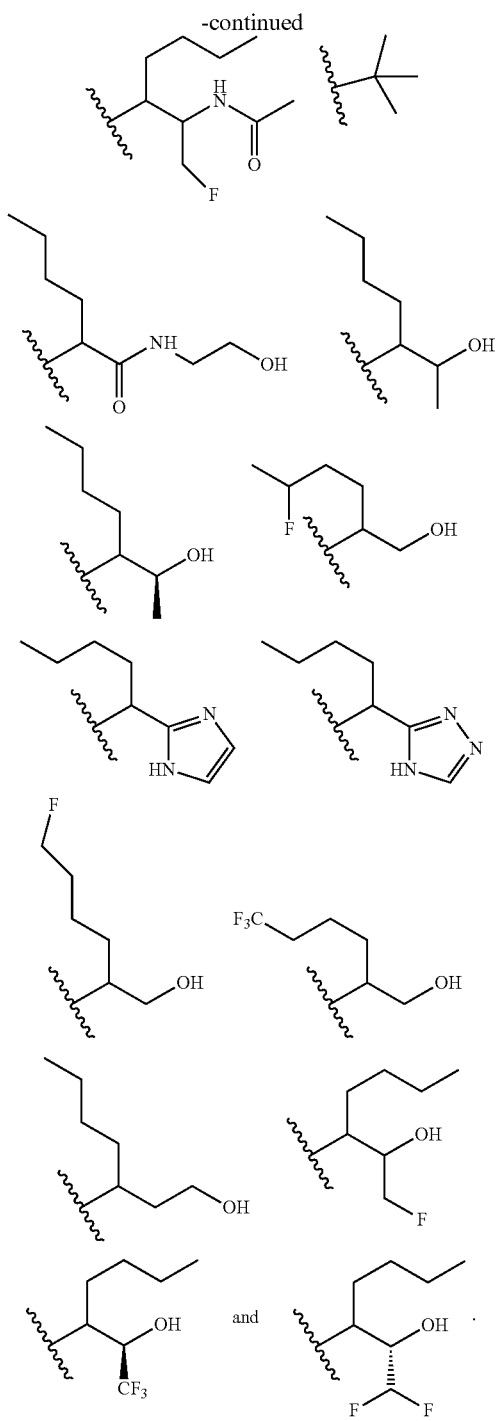
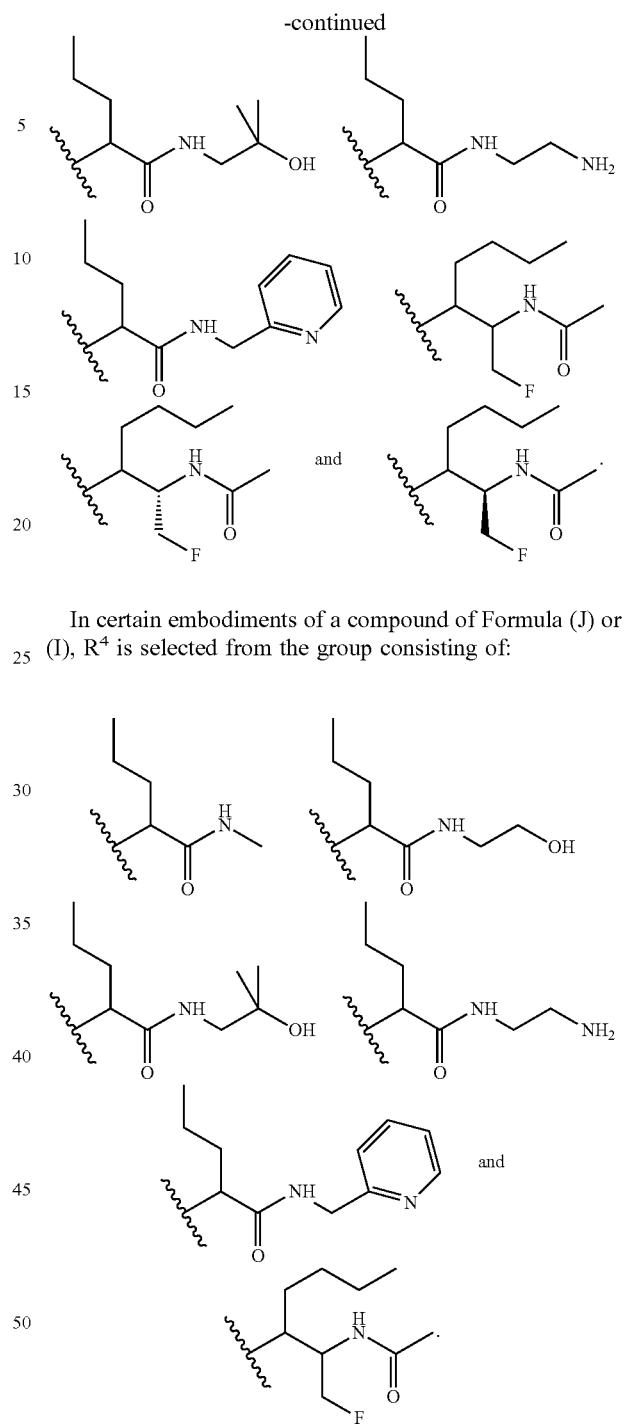
In certain embodiments of a compound of Formula (J) or (I), R⁴ is selected from the group consisting of:
In certain embodiments of a compound of Formula (J) or (I), R⁴ is selected from the group consisting of:
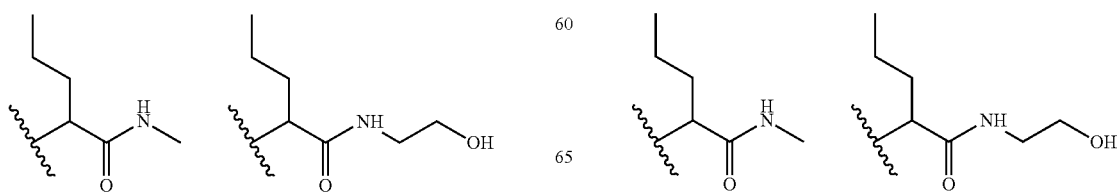

In certain embodiments of a compound of Formula (J) or (I), R⁴ is selected from the group consisting of:

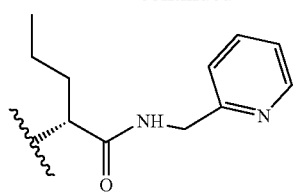
and
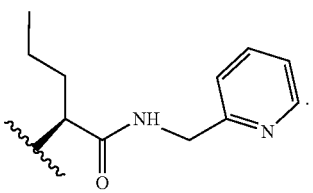
In certain embodiments of a compound of Formula (J) or (I), R⁴ is selected from the group consisting of:
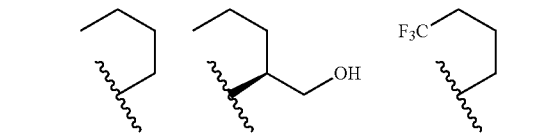
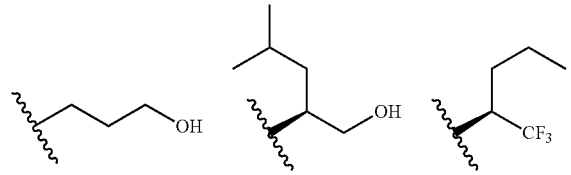
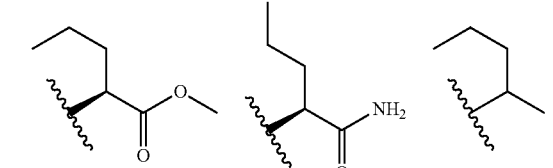
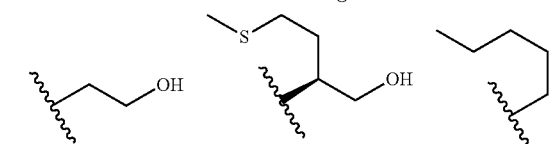
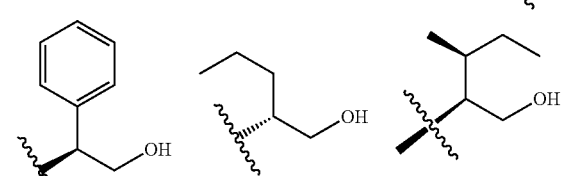
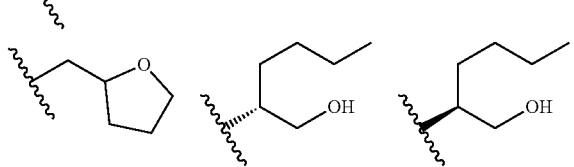
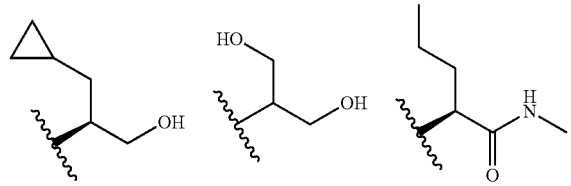
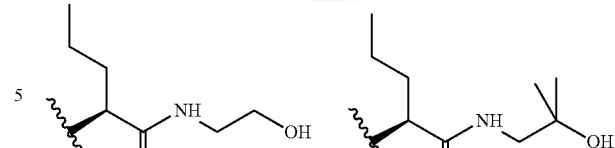
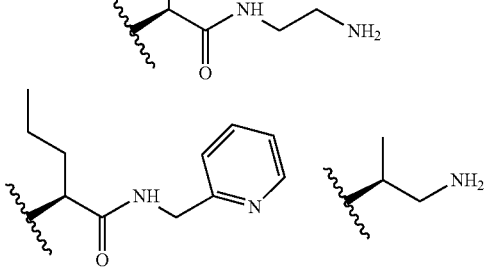
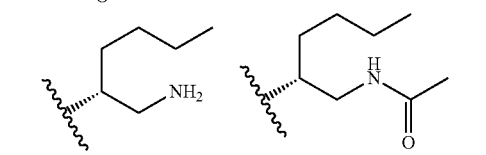
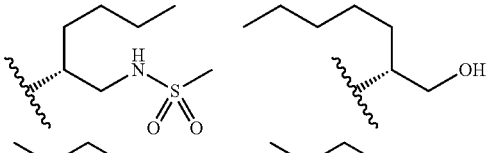
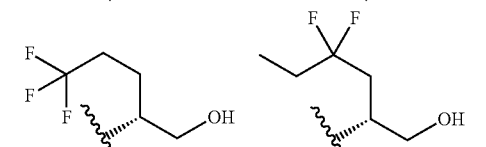
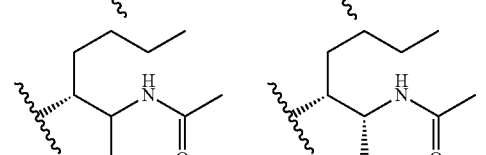
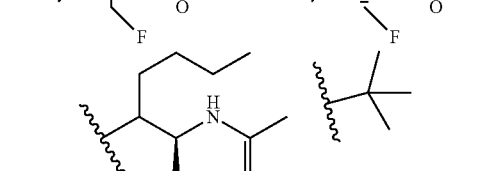
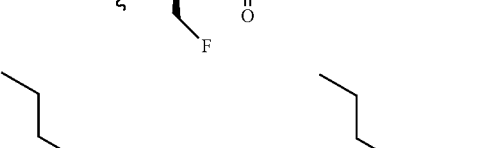
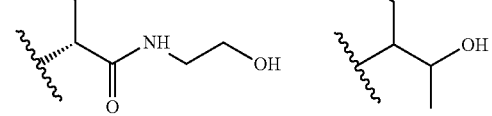

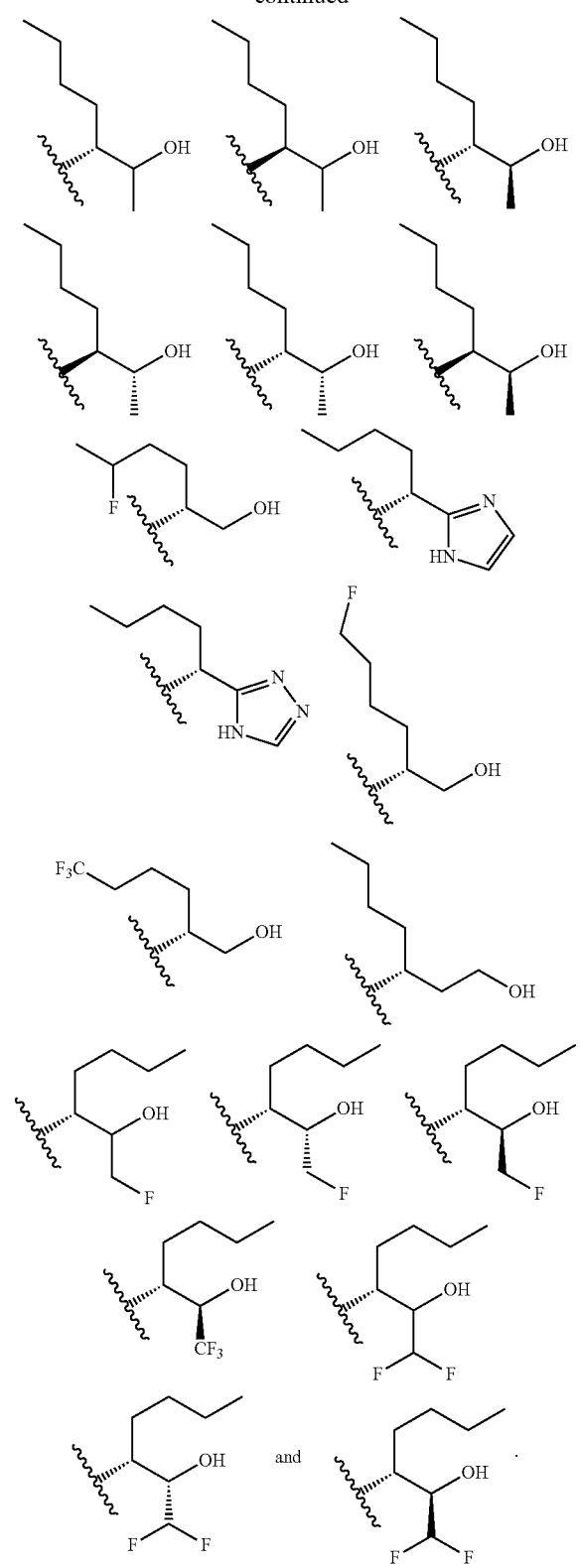
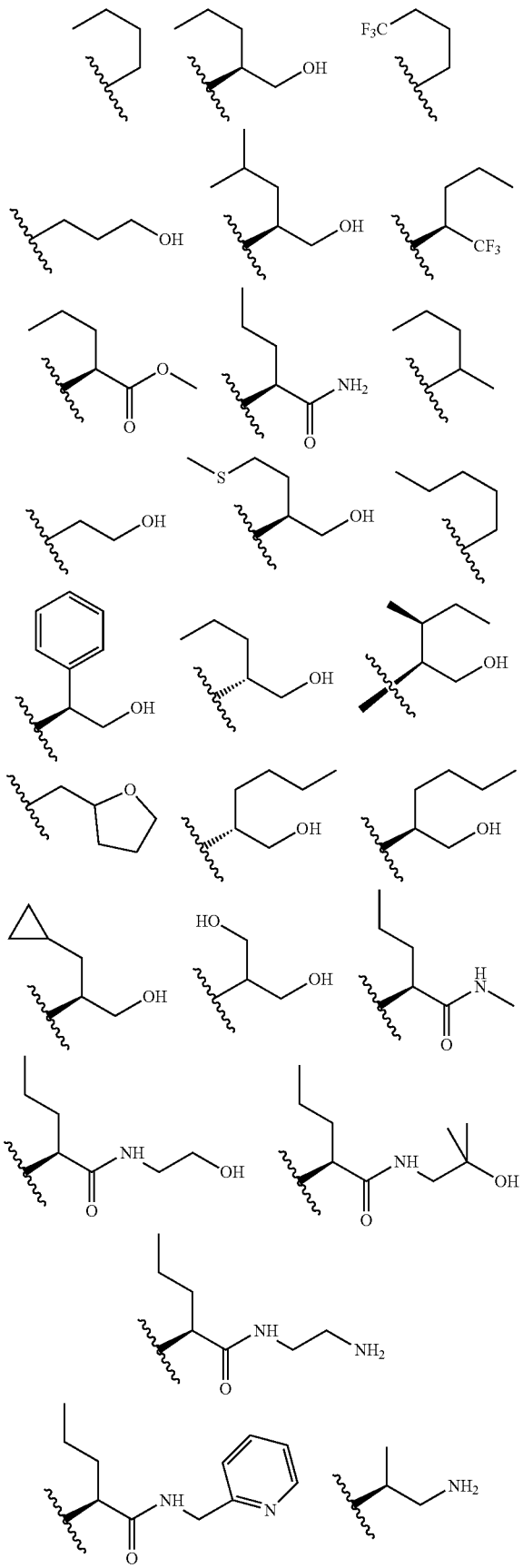
In certain embodiments of a compound of Formula (J) or (I), R⁴ is selected from the group consisting of:

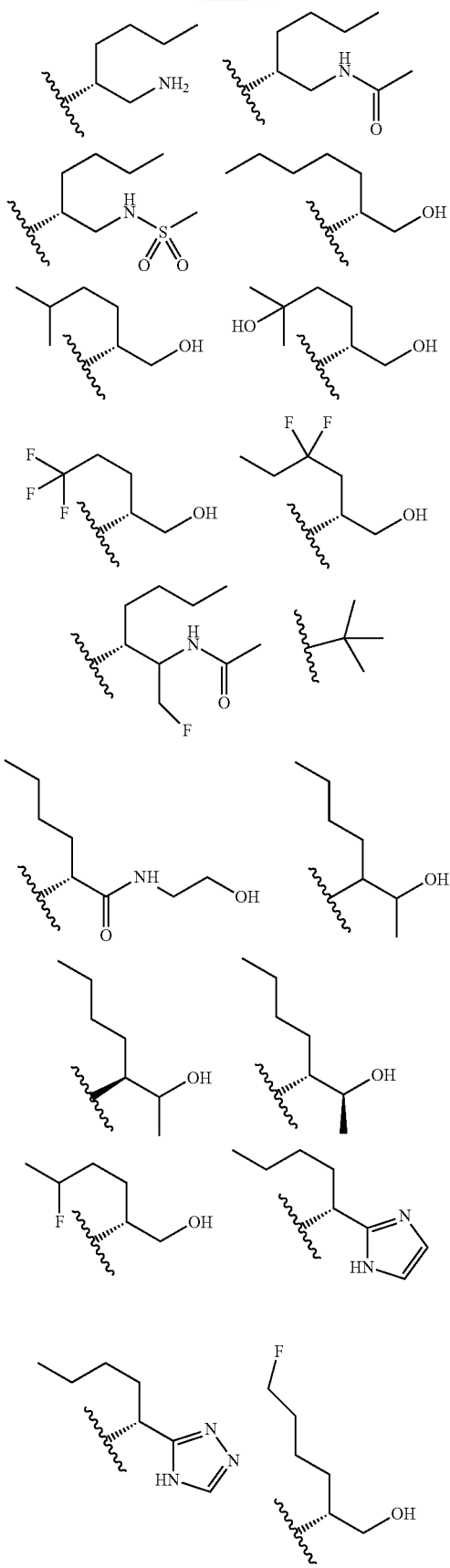
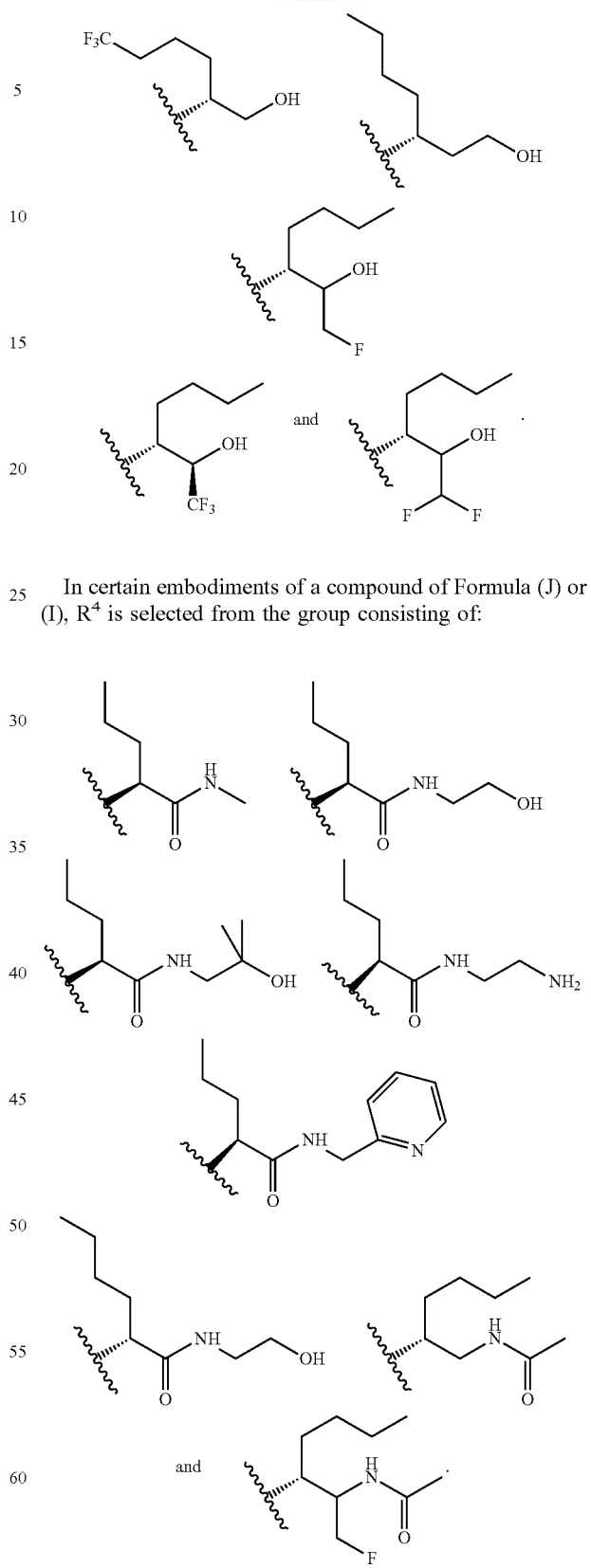
In certain embodiments of a compound of Formula (J) or (I), $R^4$ is selected from the group consisting of:
In certain embodiments of a compound of Formula (J) or (I), $R^4$ is selected from the group consisting of:

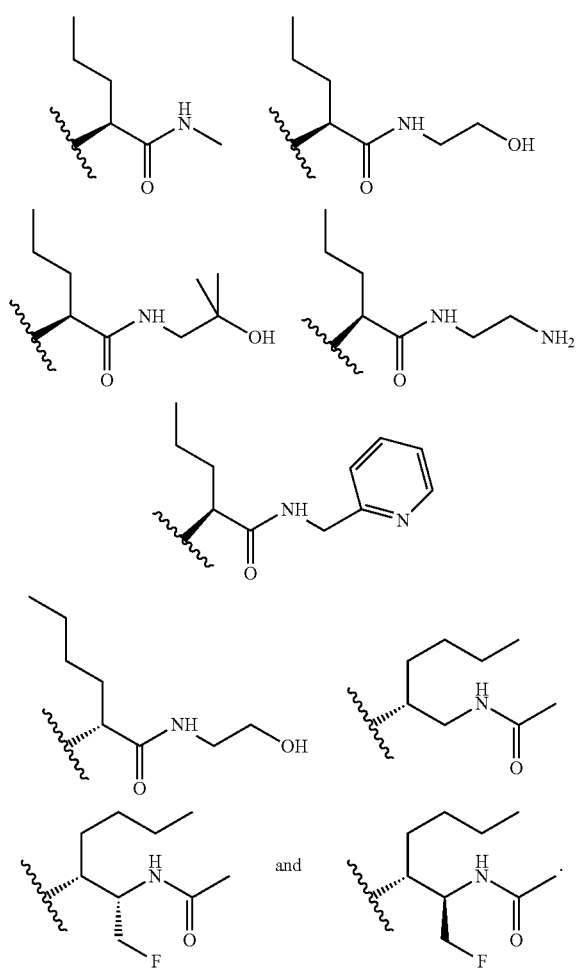
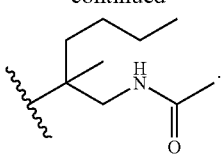
In certain embodiments of a compound of Formula (J) or (I), R⁴ is selected from the group consisting of:
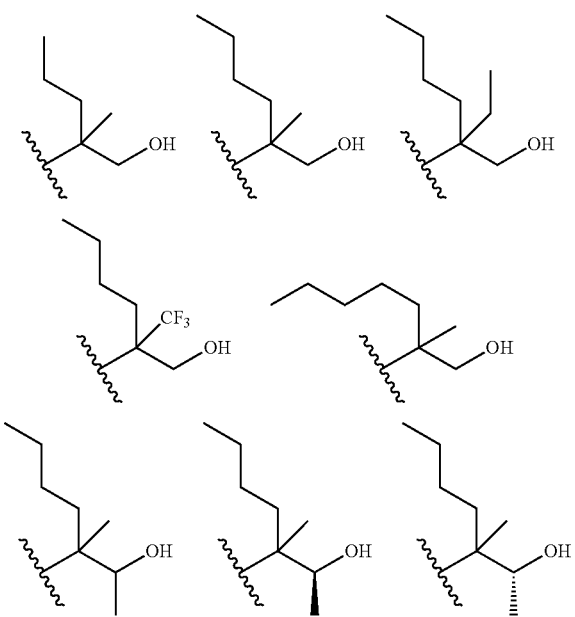
In certain embodiments of a compound of Formula (J) or (I), R⁴ is selected from the group consisting of:
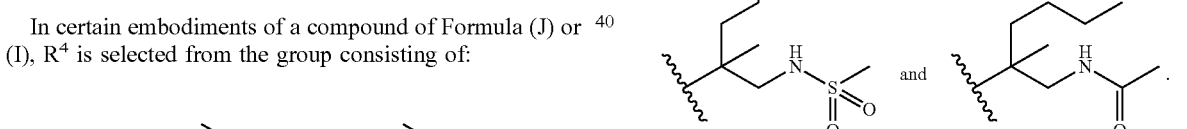
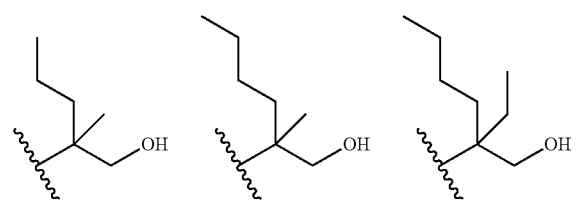
In certain embodiments of a compound of Formula (J) or (I), R⁴ is selected from the group consisting of:
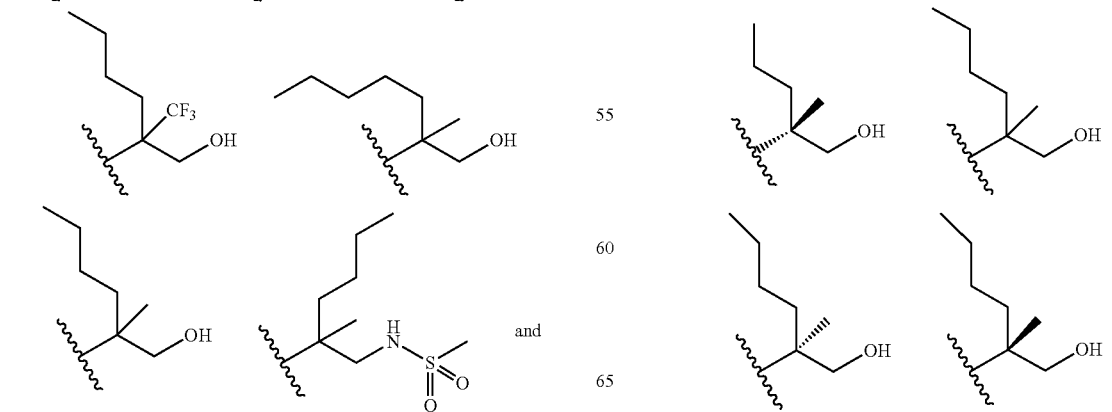

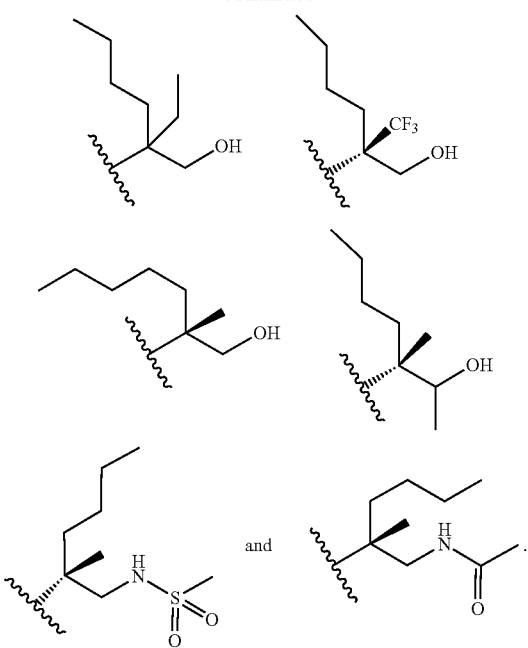
In certain embodiments of a compound of Formula (J) or (I), R[4] is selected from the group consisting of:
In certain embodiments of a compound of Formula (J) or (I), R[4] is selected from the group consisting of:
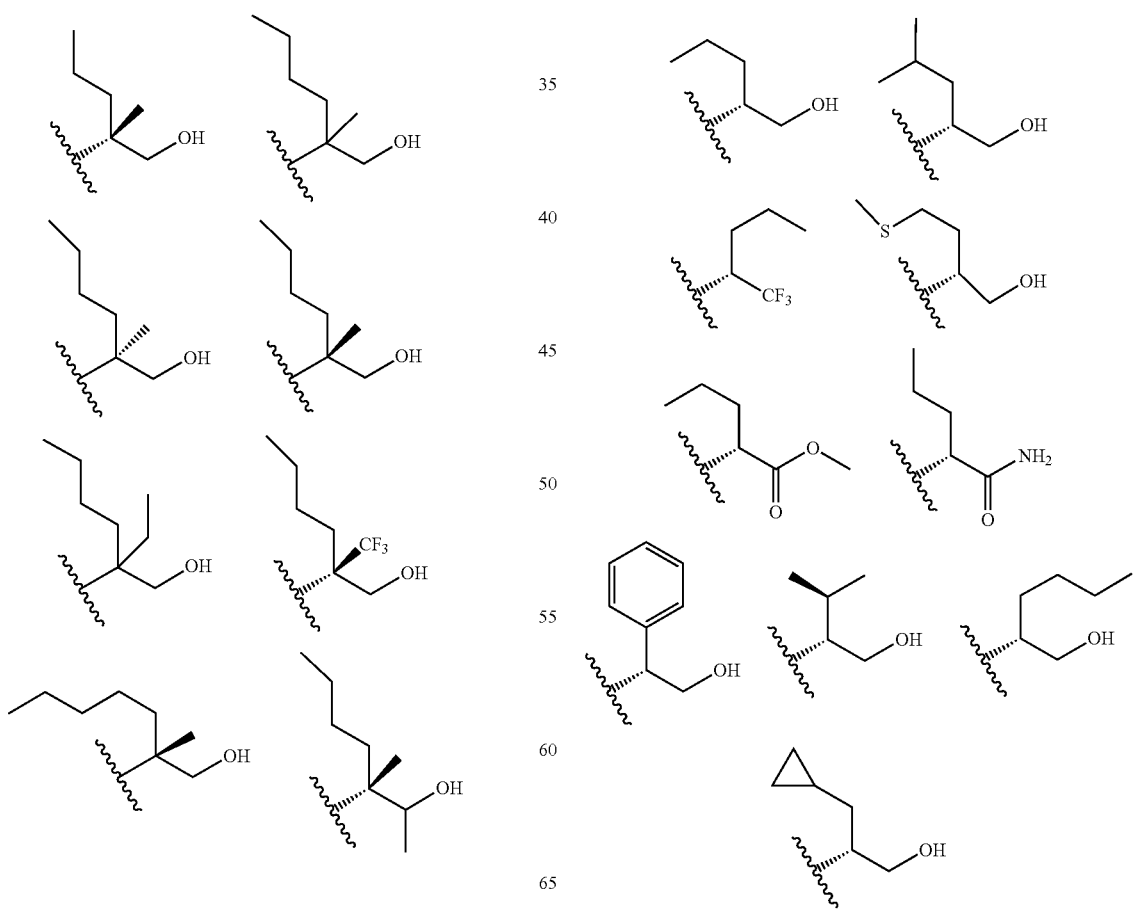

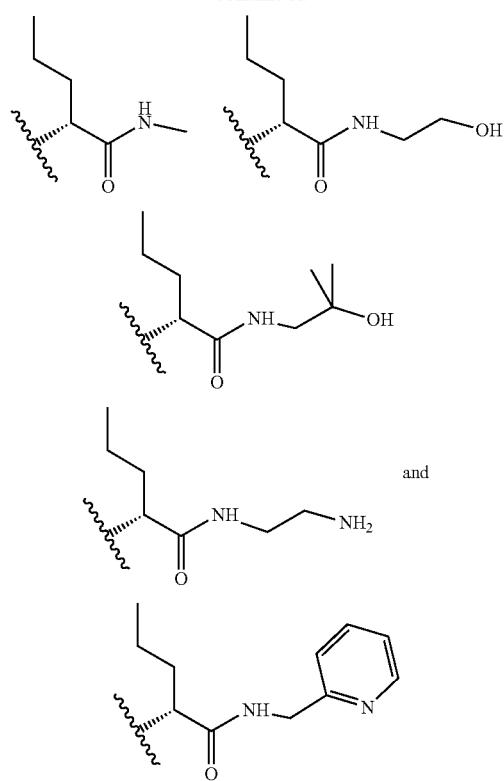
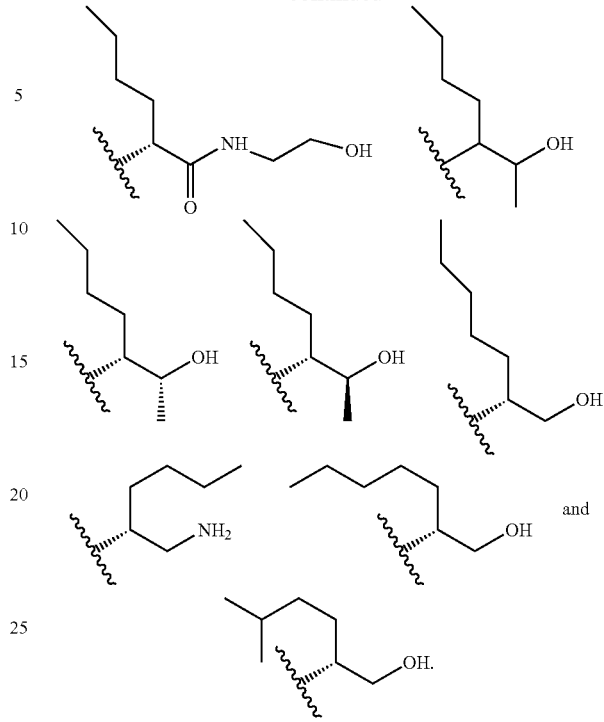
In certain embodiments of a compound of Formula (J) or (I), R⁴ is selected from the group consisting of:
In certain embodiments of a compound of Formula (J) or (I), R⁴ is selected from the group consisting of:
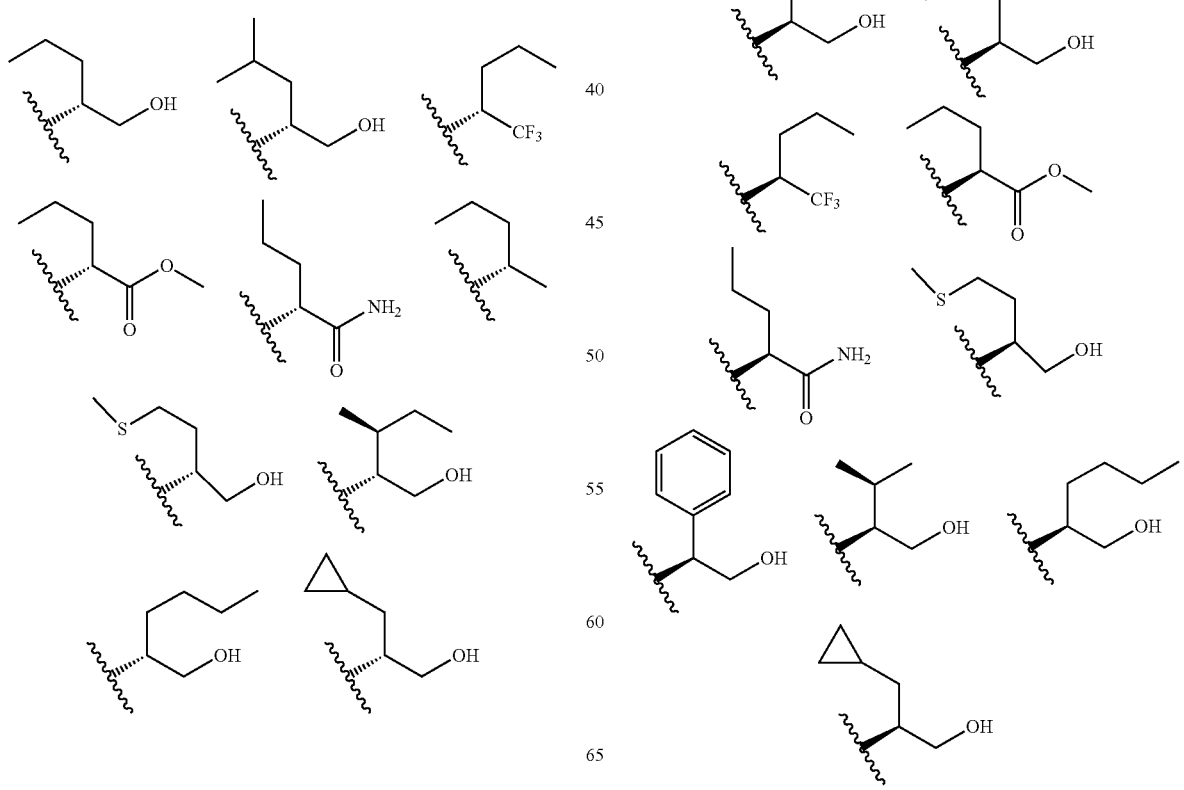

-continued
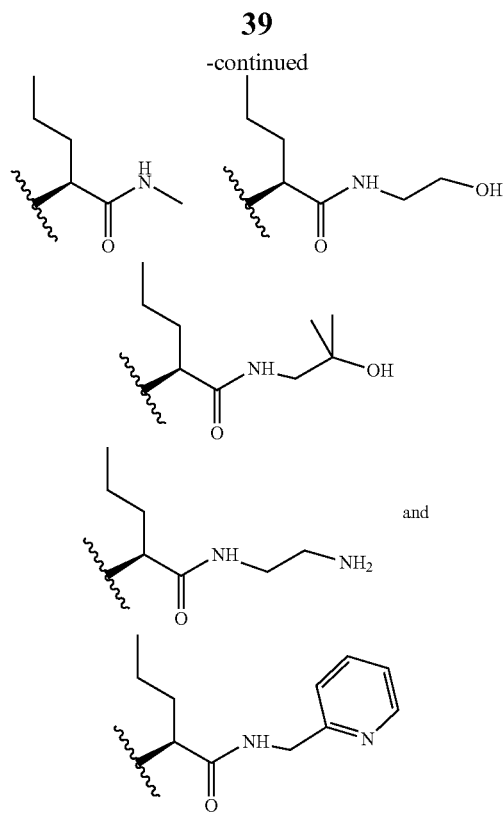
In certain embodiments of a compound of Formula (J) or (I), R⁴ is selected from the group consisting of
-continued
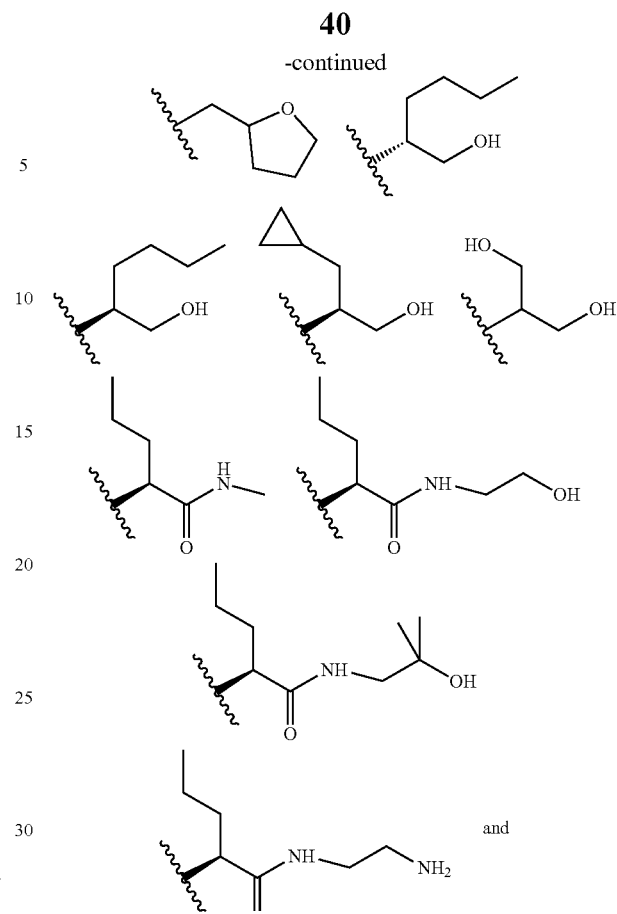
In certain embodiments of a compound of Formula (J) or (I), R⁴ is
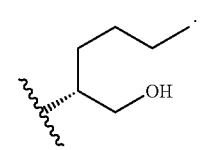 [SMILES: *[C@@H](CO)CCCC]
In certain embodiments of a compound of Formula (J) or (I), R⁴ is
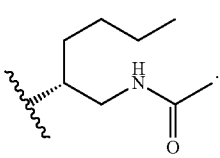 [SMILES: *[C@H](CCCC)CNC(C)=O]
In certain embodiments of a compound of Formula (J) or (I), R⁴ is
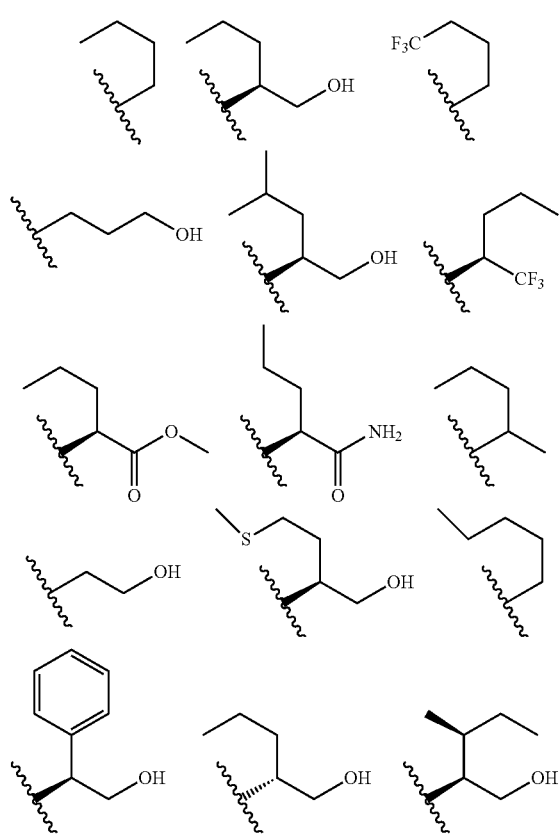

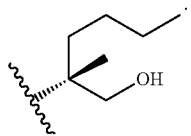

In certain embodiments of a compound of Formula (J) or (I), $R^4$ is

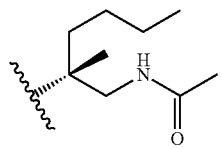

In certain embodiments of a compound of Formula (J) or (I), $R^4$ is

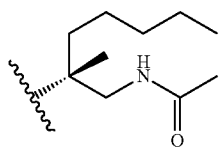

In certain embodiments, the compound of Formula (J) or (I) is a compound of Formula (II)

Formula II

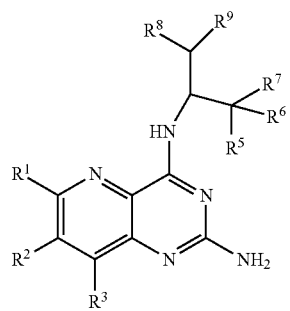

or a pharmaceutically acceptable salt thereof, wherein:
$R^5$ is selected from the group consisting of hydrogen, halogen, and methyl;
$R^6$ is selected from the group consisting of hydrogen, halogen, and methyl; or $R^5$ and $R^6$ together form an oxo group;
$R^7$ is selected from the group consisting of hydrogen, halogen, $OR^a$ and $NR^aR^b$;
$R^8$ is selected from the group consisting of hydrogen and methyl;
$R^9$ is is selected from the group consisting of $C_{1-4}$ alkyl, $C_{3-5}$cycloalkyl, and —S—$C_{1-4}$alkyl;
$R^a$ and $R^b$ are independently selected from the group consisting of hydrogen and $C_{1-6}$alkyl; wherein each $C_{1-6}$alkyl is optionally substituted with 1 to 3 substituents independently selected from the group consisting of halogen, hydroxyl, and pyridyl; and $R^1$, $R^2$, and $R^3$ are as otherwise defined herein.

For example, in Formula (II), (IIa), and (IIb), $R^1$ is selected from the group consisting of hydrogen, halogen, $C_{1-6}$alkyl, CN, —$NR^aR^b$, —$S(O)_{1-2}R^a$, and $OR^a$, wherein $C_{1-6}$alkyl is optionally substituted with 1 to 5 $R^{20}$ groups; $R^2$ is selected from the group consisting of hydrogen, halogen, $C_{1-6}$alkyl, CN, —$NR^aR^b$, —$S(O)_{1-2}R^a$ and $OR^a$, wherein $C_{1-6}$alkyl is optionally substituted with 1 to 5 $R^{20}$ groups; and $R^3$ is selected from the group consisting of hydrogen, halogen, $C_{1-6}$alkyl, CN, —$NR^aR^b$, —$S(O)_{1-2}R^a$, and $OR^a$, wherein $C_{1-6}$alkyl is optionally substituted with 1 to 5 $R^{20}$ groups;

In certain embodiments, the compound of Formula (II) is a compound of Formula (IIa)

Formula IIa

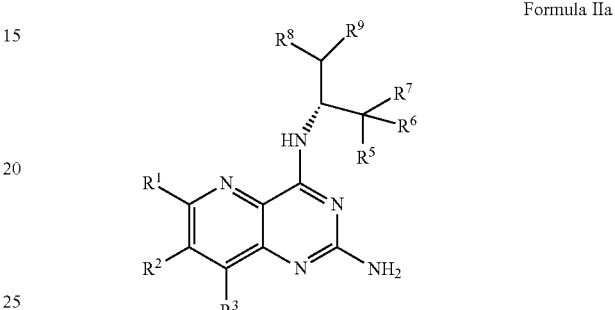

In certain embodiments, the compound of Formula (II) is a compound of Formula (IIb)

Formula IIb

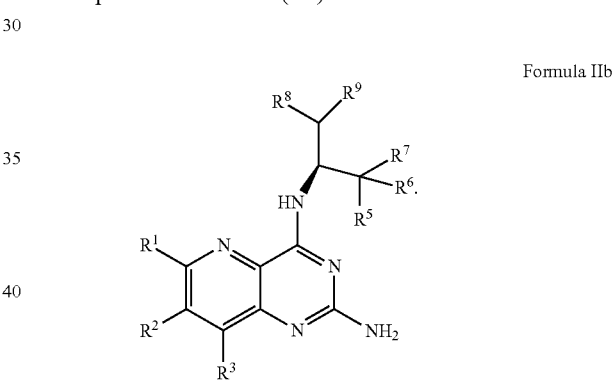

In certain embodiments of the compound of Formula (II), (IIa), or (IIb), $R^5$ is hydrogen; $R^6$ is hydrogen; or $R^5$ and $R^6$ together form an oxo group; $R^7$ is $OR^a$ or $NR^aR^b$; $R^8$ is hydrogen; $R^9$ is $C_{1-4}$ alkyl, cyclopropyl or —$SCH_3$; $R^a$ and $R^b$ are independently selected from the group consisting of hydrogen and $C_{1-4}$alkyl; wherein each $C_{1-4}$alkyl is optionally substituted with 1 to 3 substituents independently selected from halogen, hydroxyl, pyrid-2-yl, and $CF_3$, and $R^1$, $R^2$, and $R^3$ are as otherwise defined herein. In certain embodiments, $R^a$ and $R^b$ are hydrogen. In certain embodiments, $R^7$ is OH or $NH_2$. In certain embodiments, $R^1$ and $R^2$ are hydrogen.

In certain embodiments of a compound of Formula (IIa),

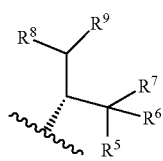

is selected from
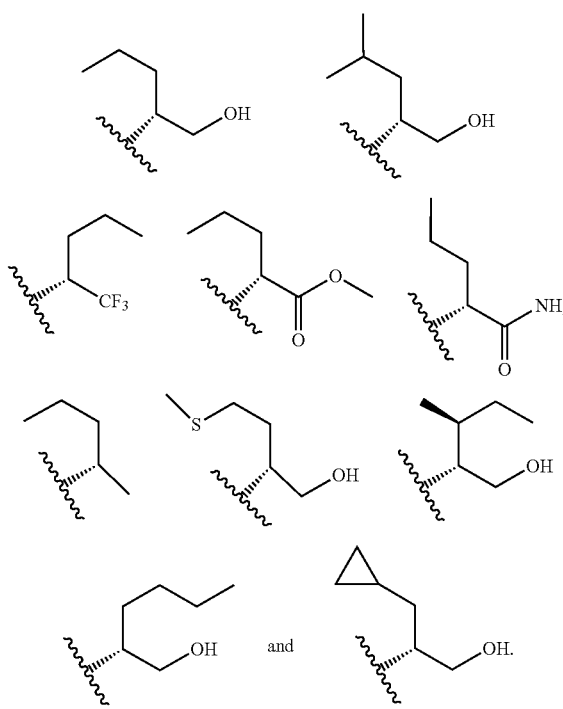
In certain embodiments of a compound of Formula (IIa),
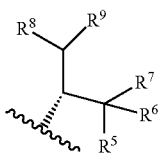
is selected from
-continued
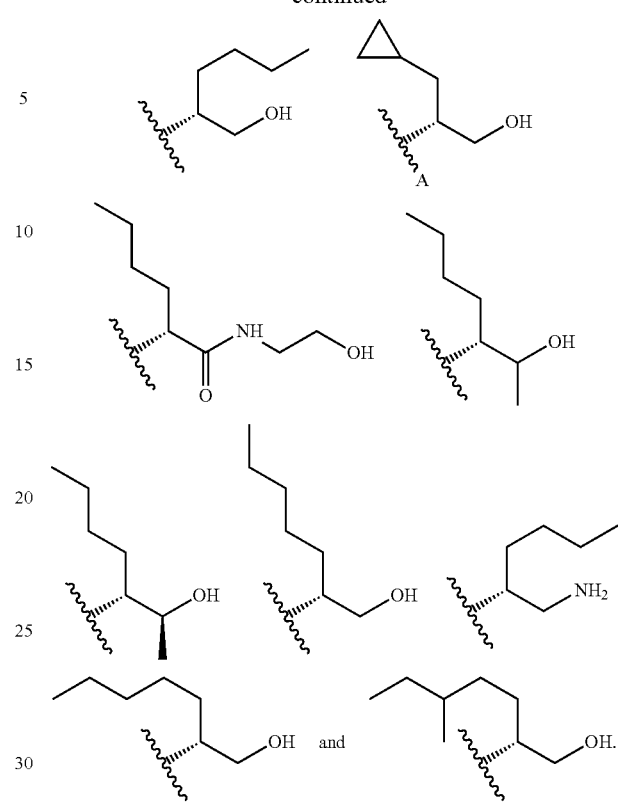
In certain embodiments of a compound of formula (IIb),
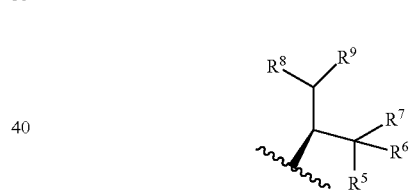
is selected from
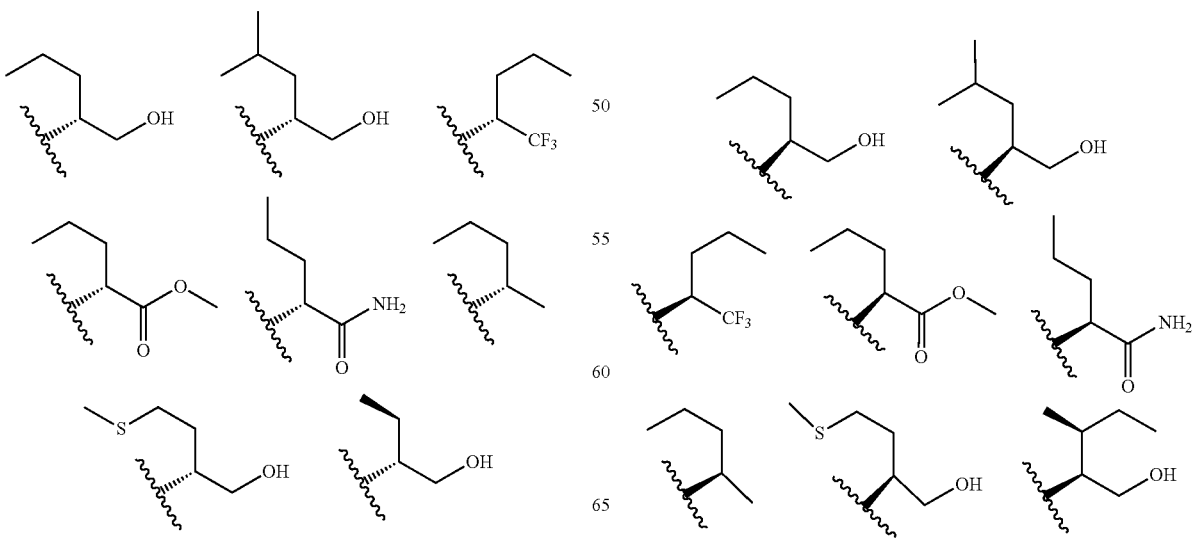

-continued

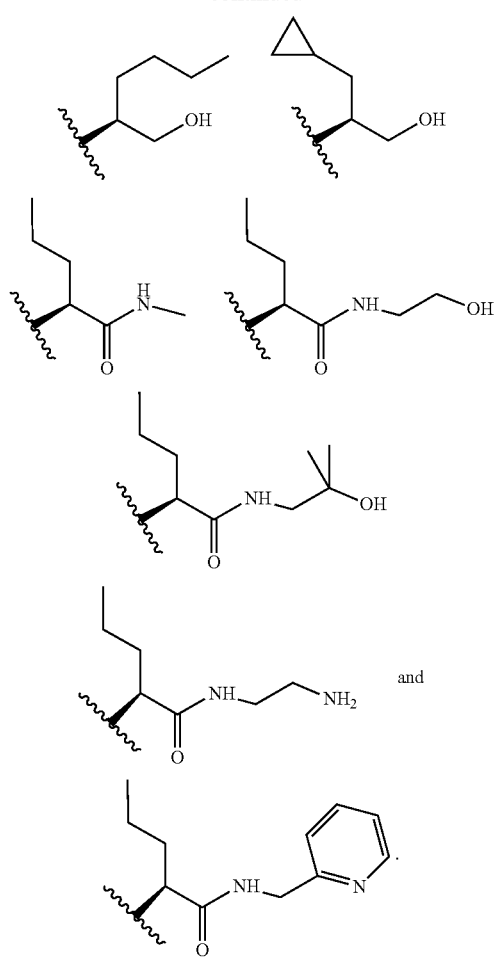

In certain embodiments of a compound of formula (IIb),

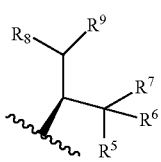

is selected from

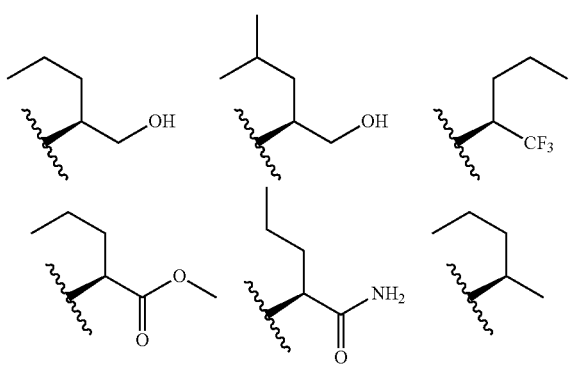

-continued

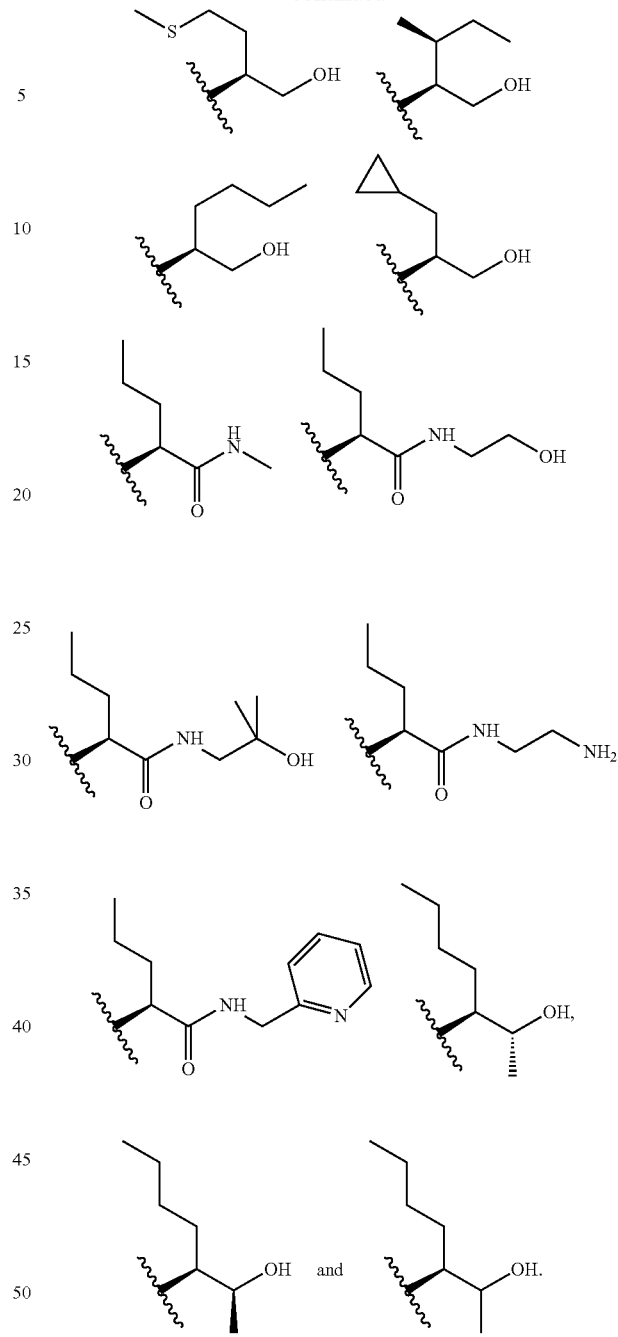

In certain embodiments of the compound of Formula (II), (IIa), or (IIb), $R^5$ is hydrogen, $R^6$ is hydrogen, or $R^5$ and $R^6$ together form an oxo group, $R^7$ is $OR^a$ or $NR^aR^b$, $R^8$ is hydrogen, $R^9$ is $C_{1-4}$alkyl, cyclopropyl or —SCH3, and $R^a$ and $R^b$ are independently selected from the group consisting of hydrogen and $C_{1-4}$alkyl; wherein each $C_{1-4}$alkyl is optionally substituted with 1 to 3 substituents independently selected from halogen, hydroxyl, pyrid-2-yl, and $CF_3$. In certain embodiments of the compound of Formula (II), (IIa), or (IIb), $R^7$ is OH or $NH_2$.

In certain embodiments of a compound of Formula (J), Formula (I), or Formula (II), the compound is a compound of Formula (III)

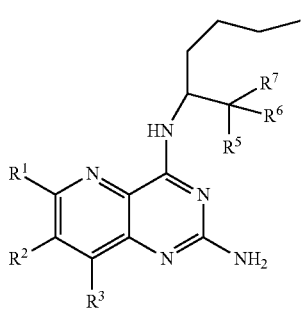

Formula (III)

wherein
R$^5$ is hydrogen;
R$^6$ is hydrogen; or R$^5$ and R$^6$ together form an oxo group;
R$^7$ is selected from the group consisting of OR$^a$ and NR$^a$R$^b$;
R$^a$ and R$^b$ are independently selected from the group consisting of hydrogen and C$_{1-3}$alkyl; wherein each C$_{1-3}$alkyl is optionally substituted with 1 to 3 substituents independently selected from the group consisting of halogen and hydroxyl and R$^1$, R$^2$, and R$^3$ are as otherwise defined herein.

In certain embodiments the compound of Formula (III) is a compound of Formula (IIIa)

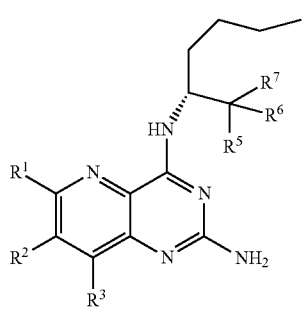

Formula (IIIa)

In certain embodiments the compound of Formula (III) is a compound of Formula (IIIb)

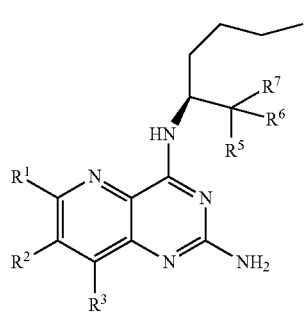

IIIb

In certain embodiments of the compound of Formula (III), (IIIa), or (IIIb), R$^5$ and R$^6$ are both hydrogen and R$^7$ is OR$^a$, wherein R$^a$ is hydrogen or C$_{1-3}$alkyl. In certain embodiments of the compound of Formula (III), (IIIa), or (IIIb), R$^5$ and R$^6$ are both hydrogen and R$^7$ is OH. In certain embodiments of the compound of Formula (III), (IIIa), or (IIIb), R$^1$, R$^2$, R$^5$, and R$^6$ are each hydrogen, and R$^7$ is OH.

In certain embodiments of the compound of Formula (III), (IIIa), or (IIIb), R$^5$ and R$^6$ together form an oxo group and R$^7$ is selected from the group consisting of OR$^a$ and NR$^a$R$^b$, wherein R$^a$ and R$^b$ are independently selected from the group consisting of hydrogen and C$_{1-3}$alkyl. In certain embodiments of the compound of Formula (III), (IIIa), or (IIIb), R$^5$ and R$^6$ together form an oxo group and R$^7$ is selected from the group consisting of OR$^a$ and NR$^a$R$^b$, wherein R$^a$ and R$^b$ are independently selected from the group consisting of hydrogen and methyl.

In certain embodiments of a compound of Formula (J), or Formula (I), the compound is a compound of Formula (IV):

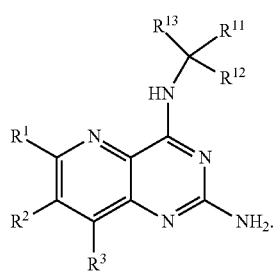

Formula (IV)

The R$^1$, R$^2$, and R$^3$ groups of Formula (IV) are as defined above for Formula (J) or (I). The R$^{11}$, R$^{12}$ and R$^{13}$ groups are as defined above for R$^4$ in Formula (J) or Formula (I).

In certain embodiments, the compound of Formula (IV), or a pharmaceutically acceptable salt thereof, is a compound of Formula (IVa):

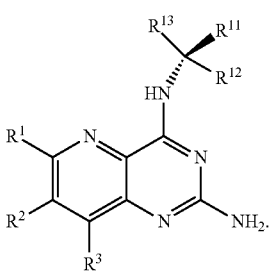

Formula (IVa)

In certain embodiments, the compound of Formula (IV), or a pharmaceutically acceptable salt thereof, is a compound of Formula (IVb):

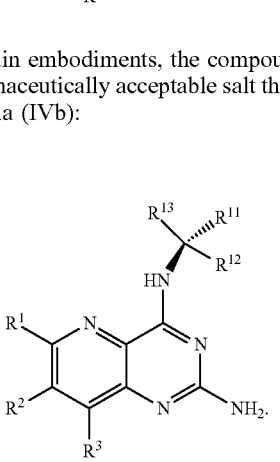

Formula (IVb)

The groups R$^1$, R$^2$, R$^3$, R$^{11}$, R$^{12}$ and R$^{13}$ of Formula (IVa) and (IVb) are as defined for Formula (J), (I) or (IV) above, or as defined below, or any combination thereof.

$R^1$ of Formula (IV), (IVa) and (IVb) can be any suitable group selected from hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups. In certain embodiments, $R^1$ is selected from hydrogen, halogen, $C_{1-6}$ alkyl, CN, and $OR^a$, wherein $C_{1-6}$ alkyl is optionally substituted with 1 to 5 $R^{20}$ groups. In certain embodiments, $R^1$ can be hydrogen, halogen, and $C_{1-3}$ alkyl, wherein $C_{1-3}$ alkyl is optionally substituted with 1 to 5 halogen groups. In certain embodiments, $R^1$ can be hydrogen, fluoro, chloro, bromo, methyl or ethyl, wherein each methyl or ethyl group is optionally substituted with 1 to 5 halogen groups. In certain embodiments, $R^1$ can be hydrogen, fluoro, chloro, bromo, methyl or ethyl, wherein each methyl or ethyl group is optionally substituted with 1 to 5 fluoro groups. In certain embodiments, $R^1$ can be hydrogen, methyl, fluoro, chloro, and $CF_3$. In certain embodiments, $R^1$ can be hydrogen. In certain embodiments, $R^1$ is selected from hydrogen, halogen, $NH_2$, $C_{1-6}$ alkyl, CN, and $OR^a$, wherein $C_{1-6}$ alkyl is optionally substituted with 1 to 5 $R^{20}$ groups.

$R^2$ of Formula (IV), (IVa) and (IVb) can be any suitable group selected from hydrogen, halogen, $C_{1-6}$alkyl, CN, $-NR^aR^b$, $-S(O)_{1-2}R^a$ and $OR^a$, wherein $C_{1-6}$alkyl is optionally substituted with 1 to 5 $R^{20}$ groups. In certain embodiments, $R^2$ is selected from hydrogen, halogen, $C_{1-6}$ alkyl, CN, and $OR^a$, wherein $C_{1-6}$ alkyl optionally substituted with 1 to 5 $R^{20}$ groups. In certain embodiments, $R^2$ is selected from hydrogen, halogen, $C_{1-3}$ alkyl, CN and $OR^a$, wherein $C_{1-3}$ alkyl is optionally substituted with 1 to 5 halogen groups. In certain embodiments, $R^2$ is selected from hydrogen, methyl, ethyl, fluoro, chloro, bromo, $CF_3$, CN, OH, OMe, and OEt. In certain embodiments, $R^2$ is selected from hydrogen, methyl, fluoro, and chloro. In certain embodiments, $R^2$ is selected from hydrogen and fluoro. In certain embodiments, $R^2$ is selected from hydrogen, halogen, $NH_2$, $C_{1-6}$ alkyl, CN, and $OR^a$, wherein $C_{1-6}$ alkyl is optionally substituted with 1 to 5 $R^{20}$ groups. In certain embodiments, $R^2$ is selected from hydrogen, methyl, ethyl, $NH_2$, fluoro, chloro, bromo, $CF_3$, CN, OH, OMe, and OEt.

$R^3$ of Formula (IV), (IVa) and (IVb) can be any suitable group selected from hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups. In certain embodiments, $R^3$ is selected from hydrogen, halogen, $C_{1-6}$ alkyl, CN, and $OR^a$, wherein $C_{1-6}$ alkyl is optionally substituted with 1 to 5 $R^{20}$ groups. In certain embodiments, $R^3$ can be selected from hydrogen, halogen, and $C_{1-3}$ alkyl. In certain embodiments, $R^3$ can be selected from hydrogen, methyl, fluoro, and chloro. In certain embodiments, $R^3$ can be selected from hydrogen and methyl. In certain embodiments, $R^3$ is selected from hydrogen, halogen, $NH_2$, $C_{1-6}$ alkyl, CN, and $OR^a$, wherein $C_{1-6}$ alkyl is optionally substituted with 1 to 5 $R^{20}$ groups.

In certain embodiments, the compound of Formula (IV), (IVa) or (IVb), or a pharmaceutically acceptable salt thereof, is the compound wherein $R^1$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups, $R^2$ is selected from the group consisting of hydrogen, halogen, $C_{1-6}$alkyl, CN, $-NR^aR^b$, $-S(O)_{1-2}R^a$ and $OR^a$, wherein $C_{1-6}$alkyl is optionally substituted with 1 to 5 $R^{20}$ groups, and $R^3$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups.

In certain embodiments, the compound of Formula (IV), (IVa) or (IVb), or a pharmaceutically acceptable salt thereof, is the compound wherein $R^1$ is selected from the group consisting of hydrogen, halogen, and $C_{1-3}$ alkyl, wherein $C_{1-3}$ alkyl is optionally substituted with 1 to 5 halogen groups, $R^2$ is selected from the group consisting of hydrogen, halogen, $C_{1-3}$ alkyl, CN and $OR^a$, wherein $C_{1-3}$ alkyl is optionally substituted with 1 to 5 halogen groups, and $R^3$ is selected from the group consisting of hydrogen, halogen, and $C_{1-3}$ alkyl.

In certain embodiments, the compound of Formula (IV), (IVa) or (IVb), or a pharmaceutically acceptable salt thereof, is the compound wherein $R^1$ is selected from the group consisting of hydrogen, methyl, fluoro, chloro, and $CF_3$, $R^2$ is selected from the group consisting of hydrogen, methyl, ethyl, fluoro, chloro, bromo, $CF_3$, CN, OH, OMe, and OEt, and $R^3$ is selected from the group consisting of hydrogen, methyl, fluoro, and chloro.

In certain embodiments, the compound of Formula (IV), (IVa) or (IVb), or a pharmaceutically acceptable salt thereof, is the compound wherein $R^1$ is selected from the group consisting of hydrogen, methyl, fluoro, chloro, and $CF_3$, $R^2$ is selected from the group consisting of hydrogen, methyl, ethyl, $NH_2$, fluoro, chloro, bromo, $CF_3$, CN, OH, OMe, and OEt, and $R^3$ is selected from the group consisting of hydrogen, methyl, fluoro, and chloro.

In certain embodiments, the compound of Formula (IV), (IVa) or (IVb), or a pharmaceutically acceptable salt thereof, is the compound wherein $R^1$ is hydrogen, $R^2$ is selected from the group consisting of hydrogen, methyl, ethyl, fluoro, chloro, and bromo, and $R^3$ is selected from the group consisting of hydrogen and methyl.

In certain embodiments, the compound of Formula (IV), (IVa) or (IVb), or a pharmaceutically acceptable salt thereof, is the compound wherein $R^1$ is hydrogen. $R^2$ is selected from the group consisting of hydrogen and fluoro, and $R^3$ is selected from the group consisting of hydrogen and methyl.

In certain embodiments, $R^{11}$ of Formula (IV), (IVa) and (IVb) can be any suitable group selected from hydrogen, $C_{1-2}$ alkyl, $C_{3-6}$ cycloalkyl, and $C_{1-3}$ haloalkyl. In certain embodiments, the compound of Formula (IV), (IVa) or (IVb), or a pharmaceutically acceptable salt thereof, is the compound wherein $R^{11}$ is selected from the group consisting of hydrogen, $C_{1-2}$ alkyl and $C_{1-2}$ haloalkyl. In certain embodiments, the compound of Formula (IV), (IVa) or (IVb), or a pharmaceutically acceptable salt thereof, is the compound wherein $R^{11}$ is selected from the group consisting of $C_{1-2}$ alkyl and $C_{1-2}$ haloalkyl. In certain embodiments, the compound of Formula (IV), (IVa) or (IVb), or a pharmaceutically acceptable salt thereof, is the compound wherein $R^{11}$ can be selected from hydrogen, methyl, ethyl or $CF_3$. In certain embodiments, the compound of Formula (IV), (IVa) or (IVb), or a pharmaceutically acceptable salt thereof, is the compound wherein $R^{11}$ can be selected from methyl, ethyl or $CF_3$. In certain embodiments, the compound of Formula (IV), (IVa) or (IVb), or a pharmaceutically acceptable salt thereof, is the compound wherein $R^{11}$ can be selected from hydrogen, methyl, or $CF_3$. In certain embodiments, the compound of Formula (IV), (IVa) or (IVb), or a pharmaceutically acceptable salt thereof, is the compound wherein $R^{11}$ can be selected from methyl, or $CF_3$. In certain embodiments, the compound of Formula (IV), (IVa) or (IVb), or a pharmaceutically acceptable salt thereof, is the compound wherein $R^{11}$ can be selected from hydrogen or methyl. In certain embodiments, the compound of Formula (IV), (IVa) or (IVb), or a pharmaceutically acceptable salt thereof, wherein $R^{11}$ is selected from the group consisting of methyl and $CF_3$. In certain embodiments, the compound of Formula (IV), (IVa) or (IVb), or a pharmaceutically acceptable salt thereof, is the compound wherein $R^{11}$ is methyl. In certain embodiments, the compound of Formula (IV), (IVa) or (IVb), or a pharmaceutically acceptable salt thereof, is the compound wherein $R^{11}$ is hydrogen.

$R^{12}$ of Formula (IV), (IVa) and (IVb) can be any suitable group selected from $C_{1-3}$ alkyl, halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-3}$ alkyl group is optionally substituted with 1 to 5 substituents independently selected from halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur.

In certain embodiments, the compound of Formula (IV), (IVa) or (IVb), or a pharmaceutically acceptable salt thereof, wherein $R^{12}$ can be selected from $C_{1-2}$ alkyl, $-C(O)NR^aR^b$, and 5 membered heteroaryl having 1 to 3 nitrogen heteroatoms, wherein $C_{1-2}$ alkyl is optionally substituted with 1 to 5 substituents independently selected from halogen, $-OH$, $-NR^aR^b$, $-NR^aC(O)R^b$, $-NR^aS(O)_2R^b$, and $C_{1-3}$ haloalkyl, and each $R^a$ and $R^b$ is independently selected from the group consisting of hydrogen and $C_{1-3}$ alkyl, wherein each $C_{1-3}$ alkyl is optionally substituted with 1 to 3 substituents independently selected from hydroxyl and amino. In certain embodiments, the compound of Formula (IV), (IVa) or (IVb), or a pharmaceutically acceptable salt thereof, wherein $R^{12}$ is $C_{1-2}$ alkyl, optionally substituted with 1 to 3 substituents independently selected from halogen, $-OH$, $-NH_2$, $-NHC(O)-C_{1-3}$ alkyl, $-NHS(O)_2-C_{1-3}$ alkyl, and $C_{1-3}$ haloalkyl. In certain embodiments, the compound of Formula (IV), (IVa) or (IVb), or a pharmaceutically acceptable salt thereof, wherein $R^{12}$ is methyl or ethyl, each optionally substituted with 1 or 2 substituents independently selected from halogen, $-OH$, $-NH_2$, $-NHC(O)-C_{1-3}$ alkyl, and $C_{1-3}$ haloalkyl. In certain embodiments, the compound of Formula (IV), (IVa) or (IVb), or a pharmaceutically acceptable salt thereof, wherein $R^{12}$ is methyl or ethyl, wherein the methyl or ethyl is substituted with 1 or 2 substituents independently selected from $-OH$ and $-NHC(O)CH_3$. In certain embodiments, the compound of Formula (IV), (IVa) or (IVb), or a pharmaceutically acceptable salt thereof, wherein $R^{12}$ can be selected from $CH_2OH$, $CH_2CH_2OH$, $CH(Me)OH$, $CH(CH_2F)OH$, $CH(CHF_2)OH$, $CH(CF_3)OH$, $CF_3$, $CH_2NH_2$, $CH_2NHC(O)Me$, $CH(CH_2F)NHC(O)Me$, $CH_2NHS(O)_2Me$, $C(O)NH_2$, $C(O)NHMe$, $C(O)NH-CH_2CH_2OH$, $C(O)NH-CH_2CH_2NH_2$, $C(O)NH$-(pyridin-2-ylmethyl), imidazolyl, and triazolyl. In certain embodiments, the compound of Formula (IV), (IVa) or (IVb), or a pharmaceutically acceptable salt thereof, wherein $R^{12}$ can be selected from $CH_2OH$, $CH(Me)OH$, $CH(CH_2F)OH$, and $CH_2NHC(O)Me$. In certain embodiments, the compound of Formula (IV), (IVa) or (IVb), or a pharmaceutically acceptable salt thereof, wherein $R^{12}$ can be selected from $CH_2OH$, $CH(Me)OH$, and $CH_2NHC(O)Me$. In certain embodiments, the compound of Formula (IV), (IVa) or (IVb), or a pharmaceutically acceptable salt thereof, wherein $R^{12}$ is $-CH_2OH$ or $-CH_2NC(O)CH_3$.

In certain embodiments, the compound of Formula (IV), (IVa) or (IVb), or a pharmaceutically acceptable salt thereof, wherein $R^{12}$ is $C_{1-2}$ alkyl substituted with $-NR^aC(O)R^b$, wherein each $R^a$ and $R^b$ is independently selected from the group consisting of hydrogen and $C_{1-3}$ alkyl, wherein each $C_{1-3}$ alkyl is optionally substituted with 1 to 3 substituents independently selected from hydroxyl and amino.

$R^{13}$ of Formula (IV), (IVa) and (IVb) can be any suitable group selected from $C_{1-6}$ alkyl, halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-6}$ alkyl is optionally substituted with 1 to 5 substituents independently selected from halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur.

In certain embodiments, the compound of Formula (IV), (IVa) or (IVb), or a pharmaceutically acceptable salt thereof, is the compound wherein $R^{13}$ is $C_{3-6}$ alkyl optionally substituted with 1 to 2 substituents independently selected from halogen and $-OH$. In certain embodiments, the compound of Formula (IV), (IVa) or (IVb), or a pharmaceutically acceptable salt thereof, is the compound wherein $R^{13}$ is $C_{3-6}$ alkyl optionally substituted with 1 to 2 halogen substituents. In certain embodiments, the compound of Formula (IV), (IVa) or (IVb), or a pharmaceutically acceptable salt thereof, is the compound wherein $R^{13}$ is $C_{3-6}$ alkyl. Representative $C_{3-6}$ alkyl groups for $R^{13}$ include, but are not limited to, n-propyl, iso-propyl, n-butyl, sec-butyl, iso-butyl, tert-butyl, n-pentyl, tert-pentyl, neopentyl, isopentyl, sec-pentyl and 3-pentyl. In certain embodiments, the compound of Formula (IV), (IVa) or (IVb), or a pharmaceutically acceptable salt thereof, is the compound wherein $R^{13}$ is propyl, butyl or pentyl. In certain embodiments, the compound of Formula (IV), (IVa) or (IVb), or a pharmaceutically acceptable salt thereof, is the compound wherein $R^{13}$ is n-propyl, n-butyl or n-pentyl. In certain embodiments, the compound of Formula (IV), (IVa) or (IVb), or a pharmaceutically acceptable salt thereof, is the compound wherein $R^{13}$ is propyl or butyl.

$R^{20}$ of Formula (IV), (IVa) and (IVb) can be any suitable group selected from halogen, $C_{1-6}$ haloalkyl, CN, $-NR^aR^b$, $S(O)_{1-2}R^a$, and $OR^a$. In certain embodiments, each $R^{20}$ can independently be selected from halogen, CN, $-NR^aR^b$, and $OR^a$. In certain embodiments, each $R^{20}$ can independently be selected from halogen, CN, $-NR^aR^b$, and $OR^a$. In certain embodiments, each $R^{20}$ can independently be halogen. In certain embodiments, each $R^{20}$ can independently be selected from fluoro, chloro, bromo, CN, $-NH_2$, OH, OMe, and OEt. In certain embodiments, each $R^{20}$ can independently be selected from fluoro and chloro.

$R^a$ and $R^b$ of Formula (IV), (IVa) and (IVb) can each independently be any suitable group selected from the group consisting of hydrogen and $C_{1-6}$alkyl; wherein each $C_{1-6}$alkyl is optionally substituted with 1 to 5 substituents independently selected from halogen, hydroxyl, amino, 5 to 10 membered heteroaryl wherein the 5 to 10 membered heteroaryl has 1 to 3 heteroatoms selected from oxygen, nitrogen, and sulfur, and $C_{1-6}$haloalkyl. In certain embodiments, $R^a$ and $R^b$ can each independently be selected from hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl. In certain embodiments, $R^a$ and $R^b$ can each independently be selected from hydrogen and $C_{1-3}$ alkyl, wherein each $C_{1-3}$ alkyl is optionally substituted with 1 to 3 substituents independently selected from hydroxyl and amino. In certain embodiments, $R^a$ and $R^b$ can each independently be selected from hydrogen and $C_{1-3}$ alkyl, wherein each $C_{1-3}$ alkyl is optionally substituted with 1 substituent selected from hydroxyl and amino. In certain embodiments, $R^a$ and $R^b$ can each independently be selected from hydrogen and $C_{1-3}$ alkyl. In certain embodiments, $R^a$ and $R^b$ can each independently be selected from hydrogen, methyl, ethyl, propyl, butyl, $CF_3$, $CH_2CF_3$, $CH_2CH_2CF_3$, $CH_2OH$, $CH_2CH_2OH$, $CH_2NH_2$, and $CH_2CH_2NH_2$. In certain embodiments, $R^a$ and $R^b$ can each independently be selected from hydrogen, methyl, ethyl, $CF_3$, $CH_2OH$, $CH_2CH_2OH$, $CH_2NH_2$, and $CH_2CH_2NH_2$. In certain embodiments, $R^a$ and $R^b$ can each independently be selected from hydrogen, methyl, ethyl, $CH_2CH_2OH$, and $CH_2CH_2NH_2$. In certain embodiments, $R^a$ and $R^b$ can each independently be selected from hydrogen, methyl and ethyl. In certain embodiments, $R^a$ and $R^b$ can each independently be selected from hydrogen and methyl.

In certain embodiments, the compound of Formula (IV), (IVa) or (IVb), or a pharmaceutically acceptable salt thereof, is the compound wherein:

$R^1$ is selected from the group consisting of hydrogen, halogen, $C_{1-6}$alkyl, CN, $-NR^aR^b$, $-S(O)_{1-2}R^a$, and $OR^a$, wherein $C_{1-4}$alkyl is optionally substituted with 1 to 5 $R^{20}$ groups;

$R^2$ is selected from the group consisting of hydrogen, halogen, $C_{1-6}$alkyl, CN, $-NR^aR^b$, $-S(O)_{1-2}R^a$ and $OR^a$, wherein $C_{1-6}$alkyl is optionally substituted with 1 to 5 $R^{20}$ groups;

$R^3$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups;

$R^{11}$ is selected from the group consisting of hydrogen, $C_{1-2}$ alkyl, $C_{3-6}$ cycloalkyl, and $C_{1-3}$ haloalkyl;

$R^{12}$ is selected from $C_{1-3}$ alkyl, halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-3}$ alkyl group is optionally substituted with 1 to 5 substituents independently selected from halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

$R^{13}$ is selected from $C_{1-6}$ alkyl, halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-6}$ alkyl is optionally substituted with 1 to 5 substituents independently selected from halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

each $R^{20}$ is independently selected from the group consisting of halogen, CN, $-NR^aR^b$, and $OR^a$; and each $R^a$ and $R^b$ is independently selected from the group consisting of hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl.

In certain embodiments, the compound of Formula (IV), (IVa) or (IVb), or a pharmaceutically acceptable salt thereof, is the compound wherein:

$R^1$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups;

$R^2$ is selected from the group consisting of hydrogen, halogen, $C_{1-6}$alkyl, CN, $-NR^aR^b$, $-S(O)_{1-2}R^a$ and $OR^a$, wherein $C_{1-6}$alkyl is optionally substituted with 1 to 5 $R^{20}$ groups;

$R^3$ is selected from the group consisting of hydrogen, halogen, $C_{1-6}$alkyl, CN, $-NR^aR^b$, $-S(O)_{1-2}R^a$, and $OR^a$, wherein $C_{1-6}$alkyl is optionally substituted with 1 to 5 $R^{20}$ groups;

$R^{11}$ is selected from the group consisting of $C_{1-2}$ alkyl, $C_{3-6}$ cycloalkyl, and $C_{1-3}$ haloalkyl;

$R^{12}$ is selected from $C_{1-3}$ alkyl, halogen, $-OR^a$, $-NR^aR^b$, CN, $-C(O)R^a$, $-C(O)OR^a$, $-C(O)NR^aR^b$, $-OC(O)NR^aR^b$, $-NR^aC(O)R^b$, $-NR^aC(O)NR^b$, $-NR^aC(O)OR^b$, $-SR^a$, $-S(O)_{1-2}R^a$, $-S(O)_2NR^aR^b$, $-NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-3}$ alkyl group is optionally substituted with 1 to 5 substituents independently selected from halogen, $-OR^a$, $-NR^aR^b$, CN, $-C(O)R^a$, $-C(O)OR^a$, $-C(O)$ $NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

$R^{13}$ is selected from $C_{1-6}$ alkyl, halogen, —$OR^a$, —$NR^aR^b$, CN, —C(O)$R^a$, —C(O)$OR^a$, —C(O)$NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-6}$ alkyl is optionally substituted with 1 to 5 substituents independently selected from halogen, —$OR^a$, —$NR^aR^b$, CN, —C(O)$R^a$, —C(O)$OR^a$, —C(O)$NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

each $R^{20}$ is independently selected from the group consisting of halogen, CN, —$NR^aR^b$, and $OR^a$; and each $R^a$ and $R^b$ is independently selected from the group consisting of hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl.

In certain embodiments, the compound of Formula (IV), (IVa) or (IVb), or a pharmaceutically acceptable salt thereof, is the compound wherein:

$R^1$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups;

$R^2$ is selected from the group consisting of hydrogen, halogen, $C_{1-6}$ alkyl, CN, and $OR^a$, wherein $C_{1-6}$ alkyl optionally substituted with 1 to 5 $R^{20}$ groups;

$R^3$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups;

$R^{11}$ is selected from the group consisting of hydrogen, $C_{1-2}$ alkyl, $C_{3-6}$ cycloalkyl, and $C_{1-3}$ haloalkyl;

$R^{12}$ is selected from $C_{1-3}$ alkyl, halogen, —$OR^a$, —$NR^aR^b$, CN, —C(O)$R^a$, —C(O)$OR^a$, —C(O)$NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-3}$ alkyl group is optionally substituted with 1 to 5 substituents independently selected from halogen, —$OR^a$, —$NR^aR^b$, CN, —C(O)$R^a$, —C(O)$OR^a$, —C(O)$NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

$R^{13}$ is selected from $C_{1-6}$ alkyl, halogen, —$OR^a$, —$NR^aR^b$, CN, —C(O)$R^a$, —C(O)$OR^a$, —C(O)$NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-6}$ alkyl is optionally substituted with 1 to 5 substituents independently selected from halogen, —$OR^a$, —$NR^aR^b$, CN, —C(O)$R^a$, —C(O)$OR^a$, —C(O)$NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-6}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur;

each $R^{20}$ is independently selected from the group consisting of halogen, CN, —$NR^aR^b$, and $OR^a$; and each $R^a$ and $R^b$ is independently selected from the group consisting of hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl.

In certain embodiments, the compound of Formula (IV), (IVa) or (IVb), or a pharmaceutically acceptable salt thereof, is the compound wherein:

$R^1$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups;

$R^2$ is selected from the group consisting of hydrogen, halogen, $C_{1-6}$ alkyl, CN, and $OR^a$, wherein $C_{1-6}$ alkyl optionally substituted with 1 to 5 $R^{20}$ groups;

$R^3$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups;

$R^{11}$ is selected from the group consisting of $C_{1-2}$ alkyl, $C_{3-6}$ cycloalkyl, and $C_{1-3}$ haloalkyl;

$R^{12}$ is selected from $C_{1-3}$ alkyl, halogen, —$OR^a$, —$NR^aR^b$, CN, —C(O)$R^a$, —C(O)$OR^a$, —C(O)$NR^aR^b$, —OC(O)$NR^aR^b$, —$NR^aC(O)R^b$, —$NR^aC(O)NR^b$, —$NR^aC(O)OR^b$, —$SR^a$, —$S(O)_{1-2}R^a$, —$S(O)_2NR^aR^b$, —$NR^aS(O)_2R^b$, $C_{1-3}$ haloalkyl, $C_{3-6}$ cycloalkyl, 3 to 6 membered heterocyclyl wherein the 3 to 6 membered heterocyclyl has 1 to 3 heteroatoms selected from oxygen, nitrogen, and sulfur, $C_{6-10}$ aryl, and 5 to 10 membered heteroaryl wherein the 5 to 10 membered heteroaryl has 1 to 3 heteroatoms selected from oxygen, nitrogen, and sulfur, wherein the $C_{1-3}$ alkyl group is optionally substituted with 1 to 5 substituents independently selected from halogen, —$OR^a$, —$NR^aR^b$, CN, —C(O)$R^a$, —C(O)$OR^a$, —C(O)

NR$^a$R$^b$, —OC(O)NR$^a$R$^b$, —NR$^a$C(O)R$^b$, —NR$^a$C(O)NR$^b$, —NR$^a$C(O)OR$^b$, —SR$^a$, —S(O)$_{1-2}$R$^a$, —S(O)$_2$NR$^a$R$^b$, —NR$^a$S(O)$_2$R$^b$, C$_{1-3}$ haloalkyl, C$_{3-6}$ cycloalkyl, 3 to 6 membered heterocyclyl wherein the 3 to 6 membered heterocyclyl has 1 to 3 heteroatoms selected from oxygen, nitrogen, and sulfur, C$_{6-10}$ aryl, and 5 to 10 membered heteroaryl wherein the 5 to 10 membered heteroaryl has 1 to 3 heteroatoms selected from oxygen, nitrogen, and sulfur;

R$^{13}$ is selected from C$_{1-6}$ alkyl, halogen, —OR$^a$, —NR$^a$R$^b$, CN, —C(O)R$^a$, —C(O)OR$^a$, —C(O)NR$^a$R$^b$, —OC(O)NR$^a$R$^b$, —NR$^a$C(O)R$^b$, —NR$^a$C(O)NR$^b$, —NR$^a$C(O)OR$^b$, —SR$^a$, —S(O)$_{1-2}$R$^a$, —S(O)$_2$NR$^a$R$^b$, —NR$^a$S(O)$_2$R$^b$, C$_{1-6}$ haloalkyl, C$_{3-6}$ cycloalkyl, 3 to 6 membered heterocyclyl wherein the 3 to 6 membered heterocyclyl has 1 to 3 heteroatoms selected from oxygen, nitrogen, and sulfur, C$_{6-10}$ aryl, and 5 to 10 membered heteroaryl wherein the 5 to 10 membered heteroaryl has 1 to 3 heteroatoms selected from oxygen, nitrogen, and sulfur, wherein the C$_{1-6}$ alkyl is optionally substituted with 1 to 5 substituents independently selected from halogen, —OR$^a$, —NR$^a$R$^b$, CN, —C(O)R$^a$, —C(O)OR$^a$, —C(O)NR$^a$R$^b$, —OC(O)NR$^a$R$^b$, —NR$^a$C(O)R$^b$, —NR$^a$C(O)NR$^b$, —NR$^a$C(O)OR$^b$, —SR$^a$, —S(O)$_{1-2}$R$^a$, —S(O)$_2$NR$^a$R$^b$, —NR$^a$S(O)$_2$R$^b$, C$_{1-6}$ haloalkyl, C$_{3-6}$ cycloalkyl, 3 to 6 membered heterocyclyl wherein the 3 to 6 membered heterocyclyl has 1 to 3 heteroatoms selected from oxygen, nitrogen, and sulfur, C$_{6-10}$ aryl, and 5 to 10 membered heteroaryl wherein the 5 to 10 membered heteroaryl has 1 to 3 heteroatoms selected from oxygen, nitrogen, and sulfur;

each R$^{20}$ is independently selected from the group consisting of halogen, CN, —NR$^a$R$^b$, and OR$^a$; and each R$^a$ and R$^b$ is independently selected from the group consisting of hydrogen and C$_{1-3}$ alkyl, wherein each C$_{1-3}$ alkyl is optionally substituted with 1 to 3 substituents independently selected from halogen, hydroxyl, amino, and C$_{1-6}$ haloalkyl.

In certain embodiments, the compound of Formula (IV), (IVa) or (IVb), or a pharmaceutically acceptable salt thereof, wherein R$^{11}$ is methyl or CF$_3$, R$^{12}$ is —CH$_2$OH, —CH(Me)OH or —CH$_2$NHC(O)CH$_3$, and R$^{13}$ is selected from the group consisting of propyl, butyl and pentyl.

In certain embodiments, the compound of Formula (IV), (IVa) or (IVb), or a pharmaceutically acceptable salt thereof, wherein R$^{11}$ is methyl or CF$_3$, R$^{12}$ is —CH$_2$OH, —CH(Me)OH, CH$_2$NHCH(CH$_3$)(CF$_3$) or —CH$_2$NHC(O)CH$_3$, and R$^{13}$ is selected from the group consisting of propyl, butyl and pentyl.

In certain embodiments, the compound of Formula (IV), (IVa) or (IVb), or a pharmaceutically acceptable salt thereof, wherein R$^{11}$ is methyl, R$^{12}$ is —CH$_2$OH or —CH$_2$NHC(O)CH$_3$, and R$^{13}$ is selected from the group consisting of propyl and butyl.

In certain embodiments, the compound of Formula (IV), or a pharmaceutically acceptable salt thereof, wherein the moiety

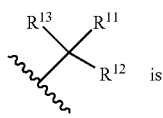

is

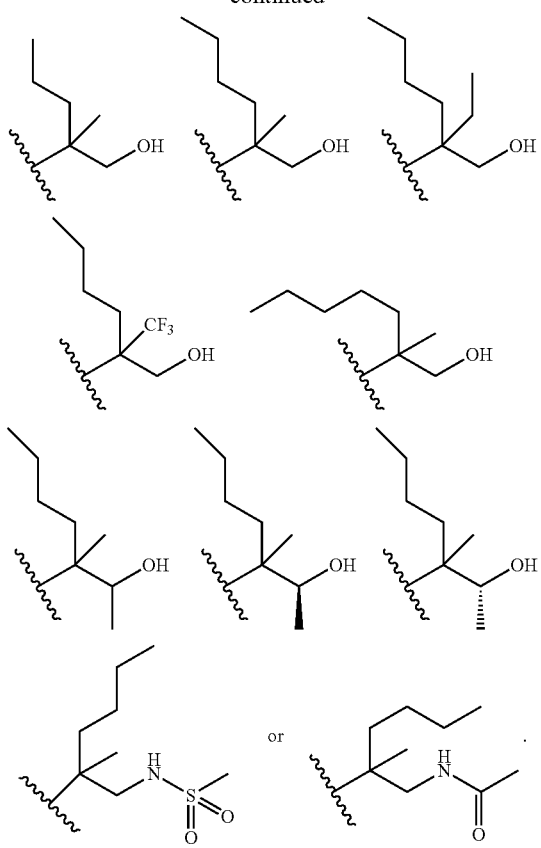

In certain embodiments, the compound of Formula (IV), or a pharmaceutically acceptable salt thereof, wherein the moiety

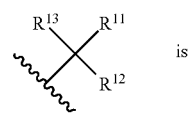

is

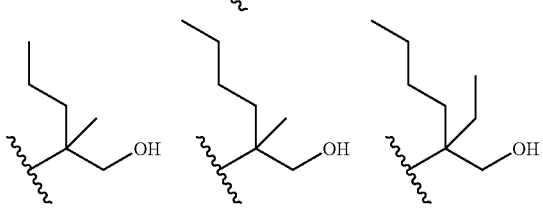

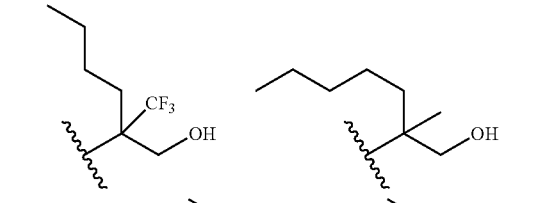

-continued

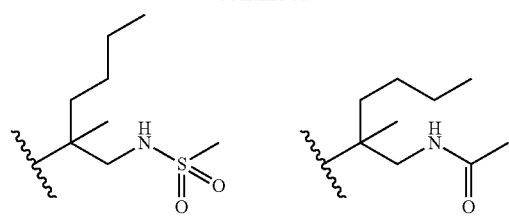

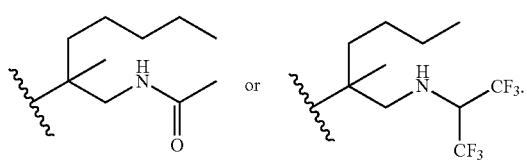

In certain embodiments, the compound of Formula (IV) or (IVa), or a pharmaceutically acceptable salt thereof, wherein the moiety

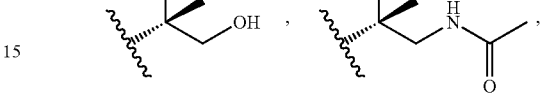

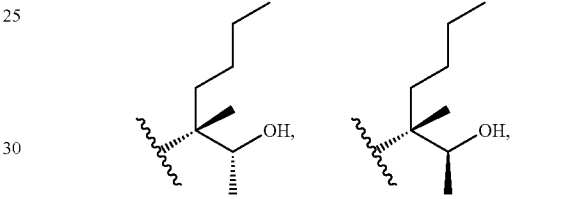


In certain embodiments, the compound of Formula (IV) or (IVa), or a pharmaceutically acceptable salt thereof, wherein the moiety

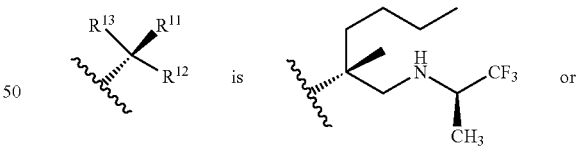

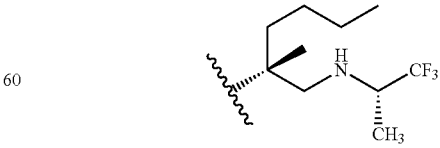

In certain embodiments, the compound of Formula (IV) or (IVa), or a pharmaceutically acceptable salt thereof, wherein the moiety In certain embodiments, the compound of Formula (IV) or (IVa), or a pharmaceutically acceptable salt thereof, wherein the moiety

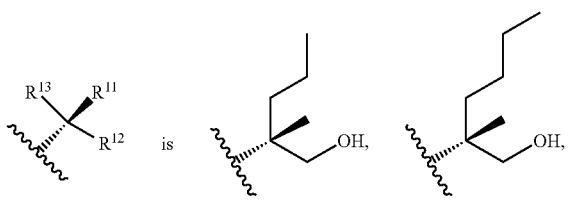 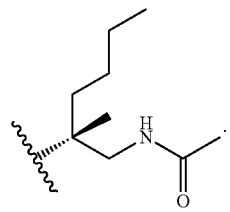

In certain embodiments, the compound of Formula (IV) or (IVa), or a pharmaceutically acceptable salt thereof, wherein the moiety

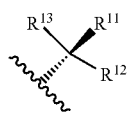

can also be drawn as the moiety

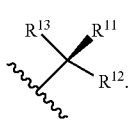

In certain embodiments, the compound of Formula (IV) or (IVb), or a pharmaceutically acceptable salt thereof, wherein the moiety

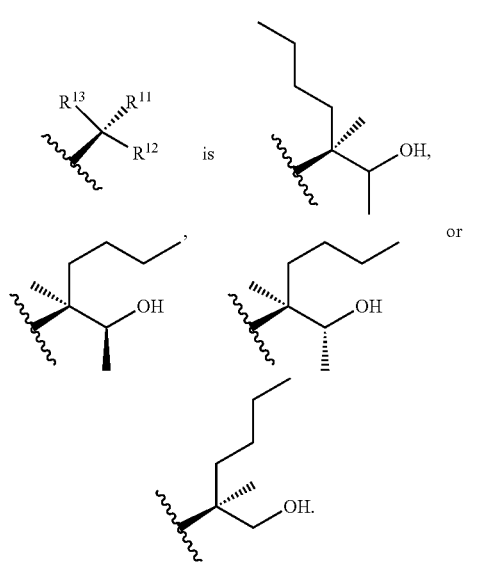

In certain embodiments, the compound of Formula (IV) or (IVb), or a pharmaceutically acceptable salt thereof, wherein the moiety

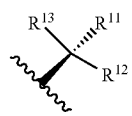

can also be drawn as the moiety

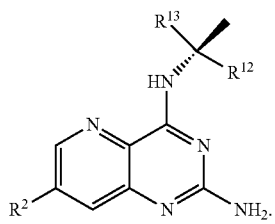

In certain embodiments, the compound of Formula (IV) or (IVa), or a pharmaceutically acceptable salt thereof, is a compound of Formula (IVc)

Formula (IVc)

The $R^2$, $R^{12}$ and $R^{13}$ groups of Formula (IVc) are as defined above for Formula (J), (I), (IV) or (IVa), or any combination thereof. For example, $R^2$ can be selected from hydrogen, halogen, $C_{1-3}$ alkyl, CN and $OR^a$, wherein $C_{1-3}$ alkyl is optionally substituted with 1 to 5 halogen groups, $R^{12}$ can be selected from $C_{1-2}$ alkyl, —C(O)$NR^aR^b$, and 5 membered heteroaryl having 1 to 3 nitrogen heteroatoms, wherein $C_{1-2}$ alkyl is optionally substituted with 1 to 5 substituents independently selected from halogen, —OH, —$NR^aR^b$, —$NR^aC(O)R^b$, —$NR^aS(O)_2R^b$, and $C_{1-3}$ haloalkyl, and $R^{13}$ can be $C_{3-6}$ alkyl optionally substituted with 1 to 2 substituents independently selected from halogen and —OH. In certain embodiments, the compound of Formula (IV), (IVa), or (IVc), or a pharmaceutically acceptable salt thereof, is a compound wherein $R^2$ can be selected from hydrogen, methyl, ethyl, fluoro, chloro, bromo, $CF_3$, CN, OH, OMe, and OEt, and $R^{12}$ can be selected $CH_2OH$, $CH_2CH_2OH$, CH(Me)OH, CH($CH_2F$)OH, CH($CHF_2$)OH, CH($CF_3$)OH, $CF_3$, $CH_2NH_2$, $CH_2NHC(O)Me$, CH($CH_2F$)NHC(O)Me, $CH_2NHS(O)_2Me$, C(O)$NH_2$, C(O)NHMe, C(O)NH—$CH_2CH_2OH$, C(O)NH—$CH_2CH_2NH_2$, C(O)NH-(pyridin-2-ylmethyl), imidazolyl, and triazolyl, and $R^{13}$ can be propyl, butyl or pentyl. In certain embodiments, the compound of Formula (IV), (IVa), or (IVc), or a pharmaceutically acceptable salt thereof, is a compound wherein $R^2$ can be selected from hydrogen, methyl, fluoro, and chloro, and $R^{12}$ can be selected $CH_2OH$, CH(Me)OH, CH($CH_2F$)OH, and $CH_2NHC(O)Me$, and $R^{13}$ can be propyl, butyl or pentyl. In certain embodiments, the compound of Formula (IV), (IVa), or (IVc), or a pharmaceutically acceptable salt thereof, is a compound wherein $R^2$ is hydrogen or fluoro, $R^{12}$ is —$CH_2OH$ or —$CH_2NHC(O)CH_3$, and $R^{13}$ is selected from propyl and butyl. In certain embodiments, the compound of Formula (IV), (IVa), or (IVc), or a pharmaceutically acceptable salt thereof, is a compound wherein $R^2$ is hydrogen, chloro, or fluoro, $R^{12}$ is —CH$_2$OH or —CH$_2$NHC(O)CH$_3$, and $R^{13}$ is selected from butyl or pentyl.

In certain embodiments, the compound of Formula (IV) or (IVa), or a pharmaceutically acceptable salt thereof, is a compound of Formula (IVd)

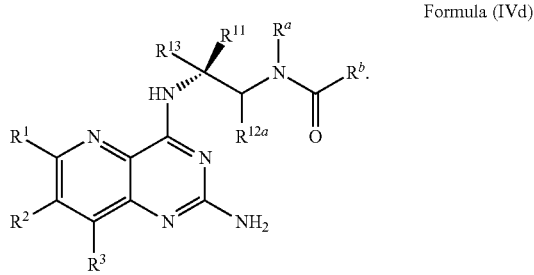

Formula (IVd)

The $R^1$, $R^2$, $R^3$, $R^{11}$, $R^{13}$, $R^a$ and $R^b$ groups of Formula (IVd) can be as defined above for Formula (J), (I), (IV), or (IVa), or any combination thereof. $R^{12a}$ can be any suitable group selected from hydrogen, $C_{1-2}$ alkyl and $C_{1-3}$ haloalkyl. In certain embodiments, the compound of Formula (IV), (IVa) or (IVd), or a pharmaceutically acceptable salt thereof, is a compound wherein $R^{12a}$ can be selected from hydrogen, $C_{1-2}$ alkyl and $C_{1-3}$ haloalkyl. In certain embodiments, the compound of Formula (IV), (IVa) or (IVd), or a pharmaceutically acceptable salt thereof, is a compound wherein $R^{12a}$ can be selected from hydrogen, methyl, ethyl and CF$_3$. In certain embodiments, the compound of Formula (IV), (IVa) or (IVd), or a pharmaceutically acceptable salt thereof, is a compound wherein $R^{12a}$ can be hydrogen.

In certain embodiments, the compound of Formula (IVd), or a pharmaceutically acceptable salt thereof, is the compound wherein $R^1$ is selected from the group consisting of hydrogen, halogen, $C_{1-6}$ alkyl, CN, and OR$^a$, wherein $C_{1-6}$ alkyl is optionally substituted with 1 to 5 $R^{20}$ groups, $R^2$ is selected from the group consisting of hydrogen, halogen, $C_{1-6}$ alkyl, CN, and OR$^a$, wherein $C_{1-6}$ alkyl optionally substituted with 1 to 5 $R^{20}$ groups, $R^3$ is selected from the group consisting of hydrogen, halogen, $C_{1-6}$ alkyl, CN, and OR$^a$, wherein $C_{1-6}$ alkyl is optionally substituted with 1 to 5 $R^{20}$ groups, $R^{11}$ is $C_{1-2}$ alkyl or CF$_3$, $R^{12a}$ is selected from the group consisting of hydrogen, $C_{1-2}$ alkyl and $C_{1-3}$ haloalkyl, $R^{13}$ is $C_{3-6}$ alkyl optionally substituted with 1 to 2 halogen substituents, each $R^{20}$ is independently selected from the group consisting of halogen, $C_{1-6}$haloalkyl, CN, —NR$^a$R$^b$, S(O)$_{1-2}$R$^a$, and OR$^a$, and each $R^a$ and $R^b$ is independently selected from the group consisting of hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl.

In certain embodiments, the compound of Formula (IVd), or a pharmaceutically acceptable salt thereof, is the compound wherein $R^1$ is selected from the group consisting of hydrogen, halogen, and $C_{1-3}$ alkyl, $R^2$ is selected from the group consisting of hydrogen, halogen, and $C_{1-3}$ alkyl, $R^3$ is selected from the group consisting of hydrogen, halogen, and $C_{1-3}$ alkyl, $R^{11}$ is $C_{1-2}$ alkyl or CF$_3$, $R^{12a}$ is selected from the group consisting of hydrogen, $C_{1-2}$ alkyl and $C_{1-3}$ haloalkyl, $R^{13}$ is $C_{3-6}$ alkyl optionally substituted with 1 to 2 halogen substituents, and each $R^a$ and $R^b$ is independently selected from the group consisting of hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl.

In certain embodiments, the compound of Formula (IVd), or a pharmaceutically acceptable salt thereof, has the structure:

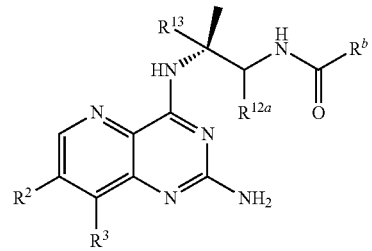

wherein $R^2$ is selected from the group consisting of hydrogen, methyl, fluoro, and chloro, $R^3$ is selected from the group consisting of hydrogen and methyl, $R^{12a}$ is selected from the group consisting of hydrogen, $C_{1-2}$ alkyl and $C_{1-3}$ haloalkyl, $R^{13}$ is $C_{3-6}$ alkyl, and $R^b$ is methyl or ethyl, each optionally substituted with hydroxyl or amino.

In certain embodiments, the compound of Formula (IVd), or a pharmaceutically acceptable salt thereof, has the structure:

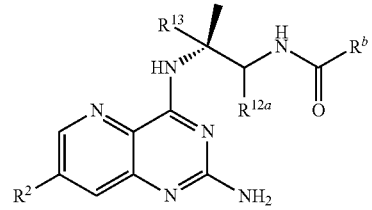

wherein $R^2$ is selected from the group consisting of hydrogen, methyl, fluoro, and chloro, $R^{12a}$ is selected from the group consisting of hydrogen, $C_{1-2}$ alkyl and $C_{1-3}$ haloalkyl, $R^{13}$ is $C_{3-6}$ alkyl, and $R^b$ is methyl or ethyl, each optionally substituted with hydroxyl or amino. In certain embodiments, $R^2$ and $R^{13}$ can be as defined above for Formula (J), (I), (IV), or (IVa), or any combination thereof.

In certain embodiments, the compound of Formula (IVd), or a pharmaceutically acceptable salt thereof, has the structure:

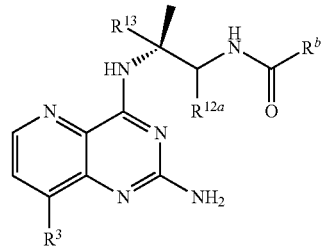

wherein $R^3$ is selected from the group consisting of hydrogen and methyl, $R^{12a}$ is selected from the group consisting of hydrogen, $C_{1-2}$ alkyl and $C_{1-3}$ haloalkyl, $R^{13}$ is $C_{3-6}$ alkyl, and $R^b$ is methyl or ethyl, each optionally substituted with hydroxyl or amino.

In certain embodiments, the compound of Formula (IVd), or a pharmaceutically acceptable salt thereof, has the structure:

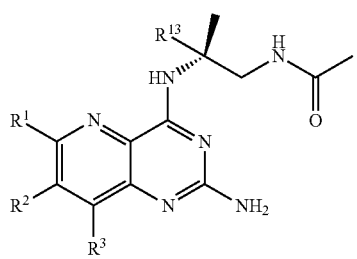

wherein $R^{13}$ is $C_{3-6}$ alkyl. $R^1$, $R^2$ and $R^3$ can be as defined above for Formula (J), (I), (IV), (IVa) or (IVd).

In certain embodiments, the compound of Formula (IVd), or a pharmaceutically acceptable salt thereof, has the structure:

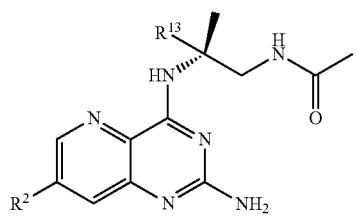

wherein $R^2$ is selected from the group consisting of hydrogen and F, and $R^{13}$ is $C_{3-6}$ alkyl. In certain embodiments, $R^2$ and $R^{13}$ can be as defined above for Formula (J), (I), (IV), or (IVa), or any combination thereof.

In certain embodiments, the compound of Formula (IVd), or a pharmaceutically acceptable salt thereof, has the structure:

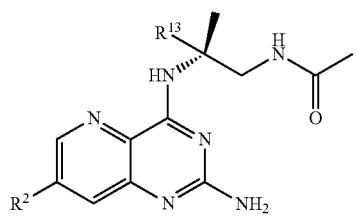

wherein $R^2$ is selected from the group consisting of hydrogen, Cl, and F, and $R^{13}$ is $C_{3-6}$ alkyl. In certain embodiments, $R^2$ and $R^{13}$ can be as defined above for Formula (J), (I), (IV), or (IVa), or any combination thereof.

In certain embodiments, the compound of Formula (IVd), or a pharmaceutically acceptable salt thereof, has the structure:

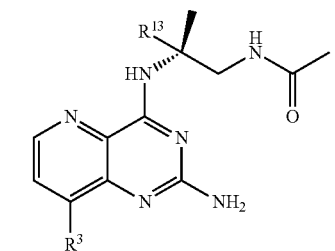

wherein $R^3$ is selected from the group consisting of hydrogen and methyl, and $R^{13}$ is $C_{3-6}$ alkyl.

In certain embodiments, the compound of Formula (J), (I), or (IV), is selected from:

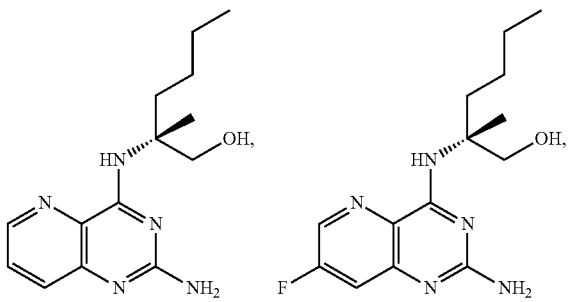

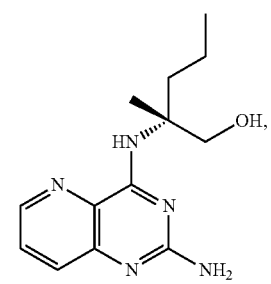

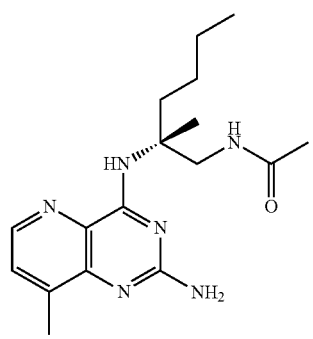

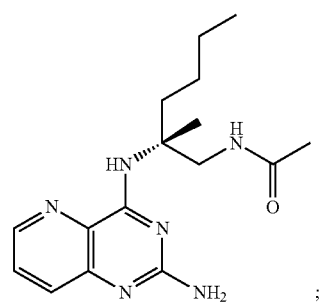

or a pharmaceutically acceptable salt thereof.

In certain embodiments, the compound of Formula (J), (I), or (IV), is selected from:

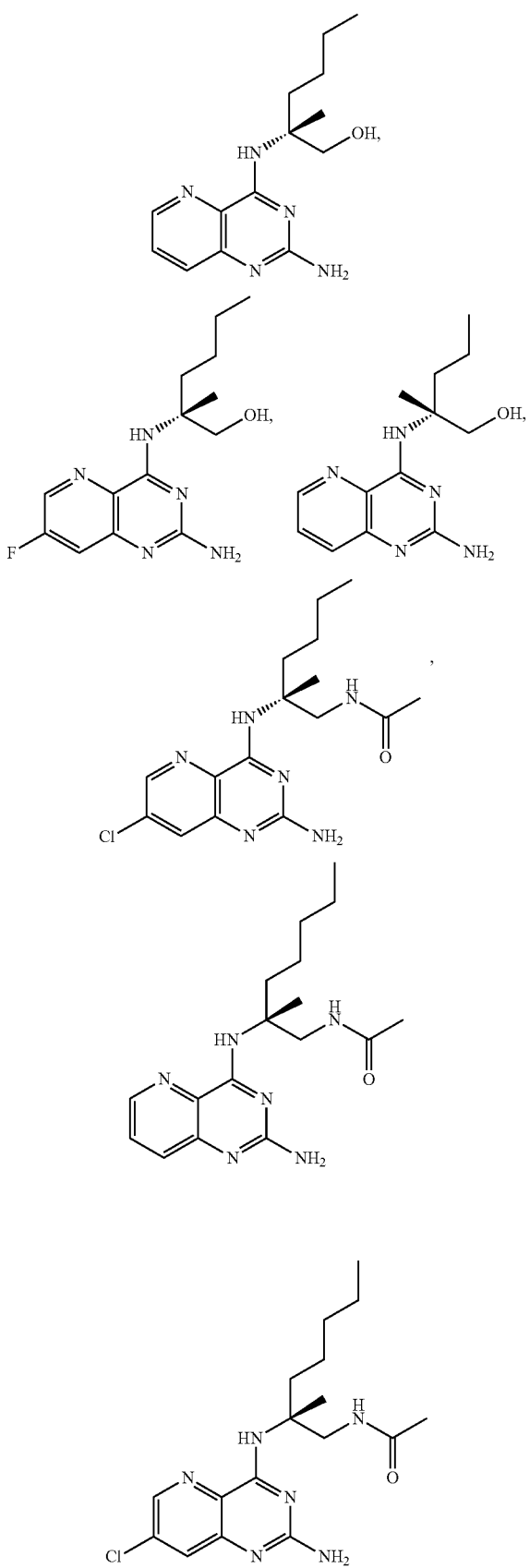

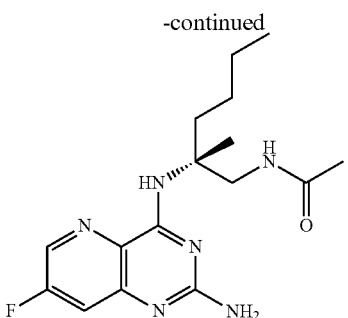

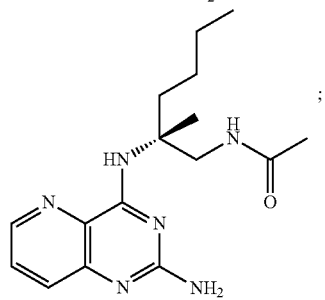

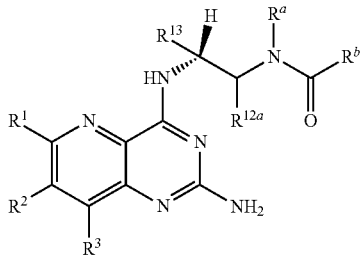

or a pharmaceutically acceptable salt thereof.

In certain embodiments, the compound of Formula (J), (I), or (IV), or a pharmaceutically acceptable salt thereof, is a compound of the following formula:

wherein $R^1$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups, $R^2$ is selected from the group consisting of hydrogen, halogen, $C_{1-6}$ alkyl, CN, and $OR^a$, wherein $C_{1-6}$ alkyl optionally substituted with 1 to 5 $R^{20}$ groups, $R^3$ is selected from the group consisting of hydrogen, halogen, $C_{1-6}$ alkyl, CN, and $OR^a$, wherein $C_{1-6}$ alkyl is optionally substituted with 1 to 5 $R^{20}$ groups, $R^{12a}$ is selected from the group consisting of hydrogen, $C_{1-2}$ alkyl and $C_{1-3}$ haloalkyl, $R^{13}$ is $C_{3-6}$ alkyl optionally substituted with 1 to 2 halogen substituents, each $R^{20}$ is independently selected from the group consisting of halogen, $C_{1-6}$haloalkyl, CN, —$NR^aR^b$, $S(O)_{1-2}R^a$, and $OR^a$, and each $R^a$ and $R^b$ is independently selected from the group consisting of hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl.

In certain embodiments, the compound of Formula (J), (I), or (IV), or a pharmaceutically acceptable salt thereof, is a compound of the following formula:

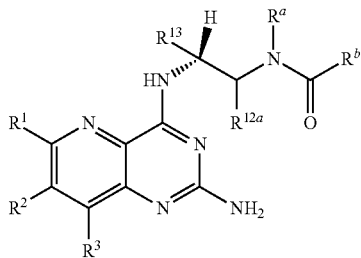

wherein R¹ is selected from the group consisting of hydrogen, halogen, and $C_{1-3}$ alkyl, R² is selected from the group consisting of hydrogen, halogen, and $C_{1-3}$ alkyl, R³ is selected from the group consisting of hydrogen, halogen, and $C_{1-3}$ alkyl, $R^{12a}$ is selected from the group consisting of hydrogen, $C_{1-2}$ alkyl and $C_{1-3}$ haloalkyl, $R^{13}$ is $C_{3-6}$ alkyl optionally substituted with 1 to 2 halogen substituents, and each $R^a$ and $R^b$ is independently selected from the group consisting of hydrogen and $C_{1-3}$ alkyl, wherein each $C_{1-3}$ alkyl is optionally substituted with 1 to 3 substituents independently selected from halogen, hydroxyl, amino, and $C_{1-6}$ haloalkyl.

In certain embodiments, the compound of Formula (J), (I), or (IV), or a pharmaceutically acceptable salt thereof, is a compound of the following formula:

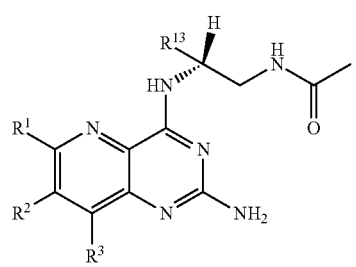

wherein $R^{13}$ is $C_{3-6}$ alkyl. R¹, R² and R³ can be as defined above for Formula (J), (I), (IV), (IVa) or (IVd).

In certain embodiments of a compound of Formula (J), (I), (II), (IIa), (IIb), (III), (IIIa), or (IIIb), R¹ is hydrogen, halogen, or $C_{1-6}$alkyl optionally substituted with 1 to 5 $R^{20}$ groups. In certain embodiments of a compound of Formula (J), (I), (II), (IIa), (IIb), (III), (IIIa), (IIIb), (IV), (IVa), (IVb), or (IVd), R¹ is hydrogen, halogen, or $C_{1-6}$alkyl optionally substituted with 1 to 5 $R^{20}$ groups.

In certain embodiments of a compound of Formula (J), (I), (II), (IIa), (IIb), (III), (IIIa), or (IIIb), R¹ is hydrogen, halogen, or $C_{1-3}$alkyl optionally substituted with 1 to 5 halogens. In certain embodiments of a compound of Formula (J), (I), (II), (IIa), (IIb), (III), (IIIa), (IIIb), (IV), (IVa), (IVb) or (IVd), R¹ is hydrogen, halogen, or $C_{1-3}$alkyl optionally substituted with 1 to 5 halogens.

In certain embodiments of a compound of Formula (J), (I), (II), (IIa), (IIb), (III), (IIIa), or (IIIb), R¹ is hydrogen, Cl, $CH_3$, or $CF_3$. In certain embodiments of a compound of Formula (J), (I), (II), (IIa), (IIb), (III), (IIIa), (IIIb), (IV), (IVa), (IVb) or (IVd), R¹ is hydrogen, Cl, $CH_3$, or $CF_3$.

In certain embodiments of a compound of Formula (J), (I), (II), (IIa), (IIb), (III), (IIIa), or (IIIb), R² is hydrogen, halogen, CN, or $C_{1-6}$alkyl optionally substituted with 1 to 5 $R^{20}$ groups. In certain embodiments of a compound of Formula (J), (I), (II), (IIa), (IIb), (III), (IIIa), (IIIb), (IV), (IVa), (IVb), (IVc), or (IVd), R² is hydrogen, halogen, CN, or $C_{1-6}$alkyl optionally substituted with 1 to 5 $R^{20}$ groups.

In certain embodiments of a compound of Formula (J), (I), (II), (IIa), (IIb), (III), (IIIa), or (IIIb), R² is hydrogen, halogen, CN or $C_{1-3}$alkyl optionally substituted with 1 to 5 halogens. In certain embodiments of a compound of Formula (J), (I), (II), (IIa), (IIb), (III), (IIIa), (IIIb), (IV), (IVa), (IVb), (IVc), or (IVd), R² is hydrogen, halogen, CN or $C_{1-3}$alkyl optionally substituted with 1 to 5 halogens.

In certain embodiments of a compound of Formula (J), (I), (II), (IIa), (IIb), (III), (IIIa), or (IIIb), R² is hydrogen, $CH_3$, $—CH_2CH_3$, F, Br, Cl, or CN. In certain embodiments of a compound of Formula (J), (I), (II), (IIa), (IIb), (III), (IIIa), (IIIb), (IV), (IVa), (IVb), (IVc), or (IVd), R² is hydrogen, $CH_3$, $—CH_2CH_3$, F, Br, Cl, or CN.

In certain embodiments of a compound of Formula (J), (I), (II), (IIa), (IIb), (III), (IIIa), or (IIIb), R³ is hydrogen, halogen, or $C_{1-6}$alkyl optionally substituted with 1 to 5 $R^{20}$ groups. In certain embodiments of a compound of Formula (J), (I), (II), (IIa), (IIb), (III), (IIIa), (IIIb), (IV), (IVa), (IVb) or (IVd), R³ is hydrogen, halogen, or $C_{1-6}$alkyl optionally substituted with 1 to 5 $R^{20}$ groups.

In certain embodiments of a compound of Formula (J), (I), (II), (IIa), (IIb), (III), (IIIa), or (IIIb), R³ is hydrogen, halogen, or $C_{1-3}$alkyl optionally substituted with 1 to 5 $R^{20}$ groups. In certain embodiments of a compound of Formula (J), (I), (II), (IIa), (IIb), (III), (IIIa), (IIIb), (IV), (IVa), (IVb) or (IVd), R³ is hydrogen, halogen, or $C_{1-3}$alkyl optionally substituted with 1 to 5 $R^{20}$ groups.

In certain embodiments of a compound of Formula (J), (I), (II), (IIa), (IIb), (III), (IIIa), or (IIIb), R³ is hydrogen, Cl, or $CH_3$. In certain embodiments of a compound of Formula (J), (I), (II), (IIa), (IIb), (III), (IIIa), (IIIb), (IV), (IVa), (IVb) or (IVd), R³ is hydrogen, Cl, or $CH_3$.

In certain embodiments of a compound of Formula (J), $R^{10}$ is hydrogen, F, Cl, or $CH_3$.

In certain embodiments of a compound of Formula (J), $R^{10}$ is hydrogen.

In certain embodiments of a compound of Formula (J), (I), (II), (IIa), (IIb), (III), (IIIa), or (IIIb), R¹, R², and R³ are hydrogen. In certain embodiments of a compound of Formula (J), (I), (II), (IIa), (IIb), (III), (IIIa), (IIIb), (IV), (IVa), (IVb), ((IVc), or (IVd), R¹, R², and R³ are hydrogen.

In certain embodiments of a compound of Formula (J), (I), (II), (IIa), (IIb), (III), (IIIa), or (IIIb), R¹ and R³ are hydrogen and R² is F. In certain embodiments of a compound of Formula (J), (I), (II), (IIa), (IIb), (III), (IIIa), (IIIb), (IV), (IVa), (IVb), (IVc), or (IVd), R and R³ are hydrogen and R² is F.

It is understood that each of the variables (e.g. R¹, R², R³, R⁴) may be combined with any other variables for Formula (J), (I), (II), (IIa) or (IIb) (e.g. R¹, R², R³, R⁴). Further, in instances describing a compound of Formula (J) or (I), it is understood that the variables also describe compounds of other formulae (e.g. Formula (II), (IIa), (IIb), (III), (IIIa), and (IIIb)) which fall within the scope of Formula (J) or (I).

It is understood that any variable for R¹ of Formula (J), (I), (II), (IIa), (IIb), (III), (IIIa), or (IIIb) may be combined with any variable of R⁴ in Formula (J), (I), (II), (IIa), (IIb), (III), (IIIa), or (IIIb), the same as if each and every combination were specifically and individually listed. For example, in one variation of Formula (J) or (I), R¹ is hydrogen, Cl, $CH_3$ or $CF_3$, and R⁴ is $C_{1-6}$ alkyl which is optionally substituted with 1 or 2 substituents independently selected from OH, $CF_3$, $—C(O)OH$, $—C(O)OCH_3$, $—C(O)NH_2$, $SCH_3$, $—C(O)NHCH_3$, $—C(O)NHCH_2CH_2NH_2$, —C(O)NHCH₂CH₂OH, —C(O)NHCH₂-pyridyl, phenyl, tetrahydrofuranyl, and cyclopropyl It is understood that any variable for R² of Formula (J), (I), (II), (IIa), (IIb), (III), (IIIa), or (IIIb) may be combined with any variable of R⁴ in Formula (J), (I), (II), (IIa), (IIb), (III), (IIIa), or (IIIb), the same as if each and every combination were specifically and individually listed. For example, in one variation of Formula (J) or (I), R² is hydrogen, CH₃, —CH₂CH₃, F, Br, Cl, or CN, and R⁴ is $C_{1-6}$ alkyl which is optionally substituted with 1 or 2 substituents independently selected from OH, CF₃, —C(O)OH, —C(O)OCH₃, —C(O)NH₂, SCH₃, —C(O)NHCH₃, —C(O)NHCH₂CH₂NH₂, —C(O)NHCH₂CH₂OH, —C(O)NHCH₂-pyridyl, phenyl, tetrahydrofuranyl, and cyclopropyl.

It is understood that any variable for R³ of Formula (J), (I), (II), (IIa), (IIb), (III), (IIIa), or (IIIb) may be combined with any variable of R⁴ in Formula (J), (I), (II), (IIa), (IIb), (III), (IIIa), or (IIIb), the same as if each and every combination were specifically and individually listed. For example, in one variation of Formula (J) or (I), R³ is hydrogen, Cl, or CH₃, and R⁴ is $C_{1-6}$ alkyl which is optionally substituted with 1 or 2 substituents independently selected from OH, CF₃, —C(O)OH, —C(O)OCH₃, —C(O)NH₂, SCH₃, —C(O)NHCH₃, —C(O)NHCH₂CH₂NH₂, —C(O)NHCH₂CH₂OH, —C(O)NHCH₂-pyridyl, phenyl, tetrahydrofuranyl, and cyclopropyl.

In certain embodiments, the compound of Formula (J) or (I), or a pharmaceutically acceptable salt thereof, has one or more features selected from:
- (a) R⁴ is $C_{1-6}$ alkyl which is optionally substituted with 1 or 2 substituents independently selected halogen, —OR$^a$, —C(O)OR$^a$, —C(O)NR$^a$R$^b$, —SR$^a$, $C_{1-3}$haloalkyl, $C_{3-6}$cycloalkyl, 3 to 6 membered heterocyclyl and $C_{6-10}$ aryl; wherein each $C_{3-6}$cycloalkyl and $C_{6-10}$ aryl is optionally substituted with 1 to 3 R²¹ groups and wherein R$^a$ and R$^b$ are each independently hydrogen or $C_{1-4}$alkyl, wherein each $C_{1-4}$ alkyl is optionally substituted with —NH₂, OH, or pyridyl;
- (b) R¹ is hydrogen, halogen, or $C_{1-6}$alkyl optionally substituted with 1 to 5 R²⁰ groups;
- (c) R² is hydrogen, halogen, CN, or $C_{1-6}$alkyl optionally substituted with 1 to 5 R²⁰ groups; and
- (d) R³ is hydrogen, halogen, or $C_{1-3}$alkyl optionally substituted with 1 to 5 R²⁰ groups.

In certain embodiments, the compound of Formula (J) or (I), or a pharmaceutically acceptable salt thereof has two or more features selected from (a)-(d), as listed above. In certain embodiments, the compound of Formula (J) or (I), or a pharmaceutically acceptable salt thereof has three or more features selected from (a)-(d), as listed above. In certain embodiments, the compound of Formula (J) or (I), or a pharmaceutically acceptable salt thereof has four features selected from (a)-(d), as listed above.

In certain embodiments, the compound of Formula (J) or (I), or a pharmaceutically acceptable salt thereof has one or more features selected from:
- (e) R⁴ is $C_{1-6}$ alkyl which is optionally substituted with 1 or 2 substituents independently selected from OH, CF₃, —C(O)OH, —C(O)OCH₃, —C(O)NH₂, SCH₃, —C(O)NHCH₃, —C(O)NHCH₂CH₂NH₂, —C(O)NHCH₂CH₂OH, —C(O)NHCH₂-pyridyl, phenyl, tetrahydrofuranyl, and cyclopropyl.
- (f) R¹ is hydrogen, halogen, or $C_{1-3}$alkyl optionally substituted with 1 to 5 halogens;
- (g) R² is hydrogen, halogen, CN or $C_{1-3}$alkyl optionally substituted with 1 to 5 halogens; and
- (h) R³ is hydrogen, halogen, or $C_{1-3}$alkyl.

In certain embodiments, the compound of Formula (J) or (I), or a pharmaceutically acceptable salt thereof has two or more features selected from (e)-(h), as listed above. In certain embodiments, the compound of Formula (J) or (I), or a pharmaceutically acceptable salt thereof has three or more features selected from (e)-(h), as listed above. In certain embodiments, the compound of Formula (J) or (I), or a pharmaceutically acceptable salt thereof has two or more features selected from (e)-(h), as listed above.

In certain embodiments, the compound of Formula (J) or (I) is selected from:

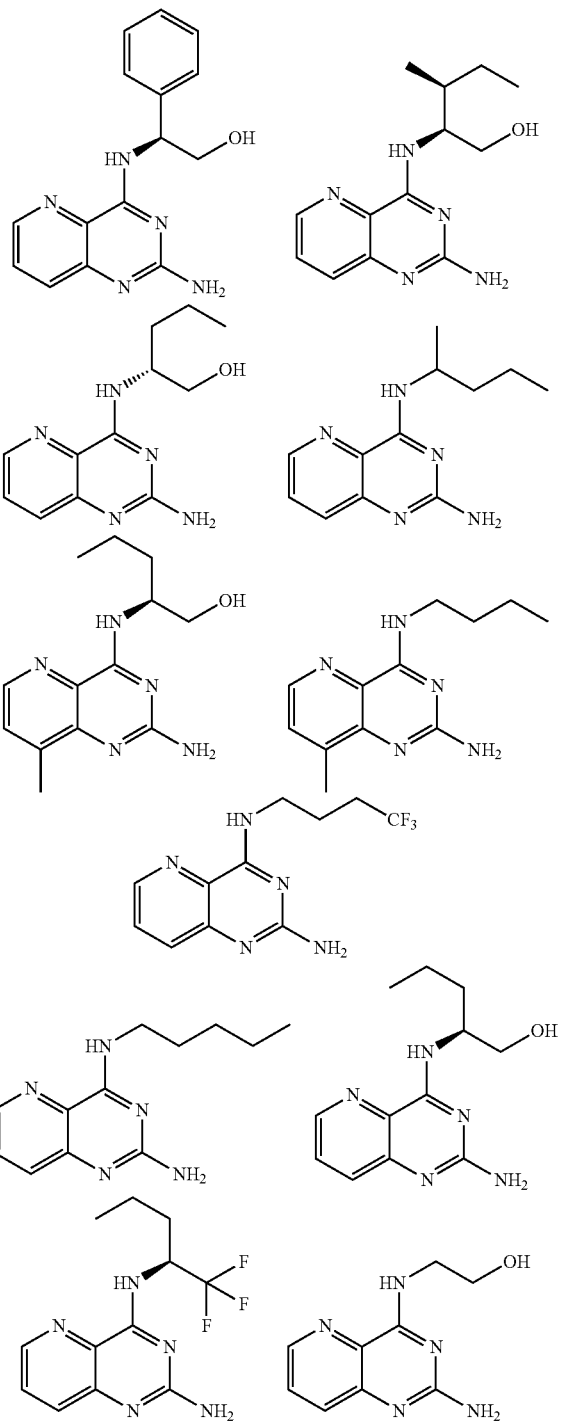

73
-continued
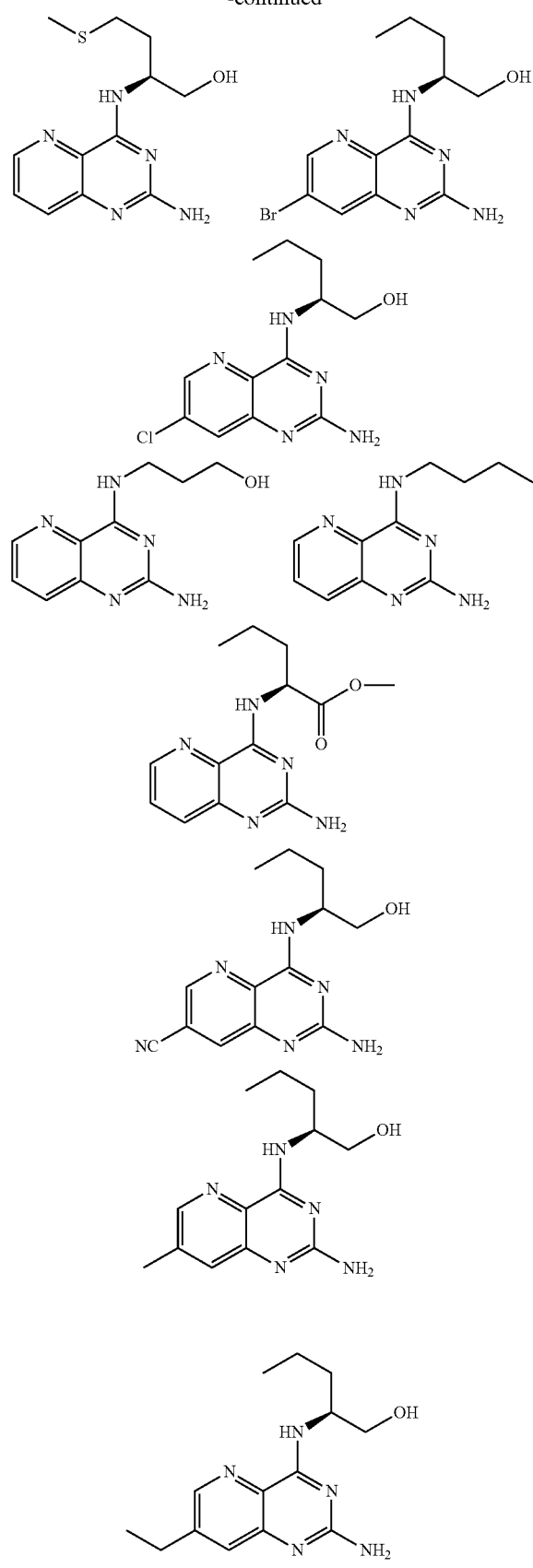
74
-continued
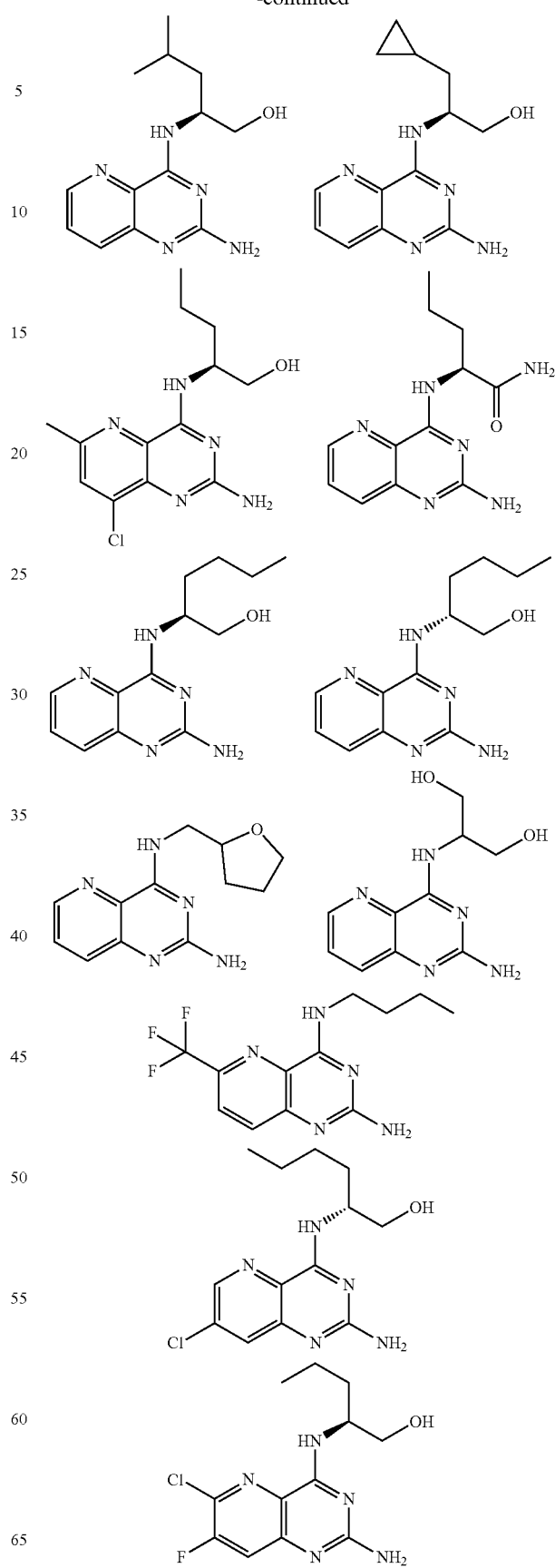

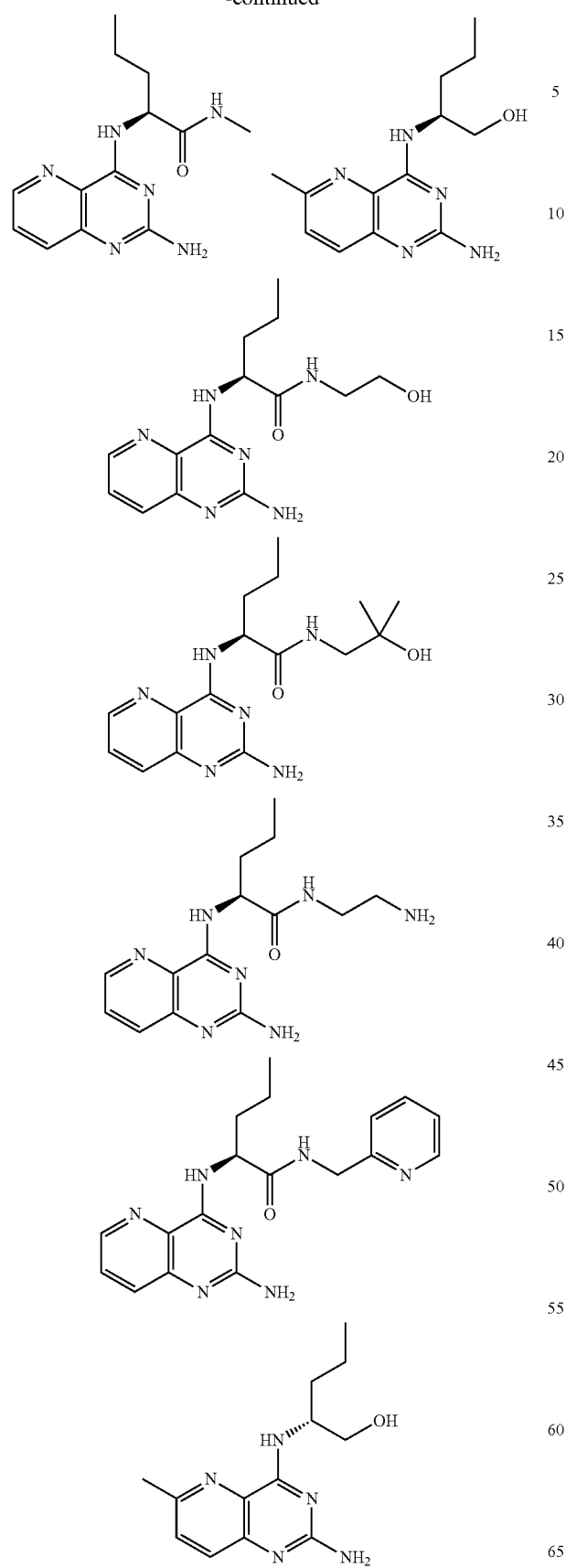
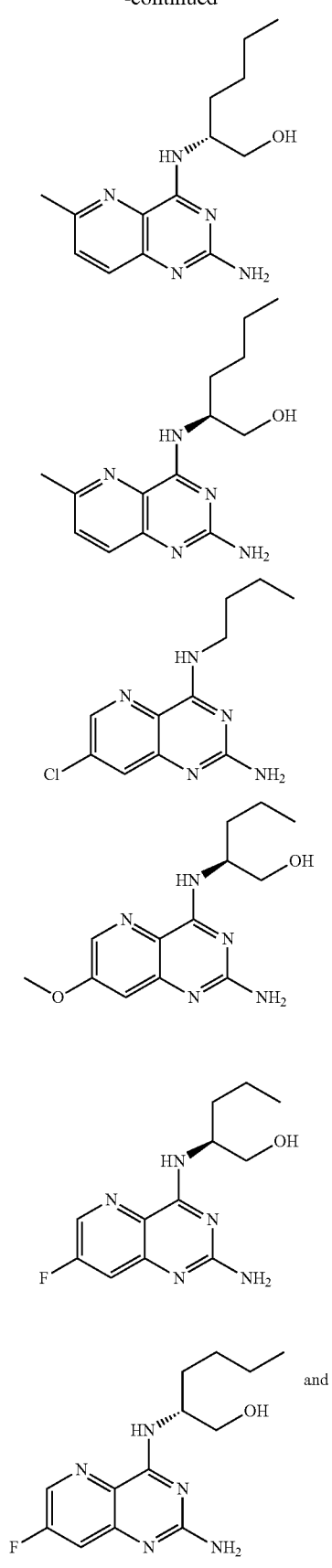

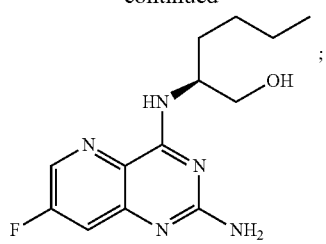
or a pharmaceutically acceptable salt thereof.
In certain embodiments, the compound of Formula (J) or (I) is selected from:
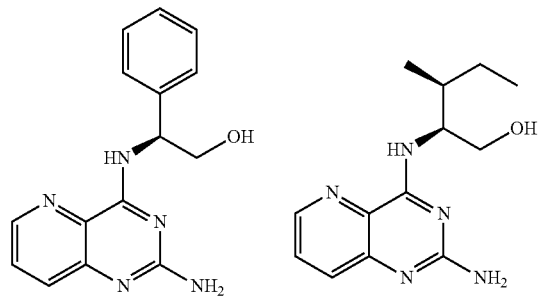
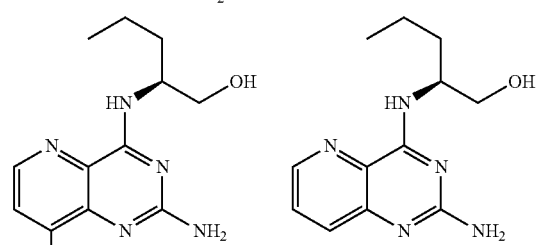
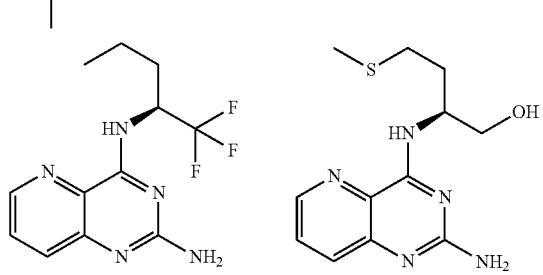
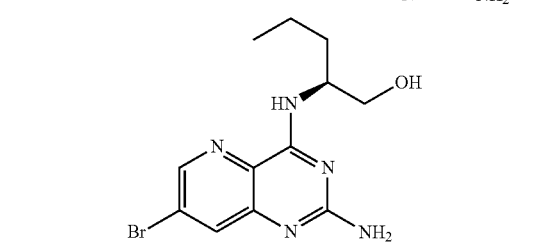
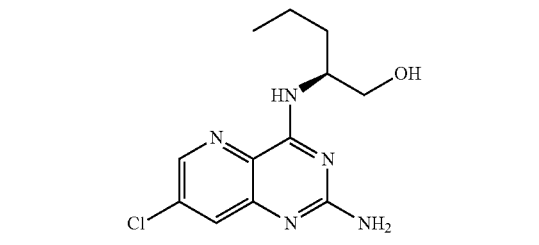
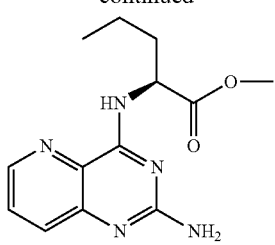
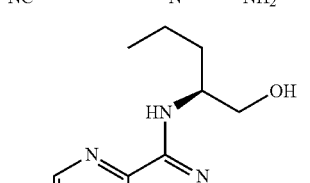
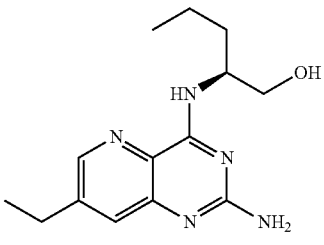
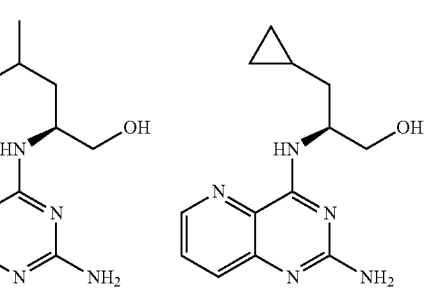
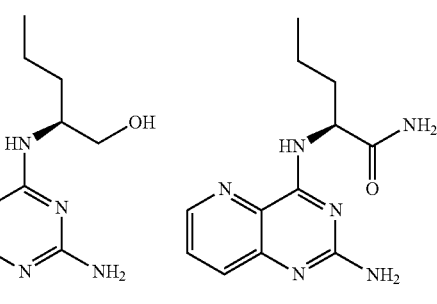

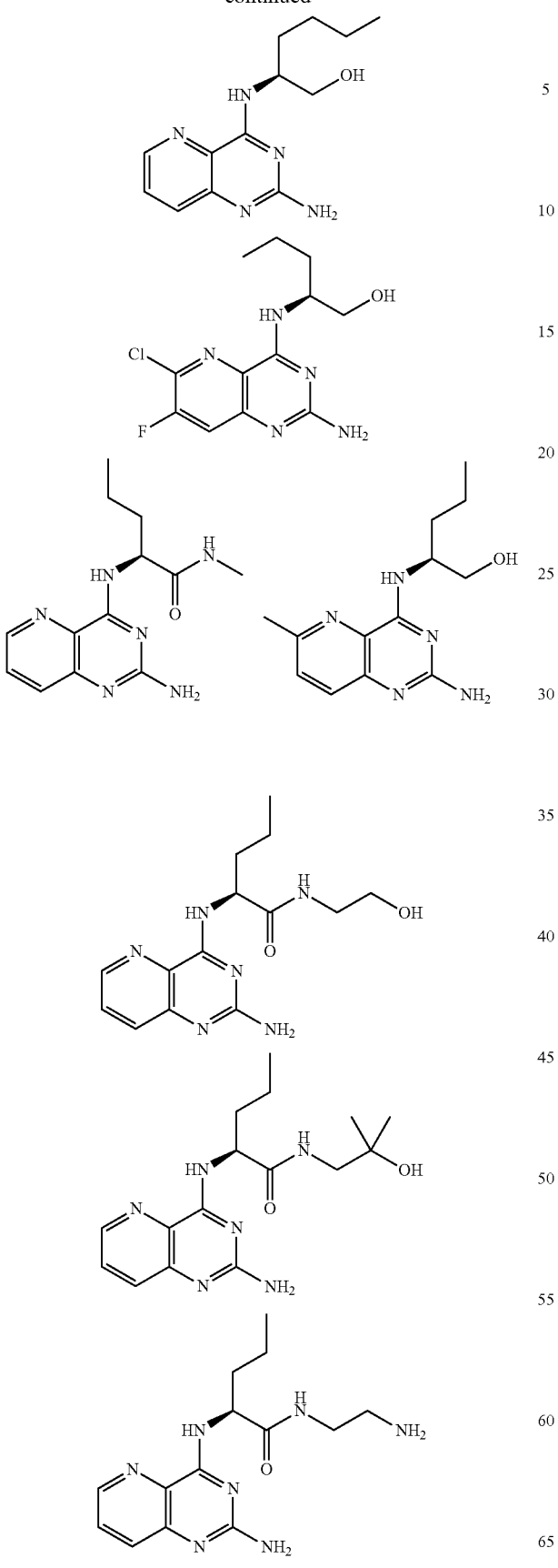
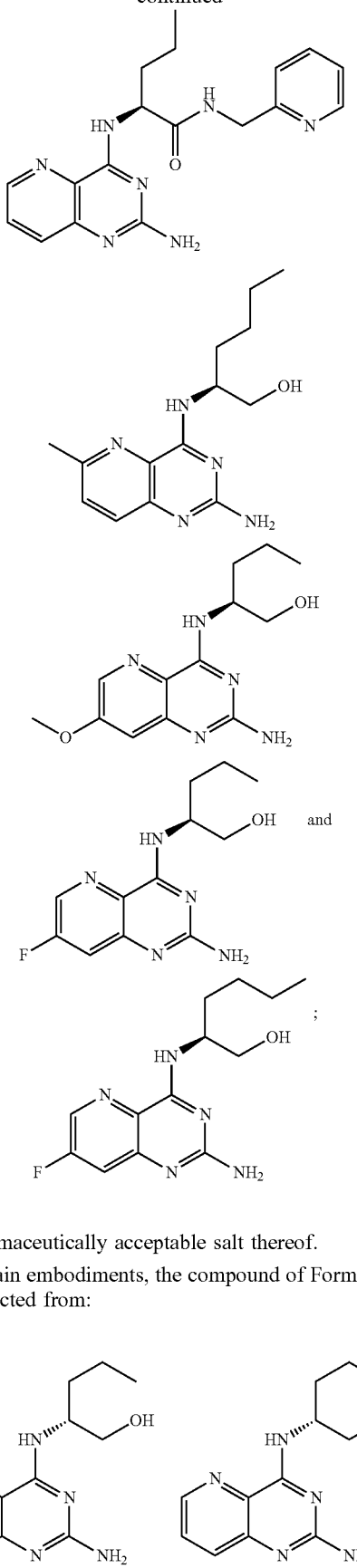
or a pharmaceutically acceptable salt thereof.
In certain embodiments, the compound of Formula (J) or (I) is selected from:

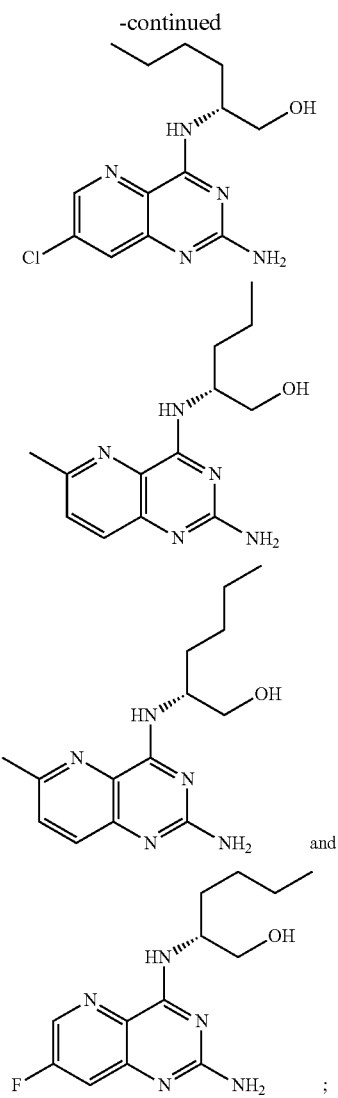
or a pharmaceutically acceptable salt thereof.
In certain embodiments, the compound of Formula (J) is selected from:
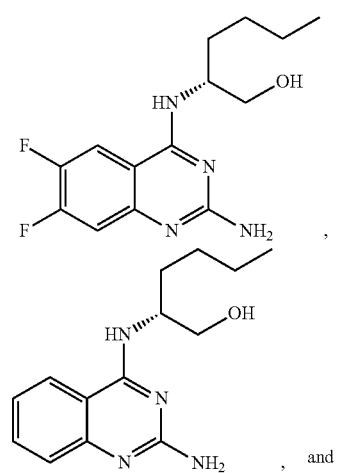
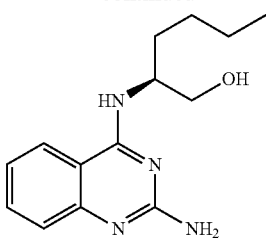
or a pharmaceutically acceptable salt thereof.
In certain embodiments, the compound of Formula (J) or (I) is selected from:

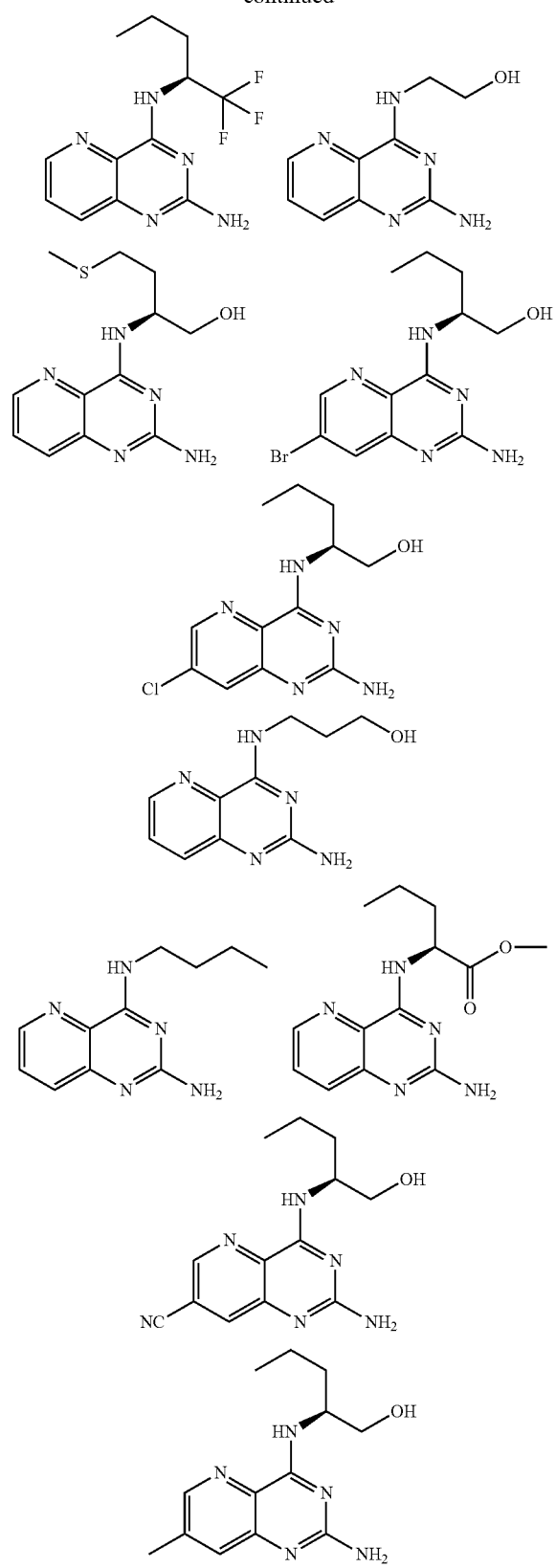
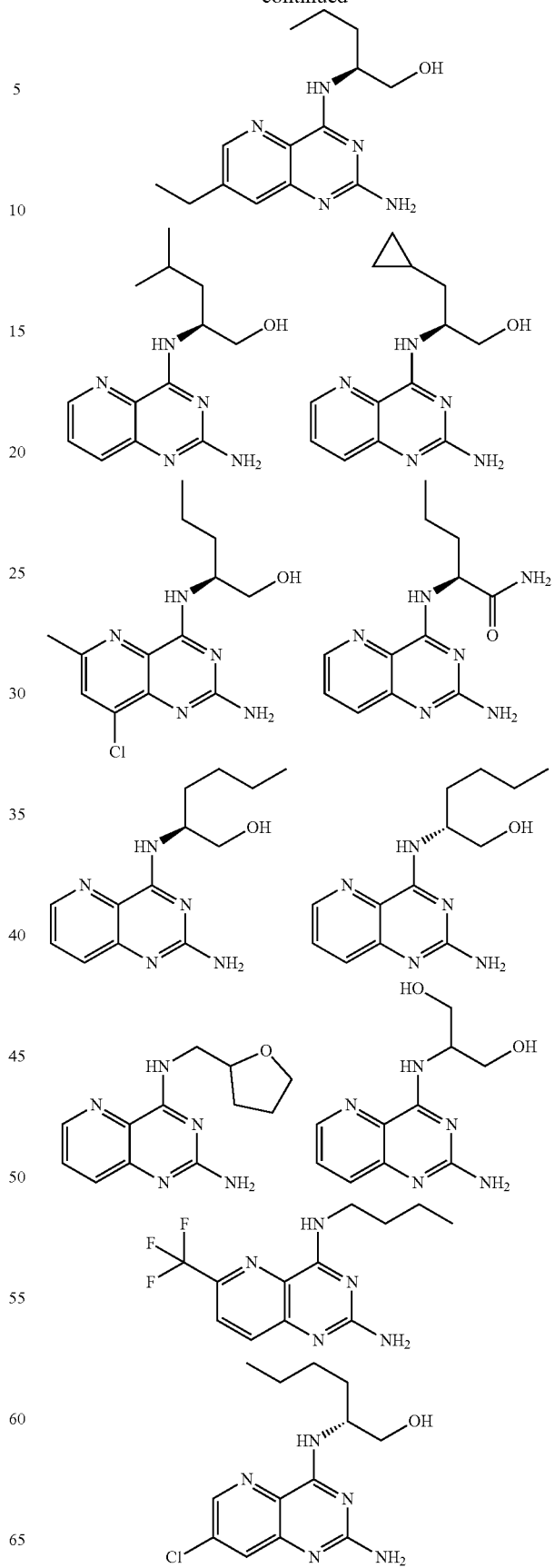

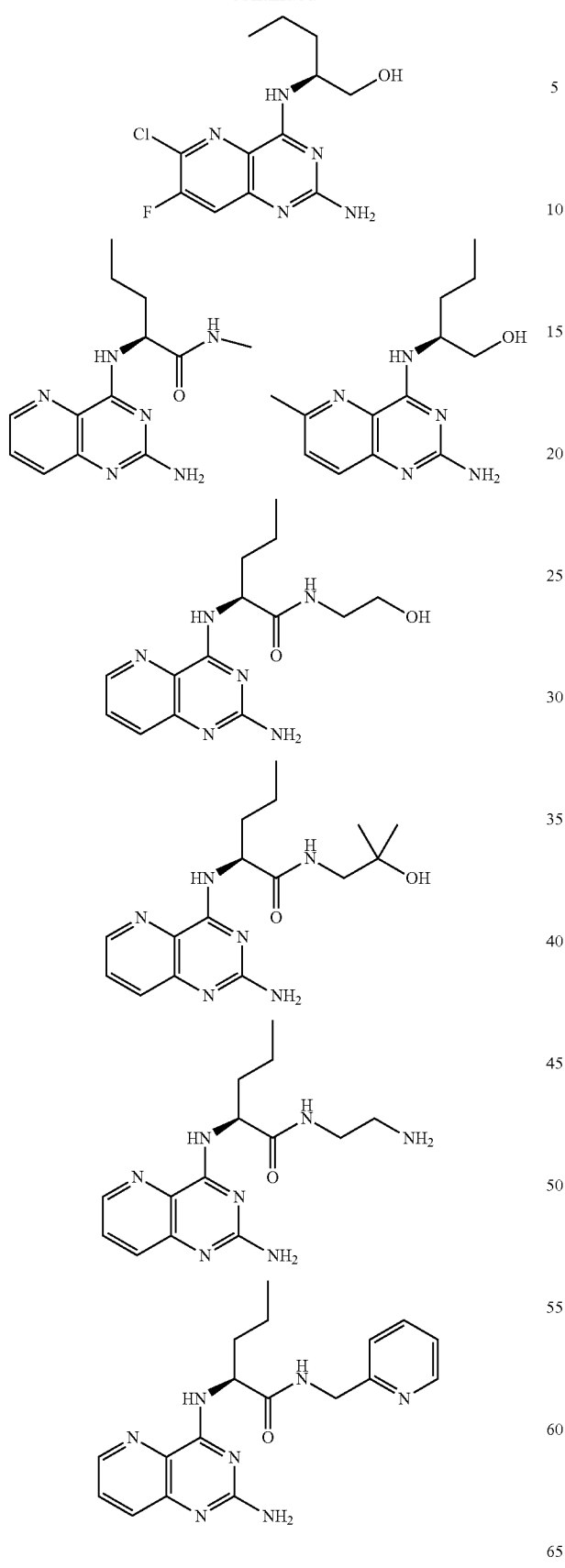
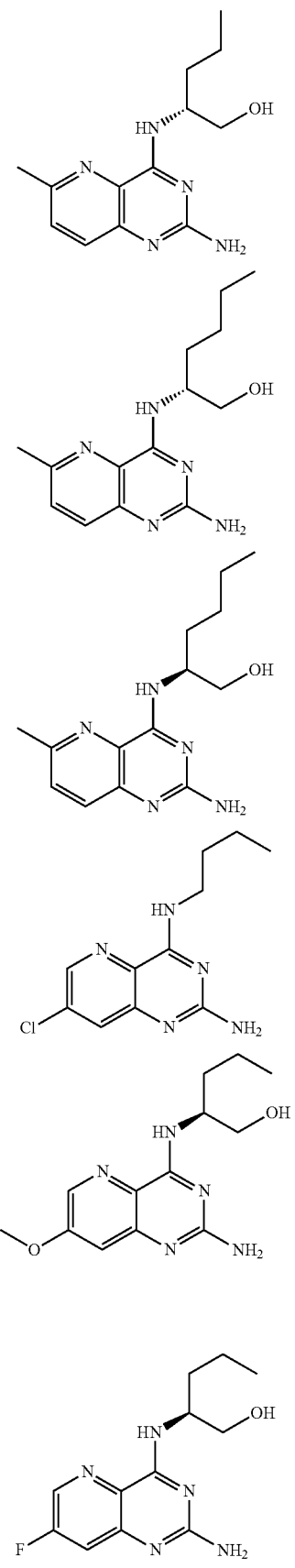

-continued
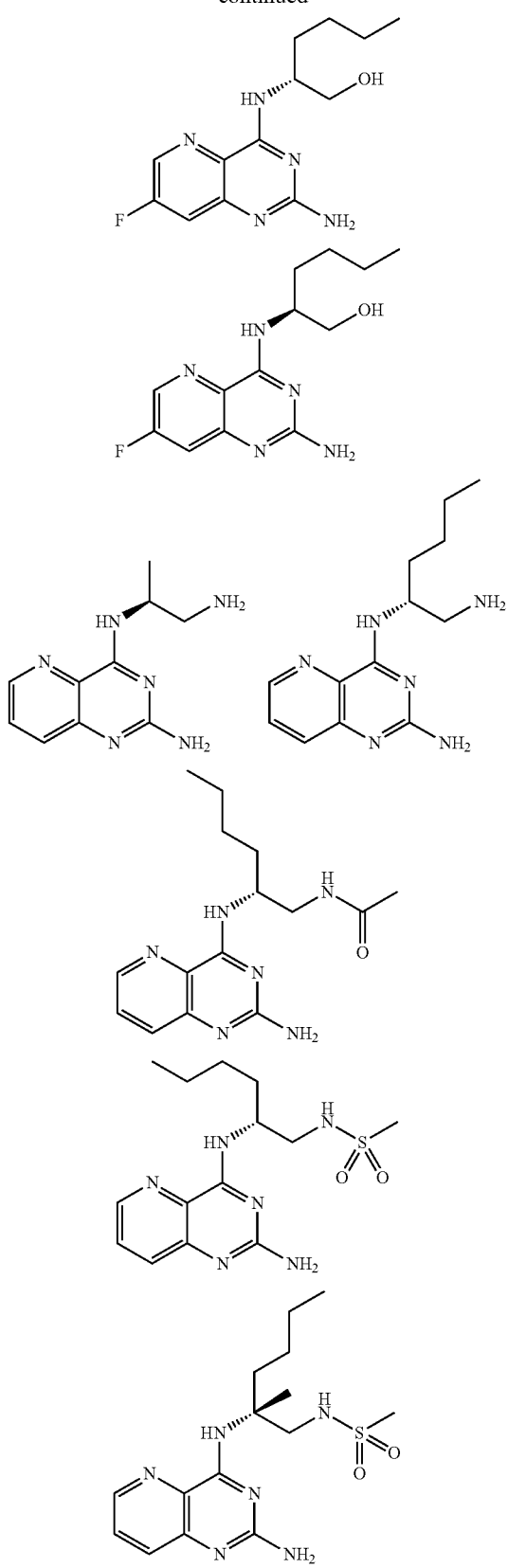
-continued
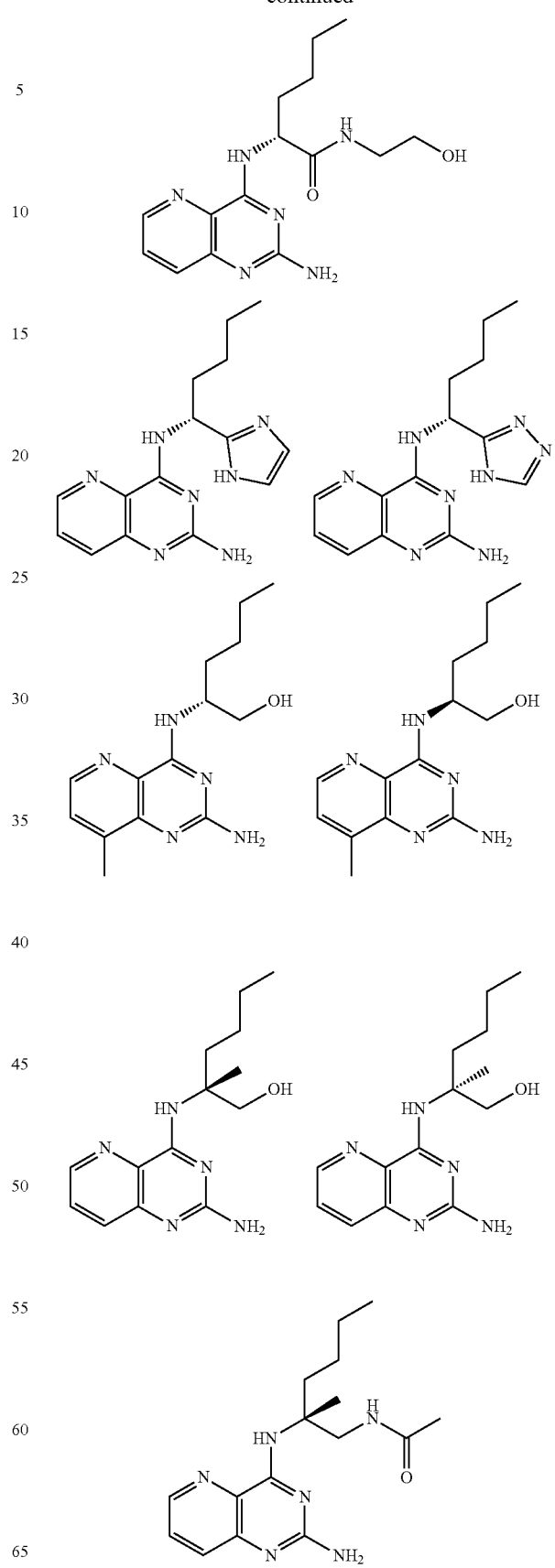

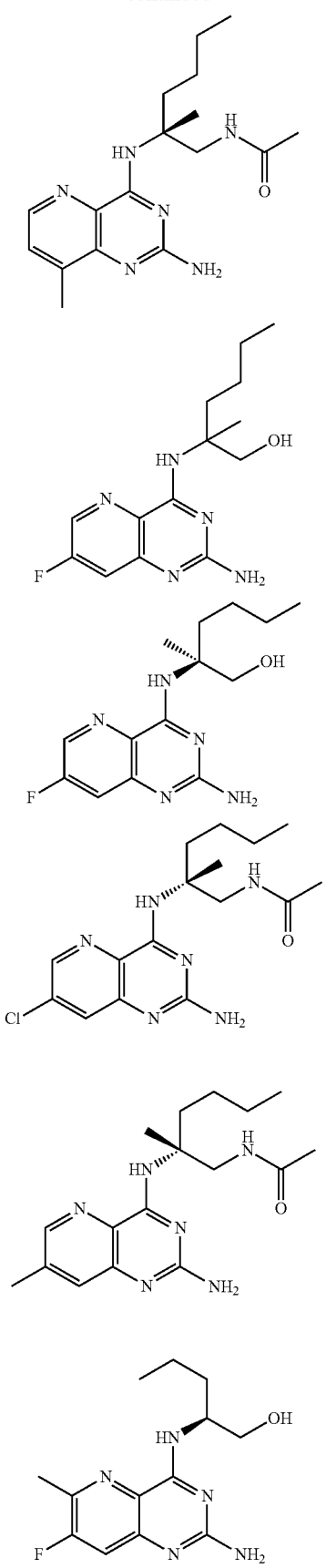
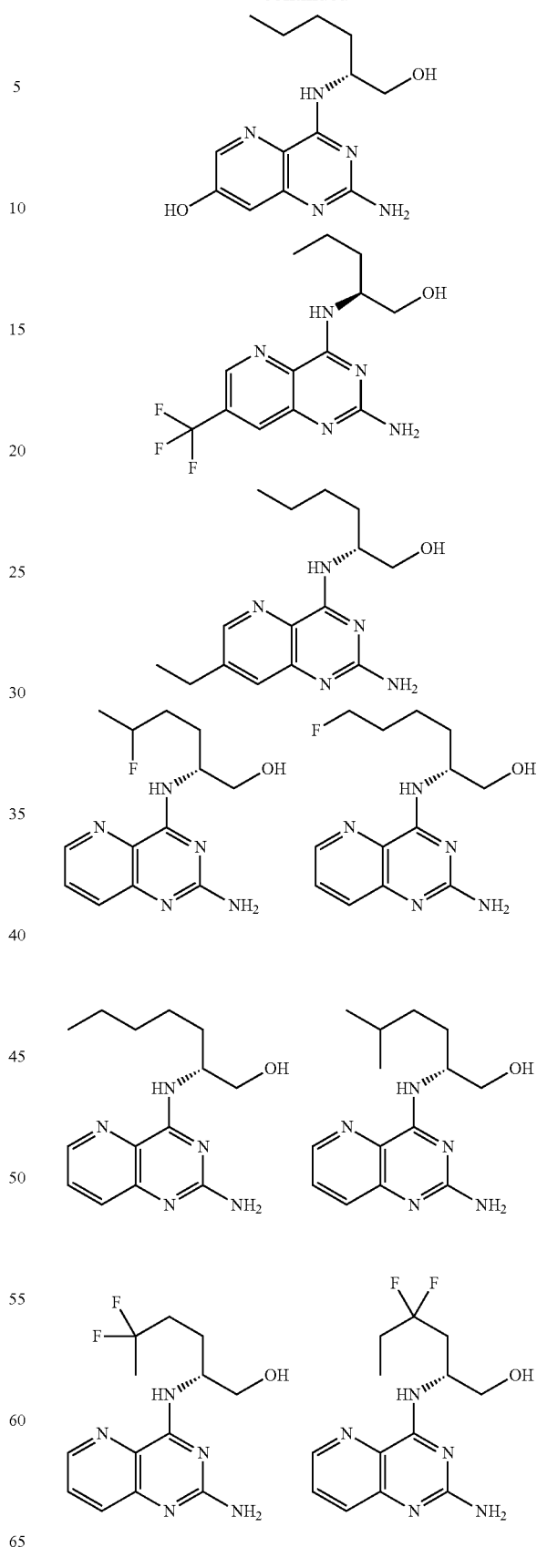

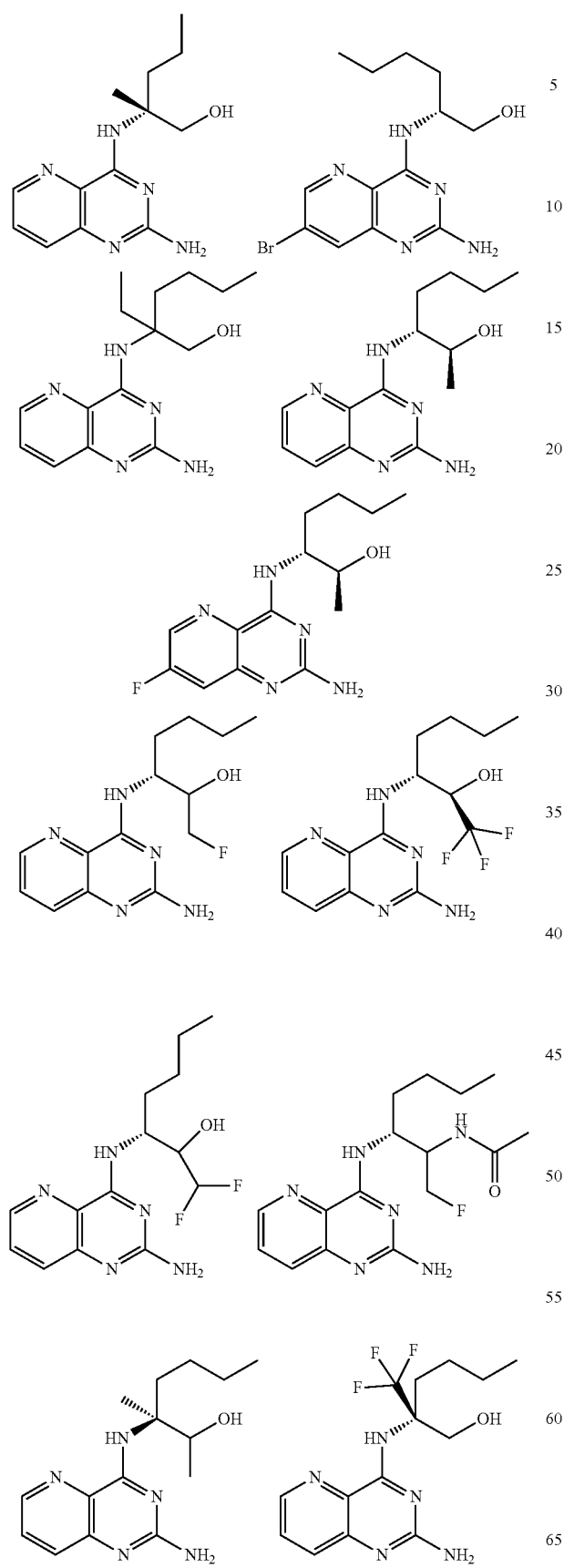
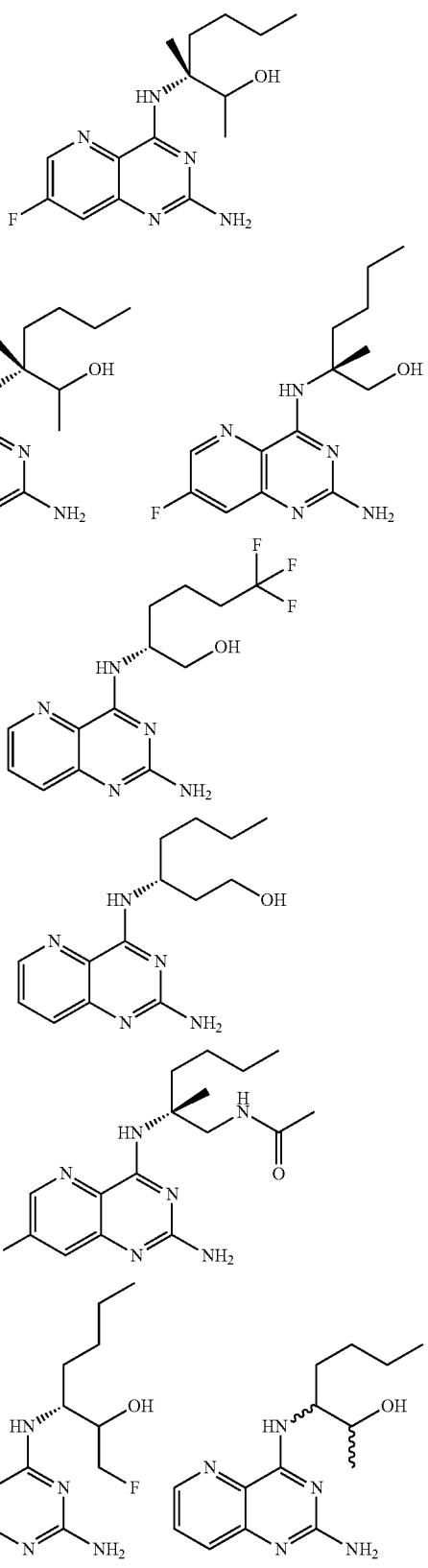

-continued
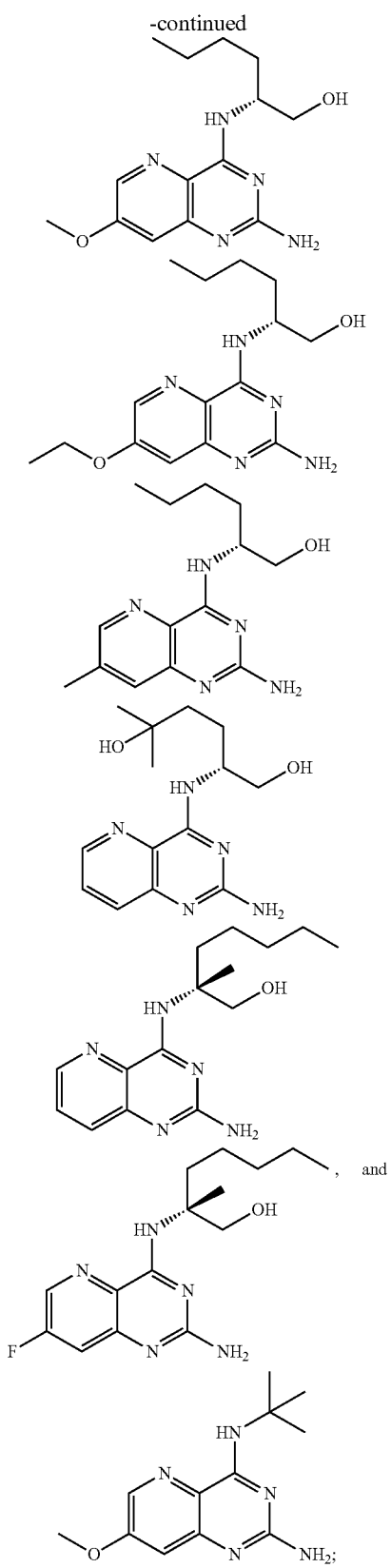
or a pharmaceutically acceptable salt thereof.
In certain embodiments, the compound of Formula (J), (I), (IV), or (IVa) is selected from:
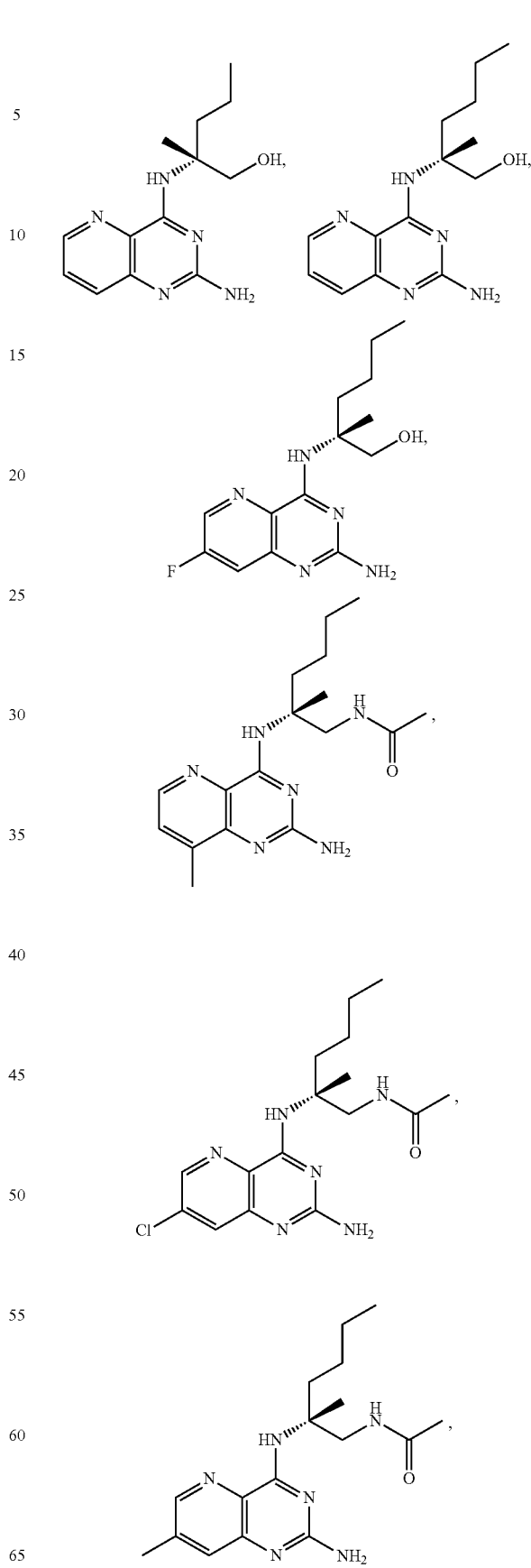

-continued

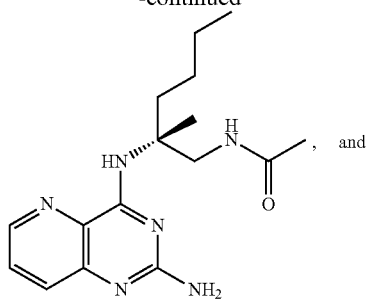, and

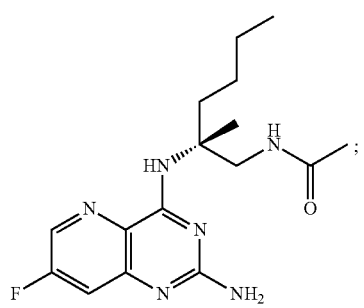;

or a pharmaceutically acceptable salt thereof.

In certain embodiments, the compound of Formula (J), (I), (IV), or (IVa) is selected from:

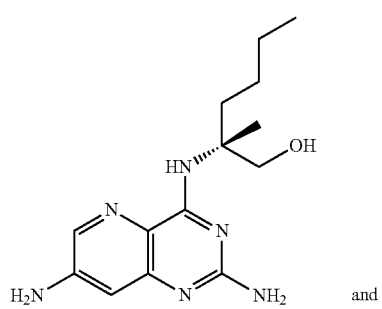 and

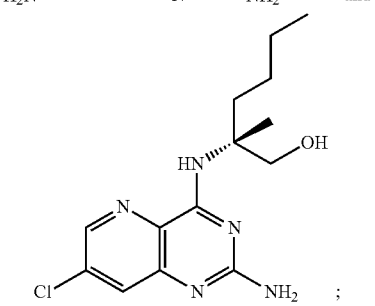;

or a pharmaceutically acceptable salt thereof.

In certain embodiments, the compound of Formula (J), (I), (IV), or (IVa) is selected from:

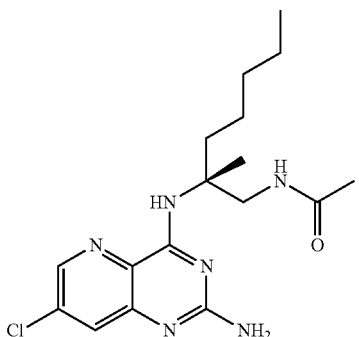 and

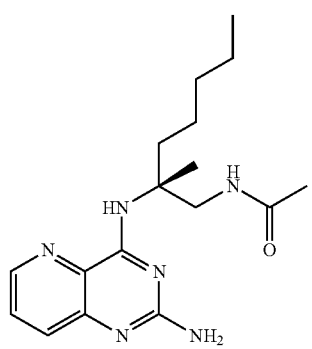;

or a pharmaceutically acceptable salt thereof.

In certain embodiments, the compound of Formula (J), (I), (IV), or (IVa) is selected from:

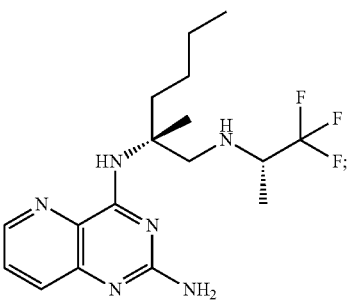

or a pharmaceutically acceptable salt thereof.

In certain embodiments, the compound of Formula (J), (I), (IV), or (IVa) is selected from:

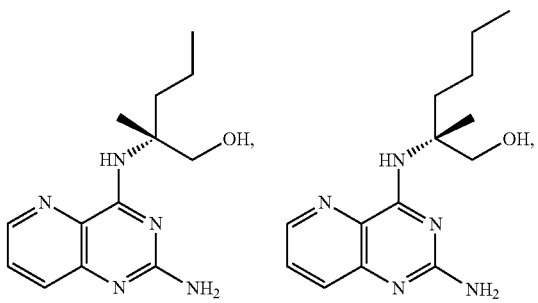

-continued

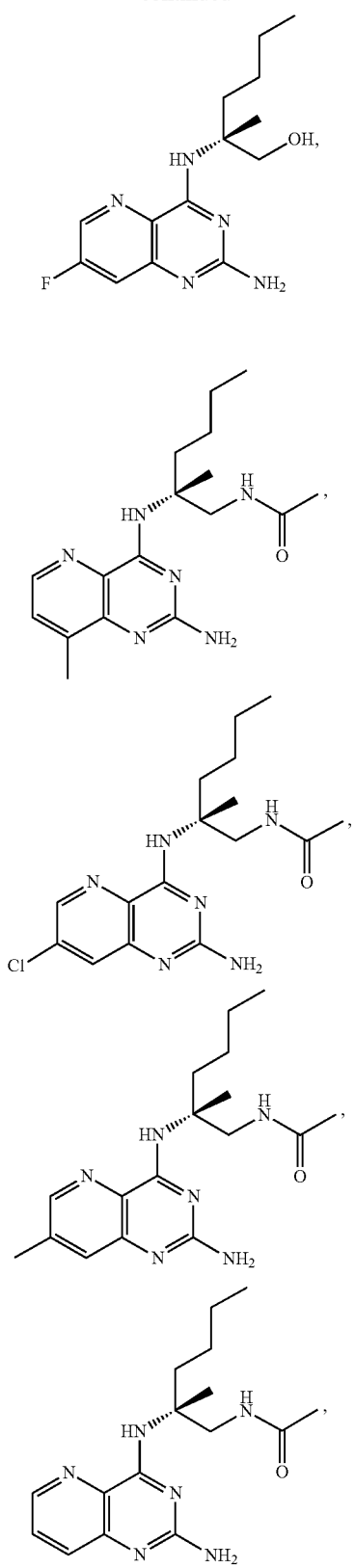

-continued

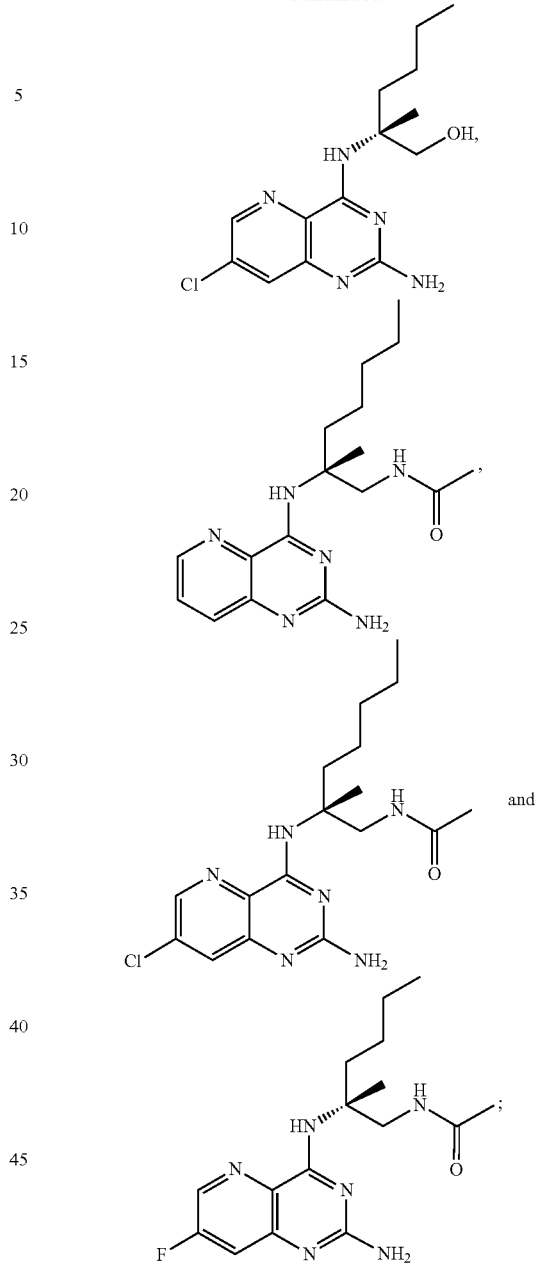

or a pharmaceutically acceptable salt thereof.

As used herein, "a compound of Formula (I)" includes compounds for Formula (II) (IIa), (IIb), (III), (IIIa), (IIIb), (IV), (IVa), (IVb), (IVc), or (IVd).

III. COMPOSITIONS

In certain embodiments, the present disclosure provides a pharmaceutical composition comprising a compound of the present disclosure (e.g. a compound of Formula (J), (I), (II), (IIa), (IIb), (III), (IIIa), (IIIb), (IV), (IVa), (IVb), (IVc), or (IVd)), or a pharmaceutically acceptable salt thereof, and a pharmaceutically acceptable excipient.

In certain embodiments, the pharmaceutical composition comprises one or more additional therapeutic agent, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, $6^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, $21^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

In certain embodiments, a composition comprising a compound of the present disclosure (e.g. a compound of Formula (J), (I), (II), (IIa), (IIb), (III), (IIIa), (IIIb), (IV), (IVa), (IVb), (IVc), or (IVd)), or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

IV. METHODS

The present disclosure provides for methods of treating diseases or conditions that are responsive to the modulation of toll-like receptors (e.g. TLR-8 receptors). While not wishing to be bound by any one theory, the presently disclosed compounds are believed to modulate TLR-8 receptors as agonists. As is understood by those of skill in the art, modulators of TLR-8 may, to some degree, modulate other toll-like receptors (e.g. TLR-7). As such, in certain embodiments, the compounds disclosed herein may also modulate TLR-7 to a measureable degree. In certain embodiments, those compounds that modulate TLR-8 to a higher degree than TLR-7 are considered selective modulators of TLR-8. Exemplary methods of measuring the each compounds respective modulation of TLR-7 and TLR-8 are described in the Examples provided herein. In certain embodiments, the compounds disclosed herein are selective modulators of TLR-8.

In certain embodiments, a method of modulating TLR-8 is provided, comprising administering a compound of the present disclosure, or a pharmaceutically acceptable salt thereof, to an individual (e.g. a human).

In certain embodiments, a method of modulating TLR-8 in vitro is provided.

In certain embodiments, the present disclosure provides a compound of the present disclosure, or a pharmaceutically acceptable salt thereof, for use as a research tool, e.g., for use in identifying modulators of TLR-8

In certain embodiments, the present disclosure provides methods for the treatment or prevention of diseases or conditions in an individual (e.g. a human) in need thereof, comprising administering a compound of the present disclosure or a pharmaceutically acceptable salt thereof. In certain embodiments, the methods comprise administering one or more additional therapeutic agents. Treatment with a compound of the present disclosure typically results in the stimulation of an immune response to the particular disease or condition being treated. Diseases or conditions contemplated by the present disclosure include those affected by the modulation of toll-like receptors (e.g. TLR-8). In certain embodiments, a method of treating or preventing a disease or condition responsive to the modulation of TLR-8 is provided, comprising administering to a human a therapeutically effective amount of a compound of the present disclosure, or a pharmaceutically acceptable salt thereof. Exemplary diseases, disorders and conditions include but are not limited to conditions involving autoimmunity, inflammation, allergy, asthma, graft rejection, graft versus host disease (GvHD), infectious diseases, cancer, and immunodeficiency.

In certain embodiments, infectious diseases include diseases such as hepatitis A, hepatitis B (HBV), hepatitis C (HCV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, leishmania infection, and respiratory syncytial virus. In certain embodiments, infectious diseases include diseases such as hepatitis A, hepatitis B (HBV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, leishmania infection, and respiratory syncytial virus.

In certain embodiments, a method of treating or preventing a viral infection is provided, comprising administering to an individual (e.g. a human) a therapeutically effective amount a compound of the present disclosure, or a pharmaceutically acceptable salt thereof. In one embodiment, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present disclosure include, among others, detecting a decrease in viral load or antigen in a subject's serum, detection of IFN-gamma-secreting peptide specific T cells, and detection of elevated levels of one or more liver enzymes, such as alanine transferase (ALT) and aspartate transferase (AST). In one embodiment, the detection of IFN-gamma-secreting peptide specific T cells is accomplished using an ELISPOT assay. Another embodiment includes reducing the viral load associated with HBV infection, including a reduction as measured by PCR testing.

In certain embodiments, the present invention provides a method for enhancing the efficacy of a vaccine by co-administering with the vaccine, a therapeutically effective amount of a compound of the present disclosure, or a pharmaceutically acceptable salt thereof, to an individual (e.g. a human). In certain embodiments, the compound of the present disclosure or a pharmaceutically acceptable salt thereof, may be co-administered with a vaccine to boost the immune response by allowing the production of a higher amount of antibodies or by allowing a longer lasting protection. In certain embodiments, the compounds of the present disclosure, or a pharmaceutically acceptable salt thereof, may be used as vaccine adjuvants to increase the efficacy and response to the immunization with a particular antigen. In certain embodiments, co-administering the compounds of the present disclosure, or a pharmaceutically acceptable salt thereof, with a vaccine, may influence the way a vaccine's antigen is presented to the immune system and enhance the vaccine's efficacy.

In certain embodiments, a compound of the present disclosure, or a pharmaceutically acceptable salt thereof, for use in medical therapy is provided. In certain embodiments, a compound of the present disclosure or a pharmaceutically acceptable salt thereof, for use in treating or preventing a disease or condition responsive to the modulation of TLR-8, is provided. In certain embodiments, the disease or condition is a viral infection as set forth herein.

In certain embodiments, the use of a compound of the present disclosure, or a pharmaceutically acceptable salt thereof, for the manufacture of a medicament for treating or preventing a disease or condition responsive to the modulation of TLR-8, is provided.

In certain embodiments, the present disclosure also provides methods for treating a hepatitis B viral infection, comprising administering to an individual (e.g. a human) infected with hepatitis B virus a therapeutically effective amount a compound of the present disclosure or a pharmaceutically acceptable salt thereof. Typically, the individual is suffering from a chronic hepatitis B infection, although it is within the scope of the present disclosure to treat people who are acutely infected with HBV.

The present disclosure also provides methods for treating a hepatitis C viral infection, comprising administering to an individual (e.g. a human) infected with hepatitis C virus a therapeutically effective amount a compound of the present disclosure or a pharmaceutically acceptable salt thereof. Typically, the individual is suffering from a chronic hepatitis C infection, although it is within the scope of the present disclosure to treat people who are acutely infected with HCV.

Treatment of HBV or HCV in accordance with the present disclosure typically results in the stimulation of an immune response against HBV or HCV in an individual (e.g. a human) being infected with HBV or HCV, respectively, and a consequent reduction in the viral load of HBV or HCV in the infected individual. Examples of immune responses include production of antibodies (e.g., IgG antibodies) and/or production of cytokines, such as interferons, that modulate the activity of the immune system. The immune system response can be a newly induced response, or can be boosting of an existing immune response. In particular, the immune system response can be seroconversion against one or more HBV or HCV antigens.

As described more fully herein, compounds of the present disclosure can be administered with one or more additional therapeutic agent(s) to an individual (e.g. a human) infected with HBV or HCV. The additional therapeutic agent(s) can be administered to the infected individual (e.g. a human) at the same time as a compound of the present disclosure or before or after administration of a compound of the present disclosure. For example, in certain embodiments, when used to treat or prevent HCV, a compound of the present disclosure may be administered with one or more additional therapeutic agent(s) selected from the group consisting of interferons, ribavirin or its analogs, HCV NS3 protease inhibitors, HCV NS4 protease inhibitors, HCV NS3/NS4 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs for treating HCV, or mixtures thereof. Specific examples are more fully described below.

Further, in certain embodiments, when used to treat or prevent HBV, a compound of the present disclosure may be administered with one or more additional therapeutic agent (s) selected from the group consisting of HBV DNA polymerase inhibitors, toll-like receptor 7 modulators, toll-like receptor 8 modulators, Toll-like receptor 7 and 8 modulators, Toll-like receptor 3 modulators, interferon alpha ligands, HBsAg inhibitors, compounds targeting HbcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, recombinant thymosin alpha-1 and hepatitis B virus replication inhibitors, and combinations thereof. Specific examples are more fully described below.

In certain embodiments, the present disclosure provides a method for ameliorating a symptom associated with an HBV infection or HCV infection, wherein the method comprises administering to an individual (e.g. a human) infected with hepatitis B virus or hepatitis C virus a therapeutically effective amount of a compound of the present disclosure, or a pharmaceutically acceptable salt thereof, wherein the therapeutically effective amount is sufficient to ameliorate a symptom associated with the HBV infection or HCV infection. Such symptoms include the presence of HBV virus particles (or HCV virus particles) in the blood, liver inflammation, jaundice, muscle aches, weakness and tiredness.

In certain embodiments, the present disclosure provides a method for reducing the rate of progression of a hepatitis B viral infection or a hepatitis C virus infection, in an individual (e.g. a human), wherein the method comprises administering to an individual (e.g. a human) infected with hepatitis B virus or hepatitis C virus a therapeutically effective amount of a compound of the present disclosure, or a pharmaceutically acceptable salt thereof, wherein the therapeutically effective amount is sufficient to reduce the rate of progression of the hepatitis B viral infection or hepatitis C viral infection. The rate of progression of the infection can be followed by measuring the amount of HBV virus particles or HCV virus particles in the blood.

In certain embodiments, the present disclosure provides a method for reducing the viral load associated with HBV infection or HCV infection, wherein the method comprises administering to an individual (e.g. a human) infected with HBV or HCV a therapeutically effective amount of a compound of the present disclosure, or a pharmaceutically acceptable salt thereof, wherein the therapeutically effective amount is sufficient to reduce the HBV viral load or the HCV viral load in the individual.

In certain embodiments, the present disclosure provides a method of inducing or boosting an immune response against hepatitis B virus or hepatitis C virus in an individual (e.g. a human), wherein the method comprises administering a therapeutically effective amount of a compound of the present disclosure, or a pharmaceutically acceptable salt thereof, to the individual, wherein a new immune response against hepatitis B virus or hepatitis C virus is induced in the individual, or a preexisting immune response against hepatitis B virus or hepatitis C virus is boosted in the individual. Seroconversion with respect to HBV or HCV can be induced in the individual. Examples of immune responses include production of antibodies, such as IgG antibody molecules, and/or production of cytokine molecules that modulate the activity of one or more components of the human immune system.

In certain embodiments, an immune response can be induced against one or more antigens of HBV or HCV. For example, an immune response can be induced against the HBV surface antigen (HBsAg), or against the small form of the HBV surface antigen (small S antigen), or against the medium form of the HBV surface antigen (medium S antigen), or against a combination thereof. Again by way of example, an immune response can be induced against the HBV surface antigen (HBsAg) and also against other HBV-derived antigens, such as the core polymerase or x-protein.

Induction of an immune response against HCV or HBV can be assessed using any technique that is known by those of skill in the art for determining whether an immune response has occurred. Suitable methods of detecting an immune response for the present disclosure include, among others, detecting a decrease in viral load in a individual's serum, such as by measuring the amount of HBV DNA or HCV DNA in a subject's blood using a PCR assay, and/or by measuring the amount of anti-HBV antibodies, or anti-HCV antibodies, in the subject's blood using a method such as an ELISA.

In certain embodiments, a compound of a compound of the present disclosure (e.g. a compound of Formula (I)), or a pharmaceutically acceptable salt thereof, for use in treating or preventing a HBV infection is provided. In certain embodiments, a compound of the present disclosure (e.g. a compound of Formula (I)), or a pharmaceutically acceptable salt thereof, for use in treating or preventing a HCV infection is provided. In certain embodiments, a compound of the present disclosure (e.g. a compound of Formula (I)), or a pharmaceutically acceptable salt thereof, for the manufacture of a medicament for treating or preventing a HBV infection is provided. In certain embodiments, a compound of the present disclosure (e.g. a compound of Formula (I)), or a pharmaceutically acceptable salt thereof, for the manufacture of a medicament for treating or preventing a HCV infection is provided.

In certain embodiments, the present disclosure also provides methods for treating a Retroviridae viral infection (e.g., an HIV viral infection) in an individual (e.g., a human), comprising administering a compound of the present disclosure, or a pharmaceutically acceptable salt thereof, to the individual.

In certain embodiments, the present disclosure also provides methods for treating a HIV infection (e.g a HIV-1 infection), comprising administering to an individual (e.g. a human) infected with HIV virus a therapeutically effective amount of a compound of the present disclosure, or a pharmaceutically acceptable salt thereof. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS.

In certain embodiments, a method for treating or preventing an HIV viral infection in an individual (e.g., a human), comprising administering a compound of the present disclosure, or a pharmaceutically acceptable salt thereof, to the individual is provided.

In certain embodiments, a method for inhibiting the replication of the HIV virus, treating AIDS or delaying the onset of AIDS in an individual (e.g., a human), comprising administering a compound of the present disclosure, or a pharmaceutically acceptable salt thereof, to the individual is provided.

In certain embodiments, a method for preventing an HIV infection in an individual (e.g., a human), comprising administering a compound of the present disclosure, or a pharmaceutically acceptable salt thereof, to the individual is provided. In certain embodiments, the individual is at risk of contracting the HIV virus, such as an individual who has one or more risk factors known to be associated with of contracting the HIV virus.

In certain embodiments, a method for treating an HIV infection in an individual (e.g., a human), comprising administering a compound of the present disclosure, or a pharmaceutically acceptable salt thereof, to the individual is provided.

In certain embodiments, a method for treating an HIV infection in an individual (e.g., a human), comprising administering to the individual in need thereof a therapeutically effective amount of a compound of the present disclosure, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof is provided.

In certain embodiments, a compound of the present invention is administered to a patient where active HIV gene expression has been suppressed by administration of antiretroviral therapy (including combination antiretroviral therapy" or "cART").

In certain embodiments, a method of reducing the latent HIV reservoir in a human infected with HIV is provided, the method comprising administering to the human a pharmaceutically effective amount of a compound of the present disclosure. In certain embodiments, the method further comprises administering one or more anti-HIV agents. In certain embodiments, the method further comprises administering antiretroviral therapy (including combination antiretroviral therapy" or "cART"). In certain embodiments, active HIV gene expression in the human has been suppressed by administration of antiretroviral therapy (including combination antiretroviral therapy" or "cART").

In certain embodiments, a compound of the present disclosure, or a pharmaceutically acceptable salt thereof for use in medical therapy of an HIV viral infection (e.g. HIV-1 or the replication of the HIV virus (e.g. HIV-1) or AIDS or delaying the onset of AIDS in an individual (e.g., a human)) is provided.

In certain embodiments, a compound of the present disclosure, or a pharmaceutically acceptable salt thereof for use in the manufacture of a medicament for treating an HIV viral infection or the replication of the HIV virus or AIDS or delaying the onset of AIDS in an individual (e.g., a human). One embodiment provides a compound of the present disclosure, or a pharmaceutically acceptable salt thereof, for use in the prophylactic or therapeutic treatment of an HIV infection or AIDS or for use in the therapeutic treatment or delaying the onset of AIDS is provided.

In certain embodiments, the use of a compound of the present disclosure (e.g. a compound of Formula (I)), or a pharmaceutically acceptable salt thereof, for the manufacture of a medicament for an HIV virus infection in an individual (e.g., a human) is provided. In certain embodiments, a compound of the present disclosure (e.g. a compound of Formula (I)), or a pharmaceutically acceptable salt thereof, for use in the prophylactic or therapeutic treatment of an HIV virus infection is provided.

In certain embodiments, in the methods of use, the administration is to an individual (e.g., a human) in need of the treatment. In certain embodiments, in the methods of use, the administration is to an individual (e.g., a human) who is at risk of developing AIDS.

Provided herein is a compound of the present disclosure (e.g. a compound of Formula (I)), or a pharmaceutically acceptable salt thereof, for use in therapy. In one embodiment, the compound of the present disclosure, or a pharmaceutically acceptable salt thereof, is for use in a method of treating an HIV viral infection or the replication of the HIV virus or AIDS or delaying the onset of AIDS in an individual (e.g., a human).

Also provided herein is a compound of the present disclosure (e.g. a compound of Formula (I)), or a pharmaceutically acceptable salt thereof, for use in a method of treating or preventing HIV in an individual in need thereof. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS.

Also provided herein is a compound of the present disclosure (e.g. a compound of Formula (I)), or a pharmaceutically acceptable salt thereof, for use in the therapeutic treatment or delaying the onset of AIDS.

Also provided herein is a compound of the present disclosure (e.g. a compound of Formula (I)), or a pharmaceutically acceptable salt thereof, for use in the prophylactic or therapeutic treatment of an HIV infection.

In certain embodiments, the HIV infection is an HIV-1 infection.

Additionally, the compounds of this disclosure are useful in the treatment of cancer or tumors (including dysplasias, such as uterine dysplasia). These includes hematological malignancies, oral carcinomas (for example of the lip, tongue or pharynx), digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In summary, the compounds of this disclosure are employed to treat any neoplasm, including not only hematologic malignancies but also solid tumors of all kinds. In certain embodiments, the compounds are useful for treating a form of cancer selected from ovarian cancer, breast cancer, head and neck cancer, renal cancer, bladder cancer, hepatocellular cancer, and colorectal cancer.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be subdivided into Hodgkin's Disease and Non-Hodgkin's lymphoma (NHL). The later group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

In certain embodiments, the compounds of the present disclosure are useful in the treatment of B-cell lymphoma, lymphoplasmacytoid lymphoma, fallopian tube cancer, head and neck cancer, ovarian cancer, and peritoneal cancer.

In certain embodiments, the compounds of the present disclosure are useful in the treatment of hepatocellular carcinoma, gastric cancer, and/or colorectal cancer. In certain embodiments, the compounds of the present disclosure are useful in the treatment of prostate cancer, breast cancer, and/or ovarian cancer. In certain embodiments, the compounds of the present disclosure are useful in the treatment of recurrent or metastatic squamous cell carcinoma.

In certain embodiments, a method of treating a hyperproliferative disease, comprising administering to an individual (e.g. a human) in need thereof a therapeutically effective amount of a compound of the present disclosure, or a pharmaceutically acceptable salt thereof, is provided. In certain embodiments, the hyperproliferative disease is cancer. In certain embodiments, the cancer is a solid tumor. In certain embodiments, the cancer is selected from ovarian cancer, breast cancer, head and neck cancer, renal cancer, bladder cancer, hepatocellular cancer, and colorectal cancer. In certain embodiments, the cancer is a lymphoma. In certain embodiments, the cancer is Hodgkin's lymphoma. In certain embodiments, the cancer is non-Hodgkin's lymphoma. In certain embodiments, the cancer is B-cell lymphoma. In certain embodiments, the cancer is selected from B-cell lymphoma; fallopian tube cancer, head and neck cancer, ovarian cancer and peritoneal cancer. In certain embodiments, the method further comprises administering one or more additional therapeutic agents as more fully described herein.

In certain embodiments, the cancer is prostate cancer, breast cancer, ovarian cancer, hepatocellular carcinoma, gastric cancer, colorectal cancer and/or recurrent or metastatic squamous cell carcinoma. In certain embodiments, the cancer is prostate cancer, breast cancer, and/or ovarian cancer. In certain embodiments, the cancer is hepatocellular carcinoma, gastric cancer, and/or colorectal cancer. In certain embodiments, the cancer is recurrent or metastatic squamous cell carcinoma.

V. ADMINISTRATION

In some embodiments, in the methods of use, the administration is to an individual (e.g., a human) in need of the treatment.

Additional examples of diseases, disorders, or conditions include psoriasis, systemic lupus erythematosus and allergic rhinitis In one embodiment, the compound of the present disclosure, or a pharmaceutically acceptable salt thereof, is for use in a method of treating a hyperproliferative disease (e.g. cancer) in an individual (e.g., a human).

Also provided herein is the use of a compound of the present disclosure (e.g. a compound of Formula (I)) or a pharmaceutically acceptable salt thereof for the manufacture of a medicament for treating a hyperproliferative disease (e.g. cancer) is provided.

VI. ADMINISTRATION

One or more of the compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure, such as a compound of Formula (I), may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In certain embodiments, the compound is administered once daily.

In certain embodiments, methods for treating or preventing a disease or condition in a human are provided, comprising administering to the human a therapeutically effective amount of a compound of the present disclosure, or a pharmaceutically acceptable salt thereof, in combination with a therapeutically effective amount of one or more (e.g., one, two, three, four, one or two, one to three, or one to four) additional therapeutic agents. As modulators of TLR-8 may be used in the treatment of various diseases or conditions, the particular identity of the additional therapeutic agents will depend on the particular disease or condition being treated.

The compound of Formula (J), (I), (II), (IIa), (IIb), (III), (IIIa), (IIIb), (IV), (IVa), (IVb), (IVc), or (IVd) can be administered by any useful route and means, such as by oral or parenteral (e.g., intravenous) administration. Therapeutically effective amounts of the compound of Formula (J), (I), (II), (IIa), (IIb), (III), (IIIa), (IIIb), (IV), (IVa), (IVb), (IVc), or (IVd) are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 30 µg to about 300 µg per day.

A compound of the present disclosure (e.g., any compound of Formula (I)) may be combined with one or more additional therapeutic agents in any dosage amount of the compound of the present disclosure (e.g., from 1 mg to 1000 mg of compound). Therapeutically effective amounts of the compound of Formula (J), (I), (II), (IIa), (IIb), (III), (IIIa), (IIIb), (IV), (IVa), (IVb), (IVc), or (IVd), are from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of Formula (J), (I), (II), (IIa), (IIb), (III), (IIIa), (IIIb), (IV), (IVa), (IVb), (IVc), or (IVd) are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of Formula (J), (I), (II), (IIa), (IIb), (III), (IIIa), (IIIb), (IV), (IVa), (IVb), (IVc), or (IVd) are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month.

The frequency of dosage of the compound of Formula (J), (I), (II), (IIa), (IIb), (III), (IIIa), (IIIb), (IV), (IVa), (IVb), (IVc), or (IVd) will be determined by the needs of the individual patient and can be, for example, once per day or twice, or more times, per day. Administration of the compound continues for as long as necessary to treat the HBV or HCV infection. For example, Compound I can be administered to a human being infected with HBV or HCV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of Formula (J), (I), (II), (IIa), (IIb), (III), (IIIa), (IIIb), (IV), (IVa), (IVb), (IVc), or (IVd), followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In certain embodiments, when a compound of the present disclosure is combined with one or more additional therapeutic agents as described herein, the components of the composition are administered as a simultaneous or sequential regimen. When administered sequentially, the combination may be administered in two or more administrations.

In certain embodiments, a compound of the present disclosure is combined with one or more additional therapeutic agents in a unitary dosage form for simultaneous administration to a patient, for example as a solid dosage form for oral administration.

In certain embodiments, a compound of the present disclosure is administered with one or more additional therapeutic agents. Co-administration of a compound of the present disclosure with one or more additional therapeutic agents generally refers to simultaneous or sequential administration of a compound of the present disclosure and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

VI. COMBINATION THERAPY FOR HBV

In certain embodiments, a method for treating or preventing an HBV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, four, one or two, one to three or one to four) additional therapeutic agents. In one embodiment, a method for treating an HBV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, four, one or two, one to three or one to four) additional therapeutic agents.

In certain embodiments, the present disclosure provides a method for treating an HBV infection, comprising administering to a patient in need thereof a therapeutically effective amount of a compound of the present disclosure, or a pharmaceutically acceptable salt thereof, in combination with a therapeutically effective amount of one or more additional therapeutic agents which are suitable for treating an HBV infection. In certain embodiments, one or more additional therapeutic agents includes, for example, one, two, three, four, one or two, one to three or one to four additional therapeutic agents.

In the above embodiments, the additional therapeutic agent may be an anti-HBV agent. For example, in some embodiments, the additional therapeutic agent is selected from the group consisting of HBV combination drugs, HBV DNA polymerase inhibitors, immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), interferon alpha receptor ligands, hyaluronidase inhibitors, recombinant IL-7, hepatitis B surface antigen (HBsAg) inhibitors, compounds targeting hepatitis B core antigen (HbcAg), cyclophilin inhibitors, HBV therapeutic vaccines, HBV prophylactic vaccines, HBV viral entry inhibitors, NTCP (Na+-taurocholate cotransporting polypeptide) inhibitors, antisense oligonucleotide targeting viral mRNA, short interfering RNAs (siRNA), miRNA gene therapy agents, endonuclease modulators, inhibitors of ribonucleotide reductase, hepatitis B virus E antigen inhibitors, recombinant scavenger receptor A (SRA) proteins, Src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), Hepatitis B virus replication inhibitors, compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), and other drugs for treating HBV, and combinations thereof. In some embodiments, the additional therapeutic agent is further selected from hepatitis B surface antigen (HBsAg) secretion or assembly inhibitors, TCR-like antibodies, IDO inhibitors, cccDNA epigenetic modifiers, IAPs inhibitors, SMAC mimetics, and compounds such as those disclosed in US20100015178 (Incyte), In certain embodiments, the additional therapeutic is selected from the group consisting of HBV combination drugs, HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, compounds targeting HbcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, BTK inhibitors, and hepatitis B virus replication inhibitors, and combinations thereof. In certain embodiments, the additional therapeutic is selected from hepatitis B surface antigen (HBsAg) secretion or assembly inhibitors and IDO inhibitors.

In certain embodiments a compound of the present disclosure (e.g a compound of Formula (I)) is formulated as a tablet, which may optionally contain one or more other compounds useful for treating HBV. In certain embodiments, the tablet can contain another active ingredient for treating HBV, such as HBV DNA polymerase inhibitors, immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), modulators of tlr7, modulators of tlr8, modulators of tlr7 and tlr8, interferon alpha receptor ligands, hyaluronidase inhibitors, hepatitis B surface antigen (HBsAg) inhibitors, compounds targeting hepatitis B core antigen (HbcAg), cyclophilin inhibitors, HBV viral entry inhibitors, NTCP (Na+-taurocholate cotransporting polypeptide) inhibitors, endonuclease modulators, inhibitors of ribonucleotide reductase, hepatitis B virus E antigen inhibitors, Src kinase inhibitors, HBx inhibitors, cccDNA inhibitors, CCR2 chemokine antagonists, thymosin agonists, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, BTK inhibitors, modulators of TIGIT, modulators of CD47, modulators of SIRP alpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, and Hepatitis B virus replication inhibitors, and combinations thereof. In certain embodiments, the tablet can contain another active ingredient for treating HBV, such as hepatitis B surface antigen (HBsAg) secretion or assembly inhibitors, cccDNA epigenetic modifiers, IAPs inhibitors, SMAC mimetics, and IDO inhibitors.

In certain embodiments, such tablets are suitable for once daily dosing.

In certain embodiments, the additional therapeutic agent is selected from one or more of.

(1) Combination drugs selected from the group consisting of tenofovir disoproxil fumarate+emtricitabine (TRUVADA®); adefovir+clevudine and GBV-015, as well as combination drugs selected from ABX-203+lamivudine+PEG-IFNalpha, ABX-203+adefovir+PEG-IFNalpha, and INO-9112+RG7944 (INO-1800);

(2) HBV DNA polymerase inhibitors selected from the group consisting of besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009 and metacavir, as well as HBV DNA polymerase inhibitors selected from AR-II-04-26 and HS-10234;

(3) Immunomodulators selected from the group consisting of rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, polymer polyethyleneimine (PEI), Gepon, VGV-1, MOR-22, BMS-936559 and IR-103, as well as immunomodulators selected from INO-9112, polymer polyethyleneimine (PEI), Gepon, VGV-1, MOR-22, BMS-936559, RO-7011785, RO-6871765 and IR-103;

(4) Toll-like receptor 7 modulators selected from the group consisting of GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795;

(5) Toll-like receptor 8 modulators selected from the group consisting of motolimod, resiquimod, 3M-051, 3M-052, MCT-465, IMO-4200, VTX-763, VTX-1463;

(6) Toll-like receptor 3 modulators selected from the group consisting of rintatolimod, poly-ICLC, MCT-465, MCT-475, Riboxxon, Riboxxim and ND-1.1;

(7) Interferon alpha receptor ligands selected from the group consisting of interferon alpha-2b (Intron A®), pegylated interferon alpha-2a (Pegasys®), interferon alpha 1b (Hapgen®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (Inferon), Multiferon®, interferon alfa-n1 (Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, Pegi-Hep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa);

(8) Hyaluronidase inhibitors selected from the group consisting of astodrimer;

(9) Modulators of IL-10;

(10) HBsAg inhibitors selected from the group consisting of HBF-0259, PBHBV-001, PBHBV-2-15, PBHBV-2-1, REP 9AC, REP-9C and REP 9AC', as well as HBsAg inhibitors selected from REP-9, REP-2139, REP-2139-Ca, REP-2165, REP-2055, REP-2163, REP-2165, REP-2053, REP-2031 and REP-006 and REP-9AC'

(11) Toll like receptor 9 modulators selected from CYT003, as well as Toll like receptor 9 modulators selected from CYT-003, IMO-2055, IMO-2125, IMO-3100, IMO-8400, IMO-9200, agatolimod, DIMS-9054, DV-1179, AZD-1419, MGN-1703, and CYT-003-QbG10;

(12) Cyclophilin inhibitors selected from the group consisting of OCB-030, SCY-635 and NVP-018;

(13) HBV Prophylactic vaccines selected from the group consisting of Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (Hansenual polymorpha yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine;

(14) HBV Therapeutic vaccines selected from the group consisting of HBsAG-HBIG complex, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, TG-1050, NU-500, HBVax, im/TriGrid/antigen vaccine, Mega-CD40L-adjuvanted vaccine, HepB-v, NO-1800, recombinant VLP-based therapeutic vaccine (HBV infection, VLP Biotech), AdTG-17909, AdTG-17910 AdTG-18202, ChronVac-B, and Lm HBV, as well as HBV Therapeutic vaccines selected from FP-02.2 and RG7944 (INO-1800);

(15) HBV viral entry inhibitor selected from the group consisting of Myrcludex B;

(16) Antisense oligonucleotide targeting viral mRNA selected from the group consisting of ISIS-HBVRx;

(17) short interfering RNAs (siRNA) selected from the group consisting of TKM-HBV (TKM-HepB), ALN-HBV, SR-008, ddRNAi and ARC-520;

(18) Endonuclease modulators selected from the group consisting of PGN-514;

(19) Inhibitors of ribonucleotide reductase selected from the group consisting of Trimidox;

(20) Hepatitis B virus E antigen inhibitors selected from the group consisting of wogonin;

(21) HBV antibodies targeting the surface antigens of the hepatitis B virus selected from the group consisting of GC-1102, XTL-17, XTL-19, XTL-001, KN-003 and fully human monoclonal antibody therapy (hepatitis B virus infection, Humabs BioMed), as well as HBV antibodies targeting the surface antigens of the hepatitis B virus selected from IV Hepabulin SN;

(22) HBV antibodies including monoclonal antibodies and polyclonal antibodies selected from the group consisting of Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088);

(23) CCR2 chemokine antagonists selected from the group consisting of propagermanium;

(24) Thymosin agonists selected from the group consisting of Thymalfasin;

(25) Cytokines selected from the group consisting of recombinant IL-7, CYT-107, interleukin-2 (IL-2, Immunex); recombinant human interleukin-2 (Shenzhen Neptunus) and celmoleukin, as well as cytokines selected from IL-15, IL-21, IL-24;

(26) Nucleoprotein inhibitors (HBV core or capsid protein inhibitors) selected from the group consisting of NVR-1221, NVR-3778, BAY 41-4109, morphothiadine mesilate and DVR-23;

(27) Stimulators of retinoic acid-inducible gene 1 selected from the group consisting of SB-9200, SB-40, SB-44, ORI-7246, ORI-9350, ORI-7537, ORI-9020, ORI-9198 and ORI-7170;

(28) Stimulators of NOD2 selected from the group consisting of SB-9200;

(29) Recombinant thymosin alpha-1 selected from the group consisting of NL-004 and PEGylated thymosin alpha 1;

(30) Hepatitis B virus replication inhibitors selected from the group consisting of isothiafludine, IQP-HBV, RM-5038 and Xingantie;

(31) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(32) cccDNA inhibitors selected from the group consisting of BSBI-25;

(33) PD-L1 inhibitors selected from the group consisting of MEDI-0680, RG-7446, durvalumab, KY-1003, KD-033, MSB-0010718C, TSR-042, ALN-PDL, STI-A1014 and BMS-936559;

(34) PD-1 inhibitors selected from the group consisting of nivolumab, pembrolizumab, pidilizumab, BGB-108 and mDX-400;

(35) BTK inhibitors selected from the group consisting of ACP-196, dasatinib, ibrutinib, PRN-1008, SNS-062, ONO-4059, BGB-3111, MSC-2364447, X-022, spebrutinib, TP-4207, HM-71224, KBP-7536, AC-0025;

(36) Other drugs for treating HBV selected from the group consisting of gentiopicrin (gentiopicroside), nitazoxanide, birinapant, NOV-205 (Molixan; BAM-205), Oligotide, Mivotilate, Feron, levamisole, Ka Shu Ning, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, Jiangantai (Ganxikang), picroside, GA5 NM-HBV, DasKloster-0039, hepulantai, IMB-2613, TCM-800B and ZH-2N, as well as other drugs for treating HBV selected from reduced glutathione, and RO-6864018; and

(37) The compounds disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167

(Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), and US20130217880 (Ono pharmaceutical), and the compounds disclosed in US20100015178 (Incyte).

Also included in the list above are:
(38) IDO inhibitors selected from the group consisting of epacadostat (INCB24360), F-001287, resminostat (4SC-201), SN-35837, NLG-919, GDC-0919, and indoximod;
(39) Arginase inhibitors selected from CB-1158, C-201, and resminostat; and
(40) Cytotoxic T-lymphocyte-associated protein 4 (ipi4) inhibitors selected from ipilumimab, belatacept, PSI-001, PRS-010, tremelimumab, and JHL-1155.

In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In a specific embodiment, a compound of the present disclosure, or a pharmaceutically acceptable salt thereof, is combined with an HBV DNA polymerase inhibitor. In another specific embodiment, a compound of the present disclosure, or a pharmaceutically acceptable salt thereof, is combined with an HBV DNA polymerase inhibitor and at least one additional therapeutic agent selected from the group consisting of: immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), interferon alpha receptor ligands, hyaluronidase inhibitors, recombinant IL-7, HBsAg inhibitors, compounds targeting HbcAg, cyclophilin inhibitors, HBV therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), and Hepatitis B virus replication inhibitors. In certain embodiments the at least one additional therapeutic agent is further selected from hepatitis B surface antigen (HBsAg) secretion or assembly inhibitors, TCR-like antibodies, cccDNA epigenetic modifiers, IAPs inhibitors, SMAC mimetics, and IDO inhibitors.

In another specific embodiment, a compound of the present disclosure, or a pharmaceutically acceptable salt thereof, is combined with an HBV DNA polymerase inhibitor and at least one additional therapeutic agent selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In another specific embodiment, a compound of the present disclosure, or a pharmaceutically acceptable salt thereof, is combined with an HBV DNA polymerase inhibitor, one or two additional therapeutic agents selected from the group consisting of: immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors). In certain embodiments one or two additional therapeutic agents is further selected from hepatitis B surface antigen (HBsAg) secretion or assembly inhibitors, TCR-like antibodies, and IDO inhibitors.

In a particular embodiment, a compound of the present disclosure, or a pharmaceutically acceptable salt thereof, is combined with one, two, three, four or more additional therapeutic agents selected from adefovir (Hepsera®), tenofovir disoproxil fumarate+emtricitabine (TRUVADA®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin In a particular embodiment, a compound of the present disclosure, or a pharmaceutically acceptable salt thereof, is combined with entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®)

In a particular embodiment, a compound of the present disclosure, or a pharmaceutically acceptable salt thereof, is combined with entecavir (Baraclude®), adefovir (Hepsera®), tenofovir disoproxil fumarate (Viread®), tenofovir alafenamide hemifumarate, telbivudine (Tyzeka®) or lamivudine (Epivir-HBV®).

In a particular embodiment, a compound of the present disclosure, or a pharmaceutically acceptable salt thereof is combined with a PD-1 inhibitor. In a particular embodiment, a compound of the present disclosure, or a pharmaceutically acceptable salt thereof is combined with a PD-L1 inhibitor. In a particular embodiment, a compound of the present disclosure, or a pharmaceutically acceptable salt thereof is combined with an IDO inhibitor. In a particular embodiment, a compound of the present disclosure, or a pharmaceutically acceptable salt thereof is combined with an IDO inhibitor and a PD-1 inhibitor. In a particular embodiment, a compound of the present disclosure, or a pharmaceutically acceptable salt thereof, is combined with an IDO inhibitor and a PD-L1 inhibitor. In a particular embodiment, a compound of the present disclosure, or a pharmaceutically acceptable salt thereof, is combined with a TLR7 modulator, such as GS-9620.

In a particular embodiment, a compound of the present disclosure, or a pharmaceutically acceptable salt thereof, is combined with a TLR7 modulator and an IDO inhibitor. In a particular embodiment, a compound of the present disclosure, or a pharmaceutically acceptable salt thereof, is combined with a TLR7 modulator such as GS-9620 and an IDO inhibitor such as epacadostat.

In a particular embodiment, a compound of the present disclosure, or a pharmaceutically acceptable salt thereof, is combined with (4-amino-2-butoxy-8-({3-[(pyrrolidin-1-yl)methyl]phenyl}methyl)-7,8-dihydropteridin-6(5H)-one) or a pharmaceutically acceptable salt thereof.

As used herein, GS-9620 (4-amino-2-butoxy-8-({3-[(pyrrolidin-1-yl)methyl]phenyl}methyl)-7,8-dihydropteridin-6 (5H)-one), includes pharmaceutically acceptable salts thereof *J Med. Chem.,* 2013, 56 (18), pp 7324-7333.

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least one additional therapeutic agent selected from the group consisting of immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), interferon alpha receptor ligands, hyaluronidase inhibitors, recombinant IL-7, HBsAg inhibitors, compounds targeting HbcAg, cyclophilin inhibitors, HBV Therapeutic vaccines, HBV prophylactic vaccines, HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), a and Hepatitis B virus replication inhibitors. In certain embodiments, the at least one additional therapeutic agent is further selected from hepatitis B surface antigen (HBsAg) secretion or assembly inhibitors, TCR-like antibodies, IDO inhibitors, cccDNA epigenetic modifiers, IAPs inhibitors, and SMAC mimetics.

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a one additional therapeutic agent selected from the group consisting of peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin.

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least one additional therapeutic agent selected from the group consisting of HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®), one or two additional therapeutic agents selected from the group consisting of: immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors). In certain embodiments, the one or two additional therapeutic agents is further selected from hepatitis B surface antigen (HBsAg) secretion or assembly inhibitors, TCR-like antibodies, and IDO inhibitors.

In certain embodiments, a compound of the present disclosure, or a pharmaceutically acceptable salt thereof, is combined with 5-30 mg tenofovir alafenamide fumarate, tenofovir alafenamide hemifumarate, or tenofovir alafenamide. In certain embodiments, a compound of the present disclosure, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound of the present disclosure, or a pharmaceutically acceptable salt thereof, is combined with 10 mg tenofovir alafenamide fumarate, tenofovir alafenamide hemifumarate, or tenofovir alafenamide. In certain embodiments, a compound of the present disclosure, or a pharmaceutically acceptable salt thereof, is combined with 25 mg tenofovir alafenamide fumarate, tenofovir alafenamide hemifumarate, or tenofovir alafenamide. A compound of the present disclosure (e.g., a compound of Formula (I)) may be combined with the agents provided herein in any dosage amount of the compound (e.g., from 50 mg to 500 mg of compound) the same as if each combination of dosages were specifically and individually listed. A compound of the present disclosure (e.g., a compound of Formula (I)) may be combined with the agents provided herein in any dosage amount of the compound (e.g. from about 1 mg to about 150 mg of compound) the same as if each combination of dosages were specifically and individually listed.

In certain embodiments, a compound of the present disclosure, or a pharmaceutically acceptable salt thereof, is combined with 100-400 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 300 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 250 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 150 mg tenofovir disoproxil fumarate, tenofovir disoproxil hemifumarate, or tenofovir disoproxil. A compound of the present disclosure (e.g., a compound of Formula (I)) may be combined with the agents provided herein in any dosage amount of the compound (e.g., from 50 mg to 500 mg of compound) the same as if each combination of dosages were specifically and individually listed. A compound of the present disclosure (e.g., a compound of Formula (I)) may be combined with the agents provided herein in any dosage amount of the compound (e.g., from about 1 mg to about 150 mg of compound) the same as if each combination of dosages were specifically and individually listed.

Also provided herein is a compound of the present disclosure (e.g., a compound of Formula (I)), or a pharmaceutically acceptable salt thereof, and one or more additional active ingredients for treating HBV, for use in a method of treating or preventing HBV.

Also provided herein is a compound of the present disclosure (e.g., a compound of Formula (I)), or a pharmaceutically acceptable salt thereof, for use in a method of treating or preventing HBV, wherein the compound, or a pharmaceutically acceptable salt thereof is administered simultaneously, separately or sequentially with one or more additional therapeutic agents fort for treating HBV.

VIII. COMBINATION THERAPY FOR HCV

In certain embodiments, a method for treating or preventing an HCV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents. In one embodiment, a method for treating an HCV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HCV infection, comprising administering to a patient in need thereof a therapeutically effective amount of a compound of the present disclosure, or a pharmaceutically acceptable salt thereof, in combination with a therapeutically effective amount of one or more additional therapeutic agents which are suitable for treating an HCV infection.

In the above embodiments, the additional therapeutic agent may be an anti-HCV agent. For example, in some embodiments, the additional therapeutic agent is selected from the group consisting of interferons, ribavirin or its analogs, HCV NS3 protease inhibitors, HCV NS4 protease inhibitors, HCV NS3/NS4 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, and pharmacokinetic enhancers, compounds such as those disclosed in US2010/0310512, US2013/0102525, and WO2013/185093, or combinations thereof.

In certain embodiments a compound of the present disclosure (e.g., a compound of Formula (I)) is formulated as a tablet, which may optionally contain one or more other compounds useful for treating HCV. In certain embodiments, the tablet can contain another active ingredient for treating HCV, such as interferons, ribavirin or its analogs, HCV NS3 protease inhibitors, HCV NS4 protease inhibitors, HCV NS3/NS4 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, and pharmacokinetic enhancers, or combinations thereof.

In certain embodiments, such tablets are suitable for once daily dosing.

In certain embodiments, the additional therapeutic agent is selected from one or more of:

(1) Interferons selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmuneribavirin and ribavirin analogs, e.g., rebetol, copegus, VX-497, and viramidine (taribavirin);

(2) Ribavirin and its analogs selected from the group consisting of ribavirin (Rebetol, Copegus), and taribavirin (Viramidine);

(3) NS5A inhibitors selected from the group consisting of Compound A.1 (described below), Compound A.2 (described below), Compound A.3 (described below), ABT-267, Compound A.4 (described below), JNJ-47910382, daclatasvir (BMS-790052), ABT-267, Samatasvir, MK-8742, MK-8404, EDP-239, IDX-719, PPI-668, GSK-2336805, ACH-3102, A-831, A-689, AZD-2836 (A-831), AZD-7295 (A-689), and BMS-790052;

(4) NS5B polymerase inhibitors selected from the group consisting of sofosbuvir (GS-7977), Compound A.5 (described below), Compound A.6 (described below), ABT-333, Compound A.7 (described below), ABT-072, Compound A.8 (described below), tegobuvir (GS-9190), GS-9669, TMC647055, ABT-333, ABT-072, setrobuvir (ANA-598), IDX-21437, filibuvir (PF-868554), VX-222, IDX-375, IDX-184, IDX-102, BI-207127, valopicitabine (NM-283), PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, BILB-1941, AL-335, AL-516 and ACH-3422;

(5) Protease (NS3, NS3-NS4) inhibitors selected from the group consisting of Compound A.9, Compound A.10, Compound A.11, ABT-450, Compound A.12 (described below), simeprevir (TMC-435), boceprevir (SCH-503034), narlaprevir (SCH-900518), vaniprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061;

(6) Alpha-glucosidase 1 inhibitors selected from the group consisting of celgosivir (MX-3253), Miglitol, and UT-231B;

(7) Hepatoprotectants selected from the group consisting of emericasan (IDN-6556), ME-3738, GS-9450 (LB-84451), silibilin, and MitoQ;

(8) TLR-7 agonists selected from the group consisting of imiquimod, 852A, GS-9524, ANA-773, ANA-975, AZD-8848 (DSP-3025), and SM-360320;
(9) Cyclophillin inhibitors selected from the group consisting of DEBIO-025, SCY-635, and NIM811;
(10) HCV IRES inhibitors selected from the group consisting of MCI-067;
(11) Pharmacokinetic enhancers selected from the group consisting of BAS-100, SPI-452, PF-4194477, TMC-41629, GS-9350, GS-9585, and roxythromycin; and
(12) Other anti-HCV agents selected from the group consisting of thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, VX-497 (merimepodib) NIM811, benzimidazole derivatives, benzo-1,2,4-thiadiazine derivatives, and phenylalanine derivatives;

Compound A.1 is an inhibitor of the HCV NS5A protein and is represented by the following chemical structure:

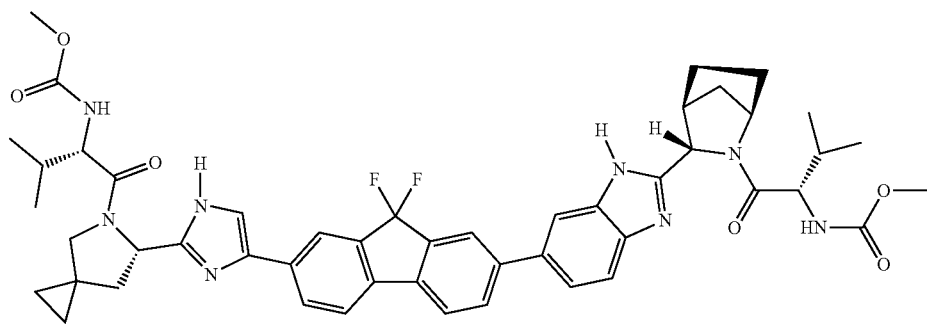

(see, e.g., U.S. Application Publication No. 20100310512 A1).

Compound A.2 is an NS5A inhibitor and is represented by the following chemical structure:

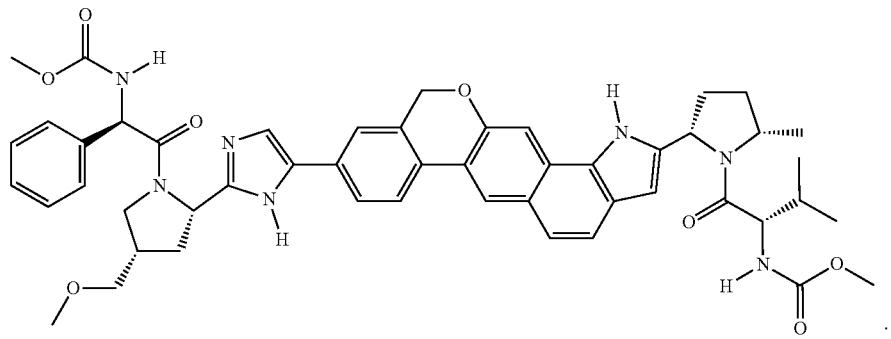 [SMILES: COC[C@H]1C[C@@H](c2ncc(-c3ccc4c(c3)COc3cc5c(ccc6cc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

Compound A.3 is an NS5A inhibitor and is represented by the following chemical structure:

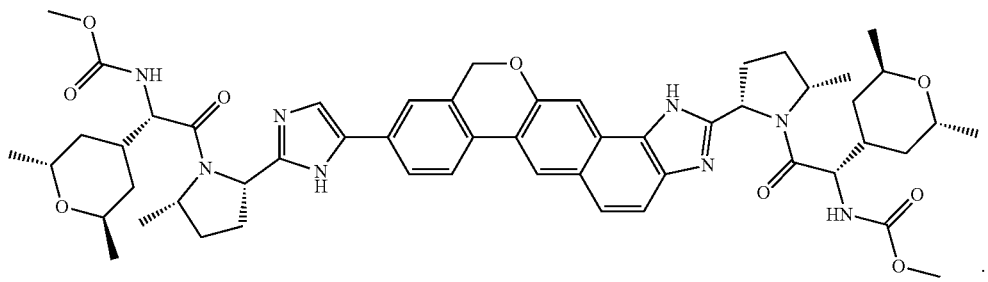

Compound A.4 is an NS5A inhibitor and is represented by the following chemical structure:

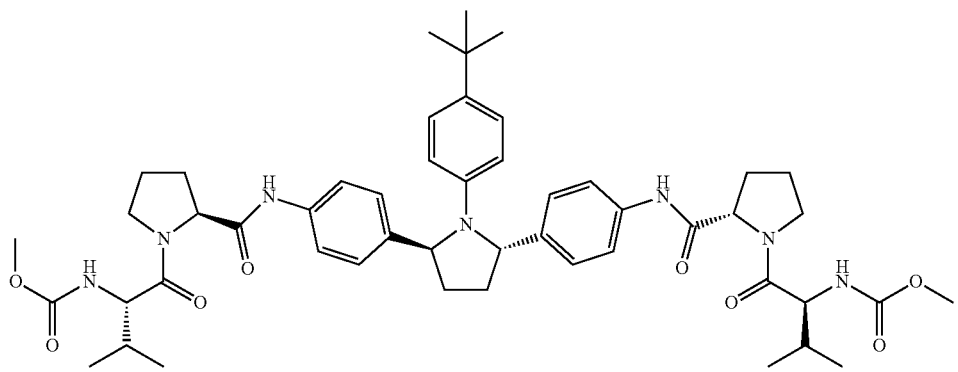 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

(see U.S. Application Publication No. 2013/0102525 and references therein.)

Compound A.5 is an NS5B Thumb II polymerase inhibitor and is represented by the following chemical structure:

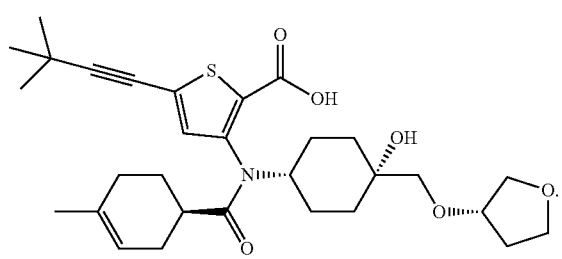 [SMILES: CC1=CC[C@H](C(=O)N(c2cc(C#CC(C)(C)C)sc2C(=O)O)[C@H]2CC[C@](O)(CO[C@H]3CCOC3)CC2)CC1]

Compound A.6 is a nucleotide inhibitor prodrug designed to inhibit replication of viral RNA by the HCV NS5B polymerase, and is represented by the following chemical structure:

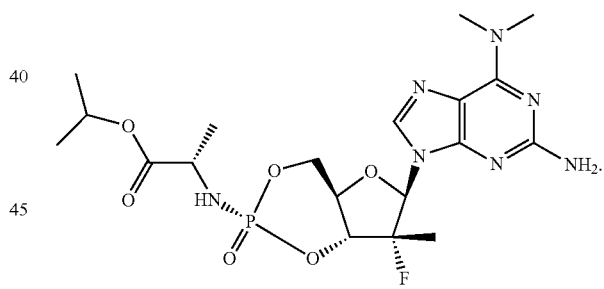

Compound A.7 is an HCV polymerase inhibitor and is represented by the following structure:

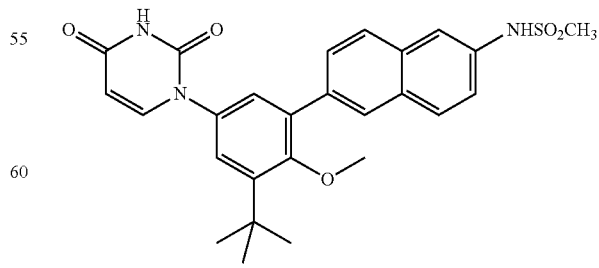

(see U.S. Application Publication No. 2013/0102525 and references therein).

Compound A.8 is an HCV polymerase inhibitor and is represented by the following structure:

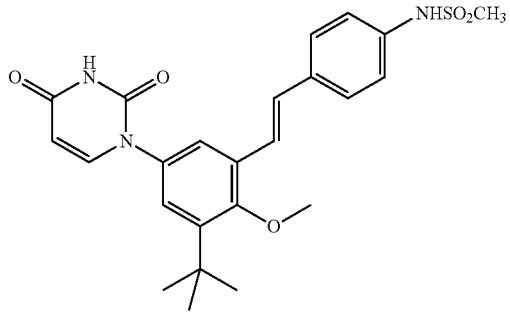

(see U.S. Application Publication No. 2013/0102525 and references therein).

Compound A.9 is an HCV protease inhibitor and is represented by the following chemical structure:

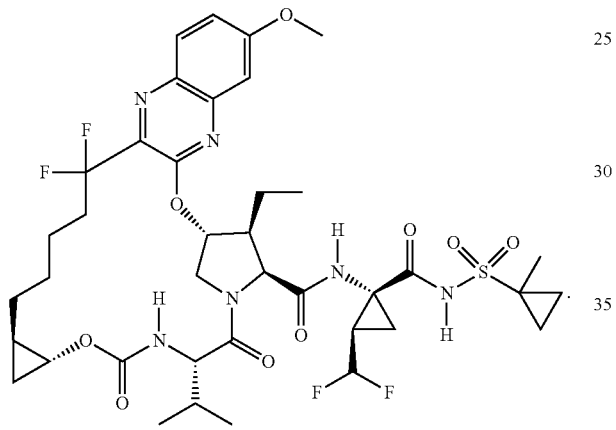

Compound A.10 is an HCV protease inhibitor and is represented by the following chemical structure:

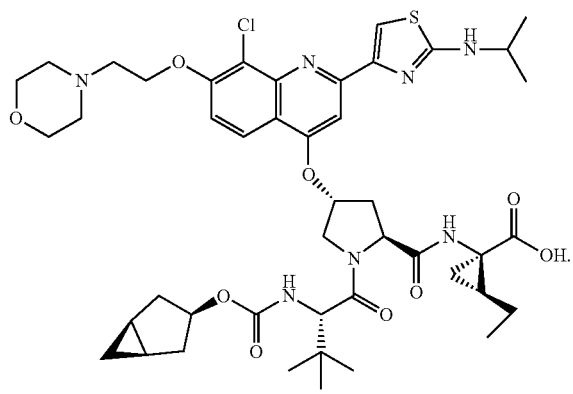

Compound A.11 is an HCV protease inhibitor and is represented by the following chemical structure:

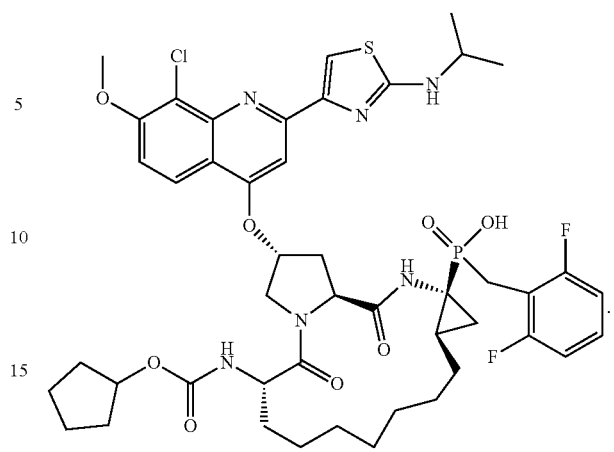

Compound A.12 is an HCV protease inhibitor and is represented by the following chemical structure:

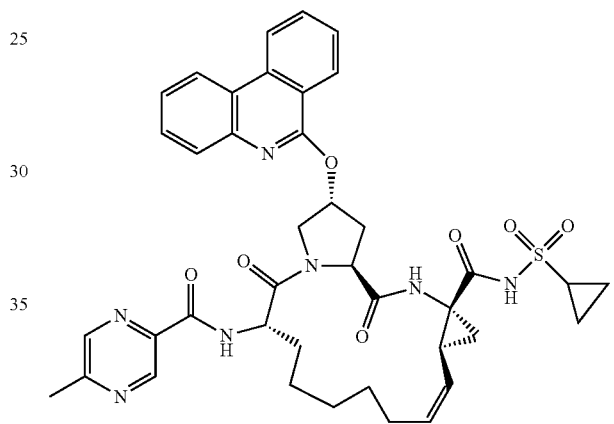

(see U.S. Application Publication No. 2013/0102525 and references therein).

In one embodiment, the additional therapeutic agent used in combination with the pharmaceutical compositions as described herein is a HCV NS3 protease inhibitor. Non-limiting examples include the following:

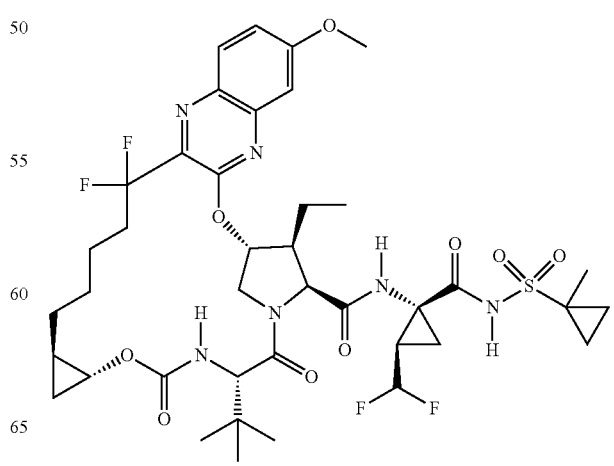

131
-continued
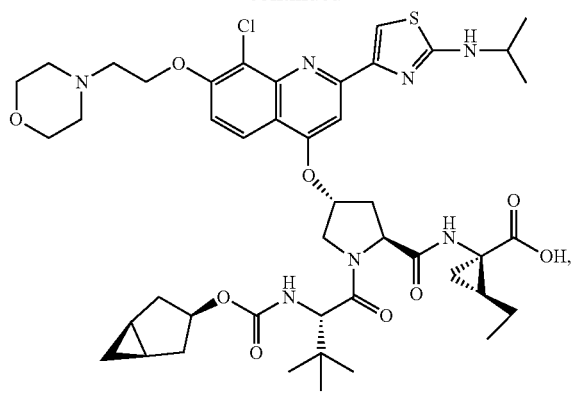
and
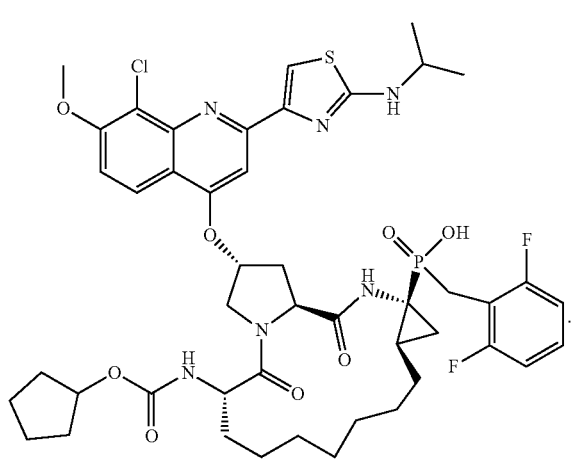 [SMILES: COc1ccc2c(O[C@@H]3C[C@H]4C(=O)N[C@]5(P(=O)(O)Cc6c(F)cccc6F)C[C@H]5CCCCCCC[C@H](NC(=O)OC5CCCC5)C(=O)N4C3)cc(-c3csc(NC(C)C)n3)nc2c1Cl]
132
-continued
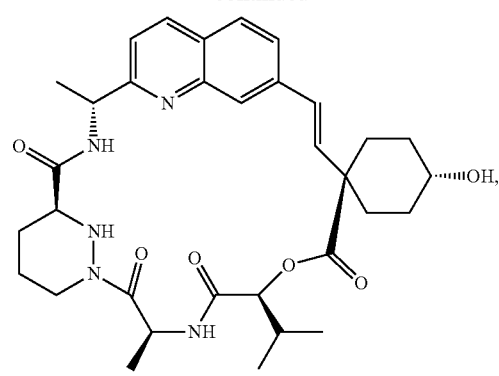
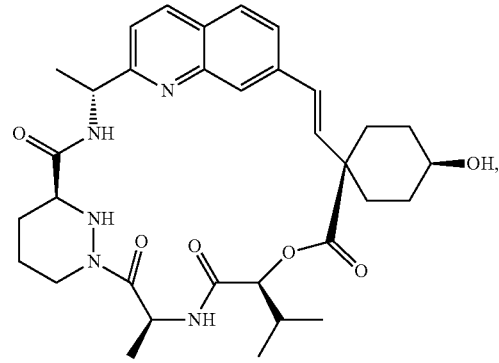
In another embodiment, the additional therapeutic agent used in combination with the pharmaceutical compositions as described herein is a cyclophillin inhibitor, including for example, a cyclophilin inhibitor disclosed in WO2013/185093. Non-limiting examples in addition to those listed above include the following:
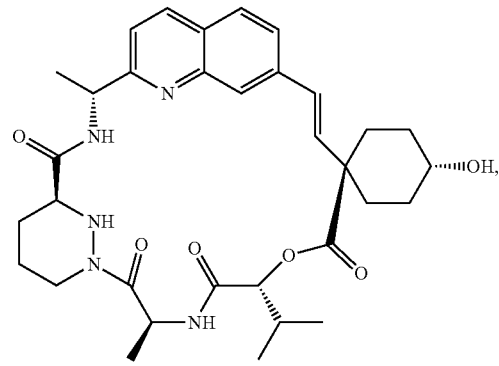
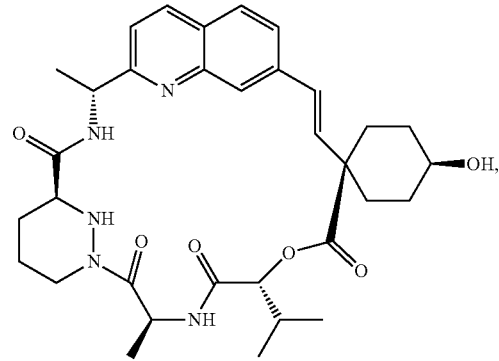

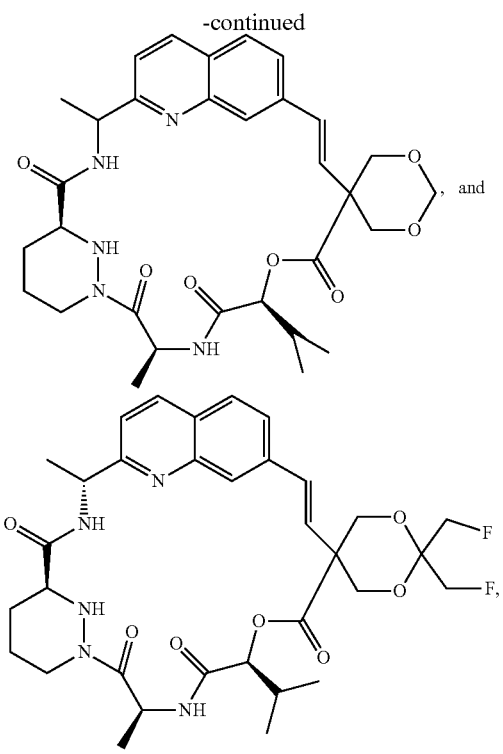

and stereoisomers and mixtures of stereoisomers thereof.

In a specific embodiment, a compound of the present disclosure, or a pharmaceutically acceptable salt thereof, is combined with a HCV NS513 polymerase inhibitor. In a specific embodiment, a compound of the present disclosure, or a pharmaceutically acceptable salt thereof, is combined with a HCV NS5B polymerase inhibitor and a HCV NS5A inhibitor. In another specific embodiment, a compound of the present disclosure, or a pharmaceutically acceptable salt thereof, is combined with a HCV NS5B polymerase inhibitor, a HCV NS3 protease inhibitor and a HCV NS5A inhibitor. In another specific embodiment, a compound of the present disclosure, or a pharmaceutically acceptable salt thereof, is combined with a HCV NS5B polymerase inhibitor, a HCV NS4 protease inhibitor and a HCV NS5A inhibitor. In another specific embodiment, a compound of the present disclosure, or a pharmaceutically acceptable salt thereof, is combined with a HCV NS5B polymerase inhibitor, a HCV NS3/NS4 protease inhibitor and a HCV NS5A inhibitor. In another specific embodiment, a compound of the present disclosure, or a pharmaceutically acceptable salt thereof, is combined with a HCV NS3 protease inhibitor and a HCV NS5A inhibitor. In another specific embodiment, a compound of the present disclosure, or a pharmaceutically acceptable salt thereof, is combined with a HCV NS4 protease inhibitor and a HCV NS5A inhibitor. In another specific embodiment, a compound of the present disclosure, or a pharmaceutically acceptable salt thereof, is combined with a HCV NS3/NS4 protease inhibitor and a HCV NS5A inhibitor. In another specific embodiment, a compound of the present disclosure, or a pharmaceutically acceptable salt thereof, is combined with a HCV NS3 protease inhibitor, a pharmacokinetic enhancer and a HCV NS5A inhibitor. In another specific embodiment, a compound of the present disclosure, or a pharmaceutically acceptable salt thereof, is combined with a HCV NS4 protease inhibitor, a pharmacokinetic enhancer and a HCV NS5A inhibitor. In another specific embodiment, a compound of the present disclosure, or a pharmaceutically acceptable salt thereof, is combined with a HCV NS3/NS4 protease inhibitor, a pharmacokinetic enhancer and a HCV NS5A inhibitor.

In a particular embodiment, a compound of the present disclosure, or a pharmaceutically acceptable salt thereof, is combined with one, two, three, four or more additional therapeutic agents selected from simeprevir, MK-8742, MK-8408, MK-5172, ABT-450, ABT-267, ABT-333, sofosbuvir, sofosbuvir+ledipasvir, sofosbuvir+GS-5816, sofosbuvir+GS-9857+ledipasvir, ABT-450+ABT-267+ritonavir, ABT-450+ABT-267+ribavirin+ritonavir, ABT-450+ABT-267+ribavirin+ABT-333+ritonavir, ABT-530+ABT-493, MK-8742+MK-5172, MK-8408+MK-3682+MK-5172, MK-8742+MK-3682+MK-5172, daclatasvir, interferon, pegylated interferon, ribavirin, samatasvir, MK-3682, ACH-3422, AL-335, IDX-21437, IDX-21459, tegobuvir, setrobuvir, valopicitabine, boceprevir, narlaprevir, vaniprevir, danoprevir, sovaprevir, neceprevir, telaprevir, faldaprevir, asunaprevir, ledipasvir, GS-5816, GS-9857, ACH-3102, ACH-3422+ACH-3102, ACH-3422+sovaprevir+ACH-3102, asunaprevir, asunaprevir+daclatasvir, AL-516, and vedroprevir.

In certain embodiments, a compound of the present disclosure, or a pharmaceutically acceptable salt thereof, is co-administered with simeprevir. In certain embodiments, a compound of the present disclosure, or a pharmaceutically acceptable salt thereof, is co-administered with MK-8742 or MK-8408. In certain embodiments, a compound of the present disclosure, or a pharmaceutically acceptable salt thereof, is co-administered with MK-5172. In certain embodiments, a compound of the present disclosure, or a pharmaceutically acceptable salt thereof, is co-administered with ABT-450, ABT-267, or ABT-333. In certain embodiments, a compound of the present disclosure, or a pharmaceutically acceptable salt thereof, is co-administered with Viekirat (a combination of ABT-450, ABT-267, and ritonavir). In certain embodiments, a compound of the present disclosure, or a pharmaceutically acceptable salt thereof, is co-administered with daclatasvir. In certain embodiments, a compound of the present disclosure, or a pharmaceutically acceptable salt thereof, is co-administered with sofosbuvir. In certain embodiments, a compound of the present disclosure, or a pharmaceutically acceptable salt thereof, is co-administered with Harvoni (sofosbuvir+ledipasvir). In certain embodiments, a compound of the present disclosure, or a pharmaceutically acceptable salt thereof, is co-administered with sofosbuvir and GS-5816. In certain embodiments, a compound of the present disclosure, or a pharmaceutically acceptable salt thereof, is co-administered with sofosbuvir+GS-9857+ledipasvir. In certain embodiments, a compound of the present disclosure, or a pharmaceutically acceptable salt thereof, is co-administered with ABT-450+ABT-267+ribavirin+ritonavir. In certain embodiments, a compound of the present disclosure, or a pharmaceutically acceptable salt thereof, is co-administered with ABT-450+ABT-267+ribavirin+ABT-333+ritonavir. In certain embodiments, a compound of the present disclosure, or a pharmaceutically acceptable salt thereof, is co-administered with ABT-530+ABT-493. In certain embodiments, a compound of the present disclosure, or a pharmaceutically acceptable salt thereof, is co-administered with MK-8408+MK-3682+MK-5172. In certain embodiments, a compound of the present disclosure, or a pharmaceutically acceptable salt thereof, is co-administered with MK-8742+MK-5172. In certain embodiments, a compound of the present disclosure, or a pharmaceutically acceptable salt thereof, is co-administered with MK-3682. In certain embodiments, a compound of the present disclosure, or a pharmaceutically acceptable salt thereof, is co-administered with ACH-3422. In certain embodiments, a compound of the present disclosure, or a pharmaceutically acceptable salt thereof, is co-administered with AL-335. In certain embodiments, a compound of the present disclosure, or a pharmaceutically acceptable salt thereof, is co-administered with ACH-3422+ACH-3102. In certain embodiments, a compound of the present disclosure, or a pharmaceutically acceptable salt thereof, is co-administered with ACH-3422+sovaprevir+ACH-3102. In certain embodiments, a compound of the present disclosure, or a pharmaceutically acceptable salt thereof, is co-administered with GS-5816. In certain embodiments, a compound of the present disclosure, or a pharmaceutically acceptable salt thereof, is co-administered with GS-9857. In certain embodiments, a compound of the present disclosure, or a pharmaceutically acceptable salt thereof, is co-administered with IDX-21459. In certain embodiments, a compound of the present disclosure, or a pharmaceutically acceptable salt thereof, is co-administered with boceprevir. In certain embodiments, a compound of the present disclosure, or a pharmaceutically acceptable salt thereof, is co-administered with ledipasvir. In certain embodiments, a compound of the present disclosure, or a pharmaceutically acceptable salt thereof, is co-administered with AL-516.

In various methods, Compound A.1 is administered in an amount ranging from about 10 mg/day to about 200 mg/day. For example, the amount of Compound A.1 can be about 30 mg/day, about 45 mg/day, about 60 mg/day, about 90 mg/day, about 120 mg/day, about 135 mg/day, about 150 mg/day, about 180 mg/day. In some methods, Compound A.1 is administered at about 90 mg/day. In various methods, Compound A.2 is administered in an amount ranging from about 50 mg/day to about 800 mg/day. For example, the amount of Compound A.2 can be about 100 mg/day, about 200 mg/day, or about 400 mg/day. In some methods, the amount of Compound A.3 is about 10 mg/day to about 200 mg/day. For example, the amount of Compound A.3 can be about 25 mg/day, about 50 mg/day, about 75 mg/day, or about 100 mg/day.

In various methods, sofosbuvir is administered in an amount ranging from about 10 mg/day to about 1000 mg/day. For example, the amount of sofosbuvir can be about 100 mg/day, about 200 mg/day, about 300 mg/day, about 400 mg/day, about 500 mg/day, about 600 mg/day, about 700 mg/day, about 800 mg/day. In some methods, sofosbuvir is administered at about 400 mg/day.

Also provided herein is a compound of the present disclosure (e.g., a compound of Formula (I)), or a pharmaceutically acceptable salt thereof, and one or more additional therapeutic agents for treating HCV, for use in a method of treating or preventing HCV.

Also provided herein is a compound of the present disclosure (e.g., a compound of Formula (I)), or a pharmaceutically acceptable salt thereof, for use in a method of treating or preventing HCV, wherein the compound or a pharmaceutically acceptable salt thereof is administered simultaneously, separately or sequentially with one or more additional therapeutic agents for treating HCV.

IX. COMBINATION THERAPY FOR HIV

In certain embodiments, a method for treating or preventing an HIV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HIV infection, comprising administering to a patient in need thereof a therapeutically effective amount of a compound of the present disclosure, or a pharmaceutically acceptable salt, thereof, in combination with a therapeutically effective amount of one or more additional therapeutic agents which are suitable for treating an HIV infection. In certain embodiments, one or more additional therapeutic agents includes, for example, one, two, three, four, one or two, one to three or one to four additional therapeutic agents.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof. In some embodiments, the additional therapeutic agent is further selected from Vif dimerization antagonists and HIV gene therapy.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of the present disclosure is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

In certain embodiments, the additional therapeutic agent is selected from one or more of (1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, TRIUMEQ® (dolutegravir+abacavir+lamivudine), lamivudine+nevirapine+zidovudine, dolutegravir+rilpivirine, atazanavir sulfate+cobicistat, darunavir+cobicistat, efavirenz+lamivudine+tenofovir disoproxil fumarate, tenofovir alafenamide hemifumarate+emtricitabine+cobicistat+elvitegravir, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), tenofovir+lamivudine and lamivudine+tenofovir disoproxil fumarate, as well as combinations drugs selected from dolutegravir+rilpivirine hydrochloride, atazanavir+cobicistat, tenofovir alafenamide hemifumarate+emtricitabine, tenofovir alafenamide+emtricitabine, tenofovir alafenamide hemifumarate+emtricitabine+rilpivirine, tenofovir alafenamide+emtricitabine+rilpivirine, doravirine+lamivudine+tenofovir disoproxil fumarate, doravirine+lamivudine+tenofovir disoproxil;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir, as well as HIV integrase inhibitors selected from JTK-351;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), TBR-220 (TAK-220), nifeviroc (TD-0232), TD-0680, and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-12, polymer polyethyleneimine (PEI), Gepon, VGV-1, MOR-22, BMS-936559, toll-like receptors modulators (TLR-1, TLR-2, TLR-3, TLR-4, TLR-5, TLR-6, TLR-7, TLR-8, TLR-9, TLR-10, TLR-11, TLR-12 and TLR-13), rintatolimod and IR-103;

(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), Remune, ITV-1, Contre Vir, Ad5-ENVA-48, DCVax-001 (CDX-2401), PEP-6409, Vacc-4x, Vacc-C5, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, Vichrepol, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHIVvac, ADVAX, MYM-V201, MVA-CMDR, ETV-01 and DNA-Ad5 gag/pol/nef/nev (HVTN505), as well as HIV vaccines selected from monomeric gp120 HIV-1 subtype C vaccine (Novartis), HIV-TriMix-mRNA, MVATG-17401, ETV-01, CDX-1401, and rcAd26.MOS1.HIV-Env;
(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8 and VRC07, as well as HIV antibodies such as VRC-07-523;
(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;
(18) HIV nucleocapsid p7 (NCp7) inhibitors selected from the group consisting of azodicarbonamide;
(19) HIV maturation inhibitors selected from the group consisting of BMS-955176 and GSK-2838232;
(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;
(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and

(22) other drugs for treating HIV selected from the group consisting of BanLec, MK-8507, AG-1105, TR-452, MK-8591, REP 9, CYT-107, alisporivir, NOV-205, IND-02, metenkefalin, PGN-007, Acemannan, Gamimune, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-shl-TAR-CCR5RZ, MazF gene therapy, BlockAide, ABX-464, SCY-635, naltrexone and PA-1050040 (PA-040); and other drugs for treating HIV selected from AAV-eCD4-Ig gene therapy, TEV-90110, TEV-90112, TEV-90111, TEV-90113, deferiprone, and HS-10234.

In certain embodiments, the additional therapeutic agent is a compound disclosed in US 2014-0221356 (Gilead Sciences, Inc.) for example (2R,5S,13aR)-N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (2S,5R,13aS)-N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (1S,4R,12aR)-N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, (1R,4S,12aR)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, and (1R,4S,12aR)-N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, US2015-0018298 (Gilead Sciences, Inc.) and US2015-0018359 (Gilead Sciences, Inc.), In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In a specific embodiment, a compound of the present disclosure, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound of the present disclosure, or a pharmaceutically acceptable salt thereof, is combined with an HIV nucleoside or nucleotide inhibitor of reverse transcriptase, and an HIV protease inhibiting compound. In a further embodiment, a compound of the present disclosure, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound of the present disclosure, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound of the present disclosure, or a pharmaceutically acceptable salt thereof, is combined with one or more additional therapeutic agents selected from HIV nucleoside inhibitor of reverse transcriptase, an integrase inhibitor, and a pharmacokinetic enhancer. In another embodiment, a compound of the present disclosure, or a pharmaceutically acceptable salt thereof, is combined with two HIV nucleoside or nucleotide inhibitors of reverse transcriptase.

In a particular embodiment, a compound of the present disclosure, or a pharmaceutically acceptable salt thereof, is combined with one, two, three, four or more additional therapeutic agents selected from Triumeq® (dolutegravir+abacavir+lamivudine), dolutegravir+abacavir sulfate+lamivudine, raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, tenofovir alafenamide and tenofovir alafenamide hemifumarate. In certain embodiments, the one, two, three, four or more additional therapeutic agents are further selected from raltegravir+lamivudine, atazanavir sulfate+cobicistat, atazanavir+cobicistat, darunavir+cobicistat, darunavir+cobicistat, atazanavir sulfate+cobicistat, atazanavir+cobicistat.

In a particular embodiment, a compound of the present disclosure, or a pharmaceutically acceptable salt thereof, is combined with one, two, three, four or more additional therapeutic agents selected from Triumeq® (dolutegravir+abacavir+lamivudine), dolutegravir+abacavir sulfate+lamivudine, raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, (2R,5S,13aR)-N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (2S,5R,13aS)-N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (1S,4R,12aR)-N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, (1R,4S,12aR)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, and (1R,4S,12aR)-N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide abacavir, abacavir sulfate, tenofovir, tenofovir disoproxil, tenofovir disoproxil fumarate, tenofovir alafenamide and tenofovir alafenamide hemifumarate.

In a particular embodiment, a compound of the present disclosure, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound of the present disclosure, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound of the present disclosure, or a pharmaceutically acceptable salt thereof, is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound of the present disclosure, or a pharmaceutically acceptable salt thereof, is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound of the present disclosure, or a pharmaceutically acceptable salt thereof, is combined with 5-30 mg tenofovir alafenamide fumarate, tenofovir alafenamide hemifumarate, or tenofovir alafenamide and 200 mg emtricitabine. In certain embodiments, a compound of the present disclosure, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound of the present disclosure, or a pharmaceutically acceptable salt thereof, is combined with 10 mg tenofovir alafenamide fumarate, tenofovir alafenamide hemifumarate, or tenofovir alafenamide and 200 mg emtricitabine. In certain embodiments, a compound of the present disclosure, or a pharmaceutically acceptable salt thereof, is combined with 25 mg tenofovir alafenamide fumarate, tenofovir alafenamide hemifumarate, or tenofovir alafenamide and 200 mg emtricitabine. A compound of the present disclosure (e.g., a compound of formula (I)) may be combined with the agents provided herein in any dosage amount of the compound (e.g., from 1 mg to 500 mg of compound) the same as if each combination of dosages were specifically and individually listed.

In certain embodiments, a compound of the present disclosure, or a pharmaceutically acceptable salt thereof, is combined with 200-400 mg tenofovir disoproxil fumarate, tenofovir disoproxil hemifumarate, or tenofovir disoproxil and 200 mg emtricitabine. In certain embodiments, a compound of the present disclosure, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound of the present disclosure, or a pharmaceutically acceptable salt thereof, is combined with 300 mg tenofovir disoproxil fumarate, tenofovir disoproxil hemifumarate, or tenofovir disoproxil and 200 mg emtricitabine. A compound of the present disclosure (e.g., a compound of formula (I)) may be combined with the agents provided herein in any dosage amount of the compound (e.g., from 50 mg to 500 mg of compound) the same as if each combination of dosages were specifically and individually listed. A compound of the present disclosure (e.g., a compound of Formula (I)) may be combined with the agents provided herein in any dosage amount of the compound (e.g. from about 1 mg to about 150 mg of compound) the same as if each combination of dosages were specifically and individually listed.

In certain embodiments a compound of the present disclosure, or a pharmaceutically acceptable salt thereof, is combined with (2R,5S,13aR)-N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (2S,5R,13aS)-N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (1S,4R,12aR)-N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, (1R,4S,12aR)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, or (1R,4S,12aR)-N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide.

Also provided herein is a compound the present disclosure (e.g., a compound of Formula (I)), or a pharmaceutically acceptable salt thereof, and one or more additional therapeutic agents for treating HIV, for use in a method of treating or preventing HIV.

Also provided herein is a compound of the present disclosure (e.g., a compound of Formula (I)), or a pharmaceutically acceptable salt thereof, for use in a method of treating or preventing HIV, wherein the compound or a pharmaceutically acceptable salt thereof is administered simultaneously, separately or sequentially with one or more additional therapeutic agents for treating HIV.

In certain embodiments, a method for treating hyperproliferative disorders such as cancer in a human is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents. In one embodiment, a method for treating hyperproliferative disorders such as cancer in a human is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents.

X. COMBINATION THERAPY FOR CANCER

In certain embodiments, the present disclosure provides a method for treating hyperproliferative disorders such as cancer, comprising administering to a patient in need thereof a therapeutically effective amount of a compound of the present disclosure, or a pharmaceutically acceptable salt, thereof, in combination with a therapeutically effective amount of one or more additional therapeutic agents which are suitable for treating hyperproliferative disorders such as cancer.

In the above embodiments, the additional therapeutic agent may be an anti-cancer agent. For example, in some embodiments, the additional therapeutic agent is selected from the group consisting of chemotherapeutic agents, immunotherapeutic agents, radiotherapeutic agents, antineoplastic agents, anti-hormonal agents, anti-angiogenic agents, anti-fibrotic agents, therapeutic antibodies, tyrosine kinase inhibitors, JAK inhibitors, Hedgehog inhibitors, HDAC inhibitors, Discoidin domain receptor (DDR) inhibitors, MMP9 inhibitors, LOXL inhibitors, ASK1 inhibitors, PI3K inhibitors, BTK inhibitors, SYK inhibitors, mTOR inhibitors, AKT inhibitors, Mitogen or Extracellular Regulated Kinase (MEK) inhibitors, blockers of Raf kinases (rafk), CDK inhibitors, JNK inhibitors, MAPK inhibitors, Raf inhibitors, ROCK inhibitors, Tie2 inhibitors, Myo-inositol signaling inhibitors, phospholipase C blockers, anti-CD19 antibodies, anti-CD20 antibodies, anti-MN-14 antibodies, Anti-TRAIL DR4 and DR5 antibodies, anti-CD74 antibodies, cancer vaccines based upon the genetic makeup of an individual patient's tumor, IDH1 inhibitors, BRD4 inhibitors, TPL2 inhibitors; A2B inhibitors; TBK1 inhibitors; IKK inhibitors; BCR inhibitors, agents inhibiting the RAS/RAF/ERK pathway, protein kinase C (PKC) modulators, modulators of growth factor receptors such as epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene, modulators of tyrosine kinases including cSrc, Lck, Fyn, Yes, cAbl, FAK (Focal adhesion kinase) and Bcr-Abl, modulators of PKB family kinases, modulators of TGF beta receptor kinases, inhibitors of Ras oncogene including inhibitors of farnesyltransferase, geranyl-geranyl transferase, and CAAX proteases, anti-sense oligonucleotides, ribozymes, Bcl-2 family protein inhibitors, proteasome inhibitors, Heat shock protein HSP90 inhibitors, combination drugs and immunotherapy, and other drugs for treating hyperproliferative disorders such as cancer, and combinations thereof.

In certain embodiments a compound of the present disclosure is formulated as a tablet, which may optionally contain one or more other compounds useful for treating cancer. In certain embodiments, the tablet can contain another active ingredient for treating cancer, such as chemotherapeutic agents, immunotherapeutic agents, radiotherapeutic agents, anti-neoplastic agents, anti-fibrotic agents, anti-hormonal agents, anti-angiogenic agents, Tyrosine kinase inhibitors, JAK inhibitors, Hedgehog inhibitors, HDAC inhibitors, Discoidin domain receptor (DDR) inhibitors, MMP9 inhibitors, LOXL inhibitors, ASK1 inhibitors, PI3K inhibitors, BTK inhibitors, SYK inhibitors, mTOR inhibitors, AKT inhibitors, Mitogen or Extracellular Regulated Kinase (MEK) inhibitors, blockers of Raf kinases (rafk), CDK inhibitors, JNK inhibitors, MAPK inhibitors, Raf inhibitors, ROCK inhibitors, Tie2 inhibitors, Myoinositol signaling inhibitors, phospholipase C blockers, IDH1 inhibitors, BRD4 inhibitors, TPL2 inhibitors; A2B inhibitors; TBK1 inhibitors; IKK inhibitors; BCR inhibitors, agents inhibiting the RAS/RAF/ERK pathway, protein kinase C (PKC) modulators, modulators of growth factor receptors such as epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene, modulators of tyrosine kinases including cSrc, Lck, Fyn, Yes, cAbl, FAK (Focal adhesion kinase) and Bcr-Abl, modulators of PKB family kinases, modulators of TGF beta receptor kinases, inhibitors of Ras oncogene including inhibitors of farnesyltransferase, geranyl-geranyl transferase, and CAAX proteases, anti-sense oligonucleotides, ribozymes, Bcl-2 family protein inhibitors, proteasome inhibitors, Heat shock protein HSP90 inhibitors, combination drugs and immunotherapy, and other drugs for treating hyperproliferative disorders such as cancer, and combinations thereof.

In certain embodiments, such tablets are suitable for once daily dosing. In certain embodiments, the additional therapeutic agent is selected from one or more of:

(1) Chemotherapeutic agents selected from the group consisting of: anti-metabolites/anti-cancer agents, such as pyrimidine analogs (floxuridine, capecitabine, and cytarabine); purine analogs, folate antagonists and related inhibitors, antiproliferative/antimitotic agents including natural products such as *vinca* alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin, trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus, sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; cell cycle inhibitors and differentiation inducers (tretinoin); inhibitors, topoisomerase inhibitors (doxorubicin (adriamycin), daunorubicin, dactinomycin, eniposide, epirubicin, idarubicin, irinotecan and mitoxantrone, topotecan, irinotecan), corticosteroids (cortisone, dexamethasone, hydrocortisone, methylpednisolone, prednisone, and prednisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators, chromatin, alkylating agents such as thiotepa and cyclophosphamide (Cytoxan, Endoxan, Endoxana, Cyclostin), alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994);

dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, PEGylated liposomal doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, paclitaxel (Taxol) and docetaxel (Taxotere); chlorambucil; gemcitabine (Gemzar); 6-thioguanine; mercaptopurine; methotrexate; platinum analogs such as cisplatin and carboplatin; platinum; ifosfamide; mitroxantrone; vancristine; vinorelbine (Navelbine); novantrone; teniposide; edatrexate; daunomycin; aminopterin; xeoloda; ibandronate; CPT-11; topoisomerase inhibitor RFS 2000; difluoromethylomithine (DMFO); retinoids such as retinoic acid; capecitabine and FOLFIRI (fluorouracil, leucovorin, and irinotecan);

(2) Anti-hormonal agents selected from the group consisting of: anti-estrogens and selective estrogen receptor modulators (SERMs), including, for example, tamoxifen (including Nolvadex), raloxifene, droloxifene, 4-hydroxytamoxifen, trioxifene, keoxifene, LY117018, onapristone, and toremifene; inhibitors of the enzyme aromatase, which regulates estrogen production in the adrenal glands, such as, for example, 4(5)-imidazoles, aminoglutethimide, megestrol acetate, exemestane, formestane, fadrozole, vorozole, letrozole and anastrozole; and anti-androgens such as flutamide, nilutamide, bicalutamide, leuprolide, and goserelin;

(3) Anti-angiogenic agents selected from the group consisting of: retinoid acid and derivatives thereof, 2-methoxyestradiol, ANGIOSTATIN, ENDOSTATIN, suramin, squalamine, tissue inhibitors of metalloproteinase-1, tissue inhibitors of metalloproteinase-2, plasminogen activator inhibitor-1, plasminogen activator inhibitor-2, cartilage-derived inhibitors, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, beta-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94, antibodies, preferably monoclonal antibodies against these angiogenic growth factors: beta-FGF, alpha-FGF, FGF-5, VEGF isoforms, VEGF-C, HGF/SF, Ang-1/Ang-2 and the compounds disclosed in Ferrara N. and Alitalo, K. "Clinical application of angiogenic growth factors and their inhibitors" (1999) Nature Medicine 5:1359-1364;

(4) Anti-fibrotic agents selected from the group consisting of: beta-aminopropionitrile (BAPN), primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone, copper chelating agents, indirect inhibitors such as compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate, the compounds disclosed in U.S. Pat. Nos. 4,965,288, 4,997,854, 4,943,593, 5,021,456; 5,5059,714; 5,120,764; 5,182,297; 5,252,608 and U.S. Patent Application No. 2004/0248871;

(5) Therapeutic antibodies selected from the group consisting of: abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, alemtuzumab, veltuzumab, apolizumab, bevacizumab, epratuzumab, tositumomab, galiximab, ibritumomab, lumiliximab, milatuzumab, obinutuzumab, ofatumumab, CC49 and 3F8, wherein the antibody may be further labeled or combined with a radioisotope particle, such as indium In 111, yttrium Y 90, iodine I-131;

(6); JAK inhibitors selected from the group consisting of: ruxolitinib, fedratinib, tofacitinib, baricitinib, lestaurtinib, pacritinib, momelotinib, XL019, AZD1480, INCB039110, LY2784544, BMS911543, and NS018;

(7) Hedgehog inhibitors selected from the group consisting of: saridegib;

(8) Histone deacetylase (HDAC) inhibitors selected from the group consisting of: pracinostat, romidepsin, vorinostat and panobinostat;

(9) Tyrosine kinase inhibitors selected from the group consisting of: lestaurtinib, gefitinib, erlotinib and sunitinib;

(10) Discoidin domain receptor (DDR) inhibitors selected from the group consisting of: the inhibitors disclosed in US2009/0142345, US2011/0287011, WO2013/027802, WO2013/034933, and U.S. Provisional Application No. 61/705,044;

(11) MMP9 inhibitors selected from the group consisting of: marimastat (BB-2516), cipemastat (Ro 32-3555), and the inhibitors described in WO2012/027721;

(12) LOXL inhibitors selected from the group consisting of: the antibodies described in WO2009/017833, the antibodies described in WO2009/017833, WO2009/035791 and WO/2011/097513;

(13) ASK1 inhibitors selected from the group consisting of: the compounds described in WO2011/008709 and WO/2013/112741;

(14) PI3K inhibitors selected from the group consisting of: the compounds described in U.S. Pat. No. 7,932,260, U.S. Provisional Application Nos. 61/543,176; 61/581,528; 61/745,429; 61/745,437; and 61/835,333, PI3K II, TGR-1202, AMG-319, GSK2269557, X-339, X-414, RP5090, KAR4141, XL499, OXY111A, duvelisib, IPI-443, GSK2636771, BAY 10824391, TGX221, RG-7666, CUDC-907, PQR-309, DS-7423, panulisib, AZD-8186, CLR-457, pictilisib, neratinib, rigosertib, rigosertib sodium, EN-3342, UCB-5857, taselisib, INCB-040093, pilaralisib, BAY-1082439, puquitinib mesylate, XL-765, gedatolisib, VS-5584, copanlisib, CAI orotate, alpelisib, buparlisib, BAY 80-6946, BYL719, PX-866, RG7604, MLN1117, WX-037, AEZS-129, PA799, ZSTK474, RP-6530, AS252424, LY294002, TG100115, LY294002, BEZ235, XL147 (SAR245408), SAR-245409, GDC-0941, BKM120, CH5132799, XL756, MLN-1117, SF-1126, RV-1729, sonolisib, GDC-0980, CLR-1401, perifosine and wortmannin;

(15) BTK inhibitors selected from the group consisting of: ibrutinib, HM71224, ONO-4059 and CC-292;

(16) SYK inhibitors selected from the group consisting of: tamatinib (R406), fostamatinib (R788), PRT062607, BAY-61-3606, NVP-QAB 205 AA, R112, R343, and the compounds described in U.S. Pat. No. 8,450,321;

(17) mTOR inhibitors selected from the group consisting of: temsirolimus, everolimus, ridaforolimus, deforolimus, OSI-027, AZD2014, CC-223, RAD001, LY294002, BEZ235, rapamycin, Ku-0063794, and PP242;

(18) AKT inhibitors selected from the group consisting of: perifosine, MK-2206, GDC-0068 and GSK795;

(19) MEK inhibitors selected from the group consisting of: trametinib, selumetinib, cobimetinib, MEK162, PD-325901, PD-035901, AZD6244, and CI-1040;

(20) CDK inhibitors selected from the group consisting of: AT-7519, alvocidib, palbociclib and SNS-032;

(21) JNK inhibitors selected from the group consisting of: CC-401;

(22) MAPK inhibitors selected from the group consisting of: VX-702, SB203580 and SB202190;

(23) Raf inhibitors selected from the group consisting of: PLX4720;

(24) ROCK inhibitors selected from the group consisting of: Rho-15;

(25) Tie2 inhibitors selected from the group consisting of: AMG-Tie2-1;

(26) Myo-inositol signaling inhibitors such as phospholipase C blockers and Myoinositol analogues described in Powis, G., and Kozikowski A., (1994) New Molecular Targets for Cancer Chemotherapy ed., Paul Workman and David Kerr, CRC press 1994, London;

(27) Bcl-2 family protein inhibitors selected from the group consisting of: ABT-263, ABT-199 and ABT-737;

(28) IKK inhibitors selected from the group consisting of: BMS-345541;

(29) Proteasome inhibitors selected from the group consisting of: bortezomib;

(30) Protein kinase C (PKC) inhibitors selected from the group consisting of: bryostatin 1 and enzastaurin;

(31) Heat shock protein HSP90 inhibitors selected from the group consisting of: Geldanamycin;

(32) Combination drugs selected from the group consisting of: FR (fludarabine, rituximab), FCR (fludarabine, cyclophosphamide, rituximab), R-CHOP (rituximab plus CHOP), R-CVP (rituximab plus CVP), R-FCM (rituximab plus FCM), R-ICE (rituximab-ICE), CHOP (cyclophosphamide, doxorubicin, vincristine, prednisone), CVP (cyclophosphamide, vincristine and prednisone), FCM (fludarabine, cyclophosphamide, mitoxantrone), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), and R MCP (R MCP); and

(33) other drugs for treating cancer selected from the group consisting of aldesleukin, alvocidib, CHIR-12.12, ha20, tiuxetan, PRO131921, SGN-40, WT-1 analog peptide vaccine, WT1 126-134 peptide vaccine, autologous human tumor-derived HSPPC-96, GTOP-99 (MyVax®), antineoplaston AS2-1, antineoplaston A10, anti-thymocyte globulin, beta alethine, arsenic trioxide, amifostine, aminocamptothecin, lenalidomide, caspofungin, clofarabine, ixabepilone, cladribine, chlorambucil, Curcumin, vinorelbine, tipifarnib, tanespimycin, sildenafil citrate, denileukin diftitox, simvastatin, epoetin alfa, fenretinide, filgrastim, mesna, mitoxantrone, lenalidomide, fludarabine, mycophenolate mofetil, nelarabine, octreotide, oxaliplatin, pegfilgrastim, recombinant interleukin-12, recombinant interleukin-11, recombinant flt3 ligand, recombinant human thrombopoietin, sargramostim, lymphokine-activated killer cells, omega-3 fatty acids, recombinant interferon alfa, therapeutic allogeneic lymphocytes and cyclosporine analogs.

In a particular embodiment, a compound of the present disclosure, or a pharmaceutically acceptable salt thereof, is combined with one, two, three, four or more additional therapeutic agents selected from ibrutinib, aldesleukin, alvocidib, antineoplaston AS2-1, antineoplaston A10, anti-thymocyte globulin, amifostine trihydrate, aminocamptothecin, arsenic trioxide, beta alethine, ABT-263, ABT-199, ABT-737, BMS-345541, bortezomib, bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, everolimus (RAD001), fenretinide, filgrastim, melphalan, mesna, flavopiridol, fludarabine (Fludara), Geldanamycin (17 AAG), ifosfamide, irinotecan hydrochloride, ixabepilone, lenalidomide (Revlimid®), lymphokine-activated killer cells, melphalan, methotrexate, mitoxantrone hydrochloride, motexafin gadolinium, mycophenolate mofetil, nelarabine, oblimersen Obatoclax, oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, selicilib, recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, temsirolimus, thalidomide, therapeutic allogeneic lymphocytes, thiotepa, tipifarnib, Vincristine, vincristine sulfate, vinorelbine ditartrate, Vorinostat (SAHA), vorinostat, FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R MCP (R MCP).

Any of the methods of treatment provided may be used to treat cancer at various stages. By way of example, the cancer stage includes but is not limited to early, advanced, locally advanced, remission, refractory, reoccurred after remission and progressive.

In addition, the subject may be a human who is undergoing one or more standard therapies, such as chemotherapy, radiotherapy, immunotherapy, surgery, or combination thereof. Accordingly, one or more anti-cancer agents may be administered before, during, or after administration of chemotherapy, radiotherapy, immunotherapy, surgery or combination thereof.

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Also provided herein is a compound of the present disclosure (e.g., a compound of Formula (I)), or a pharmaceutically acceptable salt thereof, and one or more additional therapeutic agents for treating cancer, for use in a method of treating cancer.

Also provided herein is a compound of the present disclosure (e.g., a compound of Formula (I)), or a pharmaceutically acceptable salt thereof, for use in a method of treating cancer, wherein the compound or a pharmaceutically acceptable salt thereof is administered simultaneously, separately or sequentially with one or more additional therapeutic agents for treating cancer.

XI. KITS

The present disclosure provides a kit comprising a compound of the present disclosure or a pharmaceutically acceptable salt thereof. The kit may further comprise instructions for use, e.g., for use in modulating a toll-like receptor (e.g. TLR-8), such as for use in treating a disease, disorder, or condition. In certain embodiments the use is for treating a HIV, HBV, or HCV infection. In certain embodiments the use is for treating a HBV infection. The instructions for use are generally written instructions, although electronic storage media (e.g., magnetic diskette or optical disk) containing instructions are also acceptable.

The present disclosure also provides a pharmaceutical kit comprising one or more containers comprising a compound of the present disclosure or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

XII. COMPOUND PREPARATION

Also provided are articles of manufacture comprising a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

XII. EXAMPLES

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formulas (I) or (J).

Representative syntheses of compounds of the present disclosure are described in schemes below, and the particular examples that follow.

Scheme 1 shows a representative synthesis of the compounds of the embodiments. The methodology is compatible with a wide variety of functionalities.

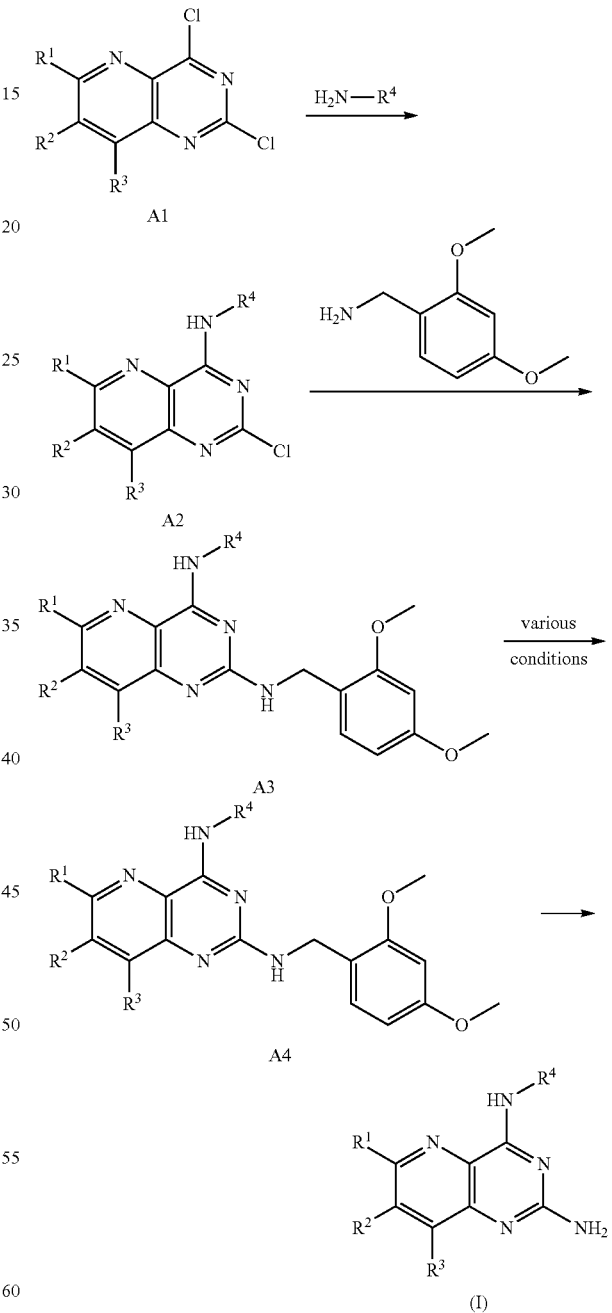

In Scheme 1, compounds of formula A1 (where R$^1$, R$^2$, and R$^3$ are as defined herein or are suitably protected derivatives of R$^1$, R$^2$, and R$^3$) are converted to the corresponding 4-amino,2-chloro heterocycle by reaction with a nuclephilic amine in the presence of a suitable base (such as DIPEA) at room temperature. The compound of formula A2 is then treated with 2,4-dimethoxybenzylamine at elevated temperature resulting in a 2,4-diaminopyrimidine of formula A3. In cases where $R^1$, $R^2$, and $R^3$ is a diversifiable chemical group such as Cl or Br, further replacement of $R^1$, $R^2$, and $R^3$ by a variety of methods including cyanation, nucleophilic aromatic displacement, and metal catalyzed cross coupling reactions such as Suzuki couplings is carried out to provide products of formula A4. Treatment with a suitable acid (such as trifluoroacetic acid) leads to certain compounds of Formula (I) or (J). Where suitable, other leaving groups may be used in place of the Cl group(s) of A1.

Scheme 2 describes a general route which is used to prepare certain compounds of Formula (I) or (J).

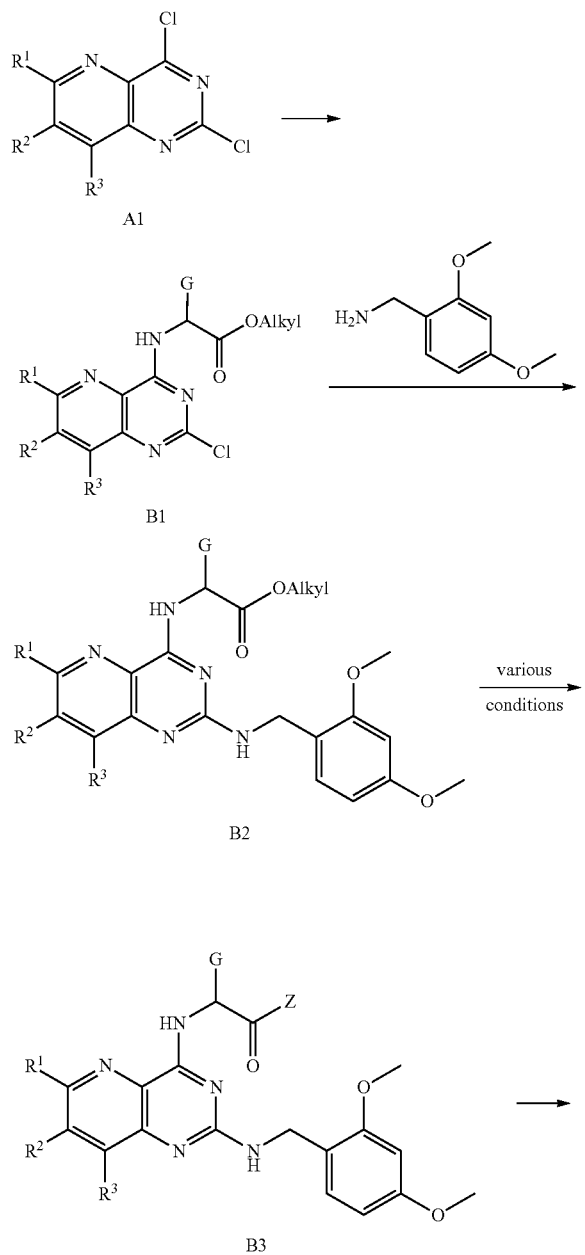

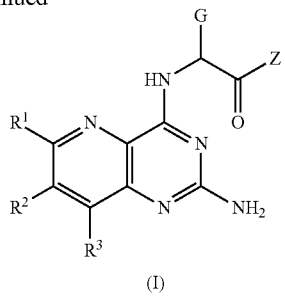

2,4-dichloro pyrido-pyrimidines of formula A1 (where $R^1$, $R^2$, and $R^3$ are as defined herein or are suitably protected derivatives of $R^1$, $R^2$, and $R^3$) are converted to the corresponding 4-amino,2-chloro heterocycle by reaction with an amino acid ester (such as L-norvaline methyl ester) in the presence of a suitable base (such as DIPEA) at room temperature to provide a compound of formula B1, where G is an the sidechain of the amino acid. The compound of formula B1 is then treated with 2,4-dimethoxybenzylamine in a microwave reactor at a suitable temperature (such as about 135° C.), resulting in a 2,4-diaminopyrimidine of formula B2. Hydrolysis of the ester group via treatment with a suitable base (such as aqueous KOH/THF) provides product of formula B3 where Z is hydroxyl. Further reaction of the resulting carboxylic acid leads to modification of Z via HATU-promoted amide formation with various amines. Protecting group removal with a suitable acid (such as trifluoroacetic acid) at room temperature then leads to certain compounds of Formula (J) or (I).

Scheme 3 shows a representative synthesis of the compounds of the embodiments. The methodology is compatible with a wide variety of functionalities.

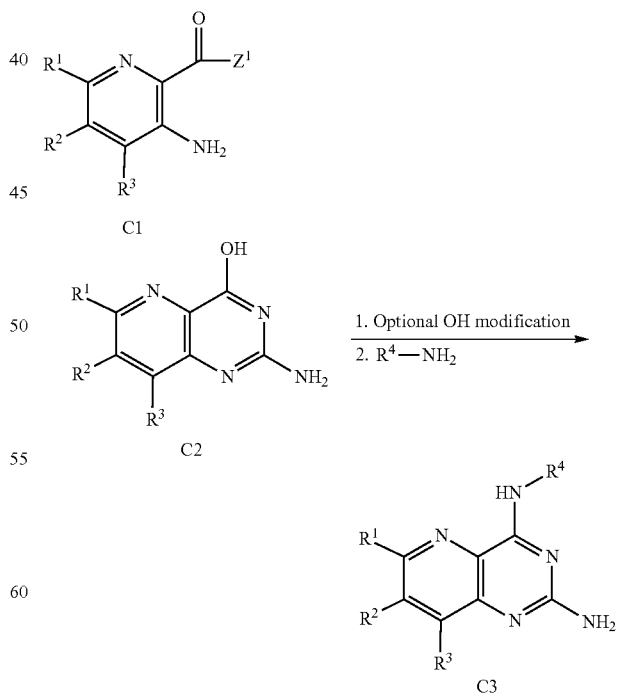

An amide of formula C1 (where $R^1$, $R^2$, and $R^3$ are as defined herein or are suitably protected derivatives of $R^1$, $R^2$, and $R^3$, and $Z^1$ is $NH^2$ or O-alkyl) is converted to a compound of formula C2, under suitable reaction conditions. For example, the compound of formula C1 is contacted with chloroformamidine hydrochloride under suitable conditions to provide C2. The hydroxyl group may be further modified, for example by introducing any suitable leaving group, such as a tosyl group, prior to contacting with $R^4$—$NH_2$. Alternatively, $R^4$—$NH_2$ may be directly coupled to C2 im the presence of a suitable coupling agent, for example, BOP reagent, under suitable conditions.

Additionally, a compound of Formula A1 (where $R^1$, $R^2$, and $R^3$ are as defined herein or are suitably protected derivatives of $R^1$, $R^2$, and $R^3$) may be prepared as described in the scheme below. It is understood that A1 may be further modified to prepare compounds of Formula (I) as more fully described herein.

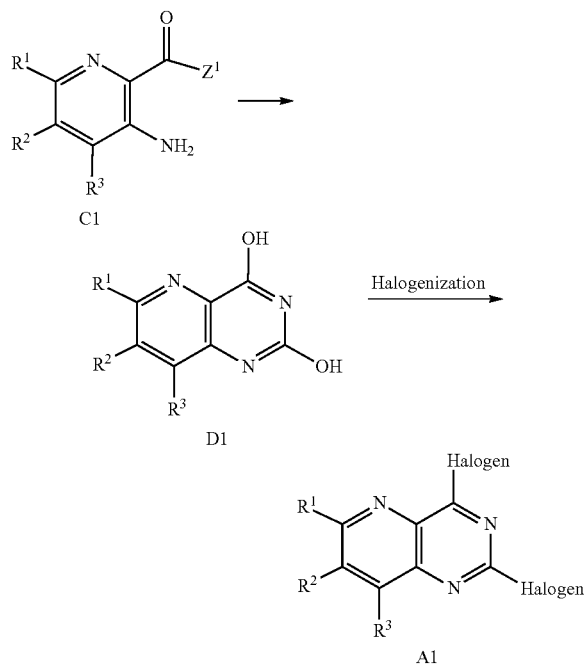

As described above C1 is contacted with a suitable agent, such as triphosgene and dioxane, to result in a compound of D1. The compound D1 may be further halogenated under suitable conditions, such as treatment with $POCl_3$ and $PCl_5$, to provide a compound of formula A1.

In certain instances, the above processes further involve the step of forming a salt of a compound of the present disclosure. Embodiments are directed to the other processes described herein; and to the product prepared by any of the processes described herein.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 5$^{th}$ edition, New York: Oxford University Press, 2009; Smith, March's Advanced Organic Chemistry: Reactions, Mechanisms, and Structure, 7$^{th}$ edition, Wiley-Interscience, 2013.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

The methods of the present invention generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Example 1

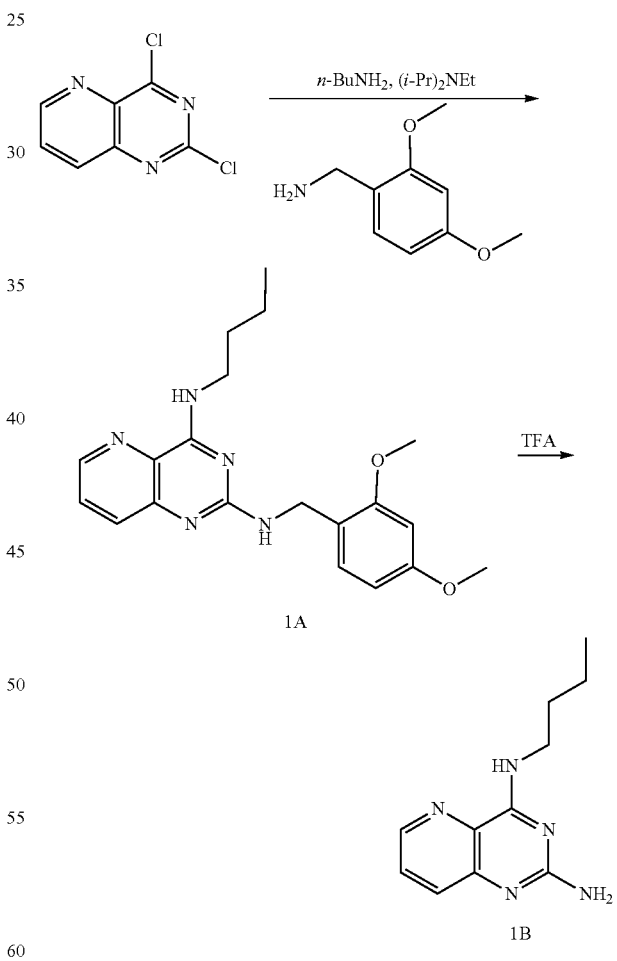

Synthesis of N$^4$-butyl-N$^2$-(2,4-dimethoxybenzyl)pyrido [3,2-d]pyrimidine 2,4-diamine (1A): To a solution of 2,4-dichloropyrido[3,2-d]pyrimidine (CAS #39551-54-7, supplied by Astatech, Inc.) (50 mg, 0.25 mmol) in THF (2 mL) was added butan-1-amine (0.03 mL, 0.28 mmol) and N,N-diisopropylethylamine (0.13 ml, 0.75 mmol). After stirring at room temperature for 30 minutes, 2,4-dimethoxybenzylamine (0.19 ml, 1.25 mmol) and N,N-diisopropylethylamine (0.13 ml, 0.75 mmol) were added and the mixture was heated to 100° C. After 16 hours, the reaction was cooled to room temperature, diluted with ethyl acetate, washed with water and brine, dried over Na$_2$SO$_4$, and concentrated in vacuo. The product (1A) was obtained after flash chromatography. MS (m/z): 368.14 [M+H]$^+$.

Synthesis of N$^4$-butylpyrido[3,2-d]pyrimidine-2,4-diamine (1B): 1A was dissolved in trifluoroacetic acid (3 mL). After 30 minutes, the reaction was diluted with water and methanol. After 60 minutes, the mixture was concentrated in vacuo. The residue was then co-evaporated with methanol three times and filtered in methanol to afford the title product 1B as a trifluoroacetic acid salt. $^1$H NMR (400 MHz, Methanol-d$_4$) δ 8.59 (dd, J=4.4, 1.4 Hz, 1H), 7.82 (dd, J=8.5, 1.4 Hz, 1H), 7.72 (dd, J=8.5, 4.4 Hz, 1H), 3.66 (t, J=7.3 Hz, 2H), 1.78-1.62 (m, 2H), 1.43 (dq, J=14.7, 7.4 Hz, 2H), 0.98 (t, J=7.4 Hz, 3H). MS (m/z): 218.10 [M+H]$^+$. $^{19}$F NMR (377 MHz, Methanol-d4) δ -77.6.

Example 2

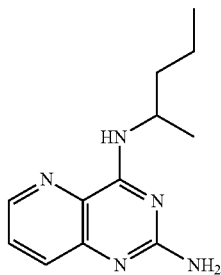

2B

Synthesis of N$^2$-(2,4-dimethoxybenzyl)-N$^4$-(pentan-2-yl) pyrido[3,2-d]pyrimidine-2,4-diamine (2A): 2A was synthesized following the procedure described above for preparation of 1A, replacing butan-1-amine with 2-aminopentane. MS (m/z) 382.17 [M+H]$^+$.

Synthesis of N$^4$-(pentan-2-yl)pyrido[3,2-d]pyrimidine-2, 4-diamine (2B): 2B was prepared following the procedure described for 1B to yield the title compound (2B) as its TFA salt. $^1$H NMR (400 MHz, Methanol-d4) δ 8.61 (dd, J=4.4, 1.4 Hz, 1H), 7.84 (dd, J=8.5, 1.4 Hz, 1H), 7.74 (dd, J=8.5, 4.4 Hz, 1H), 4.60-4.46 (m, 1H), 1.74 (dtd, J=13.5, 8.3, 6.7 Hz, 1H), 1.68-1.55 (m, 1H), 1.44 (d, J=7.4 Hz, 2H), 1.32 (d, J=6.6 Hz, 3H), 0.95 (t, J=7.4 Hz, 3H). MS (m/z) 232.11 [M+H]$^+$. $^{19}$F NMR (377 MHz, Methanol-d4) δ -77.5.

Example 3

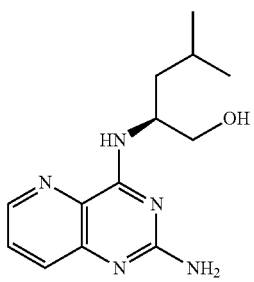

3B

Synthesis of (S)-2-((2-((2,4-dimethoxybenzyl)amino) pyrido[3,2-d]pyrimidin-4-yl)amino)-4-methylpentan-1-ol (3A): 3A was synthesized following the above procedure for 1A, replacing butan-1-amine with (S)-(+)-leucinol. MS (m/z) 412.19 [M+H]$^+$.

Synthesis of (S)-2-((2-aminopyrido[3,2-d]pyrimidin-4-yl)amino)-4-methylpentan-1-ol (3B): 3B was synthesized using the procedure described above for the preparation of 1B to yield the title compound (3B) as its TFA salt. $^1$H NMR (400 MHz, Methanol-d$_4$) δ 8.62 (dd, J=4.4, 1.3 Hz, 1H), 7.84 (dd, J=8.5, 1.4 Hz, 1H), 7.74 (dd, J=8.5, 4.4 Hz, 1H), 4.74-4.58 (m, 1H), 3.71 (h, J=6.2 Hz, 2H), 1.76-1.58 (m, 2H), 1.52 (tq, J=10.6, 3.5 Hz, 1H), 0.98 (t, J=6.4 Hz, 6H). MS (m/z) 262.15 [M+H]$^+$. $^{19}$F NMR (377 MHz, Methanol-d4) δ -77.6

Example 4

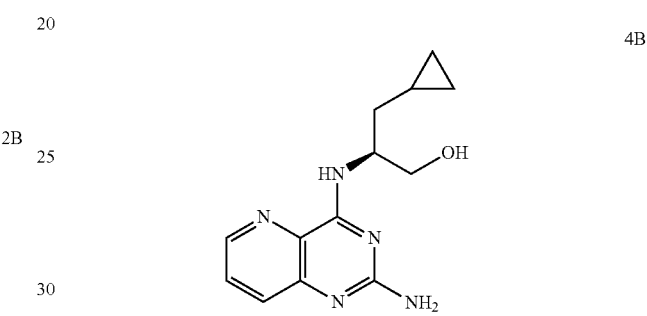

4B

Synthesis of (S)-3-cyclopropyl-2-((2-((2,4-dimethoxybenzyl)amino)pyrido[3,2-d]pyrimidin-4-yl)amino)propan-1-ol (4A): 4A was prepared using the procedure described above for the preparation of 1A, replacing butan-1-amine with (2S)-2-amino-3-cyclopropylpropan-1-ol HCl salt. MS (m/z) 410.20 [M+H]$^+$ Synthesis of (S)-2-((2-aminopyrido[3,2-d]pyrimidin-4-yl)amino)-3-cyclopropylpropan-1-ol (4B): 4B was synthesized following the procedure described above for 1B to yield the title compound (4B) as its TFA salt. $^1$H NMR (400 MHz, Methanol-d$_4$) δ 8.62 (dd, J=4.4, 1.3 Hz, 1H), 7.85 (dd, J=8.5, 1.4 Hz, 1H), 7.75 (dd, J=8.5, 4.4 Hz, 1H), 4.63 (dq, J=7.3, 5.5 Hz, 1H), 3.81 (d, J=5.2 Hz, 2H), 1.65 (h, J=7.1 Hz, 2H), 0.78 (dddd, J=15.0, 10.1, 5.1, 2.1 Hz, 1H), 0.45 (dddd, J=11.1, 9.4, 7.9, 4.6 Hz, 2H), 0.19-0.07 (m, 2H). MS (m/z) 260.15 [M+H]$^+$. $^{19}$F NMR (377 MHz, Methanol-d4) δ -77.6

Example 5

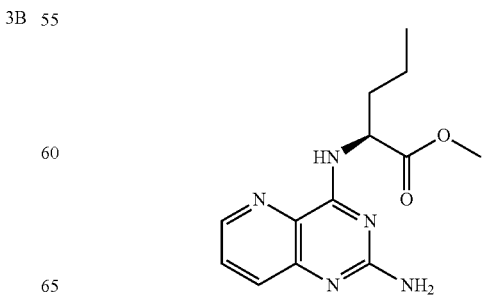

5B

Synthesis of (S)-methyl 2-((2-((2,4-dimethoxybenzyl)amino)pyrido[3,2-d]pyrimidin-4-yl)amino)pentanoate (5A): 5A was prepared following the general procedure described above for 1A, replacing butan-1-amine with (S)-methyl 2-aminopentanoate. MS (m/z) 426.19 [M+H]+.

Synthesis of (S)-methyl 2-((2-aminopyrido[3,2-d]pyrimidin-4-yl)amino)pentanoate (5B): 5B was prepared following the procedure described above for 1B to yield the title compound (5B) as its TFA salt. $^1$H NMR (400 MHz, Methanol-d$_4$) δ 8.66 (dd, J=4.4, 1.4 Hz, 1H), 7.88 (dd, J=8.5, 1.4 Hz, 1H), 7.79 (dd, J=8.5, 4.4 Hz, 1H), 5.02 (dd, J=8.7, 5.3 Hz, 1H), 3.78 (s, 3H), 2.13-1.92 (m, 2H), 1.56-1.39 (m, 2H), 0.99 (t, J=7.4 Hz, 3H). MS (m/z) 276.13 [M+H]+. $^{19}$F NMR (377 MHz, Methanol-d4) δ −77.8.

Example 6

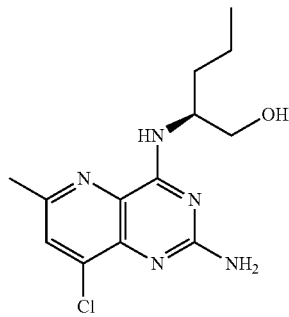

6B

Synthesis of (S)-2-((8-chloro-2-((2,4-dimethoxybenzyl)amino)-6-methylpyrido[3,2-d]pyrimidin-4-yl)amino)pentan-1-ol (6A): 6A was prepared following the procedure described above for 1A, replacing butan-1-amine with (S)-methyl 2-aminopentanoate and instead starting from 2,4,8-trichloro-6-methylpyrido[3,2-d]pyrimidine in place of 2,4-dichloropyrido[3,2-d]pyrimidine. MS (m/z) 446.20 [M+H]+.

Synthesis of (S)-2-((2-amino-8-chloro-6-methylpyrido[3,2-d]pyrimidin-4-yl)amino)pentan-1-ol (6B): 6B was prepared following the procedure described above for 1B to yield the title compound (6B) as its TFA salt. $^1$H NMR (400 MHz, Methanol-d$_4$) δ 7.84 (s, 1H), 4.55 (ddd, J=12.6, 7.2, 5.2 Hz, 1H), 3.75 (d, J=5.3 Hz, 3H), 1.79-1.67 (m, 3H), 1.51-1.35 (m, 3H), 0.98 (t, J=7.4 Hz, 4H). MS (m/z) 296.18 [M+H]+. $^{19}$F NMR (377 MHz, Methanol-d4) δ −77.6.

Example 7

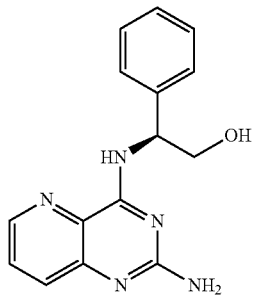

7

Compound 7, (S)-2-((2-aminopyrido[3,2-d]pyrimidin-4-yl)amino)-2-phenylethanol, was prepared following the procedure for compound 1B reported above, instead replacing butan-1-amine with (S)-2-amino-2-phenylethanol to yield the title compound (7) as its TFA salt. $^1$H NMR (400 MHz, Methanol-d4) δ 8.68 (dd, J=4.3, 1.5 Hz, 1H), 7.84 (dd, J=8.5, 1.5 Hz, 1H), 7.77 (dd, J=8.5, 4.4 Hz, 1H), 7.49-7.43 (m, 2H), 7.38-7.31 (m, 2H), 7.31-7.24 (m, 1H), 5.57 (dd, J=7.4, 4.8 Hz, 1H), 4.12-3.93 (m, 2H). $^{19}$F NMR (376 MHz, Methanol-d4) δ −77.7. MS (m/z) 282.1 [M+H]+.

Example 8

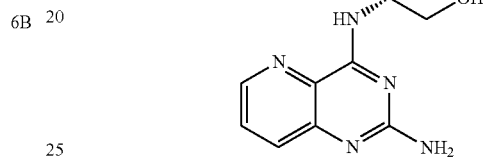

8

Compound 8, (R)-2-((2-aminopyrido[3,2-d]pyrimidin-4-yl)amino)pentan-1-ol, was prepared following the procedure for the synthesis of compound 1B reported above, instead replacing butan-1-amine with (R)-2-aminopentan-1-ol to yield the title compound (8) as its TFA salt. $^1$H NMR (400 MHz, Methanol-d4) δ 8.64 (dd, J=4.4, 1.4 Hz, 1H), 7.83 (dd, J=8.5, 1.5 Hz, 1H), 7.76 (dd, J=8.5, 4.4 Hz, 1H), 4.55 (dq, J=7.4, 5.4 Hz, 1H), 3.78-3.69 (m, 2H), 1.77-1.65 (m, 2H), 1.52-1.36 (m, 2H), 0.98 (t, J=7.3 Hz, 3H). $^{19}$F NMR (376 MHz, Methanol-d4) δ −77.56. MS (m/z) 248.1 [M+H]+.

Example 9

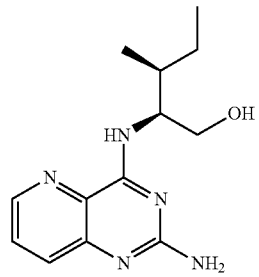

9

Compound 9, (2S,3S)-2-((2-aminopyrido[3,2-d]pyrimidin-4-yl)amino)-3-methylpentan-1-ol, was prepared following the procedure for compound 1B reported above, instead replacing butan-1-amine with (2S,3S)-2-amino-3-methylpentan-1-ol to yield the title compound (9) as its TFA salt. $^1$H NMR (400 MHz, Methanol-d4) δ 8.64 (dd, J=4.4, 1.4 Hz, 1H), 7.84 (dd, J=8.5, 1.4 Hz, 1H), 7.76 (dd, J=8.5, 4.4 Hz, 1H), 4.39 (dt, J=8.1, 5.0 Hz, 1H), 3.83 (d, J=5.0 Hz, 2H), 1.97-1.82 (m, 1H), 1.58 (dddd, J=16.8, 11.2, 7.6, 3.8 Hz, 1H), 1.33-1.16 (m, 2H), 1.03 (d, J=6.8 Hz, 3H), 0.94 (t, J=7.4 Hz, 3H). $^{19}$F NMR (376 MHz, Methanol-d4) δ −77.71. MS (m/z) 262.1 [M+H]+.

Example 10

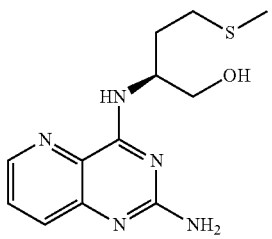

Compound 10, (S)-2-((2-aminopyrido[3,2-d]pyrimidin-4-yl)amino)-4-(methylthio)butan-1-ol, was prepared following the 2 step procedure for compound 1B reported above, replacing butan-1-amine with (S)-2-amino-4-(methylthio)butan-1-ol to yield the title compound (10) as its TFA salt. $^1$H NMR (400 MHz, Methanol-d4) δ 8.64 (dd, J=4.4, 1.4 Hz, 1H), 7.83 (dd, J=8.5, 1.4 Hz, 1H), 7.76 (dd, J=8.5, 4.4 Hz, 1H), 4.66 (dq, J=8.1, 5.4 Hz, 1H), 3.76 (d, J=5.3 Hz, 2H), 2.65-2.52 (m, 2H), 2.11-1.98 (m, 5H). $^{19}$F NMR (376 MHz, Methanol-d4) δ −77.63. MS (m/z) 280.1 [M+H]$^+$.

Example 11

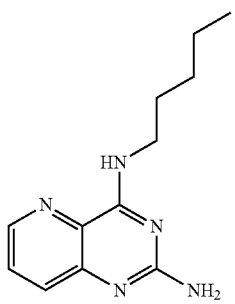

Compound 11, N$^4$-pentylpyrido[3,2-d]pyrimidine-2,4-diamine, was prepared following the procedure for compound 1B reported above, instead replacing butan-1-amine with n-pentylamine to yield the title compound (11) as its TFA salt. $^1$H NMR (400 MHz, Methanol-d4) δ 8.62 (dd, J=4.4, 1.4 Hz, 1H), 7.81 (dd, J=8.5, 1.4 Hz, 1H), 7.74 (dd, J=8.5, 4.4 Hz, 1H), 3.67 (dd, J=7.8, 6.8 Hz, 2H), 1.80-1.66 (m, 2H), 1.49-1.32 (m, 4H), 0.99-0.85 (m, 3H). $^{19}$F NMR (376 MHz, Methanol-d4) δ −77.58. MS (m/z) 232.1 [M+H]$^+$.

Example 12

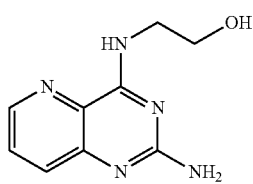

Compound 12, 2-((2-aminopyrido[3,2-d]pyrimidin-4-yl)amino)ethanol, was prepared following the procedure for compound 1B reported above, instead replacing butan-1-amine with ethanolamine to yield the title compound (12) as its TFA salt. $^1$H NMR (400 MHz, Methanol-d4) δ 8.64 (dd, J=4.3, 1.5 Hz, 1H), 7.88-7.72 (m, 2H), 3.82 (d, J=2.3 Hz, 4H). $^{19}$F NMR (376 MHz, Methanol-d4) δ −77.58. MS (m/z) 206.0 [M+H]$^+$.

Example 13

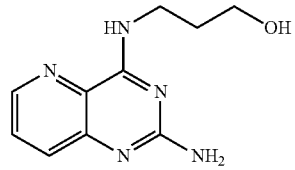

Compound 13, 3-((2-aminopyrido[3,2-d]pyrimidin-4-yl)amino)propan-1-ol, was prepared following the 2 step procedure for compound 1B reported above, instead replacing butan-1-amine with propanolamine to yield the title compound (13) as its TFA salt. $^1$H NMR (400 MHz, Methanol-d4) δ 8.62 (td, J=4.6, 1.4 Hz, 1H), 7.87-7.70 (m, 2H), 3.80 (dt, J=11.7, 6.8 Hz, 2H), 3.70 (t, J=6.0 Hz, 2H), 2.00-1.88 (m, 2H). $^{19}$F NMR (376 MHz, Methanol-d4) δ −77.58. MS (m/z) 220.1 [M+H]$^+$.

Example 14

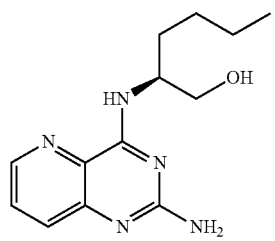

Compound 14, (S)-2-((2-aminopyrido[3,2-d]pyrimidin-4-yl)amino)hexan-1-ol, was prepared following the procedure for compound 1B reported above, instead replacing butan-1-amine with (S)-2-aminohexan-1-ol to yield the title compound (14) as its TFA salt. $^1$H NMR (400 MHz, Methanol-d4) δ 8.63 (dd, J=4.4, 1.4 Hz, 1H), 7.84 (dd, J=8.5, 1.4 Hz, 1H), 7.76 (dd, J=8.5, 4.4 Hz, 1H), 4.53 (dq, J=8.6, 5.4 Hz, 1H), 3.79-3.68 (m, 2H), 1.87-1.61 (m, 2H), 1.52-1.31 (m, 4H), 1.01-0.85 (m, 3H). $^{19}$F NMR (376 MHz, Methanol-d4) δ −77.63. MS (m/z) 262.2 [M+H]$^+$.

Example 15

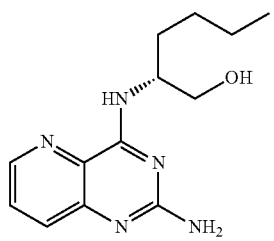

Compound 15, (R)-2-((2-aminopyrido[3,2-d]pyrimidin-4-yl)amino)hexan-1-ol, was prepared following the procedure for compound 1B reported above, instead replacing butan-1-amine with (R)-2-aminohexan-1-ol to yield the title compound (15) as its TFA salt. $^1$H NMR (400 MHz, Methanol-d4) δ 8.66-8.59 (m, 1H), 7.84 (dd, J=8.5, 1.4 Hz, 1H), 7.77 (td, J=8.8, 4.4 Hz, 1H), 4.59-4.42 (m, 1H), 3.81-3.68 (m, 2H), 1.90-1.65 (m, 2H), 1.49-1.35 (m, 4H), 1.03-0.82 (m, 3H). $^{19}$F NMR (376 MHz, Methanol-d4) δ −77.60. MS (m/z) 262.2 [M+H]$^+$.

Example 16

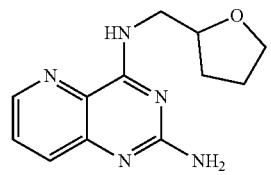

Compound 16, N$^4$-((tetrahydrofuran-2-yl)methyl)pyrido[3,2-d]pyrimidine-2,4-diamine, was prepared following the procedure for compound 1B reported above, instead replacing butan-1-amine with (tetrahydrofuran-2-yl)-methanamine to yield the title compound (16) as its TFA salt. $^1$H NMR (400 MHz, Methanol-d4) δ 8.62 (dd, J=4.4, 1.4 Hz, 1H), 7.83 (dd, J=8.5, 1.4 Hz, 1H), 7.75 (dd, J=8.5, 4.4 Hz, 1H), 4.24 (qd, J=6.8, 4.8 Hz, 1H), 3.93 (dt, J=8.3, 6.5 Hz, 1H), 3.84-3.68 (m, 3H), 2.16-1.82 (m, 3H), 1.71 (ddt, J=11.6, 8.0, 6.5 Hz, 1H). $^{19}$F NMR (376 MHz, Methanol-d4) δ −77.50. MS (m/z) 246.1 [M+H]$^+$.

Example 17

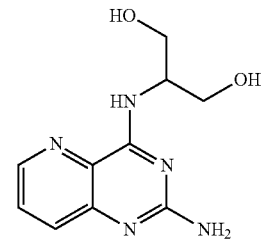

Compound 17, 2-((2-aminopyrido[3,2-d]pyrimidin-4-yl)amino)propane-1,3-diol, was prepared following the procedure for compound 1B reported above, instead replacing butan-1-amine with 2-aminopropane-1,3-diol to yield the title compound (17) as its TFA salt. $^1$H NMR (400 MHz, Methanol-d4) δ 8.64 (dd, J=4.4, 1.4 Hz, 1H), 7.85 (dd, J=8.5, 1.4 Hz, 1H), 7.77 (dd, J=8.5, 4.4 Hz, 1H), 4.54 (p, J=5.5 Hz, 1H), 3.84 (d, J=5.5 Hz, 4H). $^{19}$F NMR (376 MHz, Methanol-d4) δ −77.66. MS (m/z) 236.1 [M+H]$^+$.

Example 18

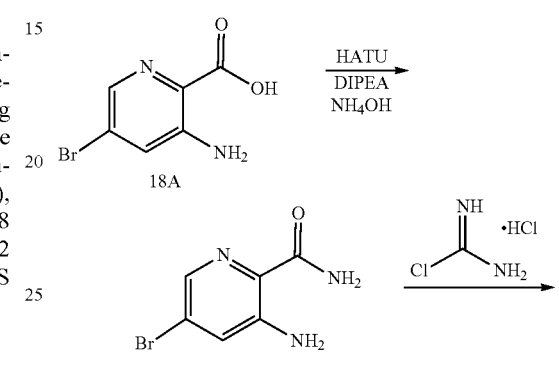

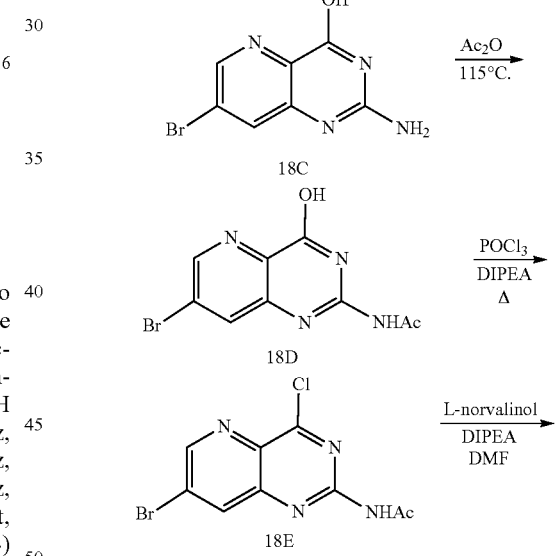

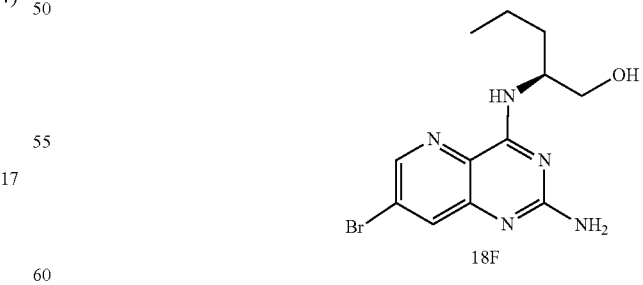

Synthesis of 3-amino-5-bromopicolinamide (18B): To a solution of 3-amino-5-bromopicolinic acid 18A (300 mg, 1.38 mmol, 1 equiv.) in DMF (11 ml, 0.1 M) was added HATU (598 mg, 1.57 mmol, 1.1 equiv.) followed by DIPEA (0.48 mL, 2.76 mmol, 2 equiv.) and ammonium hydroxide (0.8 mL, 5.55 mmol, 4 equiv.). The mixture was allowed to stir overnight. Water (50 mL) was added and the mixture then extracted with EtOAc (3 times). The organic layer was separated, dried over Na$_2$SO$_4$, filtered and concentrated under reduced pressure. The product (18B) was obtained after flash chromatography. MS (m/z): 216.8 [M+H]$^+$ Synthesis of 2-amino-7-bromopyrido[3,2-d]pyrimidin-4-ol (18C): To a flask containing 3-amino-5-bromopicolinamide (18B) (205 mg, 0.1 mmol, 1 equiv.) was added chloroformamadine hydrochloride (140 mg, 1.3 equiv.). The mixture was heated to 165° C. overnight. It was allowed to cool to room temperature, then filtered and washed with water and ethyl ether. The residue was allowed to air dry to furnish 2-amino-7-bromopyrido[3,2-d]pyrimidin-4-ol (1C) which was used without further purification. MS (m/z): 239.9 [M+H]$^+$ Synthesis of N-(7-bromo-4-hydroxypyrido[3,2-d]pyrimidin-2-yl)acetamide (18D): To a flask containing 2-amino-7-bromopyrido[3,2-d]pyrimidin-4-ol (1C) (155 mg, 0.64 mmol, 1 equiv.) was added acetic anhydride (3 mL). The mixture was heated to 115° C. for 4 hrs. It was concentrated under reduced pressure. It was filtered and washed with diethyl ether and hexane and allowed to air dry to obtain N-(7-bromo-4-hydroxypyrido[3,2-d]pyrimidin-2-yl)acetamide (18D). MS (m/z): 282.9 [M+H].$^+$ Synthesis of N-(7-bromo-4-chloropyrido[3,2-d]pyrimidin-2-yl)acetamide (18E): Into a solution of N-(7-bromo-4-hydroxypyrido[3,2-d]pyrimidin-2-yl)acetamide (18D) (200 mg, 0.71 mmol, 1 equiv.) was added acetonitrile (2 ml) and POCl$_3$ (1 ml) followed by DIPEA (0.12 mL, 0.71 mmol., 1 equiv.). The mixture was refluxed for 6 hours. The mixture was concentrated under reduced pressure. To it was added water (20 mL) then extracted with EtOAc (3 times). The organic layer was separated, dried over Na$_2$SO$_4$, filtered and concentrated under reduced pressure to afford the title product N-(7-bromo-4-chloropyrido[3,2-d]pyrimidin-2-yl)acetamide (18E). MS (m/z): 298.9 [M+H].$^+$ Synthesis of (S)-2-((2-amino-7-bromopyrido[3,2-d]pyrimidin-4-yl)amino)pentan-1-ol (18F): To a solution of N-(7-bromo-4-chloropyrido[3,2-d]pyrimidin-2-yl)acetamide (18E) (215 mg, 0.71 mmol, 1 equiv.) was added DMF (1.5 ml) followed by DIPEA (0.38 mL, 2.1 mmol, 3 equiv.) and (S)-(+)-2-Amino-1-pentanol (55 mg, 3.6 mmol, 5 equiv.). The reaction was allowed to stir overnight. It was concentrated under reduced pressure and purified by reverse phase HPLC to furnish the title compound (18F) as its TFA salt. $^1$H NMR (400 MHz, Methanol-d4) δ 8.41 (d, J=2.0 Hz, 1H), 7.83 (d, J=2.0 Hz, 1H), 4.34 (dd, J=8.5, 5.4 Hz, 1H), 3.65-3.53 (m, 3H), 1.67-1.49 (m, 3H), 1.41-1.24 (m, 3H), 0.86 (t, J=7.4 Hz, 5H). $^{19}$F NMR (377 MHz, CD$_3$OD) δ −77.52. MS (m/z): 368.2 [M+H].

Example 19

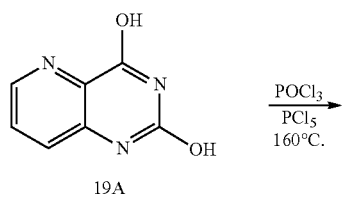

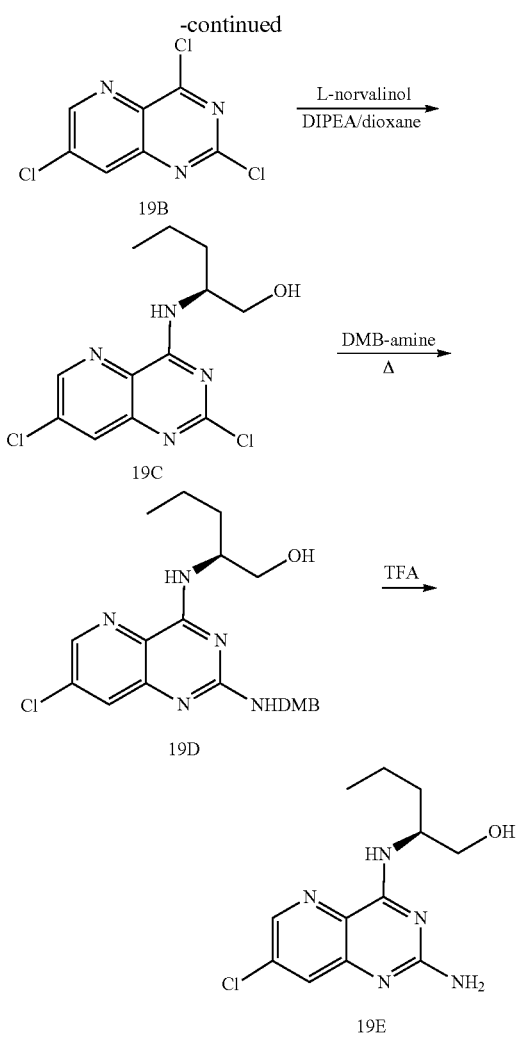

Synthesis of 2,4,7-trichloropyrido[3,2-d]pyrimidine (19B): Into a microwave vial was added pyrido[3,2-d]pyrimidine-2,4-diol (19A) (200 mg, 1.2 mmol, 1 equiv.) is added POCl$_3$ (2.5 mL) and PCl$_5$ (1.53 g, 7.4 mmol, 6 equiv.). The mixture was heated to 160° C. for 3 hr in microwave reactor. The reaction mixture was concentrated under reduced pressure and partitioned between EtOAc and H$_2$O. The organics were separated, dried, and removed in vacuo. The residue purified by column chromatography on silica to provide the title compound. MS (m/z): 236.6[M+H]$^+$.

Synthesis of (S)-2-((2,7-dichloropyrido[3,2-d]pyrimidin-4-yl)amino)pentan-1-ol (19C): To a solution of 2,4,7-trichloropyrido[3,2-d]pyrimidine (19B) (160 mg, 0.68 mmol, 1 equiv.) was added dioxane (4 ml) followed by DIPEA (0.18 mL, 1.2 mmol, 1.5 equiv.) and (S)-(+)-2-Amino-1-pentanol (85 mg, 0.82 mmol, 1.1 equiv.). The reaction was allowed to stir for an hr. It was concentrated under reduced pressure and used as is to provide the title compound. MS (m/z): 301.1 [M+H]$^+$.

Synthesis of (S)-2-((7-chloro-2-((2,4-dimethoxybenzyl)amino)pyrido[3,2-d]pyrimidin-4-yl)amino)pentan-1-ol (19D): To a solution of (R)-2-((2,7-dichloropyrido[3,2-d]pyrimidin-4-yl)amino)pentan-1-ol (19C) (206 mg, 0.68 mmol, 1 equiv.) was added dioxane (4 ml) followed by DIPEA (0.24 mL, 1.4 mmol, 2 equiv.) and 2,4-demethoxybenzylamine (0.30 mL, 2.0 mmol, 3 equiv.). The reaction was allowed heated at 120° C. overnight. The reaction mixture was partitioned between EtOAc and H₂O. The organics were separated, dried, and removed in vacuo. The residue purified by column chromatography on silica to provide the title compound. MS (m/z): 432.2 [M+H].⁺

Synthesis of (S)-2-((2-amino-7-chloropyrido[3,2-d]pyrimidin-4-yl)amino)pentan-1-ol (19E): Into a solution of (S)-2-((7-chloro-2-((2,4-dimethoxybenzyl)amino)pyrido[3,2-d]pyrimidin-4-yl)amino)pentan-1-ol (19D) (35 mg, 0.08 mmol, 1 equiv.) was added DCM (2 mL) and TFA (0.5 mL). After 3 hours the reaction mixture was concentrated under reduced pressure and purified by reverse phase HPLC to furnish the title compound (19E) as its TFA salt. ¹H NMR (400 MHz, Methanol-d4) δ 8.48 (d, J=2.0 Hz, 1H), 7.78 (d, J=2.1 Hz, 1H), 4.48 (dd, J=8.6, 5.3 Hz, 1H), 3.93-3.74 (m, 2H), 3.71 (d, J=5.2 Hz, 3H), 1.77-1.57 (m, 2H), 1.50-1.36 (m, 1H), 1.28 (s, 2H), 0.97 (t, J=7.4 Hz, 4H). ¹⁹F NMR (377 MHz, Methanol-d4) δ −77.59 (d, J=80.2 Hz). MS (m/z): 282.1 [M+H].⁺

General Scheme for Examples 20-22

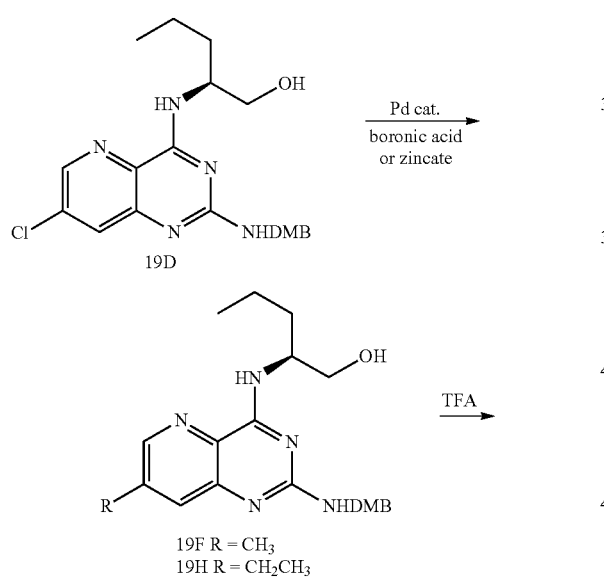

19F R = CH₃
19H R = CH₂CH₃
19J R = CN

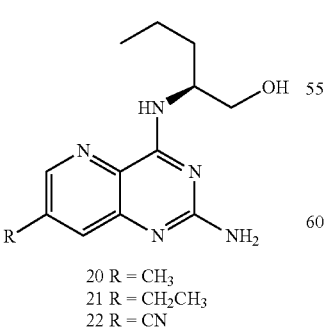

20 R = CH₃
21 R = CH₂CH₃
22 R = CN

Example 20

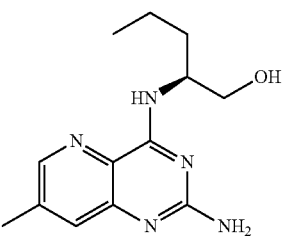

20

Synthesis of (S)-2-((2-((2,4-dimethoxybenzyl)amino)-7-methylpyrido[3,2-d]pyrimidin-4-yl)amino)pentan-1-ol (19F): Into a vial containing (S)-2-((7-chloro-2-((2,4-dimethoxybenzyl)amino)pyrido[3,2-d]pyrimidin-4-yl)amino)pentan-1-ol (19D) (25 mg, 0.06 mmol, 1 equiv.) was added methylboronic acid (8 mg, 0.14 mmol, 2.5 equiv.), potassium phosphate tribasic (37 mg, 0.17 mmol, 3 equiv.), palladium(0)-tetrakis(triphenylphosphine) (7 mg, 0.006 mmol, 0.1 equiv.) along with dioxane (2 mL) and water (2 mL). The mixture is heated to 150° C. for 1 hr in a microwave reactor. The reaction mixture was partitioned between EtOAc and H₂O. The organics were separated, dried, and removed in vacuo to furnish the title compound which was used directly. MS (m/z): 474.3 [M+H].⁺

Synthesis of (S)-2-((2-amino-7-methylpyrido[3,2-d]pyrimidin-4-yl)amino)pentan-1-ol (20): Into the a flask containing 19F was added THF (2 mL), water (2 mL) followed by 2,3-dichloro-5,6-dicyanobenzoquinone (26 mg, 20.11 mmol, 2 equiv.) After stirring overnight, the reaction mixture was partitioned between EtOAc and H₂O. The organics were separated, dried, and removed in vacuo. Purification was carried out using flash column chromatography to furnish the title compound (20). ¹H NMR (400 MHz, Methanol-d4) δ 8.35 (d, J=1.1 Hz, 1H), 7.49 (s, 1H), 4.54-4.34 (m, 1H), 3.70 (d, J=5.0 Hz, 2H), 1.84-1.61 (m, 2H), 1.56-1.35 (m, 2H), 0.97 (t, J=7.3 Hz, 3H). MS (m/z): 262.1 [M+H].⁺

Example 21

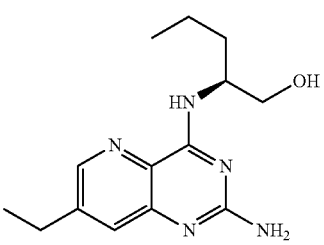

21

Synthesis of (S)-2-((2-amino-7-ethylpyrido[3,2-d]pyrimidin-4-yl)amino)pentan-1-ol (21) was prepared according to the procedure used for 20, instead using ethylboronic acid in place of methylboronic acid. ¹H NMR (400 MHz, Methanol-d4) δ 8.65-8.30 (m, 1H), 7.62 (s, 1H), 4.61-4.38 (m, 1H), 3.80-3.64 (m, 2H), 2.84 (q, J=7.6 Hz, 2H), 1.71 (tdd, J=8.3, 6.5, 2.2 Hz, 2H), 1.43 (dddd, J=12.4, 7.4, 5.1, 2.5 Hz, 2H), 1.39-1.23 (m, 4H), 0.97 (t, J=7.3 Hz, 3H). MS (m/z): 276.2 [M+H]⁺.

Example 22

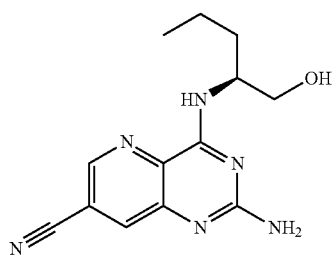

Synthesis of (S)-2-amino-4-((1-hydroxypentan-2-yl)amino)pyrido[3,2-d]pyrimidine-7-carbonitrile (22) was prepared according to the two step procedure used for 20, instead using Zn(CN)$_2$ in place of methylboronic acid. $^1$H NMR (400 MHz, DMSO-d6) δ 7.93 (d, J=1.7 Hz, 1H), 7.24 (d, J=1.7 Hz, 1H), 2.95-2.68 (m, 3H), 0.76 (d, J=7.3 Hz, 2H), 0.47 (d, J=7.6 Hz, 1H), 0.02 (t, J=7.4 Hz, 4H). MS (m/z): 273.3 [M+H].+

Example 23

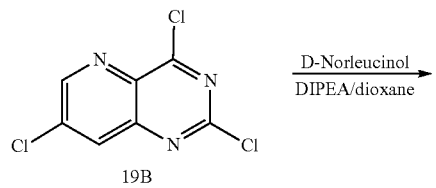

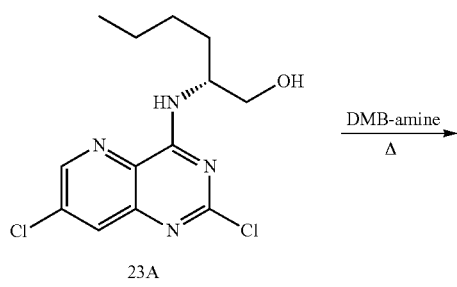

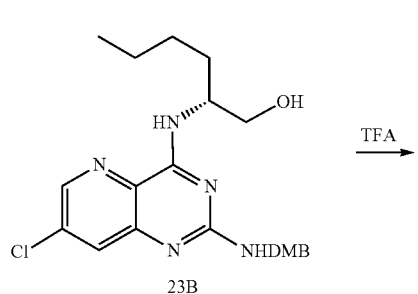

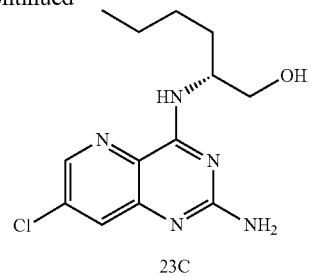

Synthesis of (R)-2-((2,7-dichloropyrido[3,2-d]pyrimidin-4-yl)amino)hexan-1-ol (23A): To a solution of 2,4,7-trichloropyrido[3,2-d]pyrimidine (19B) (45 mg, 0.19 mmol, 1 equiv.) was added dioxane (4 ml) followed by DIPEA (41 µL, 0.23 mmol, 1.2 equiv.) and (R)-(−)-2-Amino-1-hexanol 97% (24.7 mg, 0.21 mmol, 1.1 equiv.). The reaction was allowed to stir for an hr. It was concentrated under reduced pressure and used as is to provide the title compound. MS (m/z): 316.2[M+H].+

Synthesis of (R)-2-((7-chloro-2-((2,4-dimethoxybenzyl)amino)pyrido[3,2-d]pyrimidin-4-yl)amino)hexan-1-ol (23B): To a solution of (R)-2-((2,7-dichloropyrido[3,2-d]pyrimidin-4-yl)amino)hexan-1-ol (23A) (60 mg, 0.19 mmol, 1 equiv.) was added dioxane (4 ml) followed by DIPEA (68 µL, 0.38 mmol, 2 equiv.) and 2,4-demethoxybenzylamine (85 µL, 3.0 mmol, 3 equiv.). The reaction was allowed heated at 120° C. overnight. The reaction mixture partitioned between EtOAc and H$_2$O. The organics were separated, dried, and removed in vacuo. The residue purified by column chromatography on silica to provide the title compound. MS (m/z): 446.9 [M+H].+

Synthesis (R)-2-((2-amino-7-chloropyrido[3,2-d]pyrimidin-4-yl)amino)hexan-1-ol (23C): To a solution of (R)-2-((7-chloro-2-((2,4-dimethoxybenzyl)amino)pyrido[3,2-d]pyrimidin-4-yl)amino)hexan-1-ol (20B) (50 mg, 0.11 mmol, 1 equiv.) was added DCM (2 mL) and TFA (0.5 mL). After 3 hours the reaction mixture was concentrated under reduced pressure and purified by reverse phase HPLC to furnish the title compound (23C) as its TFA salt. $^1$H NMR (400 MHz, Methanol-d4) δ 8.60 (d, J=2.1 Hz, 1H), 7.90 (d, J=2.1 Hz, 1H), 4.58-4.44 (m, 1H), 3.79-3.63 (m, 3H), 1.86-1.61 (m, 2H), 1.52-1.24 (m, 5H), 1.01-0.79 (m, 4H). $^{19}$F NMR (377 MHz, Methanol-d4) δ −77.61. MS (m/z): 296.2 [M+H].+

Example 24

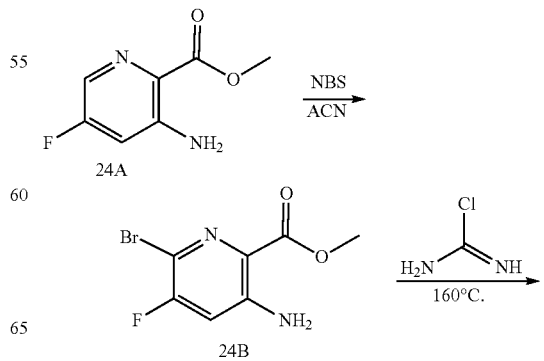

173
-continued

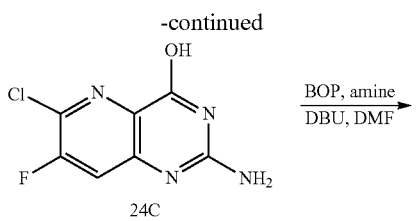

174
Example 25

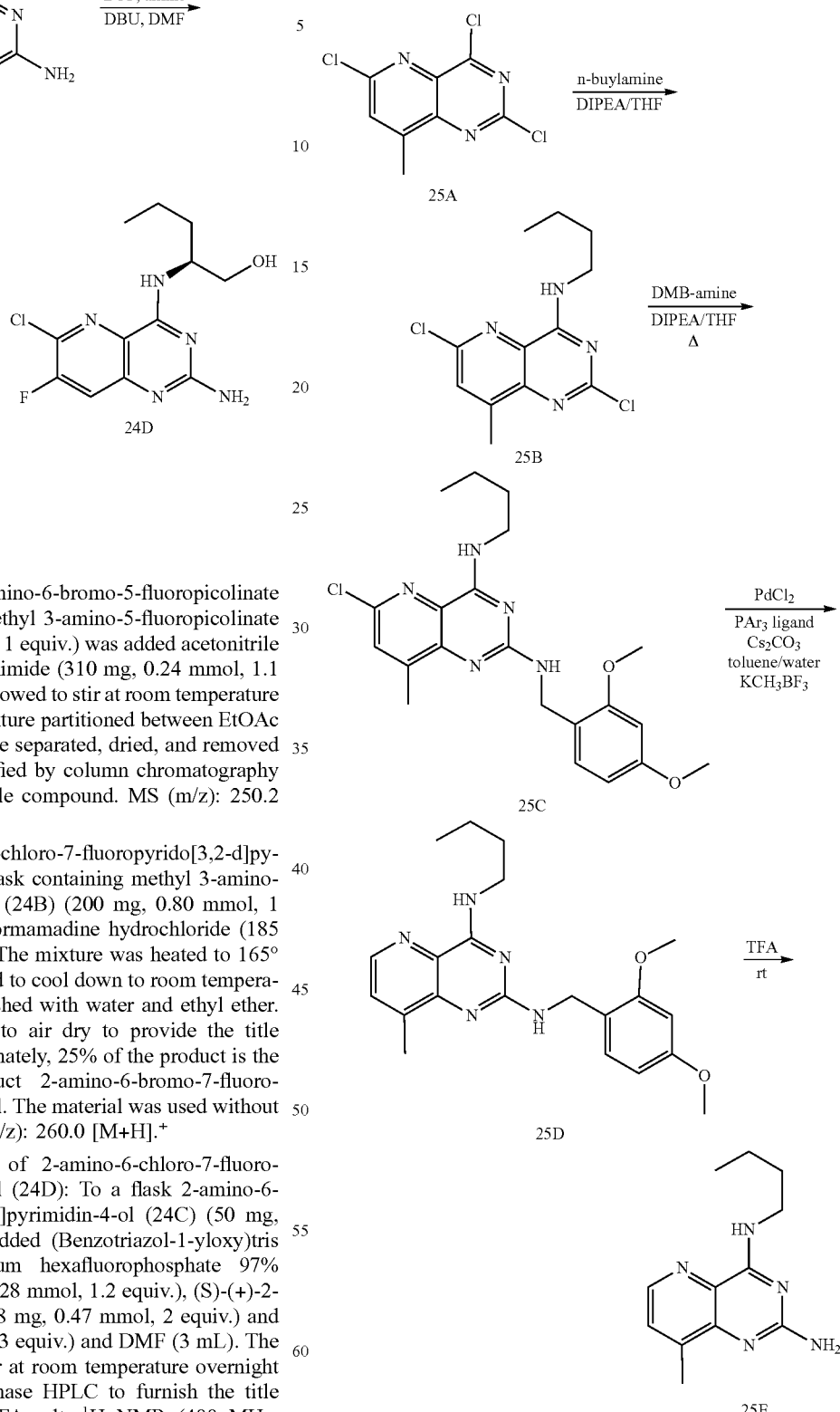

Synthesis of methyl 3-amino-6-bromo-5-fluoropicolinate (24B): To a solution of methyl 3-amino-5-fluoropicolinate (24A) (270 mg, 0.22 mmol, 1 equiv.) was added acetonitrile (5 mL) and N-bromosuccinimide (310 mg, 0.24 mmol, 1.1 equiv.). The reaction was allowed to stir at room temperature overnight. The reaction mixture partitioned between EtOAc and $H_2O$. The organics were separated, dried, and removed in vacuo. The residue purified by column chromatography on silica to provide the title compound. MS (m/z): 250.2 [M+H].+

Synthesis of 2-amino-6-chloro-7-fluoropyrido[3,2-d]pyrimidin-4-ol (24C): To a flask containing methyl 3-amino-6-bromo-5-fluoropicolinate (24B) (200 mg, 0.80 mmol, 1 equiv.) was added chloroformamadine hydrochloride (185 mg, 1.61 mmol, 2 equiv.). The mixture was heated to 165° C. overnight. It was allowed to cool down to room temperature it was filtered and washed with water and ethyl ether. The residue was allowed to air dry to provide the title compound (24C). Approximately, 25% of the product is the corresponding side product 2-amino-6-bromo-7-fluoro-pyrido[3,2-d]pyrimidin-4-ol. The material was used without further purification. MS (m/z): 260.0 [M+H].+

Synthesis of Synthesis of 2-amino-6-chloro-7-fluoro-pyrido[3,2-d]pyrimidin-4-ol (24D): To a flask 2-amino-6-chloro-7-fluoropyrido[3,2-d]pyrimidin-4-ol (24C) (50 mg, 0.23 mmol, 1 equiv.) is added (Benzotriazol-1-yloxy)tris(dimethylamino)phosphonium hexafluorophosphate 97% (BOP Reagent) (123 mg, 0.28 mmol, 1.2 equiv.), (S)-(+)-2-Amino-1-pentanol, 97% (48 mg, 0.47 mmol, 2 equiv.) and DBU (105 µL, 0.70 mmol, 3 equiv.) and DMF (3 mL). The mixture was allowed to stir at room temperature overnight and purified by reverse phase HPLC to furnish the title compound (24D) as its TFA salt. $^1$H NMR (400 MHz, Methanol-d4) δ 7.86-7.63 (m, 1H), 4.64-4.47 (m, 1H), 3.72 (d, J=5.5 Hz, 2H), 1.82-1.61 (m, 3H), 1.56-1.35 (m, 2H), 0.97 (t, J=7.4 Hz, 3H). $^{19}$F NMR (377 MHz, Methanol-d4) δ −77.54, −110.63 (d, J=8.2 Hz). MS (m/z): 300.2 [M+H]+.

Synthesis of $N^4$-butyl-8-methylpyrido[3,2-d]pyrimidine-2,4-diamine (25E). Beginning from intermediate 25A, treatment with 1.05 equiv butan-1-amine in THF/DIPEA at RT gave 25B, which was concentrated to a residue and carried forward directly. Heating with excess 2,4-dimethoxybenzylamine in THF/DIPEA led to compound 25C, with characteristic MS (m/z): 416.2 [M+H].+ Following the procedure reported by Hasnik et. al in Synthesis, 2009, 1309-1317, instead of the expected 6-methylation via potassium methyl trifluoroborate, protonolysis of the intermediate heteroaryl-Pd complex led mainly to isolation of 25D, and finally to $N^4$-butyl-8-methylpyrido[3,2-d]pyrimidine-2,4-diamine 25E upon treatment of 25D in excess TFA and final purification via HPLC to provide the title compound (25E) as its TFA salt. $^1$H NMR (400 MHz, Methanol-d4) δ 8.48 (d, J=1.1 Hz, 1H), 7.61 (d, J=1.1 Hz, 1H), 3.67 (d, J=7.2 Hz, 2H), 2.52 (s, 3H), 1.75-1.68 (m, 2H), 1.46-1.35 (m, 2H), 0.98 (t, J=7.3 Hz, 3H). $^{19}$F NMR (377 MHz, Methanol-d4) δ -77.6. MS (m/z): 232.1 [M+H].+

Example 26

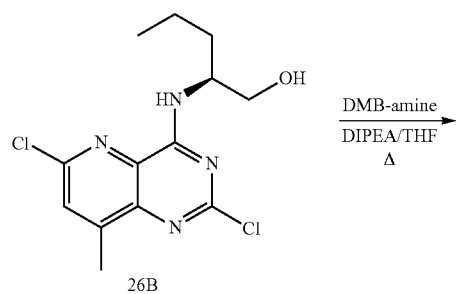

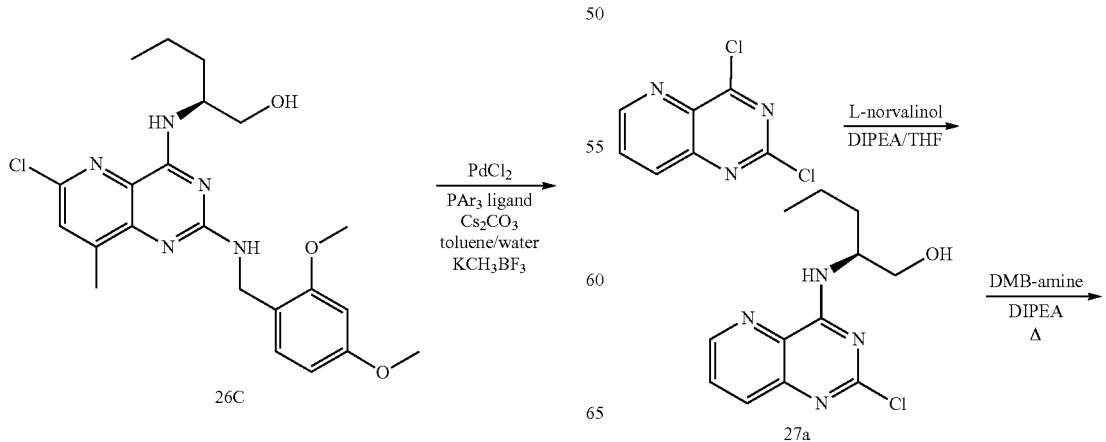

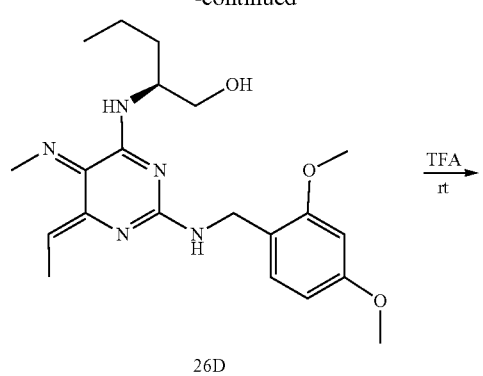

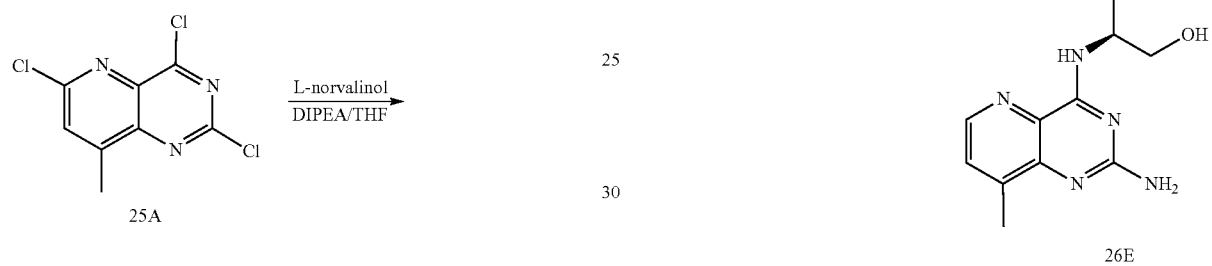

Synthesis of (S)-2-((2-amino-8-methylpyrido[3,2-d]pyrimidin-4-yl)amino)pentan-1-ol (26E): Beginning from intermediate 25A and following the synthetic sequence reported above for the synthesis of 25E, but instead using L-norvalinol in place of butan-1-amine, 26E was obtained as its TFA salt. $^1$H NMR (400 MHz, Methanol-d4) δ 8.50 (d, J=4.6 Hz, 1H), 7.63 (dq, J=4.5, 0.8 Hz, 1H), 4.60-4.49 (m, 1H), 3.78-3.70 (m, 2H), 2.53 (s, 3H), 1.81-1.64 (m, 2H), 1.52-1.34 (m, 2H), 0.97 (t, J=7.3 Hz, 3H). $^{19}$F NMR (377 MHz, Methanol-d4) δ -77.7. MS (m/z): 262.2 [M+H]+

Example 27

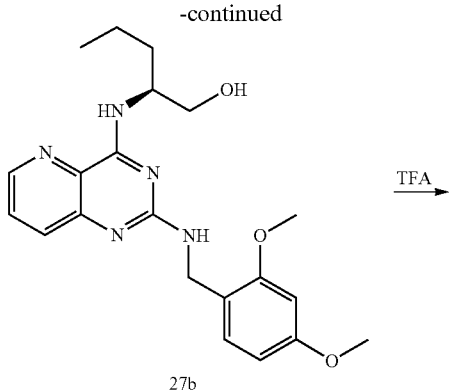

27b

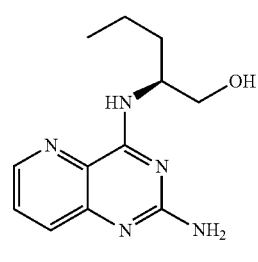

27c

Synthesis of (S)-2-((2-chloropyrido[3,2-d]pyrimidin-4-yl)amino)pentan-1-ol (27C): To a solution of 2,4-dichloropyrido[3,2-d]pyrimidine (160 mg, 0.68 mmol, 1 equiv.) was added THF (4 ml) followed by DIPEA (0.18 mL, 1.2 mmol, 1.5 equiv.) and (S)-(+)-2-amino-1-pentanol (85 mg, 0.82 mmol, 1.1 equiv.). The reaction was allowed to stir for 1h. The reaction was concentrated under reduced pressure and used as is to provide 27A. MS (m/z): 267.1[M+H].+

Synthesis of (S)-2-((2-((2,4-dimethoxybenzyl)amino)pyrido[3,2-d]pyrimidin-4-yl)amino)pentan-1-ol (27B): To a solution of (S)-2-((2-chloropyrido[3,2-d]pyrimidin-4-yl)amino)pentan-1-ol (27A) (206 mg, 0.68 mmol, 1 equiv.) was added is added THF (4 ml) followed by DIPEA (0.24 mL, 1.4 mmol, 2 equiv.) and 2,4-dimethoxybenzylamine (0.30 mL, 2.0 mmol, 3 equiv.). The reaction was heated at 135° C. via microwave reactor for 30 minutes. The reaction mixture was partitioned between EtOAc and H$_2$O. The organics were separated, dried, and removed in vacuo. The residue was purified by column chromatography on silica to provide 27B. MS (m/z): 398.2 [M+H].+

Synthesis of (S)-2-((2-amino-[3,2-d]pyrimidin-4-yl)amino)pentan-1-ol (27C): Into a solution of (S)-2-((2-((2,4-dimethoxybenzyl)amino)pyrido[3,2-d]pyrimidin-4-yl)amino)pentan-1-ol (27B) (35 mg, 0.08 mmol, 1 equiv.) was added DCM (2 mL) and TFA (0.5 mL). After 3 hours the reaction mixture was concentrated under reduced pressure and purified by reverse phase HPLC to furnish the title compound (27C) as its TFA salt. $^1$H NMR (400 MHz, Methanol-d4) δ 8.65 (dd, J=4.3, 1.5 Hz, 1H), 7.85-7.73 (m, 2H), 4.55 (s, 1H), 3.76-3.70 (m, 2H), 1.77-1.66 (m, 2H), 1.44 (td, J=7.3, 4.2 Hz, 2H), 0.98 (t, J=7.4 Hz, 3H). $^{19}$F NMR (377 MHz, Methanol-d4) δ −77.6. MS (m/z): 248.2 [M+H]+

Example 28

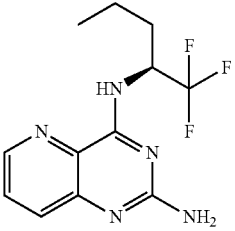

28

Following the general procedure described above for the synthesis of 1B, 2,4-dichloropyrido[3,2-d]pyrimidine was instead reacted with 1.1 equiv (S)-1,1,1-trifluoropentan-2-amine in place of 1-butan-amine and then carried through the steps as reported above in Example 1 to provide (S)—N$^4$-(1,1,1-trifluoropentan-2-yl)pyrido[3,2-d]pyrimidine-2,4-diamine (28). $^1$H NMR (400 MHz, DMSO-d6) δ 9.87 (s, 1H), 8.67 (dd, J=4.4, 1.5 Hz, 1H), 7.95-7.81 (m, 2H), 5.13 (t, J=8.9 Hz, 1H), 2.21-2.10 (m, 1H), 1.74 (dd, J=12.1, 7.1 Hz, 1H), 1.44-1.36 (m, 1H), 1.27 (dq, J=13.7, 7.1 Hz, 1H), 0.89 (t, J=7.3 Hz, 3H). $^{19}$F NMR (377 MHz, Methanol-d4) δ −73.9, −74.1. MS (m/z): 286.1 [M+H]+.

Example 29

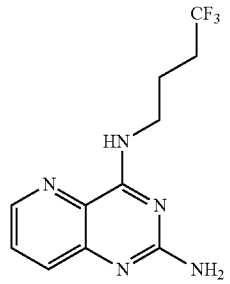

29

Following the general procedure described above for the synthesis of 1B, 2,4-dichloropyrido[3,2-d]pyrimidine was instead reacted with 1.1 equiv 4,4,4-trifluorobutylamine in place of 1-butan-amine and then carried through the steps as reported above for Example 1 to provide N$^4$-(4,4,4-trifluorobutyl)pyrido[3,2-d]pyrimidine-2,4-diamine (29) after HPLC purification as its TFA salt. $^1$H NMR (400 MHz, DMSO-d6) δ 9.74 (t, J=6.0 Hz, 1H), 8.63 (dd, J=4.4, 1.4 Hz, 1H), 8.18-7.50 (m, 2H), 3.62 (q, J=6.7 Hz, 1H), 2.39-2.27 (m, 1H), 1.93-1.84 (m, 1H). $^{19}$F NMR (377 MHz, Methanol-d4) δ −65.5, 75.6. MS (m/z): 272.1 [M+H]+

Example 30

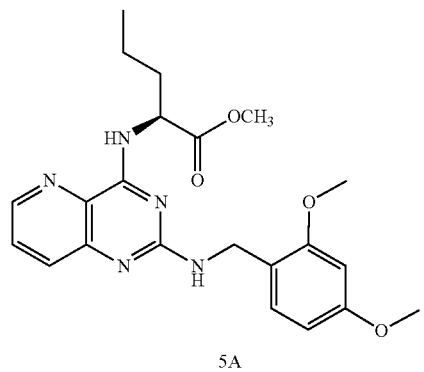

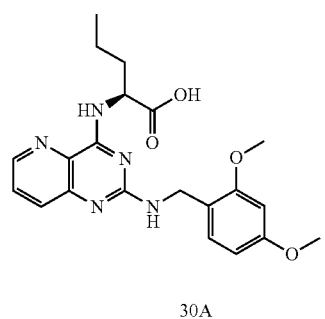

Synthesis of (S)-2-((2-aminopyrido[3,2-d]pyrimidin-4-yl)amino)pentanamide (30B). Beginning from 50 mg of the intermediate compound 5A previously described above, treatment with 1 equiv. aq. KOH in THF/MEOH (4 mL) for 1h gave, upon removal of solvent, intermediate 30A, MS (m/z): 399.1 [M+H]$^+$. 30A was treated with 1.5 equiv HATU and 3 equiv DIPEA in 2 mL DMF, with quenching by excess 2,4-dimethoxybenzylamine (DMB) to provide the intermediate amide. After global DMB removal via TFA treatment, HPLC purification of the product residue provided title compound 30B as its TFA salt. $^1$H NMR (400 MHz, Methanol-d$_4$) δ 8.67 (ddd, J=9.2, 4.3, 1.5 Hz, 1H), 7.89-7.73 (m, 2H), 4.00-3.59 (m, 1H), 2.81 (s, 2H), 2.22-1.79 (m, 2H), 1.48 (tt, J=9.8, 7.4 Hz, 2H), 0.99 (t, J=7.4 Hz, 3H). $^{19}$F NMR (377 MHz, Methanol-d4) δ −77.6. MS (m/z): 261.1 [M+H]$^+$.

Example 31

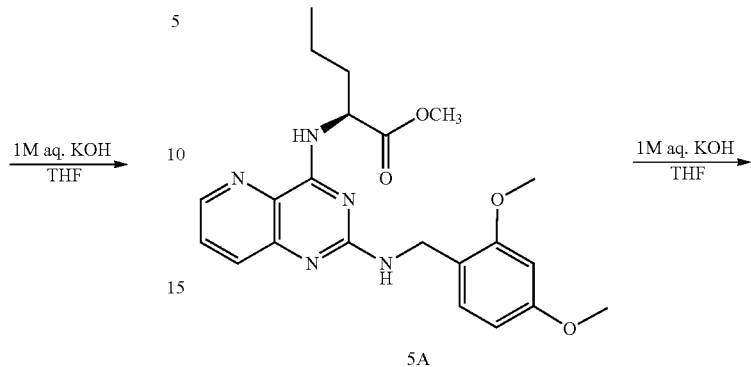

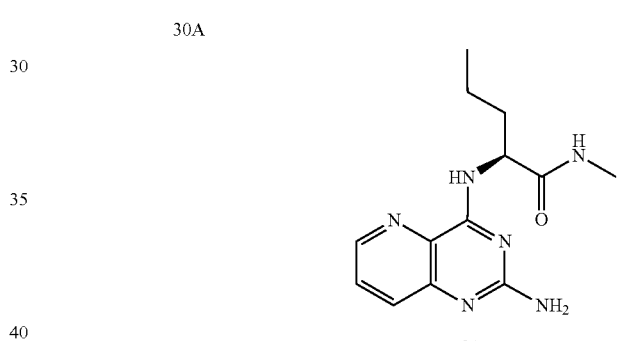

Synthesis of (S)-2-((2-aminopyrido[3,2-d]pyrimidin-4-yl)amino)-N-methylpentanamide (31). 50 mg of 30A was treated with 1.5 equiv HATU and 3 equiv DIPEA in 2 mL DMF, with quenching by 1.0 M methylamine in THF to provide the intermediate methylamide. After standard DMB removal via TFA treatment, HPLC purification of the product residue provided title compound 31 as its TFA salt. $^1$H NMR (400 MHz, Methanol-d$_4$) δ 8.68 (dd, J=4.3, 1.5 Hz, 1H), 7.89-7.76 (m, 2H), 4.85 (m, 1H), 2.76 (s, 3H), 2.08-1.85 (m, 2H), 1.45 (dddd, J=16.5, 13.8, 11.5, 7.4 Hz, 2H), 0.98 (t, J=7.4 Hz, 3H). $^{19}$F NMR (377 MHz, Methanol-d4) δ −77.9. MS (m/z): 275.1 [M+H]$^+$

Example 32

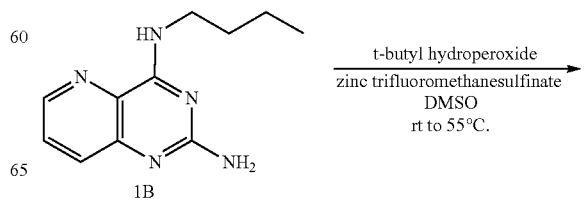

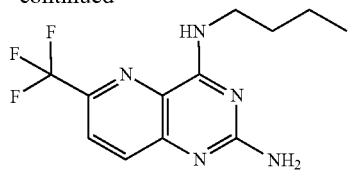

32

Synthesis of N⁴-butyl-6-(trifluoromethyl)pyrido[3,2-d]pyrimidine-2,4-diamine (32). Beginning from 10 mg compound 1B, the synthesis of which is reported in Example 1, and proceeding with chemistry described by Yining et al. in *PNAS*, 2011, 108, 14411, 1B was heated at 55° C. in DMSO in the presence of 10 equivalents of zinc trifluormethane sulfinate and 10 equiv t-butylhydroperoxide 70% aq. solution. After 24h, the reaction mixture was injected directly onto HPLC for final purification to provide the title compound (32) as the corresponding TFA salt. ¹H NMR (400 MHz, Methanol-d4) δ 8.15 (d, J=8.7 Hz, 1H), 8.01 (dd, J=8.8, 0.8 Hz, 1H), 3.82-3.56 (m, 2H), 1.83-1.61 (m, 2H), 1.58-1.31 (m, 2H), 0.99 (t, J=7.4 Hz, 3H). ¹⁹F NMR (377 MHz, Methanol-d₄) δ −69.0, −77.6. MS (m/z): 286.1 [M+H]⁺.

Example 33

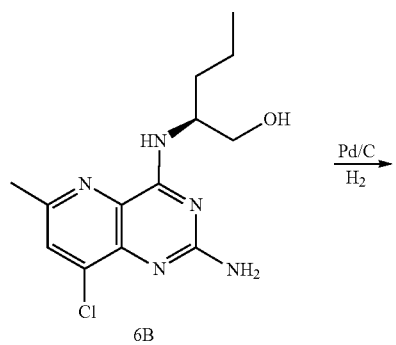

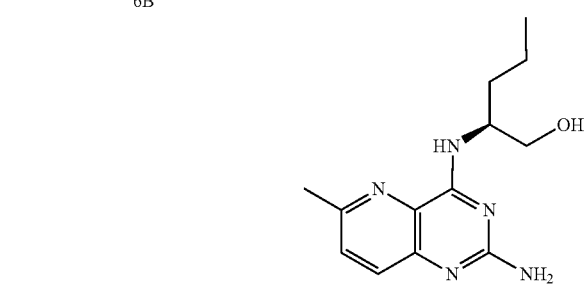

33

Synthesis of (S)-2-((2-amino-6-methylpyrido[3,2-d]pyrimidin-4-yl)amino)pentan-1-ol (33). 50 mg compound 6B, (0.11 mmol, 1 equiv) in 10 mL (1:1 EtOH/EtOAc) was reacted with 28 mg 5% Pd/C at 70° C. under 1 atm H₂. After overnight, the reaction was filtered to remove catalyst and the product chromatograped on silica gel, eluting at 25% MeOH/75% EtOAc to provide the title compound (33) as its TFA salt. ¹H NMR (400 MHz, Methanol-d4) δ 7.74 (d, J=8.6 Hz, 1H), 7.65 (d, J=8.6 Hz, 1H), 4.54 (ddd, J=12.4, 7.3, 5.2 Hz, 1H), 3.75 (d, J=5.2 Hz, 2H), 2.65 (s, 3H), 1.73 (q, J=7.5 Hz, 2H), 1.44 (ddt, J=14.6, 7.4, 4.2 Hz, 2H), 0.98 (t, J=7.3 Hz, 3H). ¹⁹F NMR (377 MHz, Methanol-d4) δ −77.7. MS (m/z) 262.14 [M+H]⁺.

Example 34

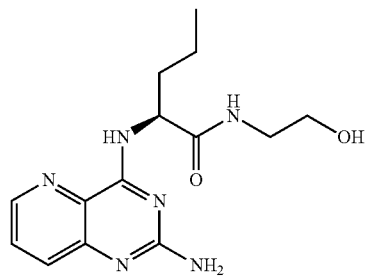

34

Synthesis of (S)-2-((2-aminopyrido[3,2-d]pyrimidin-4-yl)amino)-N-(2-hydroxyethyl)pentanamide (34): The title compound was synthesized in a similar fashion to 30B as reported in Example 30, instead replacing methanolic ammonia with ethanolamine to provide the title compound (34) as its TFA salt. ¹H NMR (400 MHz, Methanol-d₄) δ 8.68 (dd, J=4.3, 1.5 Hz, 1H), 7.86 (dd, J=8.6, 1.5 Hz, 1H), 7.80 (dd, J=8.5, 4.4 Hz, 1H), 4.88 (d, J=5.5 Hz, 1H), 3.27-3.22 (m, 2H), 2.11-1.90 (m, 3H), 1.70-1.40 (m, 5H), 1.00 (t, J=7.4 Hz, 3H). ¹⁹F NMR (377 MHz, Methanol-d4) δ −77.5. MS (m/z) 305.21 [M+H]⁺.

Example 35

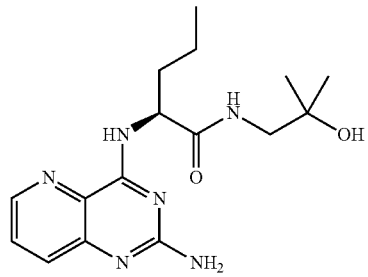

35

Synthesis of (S)-2-((2-aminopyrido[3,2-d]pyrimidin-4-yl)amino)-N-(2-hydroxy-2-methylpropyl)pentanamide (35): Compound (35) was synthesized in a similar fashion to 30B as reported in Example 30, instead replacing methanolic ammonia with 1-amino-2-methyl-2-propanol to provide the title compound (35) as its TFA salt. ¹H NMR (400 MHz, Methanol-d₄) δ 8.67 (dd, J=4.4, 1.4 Hz, 1H), 7.87 (dd, J=8.5, 1.4 Hz, 1H), 7.79 (dd, J=8.5, 4.4 Hz, 1H), 4.84-4.78 (m, 1H), 3.61 (td, J=5.9, 5.5, 1.5 Hz, 2H), 2.09-1.85 (m, 2H), 1.48 (dddd, J=18.0, 13.7, 9.7, 7.3 Hz, 2H), 1.29 (s, 6H), 0.99 (t, J=7.4 Hz, 3H). ¹⁹F NMR (377 MHz, Methanol-d4) δ −77.5. MS (m/z) 333.25 [M+H]⁺

Example 36

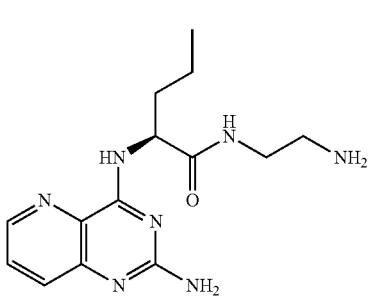

Synthesis of (S)—N-(2-aminoethyl)-2-((2-aminopyrido[3,2-d]pyrimidin-4-yl)amino)pentanamide (36): Compound 36 was synthesized in a similar fashion to 30B, instead replacing methanolic ammonia with N-Boc-ethylenediamine. Global deprotection with TFA furnished the title compound (36) as its bis-TFA salt. $^1$H NMR (400 MHz, Methanol-$d_4$) δ 8.68 (dd, J=4.4, 1.4 Hz, 1H), 7.88 (dd, J=8.5, 1.4 Hz, 1H), 7.81 (dd, J=8.5, 4.3 Hz, 1H), 4.92 (dd, J=8.6, 5.1 Hz, 1H), 3.56 (ddd, J=13.9, 12.8, 6.7 Hz, 1H), 3.45 (dt, J=14.3, 6.1 Hz, 1H), 3.08 (hept, J=6.4 Hz, 2H), 2.13-2.00 (m, 1H), 2.00-1.85 (m, 1H), 1.55-1.41 (m, 2H), 0.99 (t, J=7.4 Hz, 3H). $^{19}$F NMR (377 MHz, Methanol-d4) δ -77.6. MS (m/z) 304.05 [M+H]$^+$.

Example 37

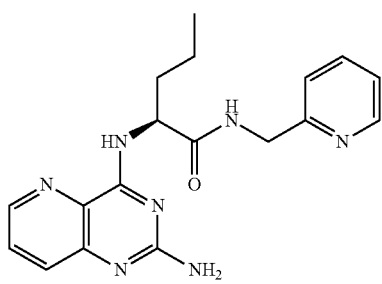

Synthesis of (S)-2-((2-aminopyrido[3,2-d]pyrimidin-4-yl)amino)-N-(pyridin-2-ylmethyl)pentanamide (37): Compound 37 was synthesized in a similar fashion to 30B, instead replacing methanolic ammonia with 2-picolylamine to provide the title compound (37) as the bis TFA salt. $^1$H NMR (400 MHz, Methanol-d4) δ 8.69 (dd, J=4.4, 1.5 Hz, 1H), 8.65-8.62 (m, 1H), 8.22 (td, J=7.8, 1.7 Hz, 1H), 7.88 (dd, J=8.5, 1.4 Hz, 1H), 7.81 (dd, J=8.5, 4.4 Hz, 1H), 7.73 (d, J=8.0 Hz, 1H), 7.67 (dd, J=7.5, 5.7 Hz, 1H), 4.93 (dd, J=8.8, 5.2 Hz, 1H), 4.65 (s, 2H), 2.13-1.94 (m, 3H), 1.57-1.40 (m, 3H), 1.00 (t, J=7.4 Hz, 3H). $^{19}$F NMR (377 MHz, Methanol-d4) δ -77.8. MS (m/z) 352.04 [M+H]$^+$.

Example 38

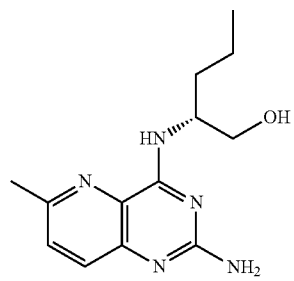

Synthesis of (R)-2-((8-chloro-2-((2,4-dimethoxybenzyl)amino)-6-methylpyrido[3,2-d]pyrimidin-4-yl)amino)pentan-1-ol (38A): 38A was synthesized in a similar fashion to 6A, instead replacing (S)-norvalinol with (R)-2-aminopentanol and 2,4-dichloropyrido[3,2-d]pyrimidine with 2,4,8-trichloro-6-methylpyrido[3,2-d]pyrimidine. MS (m/z) 446.24 [M+H]$^+$.

Synthesis of (R)-2-((2-((2,4-dimethoxybenzyl)amino)-6-methylpyrido[3,2-d]pyrimidin-4-yl)amino)pentan-1-ol (38B): 38B was synthesized in a similar fashion to 6B. MS (m/z) 412.22 [M+H]$^+$.

Synthesis of (R)-2-((2-amino-6-methylpyrido[3,2-d]pyrimidin-4-yl)amino)pentan-1-ol (38C): Compound 38C was synthesized in a similar fashion to 33, providing the title compound (38C) as its TFA salt. $^1$H NMR (400 MHz, Methanol-d4) δ 7.69 (d, J=8.5 Hz, 1H), 7.59 (d, J=8.4 Hz, 1H), 4.49 (qd, J=7.9, 6.9, 4.1 Hz, 1H), 3.71 (d, J=5.0 Hz, 2H), 2.60 (s, 3H), 1.68 (q, J=7.5 Hz, 2H), 1.44-1.33 (m, 2H), 0.93 (t, J=7.3 Hz, 3H). $^{19}$F NMR (377 MHz, Methanol-d4) δ -77.3. MS (m/z) 262.15 [M+H]$^+$.

Example 39

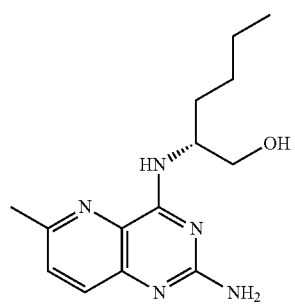

Synthesis of (R)-2-((8-chloro-2-((2,4-dimethoxybenzyl)amino)-6-methylpyrido[3,2-d]pyrimidin-4-yl)amino)hexan-1-ol (39A): 39A was synthesized in a similar fashion to 1A, instead replacing butan-1-amine with (R)-2-aminohexanol and 2,4-dichloropyrido[3,2-d]pyrimidine with 2,4,8-trichloro-6-methylpyrido[3,2-d]pyrimidine. MS (m/z) 460.21[M+H]$^+$.

Synthesis of (R)-2-((2-((2,4-dimethoxybenzyl)amino)-6-methylpyrido[3,2-d]pyrimidin-4-yl)amino)hexan-1-ol (39B): 39B was synthesized in a similar fashion to 33. MS (m/z) 426.24 [M+H]$^+$.

Synthesis of (R)-2-((2-amino-6-methylpyrido[3,2-d]pyrimidin-4-yl)amino)hexan-1-ol (39C): Compound 39C was synthesized in a similar fashion to 1B to provide the title compound (39C) as its TFA salt. $^1$H NMR (400 MHz, Methanol-d$_4$) δ 7.72 (d, J=8.5 Hz, 1H), 7.62 (d, J=8.4 Hz, 1H), 4.50 (dt, J=8.4, 5.2 Hz, 1H), 3.73 (d, J=5.1 Hz, 2H), 2.63 (s, 3H), 1.80-1.67 (m, 2H), 1.44-1.32 (m, 5H), 0.93-0.86 (m, 3H). $^{19}$F NMR (377 MHz, Methanol-d4) δ −77.3. MS (m/z) 276.17 [M+H]$^+$.

Example 40

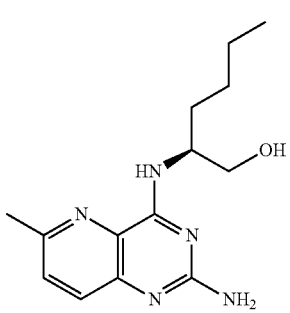

40C

Synthesis of (S)-2-((8-chloro-2-((2,4-dimethoxybenzyl)amino)-6-methylpyrido[3,2-d]pyrimidin-4-yl)amino)hexan-1-ol (40A): 40A was synthesized in a similar fashion to 1A, replacing butan-1-amine with (S)-2-aminohexanol and 2,4-dichloropyrido[3,2-d]pyrimidine with 2,4,8-trichloro-6-methylpyrido[3,2-d]pyrimidine. MS (m/z) 460.26[M+H]$^+$.

Synthesis of (S)-2-((2-((2,4-dimethoxybenzyl)amino)-6-methylpyrido[3,2-d]pyrimidin-4-yl)amino)hexan-1-ol (40b): 40b was synthesized in a similar fashion to 33. MS (m/z) 426.24 [M+H]$^+$.

Synthesis of (S)-2-((2-amino-6-methylpyrido[3,2-d]pyrimidin-4-yl)amino)hexan-1-ol (40C): Compound 40C was synthesized in a similar fashion to 1B. to provide the title compound (40C) as its TFA salt. $^1$H NMR (400 MHz, Methanol-d4) δ 7.73 (d, J=8.6 Hz, 1H), 7.63 (d, J=8.6 Hz, 1H), 4.51 (dq, J=8.5, 6.1, 5.4 Hz, 1H), 3.75 (d, J=5.2 Hz, 2H), 2.64 (s, 3H), 1.84-1.65 (m, 3H), 1.38 (qd, J=8.0, 6.4, 2.9 Hz, 5H), 0.95-0.87 (m, 4H). $^{19}$F NMR (377 MHz, Methanol-d4) δ −77.6. MS (m/z) 276.16 [M+H]$^+$.

Example 41

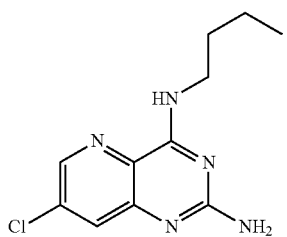

41

N$^4$-butyl-7-chloropyrido[3,2-d]pyrimidine-2,4-diamine (41). Compound 41 was synthesized following the procedure described above for preparation of 19E, instead reacting intermediate 19B with 1-butan-amine and proceeding with the reported sequence to yield the title compound (41) as the TFA salt after final HPLC purification. $^1$H NMR (400 MHz, Methanol-d4) δ 8.56 (d, J=2.1 Hz, 1H), 7.90 (d, J=2.0 Hz, 1H), 3.66 (t, J=7.3 Hz, 2H), 1.76-1.64 (m, 2H), 1.59 (s, OH), 1.43 (dq, J=14.7, 7.4 Hz, 2H), 0.98 (t, J=7.4 Hz, 3H). $^{19}$F NMR (376 MHz, Methanol-d4) δ −77.55. MS (m/z) 252.2 [M+H]$^+$.

Example 42

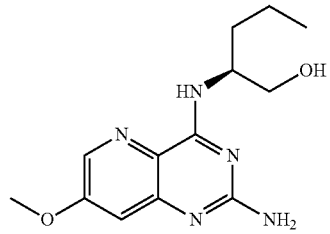

42B (S)-2-((2-amino-7-methoxypyrido[3,2-d]pyrimidin-4-yl)amino)pentan-1-ol (42B) was prepared according to the following scheme:

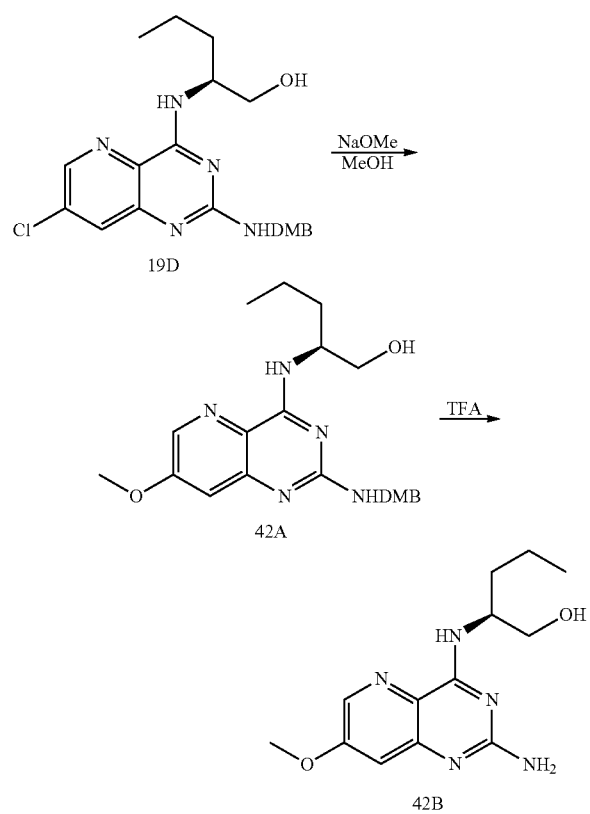

(S)-2-((2-((2,4-dimethoxybenzyl)amino)-7-methoxypyrido[3,2-d]pyrimidin-4-yl)amino)pentan-1-ol (42A): Into a vial containing (S)-2-((7-chloro-2-((2,4-dimethoxybenzyl)amino)pyrido[3,2-d]pyrimidin-4-yl)amino)pentan-1-ol (19D) (50 mg, 0.11 mmol, 1 equiv.) was added NaOMe (65 μL, 1.1 mmol, 10 equiv.) and methanol (2 mL). The mixture was heated to 150° C. for 30 min. in a microwave reactor.

The reaction mixture was partitioned between EtOAc and H₂O. The organic layer was separated, dried, and removed in vacuo. The residue was purified by column chromatography on silica to provide the title compound. MS (m/z): 428.2 [M+H].⁺

Compound 42B was synthesized via TFA treatment of 42A to yield the title compound (42B) as the TFA salt after final HPLC purification. ¹H NMR (400 MHz, Methanol-d4) δ 8.32 (d, J=2.5 Hz, 1H), 7.21 (d, J=2.5 Hz, 1H), 4.57-4.45 (m, 1H), 4.00 (s, 3H), 3.77-3.67 (m, 2H), 1.80-1.63 (m, 2H), 1.50-1.39 (m, 2H), 0.97 (t, J=7.4 Hz, 3H). ¹⁹F NMR (377 MHz, Methanol-d4) δ −77.52. MS (m/z) 278.2 [M+H]⁺.

Example 43

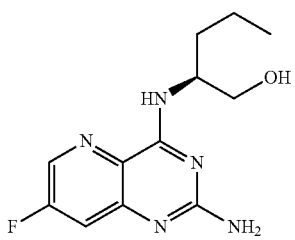
43C

Synthesis of (S)-2-((2-amino-7-fluoropyrido[3,2-d]pyrimidin-4-yl)amino)pentan-1-ol (43C):

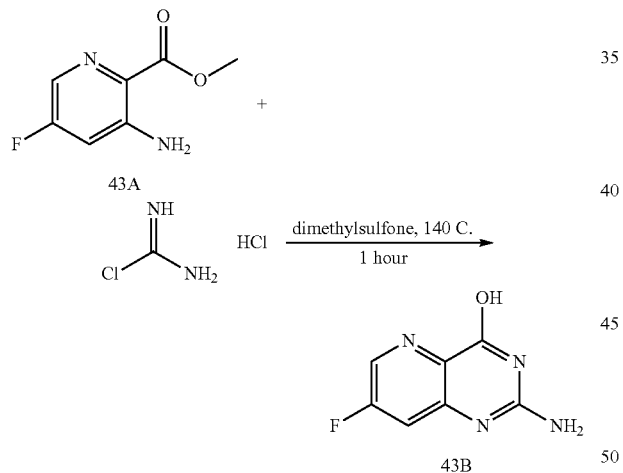

Methyl 3-amino-5-fluoropicolinate (43A) (830 mg, 4.88 mmol), chloroformamidine hydrochloride (1121.64 mg, 9.76 mmol), dimethyl sulfone (4592.09 mg, 48.78 mmol) and a stir bar were charged into a sealed pressure tube and heated to 160° C. for 1 hour. At this time reaction was allowed to cool, 50 mL of water was added and the solution stirred with heating for 30 minutes. Precipitates were filtered off and the mother liquor was purified by reverse phase HPLC using ACN/H₂O with 0.1% TFA as the eluent on a Hydro-RP column with a 2 to 5% ACN gradient. Solvents were removed under reduced pressure and the residue was azeotroped 2× with methanol, 2× with DCM before sonication in ether. Precipitates were filtered and air dried to afford 210 mg (23.9%) of 2-amino-7-fluoropyrido[3,2-d]pyrimidin-4-ol (43B) as a white solid. ¹H NMR (400 MHz, DMSO-d6) δ 8.43 (d, J=2.5 Hz, 1H), 7.48 (dd, J=10.1, 2.5 Hz, 1H), 7.23 (s, 2H). ¹⁹F NMR (376 MHz, DMSO-d6) δ −75.15, −119.96. MS (m/z) 181.0 [M+H]⁺.

Compound 43C was synthesized via a BOP-Cl promoted coupling of 43B with (S)-norvalinol, which provided the title compound (43C) as its TFA salt after final HPLC purification. ¹H NMR (400 MHz, Methanol-d4) δ 8.56 (d, J=2.4 Hz, 1H), 7.61 (dd, J=8.8, 2.5 Hz, 1H), 4.56 (dq, J=12.7, 6.4, 6.0 Hz, 1H), 3.80-3.69 (m, 2H), 1.78 (ddd, J=18.8, 11.4, 3.7 Hz, 2H), 1.53-1.33 (m, 2H), 0.97 (t, J=7.4 Hz, 3H). ¹⁹F NMR (377 MHz, Methanol-d4) δ −77.64, −118.17 (d, J=8.8 Hz). MS (m/z) 266.2 [M+H]⁺.

Example 44

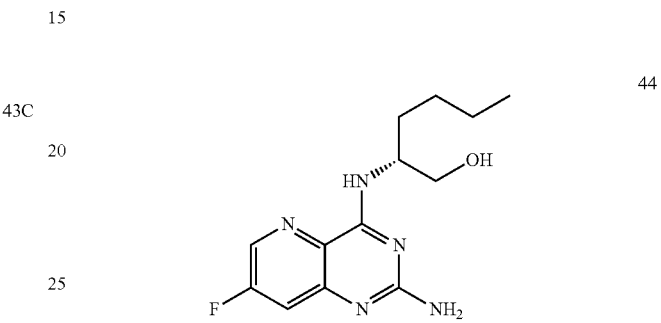
44

(R)-2-((2-amino-7-fluoropyrido[3,2-d]pyrimidin-4-yl)amino)hexan-1-ol (44). Compound 44 was synthesized following the procedure described above for preparation of 43C, instead reacting intermediate 43B with (R)-norleucinol and proceeding with the above reported sequence to yield the title compound (44) as the TFA salt after final HPLC purification. ¹H NMR (400 MHz, Methanol-d4) δ 8.57 (d, J=2.4 Hz, 1H), 7.60 (dd, J=8.8, 2.4 Hz, 1H), 4.53 (dq, J=8.7, 5.6 Hz, 1H), 3.72 (d, J=5.4 Hz, 2H), 1.72 (m, 2H), 1.52-1.28 (m, 4H), 1.04-0.82 (m, 3H). ¹⁹F NMR (377 MHz, Methanol-d4) δ −77.60, −118.13 (d, J=8.6 Hz). MS (m/z) 280.2 [M+H]⁺.

Example 45

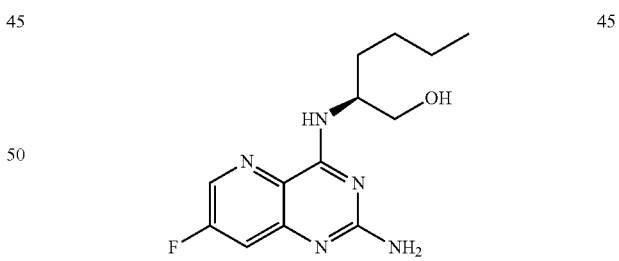
45

(S)-2-((2-amino-7-fluoropyrido[3,2-d]pyrimidin-4-yl)amino)hexan-1-ol (45). Compound 45 was synthesized following the procedure described above for preparation of 43C, instead reacting intermediate 43B with (S)-norleucinol and proceeding with the above reported sequence to yield the title compound (45) as the TFA salt after final HPLC purification. ¹H NMR (400 MHz, Methanol-d4) δ 8.57 (d, J=2.4 Hz, 1H), 7.60 (dd, J=8.8, 2.4 Hz, 1H), 4.53 (dq, J=8.7, 5.6 Hz, 1H), 3.72 (d, J=5.4 Hz, 2H), 1.72 (m, 2H), 1.52-1.28 (m, 4H), 1.04-0.82 (m, 3H). ¹⁹F NMR (376 MHz, Methanol-d4) δ −77.60, −118.13 (d, J=8.6 Hz). MS (m/z) 280.2 [M+H]⁺.

Example 46

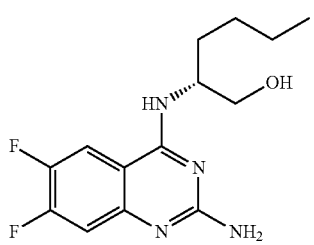

Synthesis of (R)-2-((2-amino-6,7-difluoroquinazolin-4-yl)amino)hexan-1-ol (46C)

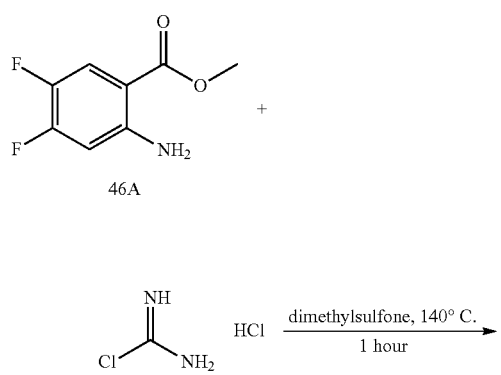

2-amino-6,7-difluoroquinazolin-4-ol (46B) was synthesized following the procedure described above for preparation of 43B, instead reacting intermediate 46A in place of 43A and proceeding with the above reported sequence to yield the title compound (46C) as the TFA salt after final HPLC purification. ¹H NMR (400 MHz, DMSO-d6)¹H NMR (400 MHz, DMSO-$d_6$) δ 7.83 (t, J=9.7 Hz, 1H), 7.31-7.22 (m, 1H), 7.19 (s, 1H). ¹⁹F NMR (376 MHz, DMSO-$d_6$) δ −74.93, −128.78, −144.35. MS (m/z) 198.0 [M+H]⁺.

Compound (46C) was synthesized via a BOP-Cl promoted coupling of 46B with (R)-norleucinol, which provided the title compound (46C) as its TFA salt after final HPLC purification. ¹H NMR (400 MHz, Methanol-d4) δ 8.29 (dd, J=11.0, 7.9 Hz, 1H), 7.35 (dd, J=10.6, 6.8 Hz, 1H), 4.67-4.53 (m, 1H), 3.80-3.59 (m, 2H), 1.77-1.63 (m, 2H), 1.49-1.30 (m, 4H), 0.91 (td, J=7.0, 6.3, 2.2 Hz, 3H). ¹⁹F NMR (376 MHz, Methanol-d4) δ −77.71, −127.97 (ddd, J=21.5, 10.6, 7.9 Hz), −142.27 (ddd, J=21.4, 11.0, 6.9 Hz). MS (m/z) 297.2 [M+H]⁺.

Example 47

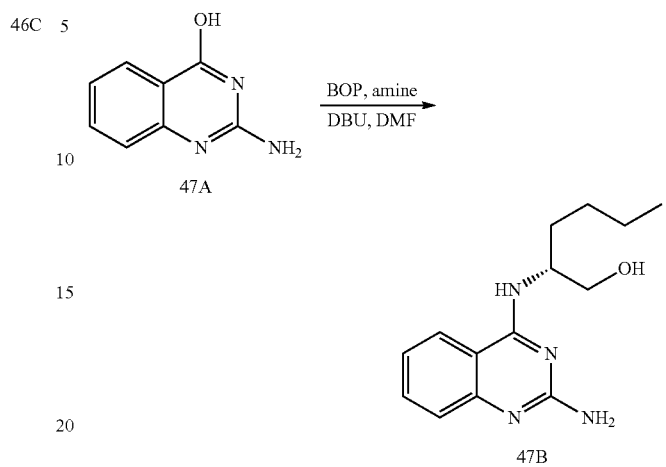

(R)-2-((2-aminoquinazolin-4-yl)amino)hexan-1-ol (47B) was synthesized via a BOP-Cl promoted coupling of 47A with (R)-norleucinol, which provided the title compound (47B) as its TFA salt after final HPLC purification. ¹H NMR (400 MHz, Methanol-d4) δ 8.22 (ddd, J=8.3, 1.3, 0.6 Hz, 1H), 7.78 (ddd, J=8.4, 7.3, 1.3 Hz, 1H), 7.50-7.33 (m, 2H), 4.71-4.56 (m, 1H), 3.80-3.61 (m, 2H), 1.81-1.64 (m, 2H), 1.47-1.31 (m, 4H), 0.92 (h, J=3.2 Hz, 3H). ¹⁹F NMR (376 MHz, Methanol-d4) δ −77.69. MS (m/z) 261.1 [M+H]⁺.

Example 48

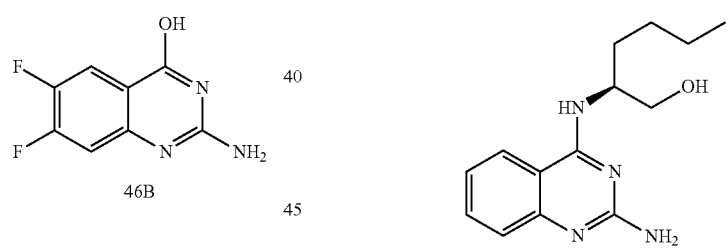

Synthesis (S)-2-((2-aminoquinazolin-4-yl)amino)hexan-1-ol (48) was prepared in a similar fashion to 47B, instead using (S)-norleucinol in place of (R)-norleucinol. ¹H NMR (400 MHz, Methanol-d4) δ 8.22 (ddd, J=8.3, 1.3, 0.6 Hz, 1H), 7.78 (ddd, J=8.4, 7.3, 1.3 Hz, 1H), 7.50-7.33 (m, 2H), 4.71-4.56 (m, 1H), 3.80-3.61 (m, 2H), 1.81-1.64 (m, 2H), 1.47-1.31 (m, 4H), 0.92 (h, J=3.2 Hz, 3H). ¹⁹F NMR (376 MHz, Methanol-d4) δ −77.69. MS (m/z) 261.1 [M+H]⁺.

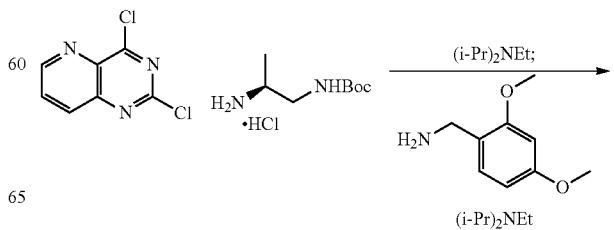

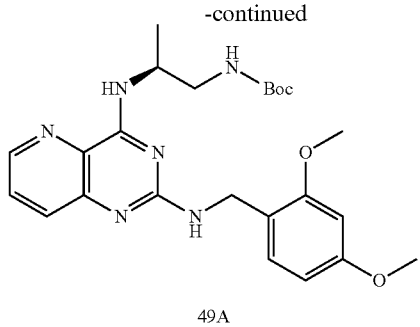

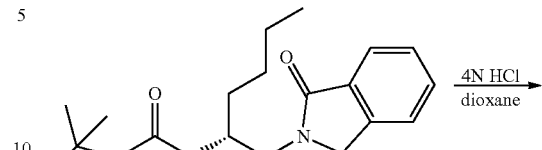

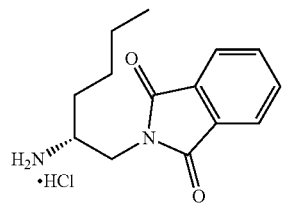

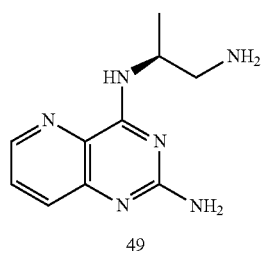

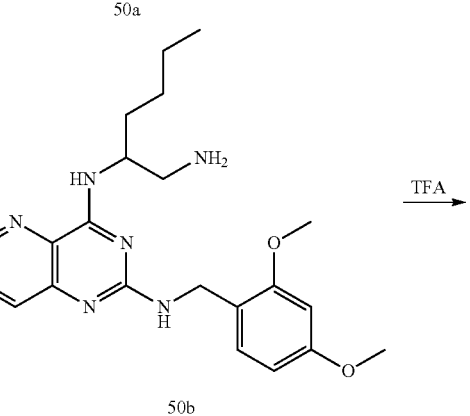

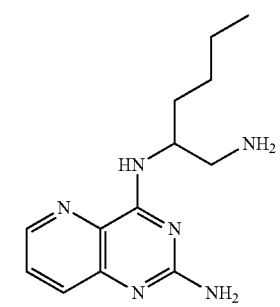

Example 49

Synthesis of (S)-tert-butyl (2-((2-((2,4-dimethoxybenzyl)amino)pyrido[3,2-d]pyrimidin-4-yl)amino)propyl)carbamate (49A). A solution of 2,4-dichloropyrido[3,2-d]pyrimidine (100 mg, 0.5 mmol) in THF (2 mL), was treated with (S)-tert-butyl (2-aminopropyl)carbamate hydrochloride butan-1-amine (CAS #959833-70-6, Fluorochem Ltd. UK), (0.03 mL, 0.56 mmol) and N,N-diisopropylethylamine (0.25 mL, 1.15 mmol). The mixture was stirred at rt for 30 minutes, 2,4-dimethoxybenzylamine (0.19 ml, 1.25 mmol) and N,N-diisopropylethylamine (0.13 mL, 0.75 mmol) were added, and the mixture was heated to 100° C. After 16 h, the reaction was cooled to rt, diluted with EtOAc, washed with water and brine, dried over $Na_2SO_4$, filtered, and concentrated in vacuo. The resulting residue was subjected to silica gel chromatography eluting with 0-100% EtOAc in hexanes to provide, after removal of volatiles in vacuo, compound 49A. LCMS (m/z): 469.18[M+H]$^+$.

Synthesis of (S)—N$^4$-(1-aminopropan-2-yl)pyrido[3,2-d]pyrimidine-2,4-diamine (49). 49A (50 mg, 0.11 mmol) was dissolved in TFA (3 mL). After 30 minutes, the reaction was diluted with water and methanol. After 60 minutes, the mixture was concentrated in vacuo. The residue was then dissolved in methanol and filtered to provide, after removal of volatiles in vacuo, compound 49 as its TFA salt. $^1$H NMR (400 MHz, Methanol-d$_4$) δ 8.67 (ddd, J=9.0, 4.2, 1.6 Hz, 1H), 7.85-7.68 (m, 2H), 4.82 (m, 1H), 3.34 (d, 2H), 1.39 (d, 3H). $^{19}$F NMR (377 MHz, Methanol-d4) δ -77.8. LCMS (m/z): 219.03 [M+H]$^+$; $t_R$=0.29 min. (LC/MS HPLC method B).

Example 50

Synthesis of (R)-2-(2-aminohexyl)isoindoline-1,3-dione hydrochloride (50a). To phthalimide 51c (180 mg, 0.53 mmol) was added 4N HCl in dioxane (20 mL). The reaction was stirred at rt for 6 h and then the volatiles were removed in vacuo to provide crude 50a which was carried forward directly into the next step without further purification. LCMS (m/z): 246.93 [M+H]$^+$.

Synthesis of (R)-methyl 2-((2-((2,4-dimethoxybenzyl)amino)pyrido[3,2-d]pyrimidin-4-yl)amino)hexanoate (50b). A solution of 2,4-dichloropyrido[3,2-d]pyrimidine (100 mg, 0.5 mmol) in THF (2 mL) was treated with 50a, (150 mg, 0.53 mmol) and N,N-diisopropylethylamine (0.25 mL, 1.15 mmol). The mixture was stirred at rt for 30 minutes, and 2,4-dimethoxybenzylamine (0.38 mL, 2.5 mmol) and N,N-diisopropylethylamine (0.13 mL, 0.75 mmol) were added and the mixture was heated to 125° C. After 24 h, the reaction was cooled to rt, diluted with EtOAc (50 mL), washed with water (25 mL), brine (25 mL), dried over Na$_2$SO$_4$, filtered and concentrated in vacuo. The resulting residue was subjected to silica gel chromatography eluting with 0-100% EtOAc in hexanes to give, after removal of volatiles in vacuo, compound 50b.

Synthesis of (R)—N$^4$-(1-aminohexan-2-yl)pyrido[3,2-d]pyrimidine-2,4-diamine (50). 50b (15 mg, 0.04 mmol) was dissolved in TFA (3 mL). After 60 minutes the mixture was concentrated to a residue in vacuo followed by co-evaporation with MeOH, to provide the title compound 50 as its bis-TFA salt. $^1$H NMR (400 MHz, MeOH-d$_4$) δ 8.68 (m, 1H), 7.81-7.83 (m, 2H), 4.89 (m, 1H), 3.91 (m, 2H), 3.61 (m, 1H) 1.92-1.79 (m, 2H), 1.55-1.48 (m, 4H), 0.98 (t, J=7.4 Hz, 3H). $^{19}$F NMR (377 MHz, MeOH-d4) δ −77.9. LCMS (m/z): 261.14 [M+H]$^+$; t$_R$=0.30 min.

Example 51

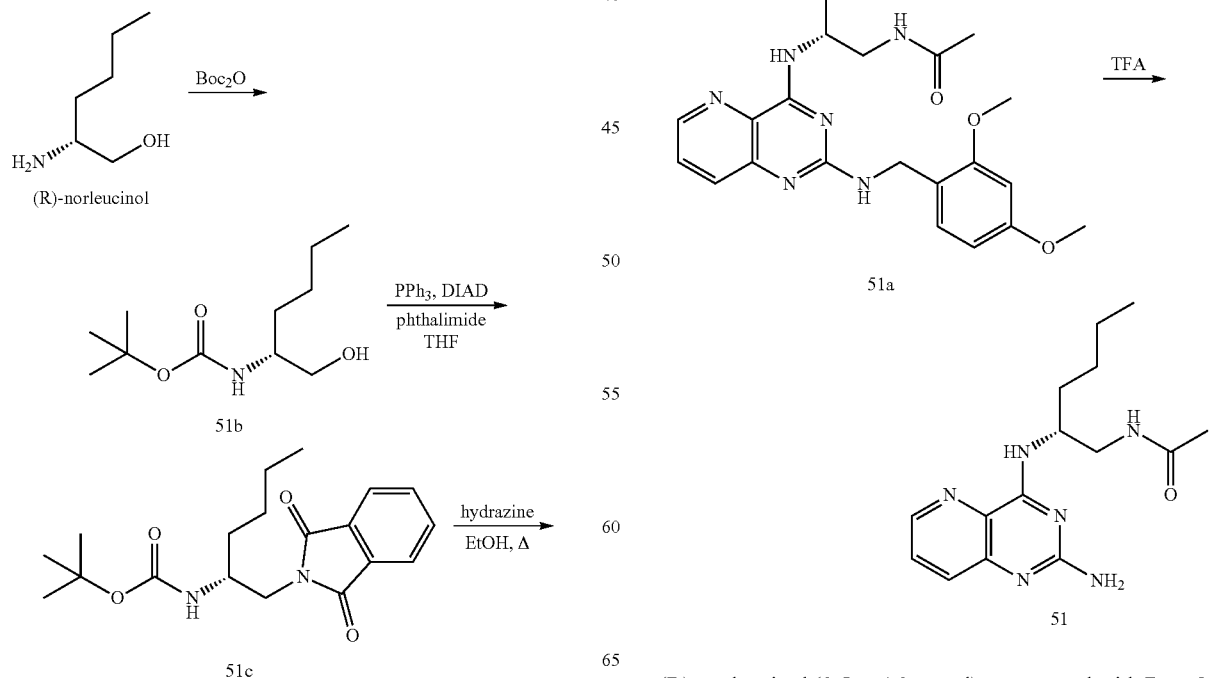

(R)-norleucinol (0.5 g, 4.3 mmol) was treated with Boc$_2$O (1.2 equiv, 5.2 mmol) and excess N,N-diisopropylethylamine in DCM (20 mL). The reaction mixture was stirred for 3h and then filtered through a silica gel plug. Removal of the volatiles provided 51b as a crude residue that was used without further purification. LCMS (m/z): 218.23 [M+H]+.

Compound 51b (0.7 g, 3.22 mmol) was reacted with PPh$_3$ (1.1 g, 3.9 mmol), phthalimide (573 mg, 3.9 mmol), and DIAD (810 mg, 4.0 mmol) in THF (30 mL). The mixture was stirred for 3 h, and then partitioned between EtOAc (200 mL) and water (200 mL). The organic layer was separated, washed with brine (100 mL), dried over Na$_2$SO$_4$, filtered and concentrated in vacuo. The residue was subjected to silica gel chromatography eluting with 0-100% EtOAc in hexanes to provide 51c. LCMS (m/z): 347.24 [M+H]+.

Imide 51c (300 mg, 0.87 mmol) was treated with excess hydrazine hydrate (0.2 mL, 6.25 mmol) in EtOH (30 mL) and refluxed for 16 h. The mixture was concentrated in vacuo to provide intermediate 51d as a crude residue that was carried forward directly. Intermediate 51d (0.87 mmol) was dissolved in DCM (10 mL) and treated with AcCl (0.1 mL, 1.2 mmol), followed by TEA (0.26 mL, 1.8 mmol). The mixture was stirred for 3 h, and then the reaction was diluted with DCM (50 mL). The mixture was then washed with water (50 mL), brine (50 mL), dried over Na$_2$SO$_4$, filtered and then concentrated under reduced pressure to provide 51e. LCMS (m/z): 259.21 [M+H]+.

Intermediate 51e (0.3 g) was treated with 4N HCl in dioxanes (20 mL) and stirred for 4 h at rt. The volatiles were removed in vacuo to provide the hydrochloride 51f which was used without further purification. LCMS (m/z): 159.45 [M+H]+.

Synthesis of (R)—N-(2-((2-((2,4-dimethoxybenzyl)amino)pyrido[3,2-d]pyrimidin-4-yl)amino)hexyl)acetamide (51a). A solution of 2,4-dichloropyrido[3,2-d]pyrimidine (100 mg, 0.5 mmol) in THF (2 mL was treated with 51f, (200 mg, 0.53 mmol) and N,N-diisopropylethylamine (0.25 mL, 1.15 mmol). After the mixture was stirred for 30 minutes, 2,4-dimethoxybenzylamine (0.38 mL, 2.5 mmol) and N,N-diisopropylethylamine (0.13 mL, 0.75 mmol) were added, and the mixture was heated to 115° C. After heating for 16 h, the reaction was cooled to rt, diluted with EtOAc (100 mL), washed with water (100 mL), brine (100 mL), dried over Na$_2$SO$_4$, filtered and concentrated in vacuo. The resulting residue was subjected to silica gel flash chromatography eluting with 0-100% EtOAc in hexanes to provide 51a. LCMS (m/z): 453.33 [M+H]+.

Synthesis of (R)—N-(2-((2-aminopyrido[3,2-d]pyrimidin-4-yl)amino)hexyl)acetamide (51). 51a (60 mg, 0.133 mmol) was dissolved in TFA (3 mL). After 60 minutes, the mixture was concentrated in vacuo. The residue was taken up in MeOH, filtered and concentrated in vacuo, to give the title compound 51 as its TFA salt. $^1$H NMR (400 MHz, MeOH-d$_4$) 8.65 (dd, J=4.3, 1.5 Hz, 1H), 7.86-7.73 (m, 2H), 4.68-4.55 (m, 4H), 3.59 (dd, J=13.9, 4.3 Hz, 4H), 3.34-3.23 (m, 3H), 1.88 (s, 3H), 1.78-1.67 (m, 2H), 1.39 (ddd, J=7.7, 5.1, 2.4 Hz, 4H), 0.91 (ddt, J=8.3, 4.7, 3.0 Hz, 3H). $^{19}$F NMR (377 MHz, MeOH-d4) δ −77.7. LCMS (m/z): 303.15 [M+H]+; $t_R$=0.68 min. (LC/MS HPLC method B).

Example 52

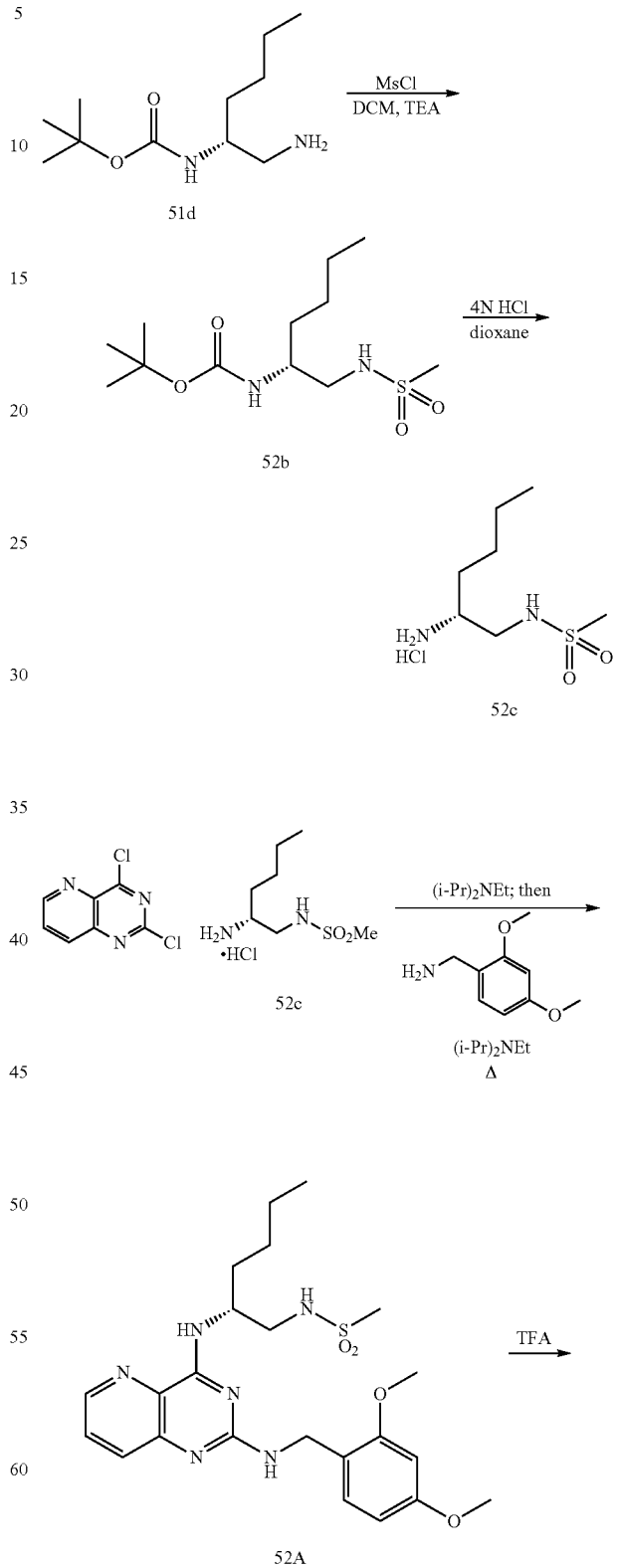

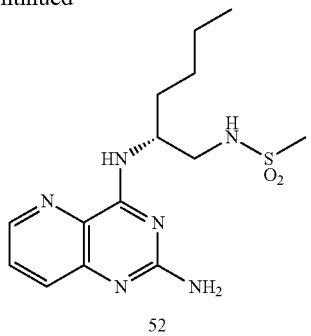

52

N-Boc-protected intermediate 51d (188 mg, 0.87 mmol) was dissolved in DCM (10 mL) and treated with methanesulfonyl chloride (0.78 μL, 114 mg, 1 mmol) and TEA (0.26 mL, 1.8 mmol). After 3 h, EtOAc (100 mL) was added and the resulting mixture washed with water (100 mL), brine (100 mL), dried over $Na_2SO_4$, filtered and concentrated in vacuo to provide 52b. LCMS (m/z): 295.24 $[M+H]^+$.

Following the synthesis of 51f from 51e, intermediate 52b (0.87 mmol) was converted to the crude hydrochloride salt 52c which was then carried forward without purification.

Synthesis of (R)—N-(2-((2-((2,4-dimethoxybenzyl)amino)pyrido[3,2-d]pyrimidin-4-yl)amino)hexyl)methanesulfonamide (52A). A solution of 2,4-dichloropyrido[3,2-d]pyrimidine (50 mg, 0.25 mmol) in THF (2 mL) was treated with crude 52c, (85 mg, 0.43 mmol) and N,N-diisopropylethylamine (0.25 mL, 1.15 mmol). The mixture was stirred at rt for 30 minutes, 2,4-dimethoxybenzylamine (0.19 mL, 1.25 mmol) and N,N-diisopropylethylamine (0.13 mL, 0.75 mmol) were added, and the mixture was heated to 115° C. After 16 h, the reaction was cooled to rt, diluted with EtOAc (100 mL), washed with de-ionised water (100 mL), brine (100 mL), dried over $Na_2SO_4$, filtered and concentrated in vacuo. The residue was subjected to silica gel chromatography eluting with 0-100% EtOAc in hexanes to provide 52A. LCMS (m/z): 489.25 $[M+H]^+$.

Synthesis of (R)—N-(2-((2-aminopyrido[3,2-d]pyrimidin-4-yl)amino)hexyl)methanesulfonamide (52). 52A (30 mg, 0.06 mmol) was dissolved in TFA (3 mL). After 60 minutes, the mixture was concentrated in vacuo. The residue was then diluted with MeOH, filtered, and concentrated in vacuo to afford the title product 52 as its TFA salt. $^1H$ NMR (400 MHz, MeOH-$d_4$) δ 8.65 (dd, J=4.4, 1.4 Hz, 1H), 7.84 (dd, J=8.5, 1.4 Hz, 1H), 7.76 (dd, J=8.5, 4.4 Hz, 1H), 4.58 (t, J=6.1 Hz, 1H), 3.52-3.26 (m, 2H), 2.93 (s, 3H), 1.75 (dd, J=9.6, 4.0 Hz, 2H), 1.39 (td, J=8.5, 7.6, 3.5 Hz, 4H), 0.91 (m, 3H). $^{19}F$ NMR (377 MHz, MeOH-d4) δ −77.7. LCMS (m/z): 339.21 $[M+H]^+$; $t_R$=0.83 min. (LC/MS HPLC method B).

Example 53

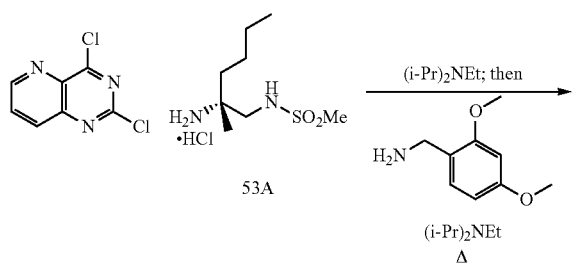

53A

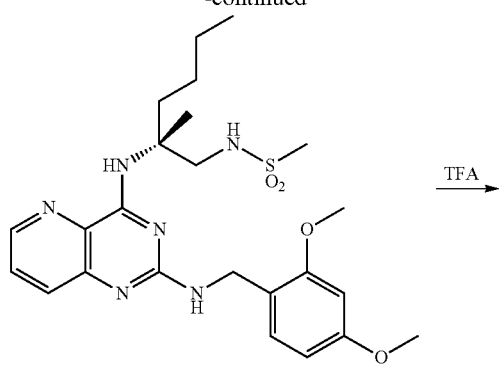

53B

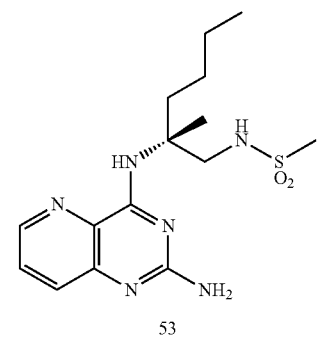

53

Compound 61C (0.22 g, 0.69 mmol) was mesylated following the procedure for the formation of 61D but instead replacing acetyl chloride with methanesulfonyl chloride (0.06 mL, 0.8 mmol) to give a quantitative yield of the corresponding mesylated intermediate. The resulting sulfonamide was then subjected to Pd/C hydrogenation followed by N-BOC removal, as described in the preparation of 61E from 61D to give the crude product 53A as its hydrochloride salt. LCMS (m/z): 209.1 $[M+H]^+$.

Synthesis of (R)—N-(2-((2-((2,4-dimethoxybenzyl)amino)pyrido[3,2-d]pyrimidin-4-yl)amino)-2-methylhexyl)methanesulfonamide (53B). A solution of 2,4-dichloropyrido[3,2-d]pyrimidine (100 mg, 0.5 mmol) in THF (4 mL) was treated with crude 53A (0.69 mmol), and N,N-diisopropylethylamine (0.5 mL, 2.3 mmol). After heating at 75° C. for 4 h, 2,4-dimethoxybenzylamine (0.4 mL, 2.5 mmol) and additional N,N-diisopropylethylamine (0.26 mL, 1.5 mmol) were added and the mixture was heated to 115° C. After 16 h, the reaction was cooled to rt, diluted with EtOAc (100 mL), washed with de-ionised water (100 mL), brine (100 mL), dried over $Na_2SO_4$, filtered and concentrated under reduced pressure. The residue was subjected to silica gel chromatography eluting with 0-100% EtOAc to give 53B. LCMS (m/z): 503.28 $[M+H]^+$.

Synthesis of (R)—N-(2-((2-aminopyrido[3,2-d]pyrimidin-4-yl)amino)-2-methylhexyl)methanesulfonamide (53). 53B (75 mg, 0.15 mmol) was dissolved in TFA (3 mL). After 60 minutes, the mixture was concentrated in vacuo. The residue was dissolved in MeOH, filtered and volatiles removed in vacuo to afford the title product 53, as its TFA salt. $^1H$ NMR (400 MHz, MeOH-$d_4$) δ 8.63 (dd, J=4.3, 1.4 Hz, 1H), 7.79 (dd, J=8.4, 1.5 Hz, 1H), 7.73 (dd, J=8.4, 4.3 Hz, 1H), 3.78 (m, 2H), 2.93 (s, 3H), 2.25 (m, 1H), 1.82 (dd, J=9.6, 4.0 Hz, 2H), 1.56 (s, 3H), 1.37 (td, J=8.4, 7.5, 3.4 Hz, 4H), 0.93 (m, 3H). $^{19}$F NMR (377 MHz, MeOH-d4) δ −77.6. LCMS (m/z): 353.18 [M+H]$^+$; $t_R$=0.83 min. (LC/MS HPLC method B).

Example 54

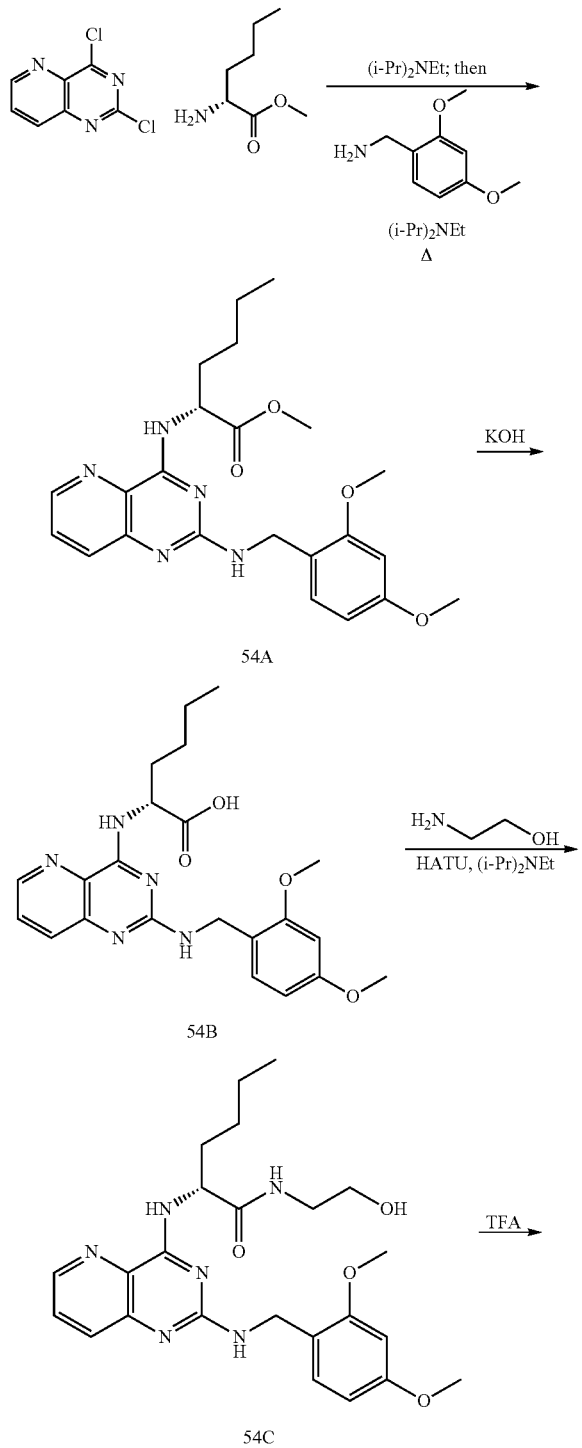

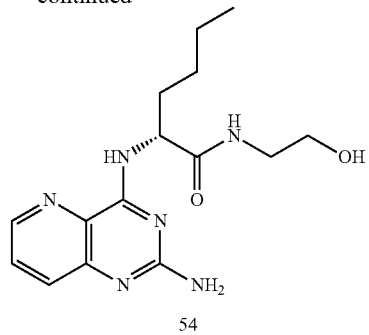

Synthesis of (R)-methyl 2-((2-((2,4-dimethoxybenzyl)amino)pyrido[3,2-d]pyrimidin-4-yl)amino)hexanoate (54A). To a solution of 2,4-dichloropyrido[3,2-d]pyrimidine (CAS #39551-54-7, supplied by Astatech, Inc.) (500 mg, 2.5 mmol) in THF (10 mL) was added D-norleucine methyl ester hydrochloride (454 mg, 2.5 mmol) and N,N-diisopropylethylamine (1.3 mL, 7.5 mmol). After stirring at rt for 30 minutes, 2,4-dimethoxybenzylamine (1.9 mL, 12.5 mmol) and N,N-diisopropylethylamine (1.3 mL, 7.5 mmol) were added and the mixture was heated to 100° C. After 16 h, the reaction was cooled to rt, diluted with EtOAc (100 mL), washed with water (100 mL), brine (100 mL), dried over Na$_2$SO$_4$, filtered and concentrated in vacuo. The residue was subjected to silica gel chromatography eluting with hexanes-EtOAc to provide 54A. $^1$H NMR (400 MHz, Chloroform-d) δ 8.33 (dd, J=4.2, 1.5 Hz, 1H), 7.68 (d, J=7.6 Hz, 1H), 7.43 (dd, J=8.5, 4.2 Hz, 1H), 7.28 (s, 1H), 6.46 (d, J=2.3 Hz, 1H), 6.41 (dd, J=8.2, 2.4 Hz, 1H), 4.88 (q, J=7.3 Hz, 1H), 4.59 (d, J=6.0 Hz, 2H), 3.85 (s, 3H), 3.79 (s, 3H), 3.75 (s, 3H), 2.04-1.95 (m, 1H), 1.88 (dq, J=14.8, 7.6 Hz, 1H), 1.40 (dddd, J=26.8, 15.8, 6.9, 2.6 Hz, 5H), 0.91 (t, J=7.1 Hz, 3H). LCMS (m/z): 440.49 [M+H]$^+$; $t_R$=0.77 min. on LC/MS Method A.

Synthesis of (R)-2-((2-((2,4-dimethoxybenzyl)amino)pyrido[3,2-d]pyrimidin-4-yl)amino)hexanoic acid (54B). To a solution of 54A (750.7 mg, 1.71 mL) in THF (3.6 mL) and MeOH (3.6 mL) was added 1N KOH$_{(aq)}$ (3.6 mL). After 4 h, the reaction was was neutralized to pH 7 using 1M HCl$_{(aq)}$. Concentration of the mixture in vacuo afforded the crude product 54B. $^1$H NMR (400 MHz, DMSO-d$_6$) δ 8.34 (d, J=4.1 Hz, 1H), 7.77 (s, 1H), 7.61 (d, J=6.5 Hz, 1H), 7.53 (dd, J=8.5, 4.2 Hz, 1H), 7.10 (s, 1H), 6.53 (d, J=2.3 Hz, 1H), 6.42 (dd, J=7.9, 2.0 Hz, 1H), 4.65 (s, 1H), 4.44 (s, 2H), 3.81 (s, 3H), 3.71 (s, 3H), 1.90 (s, 2H), 1.30 (s, 4H), 0.84 (s, 3H). LCMS (m/z): 426.16 [M+H]$^+$; $t_R$=0.67 min. on LC/MS Method A.

Synthesis of (R)-2-((2-((2,4-dimethoxybenzyl)amino)pyrido[3,2-d]pyrimidin-4-yl)amino)-N-(2-hydroxyethyl)hexanamide (54C). To a solution of crude 54B (50 mg, 0.12 mmol), N,N-diisopropylethylamine (0.15 mL, 0.86 mmol), and 2-aminoethanol (0.05 mL, 0.59 mmol) in NMP (12 mL) was added HATU (96 mg, 0.25 mmol). After 16 h the mixture was subjected to preparative HPLC (Synergi 4u Polar-RP 80A, Axia; 10% aq. acetonitrile-70% aq. acetonitrile with 0.1% TFA, over 20 min. gradient) to afford 54C as its TFA salt. LCMS (m/z): 469.23 [M+H]$^+$; $t_R$=0.70 min. on LC/MS Method A.

Synthesis of (R)-2-((2-aminopyrido[3,2-d]pyrimidin-4-yl)amino)-N-(2-hydroxyethyl)hexanamide (54). To 54C (10 mg, 0.02 mmol) was added TFA (3 mL). After 4 h, MeOH (2 mL) and water (2 mL) were added to the mixture. After 16 h, the mixture was concentrated in vacuo and then co-evaporated with MeOH three times. The residue was subjected to preparative HPLC (Synergi 4u Polar-RP 80A, Axia; 10% aq. acetonitrile-60% aq. acetonitrile with 0.1% TFA, over 20 min. gradient) to give 54 as a TFA salt. $^1$H NMR (400 MHz, MeOH-d$_4$) δ 8.68 (dd, J=4.4, 1.5 Hz, 1H), 7.86 (dd, J=8.5, 1.5 Hz, 1H), 7.80 (dd, J=8.5, 4.4 Hz, 1H), 4.81 (dd, J=8.2, 5.7 Hz, 1H), 3.66-3.56 (m, 2H), 3.43-3.32 (m, 2H), 2.12-1.90 (m, 2H), 1.49-1.36 (m, 4H), 0.98-0.89 (m, 3H). $^{19}$F NMR (377 MHz, MeOH-d$_4$) δ -77.83. LCMS (m/z): 319.23 [M+H]$^+$; t$_R$=0.49 min. on LC/MS Method A.

Example 55

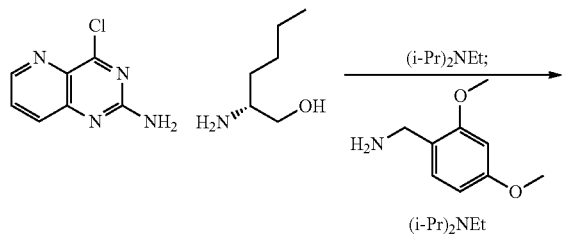

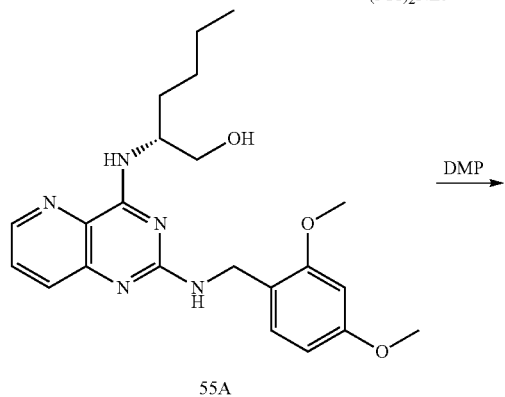

55A

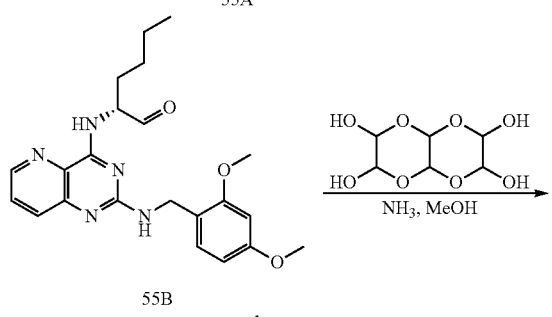

55B

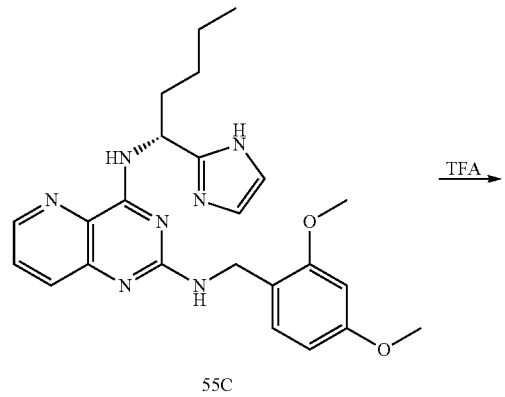

55C

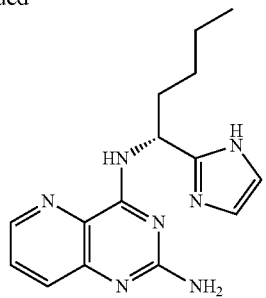

55

Synthesis of (R)-2-((2-((2,4-dimethoxybenzyl)amino)pyrido[3,2-d]pyrimidin-4-yl)amino)hexan-1-ol (55A). To a solution of 2,4-dichloropyrido[3,2-d]pyrimidine (500 mg, 2.5 mmol) in THF (15 mL) was added (R)-norleucinol (293 mg, 2.5 mmol) and N,N-diisopropylethylamine (1.3 mL, 7.5 mmol). After stirring at rt for 30 minutes, 2,4-dimethoxybenzylamine (1.9 mL, 12.5 mmol) and N,N-diisopropylethylamine (1.3 mL, 7.5 mmol) were added and the mixture was heated to 100° C. After 16 h, the reaction was cooled to rt, diluted with EtOAc (100 mL), washed with water (100 mL), brine (100 mL), dried over Na$_2$SO$_4$, filtered and concentrated in vacuo. The residue was subjected to silica gel chromatography eluting with hexanes-EtOAc to give 55A. $^1$H NMR (400 MHz, Chloroform-d) δ 8.32 (s, 1H), 7.74 (s, 1H), 7.46 (s, 1H), 6.49-6.37 (m, 3H), 4.60 (d, J=5.9 Hz, 3H), 3.86 (s, 5H), 3.79 (s, 5H), 1.55 (s, 2H), 1.45-1.33 (m, 6H), 0.91 (t, J=7.0 Hz, 4H). LCMS (m/z): 412.20 [M+H]$^+$; t$_R$=0.89 min. on LC/MS Method A.

Synthesis of (R)-2-((2-((2,4-dimethoxybenzyl)amino)pyrido[3,2-d]pyrimidin-4-yl)amino)hexanal (55B). To a solution of 55A (100 mg, 0.24 mmol) in DCM (5 mL) at 0° C. was added Dess-Martin periodinane (248 mg, 0.58 mmol). The reaction was warmed to rt and stirred for 24 h. The reaction was diluted with DCM (5 mL) and then quenched with a mixture of sat. Na$_2$S$_2$O$_{3(aq)}$ (5 mL) and sat. NaHCO$_{3(aq)}$ (5 mL). The organic layer was separated and the aqueous layer was extracted with DCM (2×10 mL). The combined organics were washed with brine (100 mL), dried over Na$_2$SO$_4$, filtered and concentrated in vacuo. The residue was subjected to silica gel chromatography eluting with hexanes-EtOAc to give 55B. LCMS (m/z): 410.19 [M+H]$^+$; t$_R$=0.97 min. on LC/MS Method A.

Synthesis of (R)—N$^4$-(1-(1H-imidazol-2-yl)pentyl)-N$^2$-(2,4-dimethoxybenzyl)pyrido[3,2-d]pyrimidine-2,4-diamine (55C). To a solution of 55B (50 mg, 0.12 mmol) in MeOH (2 mL) was added gyloxal trimer dihydrate (12 mg, 0.06 mg) and ammonia in MeOH (2M, 0.28 mL, 0.55 mmol). After 24 h, additional gyloxal trimer dihydrate (12 mg, 0.06 mg) and ammonia in MeOH (2M, 0.28 mL, 0.55 mmol) were added. After 18 h, the mixture was concentrated in vacuo. The residue was diluted with water (10 mL) and extracted with EtOAc (4×10 mL). The combined organics were dried over Na$_2$SO$_4$, filtered and concentrated in vacuo to afford the crude 55C. LCMS (m/z): 448.15 [M+H]$^+$; t$_R$=0.62 min. on LC/MS Method A.

Synthesis of (R)—N$^4$-(1-(1H-imidazol-2-yl)pentyl)pyrido[3,2-d]pyrimidine-2,4-diamine (55). To 55C (50 mg, 0.11 mmol) was added TFA (2 mL). After 90 minutes, MeOH (2 mL) and water (2 mL) were added to the mixture. After 16 h, the mixture was concentrated in vacuo and co-evaporated with MeOH (×3). The residue was subjected to preparative HPLC (Synergi 4u Polar-RP 80A, Axia; 10% aq. acetonitrile-60% aq. acetonitrile with 0.1% TFA, over 20 min. gradient) to give 55 as a TFA salt. $^1$H NMR (400 MHz, MeOH-d$_4$) δ 8.70 (dd, J=4.4, 1.4 Hz, 1H), 7.93 (dd, J=8.5, 1.4 Hz, 1H), 7.83 (dd, J=8.5, 4.4 Hz, 1H), 7.52 (s, 2H), 5.92-5.71 (m, 1H), 2.30 (td, J=9.3, 8.7, 4.3 Hz, 2H), 1.64-1.34 (m, 4H), 0.95 (t, J=7.0 Hz, 3H). $^{19}$F NMR (377 MHz, MeOH-d$_4$) δ −77.73. LCMS (m/z): 298.05[M+H]$^+$; $t_R$=0.46 min. on LC/MS Method A.

Example 56

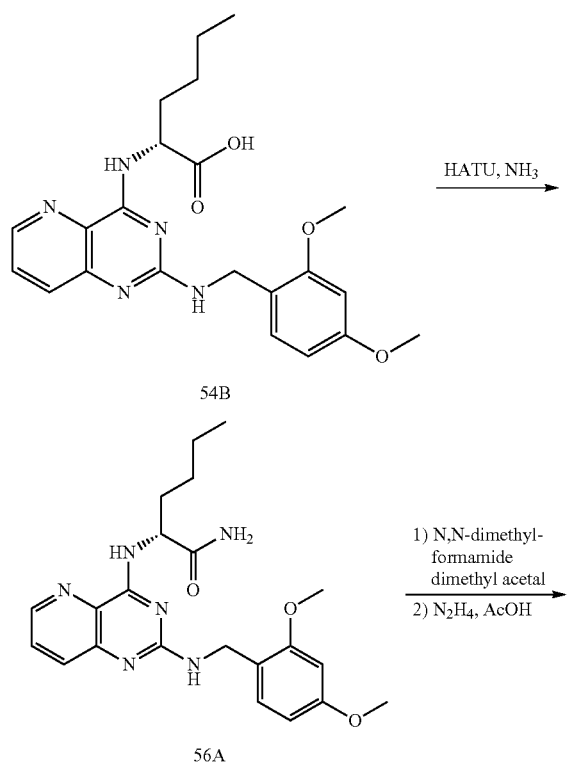

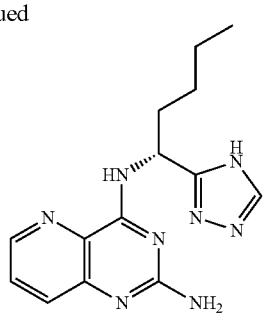

Synthesis of (R)-2-((2-((2,4-dimethoxybenzyl)amino)pyrido[3,2-d]pyrimidin-4-yl)amino)hexanamide (56A). To a solution of 54B (50 mg, 0.12 mmol), N,N-diisopropylethylamine (0.1 mL, 0.57 mmol), and ammonia in dioxane (0.5 M, 1.2 mL, 0.59 mmol) in NMP (6 mL) was added HATU (174 mg, 0.46 mmol). After 4 h the mixture was subjected to preparative HPLC (Synergi 4u Polar-RP 80A, Axia; 10% aq. acetonitrile-70% aq. acetonitrile with 0.1% TFA, over 20 min. gradient) to afford 56A as a TFA salt. LCMS (m/z): 425.18 [M+H]$^+$; $t_R$=0.69 min. on LC/MS Method A.

Synthesis of (R)—N$^4$-(1-(4H-1,2,4-triazol-3-yl)pentyl)-N$^2$-(2,4-dimethoxybenzyl)pyrido[3,2-d]pyrimidine-2,4-diamine (56B). A mixture of 56A (70 mg, 0.17 mmol) and N,N-dimethylformamide dimethyl acetal (2 mL, 16 mmol) was heated to 120° C. After 2 h, the mixture was cooled to rt and concentrated in vacuo. The crude residue was dissolved in AcOH (2 mL) and treated with hydrazine monohydrate (0.02 mL, 0.42 mmol). The mixture was heated to 90° C. for 24 h. The mixture was concentrated in vacuo to afford the crude 56B which was used without further purification. LCMS (m/z): 449.23 [M+H]$^+$; $t_R$=0.83 min. on LC/MS Method A.

Synthesis of (R)—N$^4$-(1-(4H-1,2,4-triazol-3-yl)pentyl)pyrido[3,2-d]pyrimidine-2,4-diamine (56). To crude 56B was added TFA (3 mL). After 60 minutes, the mixture was concentrated in vacuo and the residue was diluted with MeOH (3.5 mL) and water (3.5 mL). After 90 min., the mixture was concentrated and then subjected to preparative HPLC (Synergi 4u Polar-RP 80A, Axia; 10% aq. acetonitrile-60% aq. acetonitrile with 0.1% TFA, over 20 min. gradient) to afford 56 as a TFA salt. $^1$H NMR (400 MHz, MeOH-d$_4$) δ 8.67 (dd, J=4.4, 1.4 Hz, 1H), 8.47 (s, 1H), 7.86 (dd, J=8.5, 1.4 Hz, 1H), 7.79 (dd, J=8.5, 4.4 Hz, 1H), 5.72 (dd, J=8.4, 6.3 Hz, 1H), 2.30-2.09 (m, 2H), 1.49-1.34 (m, 4H), 0.96-0.89 (m, 3H). $^{19}$F NMR (377 MHz, MeOH-d$_4$) δ −77.98. LCMS (m/z): 299.15 [M+H]$^+$; $t_R$=0.62 min. on LC/MS Method A.

Example 57

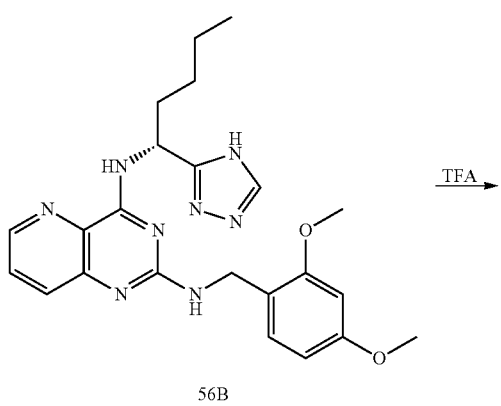

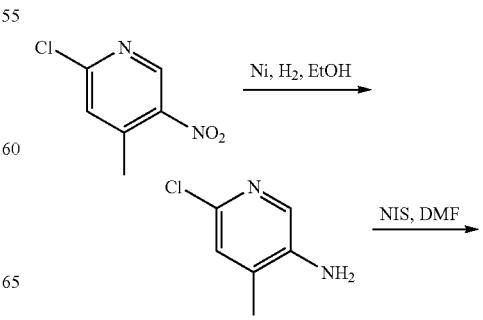

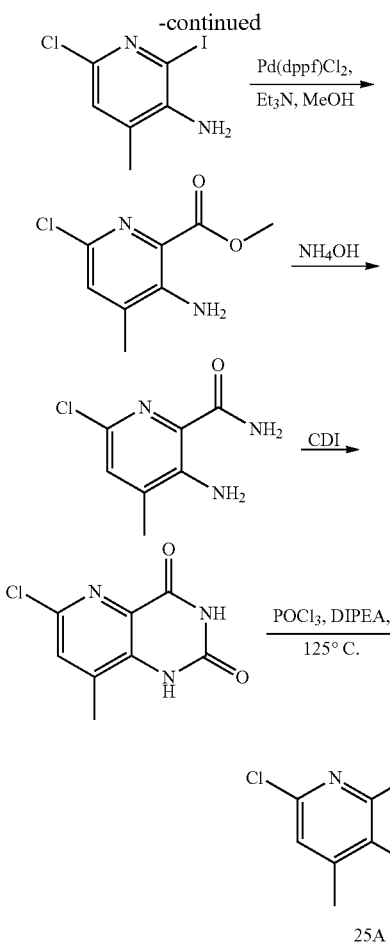

2-Chloro-4-methyl-5-nitropyridine (10.0 g, 57.8 mmol) was dissolved in EtOH (100 mL) and Raney nickel (3 g) was added. The reaction mixture was stirred under H₂ overnight. The mixture was filtered, concentrated under vacuum, and washed with petroleum ether/EtOAc=5:1 (50 mL) to give crude 6-chloro-4-methylpyridin-3-amine.

6-Chloro-4-methylpyridin-3-amine (22.0 g, 154.9 mmol) was dissolved in DMF (150 mL) and treated with NIS (41.8 g, 185.9 mmol). The reaction mixture was stirred at rt overnight, then water (200 mL) was added, and the mixture was extracted with EtOAc (3×200 mL). The combined organics were concentrated in vacuo and the residue was subjected to silica gel flash chromatography eluting with Et₂O-EtOAc to give 6-chloro-2-iodo-4-methylpyridin-3-amine. ¹H NMR (DMSO-d₆, 400 MHz): δ 7.11 (s, 1H), 5.23 (s, 2H), 2.15 (s, 3H) ppm.

To a solution of 6-chloro-2-iodo-4-methylpyridin-3-amine (30.0 g, 111.7 mmol) in MeOH (200 mL) was added Pd(dppf)Cl₂ (4.09 g, 5.5 mmol), Et₃N (45.1 g, 447 mmol) and the reaction mixture was stirred at rt overnight. The residue was subjected to silica gel chromatography eluting with Et₂O-EtOAc to give 6-chloro-2-iodo-4-methylpyridin-3-amine. ¹H NMR (DMSO-d₆, 400 MHz): δ 7.33 (d, J=0.8, 1H), 6.74 (s, 2H), 3.82 (s, 3H), 3.18 (d, J=0.4, 3H) ppm.

To a solution of 6-chloro-2-iodo-4-methylpyridin-3-amine (18.8 g, 94 mmol) in NH₄OH (180 mL) was added MeOH (10 mL) and the reaction mixture was stirred at rt overnight. The mixture was filtered and the collected solid washed with petroleum ether/EtOAc (5:1, 50 mL) to afford 3-amino-6-chloro-4-methylpicolinamide. ¹H NMR (DMSO-d₆, 400 MHz): δ 7.76 (s, 1H), 7.43 (s, 1H), 7.27 (s, 1H), 6.92 (s, 2H), 2.15 (s, 3H) ppm.

A solution of 3-amino-6-chloro-4-methylpicolinamide (10 g, 54.1 mmol) and CDI (8.02 g; 27.02 mmol) in 1,4-dioxane (200 mL) was stirred at 110° C. for 30 minutes. The mixture was filtered and the collected solids were washed with EtOAc (30 mL). The organics were concentrated in vacuo to give crude 6-chloro-8-methylpyrido[3,2-d]pyrimidine-2,4(1H,3H)-dione. ¹H NMR (CDCl₃, 400 MHz) δ 7.70 (d, J=1.2 Hz, 1H), 2.76 (d, J=0.8 Hz, 3H) ppm.

Synthesis of 2,4,6-trichloro-8-methylpyrido[3,2-d]pyrimidine (25A). A solution of 6-chloro-8-methylpyrido[3,2-d]pyrimidine-2,4(1H,3H)-dione (32 g, 151.6 mmol) and N,N-diisopropylethylamine (50 mL) in POCl₃ (320 mL) was stirred at 125° C. overnight. The mixture was concentrated in vacuo and the residue was subjected to silica gel flash chromatography eluting with Et₂O-EtOAc to give 25A. ¹H NMR (CDCl₃, 400 MHz) δ 7.70 (d, J=1.2 Hz, 1H), 2.76 (d, J=0.8 Hz, 3H) ppm.

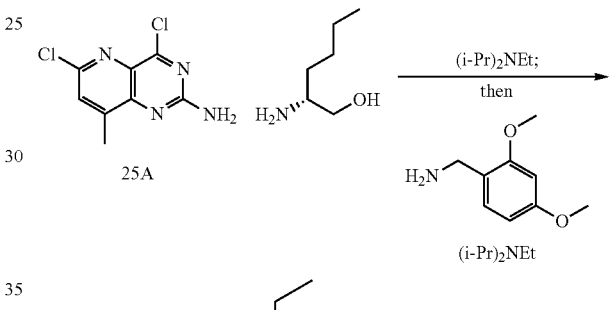

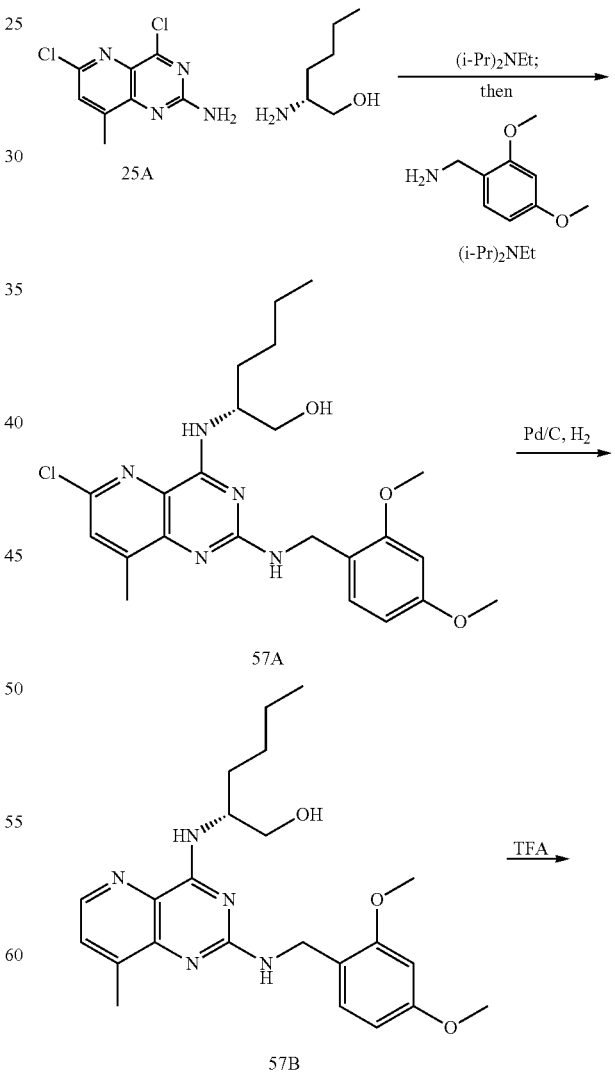

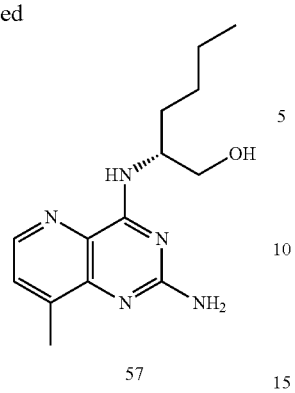

57

Synthesis of (R)-2-((6-chloro-2-((2,4-dimethoxybenzyl) amino)-8-methylpyrido[3,2-d]pyrimidin-4-yl)amino)hexan-1-ol (57A). To a solution of 25A (50 mg, 0.20 mmol) in THF (15 mL) was added D-norleucinol (24 mg, 0.20 mmol) and N,N-diisopropylethylamine (1.1 mL, 6.0 mmol). After stirring at rt for 30 minutes, 2,4-dimethoxybenzylamine (0.2 mL, 1.1 mmol) and additional N,N-diisopropylethylamine (0.26 mL, 1.5 mmol) was added and the mixture was heated to 100° C. After 16 h, the reaction was cooled to rt, diluted with EtOAc (100 mL), washed with water (100 mL), brine (100 mL), dried over $Na_2SO_4$, filtered and concentrated in vacuo. The crude residue was subjected to silica gel chromatography eluting with hexanes-EtOAc to provide 57A. $^1$H NMR (400 MHz, Chloroform-d) δ 7.30 (d, J=8.2 Hz, 1H), 7.25 (s, 1H), 6.75 (d, J=6.0 Hz, 1H), 6.46 (d, J=2.3 Hz, 1H), 6.41 (dd, J=8.2, 2.4 Hz, 1H), 5.39 (s, 1H), 4.57 (d, J=6.0 Hz, 2H), 3.85 (s, 4H), 3.81 (d, J=3.1 Hz, 1H), 3.79 (s, 4H), 3.68 (q, J=7.7, 7.2 Hz, 1H), 2.51 (s, 3H), 1.72-1.60 (m, 3H), 1.46-1.30 (m, 5H), 0.95-0.86 (m, 4H). LCMS (m/z): 460.25 [M+H]$^+$; $t_R$=1.26 min. on LC/MS Method A.

Synthesis of (R)-2-((2-((2,4-dimethoxybenzyl)amino)-8-methylpyrido[3,2-d]pyrimidin-4-yl)amino)hexan-1-ol (57B). A solution of 57A (35 mg, 0.08 mmol) in EtOAc (4 mL) and EtOH (4 mL) was purged with Ar, and then Pd/C (Degussa 10 wt %, 25 mg) was added. The mixture was then purged with $H_2$ and heated to 70° C. After 1 h, the reaction was cooled, purged with Ar, filtered through Celite, and the Celite rinsed with EtOAc. The organics were concentrated in vacuo and the residue was subjected to silica gel chromatography eluting with EtOAc-MeOH to afford 57B. LCMS (m/z): 426.16 [M+H]$^+$; $t_R$=1.18 min. on LC/MS Method A.

Synthesis of (R)-2-((2-amino-8-methylpyrido[3,2-d]pyrimidin-4-yl)amino)hexan-1-ol (57). To 57B (21 mg, 0.05 mmol) was added TFA (3 mL). After 60 minutes, MeOH (5 mL) and water (5 mL) were added to the mixture. After 4 h, the mixture was concentrated in vacuo and co-evaporated with MeOH (×3). The residue was subjected to preparative HPLC (Synergi 4u Polar-RP 80A, Axia; 10% aq. acetonitrile-70% aq. acetonitrile with 0.1% TFA, over 20 min. gradient) to provide 57 as a TFA salt. $^1$H NMR (400 MHz, MeOH-d$_4$) δ 8.50 (d, J=4.6 Hz, 1H), 7.63 (dd, J=4.6, 1.0 Hz, 1H), 4.53 (dq, J=8.6, 5.2 Hz, 1H), 3.74 (d, J=5.3 Hz, 2H), 2.53 (d, J=0.8 Hz, 4H), 1.83-1.64 (m, 3H), 1.45-1.33 (m, 5H), 0.97-0.87 (m, 4H). $^{19}$F NMR (377 MHz, MeOH-d$_4$) δ −77.78. LCMS (m/z): 276.26 [M+H]$^+$; $t_R$=0.88 min. on LC/MS Method A.

Example 58

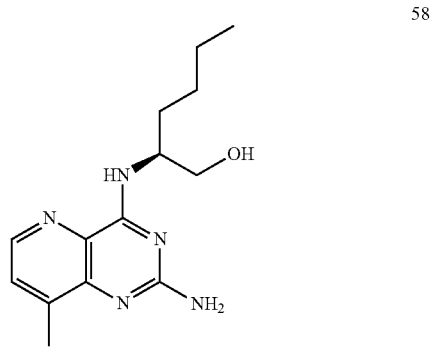 [SMILES: CCCC[C@@H](CO)Nc1nc(N)nc2c(C)ccnc12]

58

Synthesis of (S)-2-((2-amino-8-methylpyrido[3,2-d]pyrimidin-4-yl)amino)hexan-1-ol (58). 58 was synthesized in a 3 step procedure similar to that described for Example 57, instead replacing D-norleucinol with L-norleucinol (24 mg, 0.204 mmol), affording 58 as a TFA salt. $^1$H NMR (400 MHz, MeOH-d$_4$) δ 8.48 (d, J=4.6 Hz, 1H), 7.60 (dd, J=4.6, 1.0 Hz, 1H), 4.52 (dq, J=8.7, 5.4 Hz, 1H), 3.74 (d, J=5.8 Hz, 2H), 2.52 (d, J=0.8 Hz, 3H), 1.86-1.61 (m, 3H), 1.47-1.32 (m, 5H), 0.95-0.86 (m, 4H). $^{19}$F NMR (377 MHz, MeOH-d$_4$) δ −77.64. LCMS (m/z): 276.17 [M+H]$^+$; $t_R$=0.88 min. on LC/MS Method A.

Example 59

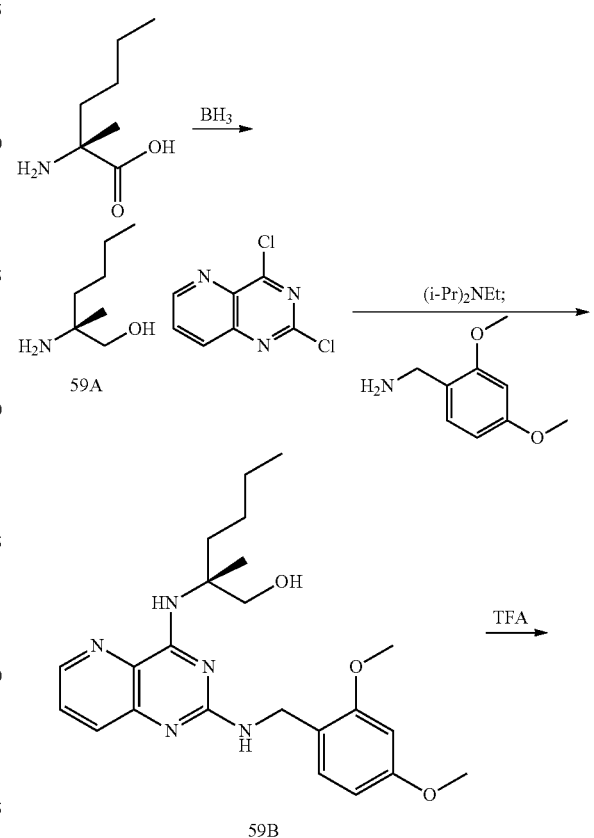

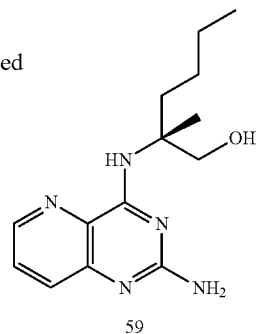

Synthesis of (R)-2-amino-2-methylhexan-1-ol (59A). To (2R)-2-amino-2-methylhexanoic acid hydrochloride (250 mg, 1.4 mmol, supplied by Astatech) in THF (5 mL) was added borane-tetrahydrofuran complex solution in THF (1M, 5.5 mL) dropwise over 5 minutes. After 24 h, the reaction was quenched with MeOH (1 mL) and concentrated in vacuo. The residue was diluted with DCM, filtered, and concentrated in vacuo to afford crude 59A which was carried forward into the next step directly. LCMS (m/z): 131.92 [M+H]$^+$; $t_R$=0.58 min. on LC/MS Method A.

Synthesis of (R)-2-((2-((2,4-dimethoxybenzyl)amino)pyrido[3,2-d]pyrimidin-4-yl)amino)-2-methylhexan-1-ol (59B). To a solution of 2,4-dichloropyrido[3,2-d]pyrimidine (50 mg, 0.25 mmol) in THF (10 mL) was added 59A (50 mg, 0.38 mmol) and N,N-diisopropylethylamine (0.13 mL, 0.75 mmol). After stirring at 80° C. for 18 h, 2,4-dimethoxybenzylamine (0.19 mL, 1.25 mmol) was added and the mixture was heated to 100° C. After 18 h, the reaction was cooled to rt, diluted with EtOAc, washed with water and brine, dried over Na$_2$SO$_4$, then filtered and concentrated in vacuo. The residue was subjected to silica gel chromatography eluting with hexanes-EtOAc to provide 59B. LCMS (m/z): 426.21 [M+H]$^+$; $t_R$=0.91 min. on LC/MS Method A.

Synthesis of (R)-2-((2-aminopyrido[3,2-d]pyrimidin-4-yl)amino)-2-methylhexan-1-ol (59). To 59B was added TFA (3 mL). After 2 h, the reaction mixture was concentrated in vacuo. The residue was subjected to preparative HPLC (Synergi 4u Polar-RP 80A, Axia; 10% aq. acetonitrile-70% aq. acetonitrile with 0.1% TFA, over 20 min. gradient) to provide 59 as a TFA salt. $^1$H NMR (400 MHz, Methanol-d4) δ 8.62 (dd, J=4.2, 1.6 Hz, 1H), 7.81 (dd, J=8.5, 1.6 Hz, 1H), 7.77 (dd, J=8.5, 4.2 Hz, 1H), 3.97 (d, J=11.2 Hz, 1H), 3.72 (d, J=11.2 Hz, 1H), 2.18-2.03 (m, 1H), 1.99-1.86 (m, 1H), 1.54 (s, 3H), 1.41-1.30 (m, 4H), 0.92 (t, J=6.9 Hz, 2H). $^{19}$F NMR (377 MHz, MeOH-d$_4$) δ −77.98. LCMS (m/z): 276.13 [M+H]$^+$; $t_R$=0.65 min. on LC/MS Method A.

Example 60

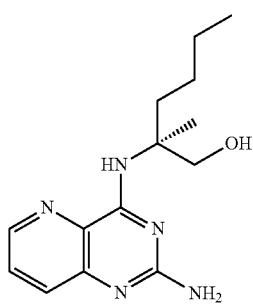

Synthesis of (S)-2-((2-aminopyrido[3,2-d]pyrimidin-4-yl)amino)-2-methylhexan-1-ol (60). Compound 60 was synthesized in a procedure similar to that reported for 59, replacing (2R)-2-amino-2-methylhexanoic acid hydrochloride with (2S)-2-amino-2-methylhexanoic acid hydrochloride (250 mg, 1.38 mmol, supplied by Astatech, Inc.). Final purification with preparative HPLC (Synergi 4u Polar-RP 80A, Axia; 10% aq. acetonitrile-70% aq. acetonitrile with 0.1% TFA, over 20 min. gradient) provided 60 as a TFA salt. $^1$H NMR (400 MHz, Methanol-d$_4$) δ 8.63 (dd, J=4.3, 1.5 Hz, 1H), 7.82 (dd, J=8.5, 1.5 Hz, 1H), 7.77 (dd, J=8.5, 4.3 Hz, 1H), 3.98 (d, J=11.2 Hz, 1H), 3.73 (d, J=11.2 Hz, 1H), 2.19-2.04 (m, 1H), 2.01-1.88 (m, 1H), 1.55 (s, 3H), 1.50-1.29 (m, 4H), 0.93 (t, J=6.9 Hz, 3H). $^{19}$F NMR (377 MHz, MeOH-d$_4$) δ −77.98. LCMS (m/z): 276.10 [M+H]$^+$; $t_R$=0.65 min. on LC/MS Method A.

Example 61

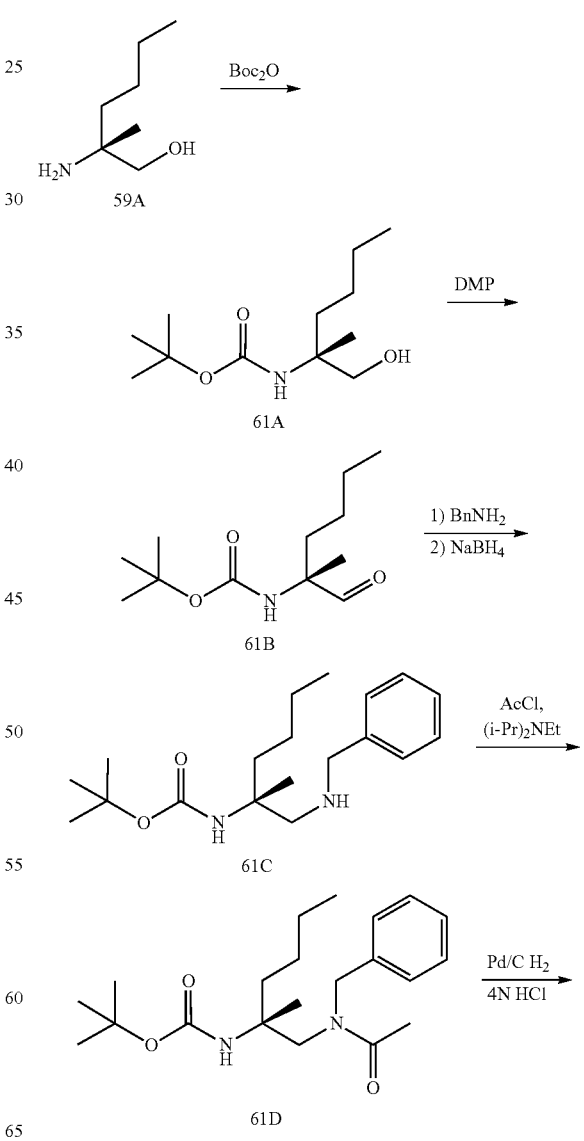

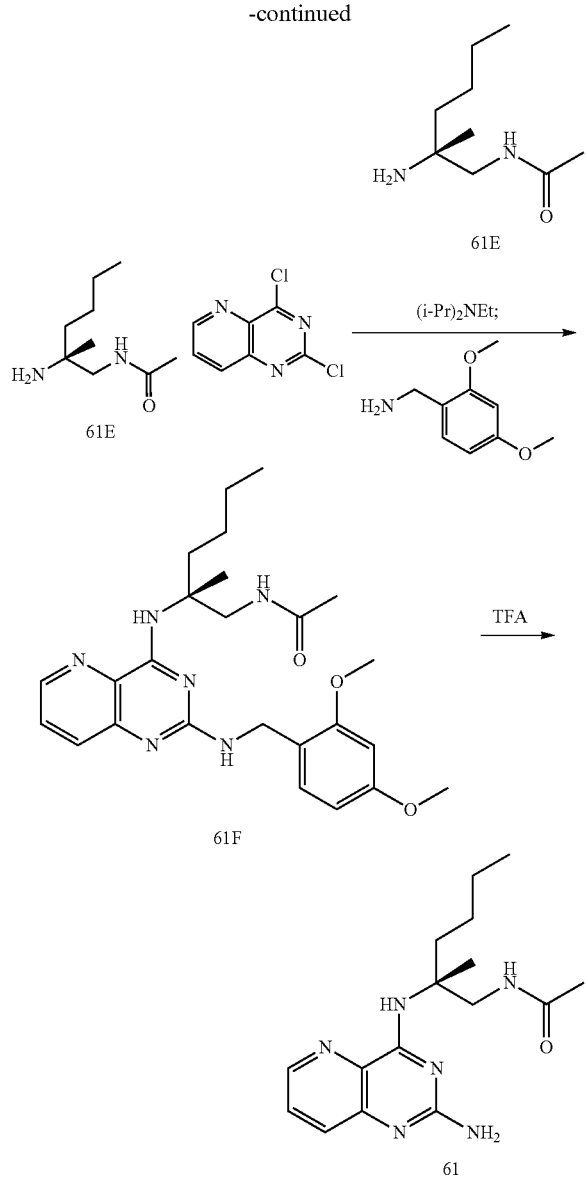

Synthesis of (R)-tert-butyl (1-hydroxy-2-methylhexan-2-yl)carbamate (61A). To a solution of 59A (1 g, 7.6 mmol) in THF (35 mL) was added sat. NaHCO$_{3(aq)}$ (35 mL) followed by di-tert-butyl dicarbonate (3.33 g, 15.24 mmol). After 24 h, the organic solvents were removed in vacuo. The resulting slurry was diluted with water (50 mL), extracted with EtOAc (100 mL), washed with brine (10 mL), dried over Na$_2$SO$_4$, and concentrated in vacuo. The residue was subjected to silica gel chromatography using an ELSD eluting with hexanes-EtOAc to provide 61A. LCMS (m/z): 231.61 [M+H]$^+$; t$_R$=1.09 min. on LC/MS Method A.

Synthesis of (R)-tert-butyl (2-methyl-1-oxohexan-2-yl)carbamate (61B). To a solution of 61A (2.1 g, 9.0 mmol) in DCM (100 mL) was added Dess-Martin periodinane (5.7 g, 14 mmol). After 2 h the reaction was quenched with sat. Na$_2$S$_2$O$_{3(aq)}$ (75 mL). The mixture was separated and the aqueous layer was extracted with DCM (100 mL). The combined organics were washed with water (100 mL) and brine (100 mL), dried over Na$_2$SO$_4$, then filtered and concentrated in vacuo. The residue was subjected to silica gel chromatography using an ELSD eluting with hexanes-EtOAc to provide 61B. LCMS (m/z): 173.75 [M+H-(t-Bu)]$^+$; t$_R$=1.18 min. on LC/MS Method A.

Synthesis of (R)-tert-butyl (1-(benzylamino)-2-methylhexan-2-yl)carbamate (61C). To a solution of 61B (1.9 g, 8.4 mmol) in dry MeOH (50 mL) was added benzylamine (1.0 mL, 8.35 mmol). After 18 h, sodium borohydride (500 mg, 13 mmol) was added portionwise. At 60 minutes, the mixture was concentrated in vacuo. The resulting residue was dissolved in EtOAc (50 mL), washed with 1M NaOH$_{(aq)}$ (50 mL), 10% Rochelle's salt aq. solution (50 mL, solid supplied by Sigma-Aldrich), and brine (50 mL), dried over Na$_2$SO$_4$, then filtered and concentrated in vacuo to afford 61C. LCMS (m/z): 321.03 [M+H]$^+$; t$_R$=0.94 min. on LC/MS Method A.

Synthesis of (R)-tert-butyl (1-(N-benzylacetamido)-2-methylhexan-2-yl)carbamate (61D). To a solution of 61C (2.2 g, 6.9 mmol) in THF (50 mL) was added N,N-diisopropylethylamine (2.4 mL, 14 mmol) followed by acetyl chloride (0.75 mL, 11 mmol). After 60 minutes, the mixture was diluted with EtOAc (150 mL), washed with sat. NaHCO$_{3(aq)}$ (100 mL) and brine (100 mL), dried over Na$_2$SO$_4$, then filtered and concentrated in vacuo. The residue was subjected to silica gel chromatography eluting with hexanes-EtOAc to provide 61D. LCMS (m/z): 362.82 [M+H]$^+$; t$_R$=1.32 min. on LC/MS Method A.

Synthesis of (R)—N-(2-amino-2-methylhexyl)acetamide (61E). To a solution of 61D (2.0 g, 5.4 mmol) in EtOH (55 mL) and hydrochloric acid solution in dioxane (4M, 2 mL) that was purged with Ar, was added palladium hydroxide on carbon (20 wt %, 2.0 g). The mixture was purged with H$_2$ and heated to 60° C. After 24 h, the reaction mixture was filtered through Celite, rinsed with EtOAc, and concentrated in vacuo to afford 61E as a HCl salt. LCMS (m/z): 172.92 [M+H]$^+$; t$_R$=0.50 min. on LC/MS Method A.

Synthesis of (R)—N-(2-((2-((2,4-dimethoxybenzyl)amino)-7-fluoropyrido[3,2-d]pyrimidin-4-yl)amino)-2-methylhexyl)acetamide (61F). To a solution of 2,4-dichloropyrido[3,2-d]pyrimidine (30 mg, 0.15 mmol) in THF (10 mL) was added 61E (25 mg, 0.15 mmol) and N,N-diisopropylethylamine (0.08 mL, 0.44 mmol). After stirring at 80° C. for 18 h, 2,4-dimethoxybenzylamine (0.1 mL, 0.73 mmol) was added and the mixture heated to 100° C. After 18 h, the reaction was cooled to rt, diluted with EtOAc, washed with water and brine, dried over Na$_2$SO$_4$, and concentrated in vacuo. The residue was subjected to silica gel chromatography eluting with EtOAc-MeOH to provide 61F. LCMS (m/z): 467.24 [M+H]$^+$; t$_R$=1.02 min. on LC/MS Method A.

Synthesis of (R)—N-(2-((2-amino-7-fluoropyrido[3,2-d]pyrimidin-4-yl)amino)-2-methylhexyl)acetamide (61). To 61F (33 mg, 0.07 mmol) was added TFA (3 mL). After 60 minutes, the mixture was concentrated in vacuo and co-evaporated with MeOH (×3). The residue was suspended in MeOH, filtered, and concentrated in vacuo to provide 61 as a TFA salt. $^1$H NMR (400 MHz, MeOH-d$_4$) δ 8.63 (dd, J=4.4, 1.4 Hz, 1H), 7.84 (dd, J=8.5, 1.4 Hz, 1H), 7.76 (dd, J=8.5, 4.4 Hz, 1H), 3.95 (d, J=14.0 Hz, 1H), 3.57 (d, J=14.0 Hz, 1H), 2.25-2.12 (m, 1H), 1.95 (s, 3H), 1.95-1.86 (m, 1H), 1.54 (s, 3H), 1.41-1.32 (m, 4H), 0.95-0.90 (m, 3H). $^{19}$F NMR (377 MHz, MeOH-d$_4$) δ −77.77. LCMS (m/z): 317.24 [M+H]$^+$; t$_R$=0.71 min. on LC/MS Method A.

Example 62

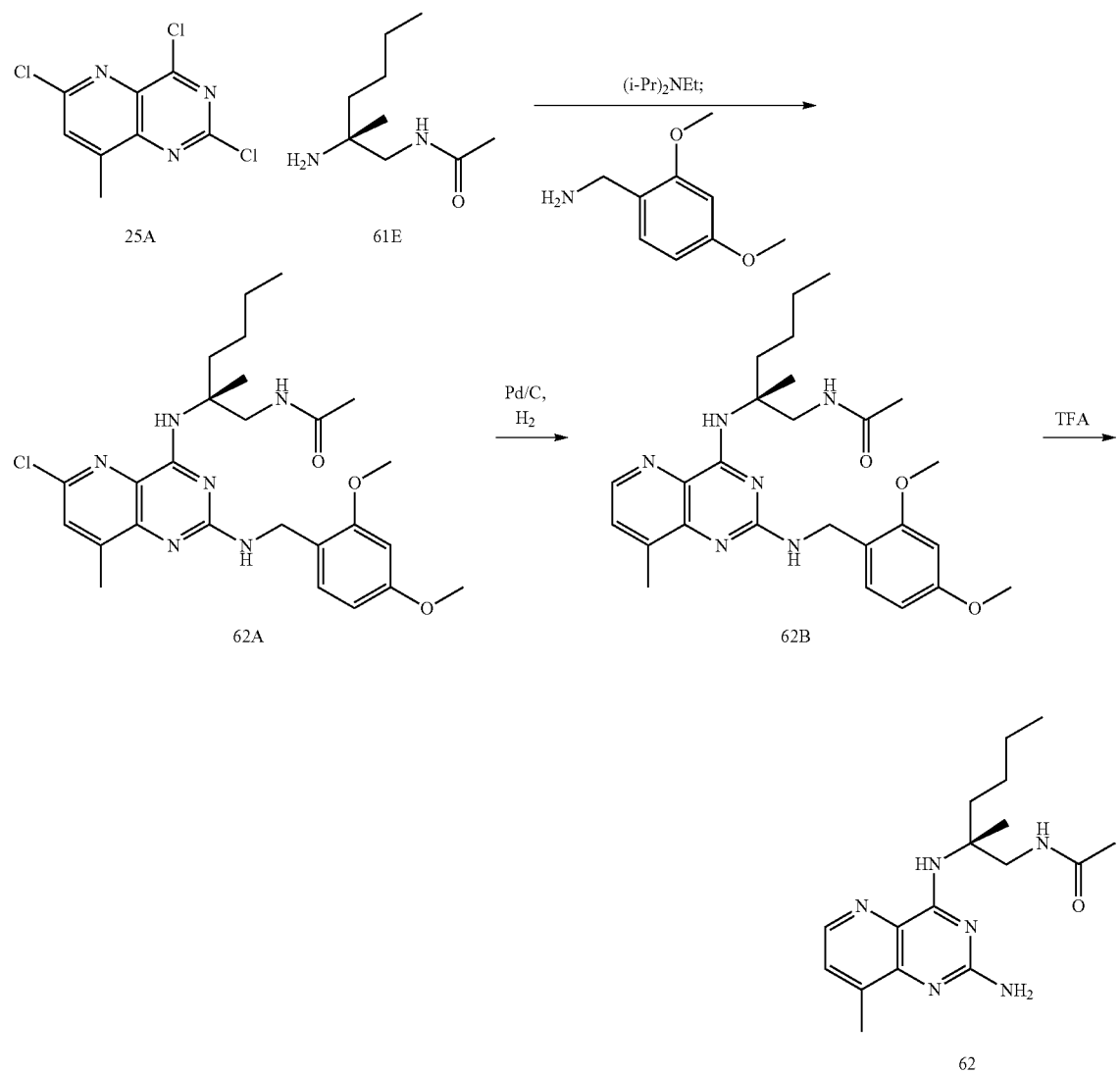

Synthesis of (R)—N-(2-((6-chloro-2-((2,4-dimethoxybenzyl)amino)-8-methylpyrido[3,2-d]pyrimidin-4-yl)amino)-2-methylhexyl)acetamide (62A). To a solution of 25A (37 mg, 0.15 mmol) in THF (5 mL) was added 61E (25 mg, 0.15 mmol) and N,N-diisopropylethylamine (0.4 mL, 0.43 mmol). After stirring at 80° C. for 18 h, 2,4-dimethoxybenzylamine (0.1 mL, 0.63 mmol) was added and the mixture was heated to 100° C. After 18 h, the reaction was cooled to rt, diluted with EtOAc, washed with water (50 mL) and brine (50 mL), dried over $Na_2SO_4$, then filtered and concentrated in vacuo. The residue was subjected to silica gel chromatography eluting with EtOAc-MeOH to provide 62A (49 mg, 75%). LCMS (m/z): 515.17 [M+H]$^+$; $t_R$=0.86 min. on LC/MS Method A.

Synthesis of (R)—N-(2-((2-((2,4-dimethoxybenzyl)amino)-8-methylpyrido[3,2-d]pyrimidin-4-yl)amino)-2-methylhexyl)acetamide (62B). To a solution of 62A (49 mg, 0.1 mmol) in EtOAc (4 mL) and EtOH (4 mL) that was purged with Ar, was added Pd/C (Degussa 10 wt %, 25 mg). The mixture was then purged with $H_2$ and heated to 70° C. After 1 h, the reaction was allowed to cool to rt, purged with Ar, filtered through Celite, rinsed with EtOAc (50 mL), and concentrated in vacuo to provide 62B (46 mg, 100%). LCMS (m/z): 481.25 [M+H]$^+$; $t_R$=1.10 min. on LC/MS Method A.

Synthesis of (R)-2-((2-amino-8-methylpyrido[3,2-d]pyrimidin-4-yl)amino)hexan-1-ol (62). To 62B (46 mg, 0.1 mmol) was added TFA (3 mL). After 18 h, the mixture was concentrated in vacuo and co-evaporated with MeOH (3×10 mL). The residue was suspended in 10 mL MeOH, filtered, and concentrated in vacuo to provide 62 as a TFA salt. $^1$H NMR (400 MHz, MeOH-d$_4$) δ 8.48 (d, J=4.6 Hz, 1H), 7.61 (dd, J=4.7, 1.0 Hz, 1H), 3.95 (d, J=14.0 Hz, 1H), 3.56 (d, J=14.0 Hz, 1H), 2.52 (d, J=0.8 Hz, 3H), 2.18 (ddd, J=13.5, 11.3, 4.5 Hz, 1H), 1.95 (s, 3H), 1.89 (ddd, J=13.5, 11.6, 4.8 Hz, 1H), 1.54 (s, 3H), 1.42-1.31 (m, 5H), 0.96-0.89 (m, 4H). $^{19}$F NMR (377 MHz, MeOH-d$_4$) δ −77.85. LCMS (m/z): 331.16 [M+H]$^+$; $t_R$=0.79 min. on LC/MS Method A.

Example 63

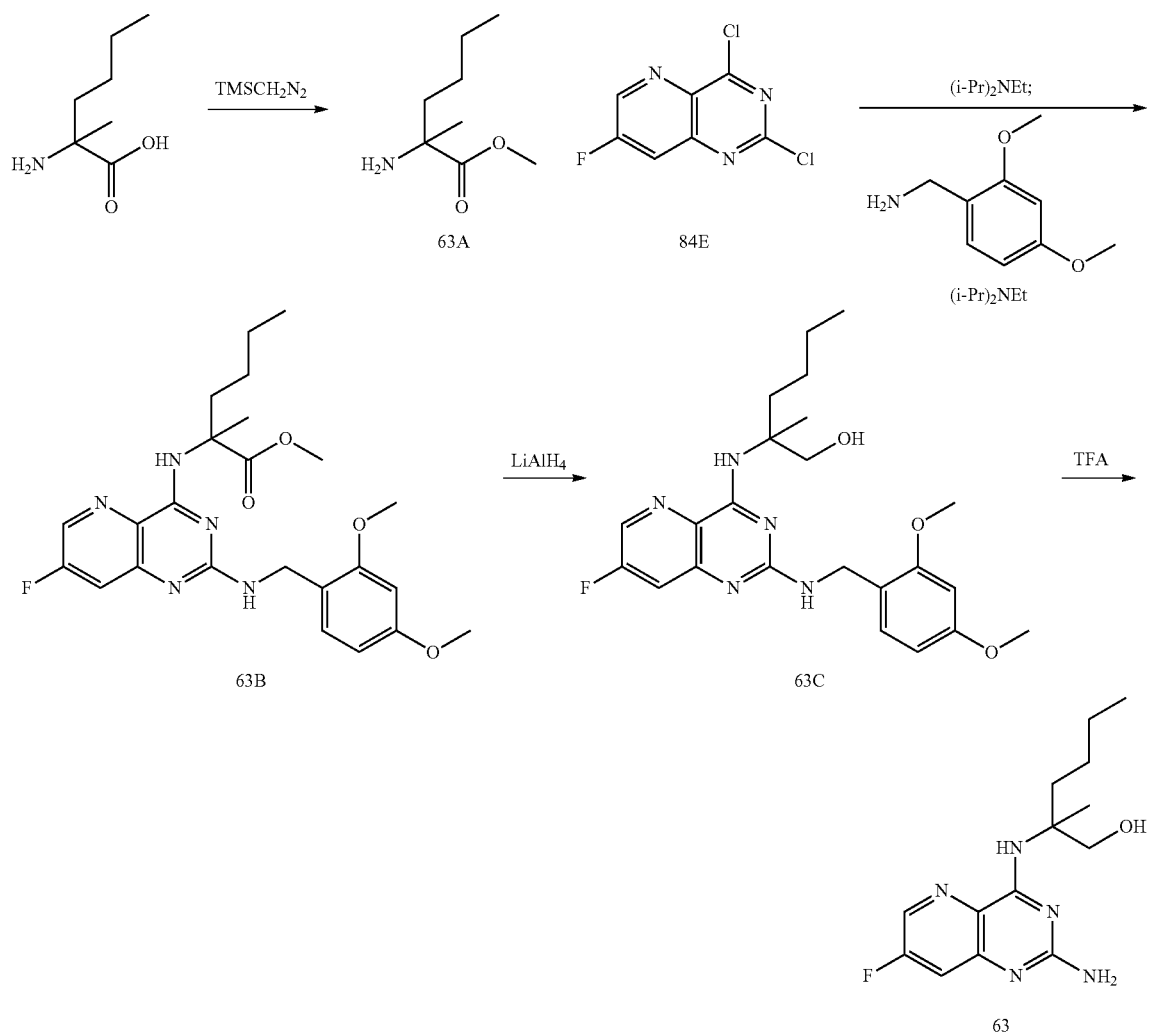

Synthesis of methyl 2-amino-2-methylhexanoate (63A). To a mixture of (2R)-2-amino-2-methylhexanoic acid hydrochloride (50 mg, 0.28 mmol) and (2S)-2-amino-2-methylhexanoic acid hydrochloride (50 mg, 0.28 mmol) in MeOH (5.0 mL) was added (trimethylsilyl) diazomethane in hexanes (2 M, 0.41 mL, 0.83 mmol) dropwise. After 6 h, the reaction was quenched with AcOH (100 µL). The mixture was concentrated in vacuo to provide 63A that was used without further isolation. LCMS (m/z): 159.91 [M+H]$^+$; $t_R$=0.57 min. on LC/MS Method A.

Synthesis of methyl 2-((2-((2,4-dimethoxybenzyl) amino)-7-fluoropyrido[3,2-d]pyrimidin-4-yl)amino)-2-methylhexanoate (63B). To a solution of 84E (120 mg, 0.55 mmol) in THF (5 mL) was added 63A (88 mg, 0.55 mmol) and N,N-diisopropylethylamine (0.3 mL, 1.7 mmol). After stirring at 80° C. for 18 h, the reaction was cooled to rt, diluted with EtOAc (50 mL), washed with water (50 mL) and brine (50 mL), dried over Na$_2$SO$_4$, then filtered and concentrated in vacuo. The crude residue was then diluted with THF (10 mL) and 2,4-dimethoxybenzylamine (0.4 mL, 2.6 mmol) and N,N-diisopropylethylamine (0.3 mL, 1.7 mmol) were added. After stirring at 100° C. for 18 h, the reaction was cooled to rt, diluted with EtOAc (50 mL), washed with water and brine, dried over Na$_2$SO$_4$, then filtered and concentrated in vacuo. The residue was subjected to silica gel chromatography eluting with hexanes-EtOAc to provide 63B. $^1$H NMR (400 MHz, Chloroform-d) δ 8.14 (d, J=2.5 Hz, 1H), 7.36 (s, 1H), 7.28-7.24 (m, 2H), 6.46 (d, J=2.3 Hz, 1H), 6.41 (dd, J=8.3, 2.4 Hz, 1H), 4.54 (dd, J=6.2, 2.7 Hz, 2H), 3.84 (s, 3H), 3.78 (s, 3H), 3.69 (s, 3H), 2.27-2.16 (m, 1H), 2.02 (s, 1H), 1.71 (s, 3H), 1.34-1.23 (m, 5H), 0.88 (t, J=6.9 Hz, 3H). $^{19}$F NMR (376 MHz, Chloroform-d) δ -121.51 (d, J=422.9 Hz). LCMS (m/z): 472.21 [M+H]$^+$; $t_R$=0.91 min. on LC/MS Method A.

Synthesis of 2-((2-((2,4-dimethoxybenzyl)amino)-7-fluoropyrido[3,2-d]pyrimidin-4-yl)amino)-2-methylhexan-1-ol (63C). To a solution of 63B (104 mg, 0.22 mmol) in THF (5 mL) was added lithium aluminum hydride in Et$_2$O (2M, 0.30 mL, 0.60 mmol). After 5 h the reaction was quenched with H$_2$O (1 mL) and 2M NaOH$_{(aq)}$, and then filtered. The mother liquor was then diluted with EtOAc (30 mL), washed with sat. Rochelle's salt solution (25 mL), H$_2$O (25 mL), and brine (25 mL), dried over Na$_2$SO$_4$, then filtered and concentrated in vacuo. The residue was subjected to silica gel chromatography eluting with hexanes-EtOAc to provide 63C. ¹H NMR (400 MHz, Chloroform-d) δ 8.12 (d, J=2.5 Hz, 1H), 7.32 (s, 1H), 7.28 (s, 1H), 6.46 (d, J=2.4 Hz, 1H), 6.42 (dd, J=8.2, 2.4 Hz, 1H), 4.57-4.52 (m, 2H), 3.84 (s, 3H), 3.79 (s, 4H), 3.75 (s, 2H), 1.92 (d, J=14.1 Hz, 1H), 1.74 (t, J=12.6 Hz, 1H), 1.40-1.37 (m, 3H), 1.32 (td, J=13.4, 12.4, 6.3 Hz, 4H), 0.91 (t, J=7.0 Hz, 3H). ¹⁹F NMR (377 MHz, Chloroform-d) δ −121.34. LCMS (m/z): 444.20 [M+H]⁺; $t_R$=0.94 min. on LC/MS Method A.

Synthesis of 2-((2-amino-7-fluoropyrido[3,2-d]pyrimidin-4-yl)amino)-2-methylhexan-1-ol (63). To 63C (22 mg, 0.05 mmol) was added TFA (3 mL). After 30 minutes, the reaction mixture was diluted with MeOH (5 mL). After stirring for 18 h, the mixture was filtered and concentrated in vacuo. Co-evaporation with MeOH (×3) provided 63 as a TFA salt. ¹H NMR (400 MHz, MeOH-d₄) δ 8.53 (d, J=2.4 Hz, 1H), 8.20 (s, 1H), 7.65 (dd, J=8.8, 2.4 Hz, 1H), 3.95 (s, 1H), 3.70 (d, J=11.2 Hz, 1H), 2.09 (ddd, J=13.9, 10.9, 5.3 Hz, 1H), 1.96-1.86 (m, 1H), 1.53 (s, 3H), 1.42-1.28 (m, 6H), 0.95-0.87 (m, 3H). ¹⁹F NMR (377 MHz, MeOH-d₄) δ −77.47, −118.23 (d, J=8.6 Hz). LCMS (m/z): 294.12 [M+H]⁺; $t_R$=0.68 min. on LC/MS Method A.

Example 64

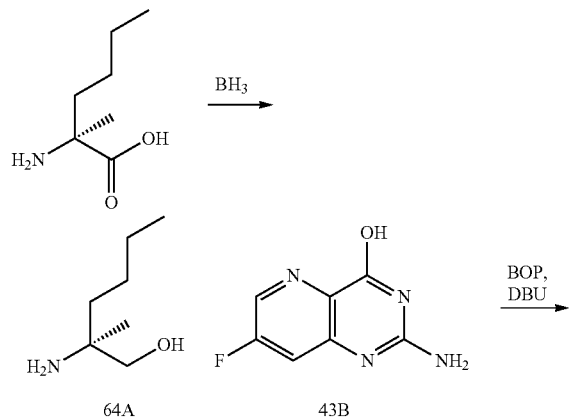

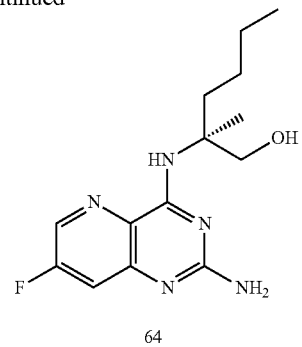

Synthesis of (S)-2-amino-2-methylhexan-1-ol (64A). To (2S)-2-amino-2-methylhexanoic acid hydrochloride (250 mg, 1.4 mmol, supplied by Astatech) in THF (5 mL) was added borane-tetrahydrofuran complex solution in THF (1M, 5.5 mL) dropwise over 5 minutes. After 24 h, the reaction was quenched with MeOH (1 mL) and concentrated in vacuo. The residue was taken up in DCM (10 mL), filtered, and concentrated in vacuo to provide crude 64A. LCMS (m/z): 131.92 [M+H]⁺; $t_R$=0.57 min. on LC/MS Method A.

Synthesis of (S)-2-((2-amino-7-fluoropyrido[3,2-d]pyrimidin-4-yl)amino)-2-methylhexan-1-ol (64). To a solution of 43B (140 mg, 78 mmol) and 64A (125 mg, 0.95 mmol) in NMP (7.5 mL), was added DBU (0.35 mL, 2.4 mmol) followed by BOP (419 mg, 0.95 mmol). After 16 h, the reaction mixture was subjected to prep HPLC (Gemini 10u C18 110A, AXIA; 10% aq. acetonitrile-50% aq. acetonitrile with 0.1% TFA, over 20 min. gradient) to provide, after removal of volatiles in vacuo, 64 as a TFA salt. ¹H NMR (400 MHz, MeOH-d₄) δ 8.55 (d, J=2.4 Hz, 1H), 8.22 (s, 1H), 7.64 (dd, J=8.7, 2.5 Hz, 1H), 3.97 (d, J=11.2 Hz, 1H), 3.71 (d, J=11.2 Hz, 1H), 2.09 (ddd, J=13.9, 10.8, 5.2 Hz, 1H), 1.92 (ddd, J=13.6, 10.9, 5.4 Hz, 1H), 1.54 (s, 4H), 1.40-1.31 (m, 5H), 1.00-0.85 (m, 3H). ¹⁹F NMR (377 MHz, MeOH-d₄) δ −77.62, −118.22 (d, J=8.7 Hz). LCMS (m/z) 294.09 [M+H]⁺; $t_R$=0.79 min. on LC/MS Method A.

Example 65

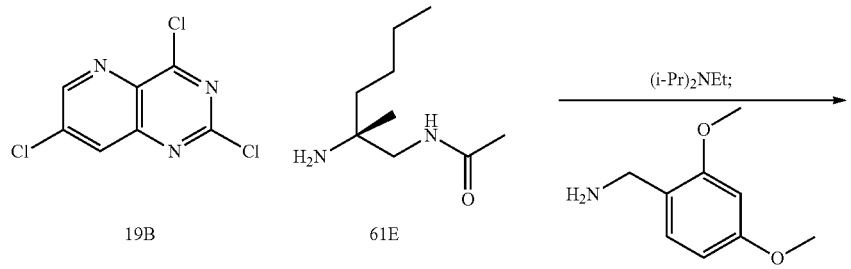

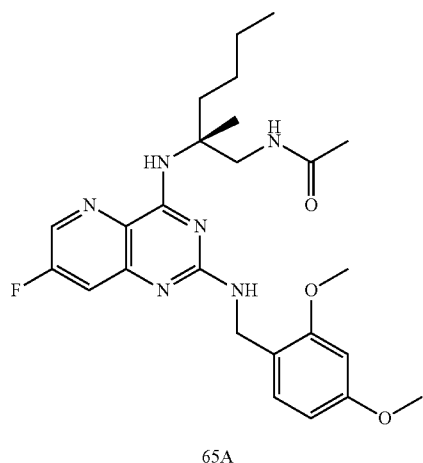

65A

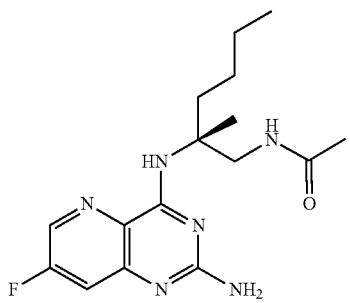

65

Synthesis of (R)—N-(2-((2-amino-7-chloropyrido[3,2-d]pyrimidin-4-yl)amino)-2-methylhexyl)acetamide (65A). To a solution of 19B (112 mg, 0.48 mmol) in THF (5 mL) was added 61E (100 mg, 0.48 mmol) and N,N-diisopropylethylamine (0.25 mL, 1.4 mmol). After stirring at 80° C. for 18 h, 2,4-dimethoxybenzylamine (0.75 mL, 5.0 mmol) was added and the mixture was heated to 100° C. After 18 h, the reaction was cooled to rt, diluted with EtOAc (50 mL), washed with water (50 mL) and brine (50 mL), dried over $Na_2SO_4$, then filtered and concentrated in vacuo. The residue was subjected to silica gel chromatography eluting with hexanes-EtOAc to provide 65A LCMS (m/z): 509.30[M+H]$^+$; $t_R$=0.89 min. on LC/MS Method A.

Synthesis of (R)—N-(2-((2-amino-7-chloropyrido[3,2-d]pyrimidin-4-yl)amino)-2-methylhexyl)acetamide (65). To 65A (21 mg, 0.04 mmol) was added TFA (3 mL). After 30 minutes, the mixture was concentrated in vacuo and the residue co-evaporated with MeOH (10 mL×3). The resulting residue was suspended in MeOH (10 mL), filtered, and concentrated in vacuo to provide 65 as a TFA salt. $^1$H NMR (400 MHz, MeOH-d$_4$) δ 8.59 (d, J=2.1 Hz, 1H), 8.58 (s, 1H), 7.91 (d, J=2.1 Hz, 1H), 3.93 (d, J=14.0 Hz, 1H), 3.52 (d, J=14.0 Hz, 1H), 2.22-2.10 (m, 1H), 1.96 (s, 3H), 1.95-1.87 (m, 1H), 1.54 (s, 3H), 1.34 (dd, J=7.5, 3.9 Hz, 5H), 0.94-0.89 (m, 3H). $^{19}$F NMR (377 MHz, MeOH-d$_4$) δ −77.91. LCMS (m/z): 351.29 [M+H]$^+$; $t_R$=0.69 min. on LC/MS Method A.

Example 66

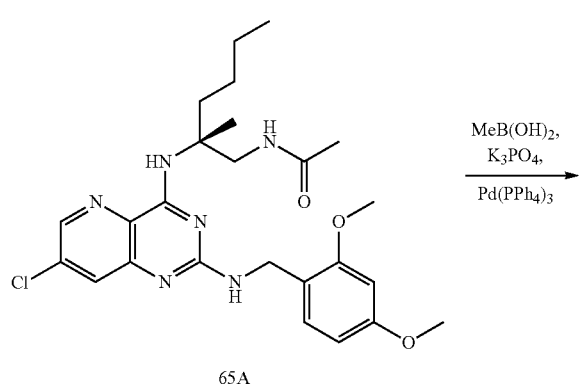

65A

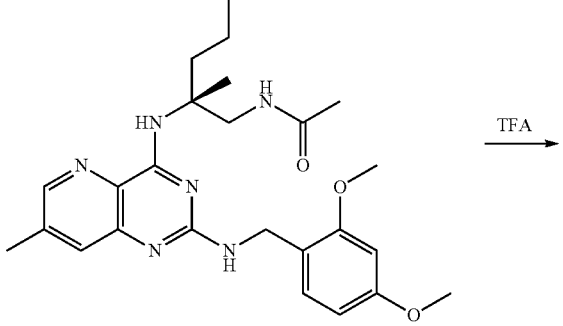

66A

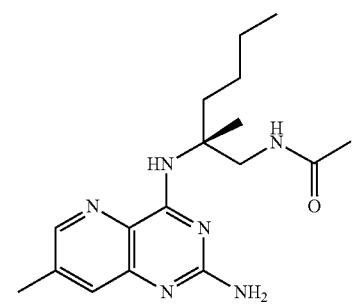

66

Synthesis of (R)—N-(2-((2-((2,4-dimethoxybenzyl)amino)-7-methylpyrido[3,2-d]pyrimidin-4-yl)amino)-2-methylhexyl)acetamide (66A). To 65A (128 mg, 0.26 mmol) in 1,4-dioxane (10 mL) and water (10 mL) was added methylboronic acid (61 mg, 1.0 mmol), tetrakis(triphenylphosphine)palladium(0) (51 mg, 0.05 mmol), and potassium phosphate tribasic (163 mg, 0.77 mmol). The reaction mixture was heated to 150° C. in a microwave reactor for 30 minutes. The reaction mixture was diluted with water (50 mL) and extracted with EtOAc (3×25 mL). The combined organics were washed with water (50 mL) and brine (50 mL), dried over $Na_2SO_4$, and concentrated in vacuo. The residue was subjected to silica gel chromatography eluting with EtOAc-MeOH, to provide 66A. LCMS (m/z): 481.30 [M+H]$^+$; $t_R$=0.89 min. on LC/MS Method A.

Synthesis of (R)—N-(2-((2-amino-7-methylpyrido[3,2-d]pyrimidin-4-yl)amino)-2-methylhexyl)acetamide (66). To 66A (54 mg, 0.11 mmol) was added TFA (3 mL). After 60 minutes, the mixture was concentrated in vacuo and co-evaporated with MeOH (10 mL×3). The resulting residue was suspended in MeOH (10 mL), filtered, and concentrated in vacuo to provide 66 as a TFA salt. $^1$H NMR (400 MHz, MeOH-d$_4$) δ 8.48 (d, J=1.8 Hz, 1H), 7.64 (s, 1H), 3.94 (d, J=14.0 Hz, 1H), 3.57 (d, J=13.9 Hz, 1H), 2.50 (s, 3H), 2.17 (ddd, J=13.4, 11.4, 4.7 Hz, 1H), 1.95 (s, 3H), 1.88 (ddd, J=16.1, 8.9, 4.4 Hz, 1H), 1.53 (s, 3H), 1.39-1.29 (m, 4H), 0.97-0.86 (m, 3H). $^{19}$F NMR (377 MHz, MeOH-d$_4$) δ −77.86. LCMS (m/z): 331.34 [M+H]$^+$; $t_R$=0.93 min. on LC/MS Method A.

Example 67

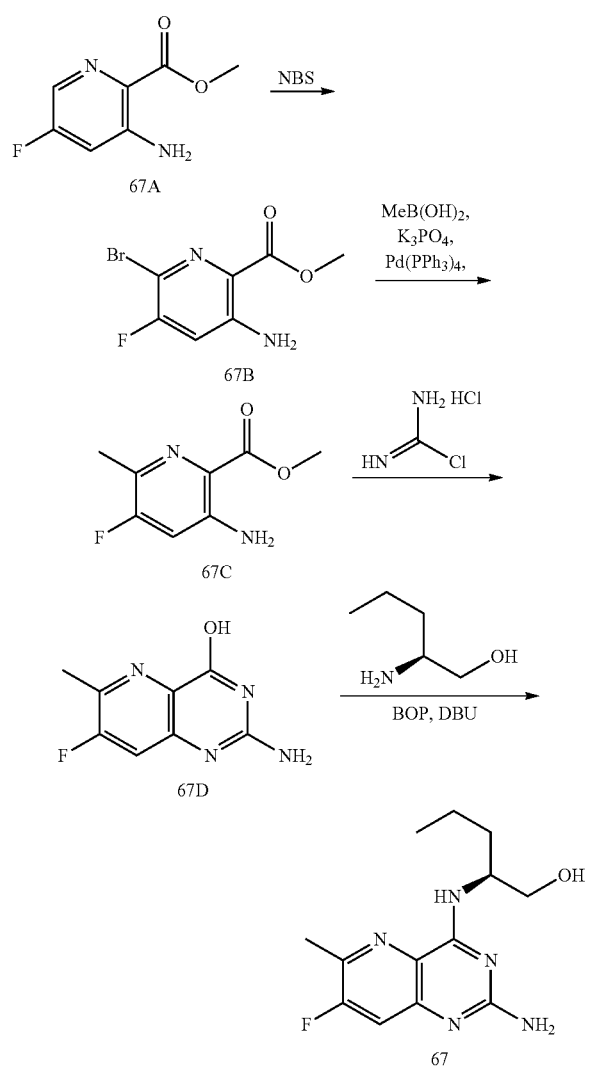

Synthesis of methyl 3-amino-6-bromo-5-fluoropicolinate (67B). To a solution of methyl 3-amino-5-fluoropicolinate 67A (270 mg, 2 mmol, 1.0 equiv., supplied by Astatech, Inc.) in acetonitrile (2 mL, 0.1M solution) was added NBS (311 mg, 2.2 mmol, 1.1 equiv.) over 2 minutes at rt. After 18 h, the reaction was quenched with water (50 mL) and the mixture was extracted with EtOAc (50 mL), washed with water (50 mL) and brine (50 mL), then dried over Na$_2$SO$_4$, filtered and then concentrated in vacuo. The residue was subjected to silica column chromatography eluting with 0% to 100% EtOAc in hexanes to provide 67B. LCMS (m/z): 250.1 [M+H]$^+$; $t_R$=0.71 min. on LC/MS Method A.

Synthesis of methyl 3-amino-5-fluoro-6-methylpicolinate (67C). Methyl 3-amino-6-bromo-5-fluoropicolinate 67B (50 mg, 0.2 mmol, 1 equiv.) in a microwave vial was treated with dioxane (2 mL) and water (2 mL), along with methylboronic acid (36.05 mg, 0.06 mmol, 3 equiv.), potassium phosphate tribasic (85.23 mg, 0.4 mmol, 2 equiv.) and palladium(O) tetrakis(triphenylphosphine) (46.4 mg, 0.04 mmol, 0.2 equiv.). The mixture was heated to 120° C. for 20 min. and the reaction mixture was partitioned between EtOAc (20 mL) and H$_2$O (20 mL). The organic layers were combined, dried over MgSO$_4$ then filtered and volatiles removed in vacuo. The resulting residue was subjected to silica gel chromatography eluting with 0-100% EtOAc in hexanes to provide 67C. LCMS (m/z): 184.88 [M+H]$^+$; $t_R$=0.54 min. on LC/MS Method A.

Synthesis of 2-amino-7-fluoro-6-methylpyrido[3,2-d]pyrimidin-4-ol (67D). A flask containing methyl 3-amino-5-fluoro-6-methylpicolinate 67C (95 mg, 0.52 mmol) was treated with chloroformamidine hydrochloride (118 mg, 1.03 mmol, supplied by Oakwood Scientific, Inc.). The mixture was heated to 160° C. overnight. The mixture was allowed to cool to rt, diluted with EtOAc (100 mL), filtered, and then the collected solids washed with water (50 mL) and diethyl ether (50 mL). The solid was allowed to air dry to furnish 67D which was used without further purification. LCMS (m/z): 195.03 [M+H]$^+$; $t_R$=0.31 min. on LC/MS Method A.

Synthesis of (S)-2-((2-amino-7-fluoro-6-methylpyrido[3,2-d]pyrimidin-4-yl)amino)pentan-1-ol (67). To a flask containing 2-amino-7-fluoro-6-methylpyrido[3,2-d]pyrimidin-4-ol 67D (5 mg, 0.026 mmol) was added DMF (2 mL) along with 1,8-diazabicyclo[5.4.0]undec-7-ene solution 1M in THF (0.01 mL, 0.08 mmol), (benzotriazol-1-yloxy)tris(dimethylamino)phosphonium hexafluorophosphate (22.78 mg, 0.05 mmol) and (S)-(+)-2-amino-1-pentanol, (10.63 mg, 0.1 mmol). The reaction was allowed to stir overnight and then subjected to HPLC (10% to 70% MeCN in water with 0.1% TFA using a Hydro-RP column) to provide, after removal of volatiles in vacuo, 67 as its TFA salt; $t_R$=0.57 min. on LC/MS Method A. $^1$H NMR (400 MHz, MeOH-d$_4$) δ 7.52 (d, J=9.4 Hz, 1H), 4.54 (s, 1H), 3.73 (d, J=5.3 Hz, 2H), 2.61 (d, J=2.9 Hz, 3H), 1.71 (q, J=7.6 Hz, 2H), 1.49-1.37 (m, 1H), 1.29 (s, 5H), 0.97 (t, J=7.4 Hz, 3H). $^{19}$F NMR (377 MHz, MeOH-d$_4$) δ −77.42; LCMS (m/z): 280.1 [M+H]$^+$ Example 68

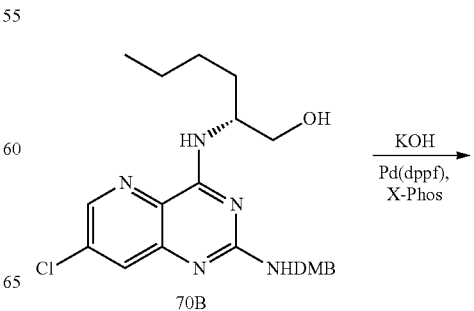

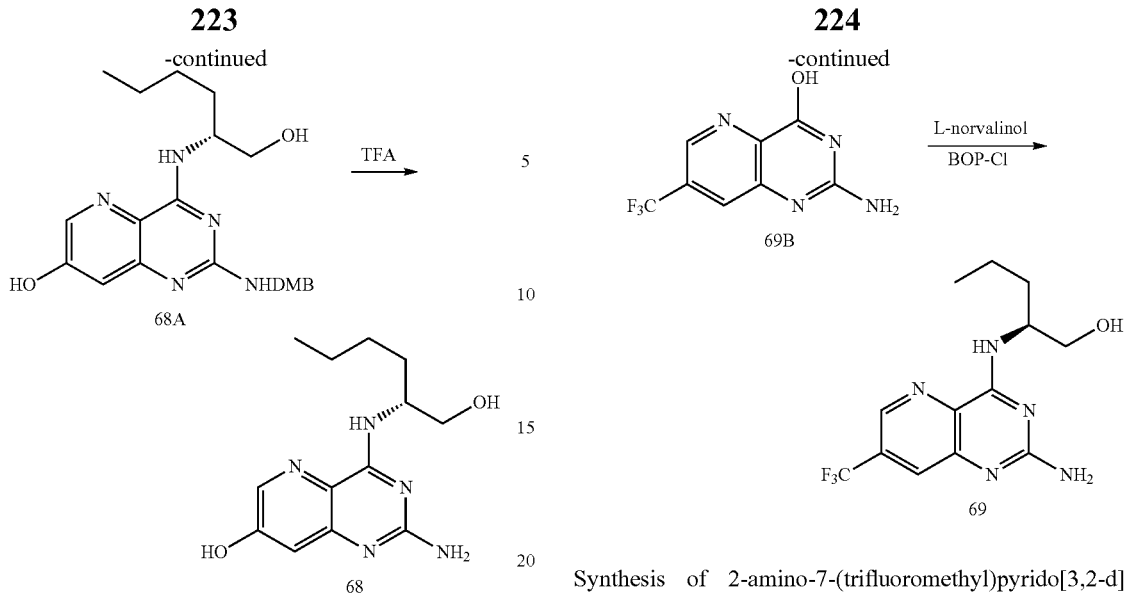

Synthesis of (R)-2-((2,4-dimethoxybenzyl)amino)-4-((1-hydroxyhexan-2-yl)amino)pyrido[3,2-d]pyrimidin-7-ol (68A). Into a microwave vial containing (R)-2-((7-chloro-2-((2,4-dimethoxybenzyl)amino)pyrido[3,2-d]pyrimidin-4-yl)amino)hexan-1-ol 70B (22 mg, 0.049 mmol, 1 equiv.) was added 2-(dicyclohexylphosphino)-2',4',6'-triisopropylbiphenyl (2.35 mg, 0.01 mmol), tris(dibenzylideneacetone)dipalladium(0) (0.9 mg, 0.005 mmol, 20 mol %) along with dioxane (2.5 mL) and KOH$_{(aq)}$ (1 mL, 0.08M). The mixture was heated to 150° C. for 30 min. in a microwave reactor. The reaction mixture was partitioned between EtOAc (50 ml) and H$_2$O (50 mL). The organic layer was separated, dried over MgSO$_4$, filtered and concentrated in vacuo. The crude material 68A was used without further purification. LCMS (m/z): 428.2 [M+H]$^+$; t$_R$=0.78 min. on LC/MS Method A.

Synthesis of (R)-2-amino-4-((1-hydroxyhexan-2-yl)amino)pyrido[3,2-d]pyrimidin-7-ol (68). A solution of (R)-2-((2,4-dimethoxybenzyl)amino)-4-((1-hydroxyhexan-2-yl)amino)pyrido[3,2-d]pyrimidin-7-ol 68A (21 mg, 0.05 mmol, 1 equiv.) in DCM (2 mL) was treated with TFA (0.5 mL). After 3 h the reaction mixture was concentrated under reduced pressure and the residue subjected to reverse phase HPLC (10% to 70% MeCN in water with 0.1% TFA using a Hydro-RP column) to furnish, after product fraction collection and the removal of volatiles in vacuo, 68 as its TFA salt. LCMS (m/z): 278.3 [M+H]$^+$; t$_R$=0.55 min. on LC/MS Method A. $^1$H NMR (400 MHz, MeOH-d$_4$) δ 8.61-8.34 (m, 1H), 8.19-7.98 (m, 1H), 4.39 (ddd, J=18.0, 9.2, 5.3 Hz, 2H), 3.77 (dt, J=8.3, 6.5 Hz, 1H), 1.74-1.50 (m, 6H), 1.34-1.09 (m, 10H), 0.79 (tt, J=6.9, 1.3 Hz, 6H), 0.59 (d, J=5.6 Hz, 2H). $^{19}$F NMR (377 MHz, MeOH-d$_4$) δ −77.55

Example 69

Synthesis of 2-amino-7-(trifluoromethyl)pyrido[3,2-d]pyrimidin-4-ol (69B). Methyl 3-amino-5-(trifluoromethyl)picolinate 69A (300 mg, 0.001 mol, 1 equiv., supplied by J&W Pharmlab, LLC) was treated with chloroformamadine hydrochloride (390 mg, 0.003 mmol, 2.5 equiv.) and dimethyl sulfone (1.28 g, 0.014 mol, 10 equiv.). The mixture was heated to 200° C. overnight. The reaction mixture was allowed to cool to rt, filtered, and washed with water (50 mL) and diethyl ether (50 mL). The residue was allowed to air dry to furnish 69B which was used without further purification. LCMS (m/z): 231 [M+H]$^+$; t$_R$=0.48 min. on LC/MS Method A.

Synthesis of (S)-2-((2-amino-7-(trifluoromethyl)pyrido[3,2-d]pyrimidin-4-yl)amino)hexan-1-ol (69). 2-amino-7-(trifluoromethyl)pyrido[3,2-d]pyrimidin-4-ol, 69B (100 mg, 0.44 mmol, 1 equiv.) was treated with 1,8-diazabicyclo[5.4.0]undec-7-ene solution 1M in THF (0.19 mL, 1.3 mmol, 3 equiv.). (Benzotriazol-1-yloxy)tris(dimethylamino)phosphonium hexafluorophosphate (249.83 mg, 0.56 mmol, 1.3 equiv.) was added followed by (S)-(+)-2-Amino-1-pentanol (112.06 mg, 1.09 mmol, 2.5 equiv.)), and DMF (5 mL). After stirring 16 h, the reaction mixture was diluted with water (5 mL) and subjected to reverse phase HPLC (10% to 70% MeCN in water with 0.1% TFA using a Hydro-RP column) to furnish, after product fractions were collected and the volatiles removed in vacuo, the title compound 69 as its TFA salt. LCMS (m/z): 316.16 [M+H]$^+$; t$_R$=0.59 min. on LC/MS Method A. $^1$H NMR (400 MHz, MeOH-d$_4$) δ 8.94-8.53 (m, 1H), 8.01 (dd, J=1.8, 0.9 Hz, 1H), 4.45 (t, J=6.5 Hz, 1H), 3.71-3.54 (m, 2H), 3.42-3.24 (m, 2H), 2.72-2.55 (m, 2H), 1.59 (td, J=8.2, 6.6 Hz, 3H), 1.37-1.20 (m, 2H), 0.85 (t, J=7.3 Hz, 4H). $^{19}$F NMR (377 MHz, MeOH-d$_4$) δ −64.83, −77.69.

Example 70 & Example 71

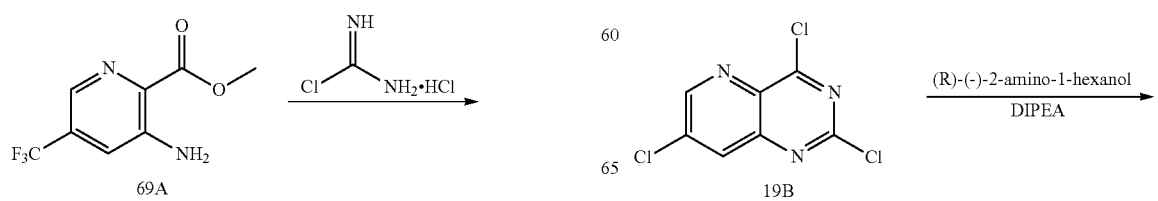

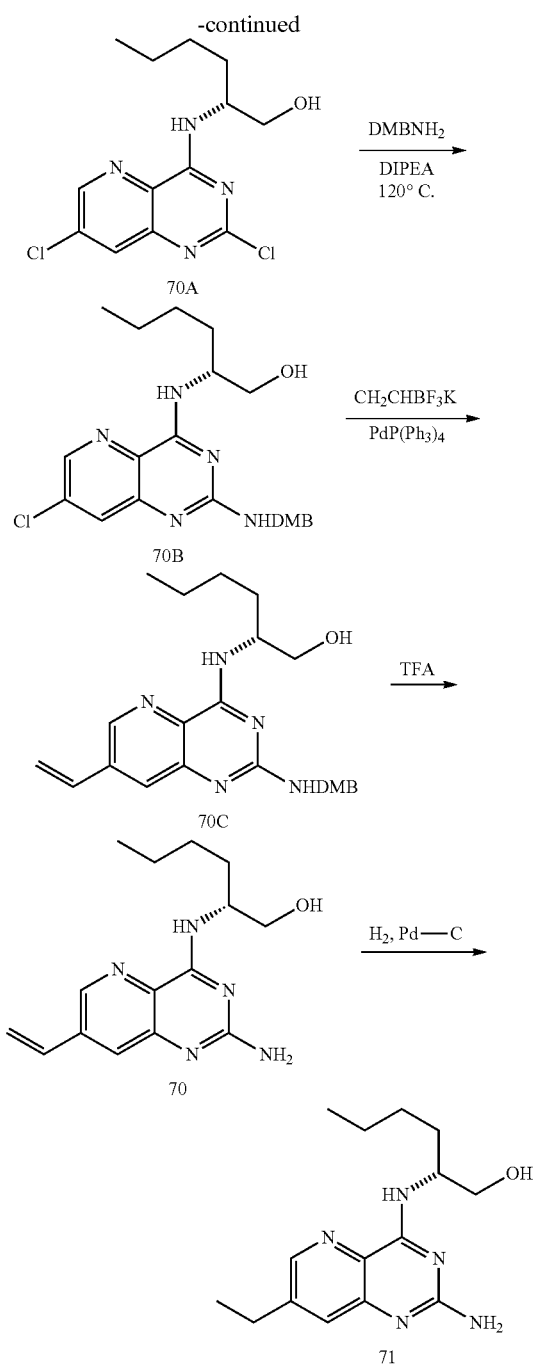

Synthesis of (R)-2-((2,7-dichloropyrido[3,2-d]pyrimidin-4-yl)amino)hexan-1-ol (70A). A solution of 2,4,7-trichloropyrido[3,2-d]pyrimidine 19B (250 mg, 1.06 mmol, 1 equiv.) in dioxane (4 mL) was treated with N,N-diisopropylethylamine (0.22 mL, 1.2 mmol, 1.5 equiv.) and (R)-(−)-2-amino-1-hexanol (312.38 mg, 3.02 mmol, 2.5 equiv.). The reaction was allowed to stir for 1 h and the product that formed, 70A, was carried forward directly into the following reaction without isolation.

Synthesis of (R)-2-((7-chloro-2-((2,4-dimethoxybenzyl)amino)pyrido[3,2-d]pyrimidin-4-yl)amino)hexan-1-ol (70B). The solution of (R)-2-((2,7-dichloropyrido[3,2-d]pyrimidin-4-yl)amino)hexan-1-ol 70A (315 mg, 1.06 mmol, 1 equiv.) prepared as described, was treated with dioxane (4 mL) followed by N,N-diisopropylethylamine (0.38 mL, 2 mmol, 2 equiv.) and 2,4-dimethoxybenzylamine (0.47 mL, 3.1 mmol, 3 equiv.). The reaction was heated at 120° C. overnight. The reaction mixture partitioned between EtOAc (50 mL) and H$_2$O (50 mL). The organics layer was separated, dried over Na$_2$SO$_4$, then filtered and concentrated in vacuo. The residue was subjected to silica gel chromatography eluting with 0% to 100% EtOAc in hexanes to provide the title compound 70B. LCMS (m/z): 446.9 [M+H]$^+$; t$_R$=0.78 min. on LC/MS Method A.

Synthesis of (R)-2-((2-((2,4-dimethoxybenzyl)amino)-7-vinylpyrido[3,2-d]pyrimidin-4-yl)amino)hexan-1-ol (70C). A microwave vial containing (R)-2-((7-chloro-2-((2,4-dimethoxybenzyl)amino)pyrido[3,2-d]pyrimidin-4-yl)amino) hexan-1-ol 70B (50 mg, 0.11 mmol, 1 equiv.) was treated with potassium vinyltrifluoroborate (26.59 mg, 0.28 mmol, 2.5 equiv.), potassium phosphate tribasic (71.4 mg, 0.34 mmol, 3 equiv.), palladium(0) tetrakis(triphenylphosphine) (25.91 mg, 0.02 mmol, 0.2 equiv.), dioxane (2.0 mL), and water (2 mL). The mixture was heated to 150° C. for 60 min. in a microwave reactor. The reaction mixture was partitioned between EtOAc (50 mL) and H$_2$O (50 mL). The organic layer was separated, dried over Na$_2$SO$_4$, filtered and concentrated in vacuo to provide the crude material 70C which was used without further purification. LCMS (m/z): 438.27 [M+H]$^+$; t$_R$=0.82 min. on LC/MS Method A.

Synthesis of (R)-2-((2-amino-7-vinylpyrido[3,2-d]pyrimidin-4-yl)amino)hexan-1-ol (70). A solution of (R)-2-((2-((2,4-dimethoxybenzyl)amino)-7-vinylpyrido[3,2-d]pyrimidin-4-yl)amino)hexan-1-ol, 70C (49 mg, 0.08 mmol, 1 equiv.) in DCM (2 mL) was treated with TFA (0.5 mL). After 3 h the reaction mixture was concentrated under reduced pressure and the residue subjected to reverse phase HPLC (10% to 70% MeCN in water with 0.1% TFA using a Hydro-RP column) to furnish, after product fractions were collected and removal of volatiles in vacuo, 70 as its TFA salt. LCMS (m/z): 288.17 [M+H]$^+$; t$_R$=0.61 min. on LC/MS Method A. $^1$H NMR (400 MHz, MeOH-d$_4$) δ 8.61 (d, J=1.8 Hz, 1H), 7.75-7.62 (m, 1H), 6.80 (dd, J=17.7, 11.1 Hz, 1H), 6.05 (d, J=17.7 Hz, 1H), 5.54 (d, J=11.1 Hz, 1H), 4.47-4.31 (m, 1H), 3.71-3.51 (m, 2H), 1.77-1.47 (m, 2H), 1.35-1.16 (m, 5H), 0.93-0.71 (m, 4H). $^{19}$F NMR (377 MHz, MeOH-d$_4$) δ −77.60.

Synthesis of (R)-2-((2-amino-7-ethylpyrido[3,2-d]pyrimidin-4-yl)amino)hexan-1-ol (71). (R)-2-((2-amino-7-vinylpyrido[3,2-d]pyrimidin-4-yl)amino)hexan-1-ol, 70 (25 mg, 0.09 mmol, 1 equiv.) was treated with Pd/C (Degussa 10 wt %, 50 mg) and EtOH (5 mL) and the mixture stirred under hydrogen. After several h the solid was filtered off and the filtrate was concentrated under reduced pressure. The residue was subjected to reverse phase HPLC (10% to 50% MeCN in water with 0.1% TFA using a Gemini C18 column) to furnish, after product fractions were collected and the removal of volatiles in vacuo, 71 as its TFA salt. LCMS (m/z): 290.42 [M+H]$^+$; t$_R$=0.70 min. on LC/MS Method A. $^1$H NMR (400 MHz, MeOH-d$_4$) δ 8.60-8.42 (m, 1H), 7.63 (td, J=1.6, 0.9 Hz, 1H), 4.61-4.44 (m, 1H), 3.82-3.63 (m, 2H), 2.85 (q, J=7.6 Hz, 2H), 1.84-1.64 (m, 3H), 1.46-1.15 (m, 9H), 0.97-0.81 (m, 4H). $^{19}$F NMR (377 MHz, MeOH-d$_4$) δ −77.47.

Example 72

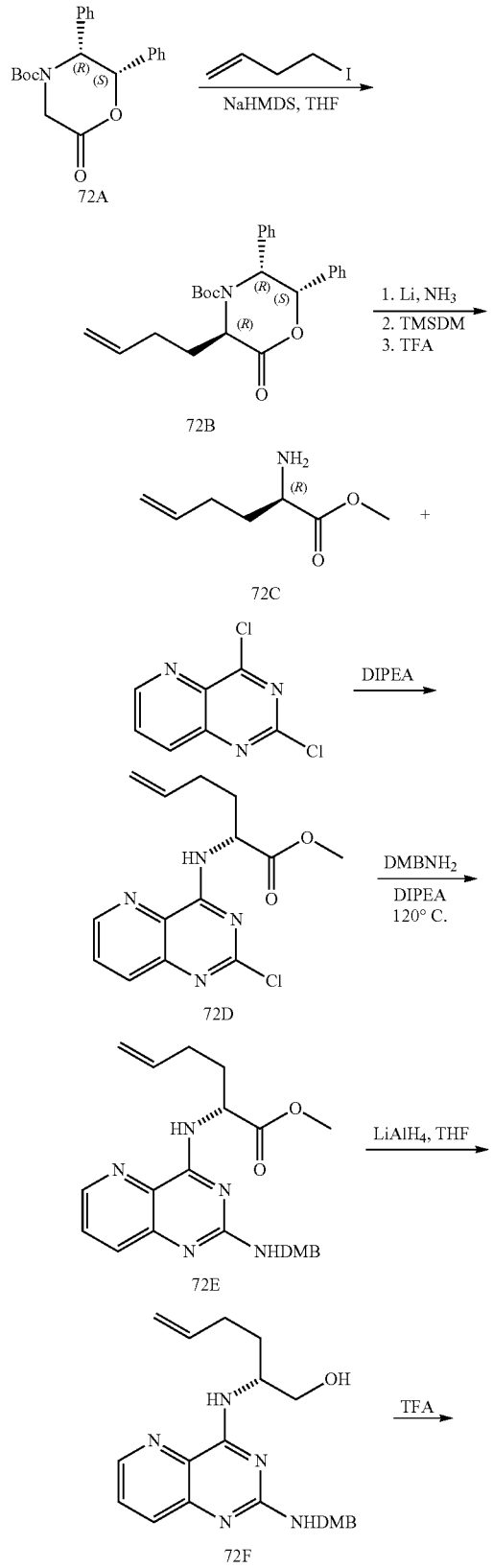

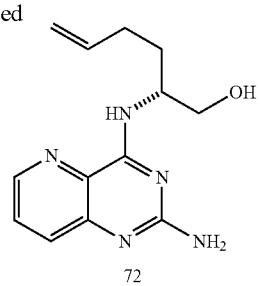

Synthesis of (3R,5R,6S)-tert-butyl 3-(but-3-en-1-yl)-2-oxo-5,6-diphenylmorpholine-4-carboxylate (72B). Starting with a stirred solution of (2S,3R)-tert-butyl 6-oxo-2,3-diphenylmorpholine-4-carboxylate 72A (1500 mg, 4 mmol, 1 equiv., supplied by Sigma-Aldrich) and 4-iodobutene (3862.41 mg, 0.02 mol, 5 equiv., supplied by Sigma-Aldrich) in anhydrous THF (24 mL) and HMPA (2.5 mL), cooled to −78° C., 1M sodium bis(trimethylsilyl) amide in THF (6.37 mL, 6.37 mmol, 1.5 equiv.) was added dropwise under argon. After 10 min. the reaction mixture was stirred at −40° C. for 4 h. The reaction was quenched with EtOAc (50 mL) and poured into a mixture of EtOAc (50 mL) and an aqueous solution of 1M NH$_4$Cl (50 mL). The organic layer was separated, washed with water (50 mL) and brine (50 mL), dried with Na$_2$SO$_4$, filtered and volatiles removed in vacuo to give a residue. The residue was subjected to silica gel chromatography eluting with 0% to 100% EtOAc in hexanes to afford the title compound 72B. LCMS (m/z): 307.98 [M+H−Boc]$^+$; t$_R$=1.28 min. on LC/MS Method A.

Synthesis of (R)-methyl 2-aminohex-5-enoate (72C). A 2-neck flask containing lithium (91.98 mg, 13.25 mmol, 15 equiv.) was cooled to −40° C. before liquid ammonia (15 mL) was added to the flask via condensation using a cold-finger apparatus. Intermediate 72B (360 mg, 0.88 mmol, 1 equiv.) in THF (2 mL) was then added. The reaction was maintained at −40° C. for 1 h, and then slowly quenched with NH$_4$Cl solution (5 mL), after which time it was allowed to warm to rt. The reaction was then diluted with diethyl ether (50 mL) and water (50 mL) and the diethyl ether layer separated. To the aqueous layer was then added 1 N HCl until pH 5 followed by extraction with EtOAc (50 mL). Each of the organic layers was washed with saturated NH$_4$Cl (50 mL) separately, and then combined, dried over MgSO$_4$, filtered and concentrated in vacuo. DCM (10 mL) was added to the residue followed by MeOH (1 mL), (trimethylsilyl)diazomethane (2.0M solution in hexanes) (0.29 mL, 2.20 mmol, 12 equiv.). After stirring for 1 h the reaction was concentrated under reduced pressure. The crude residue was treated with DCM (5 mL) and TFA (5 mL). After stirring for 2 h, the reaction was concentrated under reduced pressure to give 72C that was used without further purification.

Synthesis of (R)-2-((2,7-dichloropyrido[3,2-d]pyrimidin-4-yl)amino)hexan-1-ol (72D). A solution of 2,4,-dichloropyrido[3,2-d]pyrimidine (110 mg, 0.55 mmol, 1.1 equiv) in dioxane (4 mL) was treated with N,N-diisopropylethylamine (0.14 mL, 0.9 mmol, 2 equiv.) and then the crude (R)-methyl 2-aminopent-4-enoate 72C (112 mg, 0.46 mmol, 1 equiv.). The reaction was allowed to stir for 1 h to provide 72D that was used directly in solution. LCMS (m/z): 307.80 [M+H]$^+$; t$_R$=1.09 min. on LC/MS Method A.

Synthesis of (R)-methyl 2-((2-((2,4-dimethoxybenzyl)amino)pyrido[3,2-d]pyrimidin-4-yl)amino)hex-5-enoate (72E). The crude solution containing (R)-2-((2,7-dichloropyrido[3,2-d]pyrimidin-4-yl)amino)hexan-1-ol 72D (128 mg, 0.42 mmol, 1 equiv.) was treated with additional N,N-diisopropylethylamine (0.15 mL, 0.84 mmol, 2 equiv.) and then 2,4-dimethoxybenzylamine (0.47 mL, 0.85 mmol, 2 equiv.). The reaction was heated at 120° C. overnight. The reaction mixture was then partitioned between EtOAc (50 mL) and H$_2$O (50 mL). The organic layer was separated, dried over Na$_2$SO$_4$, filtered, and then concentrated in vacuo. The residue was subjected to silica gel chromatography eluting with 0% to 100% EtOAc in hexanes to provide the title compound 72E. LCMS (m/z): 438.52 [M+H]$^+$; t$_R$=0.91 min. on LC/MS Method A.

Synthesis of (R)-2-((2-((2,4-dimethoxybenzyl)amino)pyrido[3,2-d]pyrimidin-4-yl)amino)hex-5-en-1-ol (72F). (R)-methyl 2-((2-((2,4-dimethoxybenzyl)amino)pyrido[3,2-d]pyrimidin-4-yl)amino)hex-5-enoate 72E (43 mg, 0.1 mmol, 1 equiv.) was dissolved in THF (5 mL) and 1M lithium aluminum hydride in diethyl ether (0.29 mL, 0.29 mmol, 3 equiv.) was added. The reaction mixture was stirred at rt for 2 h. The reaction mixture was quenched with water (50 mL) and extracted with EtOAc (50 mL). The organic layer was dried over Na$_2$SO$_4$, filtered, and then concentrated in vacuo. The crude residue 72F (40 mg) was then used without further purification. LCMS (m/z): 410.52 [M+H]$^+$; t$_R$=0.85 min. on LC/MS Method A.

Synthesis of (R)-2-((2-aminopyrido[3,2-d]pyrimidin-4-yl)amino)hex-5-en-1-ol (72). (R)-2-((2-((2,4-dimethoxybenzyl)amino)pyrido[3,2-d]pyrimidin-4-yl)amino)hex-5-en-1-ol 72F (40 mg, 0.09 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, 72 as its TFA salt. LCMS (m/z): 260.14 [M+H]$^+$; t$_R$=0.58 min. on LC/MS Method A. $^1$H NMR (400 MHz, MeOH-d$_4$) δ 8.66 (ddd, J=10.3, 4.2, 1.5 Hz, 1H), 7.94-7.65 (m, 2H), 5.86 (ddt, J=16.9, 10.3, 6.7 Hz, 1H), 5.15-4.90 (m, 2H), 4.63-4.43 (m, 1H), 2.29-2.06 (m, 2H), 2.00-1.71 (m, 2H). $^{19}$F NMR (377 MHz, Methanol-d4) δ −77.31, −77.69.

Example 73

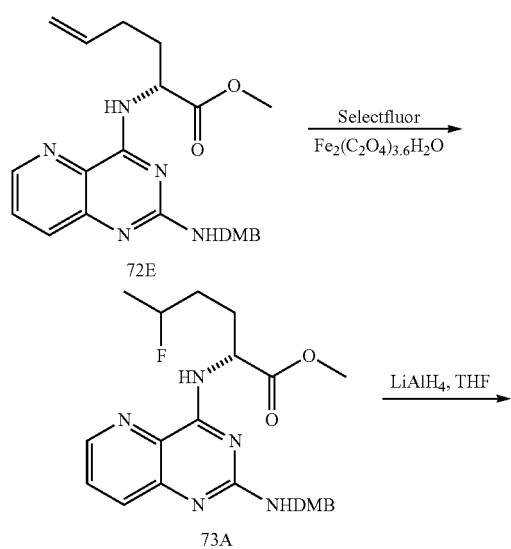

Synthesis of (2R)-methyl 2-((2-((2,4-dimethoxybenzyl)amino)pyrido[3,2-d]pyrimidin-4-yl)amino)-5-fluorohexanoate (73A). Iron(III) oxalate hexahydrate (172 mg, 0.36 mmol, 2 equiv.) was stirred in water (10 mL) until completely dissolved (typically 1-2 h). The clear yellow solution was cooled to 0° C. and degassed for 10 min. Selectfluor (126 mg, 0.36 mmol, 2 equiv.) and MeCN (5 mL) were added to the reaction mixture. A solution of (R)-methyl 2-((2-((2,4-dimethoxybenzyl)amino)pyrido[3,2-d]pyrimidin-4-yl)amino)hex-5-enoate 72E (78 mg, 0.18 mmol, 1 equiv.) in MeCN (5 mL) was added to the reaction mixture followed by sodium borohydride (23.6 mg, 0.62 mmol, 3.5 equiv.) at 0° C. After 2 min, the reaction mixture was treated with an additional portion of NaBH$_4$ (24 mg, 0.62 mmol, 3.5 equiv.). The resulting mixture was stirred for 30 min. and then quenched by the addition of 28-30% aqueous NH$_4$OH (4 mL). The mixture was extracted with 10% MeOH in CH$_2$Cl$_2$ and the organic layer was dried over Na$_2$SO$_4$, filtered and concentrated under reduced pressure. The residue was subjected to silica gel chromatography eluting with 0% to 100% EtOAc in hexanes, to provide 73A. LCMS (m/z): 458.63 [M+H]$^+$; t$_R$=0.91 min. on LC/MS Method A.

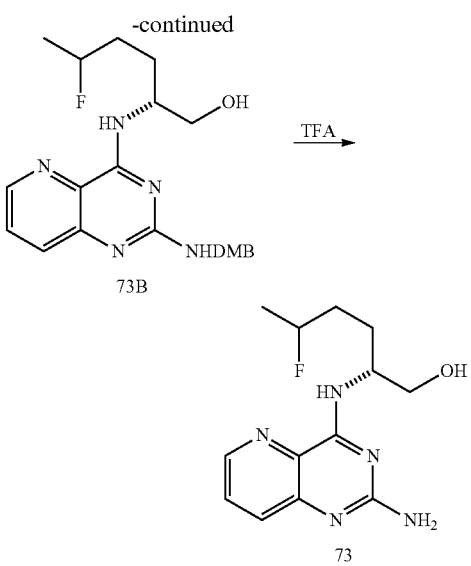

Synthesis of (2R)-2-((2-((2,4-dimethoxybenzyl)amino)pyrido[3,2-d]pyrimidin-4-yl)amino)-5-fluorohexan-1-ol (73B). (2R)-methyl 2-((2-((2,4-dimethoxybenzyl)amino)pyrido[3,2-d]pyrimidin-4-yl)amino)-5-fluorohexanoate 73A (43 mg, 0.1 mmol, 1 equiv.) was treated with THF (5 mL) and 1M lithium aluminum hydride in ether (0.29 mL, 0.29 mmol, 3 equiv.). The reaction mixture was allowed to stir at rt for 2 h. The reaction mixture was quenched with water (50 mL) and extracted with EtOAc (50 mL). The organics were combined, dried over Na$_2$SO$_4$, and concentrated in vacuo. The crude material 73B was used without further purification. LCMS (m/z): 430.19 [M+H]$^+$; t$_R$=0.82 min. on LC/MS Method A.

Synthesis of (2R)-2-((2-aminopyrido[3,2-d]pyrimidin-4-yl)amino)-5-fluorohexan-1-ol (73). (2R)-2-((2-((2,4-dimethoxybenzyl)amino)pyrido[3,2-d]pyrimidin-4-yl)amino)-5-fluorohexan-1-ol 73B (40 mg, 0.09 mmol, 1 equiv.) was treated with DCM (2 mL) and TFA (0.5 mL). After 3 h the reaction mixture was concentrated under reduced pressure and the residue subjected to reverse phase HPLC (10% to 70% MeCN in water with 0.1% TFA using a Hydro-RP column) to furnish, after collection of product fractions and removal of volatiles in vacuo, 73 as its TFA salt. LCMS (m/z): 280.12 [M+H]$^+$; $t_R$=0.59 min. on LC/MS Method A. $^1$H NMR (400 MHz, Methanol-d$_4$) δ 8.64 (dd, J=4.3, 1.4 Hz, 1H), 7.84 (dd, J=8.5, 1.4 Hz, 1H), 4.63-4.50 (m, 1H), 4.47 (t, J=6.0 Hz, 1H), 4.35 (t, J=6.0 Hz, 1H), 3.74 (d, J=5.3 Hz, 2H), 1.89-1.61 (m, 4H), 1.60-1.39 (m, 2H). $^{19}$F NMR (377 MHz, Methanol-d$_4$) δ -77.66, -220.85 (ddd, J=47.6, 25.5, 22.1 Hz).

Example 74

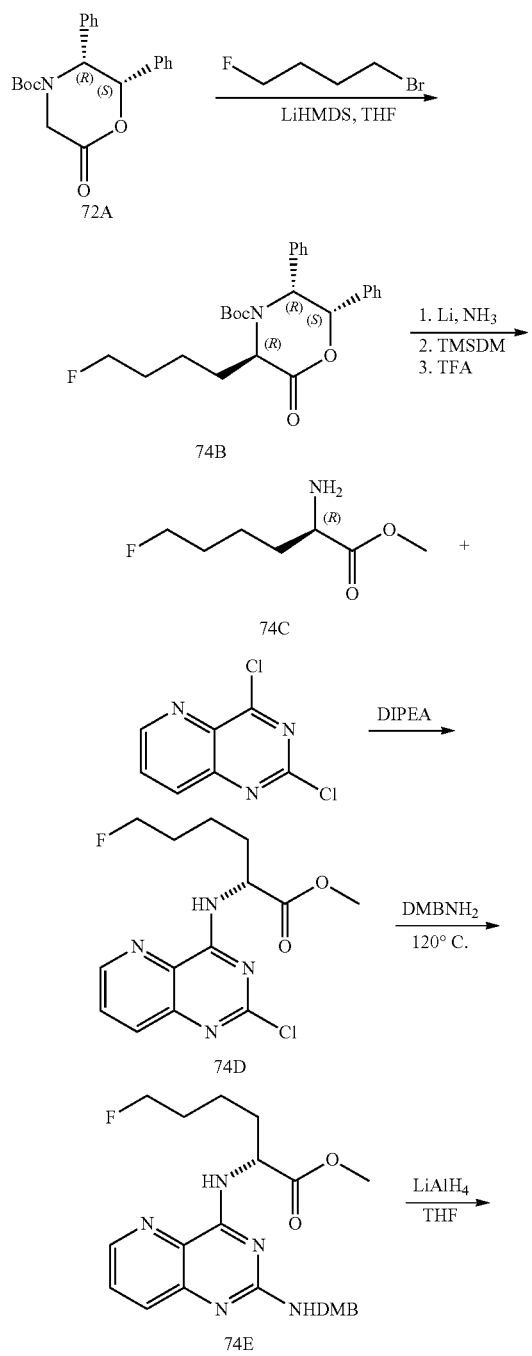

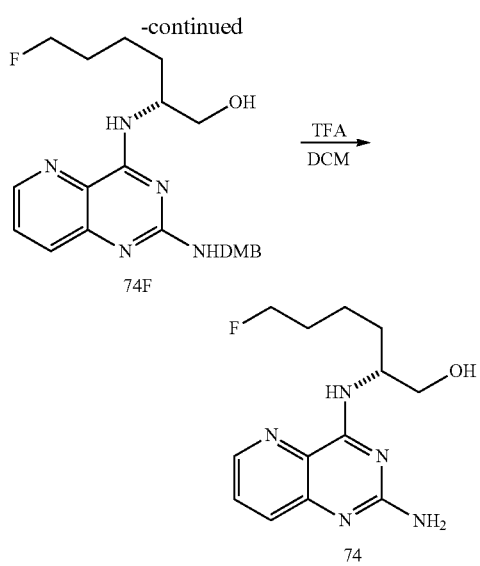

Synthesis of (3R,5R,6S)-tert-butyl 3-(4-fluorobutyl)-2-oxo-5,6-diphenylmorpholine-4-carboxylate (74B). A stirred solution of (2S,3R)-tert-butyl 6-oxo-2,3-diphenylmorpholine-4-carboxylate 72A (1000 mg, 2.8 mmol, 1 equiv.) and 1-bromo-4-fluorobutane (2.57 g, 13.5 mmol, 4.5 equiv., supplied by Sigma-Aldrich) in anhydrous THF (10 mL) and HMPA (1 mL) was cooled to -78° C. and treated dropwise with 1M Lithium bis(trimethylsilyl) amide in THF (4.2 mL, 4.2 mmol, 1.5 equiv.) under argon. After 10 min. the reaction mixture was stirred at -40° C. for 4 h. The reaction was quenched with EtOAc and poured into a mixture of EtOAc (50 mL) and an aqueous solution of NH$_4$Cl (50 mL, 1 M). The organic layer was separated and concentrated in vacuo to provide a crude residue which was subjected to silica gel chromatography eluting with 0% to 100% EtOAc in hexanes, to afford the title compound 74B LCMS (m/z): 328.9 [M+H−Boc]$^+$; $t_R$=1.38 min. on LC/MS Method A.

Synthesis of (R)-methyl 2-amino-6-fluorohexanoate (74C). A 2-neck flask containing lithium (170 mg, 24.5 mmol, 15 equiv.) was cooled at -40° C. before liquid ammonia (15 mL) was added via a cold-finger. To the deep blue mixture (3R,5R,6s)-tert-butyl 3-(4-fluorobutyl)-2-oxo-5,6-diphenylmorpholine-4-carboxylate 74B (700 mg, 1.6 mmol, 1 equiv.) was added. The reaction mixture was maintained at this temperature for 1 h and then allowed to warm up to rt. The reaction was slowly quenched with NH$_4$Cl solution and diluted with diethyl ether and the organic layer separated. The aqueous layer was adjusted to pH 5 with 1N HCl and was then extracted with EtOAc. The organic layers were washed with saturated NH$_4$Cl, dried over MgSO$_4$, filtered, and concentrated under reduced pressure. The organic residues were combined and treated with DCM (10 mL) and MeOH (1 mL) along with (trimethylsilyl) diazomethane (2.0M solution in hexanes, 0.50 mL, 3.2 mmol, 4 equiv.). After 1 h the reaction mixture was concentrated under reduced pressure. The crude residue material was treated with DCM (5 mL) and TFA (5 mL). The mixture was stirred for 2 h and then concentrated under reduced pressure to provide crude 74C that was used without further purification.

Synthesis of (R)-methyl 2-((2-chloropyrido[3,2-d]pyrimidin-4-yl)amino)-6-fluorohexanoate (74D). 2,4,-dichloropyrido[3,2-d]pyrimidine (163 mg, 0.82 mmol, 1.1 equiv.) was dissolved in dioxane (6 mL), N,N-diisopropylethylamine (0.53 mL, 2.9 mmol, 4 equiv.) and (R)-methyl 2-amino-6-fluorohexanoate 74C (205 mg, 0.74 mmol, 1 equiv.). The reaction mixture was stirred for 1h and then the mixture of 74D used directly. LCMS (m/z): 326.80 [M+H]⁺; $t_R$=1.04 min. on LC/MS Method A.

Synthesis of (R)-methyl 2-((2-((2,4-dimethoxybenzyl)amino)pyrido[3,2-d]pyrimidin-4-yl)amino)-6-fluorohexanoate (74E). A solution of (R)-methyl 2-((2-((2,4-dimethoxybenzyl)amino)pyrido[3,2-d]pyrimidin-4-yl)amino)-6-fluorohexanoate 74D (243 mg, 0.74 mmol, 1 equiv.) prepared as described, was treated with 2,4-dimethoxybenzylamine (0.22 mL, 1.49 mmol, 2 equiv.). The reaction was heated at 120° C. overnight. The reaction mixture was partitioned between EtOAc (50 mL) and H₂O (50 mL). The organic layer was separated, dried over Na₂SO₄, and concentrated in vacuo. The residue was subjected to silica gel chromatography eluting with 0% to 100% EtOAc in hexanes to provide 74E. LCMS (m/z): 445.61 [M+H]⁺; $t_R$=0.87 min. on LC/MS Method A.

Synthesis of (R)-2-((2-((2,4-dimethoxybenzyl)amino)pyrido[3,2-d]pyrimidin-4-yl)amino)-6-fluorohexan-1-ol (74F). (R)-methyl 2-((2-((2,4-dimethoxybenzyl)amino)pyrido[3,2-d]pyrimidin-4-yl)amino)-6-fluorohexanoate 74E (236 mg, 0.52 mmol, 1 equiv) was treated with THF (5 mL) and 1M lithium aluminum hydride in ether (1.5 mL, 1.54 mmol, 3 equiv.). The reaction was stirred at rt. After 2 h, the reaction was quenched with water (50 mL) and extracted with EtOAc (50 mL). The organic layer was dried over Na₂SO₄, and concentrated in vacuo. The crude material 74F was used without further purification. LCMS (m/z): 430.52 [M+H]⁺; $t_R$=0.79 min. on LC/MS Method A.

Synthesis of (R)-2-((2-aminopyrido[3,2-d]pyrimidin-4-yl)amino)-6-fluorohexan-1-ol (74). (R)-2-((2-((2,4-dimethoxybenzyl)amino)pyrido[3,2-d]pyrimidin-4-yl)amino)-6-fluorohexan-1-ol 74F (80 mg, 0.18 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.10% TFA using a Hydro-RP column) to furnish, after collection of product fractions and removal of volatiles in vacuo, 74 as its TFA salt. LCMS (m/z): 280.15 [M+H]⁺; $t_R$=0.56 min. on LC/MS Method A. ¹H NMR (400 MHz, Methanol-d4) δ 8.64 (dd, J=4.3, 1.4 Hz, 1H), 7.84 (dd, J=8.5, 1.4 Hz, 1H), 4.63-4.50 (m, 1H), 4.47 (t, J=6.0 Hz, 1H), 4.35 (t, J=6.0 Hz, 1H), 3.74 (d, J=5.3 Hz, 2H), 1.89-1.61 (m, 4H), 1.60-1.39 (m, 2H). ¹⁹F NMR (377 MHz, Methanol-d4) δ -77.66, -220.85 (ddd, J=47.6, 25.5, 22.1 Hz).

Example 75

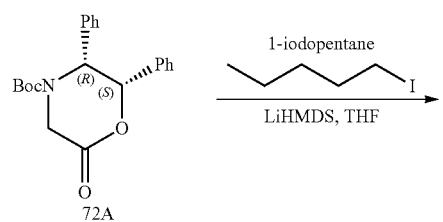

Synthesis of (3R,5R,6S)-tert-butyl 2-oxo-3-pentyl-5,6-diphenylmorpholine-4-carboxylate (75B). A stirred solution of (2S,3R)-tert-butyl 6-oxo-2,3-diphenylmorpholine-4-carboxylate 72A (1000 mg, 2.8 mmol, 1 equiv., supplied by Sigma-Aldrich) and 1-iodopentane (1.8 mL, 14.2 mmol, 5 equiv., supplied by Sigma-Aldrich) in anhydrous THF (15 mL) and HMPA (1.5 mL) cooled to −78° C., was treated dropwise with 1M lithium bis(trimethylsilyl) amide in THF (4.2 ml, 1.5 equiv.) under argon. After 10 min. the reaction mixture was stirred at −40° C. for 4 h. The reaction mixture was quenched with EtOAc and poured into a mixture of EtOAc (50 mL) and an aqueous solution of NH$_4$Cl (50 mL, 1 M). The organic layer was separated and concentrated in vacuo to provide a crude residue which was subjected to silica gel chromatography eluting with 0% to 100% EtOAc in hexanes to afford 75B. LCMS (m/z): 310.08 [M+H]$^+$; t$_R$=0.1.33 min. on LC/MS Method A.

Synthesis of (R)-methyl 2-aminoheptanoate (75C). A 2-neck flask containing lithium (110 mg, 15.9 mmol, 15 equiv.) was cooled at −40° C. before liquid ammonia (15 mL) was added via a cold-finger. To the deep blue mixture was added (3R,5R,6S)-tert-butyl 2-oxo-3-pentyl-5,6-diphenylmorpholine-4-carboxylate 75B (450 mg, 1.06 mmol, 1 equiv.). The reaction was maintained at this temperature for 1h and then allowed to warm to rt. The reaction was slowly quenched with NH$_4$Cl (5 mL) solution and diluted with ether (50 mL) and separated. To the aqueous layer was added 1N HCl to pH 5 which was then extracted with EtOAc (50 mL). Each of the organic layers was then washed separately with saturated NH$_4$Cl, then combined, dried over MgSO$_4$, filtered, and concentrated under reduced pressure. The residue was treated with DCM (10 mL) and MeOH (1 mL) along with (trimethylsilyl)diazomethane, 2.0M solution in hexanes (1.1 mL, 2.1 mmol, 4 equiv.). After 1 h the reaction was concentrated under reduced pressure and the residue dissolved in DCM (5 mL) and TFA (5 mL). The mixture was stirred for 2 h and then concentrated under reduced pressure to afford crude 75C which was used without further purification.

Synthesis of (R)-methyl 2-((2-chloropyrido[3,2-d]pyrimidin-4-yl)amino)heptanoate (75D). A solution of 2,4,-dichloropyrido[3,2-d]pyrimidine (89 mg, 0.44 mmol, 1.2 equiv.) in THF (5 mL) was treated with N,N-diisopropylethylamine (0.26 mL, 1.76 mmol, 4 equiv.) and (R)-methyl 2-aminoheptanoate 75C (71 mg, 0.44 mmol, 1 equiv., TFA salt). The reaction was stirred for 1 h and then the mixture containing 75D was used without purification. LCMS (m/z): 323.8 [M+H]$^+$; t$_R$=1.32 min. on LC/MS Method A.

Synthesis of (R)-methyl 2-((2-((2,4-dimethoxybenzyl)amino)pyrido[3,2-d]pyrimidin-4-yl)amino)heptanoate (75E). To the solution containing (R)-methyl 2-((2-chloropyrido[3,2-d]pyrimidin-4-yl)amino)heptanoate 75D (120 mg, 0.37 mmol, 1 equiv.) prepared as described, was added 2,4-dimethoxybenzylamine (0.17 mL, 1.1 mmol, 3 equiv.). The reaction mixture was heated at 120° C. overnight. The reaction mixture partitioned between EtOAc (50 mL) and H$_2$O (50 mL). The organic layer was separated, dried, and concentrated in vacuo. The residue was subjected to silica gel chromatography eluting with 0% to 100% EtOAc in hexanes to provide the title compound 75E. LCMS (m/z): 454.6 [M+H]$^+$; t$_R$=1.02 min. on LC/MS Method A.

Synthesis of (R)-2-((2-((2,4-dimethoxybenzyl)amino)pyrido[3,2-d]pyrimidin-4-yl)amino)heptan-1-ol (75F). (R)-methyl 2-((2-((2,4-dimethoxybenzyl)amino)pyrido[3,2-d]pyrimidin-4-yl)amino)heptanoate 75E (169 mg, 0.37 mmol, 1 equiv.) was dissolved in THF (5 mL) and treated with 1M lithium aluminum hydride in ether (1.1 mL, 1.1 mmol, 3 equiv.). The reaction mixture was stirred at rt. After 2 h, the reaction was quenched with water and extracted with EtOAc. The organics were separated, dried, and concentrated in vacuo. The crude product 75F was used without further purification. LCMS (m/z): 426.4 [M+H]$^+$; t$_R$=0.95 min. on LC/MS Method A.

Synthesis of (R)-2-((2-aminopyrido[3,2-d]pyrimidin-4-yl)amino)heptan-1-ol (75). (R)-2-((2-((2,4-dimethoxybenzyl)amino)pyrido[3,2-d]pyrimidin-4-yl)amino)heptan-1-ol 75F (20 mg, 0.05 mmol, 1 equiv.) was dissolved in DCM (2 mL) and TFA (0.5 mL). After 3 h the reaction mixture was concentrated under reduced pressure and the residue subjected to reverse phase HPLC (10% to 70% MeCN in water with 0.1% TFA using a Hydro-RP column) to furnish, after collection of product fractions and removal of volatiles in vacuo, 75 as its TFA salt. LCMS (m/z): 276.4 [M+H]$^+$; t$_R$=0.71 min. on LC/MS Method A. $^1$H NMR (400 MHz, Methanol-d$_4$) δ 8.65 (dd, J=4.3, 1.6 Hz, 1H), 7.92-7.66 (m, 2H), 4.66-4.43 (m, 1H), 3.73 (d, J=5.3 Hz, 2H), 1.81-1.57 (m, 2H), 1.51-1.20 (m, 9H), 0.89 (t, J=7.0 Hz, 3H). $^{19}$F NMR (377 MHz, Methanol-d$_4$) δ −77.55.

Example 76 and Example 77

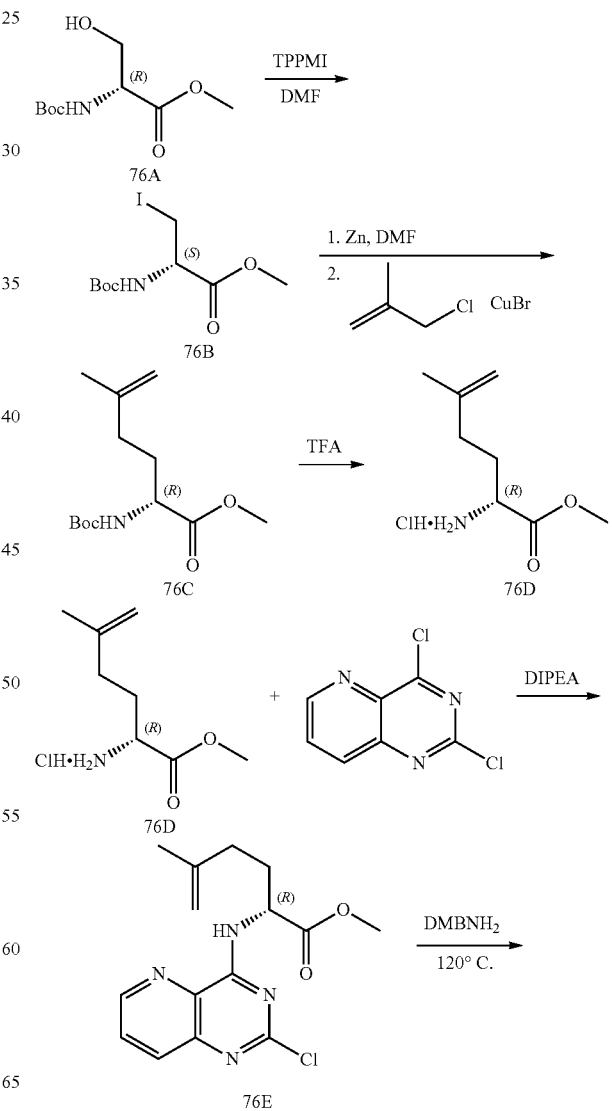

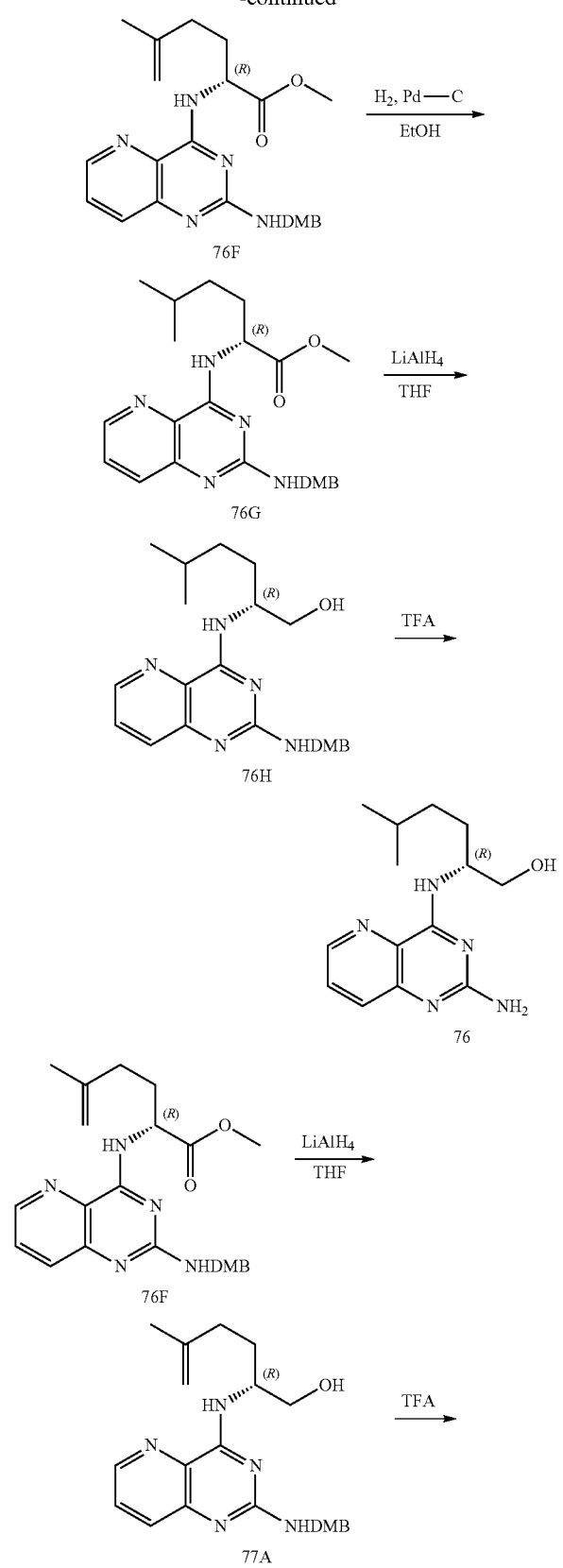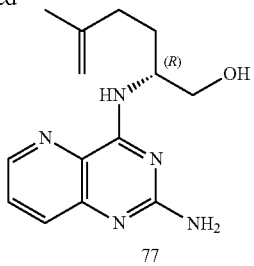

Synthesis of (S)-methyl 2-((tert-butoxycarbonyl)amino)-3-iodopropanoate (76B). (R)-methyl 2-((tert-butoxycarbonyl)amino)-3-hydroxypropanoate 76A (6 g, 27.37 mmol, supplied by Sigma-Aldrich) was treated with DMF (100 mL) and cooled to 0° C. before methyltriphenoxyphosphonium iodide (16.1 g, 35.58 mmol, 1.3 equiv., supplied by Sigma-Aldrich) was slowly added. The reaction mixture was stirred overnight and solid NaHCO₃ (14 g) and water (100 mL) were added to the reaction. The reaction mixture was stirred for 15 min. and then the mixture was extracted with hexanes in diethyl ether, (1:1) (2×250 mL). The combined organic extracts were washed with 0.5M NaOH solution (3×75 mL) and saturated NH₄Cl (75 mL), dried over MgSO₄, filtered and concentrated under reduced pressure to afford the crude product 76B. LCMS (m/z): 331.13 [M+H]⁺; $t_R$=1.16 min. on LC/MS Method A.

Synthesis of (R)-methyl 2-((tert-butoxycarbonyl)amino)-5-methylhex-5-enoate (76C). Zinc dust (2.4 g, 36.4 mmol, 4 equiv.) was added to iodine (93 mg, 0.37 mmol, 0.04 equiv.) in a three-neck round-bottomed flask and heated under vacuum for 10 min. The flask was flushed with nitrogen and evacuated three times. (S)-methyl 2-((tert-butoxycarbonyl)amino)-3-iodopropanoate 76B (3000 mg, 9.11 mmol) was dissolved in dry DMF (5 mL) and added to the zinc slurry at 0° C. The reaction mixture was stirred at rt for 1 h. Copper (I) bromide-dimethylsulfide complex (187.39 mg, 0.91 mmol, 0.1 equiv., supplied by Sigma-Aldrich) was placed in a separate three-necked flask and gently dried under vacuum until a color change from white to green was observed. Dry DMF (4 mL) and 3-chloro-2-methylpropene (1.34 mL, 13.67 mmol, supplied by Sigma-Aldrich) were added, and the reaction was cooled to −15° C. Once zinc insertion in the first step was complete, stirring was stopped, and the zinc allowed to settle. The supernatant was removed via syringe and added dropwise to the electrophile and Cu catalyst mixture at −15° C. The cold bath was removed, and the reaction mixture was stirred at rt for 2 days. EtOAc (100 mL) was added, and the reaction was stirred for 15 min. The reaction mixture was washed with 1M Na₂S₂O₃ (100 mL), water (2×100 mL), and brine (100 mL), dried over MgSO₄, filtered, and concentrated reduced pressure. The residue was subjected to silica gel chromatography eluting with 0% to 100% EtOAc in hexane to provide 76C. LCMS (m/z): 157.95 [M+H−Boc]⁺; $t_R$=1.16 min. on LC/MS Method A.

Synthesis of (R)-methyl 2-amino-5-methylhex-5-enoate (76D). (R)-methyl 2-((tert-butoxycarbonyl)amino)heptanoate 76C (655 mg, 3 mmol) was treated with DCM (5 mL) and TFA (5 mL) and stirred for 2 h. The mixture was then concentrated under reduced pressure to provide 76D that was used without further purification.

Synthesis of (R)-methyl 2-((2-chloropyrido[3,2-d]pyrimidin-4-yl)amino)-5-methylhex-5-enoate (76E). 2,4,-dichloropyrido[3,2-d]pyrimidine (466 mg, 2 mmol, 1 equiv.) was treated with THF (10 mL) followed by N,N-diisopropylethylamine (1.66 mL, 9 mmol, 4 equiv.), and then (R)-methyl 2-amino-5-methylhex-5-enoate 76D (593 mg, 2 mmol, 1 equiv., TFA salt). The reaction mixture was stirred for 1 h and then the product 76E was used directly. LCMS (m/z): 321.2 [M+H]$^+$; $t_R$=1.19 min. on LC/MS Method A.

Synthesis of (R)-methyl 2-((2-((2,4-dimethoxybenzyl)amino)pyrido[3,2-d]pyrimidin-4-yl)amino)-5-methylhex-5-enoate (76F). The solution of (R)-methyl 2-((2-chloropyrido[3,2-d]pyrimidin-4-yl)amino)-5-methylhex-5-enoate 76E (748 mg, 2 mmol, 1 equiv.) prepared as described, was treated with 2,4-dimethoxybenzylamine (0.69 mL, 5 mmol, 2 equiv.) and N,N-diisopropylethylamine (1.66 mL, 9 mmol, 4 equiv.). The reaction mixture was heated at 120° C. overnight. The reaction mixture was partitioned between EtOAc (50 mL) and H$_2$O (50 mL). The organic layer was separated, dried over MgSO$_4$, and concentrated in vacuo. The residue was subjected to silica gel chromatography eluting with 0% to 100% EtOAc in hexane to provide the title compound 76F (LCMS (m/z): 452.55 [M+H]$^+$; $t_R$=0.97 min. on LC/MS Method A.

Synthesis of (R)-methyl 2-((2-((2,4-dimethoxybenzyl)amino)pyrido[3,2-d]pyrimidin-4-yl)amino)-5-methylhexanoate (76G). (R)-methyl 2-((2-((2,4-dimethoxybenzyl)amino)pyrido[3,2-d]pyrimidin-4-yl)amino)-5-methylhex-5-enoate 76F (35 mg, 0.08 mmol) was treated with Pd/C (50 mg) and EtOH (5 mL) and then stirred under hydrogen. After 4 h the solid was removed by filtration and the filtrate was concentrated under reduced pressure. The resulting residue of 76G was used without further purification. LCMS (m/z): 454.24 [M+H]$^+$; $t_R$=1.06 min. on LC/MS Method A.

Synthesis of (R)-2-((2-((2,4-dimethoxybenzyl)amino)pyrido[3,2-d]pyrimidin-4-yl)amino)-5-methylhexan-1-ol (76H). (R)-methyl 2-((2-((2,4-dimethoxybenzyl)amino)pyrido[3,2-d]pyrimidin-4-yl)amino)-5-methylhexanoate 76G (32 mg, 0.37 mmol, 1 equiv.) was treated with THF (5 mL) and 1M lithium aluminum hydride in ether (0.2 mL, 0.2 mmol, 3 equiv.). The reaction mixture was stirred for 2 h and then quenched with water (50 mL) and extracted with EtOAc (50 mL). The organic layer was separated, dried over MgSO$_4$, and concentrated in vacuo. The crude material 76H was used without further purification. LCMS (m/z): 426.23 [M+H]$^+$; $t_R$=0.96 min. on LC/MS Method A.

Synthesis of (R)-2-((2-aminopyrido[3,2-d]pyrimidin-4-yl)amino)-5-methylhexan-1-ol. (R)-2-((2-((2,4-dimethoxybenzyl)amino)pyrido[3,2-d]pyrimidin-4-yl)amino)-5-methylhexan-1-ol (76). Compound 76H (25 mg, 0.05 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP) to furnish, after collection of product fractions and removal of volatiles in vacuo, 76. LCMS (m/z): 276.13 [M+H]$^+$; $t_R$=0.70 min. on LC/MS Method A.

Synthesis of (R)-2-((2-((2,4-dimethoxybenzyl)amino)pyrido[3,2-d]pyrimidin-4-yl)amino)-5-methylhex-5-en-1-ol (77A). (R)-methyl 2-((2-((2,4-dimethoxybenzyl)amino)pyrido[3,2-d]pyrimidin-4-yl)amino)-5-methylhex-5-enoate 76F (40 mg, 90 mmol, 1 equiv.) was treated with THF (5 mL) and 1M lithium aluminum hydride in ether (0.27 mL, 0.27 mmol, 3 equiv.). The reaction mixture was stirred for 2 h and then quenched with water (50 ml) and extracted with EtOAc (50 mL). The organics were separated, dried, and concentrated in vacuo to provide a residue of 77A that was used without further purification. LCMS (m/z): 424.20 [M+H]$^+$; $t_R$=0.88 min. on LC/MS Method A.

Synthesis of (R)-2-((2-aminopyrido[3,2-d]pyrimidin-4-yl)amino)-5-methylhex-5-en-1-ol (77). 77A (40 mg, 0.095 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, the title compound 77 as its TFA salt. LCMS (m/z): 274.43 [M+H]$^+$; $t_R$=0.65 min. on LC/MS Method A. $^1$H NMR (400 MHz, Methanol-d4) δ 8.59-8.42 (m, 1H), 7.75-7.52 (m, 2H), 4.45-4.13 (m, 1H), 3.87-3.69 (m, 1H), 3.65-3.44 (m, 2H), 2.30 (dq, J=15.0, 7.1 Hz, 1H), 2.01-1.73 (m, 2H), 1.68-1.41 (m, 4H), 1.26-1.05 (m, 6H). $^{19}$F NMR (377 MHz, Methanol-d4) δ −77.52.

Example 78

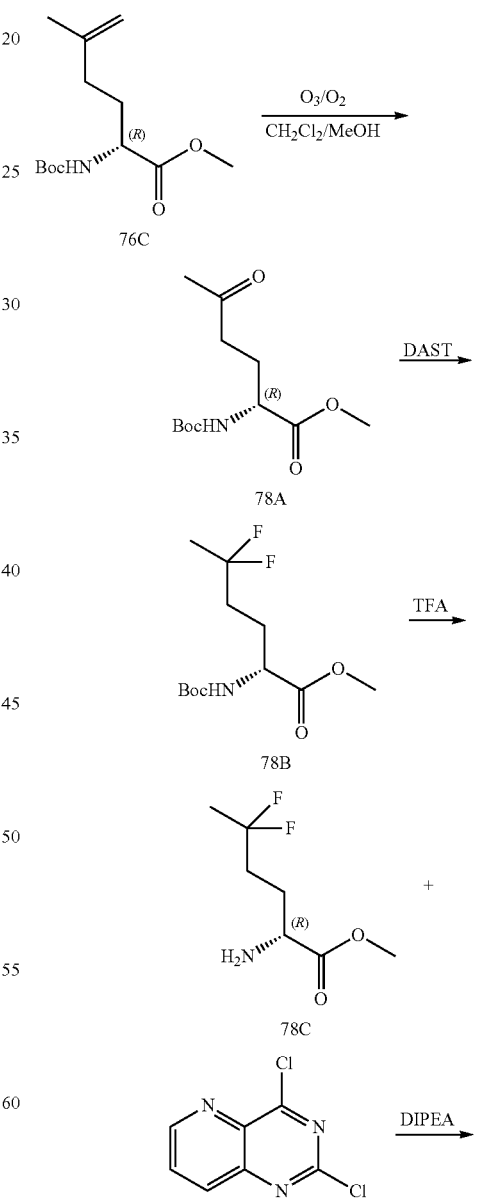

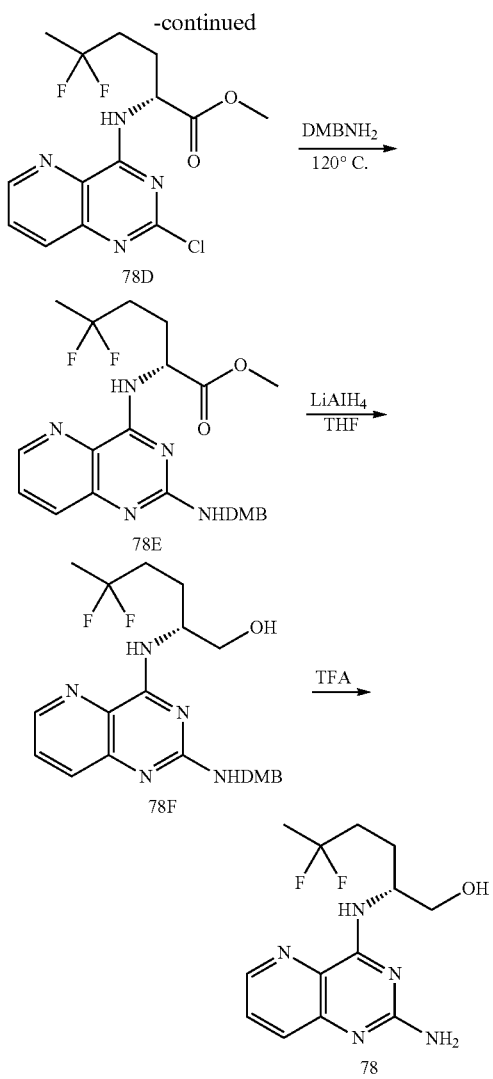

Synthesis of (R)-methyl 2-((tert-butoxycarbonyl)amino)-5-oxohexanoate (78A). (R)-methyl 2-((tert-butoxycarbonyl)amino)-5-methylhex-5-enoate 76C (775 mg, 3.01 mmol) was treated with DCM (20 mL) and MeOH (5 mL) before cooling to −78° C. Ozone was bubbled through the reaction mixture. After 10 min., the mixture was quenched with dimethyl sulfide (0.90 mL, 12 mmol, 4 equiv.) and allowed to warm up to rt. EtOAc (100 mL) was added, and the reaction was stirred for 15 min. The mixture was washed with 1M Na$_2$S$_2$O$_3$ (100 mL), water (2×100 mL), and brine (100 mL) and dried over MgSO$_4$. The organic solution was filtered and concentrated under reduced pressure, and the resulting residue was subjected to silica gel chromatography eluting with 0% to 100% EtOAc in hexane to provide 78A $^1$H NMR (400 MHz, Chloroform-d) δ 5.11 (d, J=8.3 Hz, 1H), 4.33-4.20 (m, 1H), 3.73 (s, 4H), 2.63-2.42 (m, 3H), 2.14 (s, 4H), 2.12-2.05 (m, 1H), 1.94-1.81 (m, 1H), 1.42 (s, 13H).

Synthesis of (R)-methyl 2-((tert-butoxycarbonyl)amino)-5,5-difluorohexanoate (78B). (R)-methyl 2-((tert-butoxycarbonyl)amino)-5-oxohexanoate 78A (235 mg, 0.91 mmol) was dissolved in DCM (10 mL), then treated with DAST 95% (0.36 mL, 2.72 mmol). The reaction was stirred for 16 h. EtOAc (50 mL) and NaHCO$_3$ solution (5 mL) were added and the reaction was stirred for 5 min. The reaction mixture was washed with 1M Na$_2$S$_2$O$_3$ (100 mL), water (2×100 mL), and brine (100 mL) and dried over MgSO$_4$. The solvent was removed under reduced pressure and the residue subjected to silica gel chromatography eluting with 0% to 100% EtOAc in hexanes to afford 78B. $^1$H NMR (400 MHz, Chloroform-d) δ 5.04 (s, 1H), 4.32 (s, 1H), 3.76 (s, 5H), 2.16-1.99 (m, 2H), 1.98-1.75 (m, 5H), 1.69-1.52 (m, 7H), 1.44 (s, 16H), 1.34-1.20 (m, 2H), 0.92-0.80 (m, 1H). $^{19}$F NMR (377 MHz, Chloroform-d) δ −92.14 (dq, J=50.1, 17.0 Hz).

Synthesis of (R)-methyl 2-amino-5,5-difluorohexanoate (78C). (R)-methyl 2-((tert-butoxycarbonyl)amino)-5,5-difluorohexanoate 78B (36 mg, 0.13 mmol, 1 equiv.) was treated with DCM (2 mL) and TFA (0.5 mL). After 3 h the reaction mixture was concentrated under reduced pressure and the crude product 78C was used without further purification.

Synthesis of (R)-methyl 2-((2-chloropyrido[3,2-d]pyrimidin-4-yl)amino)-5,5-difluorohexanoate (78D). 2,4,-dichloropyrido[3,2-d]pyrimidine (33 mg, 0.16 mmol, 1.25 equiv.) was treated with THF (10 mL) followed by N,N-diisopropylethylamine (0.18 mL, 1.0 mmol, 8 equiv.), and (R)-methyl 2-amino-5,5-difluorohexanoate 78C (36 mg, 0.13 mmol, 1 equiv., TFA salt). The reaction mixture was stirred for 1 h to generate 78D and then this mixture was used directly. LCMS (m/z): 345.13 [M+H]$^+$; t$_R$=1.08 min. on LC/MS Method A.

Synthesis of (R)-methyl 2-((2-((2,4-dimethoxybenzyl)amino)pyrido[3,2-d]pyrimidin-4-yl)amino)-5,5-difluorohexanoate (78E). (R)-methyl 2-((2-chloropyrido[3,2-d]pyrimidin-4-yl)amino)-5,5-difluorohexanoate 78D (45 mg, 0.13 mmol, 1 equiv.) solution as described, was treated with 2,4-dimethoxybenzylamine (0.077 mL, 0.52 mmol, 4 equiv.). The reaction was heated at 120° C. overnight. The reaction mixture was partitioned between EtOAc (100 mL) and H$_2$O (100 mL). The organics were separated, dried, and concentrated in vacuo. The residue was subjected to silica gel chromatography eluting with 0% to 100% EtOAc in hexane to provide the title compound 78E. LCMS (m/z): 476.13 [M+H]$^+$; t$_R$=0.99 min. on LC/MS Method A.

Synthesis of (R)-2-((2-((2,4-dimethoxybenzyl)amino)pyrido[3,2-d]pyrimidin-4-yl)amino)-5,5-difluorohexan-1-ol (78F). (R)-methyl 2-((2-((2,4-dimethoxybenzyl)amino)pyrido[3,2-d]pyrimidin-4-yl)amino)-5,5-difluorohexanoate 78E (26 mg, 0.055 mmol, 1 equiv.) was treated with THF (5 mL) and 1M lithium aluminum hydride in ether (0.2 mL, 0.2 mmol, 4 equiv.). The reaction mixture was stirred at rt for 2 h and then the reaction was quenched with water (50 mL) and extracted with EtOAc (50 mL). The organics were separated, dried, and concentrated in vacuo. The crude material 78E was used without further purification. LCMS (m/z): 448.12 [M+H]$^+$; t$_R$=0.91 min. on LC/MS Method A.

Synthesis of (R)-2-((2-aminopyrido[3,2-d]pyrimidin-4-yl)amino)-5,5-difluorohexan-1-ol (78). (R)-2-((2-((2,4-dimethoxybenzyl)amino)pyrido[3,2-d]pyrimidin-4-yl)amino)-5,5-difluorohexan-1-ol 78F (24 mg, 0.055 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, 78. LCMS (m/z): 298.10 [M+H]$^+$; t$_R$=0.60 min. on LC/MS Method A. $^1$H NMR (400 MHz, Methanol-d$_4$) δ 8.66 (dd, J=4.3, 1.5 Hz, 5H), 7.86-7.73 (m, 10H), 4.55 (dd, J=9.0, 4.7 Hz, 5H), 4.30 (s, 1H), 3.83 (s, 2H), 3.76 (t, J=5.1 Hz, 12H), 3.34 (s, 3H), 2.05-1.85 (m, 23H), 1.58 (t, J=18.5 Hz, 17H), 1.41-1.26 (m, 17H), 1.14

(s, 1H), 0.96-0.88 (m, 4H), 0.87 (s, 2H). $^{19}$F NMR (377 MHz, Methanol-d4) δ −77.67, −92.96 (p, J=17.4 Hz).

Example 79

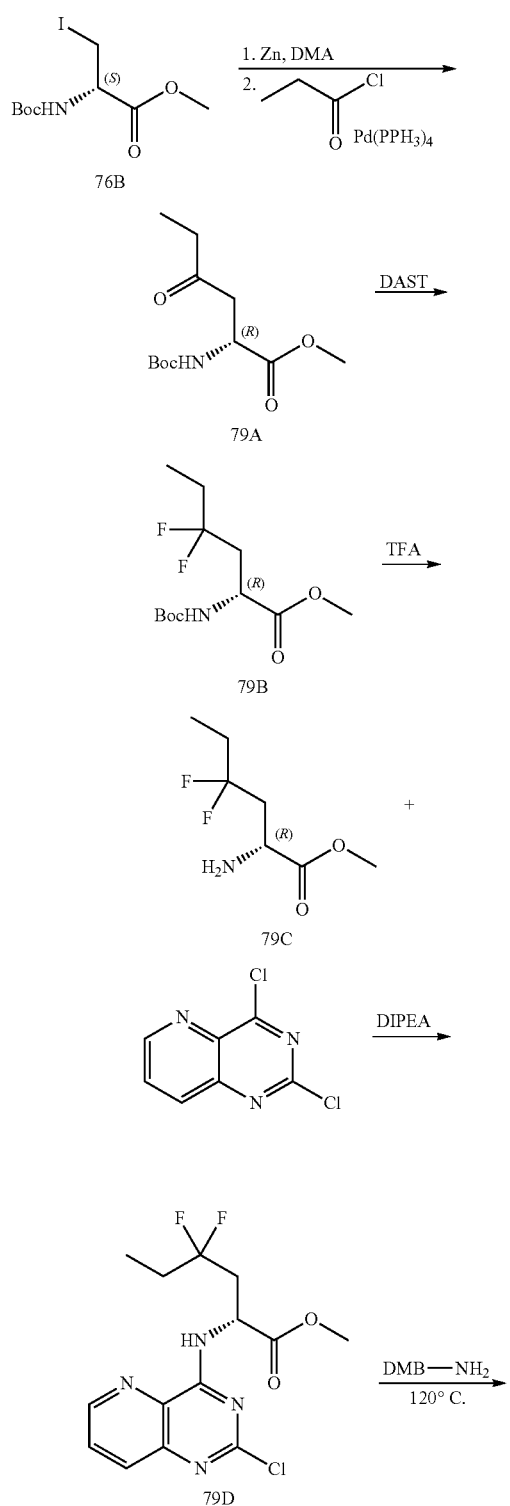

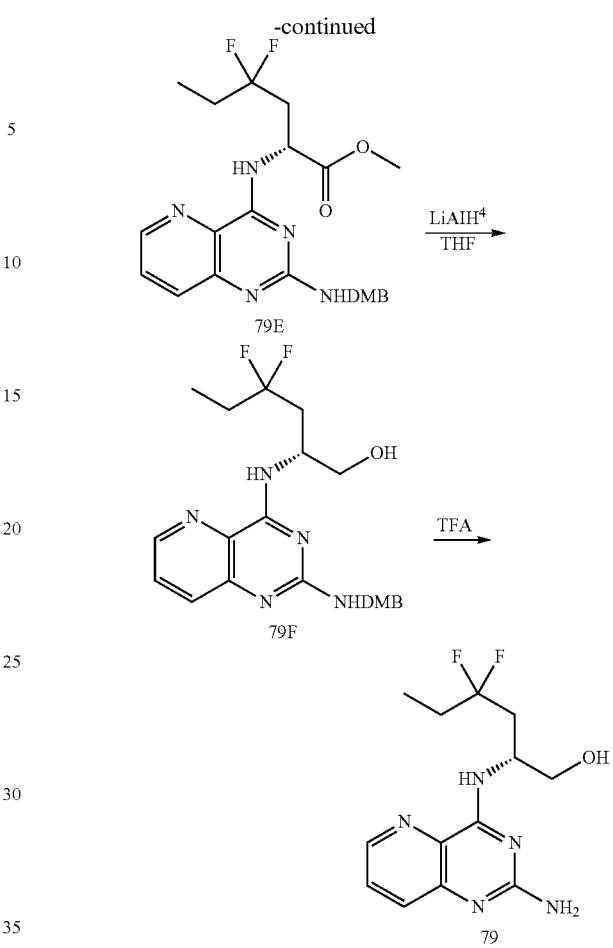

Synthesis of (R)-methyl 2-((tert-butoxycarbonyl)amino)-4-oxohexanoate (79A). Zinc dust (1.58 g, 24.3 mmol, 4 equiv.) was added to iodine (61 mg, 0.24 mmol, 0.04 equiv.) in a three-neck round-bottomed flask and heated under vacuum for 10 min. The flask was flushed with nitrogen and evacuated three times. After cooling, benzene (10 mL) and DMA (1 mL) were added. 1,2-bromoethane (0.05 mL, 0.61 mmol) and chlorotrimethylsilane (33.01 mg, 0.3 mmol) were then added consecutively and this process repeated three times in the course of 1 hour. (S)-methyl 2-((tert-butoxycarbonyl)amino)-3-iodopropanoate 76B (2400 mg, 0.6 mmol, 1 equiv.) was dissolved in benzene (10 mL) and DMA (1 mL) and added to the zinc slurry. After about 1 h, bis(triphenylphosphine) palladium (II) dichloride, (106.62 mg, 0.025 equiv.) and Tetrakis(triphenylphosphine)palladium(0) (175.68 mg, 0.025 equiv.) were added followed by propionyl chloride (0.8 mL, 0.01 mol, 1.5 equiv.). The reaction mixture was warmed to 70° C. and stirred for 1 h. EtOAc (100 mL) was added, and the reaction mixture was filtered over a pad of Celite. The filtrate was washed with water (2×100 mL), brine (100 mL), dried over MgSO$_4$, filtered and concentrated under reduced pressure. The residue was subjected to silica gel chromatography eluting with 0% to 100% EtOAc in hexane to afford 79A. $^1$H NMR (400 MHz, Chloroform-d) δ 5.48 (d, J=8.6 Hz, 1H), 4.46 (dt, J=8.7, 4.4 Hz, 1H), 3.69 (s, 3H), 3.10 (dd, J=18.0, 4.5 Hz, 1H), 2.89 (dd, J=17.9, 4.4 Hz, 1H), 2.40 (qd, J=7.3, 1.7 Hz, 2H), 1.40 (s, 10H), 1.01 (t, J=7.3 Hz, 3H).

Synthesis of (R)-methyl 2-((tert-butoxycarbonyl)amino)-4,4-difluorohexanoate (79B). (R)-methyl 2-((tert-butoxycarbonyl)amino)-4-oxohexanoate 79A (475 mg, 1.8 mmol, 1 equiv.) was treated with DAST (0.97 mL, 7.3 mmol, 4 equiv.). The reaction mixture was stirred for 16 h. EtOAc (50 mL) and NaHCO₃ solution (5 mL) were added and the reaction was stirred for 5 min. The reaction mixture was washed with 1M Na₂S₂O₃ (100 mL), water (2×100 mL), brine (100 mL), dried over MgSO₄, filtered, and concentrated under reduced pressure. The residue was subjected to silica gel chromatography eluting with 0% to 100% EtOAc in hexane to afford 79B. $^1$H NMR (400 MHz, Chloroform-d) δ 5.20 (d, J=8.3 Hz, 1H), 4.51 (d, J=7.0 Hz, 1H), 3.82 (s, 1H), 3.75 (d, J=0.5 Hz, 5H), 3.35-3.17 (m, 2H), 3.11 (q, J=7.1 Hz, 2H), 2.52-2.27 (m, 3H), 1.89 (ddt, J=24.1, 16.8, 7.5 Hz, 3H), 1.44 (d, J=0.6 Hz, 15H), 1.23-1.13 (m, 4H), 1.00 (dt, J=10.7, 7.5 Hz, 6H). $^{19}$F NMR (377 MHz, Chloroform-d) δ −93.56−−109.28 (m).

Synthesis of (R)-methyl 2-amino-5,5-difluorohexanoate. (R)-methyl 2-((tert-butoxycarbonyl)amino)-4,4-difluorohexanoate (79C). Compound 79B (98 mg, 0.35 mmol, 1 equiv.) was treated with DCM (2 mL) and TFA (0.5 mL). After 3 h the reaction mixture was concentrated under reduced pressure and the crude product 79C as its TFA salt was used without further purification.

Synthesis of (R)-methyl 2-((2-chloropyrido[3,2-d]pyrimidin-4-yl)amino)-4,4-difluorohexanoate (79D). 2,4,-dichloropyrido[3,2-d]pyrimidine (80 mg, 0.39 mmol, 1 equiv.) was treated with THF (10 ml) followed by N,N-diisopropylethylamine (0.28 mL, 1.5 mmol, 4 equiv.), and then (R)-methyl 2-amino-5,5-difluorohexanoate 79C (110 mg, 0.39 mmol, 1 equiv., TFA salt). The reaction mixture was stirred for 1 h to form 79D and then this solution was used directly. LCMS (m/z): 345.11 [M+H]⁺; $t_R$=1.09 min. on LC/MS Method A.

Synthesis of (R)-methyl 2-((2-((2,4-dimethoxybenzyl)amino)pyrido[3,2-d]pyrimidin-4-yl)amino)-4,4-difluorohexanoate (79E). (R)-methyl 2-((2-chloropyrido[3,2-d]pyrimidin-4-yl)amino)-5,5-difluorohexanoate 79D solution prepared as described, was treated with 2,4-dimethoxybenzylamine (0.077 mL, 0.52 mmol, 4 equiv.). The reaction was heated at 120° C. overnight. The reaction mixture partitioned between EtOAc (50 mL) and H₂O (50 mL). The organics were separated, dried over MgSO₄, and concentrated in vacuo. The residue was subjected to silica gel chromatography eluting with 0% to 100% EtOAc in hexane to provide 79E. LCMS (m/z): 476.32 [M+H]⁺; $t_R$=0.96 min. on LC/MS Method A.

Synthesis of (R)-2-((2-((2,4-dimethoxybenzyl)amino)pyrido[3,2-d]pyrimidin-4-yl)amino)-4,4-difluorohexan-1-ol (79F). (R)-methyl 2-((2-((2,4-dimethoxybenzyl)amino)pyrido[3,2-d]pyrimidin-4-yl)amino)-4,4-difluorohexanoate 79E (35 mg, 0.074 mmol, 1 equiv.) was treated with THF (5 mL) and 1M lithium aluminum hydride in ether (0.29 mL, 0.29 mmol, 4 equiv.). The reaction mixture was stirred for 2 h and then the reaction was quenched with water (50 mL) and extracted with EtOAc (50 mL). The organic layer was separated, dried over MgSO₄, and concentrated in vacuo. The crude material 79F was used without further purification. LCMS (m/z): 448.20 [M+H]⁺; $t_R$=0.86 min. on LC/MS Method A.

Synthesis of (R)-2-((2-aminopyrido[3,2-d]pyrimidin-4-yl)amino)-4,4-difluorohexan-1-ol (79). (R)-2-((2-((2,4-dimethoxybenzyl)amino)pyrido[3,2-d]pyrimidin-4-yl)amino)-4,4-difluorohexan-1-ol 79F (24 mg, 0.055 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, 79 as its TFA salt. LCMS (m/z): 298.11 [M+H]⁺; $t_R$=0.63 min. on LC/MS Method A. $^1$H NMR (400 MHz, Methanol-d₄) δ 8.51 (dd, J=4.3, 1.5 Hz, 1H), 7.77-7.54 (m, 2H), 3.60 (d, J=5.7 Hz, 2H), 2.37-2.11 (m, 2H), 1.93-1.69 (m, 2H), 0.87 (t, J=7.5 Hz, 3H). $^{19}$F NMR (377 MHz, Methanol-d₄) δ −77.80, −98.15, −105.45 (m).

Example 80 and Example 81

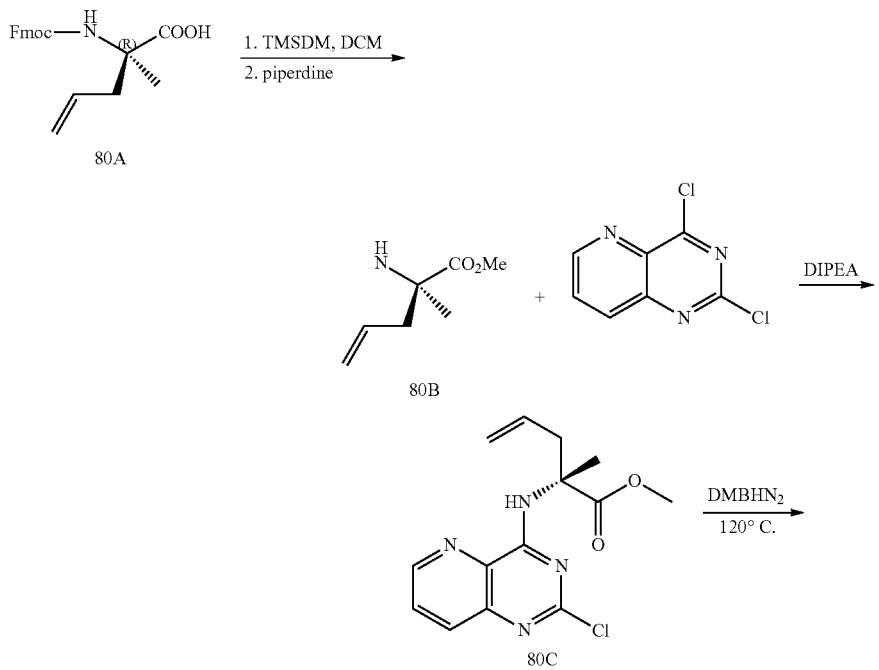

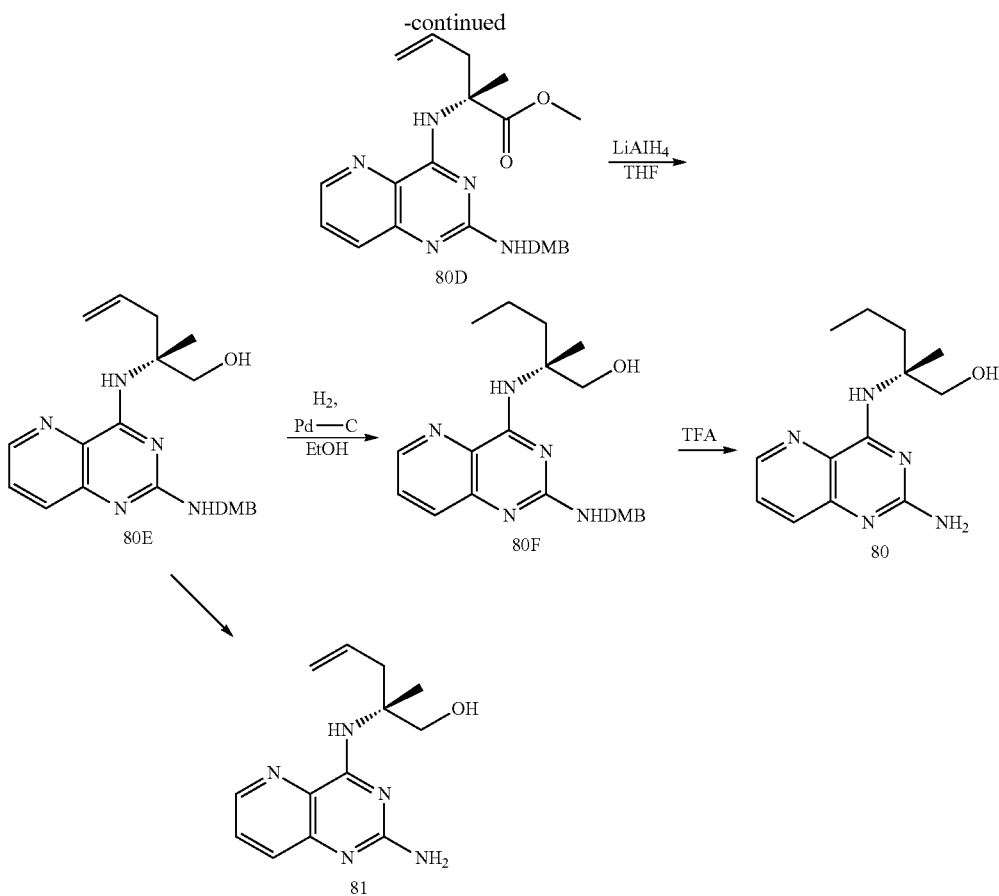

Synthesis of (R)-methyl 2-amino-2-methylpent-4-enoate (80B). (R)-2-((((9H-fluoren-9-yl)methoxy)carbonyl)amino)-2-methylpent-4-enoic acid 80A (1 g, 2.8 mmol, 1 equiv., provided by Okeanos Inc.) was treated with DCM (10 mL) and MeOH (1 mL) along with (trimethylsilyl)diazomethane (2.0M solution in hexanes, 2.3 mL, 5.6 mmol, 2.5 equiv.). After 1 h the reaction mixture was concentrated under reduced pressure to provide a residue. The residue was treated with THF (10 mL) followed by piperidine (0.56 mL, 0.006 mol, 2 equiv.). The mixture was stirred for 2 h and then concentrated under reduced pressure to provide 80B that was used without further purification.

Synthesis of (R)-methyl 2-((2-chloropyrido[3,2-d]pyrimidin-4-yl)amino)-2-methylpent-4-enoate (80C). 2,4,-dichloropyrido[3,2-d]pyrimidine (540 mg, 2.71 mmol, 1 equiv.) was treated with dioxane (15 ml) followed by N,N-diisopropylethylamine (1.9 mL, 10.8 mmol, 4 equiv.), and then (R)-methyl 2-amino-2-methylpent-4-enoate 80B (486 mg, 2.71 mmol, 1 equiv.). The reaction mixture was stirred at 80° C. for 15 minutes, then more 2,4,-dichloropyrido[3,2-d]pyrimidine (250 mg, 1.25 mmol) was added. The mixture was stirred at 80° C. overnight to form 80C which was then used directly. LCMS (m/z): 307.12 [M+H]$^+$; $t_R$=1.14 min. on LC/MS Method A.

Synthesis of (R)-methyl 2-((2-((2,4-dimethoxybenzyl)amino)pyrido[3,2-d]pyrimidin-4-yl)amino)-2-methylpent-4-enoate (80D). (R)-methyl 2-((2-chloropyrido[3,2-d]pyrimidin-4-yl)amino)-2-methylpent-4-enoate 80C solution prepared as described was treated with 2,4-dimethoxybenzylamine (0.80 mL, 5.0 mmol, 2 equiv.). The reaction was heated at 120° C. overnight. The reaction mixture was partitioned between EtOAc (50 mL) and H$_2$O (50 mL). The organics were separated, dried over MgSO$_4$, and concentrated in vacuo. The residue was subjected to silica gel chromatography eluting with 0% to 100% EtOAc in hexane to provide 80D. LCMS (m/z): 438.20 [M+H]$^+$; $t_R$=1.04 min. on LC/MS Method A.

Synthesis of (R)-2-((2-((2,4-dimethoxybenzyl)amino)pyrido[3,2-d]pyrimidin-4-yl)amino)-2-methylpent-4-en-1-ol (80E). (R)-methyl 2-((2-((2,4-dimethoxybenzyl)amino)pyrido[3,2-d]pyrimidin-4-yl)amino)-2-methylpent-4-enoate 80D (634 mg, 1.44 mmol, 1 equiv.) was treated with THF (20 mL) and 1M lithium aluminum hydride in ether (3.6 mL, 3.62 mmol, 2.5 equiv.). The reaction mixture was stirred for 2 h and then the reaction was quenched with water (100 mL) and extracted with EtOAc (100 mL). The organic layer was separated, dried over MgSO$_4$, and concentrated in vacuo. The residue was subjected to silica gel chromatography eluting with 0% to 100% EtOAc in hexane to provide the 80E. LCMS (m/z): 410.17 [M+H]$^+$; $t_R$=0.97 min. on LC/MS Method A.

Synthesis of (R)-2-((2-((2,4-dimethoxybenzyl)amino)pyrido[3,2-d]pyrimidin-4-yl)amino)-2-methylpentan-1-ol (80F). (R)-methyl 2-((2-((2,4-dimethoxybenzyl)amino)pyrido[3,2-d]pyrimidin-4-yl)amino)-5-methylhex-5-enoate 80E (35 mg, 0.09 mmol) was treated with Pd/C (60 mg) and EtOH (5 mL) and then stirred under hydrogen. After 24 h, the solid was filtered off and the filtrate was concentrated under reduced pressure. The resulting residue 80F was used without further purification. LCMS (m/z): 454.24 [M+H]$^+$; $t_R$=1.06 min. on LC/MS Method A.

Synthesis of (R)-2-((2-aminopyrido[3,2-d]pyrimidin-4-yl)amino)-2-methylpentan-1-ol (80). (R)-2-((2-((2,4-dimethoxybenzyl)amino)pyrido[3,2-d]pyrimidin-4-yl)amino)-2-methylpentan-1-ol 80F (35 mg, 0.09 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, 80 as its TFA salt. LCMS (m/z): 262.13 [M+H]$^+$; $t_R$=0.64 min. on LC/MS Method A.

Synthesis of (R)-2-((2-aminopyrido[3,2-d]pyrimidin-4-yl)amino)-2-methylpent-4-en-1-ol (81). (R)-methyl 2-((2-((2,4-dimethoxybenzyl)amino)pyrido[3,2-d]pyrimidin-4-yl)amino)-5-methylhex-5-enoate 80E (40 mg, 0.10 mmol, 1 equiv.) was treated with DCM (2 mL) and TFA (0.5 mL). After 4 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, 81 as its TFA salt. LCMS (m/z): 260.10 [M+H]$^+$; $t_R$=0.63 min. on LC/MS Method A. $^1$H NMR (400 MHz, Methanol-d4) δ 8.59 (dd, J=4.4, 1.4 Hz, 1H), 7.84 (dd, J=8.5, 1.4 Hz, 1H), 7.75 (dd, J=8.5, 4.4 Hz, 1H), 5.87 (ddt, J=17.5, 10.1, 7.4 Hz, 1H), 5.33-4.94 (m, 2H), 3.94 (d, J=11.2 Hz, 1H), 3.78 (d, J=11.2 Hz, 1H), 2.97-2.76 (m, 1H), 2.70 (ddt, J=13.9, 7.3, 1.2 Hz, 1H), 1.55 (s, 3H). $^{19}$F NMR (377 MHz, Methanol-d4) δ -77.56.

Example 82

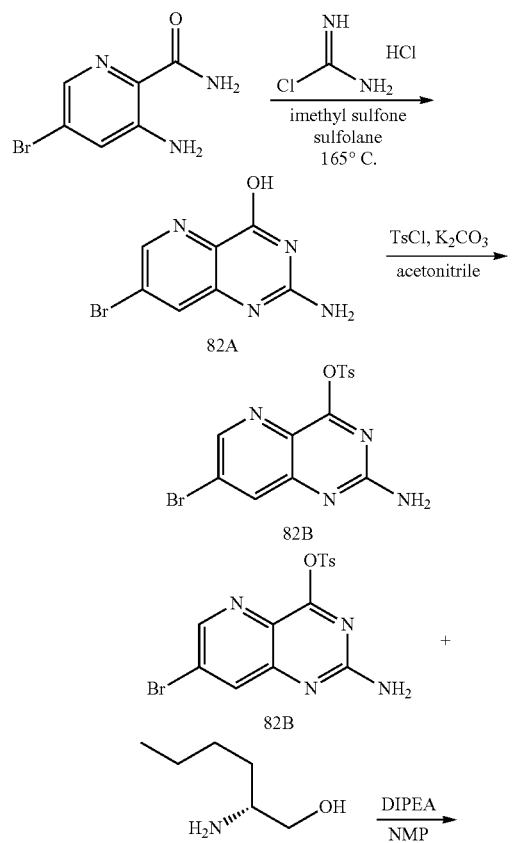

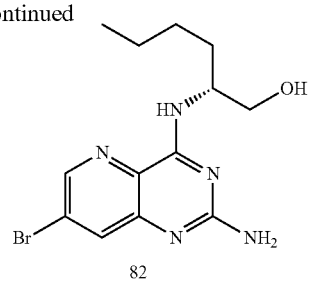

Synthesis of 2-amino-7-bromopyrido[3,2-d]pyrimidin-4-ol (82A). A mixture of 3-amino-5-bromopyridine-2-carboxamide (3.0 g, 13.9 mmol, 1 equiv., supplied by Combi-Blocks Inc.), chloroformamidine hydrochloride (3192.9 mg, 27.8 mmol, 2 equiv.), methyl sulfone (13.1 g, 139 mmol, 10 equiv.) in sulfolane (1 mL) in a sealed tube, was heated at 165° C. After 24 h, the mixture was diluted with water and then cooled to rt. The reaction was adjusted to pH 12 using NH$_4$OH and stirred for 20 minutes. The precipitates were then filtered, rinsed with water, hexanes, and ether, and dried in a vacuum oven at 100° C. overnight to afford 82A that was used without further purification. LCMS (m/z): 242.92 [M+H]$^+$; $t_R$=0.55 min. on LC/MS Method A.

Synthesis of 2-amino-7-bromopyrido[3,2-d]pyrimidin-4-yl 4-methylbenzenesulfonate (82B). 2-amino-7-bromopyrido[3,2-d]pyrimidin-4-ol 82A (1000 mg, 4.2 mmol, 1 equiv.) was treated with acetonitrile (40 mL) followed by potassium carbonate (1433.4 mg, 10.37 mmol, 2.5 equiv.) and p-toluenesulfonyl chloride (1186.38 mg, 6.22 mmol, 1.5 equiv.). The reaction mixture was heated to 100° C. and stirred overnight. The mixture was allowed to cool and then diluted with EtOAc, washed with water and saturated NH$_4$Cl. The organic layer was dried over MgSO$_4$, filtered, and concentrated under reduced pressure to afford 82B that was used without further purification. LCMS (m/z): 396.98 [M+H]$^+$; $t_R$=1.15 min. on LC/MS Method A.

Synthesis of (R)-2-((2-amino-7-bromopyrido[3,2-d]pyrimidin-4-yl)amino)hexan-1-ol (82). 2-Amino-7-bromopyrido[3,2-d]pyrimidin-4-yl 4-methylbenzenesulfonate 82B (50 mg, 0.13 mmol, 1 equiv.) was treated with acetonitrile (5 mL), N,N-diisopropylethylamine (0.07 mL, 0.38 mmol, 3 equiv.) and (R)-(–)-2-amino-1-hexanol (44.48 mg, 0.38 mmol, 3 equiv.). After 16 h, the reaction mixture was concentrated under reduced pressure and subjected to reverse phase HPLC (10% to 70% MeCN in water using a Hydro-RP column) to furnish, after collection of product fractions and removal of volatiles in vacuo, 82 as its TFA salt. LCMS (m/z): 342.1 [M+H]$^+$; $t_R$=0.90 min. on LC/MS Method A. $^1$H NMR (400 MHz, Methanol-d$_4$) δ 8.69 (d, J=1.9 Hz, 1H), 8.06 (d, J=1.9 Hz, 1H), 4.52 (dq, J=8.7, 5.5 Hz, 1H), 3.86-3.54 (m, 2H), 1.95-1.63 (m, 2H), 1.57-1.29 (m, 5H), 1.11-0.76 (m, 3H). $^{19}$F NMR (377 MHz, Methanol-d4) δ -77.42.

Example 83

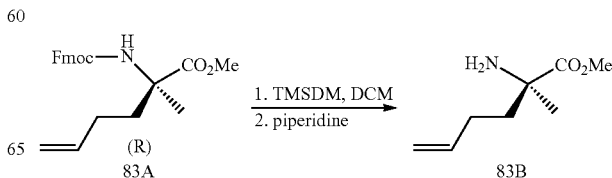

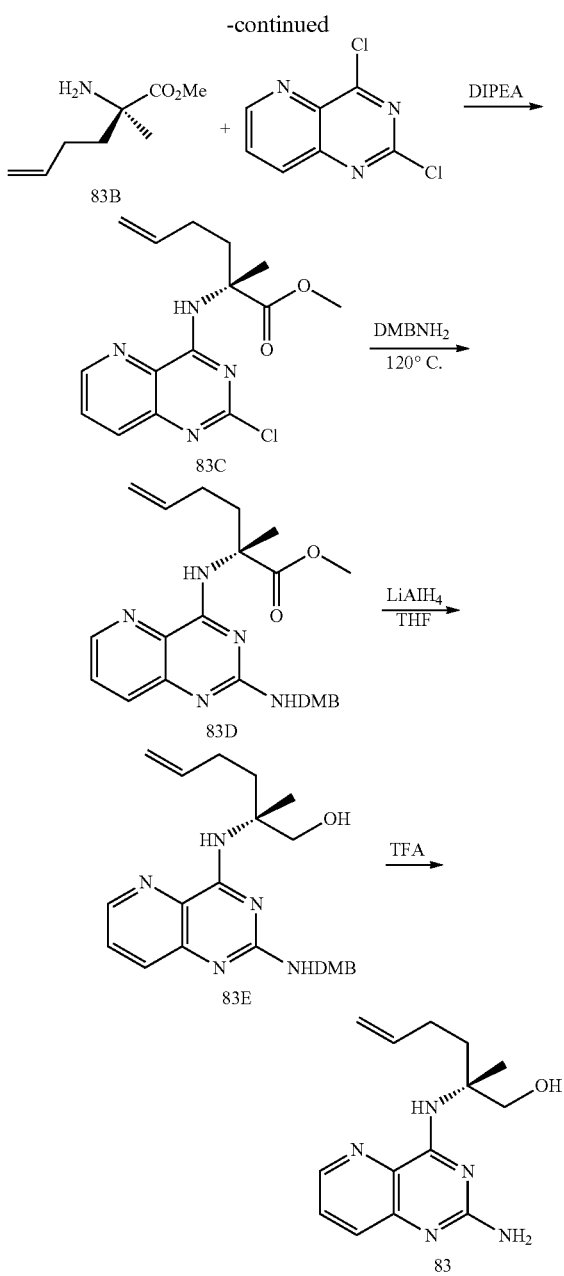

Synthesis of (R)-methyl 2-amino-2-methylhex-5-enoate (83B). (R)-methyl 2-(((((9H-fluoren-9-yl)methoxy)carbonyl)amino)-2-methylhex-5-enoate 83A (2 g, 5.5 mmol, 1 equiv., provided by Okeanos Inc.) was treated with DCM (20 mL) and MeOH (4 mL) along with (trimethylsilyl)diazomethane (2.0M solution in hexanes, 4.4 mL, 11.0 mmol, 2.5 equiv.). After 30 minutes, the reaction mixture was concentrated under reduced pressure to provide a residue. The residue was treated with THF (33 mL) followed by piperidine (1.9 mL, 0.02 mol, 3.5 equiv.). The mixture was stirred for 3 days and then concentrated under reduced pressure. The residue was subjected to silica gel chromatography eluting with 0% to 20% MeOH in DCM to provide 83B. LCMS (m/z): 157.91 [M+H]$^+$; $t_R$=0.59 min. on LC/MS Method A.

Synthesis of (R)-methyl 2-((2-chloropyrido[3,2-d]pyrimidin-4-yl)amino)-2-methylhex-5-enoate (83C). 2,4,-dichloropyrido[3,2-d]pyrimidine (55 mg, 0.28 mmol, 1 equiv.) was treated with dioxane (15 ml) followed by N,N-diisopropylethylamine (0.25 mL, 1.4 mmol, 4 equiv.), and then (R)-methyl 2-amino-2-methylhex-5-enoate 83B (47.6 mg, 0.30 mmol, 1 equiv.). The mixture was stirred at 80° C. overnight to form 83C which was used directly. LCMS (m/z): 321.14 [M+H]$^+$; $t_R$=1.21 min. on LC/MS Method A.

Synthesis of (R)-methyl 2-((2-((2,4-dimethoxybenzyl)amino)pyrido[3,2-d]pyrimidin-4-yl)amino)-2-methylhex-5-enoate (83D). (R)-methyl 2-((2-chloropyrido[3,2-d]pyrimidin-4-yl)amino)-2-methylhex-5-enoate 83C solution prepared as described, was treated with 2,4-dimethoxybenzylamine (0.10 mL, 0.69 mmol, 2.5 equiv.). The reaction was heated at 120° C. overnight. The reaction mixture was partitioned between EtOAc (50 mL) and H$_2$O (50 mL). The organics were separated, dried over MgSO$_4$, and concentrated in vacuo. The residue was subjected to silica gel chromatography eluting with 0% to 100% EtOAc in hexane to provide 83D. LCMS (m/z): 452.21 [M+H]$^+$; $t_R$=1.22 min. on LC/MS Method A.

Synthesis of (R)-2-((2-((2,4-dimethoxybenzyl)amino)pyrido[3,2-d]pyrimidin-4-yl)amino)-2-methylhex-5-en-1-ol (83E). (R)-methyl 2-((2-((2,4-dimethoxybenzyl)amino)pyrido[3,2-d]pyrimidin-4-yl)amino)-2-methylhex-5-enoate 83D (25 mg, 0.06 mmol, 1 equiv.) was treated with THF (20 mL) and 1M lithium aluminum hydride in ether (0.14 mL, 0.14 mmol, 2.5 equiv.). The reaction mixture was stirred for 2 h and then the reaction was quenched with water (100 mL) and extracted with EtOAc (100 mL). The organic layer was separated, dried over MgSO$_4$, and concentrated in vacuo to provide the 83E that was used without further purification. LCMS (m/z): 424.14 [M+H]$^+$; $t_R$=1.12 min. on LC/MS Method A.

Synthesis of (R)-2-((2-aminopyrido[3,2-d]pyrimidin-4-yl)amino)-2-methylhex-5-en-1-ol (83). (R)-2-((2-((2,4-dimethoxybenzyl)amino)pyrido[3,2-d]pyrimidin-4-yl)amino)-2-methylhex-5-en-1-ol 83E (23 mg, 0.05 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, 83 (10 mg, 65%) as its TFA salt. LCMS (m/z): 274.7 [M+H]$^+$; $t_R$=0.73 min. on LC/MS Method A. $^1$H NMR (400 MHz, Methanol-d$_4$) δ 9.01 (d, J=4.5 Hz, 1H), 8.33-8.09 (m, 2H), 6.23 (ddt, J=16.4, 11.0, 5.8 Hz, 1H), 5.42 (d, J=17.1 Hz, 1H), 4.40 (d, J=11.3 Hz, 1H), 4.26-4.03 (m, 2H), 2.57 (ddd, J=29.2, 14.7, 8.4 Hz, 3H), 2.42 (dq, J=10.9, 6.9 Hz, 1H), 1.96 (s, 3H). $^{19}$F NMR (377 MHz, Methanol-d$_4$) δ -77.19 (d, J=144.5 Hz).

Example 84

Synthesis of Intermediate Compound 84E

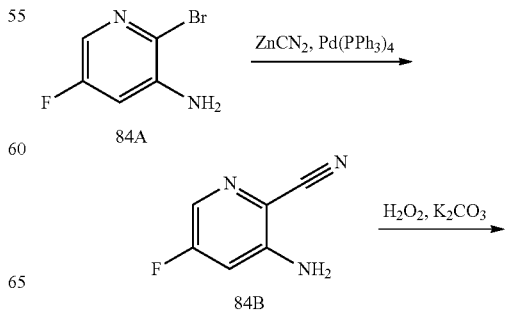

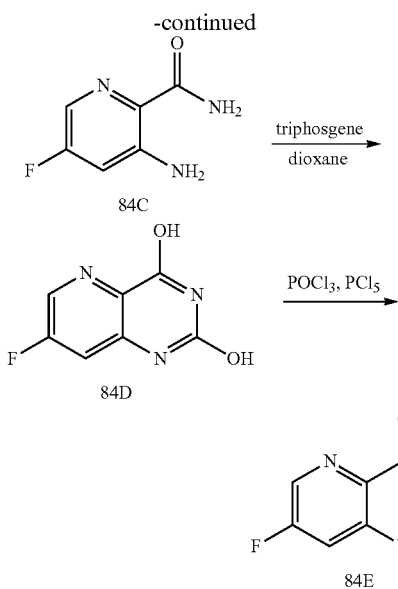

reduced pressure and azeotroped with toluene. The resultant solid was treated with EtOAc (500 mL) and ice-water (500 mL). The organic layer was separated and washed with saturated NaHCO₃ solution (500 mL), water (500 mL), and saturated NH₄Cl (500 mL). The organic solution was dried over MgSO₄, filtered and concentrated under reduced pressure to furnish the crude product 84E. LCMS (m/z): 213.9 [M+H+2(OMe)-2Cl]⁺; $t_R$=0.82 min. on LC/MS Method A. ¹H NMR (400 MHz, Chloroform-d) δ 9.01 (d, J=2.6 Hz, 1H), 7.94 (dd, J=7.9, 2.7 Hz, 1H). ¹⁹F NMR (377 MHz, Chloroform-d) δ −111.79 (d, J=7.9 Hz).

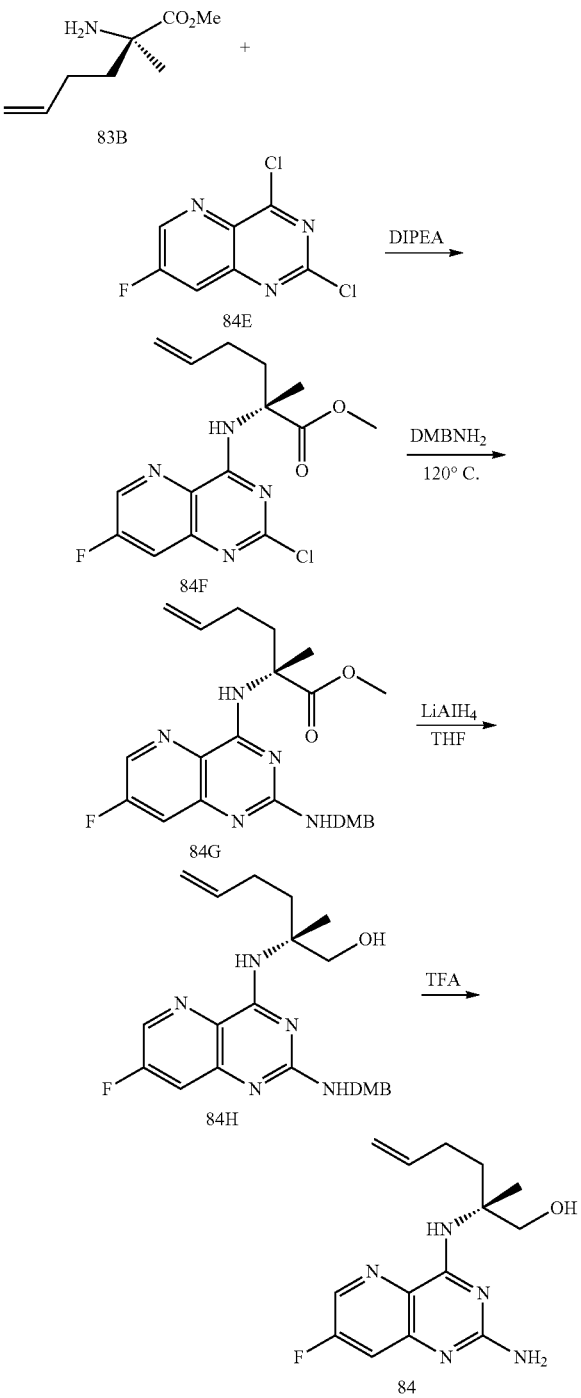

Synthesis of 3-amino-5-fluoropicolinonitrile (84B). 3-amino-2-bromo-5-fluoropyridine 84A (25 g, 131 mmol, Astatech Chemical, Inc) was treated with ZnCN₂ (16.9 g, 1.1 equiv., 144 mmol), Pd(Ph₃)₄ (11.3 g, 0.075 equiv., 9.8 mmol) and DMF (200 mL) and then heated to 115° C. After 6 h, the reaction mixture was allowed to cool and then concentrated under reduced pressure to a solid. The solid was washed with EtOAc (2×100 mL). The organic layers were combined and washed with water (3×100 mL), saturated NH₄Cl solution (100 mL), dried over MgSO₄, filtered and concentrated under reduced pressure to provide 84B that was used without further purification. LCMS (m/z): 138.87 [M+H]⁺; $t_R$=0.59 min. on LC/MS Method A.

Synthesis of 3-amino-5-fluoropicolinamide (84C). Compound 84B (2.6 g, 19.0 mmol, 1 equiv.) was treated with DMSO (10 mL) and cooled to 0° C. before K₂CO₃ (524 mg, 0.2 equiv., 3.8 mmol) was added. H₂O₂ (2.3 mL, 1.2 equiv., 22.8 mmol, 30% water) was then slowly added. The cooling bath was removed and the reaction was stirred for 1 h. The reaction mixture was diluted with water (100 mL) and extracted with EtOAc (3×100). The combined organic layers were washed with water (3×500) and saturated NH₄Cl solution (500 mL), dried over MgSO₄, filtered and concentrated under reduced pressure. The crude material 84C was used without further purification. LCMS (m/z): 155.87 [M+H]⁺; $t_R$=0.62 min. on LC/MS Method A.

The following procedure was adapted from De Jonghe, WO 2006/1359931.

Synthesis of 7-fluoropyrido[3,2-d]pyrimidine-2,4-diol (84D). Carboxamide 84C (1 g, 1 equiv., 6.4 mmol) was treated with triphosgene (1.9 g, 1.0 equiv., 6.4 mmol) and dioxane (20 mL). The reaction mixture was heated to 110° C. for 30 min. The reaction mixture was allowed to cool and concentrated under reduced pressure. The crude solid residue was washed with DCM and diethyl ether and allowed to air dry to provide 84D. LCMS (m/z): 181.95 [M+H]⁺; $t_R$=0.62 min. on LC/MS Method A.

Synthesis of 2,4-dichloro-7-fluoropyrido[3,2-d]pyrimidine (84E). Dione 84D (13.7 g, 75.6 mmol, 1 equiv.) was treated with phosphorus pentachloride (63.0 g, 302.6 mmol, 4 equiv.) and phosphorus (V) oxychloride (141 mL, 20 equiv.) and heated to 110° C. under a under reflux condenser for 8 h. The reaction mixture was concentrated under Synthesis of (R)-methyl 2-((2-chloro-7-fluoropyrido[3,2-d]pyrimidin-4-yl)amino)-2-methylhex-5-enoate (84F). 2,4-dichloro-7-fluoropyrido[3,2-d]pyrimidine 84E (75 mg, 0.34 mmol, 1 equiv.) was treated with dioxane (15 ml) followed by N,N-diisopropylethylamine (0.31 mL, 1.7 mmol, 5 equiv.), and then (R)-methyl 2-amino-2-methylhex-5-enoate 83B (59.5 mg, 0.38 mmol, 1 equiv.). The mixture was stirred at 80° C. overnight to form 84F in solution which was then used directly. LCMS (m/z): 339.1 [M+H]$^+$; $t_R$=1.23 min. on LC/MS Method A.

Synthesis of (R)-methyl 2-((2-((2,4-dimethoxybenzyl)amino)-7-fluoropyrido[3,2-d]pyrimidin-4-yl)amino)-2-methylhex-5-enoate (84G). (R)-methyl 2-((2-chloro-7-fluoropyrido[3,2-d]pyrimidin-4-yl)amino)-2-methylhex-5-enoate 84F solution prepared as described, was treated with 2,4-dimethoxybenzylamine (0.10 mL, 0.69 mmol, 2.5 equiv.). The reaction was heated at 120° C. overnight. The reaction mixture partitioned between EtOAc (50 mL) and H$_2$O (50 mL). The organics were separated, dried over MgSO$_4$, and concentrated in vacuo. The residue was subjected to silica gel chromatography eluting with 0% to 100% EtOAc in hexane to provide 84G. LCMS (m/z): 470.25 [M+H]$^+$; $t_R$=1.12 min. on LC/MS Method A.

Synthesis of (R)-2-((2-((2,4-dimethoxybenzyl)amino)-7-fluoropyrido[3,2-d]pyrimidin-4-yl)amino)-2-methylhex-5-en-1-ol (84H). (R)-methyl 2-((2-((2,4-dimethoxybenzyl)amino)-7-fluoropyrido[3,2-d]pyrimidin-4-yl)amino)-2-methylhex-5-enoate 83G (85 mg, 0.18 mmol, 1 equiv.) was treated with THF (5 mL) and 1M lithium aluminum hydride in ether (0.54 mL, 0.54 mmol, 3 equiv.). The reaction mixture was stirred for 2 h and then the reaction was quenched with water (100 mL) and extracted with EtOAc (100 mL). The organic layer was separated, dried over MgSO$_4$, and concentrated in vacuo to provide 84H that was used without further purification. LCMS (m/z): 442.16 [M+H]$^+$; $t_R$=1.07 min. on LC/MS Method A.

Synthesis of (R)-2-((2-amino-7-fluoropyrido[3,2-d]pyrimidin-4-yl)amino)-2-methylhex-5-en-1-ol (84). (R)-2-((2-((2,4-dimethoxybenzyl)amino)-7-fluoropyrido[3,2-d]pyrimidin-4-yl)amino)-2-methylhex-5-en-1-ol 84H (35 mg, 0.08 mmol, 1 equiv.) was treated with DCM (2 mL) and TFA (0.5 mL). After 3 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, as its TFA salt. LCMS (m/z): 292.13 [M+H]$^+$; $t_R$=0.62 min. on LC/MS Method A. $^1$H NMR (400 MHz, Methanol-d$_4$) δ 8.55 (d, J=2.4 Hz, 1H), 8.25 (s, 1H), 7.63 (dd, J=8.7, 2.5 Hz, 1H), 5.83 (ddt, J=16.6, 10.2, 6.2 Hz, 1H), 5.02 (dq, J=17.1, 1.5 Hz, 1H), 4.92 (ddt, J=10.2, 2.1, 1.1 Hz, 8H), 4.08-3.88 (m, 1H), 3.69 (d, J=11.3 Hz, 1H), 2.34-1.90 (m, 4H), 1.56 (s, 3H). $^{19}$F NMR (377 MHz, Methanol-d$_4$) δ −77.54, −118.17 (dd, J=8.8, 4.3 Hz).

Example 85

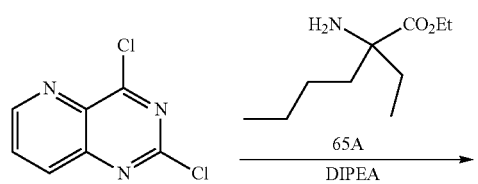

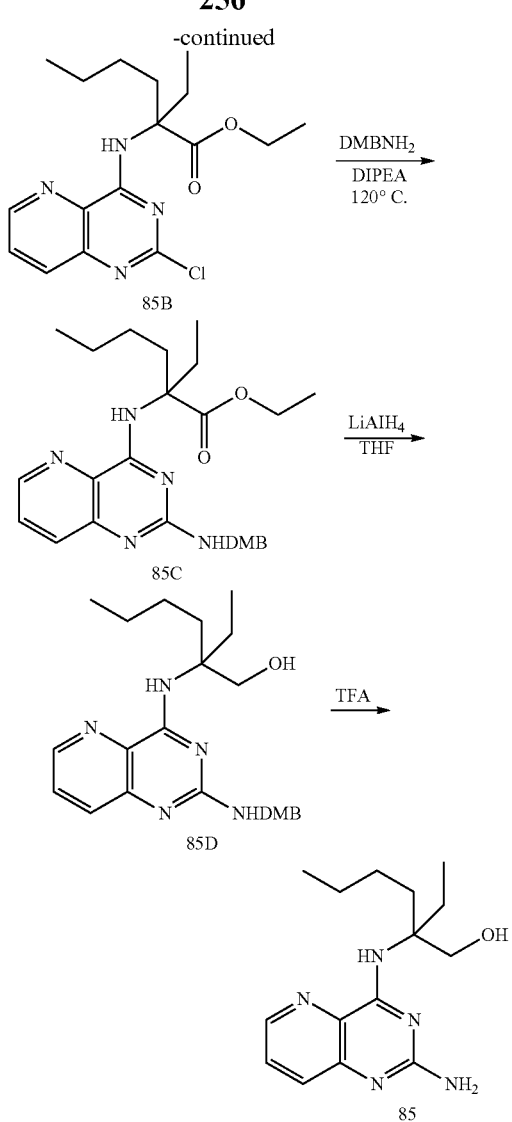

Synthesis of ethyl 2-((2-chloropyrido[3,2-d]pyrimidin-4-yl)amino)-2-ethylhexanoate (85B). 2,4,-dichloropyrido[3,2-d]pyrimidine (1068 mg, 5.34 mmol, 1 equiv.) was treated with dioxane (10 ml) followed by N,N-diisopropylethylamine (5.7 mL, 32.0 mmol, 6 equiv.), and then 2-amino-2-ethyl-hexanoic acid ethyl ester 85A (1000 mg, 5.34 mmol, 1 equiv., supplied by J&W Pharmlab, LLC). The mixture was stirred at 80° C. overnight. The reaction mixture partitioned between EtOAc (50 mL) and H$_2$O (50 mL). The organics were separated, dried over MgSO$_4$, and concentrated in vacuo to afford 85B that was then used directly. LCMS (m/z): 351.23 [M+H]$^+$; $t_R$=1.43 min. on LC/MS Method A.

Synthesis of ethyl 2-((2-((2,4-diethylbenzyl)amino)pyrido[3,2-d]pyrimidin-4-yl)amino)-2-ethylhexanoate (85C). Ethyl 2-((2-chloropyrido[3,2-d]pyrimidin-4-yl)amino)-2-ethylhexanoate 85B prepared as described, was treated with dioxane (10 mL), N,N-diisopropylethylamine (1.7 mL, 9.5 mmol, 3 equiv.), and 2,4-dimethoxybenzylamine (0.94 mL, 6.3 mmol, 2 equiv.). The reaction was heated at 120° C. overnight. The reaction mixture partitioned between EtOAc (50 mL) and H$_2$O (50 mL). The organics were separated, dried over MgSO$_4$, and concentrated in vacuo. The residue was subjected to silica gel chromatography eluting with 0% to 100% EtOAc in hexane to provide 85C. LCMS (m/z): 482.27 [M+H]+; $t_R$=1.02 min. on LC/MS Method A.

Synthesis of 2-((2-((2,4-diethylbenzyl)amino)pyrido[3,2-d]pyrimidin-4-yl)amino)-2-ethylhexan-1-ol (85D). Ethyl 2-((2-((2,4-diethylbenzyl)amino)pyrido[3,2-d]pyrimidin-4-yl)amino)-2-ethylhexanoate 85C (111 mg, 0.23 mmol, 1 equiv.) was treated with THF (10 mL) and 1M lithium aluminum hydride in ether (0.92 mL, 0.92 mmol, 4 equiv.). The reaction mixture was stirred for 2 h and then the reaction was quenched with water (100 mL) and extracted with EtOAc (100 mL). The organic layer was separated, dried over MgSO4, and concentrated in vacuo. The residue was subjected to silica gel chromatography eluting with 0% to 100% EtOAc in hexane to provide 85D. LCMS (m/z): 440.24 [M+H]+; $t_R$=0.94 min. on LC/MS Method A.

Synthesis of 2-((2-aminopyrido[3,2-d]pyrimidin-4-yl)amino)-2-ethylhexan-1-ol (85). 2-((2-((2,4-Diethylbenzyl)amino)pyrido[3,2-d]pyrimidin-4-yl)amino)-2-ethylhexan-1-ol 85D (16 mg, 0.04 mmol, 1 equiv.) was treated with DCM (2 mL) and TFA (0.5 mL). After 6 h the reaction mixture was concentrated under reduced pressure and subjected to reverse phase HPLC (10% to 70% MeCN in water with 0.1% TFA using a Hydro-RP column) to furnish, after collection of product fractions and removal of volatiles in vacuo, 85 as its TFA salt. LCMS (m/z): 290.15 [M+H]+; $t_R$=0.73 min. on LC/MS Method A. $^1$H NMR (400 MHz, Methanol-d4) δ 8.62 (dd, J=4.4, 1.4 Hz, 1H), 7.93-7.61 (m, 2H), 3.98 (s, 3H), 3.91 (s, 2H), 2.10-1.82 (m, 4H), 1.46-1.20 (m, 4H), 1.10-0.71 (m, 5H). $^{19}$F NMR (377 MHz, Methanol-d4) δ −77.69 (d, J=231.2 Hz).

Example 86

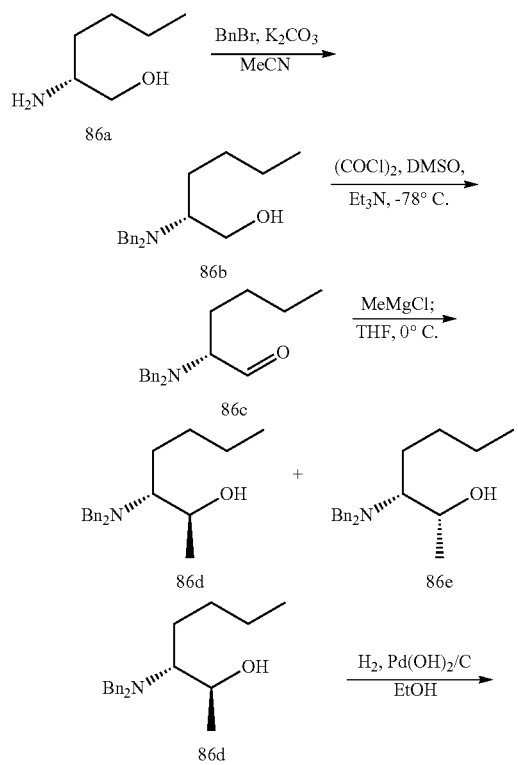

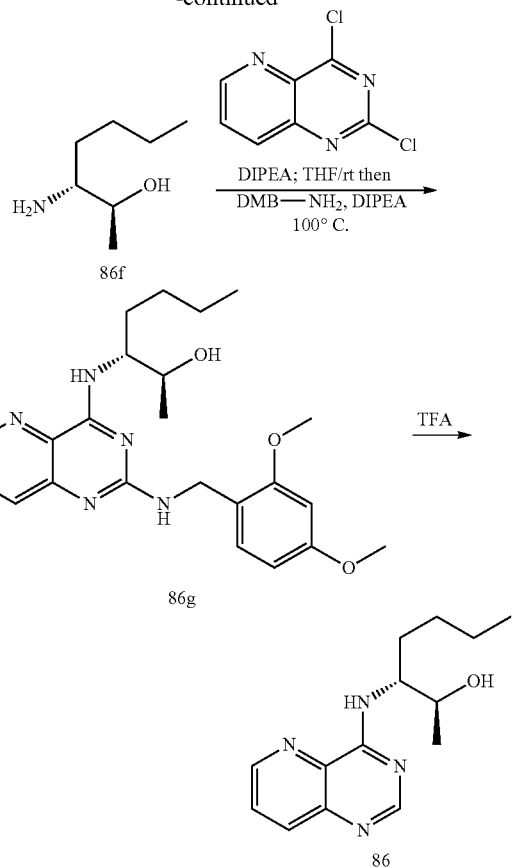

Synthesis of (R)-2-(Dibenzylamino)hexan-1-ol (86b). (R)-norleucinol (86a, 2046.4 mg, 17.46 mmol) was treated with acetonitrile (40 mL) and K2CO3 (4842.4 mg, 35.04 mmol) followed by benzyl bromide (6.222 mL, 52.39 mmol) at 0° C. The resulting mixture was stirred at rt. After 18 h, the precipitate was filtered and the solids were washed with EtOAc (30 mL). Filtrates were concentrated under reduced pressure and the resultant residue was subjected to silica gel chromatography eluting with 0-70% EtOAc in hexanes to provide 86b LCMS-ESI+ (m/z): [M+H]+ calculated for C20H28NO: 298.22; found: 298.16; $t_R$=0.82 min on LC/MS Method A.

Synthesis of (R)-2-(dibenzylamino)hexanal (86c). Oxalyl chloride (0.18 mL, 2.10 mmol) in DCM (3 mL) was cooled in an acetone-dry ice bath and then treated with DMSO (0.3 mL, 4.22 mmol) in DCM (1 mL) dropwise over 2 minutes. After 10 min, a solution of compound 86b (503.5 mg, 1.69 mmol) in DCM (2 mL) was added and resulting mixture was allowed to stir for 30 min. before addition of triethylamine (1.2 mL, 8.61 mmol). After 1 h at −70~−55° C., the reaction mixture was allowed to warm to rt, diluted with EtOAc (30 mL), and washed with water (30 mL×2). The aqueous fractions were extracted with EtOAc (×1), and the combined organic fractions were then dried (MgSO4), concentrated under reduced pressure, and the residue vacuum dried to obtain compound 86c, which was used without further purification LCMS-ESI+ (m/z): [M+H]+ calculated for C20H26NO: 296.20; found: 296.16; $t_R$=1.12 min on LC/MS Method A.

Synthesis of (2S,3R)-3-(Dibenzylamino)heptan-2-ol (86d) and (2R,3R)-3-(Dibenzylamino)heptan-2-ol (86e).

Compound 86c (134.87 mg, 0.457 mmol) in diethyl ether (4 mL) was stirred at −15° C. and a 1.6 M solution of methyl lithium in diethyl ether (4.2 mL, 6.72 mmol) was added. After 0.5 h, the reaction mixture was quenched with saturated aqueous ammonium chloride (10 mL) and water (10 mL), and the product was extracted with EtOAc (20 mL×2). The organic extracts were washed with water (20 mL×1), combined, dried ($MgSO_4$), and then concentrated under reduced pressure. The crude residue was subjected to silica gel chromatography eluting with 5-30% EtOAc in hexanes to obtain 86d (first eluting compound) and compound 86e second eluting compound.

(2S,3R)-3-(Dibenzylamino)heptan-2-ol (86d): $^1$H NMR (400 MHz, Chloroform-d) δ 7.37-7.17 (m, 10H), 4.33 (s, 1H), 3.86 (d, J=13.3 Hz, 1.9H), 3.73 (d, J=13.7 Hz, 0.1H), 3.67-3.55 (m, 1H), 3.45 (d, J=13.3 Hz, 2H), 2.64 (d, J=5.8 Hz, 0.05H), 2.33 (dt, J=9.3, 5.5 Hz, 0.95H), 1.72 (ddd, J=14.8, 12.0, 6.5 Hz, 1H), 1.50-1.20 (m, 6H), 1.18 (d, J=6.7 Hz, 0.15H), 1.09 (d, J=6.0 Hz, 2.85H), 0.96 (t, J=7.1 Hz, 3H). LCMS-ESI$^+$ (m/z): [M+H]$^+$ calculated for $C_{21}H_{30}NO$: 312.23; found: 312.16; $t_R$=0.98 min on LC/MS Method A.

(2R,3R)-3-(Dibenzylamino)heptan-2-ol (86e): $^1$H NMR (400 MHz, Chloroform-d) δ 7.44-7.13 (m, 10H), 3.88 (dt, J=8.6, 5.8 Hz, 1H), 3.73 (d, J=13.6 Hz, 2H), 3.63 (d, J=13.6 Hz, 2H), 2.65 (td, J=6.5, 4.3 Hz, 1H), 2.31 (s, 1H), 1.73 (td, J=11.0, 9.8, 5.8 Hz, 1H), 1.50-1.22 (m, 6H), 1.18 (d, J=6.6 Hz, 3H), 0.92 (t, J=7.0 Hz, 3H). LCMS-ESI$^+$ (m/z): [M+H]$^+$ calculated for $C_{21}H_{30}NO$: 312.23; found: 312.16; $t_R$=0.93 min on LC/MS Method A.

Synthesis of (2S,3R)-3-aminoheptan-2-ol (86f). Diastereomer 86d (108.9 mg, 0.349 mmol) and 20% palladium hydroxide on carbon (25.3 mg) in EtOH (4 mL) was stirred under $H_2$ atmosphere for 16 h. The resulting mixture was filtered and the filtrate was concentrated under reduced pressure to provide compound 86f contaminated with some EtOH, which was used without further purification. $^1$H NMR (400 MHz, Methanol-$d_4$) δ 3.51 (p, J=6.3 Hz, 1H), 2.49 (ddd, J=8.2, 6.0, 4.0 Hz, 1H), 1.57-1.20 (m, 6H), 1.15 (d, J=6.4 Hz, 3H), 0.97-0.87 (m, 3H).

Synthesis of (2S,3R)-3-((2-((2,4-dimethoxybenzyl)amino)pyrido[3,2-d]pyrimidin-4-yl)amino)heptan-2-ol (86g). Compound 86f prepared as described and 2,4-dichloropyrido[3,2-d]pyrimidine (73.2 mg, 0.350 mmol, Astatech, Inc.) in THF (3 mL) were treated with N,N-diisopropylethylamine (0.19 mL, 1.091 mmol) and the resulting mixture stirred for 1.5 h. Additional THF (3 mL), N,N-diisopropylethylamine (0.19 mL, 1.091 mmol), and 2,4-dimethoxybenzylamine (0.27 mL, 1.797 mmol) were added. The reaction mixture was stirred at 100° C. for 15.5 h and then cooled to rt. The reaction mixture was diluted with DCM (30 mL), washed with water (30 mL×2). The aqueous fractions were then extracted with DCM (20 mL×1), and the combined organic fractions, dried ($MgSO_4$), and concentrated in vacuo. The residue was subjected to silica gel chromatography eluting with 0-20% methanol in DCM to provide crude 86g. The crude 86g was further subjected to preparative HPLC (Gemini 10u C18 110A, AXIA; 10% aq. acetonitrile-80% aq. acetonitrile with 0.1% TFA, over 20 min. gradient). The collected fractions were neutralized with $NaHCO_3$ before concentration. The residue was dissolved in EtOAc, washed with water, dried ($MgSO_4$), and concentrated under reduced pressure to provide compound 86g. LCMS-ESI$^+$ (m/z): [M+H]$^+$ calculated for $C_{23}H_{32}N_5O_3$: 426.25; found: 426.14; $t_R$=1.23 min on LC/MS Method A.

Synthesis of (2S,3R)-3-(2-aminopyrido[3,2-d]pyrimidin-4-yl)amino)heptan-2-ol (86). Compound 86g (76.0 mg, 0.179 mmol) was dissolved in TFA (2 mL) and stirred at rt for 1 h. The reaction mixture was concentrated and co-evaporated with methanol (10 mL×1). The resulting residue was dissolved in methanol (2 mL) and concentrated ammonium hydroxide (0.2 mL) was added to the solution. After 10 min. at rt, the mixture was concentrated to dryness, and the residue was dissolved in methanol (3 mL) and water (3 mL). The insoluble material was removed by filtration, and the filtrate was subjected to preparative HPLC (Gemini 10u C18 110A, AXIA; 10% aq. acetonitrile-70% aq. acetonitrile with 0.1% TFA, over 20 min. gradient) to provide, after collection of product fractions and removal of volatiles in vacuo, compound 86 as its TFA salt. $^1$H NMR (400 MHz, Methanol-d4) δ 8.64 (dd, J=4.4, 1.4 Hz, 1H), 7.84 (dd, J=8.5, 1.5 Hz, 1H), 7.77 (dd, J=8.5, 4.4 Hz, 1H), 4.37 (td, J=7.2, 3.4 Hz, 1H), 3.99 (qd, J=6.4, 3.4 Hz, 1H), 1.76 (q, J=7.4 Hz, 2H), 1.48-1.26 (m, 4H), 1.18 (d, J=6.4 Hz, 3H), 0.97-0.82 (m, 3H). LCMS-ESI$^+$ (m/z): [M+H]$^+$ calculated for $C_{1-4}H_{22}N_5O$: 276.18; found: 276.15; $t_R$=0.67 min on LC/MS Method A.

Example 87

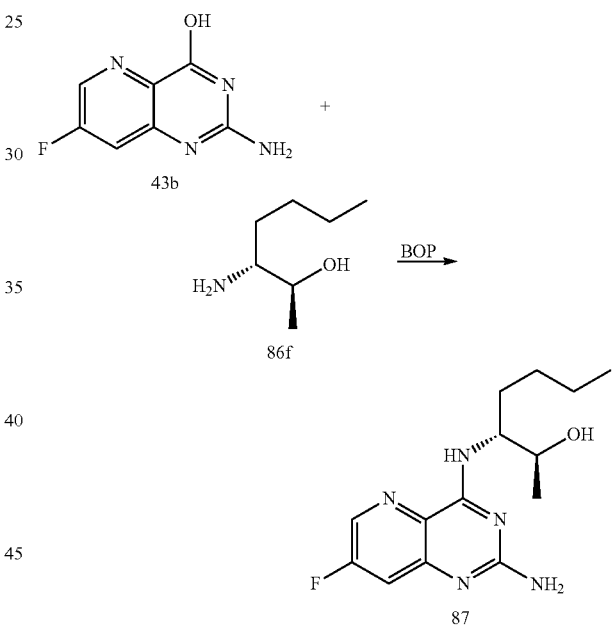

Synthesis of (2S,3R)-3-((2-amino-7-fluoropyrido[3,2-d]pyrimidin-4-yl)amino)heptan-2-ol (87). A solution of 2-amino-7-fluoropyrido[3,2-d]pyrimidin-4-ol (43B, 20.0 mg, 0.068 mmol), compound 86f (27.2 mg, 0.207 mmol), and (benzotriazol-1-yloxy)tris(dimethylamino)phosphonium hexafluorophosphate (BOP, 58.9 mg, 0.133 mmol) in DMF (3 mL) was stirred at rt and 1,8-diazabicyclo[5.4.0]undec-7-ene (DBU, 0.05 mL, 0.333 mmol) was added. After 24 h stirring at rt, the reaction mixture was diluted with water (2 mL) and 1 N HCl (1 mL), and the resulting solution filtered. The filtrate was subjected to preparative HPLC (Gemini 10u C18 110A, AXIA; 10% aq. acetonitrile-70% aq. acetonitrile with 0.1% TFA, over 20 min. gradient). The concentrated fractions containing product were concentrated, co-evaporated with methanol (10 mL×3), and then dried in vacuo to obtain compound 87 as its TFA salt. $^1$H NMR (400 MHz, Methanol-d4) δ 8.56 (d, J=2.4 Hz, 1H), 7.64 (dd, J=8.8, 2.4 Hz, 1H), 4.36 (td, J=7.2, 3.6 Hz, 1H), 4.03-3.91 (m, 1H), 1.82-1.69 (m, 2H), 1.37 (tddd, J=12.8, 10.3, 7.7, 5.0 Hz, 4H), 1.18 (d, J=6.4 Hz, 3H), 0.94-0.85 (m, 3H). $^{19}$F NMR (376 MHz, Methanol-d$_4$) δ −77.82, −117.98 (d, J=8.8 Hz). LCMS-ESI$^+$ (m/z): [M+H]$^+$ calculated for C$_{1-4}$H$_{21}$FN$_5$O: 294.17; found: 294.13; t$_R$=0.71 min on LC/MS Method A.

Example 88

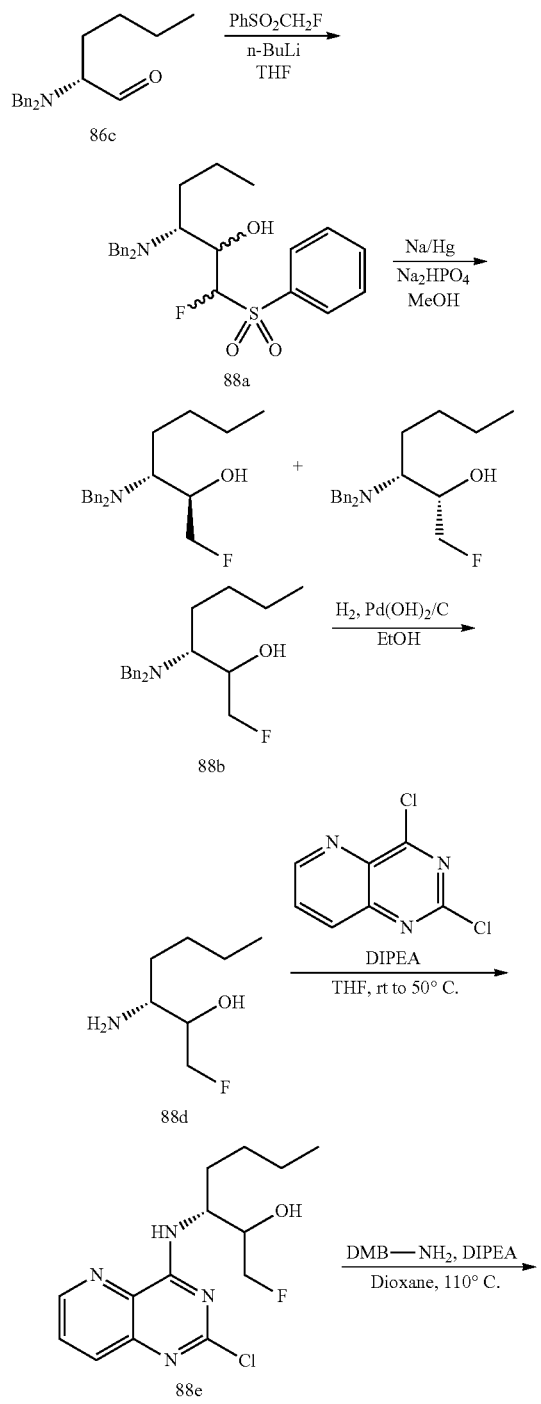

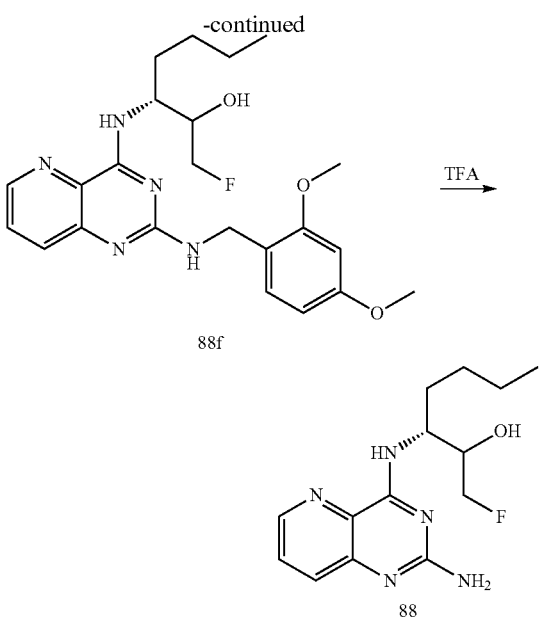

Synthesis of (3R)-3-(dibenzylamino)-1-fluoro-1-(phenylsulfonyl)heptan-2-ol (88a). A solution of fluoromethyl phenyl sulphone (935.6 mg, 5.371 mmol) in THF (3 mL) was stirred in an acetone-dry ice bath and 2.5 M n-butyllithium in hexane (2.15 mL) was added. After 30 min, the crude compound 86c (393.9 mg, 1.333 mmol) in THF (2 mL) was added and the resulting solution stirred with cooling by an acetone-dry ice bath. After 30 minutes, the reaction mixture was quenched with saturated NH$_4$Cl (15 mL), diluted with EtOAc (30 mL), and warmed up to rt before the two fractions were separated. The aqueous fraction was extracted with EtOAc (20 mL×1), and the organic fractions were then washed with water (30 mL×1), before being combined, dried (MgSO$_4$), and concentrated under reduced pressure. The residue was subjected to silica gel chromatography eluting with 0-40% EtOAc in hexanes to provide compound 88a, as a mixture of 4 diastereomers. LCMS-ESI$^+$ (m/z): [M+H]$^+$ calculated for C$_{27}$H$_{33}$FNO$_3$S: 470.22; found: 470.24; t$_R$=1.40-1.45 min.

Synthesis of (2R,3R)-3-(dibenzylamino)-1-fluoroheptan-2-ol and (2S,3R)-3-(dibenzylamino)-1-fluoroheptan-2-ol (88b and 88c). A suspension of compound 88a (635.4 mg, 1.333 mmol) and Na$_2$HPO$_4$ (1325.9 mg, 9.340 mmol) in methanol (10 mL) was stirred in −30~−40° C. bath as sodium-mercury amalgam (1853.9 mmol, 8.060 mmol) was added. The reaction mixture was slowly warmed to ~5° C. over 2 h and then stirred 1 h at ~5° C. The mixture was then filtered through a Celite pad and the filtrate was concentrated in vacuo. The residue was dissolved in EtOAc and water (20 mL each), and the two fractions separated. The aqueous fraction was extracted with EtOAc (20 mL×1). The organic fractions were washed with water (30 mL×1), then combined, dried (MgSO$_4$), and concentrated under reduced pressure. The residue was subjected to repeated silica gel chromatography eluting with 5-20% EtOAc in hexanes to provide compound 88b, as the first eluting fraction, and compound 88c as the second eluting fraction.

Compound 88b: $^1$H NMR (400 MHz, Chloroform-d) δ 7.63-6.91 (m, 10H), 4.53-4.27 (m, 2H), 4.16 (s, 1H), 3.90 (d, J=13.2 Hz, 2H), 3.66 (dt, J=22.5, 5.7 Hz, 1H), 3.49 (d, J=13.3 Hz, 2H), 2.69 (dt, J=9.2, 5.3 Hz, 1H), 1.90-1.70 (m, 1H), 1.39 (tdd, J=12.6, 8.2, 5.5 Hz, 5H), 0.97 (t, J=7.0 Hz, 3H). $^{19}$F NMR (376 MHz, Chloroform-d) δ −230.59 (td, J=47.8, 23.5 Hz). LCMS-ESI$^+$ (m/z): [M+H]$^+$ calculated for $C_{21}H_{29}FNO$: 330.22; found: 330.17; $t_R$=0.96 min on LC/MS Method A.

Compound 88c: $^1$H NMR (400 MHz, Chloroform-d) δ 7.54-6.94 (m, 10H), 4.54 (ddd, J=47.2, 9.4, 3.4 Hz, 1H), 4.25 (ddd, J=48.2, 9.4, 7.3 Hz, 1H), 4.01 (d, J=18.6 Hz, 1H), 3.66 (d, J=2.5 Hz, 4H), 2.68 (q, J=6.1 Hz, 1H), 2.35 (s, 1H), 1.88-1.70 (m, 1H), 1.53-1.21 (m, 5H), 1.00-0.80 (m, 3H). $^{19}$F NMR (376 MHz, Chloroform-d) δ −228.21 (td, J=47.7, 18.4 Hz). LCMS-ESI$^+$ (m/z): [M+H]$^+$ calculated for $C_{21}H_{29}FNO$: 330.22; found: 330.13; $t_R$=1.07 min on LC/MS Method A.

Synthesis of (3R)-3-amino-1-fluoroheptan-2-ol (88d). A mixture of compound 88b (38.25 mg, 0.116 mmol) and 20% palladium hydroxide on carbon (15.61 mg) in EtOH (2 mL) was stirred under H$_2$ atmosphere. After 20.5 h, the reaction mixture was filtered and the solids washed with EtOH (10 mL). After the filtrate and washing was concentrated, the residue was co-evaporated with toluene (5 mL×2) to obtain compound 88d. LCMS-ESI$^+$ (m/z): [M+H]$^+$ calculated for $C_7H_{17}FNO$: 150.13; found: 149.97; $t_R$=0.40 min on LC/MS Method A.

Synthesis of (3R)-3-((2-chloropyrido[3,2-d]pyrimidin-4-yl)amino)-1-fluoroheptan-2-ol (88e). To a solution of compound 88d (14.9 mg, 0.100 mmol) and 2,4-dichloropyrido[3,2-d]pyrimidine (11.6 mg, 0.158 mmol) in THF (2 mL) was added N,N-diisopropylethylamine (0.1 mL, 0.574 mmol). The mixture was stirred at rt for 1.5 h and at 50° C. for 30 min. The reaction mixture was then concentrated in vacuo, and the residue subjected to silica gel chromatography eluting with 20-70% EtOAc in hexanes to obtain compound 88e. LCMS-ESI$^+$ (m/z): [M+H]$^+$ calculated for $C_{14}H_{19}ClFN_4O$: 313.12; found: 313.14; $t_R$=1.06 min on LC/MS Method A.

Synthesis of (3R)-3-((2-((2,4-dimethoxybenzyl)amino)pyrido[3,2-d]pyrimidin-4-yl)amino)-1-fluoroheptan-2-ol (88f). To solution of compound 88e (22.0 mg, 0.070 mmol) in dioxane (2 mL), N,N-diisopropylethylamine (0.06 mL, 0.344 mmol), and 2,4-dimethoxybenzylamine (0.04 mL, 0.266 mmol) were added. The resulting solution was refluxed at 110° C. for 19 h. After the reaction mixture was concentrated, the residue was subjected to silica gel chromatography eluting with hexanes-EtOAc to provide crude product 88f. The crude product was then subjected to preparative HPLC (Gemini 10u C18 110A, AXIA; 10% aq. acetonitrile-80% aq. acetonitrile with 0.1% TFA, over 20 min. gradient). The combined product fractions were neutralized by the addition of saturated aqueous NaHCO$_3$ (1 mL), concentrated to remove acetonitrile, and then extracted with EtOAc (20 mL×2). The organic extracts were washed with water (×1), combined, dried (MgSO$_4$), and concentrated under reduced pressure to obtain compound 88f LCMS-ESI$^+$ (m/z): [M+H−C$_2$H$_4$]$^+$ calculated for $C_{23}H_{31}FN_5O_3$: 444.24; found: 444.18; $t_R$=0.95 min on LC/MS Method A.

Synthesis of (3R)-3-((2-aminopyrido[3,2-d]pyrimidin-4-yl)amino)-1-fluoroheptan-2-ol (88). Compound 88f (8.7 mg, 30.44 umol) was dissolved in TFA (1 mL) and stirred at rt for 1 h. The reaction mixture was concentrated in vacuo and co-evaporated with methanol (10 mL). The residue was dissolved in methanol (1 mL) and concentrated ammonium hydroxide (0.1 mL) was added. The resulting mixture was stirred at rt for 10 min, concentrated under reduced pressure. The residue was triturated in 1 N HCl (0.5 mL) and methanol (2 mL), filtered, and diluted with water (3 mL) before subjecting to preparative HPLC (Gemini 10u C18 110A, AXIA; 10% aq. acetonitrile-70% aq. acetonitrile with 0.1% TFA, over 20 min. gradient). The product fractions were combined, concentrated in vacuo, co-evaporated with methanol (10 mL×3) and dried in vacuo to obtain compound 88 as its TFA salt. $^1$H NMR (400 MHz, Methanol-d4) δ 8.64 (dd, J=4.4, 1.4 Hz, 1H), 7.84 (dd, J=8.5, 1.4 Hz, 1H), 7.77 (dd, J=8.5, 4.4 Hz, 1H), 4.59 (ddd, J=8.0, 6.5, 3.0 Hz, 1H), 4.51-4.38 (m, 1H), 4.38-4.26 (m, 1H), 4.04 (dddd, J=16.2, 6.1, 4.9, 3.1 Hz, 1H), 1.89-1.73 (m, 2H), 1.39 (dtd, J=10.4, 6.9, 6.3, 3.4 Hz, 4H), 0.96-0.84 (m, 3H). $^{19}$F NMR (376 MHz, Methanol-d$_4$) δ −77.56, −231.26 (td, J=47.3, 16.2 Hz). LCMS-ESI$^+$ (m/z): [M+H]$^+$ calculated for $C_{14}H_{21}FN_5O$: 294.17; found: 294.15; $t_R$=0.69 min on LC/MS Method A.

Example 89

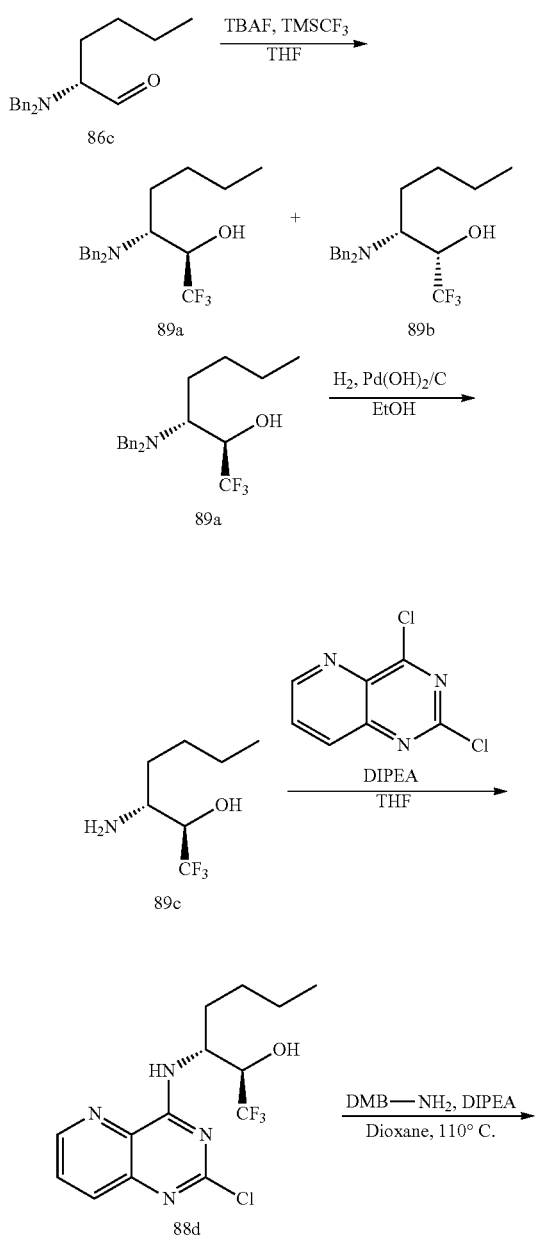

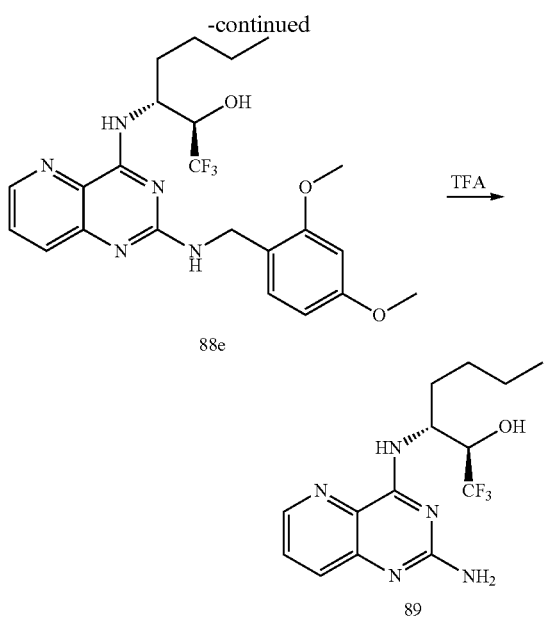

Synthesis of (2S,3R)-3-(dibenzylamino)-1,1,1-trifluoroheptan-2-ol (89a) and (2R,3R)-3-(dibenzylamino)-1,1,1-trifluoroheptan-2-ol (89b). A solution of compound 86c (492.7 mg, 1.668 mmol) and tetrabutylammonium fluoride (TBAF, 21.8 mg, 0.083 mmol) in THF (4 mL) was stirred at 0° C. and trimethyl(trifluoromethyl)silane (0.76 mL, 5.17 mmol) was added. After the resulting mixture was stirred at 0° C. for 30 min, additional TBAF (87.2 mg, 0.334 mmol) was added and the reaction mixture was stirred for 1h at rt. The reaction mixture was quenched with saturated aqueous $NH_4Cl$ (10 mL). The resulting solution was diluted with EtOAc (20 mL) and two layers were separated. The aqueous fraction was extracted with EtOAc (20 mL×3) and the organic fractions were washed with brine (20 mL×1), combined, dried ($MgSO_4$), and concentrated in vacuo. The residue was then subjected to silica gel chromatography eluting with 0-20% EtOAc in hexanes to obtain compound 89a, as the first eluting product and compound 89b as the second eluting product.

Compound 89a: $^1$H NMR (400 MHz, Chloroform-d) δ 7.36-7.26 (m, 10H), 5.30 (s, 1H), 3.90 (d, J=13.1 Hz, 2H), 3.74-3.64 (m, 1H), 3.60 (d, J=13.1 Hz, 2H), 2.97 (d, J=9.3 Hz, 1H), 1.94-1.80 (m, 1H), 1.60-1.44 (m, 3H), 1.38 (h, J=7.4 Hz, 2H), 0.98 (t, J=7.2 Hz, 3H). $^{19}$F NMR (376 MHz, Chloroform-d) δ −76.57 (d, J=6.3 Hz). LCMS-ESI$^+$ (m/z): [M+H]$^+$ calculated for $C_{21}H_{27}F_3NO$: 366.20; found: 366.15; TR=1.46 min.

Compound 89b: $^1$H NMR (400 MHz, Chloroform-d) δ 7.32 (d, J=4.8 Hz, 10H), 4.22 (s, 1H), 3.82 (d, J=13.6 Hz, 2H), 3.50 (d, J=13.6 Hz, 2H), 3.00 (d, J=9.4 Hz, 1H), 2.66 (s, 1H), 1.79 (q, J=9.1 Hz, 1H), 1.49 (s, 2H), 1.35-1.11 (m, 4H), 0.87 (t, J=7.2 Hz, 3H). $^{19}$F NMR (376 MHz, Chloroform-d) δ −76.53 (d, J=8.3 Hz). LCMS-ESI$^+$ (m/z): [M+H]$^+$ calculated for $C_{21}H_{27}F_3NO$: 366.20; found: 366.15; $t_R$=1.49 min on LC/MS Method A.

Synthesis of (2R,3R)-3-amino-1,1,1-trifluoroheptan-2-ol (89c). To a stirred solution of compound 89a (121.35 mg, 0.332 mmol) in EtOH (4 mL) was added 20% palladium hydroxide on carbon (52 mg, 0.074 mmol). The resulting mixture was stirred under $H_2$ atmosphere for 20 h. The reaction mixture was then filtered and washed with ethanol (10 mL). The filtrate was then concentrated in vacuo to obtain compound 89c. LCMS-ESI$^+$ (m/z): [M+H]$^+$ calculated for $C_7H_{15}F_3NO$: 186.11; found: 185.96; $t_R$=0.55 min on LC/MS Method A.

Synthesis of (2R,3R)-3-((2-chloropyrido[3,2-d]pyrimidin-4-yl)amino)-1,1,1-trifluoroheptan-2-ol (89d). To a solution of compound 89c (53.4 mg, 0.288 mmol) and 2,4-dichloropyrido[3,2-d]pyrimidine (57.68 mg, 0.288 mmol) in THF (3 mL) was added N,N-diisopropylethylamine (0.151 mL, 0.865 mmol) and the mixture heated to 80° C. After 2 h, the reaction mixture was allowed to cool to rt and then concentrated in vacuo and the residue subjected to silica gel chromatography eluting with 0-100% EtOAc in hexanes to afford compound 89d.

Synthesis of (2R,3R)-3-((2-((2,4-dimethoxybenzyl)amino)pyrido[3,2-d]pyrimidin-4-yl)amino)-1,1,1-trifluoroheptan-2-ol (89e). To a solution of compound 89d (106.7 mg, 0.346 mmol) in dioxane (3 mL) was added N,N-diisopropylethylamine (0.160 mL, 0.918 mmol) and 2,4-dimethoxybenzylamine (0.230 mL, 1.530 mmol). The resulting solution was refluxed at 110° C. and stirred for 20 h. The reaction mixture was then cooled to rt and diluted with EtOAc (20 mL), washed with water (20 mL×3) and brine (20 mL×1), dried ($MgSO_4$), filtered and then concentrated in vacuo. The residue was subjected to silica gel chromatography eluting with 0-100% EtOAc in hexanes to afford compound 89e. LCMS-ESI$^+$ (m/z): [M+H−$C_2H_4$]$^+$ calculated for $C_{23}H_{29}F_3N_5O_3$: 480.22; found: 480.17; $t_R$=1.03 min on LC/MS Method A.

Synthesis of (2R,3R)-3-((2-aminopyrido[3,2-d]pyrimidin-4-yl)amino)-1,1,1-trifluoroheptan-2-ol (89). Compound 89e (12 mg, 25.0 umol) was dissolved in TFA (1 mL) and stirred at rt for 1 h. The reaction mixture was concentrated in vacuo and co-evaporated with methanol (10 mL). The resulting residue was dissolved in aqueous methanol (1 mL), filtered through a Celite-membrane filter to remove insoluble material, and the filtrate subjected to preparative HPLC (Gemini 10u C18 110A, AXIA; 10% aq. acetonitrile-70% aq. acetonitrile with 0.1% TFA, over 20 min. gradient). The collected product fractions were concentrated in vacuo, and the residue was co-evaporated with methanol (10 mL×3), and dried in vacuum overnight to obtain compound 89 as its TFA salt. $^1$H NMR (400 MHz, Methanol-d4) δ 8.65 (dd, J=4.4, 1.4 Hz, 1H), 7.85 (dd, J=8.5, 1.4 Hz, 1H), 7.79 (dd, J=8.5, 4.4 Hz, 1H), 4.82 (ddd, J=8.3, 6.5, 2.1 Hz, 1H), 4.22 (qd, J=7.3, 1.9 Hz, 1H), 1.92-1.74 (m, 2H), 1.50-1.31 (m, 4H), 0.96-0.87 (m, 3H). $^{19}$F NMR (376 MHz, Methanol-d$_4$) δ −77.56, −79.32 (d, J=7.3 Hz). LCMS-ESI$^+$ (m/z): [M+H]$^+$ calculated for $C_{14}H_{19}F_3N_5O$: 330.15; found: 330.15; $t_R$=0.77 min on LC/MS Method A.

Example 90

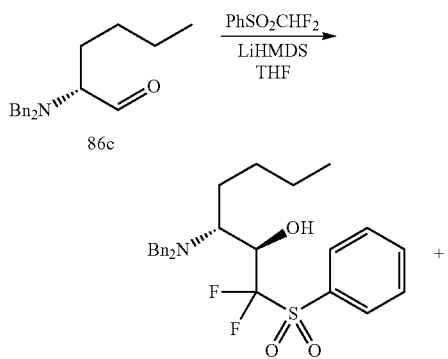

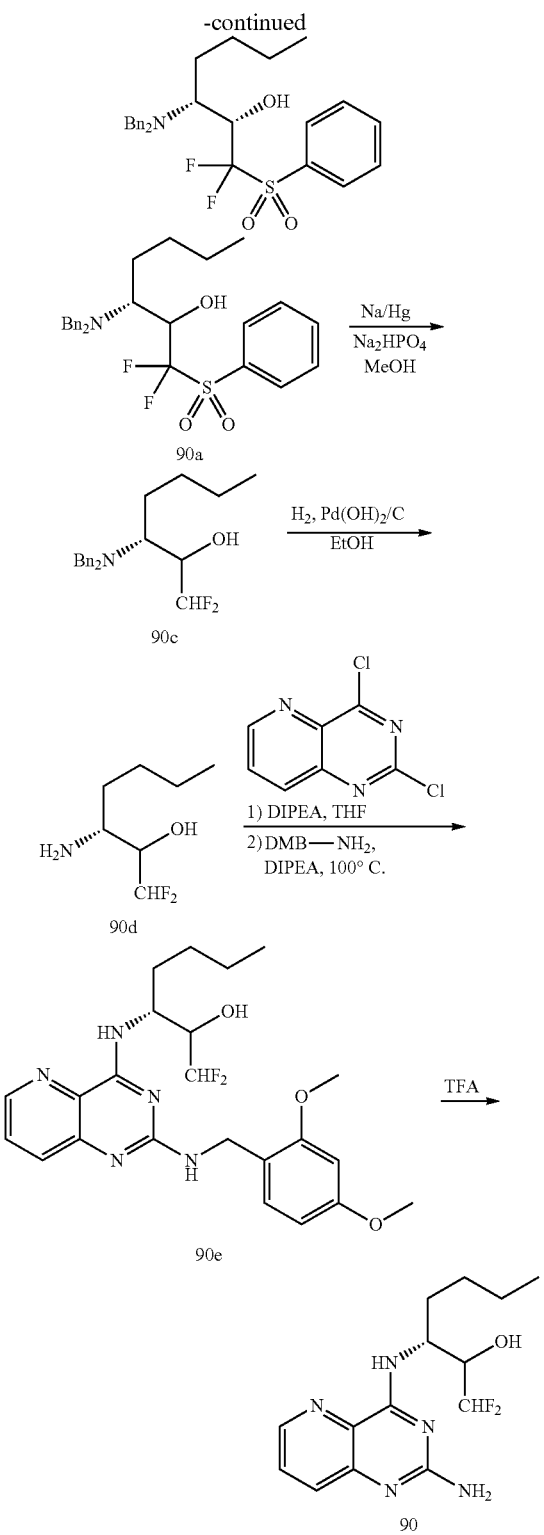

warmed to rt. before quenching with saturated aqueous NH₄Cl solution (15 mL). The resulting solution was diluted with EtOAc (25 mL) and the two layers separated. The separated aqueous fraction was back extracted with EtOAc (15 mL×2). The separate organic fractions were washed with water (25 mL×2), brine (25 mL), then combined, dried over MgSO₄, filtered and concentrated in vacuo. The residue was subjected to silica gel chromatography eluting with 0-30% EtOAc in hexanes to afford of compound 90a as the first eluting isomer, and compound 90b as the second eluting isomer.

Compound 90a. LCMS-ESI⁺ (m/z): [M+H]⁺ calculated for $C_{27}H_{32}F_2NO_3S$: 488.21; found: 488.20; $t_R$=1.50 min on LC/MS Method A.

Compound 90b. LCMS-ESI⁺ (m/z): [M+H]⁺ calculated for $C_{27}H_{32}F_2NO_3S$: 488.21; found: 488.23; $t_R$=1.52 min on LC/MS Method A.

Synthesis of (3R)-3-(dibenzylamino)-1,1-difluoroheptan-2-ol (90c). To a solution of compound 90a (132.9 mg, 0.273 mmol) in methanol (2 mL) at −40° C. was added Na₂HPO₄ (236.3 mg, 1.664 mmol) and 5% sodium mercury-amalgam beads (646.1 mg, 1.41 mmol). The resulting mixture was stirred for 2 h in a cold bath, and then filtered through a Celite pad. The filtrate was concentrated in vacuo and the residue was treated with EtOAc (20 mL) and water (20 mL). The two layers were separated and the aqueous fraction was extracted with EtOAc (20 mL×2). The organic fractions were washed with water (20 mL×1), then combined, dried (MgSO₄), filtered and concentrated under reduced pressure. The residue was subjected to silica gel chromatography eluting with 0-30% EtOAc in hexanes to provide compound 90c. LCMS-ESI⁺ (m/z): [M+H]⁺ calculated for $C_{21}H_{28}F_2NO$: 348.21; found: 348.16; $t_R$=1.26 min on LC/MS Method A.

Synthesis of (3R)-3-amino-1,1-difluoroheptan-2-ol (90d). To a solution of compound 90c (27.2 mg, 0.078 mmol) in EtOH (1 mL) was added 20% palladium hydroxide on carbon (15.9 mg, 0.023 mmol). The resulting mixture was stirred under H₂ atmosphere for 20 h. The reaction mixture was then filtered and washed with EtOH (5 mL). The filtrate was concentrated in vacuo to obtain compound 90d. LCMS-ESI+(m/z): [M+H]⁺ calculated for $C_7H_{116}F_2NO$: 168.12; found: 167.94; $t_R$=0.49 min on LC/MS Method A.

Synthesis of (3R)-3-((2-((2,4-dimethoxybenzyl)amino)pyrido[3,2-d]pyrimidin-4-yl)amino)-1,1-difluoroheptan-2-ol (90e). To a solution of compound 90d (12.4 mg, 0.074 mmol) and 2,4-dichloropyrido[3,2-d]pyrimidine (11.8 mg, 0.059 mmol) in THF (1 mL) was added N,N-diisopropylethylamine (0.039 mL, 0.222 mmol). The mixture was stirred for 2 h at rt, then additional THF (1 mL), N,N-diisopropylethylamine (0.039 mL, 0.222 mmol), and 2,4-dimethoxybenzylamine (0.056 mL, 0.371 mmol) were added, and the resulting mixture heated to 100° C. for 20 h. The reaction mixture was cooled to rt, diluted with EtOAc (~20 mL), washed with water (20 mL×3) and brine (20 mL×1), dried (MgSO₄), filtered and concentrated in vacuo. The residue was subjected to silica gel chromatography eluting with 0-100% EtOAc in hexanes to isolate impure 90e. The impure material was then subjected to preparative HPLC purification (column, Gemini 10u C18 110A, AXIA; 10% aq. acetonitrile-80% aq. acetonitrile with 0.1% TFA, over 20 min. gradient) to afford compound 90e LCMS-ESI⁺ (m/z): [M+H]⁺ calculated for $C_{23}H_{30}F_2N_5O_3$: 462.23; found: 462.17; $t_R$=1.00 min on LC/MS Method A.

Synthesis of (2R,3R)-3-(dibenzylamino)-1,1-difluoro-1-(phenylsulfonyl)heptan-2-ol and (2S,3R)-3-(dibenzylamino)-1,1-difluoro-1-(phenylsulfonyl)heptan-2-ol (90a and 90b). A solution of compound 86c (235.6 mg, 0.798 mmol) and difluoromethyl phenyl sulfone (153.3 mg, 0.80 mmol) in THF (5 mL) was stirred at −78° C. and then 1.0 M LHMDS in THF (1.60 mL, 1.60 mmol) was added slowly. The reaction mixture was stirred for 2 h at −78° C., and Synthesis of (3R)-3-((2-aminopyrido[3,2-d]pyrimidin-4-yl)amino)-1,1-difluoroheptan-2-ol (90). Compound 90e (16 mg, 34.67 umol) was dissolved in TFA (1 mL) and stirred at rt. After 1 h, the mixture was concentrated in vacuo, and the residue was triturated in methanol (1 mL×3), filtered, and diluted with water (~6 mL). The mixture was subjected to preparative HPLC (Gemini 10u C18 110A, AXIA; 10% aq. acetonitrile-70% aq. acetonitrile with 0.1% TFA, over 20 min. gradient). Collected product fractions were concentrated in vacuo, co-evaporated with methanol (10 mL×3) and dried in vacuo to obtain compound 90 as its TFA salt. $^1$H NMR (400 MHz, Methanol-$d_4$) δ 8.64 (dd, J=4.3, 1.4 Hz, 1H), 7.84 (dd, J=8.5, 1.5 Hz, 1H), 7.78 (dd, J=8.5, 4.3 Hz, 1H), 5.73 (td, J=55.6, 4.9 Hz, 1H), 4.70 (t, J=7.4 Hz, 1H), 3.98-3.82 (m, 1H), 1.90-1.72 (m, 2H), 1.54-1.31 (m, 4H), 1.00-0.82 (m, 3H). $^{19}$F NMR (376 MHz, Methanol-d4) δ −77.78, −129.57 (ddd, J=289.8, 55.1, 8.6 Hz), −132.42 (ddd, J=290.1, 56.0, 12.5 Hz). LCMS-ESI$^+$ (m/z): [M+H]$^+$ calculated for $C_{14}H_{20}F_2N_5O$: 312.16; found: 312.15; $t_R$=0.74 min on LC/MS Method A.

Example 91

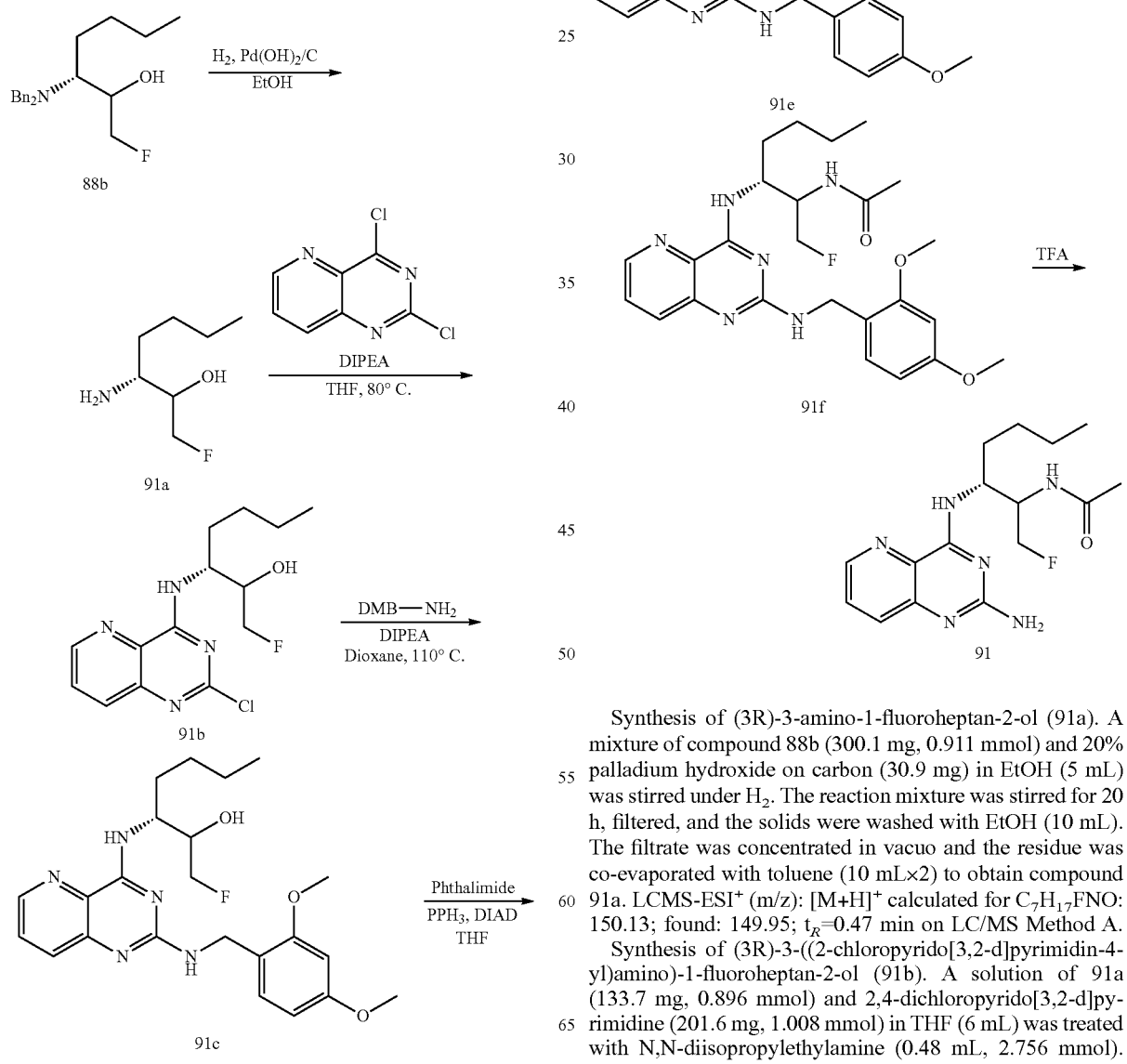

Synthesis of (3R)-3-amino-1-fluoroheptan-2-ol (91a). A mixture of compound 88b (300.1 mg, 0.911 mmol) and 20% palladium hydroxide on carbon (30.9 mg) in EtOH (5 mL) was stirred under $H_2$. The reaction mixture was stirred for 20 h, filtered, and the solids were washed with EtOH (10 mL). The filtrate was concentrated in vacuo and the residue was co-evaporated with toluene (10 mL×2) to obtain compound 91a. LCMS-ESI$^+$ (m/z): [M+H]$^+$ calculated for $C_7H_{17}FNO$: 150.13; found: 149.95; $t_R$=0.47 min on LC/MS Method A.

Synthesis of (3R)-3-((2-chloropyrido[3,2-d]pyrimidin-4-yl)amino)-1-fluoroheptan-2-ol (91b). A solution of 91a (133.7 mg, 0.896 mmol) and 2,4-dichloropyrido[3,2-d]pyrimidine (201.6 mg, 1.008 mmol) in THF (6 mL) was treated with N,N-diisopropylethylamine (0.48 mL, 2.756 mmol). The mixture was stirred at rt for 2.75 h. The reaction mixture was concentrated in vacuo, and the residue was subjected to silica gel chromatography eluting with 20-70% EtOAc in hexanes to obtain, after removal of solvent in vacuo, compound 91b. LCMS-ESI$^+$ (m/z): [M+H–C$_2$H$_4$]$^+$ calculated for C$_{14}$H$_{19}$ClFN$_4$O: 313.12; found: 313.14; t$_R$=1.04 min on LC/MS Method A.

Synthesis of (3R)-3-((2-((2,4-dimethoxybenzyl)amino)pyrido[3,2-d]pyrimidin-4-yl)amino)-1-fluoroheptan-2-ol (91c). To a solution of compound 91b (233.6 mg, 0.747 mmol) in dioxane (7 mL) was added N,N-diisopropylethylamine (0.64 mL, 3.674 mmol), and 2,4-dimethoxybenzylamine (0.45 mL, 2.995 mmol). The resulting solution was refluxed at 110° C. bath for 24 h. The reaction mixture was concentrated in vacuo, and the residue was dissolved in DCM (30 mL), and washed with water (30 mL×1). The aqueous fraction was extracted with DCM (30 mL×1), and the organic fractions were combined, dried (MgSO$_4$), filtered and concentrated in vacuo. The residue was subjected to silica gel chromatography eluting with 20-100% EtOAc in hexanes. The collected fractions were concentrated under reduced pressure and the residue was subjected to preparative HPLC (Gemini 10u C18 110A, AXIA; 10% aq. acetonitrile-80% aq. acetonitrile with 0.1% TFA, over 20 min. gradient). The collected product fractions were combined, neutralized by saturated aqueous NaHCO$_3$ solution (1 mL), partially concentrated in vacuo to remove acetonitrile and then extracted with EtOAc (20 mL×2). The organic extracts were washed with water (20 mL), combined, dried over MgSO$_4$, filtered and concentrated in vacuo to obtain compound 91c. LCMS-ESI$^+$ (m/z): [M+H–C$_2$H$_4$]$^+$ calculated for C$_{23}$H$_{31}$FN$_5$O$_3$: 444.24; found: 444.19; t$_R$=0.97 min on LC/MS Method A.

Synthesis of 2-((3R)-3-((2-((2,4-dimethoxybenzyl)amino)pyrido[3,2-d]pyrimidin-4-yl)amino)-1-fluoroheptan-2-yl)isoindoline-1,3-dione (91d). To a solution of compound 91c (654 mg, 1.475 mmol), phthalimide (347.1 mg, 2.359 mmol), and triphenylphosphine (874.8 mg, 3.359 mmol) in THF (24 mL) at 0° C. was added diisopropyl azodicarboxylate (0.697 mL, 3.539 mmol). The reaction mixture was warmed to rt and stirred for 2 h. After the reaction mixture was concentrated under reduced pressure, the residue was subjected to silica gel chromatography eluting with 0-100% EtOAc in hexanes to obtain, after removal of volatiles in vacuo, compound 91d. LCMS-ESI$^+$ (m/z): [M+H]$^+$ calculated for C$_{31}$H$_{34}$FN$_6$O$_4$: 573.26; found: 573.20; t$_R$=1.27 min on LC/MS Method A.

Synthesis of N$^4$-((3R)-2-amino-1-fluoroheptan-3-yl)-N$^2$-(2,4-dimethoxybenzyl)pyrido[3,2-d]pyrimidine-2,4-diamine (91e). To a solution of compound 91d (489.3 mg, 0.854 mmol) in EtOH (5 mL) was added hydrazine hydrate (0.07 mL, 1.28 mmol) at rt. The reaction mixture was refluxed for 3.5 h, the precipitates were removed by filtration and then the solid washed with EtOH (15 mL). The filtrates were concentrated in vacuo and the residue was dissolved in DCM (30 mL), washed with water (30 mL×2), dried over MgSO$_4$, filtered and concentrated in vacuo to obtain compound 91e. LCMS-ESI$^+$ (m/z): [M+H]$^+$ calculated for C$_{23}$H$_{32}$FN$_6$O$_2$: 443.26; found: 443.20; t$_R$=0.79 min on LC/MS Method A.

Synthesis of N-((3R)-3-((2-((2,4-dimethoxybenzyl)amino)pyrido[3,2-d]pyrimidin-4-yl)amino)-1-fluoroheptan-2-yl)acetamide (91f). To a solution of 91e (395.3 mg, 0.893 mmol) and N,N-diisopropylethylamine (0.311 mL, 1.787 mmol) in THF (8 mL) was added acetic anhydride (0.127 mL, 1.340 mmol), and the reaction was stirred for 30 min. at rt. The mixture was then diluted with EtOAc (30 mL), washed with saturated aqueous NaHCO$_3$ solution (30 mL), brine (30 mL), dried over MgSO$_4$, filtered and concentrated under reduced pressure. The residue was subjected to silica gel chromatography eluting with 0-100% EtOAc in hexanes, followed by elution with 0-20% methanol in EtOAc. The collected product fractions were concentrated in vacuo and then subjected to preparative HPLC purification (Gemini 10u C18 110A, AXIA; 10% aq. acetonitrile-70% aq. acetonitrile with 0.1% TFA, over 20 min. gradient) to obtain, after removal of volatiles in vacuo, compound 91f. LCMS-ESI$^+$ (m/z): [M+H]$^+$ calculated for C$_{25}$H$_{34}$FN$_6$O$_3$: 485.27; found: 485.23; t$_R$=1.28 min on LC/MS Method A.

Synthesis of N-((3R)-3-((2-aminopyrido[3,2-d]pyrimidin-4-yl)amino)-1-fluoroheptan-2-yl)acetamide (91). Compound 91f (50 mg, 0.103 mmol) was dissolved in TFA (3 mL) and stirred at rt for 11 h. The mixture was concentrated under reduced pressure, and the residue was triturated with methanol (1 mL×3). After the insoluble material was removed by filtration and the filtrate was diluted with water (3 mL), the resulting solution was subjected to preparative HPLC (Gemini 10u C18 110A, AXIA; 10% aq. acetonitrile-70% aq. acetonitrile with 0.1% TFA, over 20 min. gradient). Product-containing fractions were combined, concentrated under reduced pressure to dryness, co-evaporated with methanol (×3), and finally dried under high vacuum to provide 91 as its TFA salt. $^1$H NMR (400 MHz, Methanol-d$_4$) δ 8.67 (ddd, J=4.3, 1.4, 0.6 Hz, 1H), 7.96-7.69 (m, 2H), 4.82-4.67 (m, 1H), 4.60 (d, J=5.1 Hz, 1H), 4.48 (d, J=5.0 Hz, 1H), 4.41 (dq, J=21.7, 5.1 Hz, 1H), 1.96 (d, J=4.2 Hz, 3H), 1.78 (td, J=8.6, 4.6 Hz, 1H), 1.48-1.24 (m, 4H), 0.90 (tt, J=5.5, 2.3 Hz, 3H). LCMS-ESI$^+$ (m/z): [M+H]$^+$ calculated for C$_{16}$H$_{27}$FN$_6$O: 335.19; found: 335.19; t$_R$=0.82 min on LC/MS Method A.

Example 92

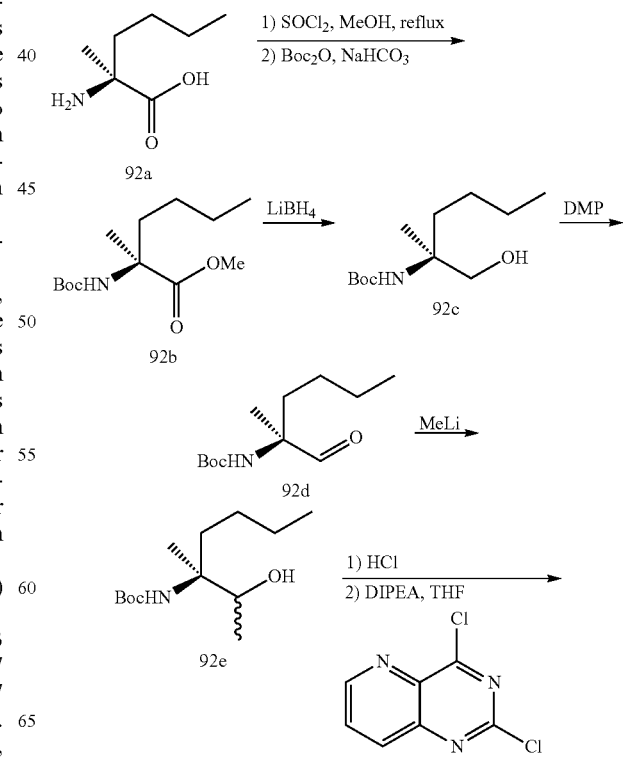

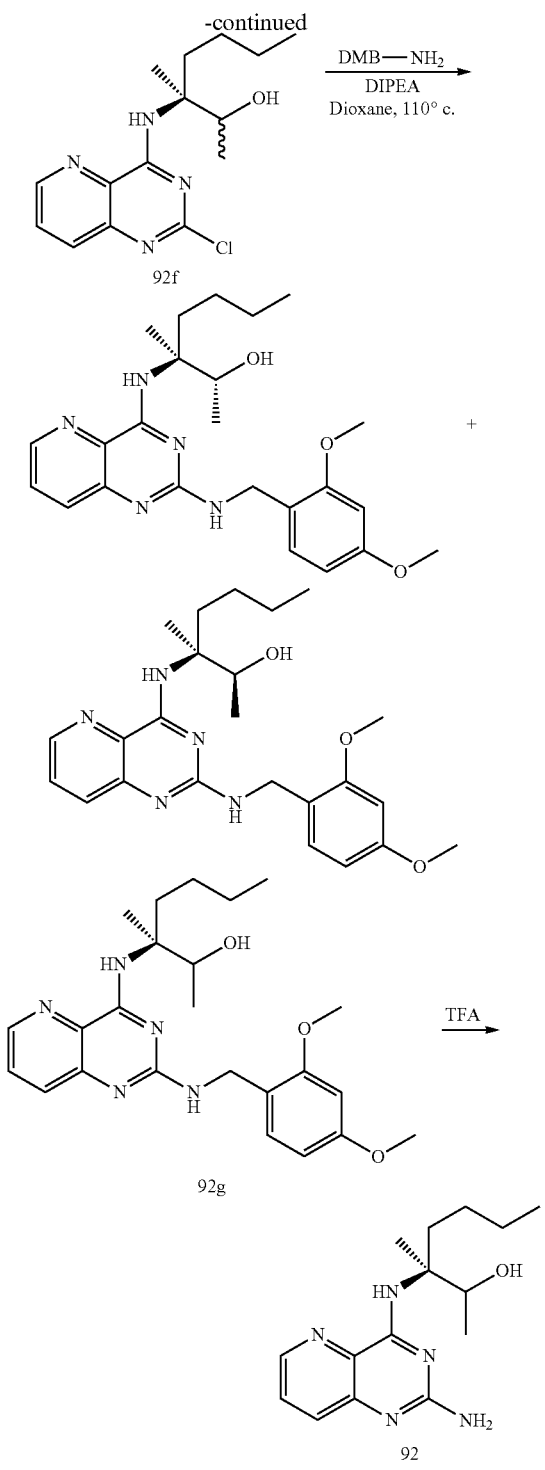

mg, 13.43 mmol) was added and the mixture stirred for 4 h. Additional NaHCO$_3$ (1014.6 mg, 12.08 mmol) and di-tert-butyl dicarbonate (1234.0 mg, 5.654 mmol) were then added and the resulting suspension was stirred at rt overnight. The reaction mixture was then diluted with water (100 mL) and extracted with EtOAc (100 mL×2). The organic extracts were washed with water (100 mL), then combined, dried over MgSO$_4$ filtered and concentrated in vacuo. The residue was subjected to silica gel chromatography eluting with 0-20% EtOAc in hexanes to obtain compound 92b. LCMS-ESI$^+$ (m/z): [M+H–C$_4$H$_8$]$^+$ calculated for C$_9$H$_{18}$NO$_4$: 204.12; found: 203.68; $t_R$=1.24 min on LC/MS Method A.

Synthesis of (S)-tert-butyl (1-hydroxy-2-methylhexan-2-yl)carbamate (92c). To a stirred solution of compound 92b (2515.4 mg, 9.699 mmol) in THF (20 mL) and methanol (2.8 mL) at 0° C., was added 2.0 M LiBH$_4$ in THF (9.7 mL, 19.4 mmol). The solution was stirred at rt for 5 h, was and then diluted with water (100 mL) at 0° C., and extracted with EtOAc (100 mL×2). The combined extracts were washed with water (100 mL), dried over MgSO$_4$, filtered and concentrated in vacuo. The residue was subjected to silica gel chromatography eluting with 0-40% EtOAc in hexanes to provide compound 92c LCMS-ESI$^+$ (m/z): [M+H–C$_4$H$_8$]$^+$ calculated for C$_{12}$H$_{26}$NO$_3$: 232.19; found: 231.60; $t_R$=1.07 min on LC/MS Method A.

Synthesis of (S)-tert-butyl (2-methyl-1-oxohexan-2-yl) carbamate (92d). To a solution of compound 92c (543.3 mg, 2.349 mmol) in DCM (20 mL) was added Dess-Martin Periodinane (1495.1 mg, 3.525 mmol) and the resulting mixture stirred for 3 h. The reaction mixture was diluted with DCM (30 mL) and filtered through a pad of Celite. The filtrate was washed with saturated aqueous Na$_2$S$_2$O$_3$ (50 mL), water (50 mL), and brine (50 mL). The aqueous fraction was re-extracted with DCM (30 mL×2), and the combined organic fractions were dried over Na$_2$SO$_4$, filtered and concentrated in vacuo. The residue was subjected to silica gel chromatography eluting with 0-70% EtOAc in hexanes to obtain compound 92d. LCMS-ESI$^+$ (m/z): [M+H–C$_4$H$_8$]$^+$ calculated for C$_8$H$_{16}$NO$_3$: 174.11; found: 174.76, $t_R$=1.28 min on LC/MS Method A.

Synthesis of tert-butyl ((3S)-2-hydroxy-3-methylheptan-3-yl)carbamate (92e). To a solution of compound 92d (511.8 mg, 2.232 mmol) in diethyl ether (5 mL) cooled in an ice-salt bath (−15° C.), was added 1.6 M solution of MeLi in diethyl ether (5.58 mL, 8.927 mmol) dropwise over 5 min. After 30 min, the reaction mixture was quenched with saturated aqueous NH$_4$Cl solution (15 mL). The resulting mixture was diluted with water and the product was extracted with EtOAc (25 mL×2). The combined extracts were dried over MgSO$_4$, filtered and concentrated in vacuo. The residue was then subjected to silica gel chromatography eluting with 0-70% EtOAc in hexanes to provide compound 92e as a mixture of two diastereomers. LCMS-ESI$^+$ (m/z): [M+H]$^+$ calculated for C$_{13}$H$_{28}$NO$_3$: 246.21; found: 245.63; $t_R$=1.28 min on LC/MS Method A.

Synthesis of (3S)-3-((2-chloropyrido[3,2-d]pyrimidin-4-yl)amino)-3-methylheptan-2-ol (92f). Compound 92e (347 mg, 1.414 mmol) was dissolved in 4M HCl in dioxane (3.1 mL) and stirred at rt for 4 h. The reaction mixture was then concentrated in vacuo. The residue in THF (10.5 mL) was treated with 2,4-dichloropyrido[3,2-d]pyrimidine (259.1 mg, 1.295 mmol) and N,N-diisopropylethylamine (1.18 mL, 6.77 mmol), and placed in 80° C. bath for 1 h. The reaction mixture was cooled to rt, concentrated under reduced pressure, and the residue subjected to silica gel chromatography eluting with 0-70% EtOAc in hexanes to obtain compound Synthesis of (S)-methyl 2-((tert-butoxycarbonyl)amino)-2-methylhexanoate (92b). To a suspension of (S)-2-amino-2-methylhexanoic acid 92a (2018.9 mg, 11.11 mmol, Asiba Pharmatech Inc.) in methanol (30 mL) was added thionyl chloride (1.62 mL) dropwise, and the resulting solution was refluxed for 41 h. The solution was concentrated under reduced pressure and the residue was co-evaporated with methanol (30 mL×2). The residue was treated with NaHCO$_3$ (4.6964 g, 55.90 mmol) in water (30 mL) and methanol (5 mL) and was stirred at rt. Di-tert-butyl dicarbonate (2932

92f. LCMS-ESI⁺ (m/z): [M+H]⁺ calculated for $C_{15}H_{21}ClN_4O$: 309.15; found: 309.12; $t_R$=1.32 min on LC/MS Method A.

Synthesis of (2R,3S)-3-((2-((2,4-dimethoxybenzyl)amino)pyrido[3,2-d]pyrimidin-4-yl)amino)-3-methylheptan-2-ol and (2S,3S)-3-((2-((2,4-dimethoxybenzyl)amino)pyrido[3,2-d]pyrimidin-4-yl)amino)-3-methylheptan-2-ol (92g and 92h). To a solution of compound 92f (331.8 mg, 1.074 mmol) in dioxane (11 mL) was added N,N-diisopropylethylamine (0.561 mL, 3.223 mmol) and 2,4-dimethoxybenzylamine (0.807 mL, 5.372 mmol). The resulting mixture was refluxed at 110° C. bath for 17 h. The mixture was then concentrated in vacuo and the resulting residue dissolved in EtOAc (50 mL) and washed with water (50 mL×2) and brine (50 mL). The organic fraction was dried over $Na_2SO_4$, filtered and then concentrated in vacuo. The resulting residue was subjected to silica gel chromatography eluting with 0-100% EtOAc in hexanes. The collected product was then concentrated in vacuo and resubjected to column chromatography on silica gel eluting with 0-20% MeOH in DCM to obtain a mixture of compound 92g and 92h. The mixture was then concentrated in vacuo and the residue subjected to preparative chiral SFC (SFC IC-5 um-4.6×100 mm, 40% EtOH-ammonia) to obtain after removal of volatiles in vacuo compound 92g eluting first, and compound 92h eluting second.

Compound 92g: ¹H NMR (400 MHz, Chloroform-d) δ 8.29 (dd, J=4.5, 1.5 Hz, 1H), 7.71 (d, J=8.4 Hz, 1H), 7.44 (dd, J=8.5, 4.3 Hz, 1H), 7.29 (d, J=8.2 Hz, 1H), 6.46 (d, J=2.4 Hz, 1H), 6.42 (dd, J=8.2, 2.4 Hz, 1H), 4.56 (d, J=5.8 Hz, 2H), 3.84 (s, 3H), 3.79 (s, 3H), 2.13 (t, J=12.7 Hz, 1H), 1.88 (t, J=11.5 Hz, 1H), 1.45 (ddd, J=12.9, 9.7, 5.5 Hz, 1H), 1.38 (s, 3H), 1.35-1.22 (m, 2H), 1.21 (d, J=6.3 Hz, 4H), 0.87 (t, J=7.2 Hz, 3H). LCMS-ESI⁺ (m/z): [M+H]⁺ calculated for $C_{24}H_{34}N_5O_3$: 440.27; found: 440.18; $t_R$=1.29 min on LC/MS Method A.

Compound 92h: ¹H NMR (400 MHz, Chloroform-d) δ 8.29 (dd, J=4.3, 1.5 Hz, 1H), 7.70 (d, J=8.4 Hz, 1H), 7.43 (dd, J=8.5, 4.3 Hz, 1H), 7.29 (d, J=8.2 Hz, 1H), 7.20 (s, 1H), 6.46 (d, J=2.4 Hz, 1H), 6.42 (dd, J=8.2, 2.4 Hz, 1H), 4.56 (d, J=5.7 Hz, 2H), 3.84 (s, 3H), 3.79 (s, 3H), 1.97 (d, J=10.6 Hz, 1H), 1.59 (dt, J=13.9, 7.2 Hz, 1H), 1.48 (s, 3H), 1.36 (qd, J=7.2, 6.7, 4.0 Hz, 4H), 1.26 (d, J=1.4 Hz, 1H), 1.18 (d, J=6.4 Hz, 3H), 0.97-0.90 (m, 3H). LCMS-ESI⁺ (m/z): [M+H]⁺ calculated for $C_{24}H_{34}N_5O_3$: 440.27; found: 440.18; $t_R$=1.28 min on LC/MS Method A.

Synthesis of (3S)-3-((2-aminopyrido[3,2-d]pyrimidin-4-yl)amino)-3-methylheptan-2-ol (92). Compound 92g (74.1 mg, 0.169 mmol) was dissolved in TFA (3 mL) and stirred at rt for 0.75 h. The reaction mixture was carefully concentrated under reduced pressure to dryness. The residue was triturated with 50% aq. methanol and filtered through a Celite-membrane filter. The filtrate was then subjected to preparative HPLC (Gemini 10u C18 110A, AXIA; 10% aq. acetonitrile-70% aq. acetonitrile with 0.1% TFA, over 20 min. gradient). The product fractions were combined, concentrated in vacuo, then co-evaporated with methanol (10 mL×3), and dried under vacuum to provide compound 92 as its TFA salt. ¹H NMR (400 MHz, Methanol-d4) δ 8.61 (dd, J=4.4, 1.4 Hz, 1H), 7.84 (dd, J=8.5, 1.4 Hz, 1H), 7.76 (dd, J=8.5, 4.4 Hz, 1H), 4.36 (q, J=6.5 Hz, 1H), 2.30 (dt, J=16.4, 6.8 Hz, 1H), 1.91-1.78 (m, 1H), 1.56 (s, 3H), 1.46-1.29 (m, 4H), 1.23 (d, J=6.5 Hz, 3H), 0.97-0.85 (m, 3H). ¹⁹F NMR (376 MHz, Methanol-d4) δ −77.60. LCMS-ESI⁺ (m/z): [M+H]⁺ calculated for $C_{15}H_{24}N_5O$: 290.20; found: 290.14; $t_R$=0.82 min on LC/MS Method A.

Example 93

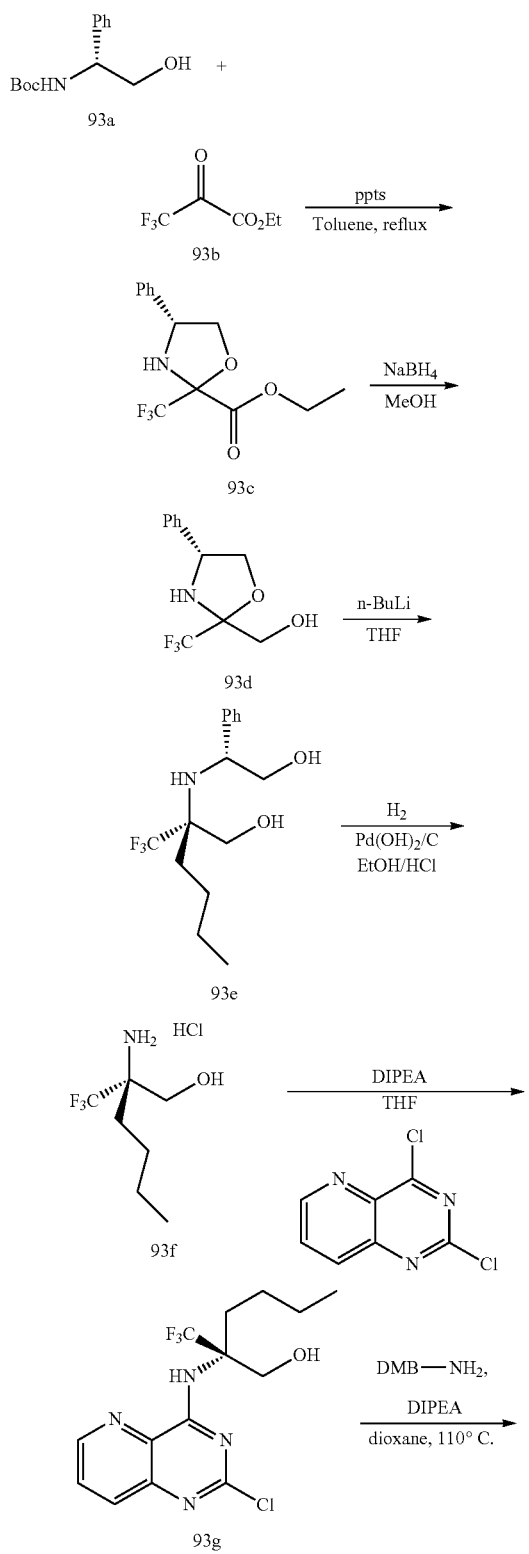

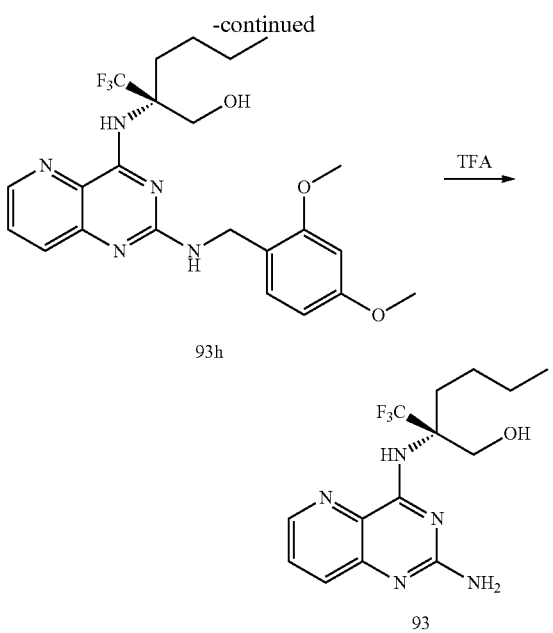

Synthesis of (4R)-ethyl 4-phenyl-2-(trifluoromethyl)oxazolidine-2-carboxylate (93c). A solution of (R)—N-Boc-phenylglycinol 93a (522.4 mg, 2.249 mmol, Combi-Blocks, Inc.), ethyl trifluoropyruvate 93b (0.328 mL, 2.474 mmol, Oakwood Products), and pyridinium p-toluenesulfonate (113.1 mg, 0.450 mmol) in toluene (20 mL) was refluxed with a Dean-Stark apparatus for 20 h. The reaction mixture was then cooled to 0° C. using an ice-water bath and filtered through a pad of Celite. After the filtrate was concentrated in vacuo, the residue was subjected to silica gel chromatography eluting with 0-30% EtOAc in hexanes to obtain compound 93c. LCMS-ESI$^+$ (m/z): [M+H]$^+$ calculated for $C_{13}H_{15}F_3NO_3$: 290.10; found: 289.84; $t_R$=1.21 min on LC/MS Method A.

Synthesis of ((4R)-4-phenyl-2-(trifluoromethyl)oxazolidin-2-yl)methanol (93d). To a solution of compound 93c (384.9 mg, 1.331 mmol) in MeOH (6 mL) at 0° C. was added sodium borohydride (50.3 mg, 1.331 mmol). The reaction mixture was warmed to rt and stirred for 30 min. before quenching with aqueous saturated NH$_4$Cl (15 mL). After methanol was removed under reduced pressure, the resulting aqueous solution was extracted with EtOAc (25 mL×3). The organic extracts were washed with water (25 mL×2) and brine (25 mL), combined, dried over MgSO$_4$, filtered and then concentrated in vacuo. The residue was subjected to silica gel chromatography eluting with 0-40% EtOAc in hexanes to obtain compound 93d LCMS-ESI$^+$ (m/z): [M+H]$^+$ calculated for $C_{11}H_{13}F_3NO_2$: 248.09; found: 247.90; $t_R$=0.96 min on LC/MS Method A.

Synthesis of (R)-2-(((R)-2-hydroxy-1-phenylethyl)amino)-2-(trifluoromethyl)hexan-1-ol (93e). To a solution of compound 93d (264.7 mg, 1.071 mmol) in THF (13 mL) at −78° C. was added n-butyllithium (2.5 M in hexane, 1.713 mL, 4.283 mmol) dropwise. The resulting solution was stirred in a cold bath for 2 h before quenching with aqueous saturated NH$_4$Cl (30 mL). The mixture was extracted with EtOAc (30 mL×3) and the extracts were washed with water (30 mL×2) and brine (30 mL×1). The organic fractions were combined, dried over MgSO$_4$, filtered and concentrated in vacuo. The residue was subjected to silica gel chromatography eluting with 0-70% EtOAc in hexanes to obtain compound 93e LCMS-ESI$^+$ (m/z): [M+H]$^+$ calculated for $C_{15}H_{23}F_3NO_2$: 306.17; found: 305.90, $t_R$=1.13 min on LC/MS Method A.

Synthesis of (R)-2-amino-2-(trifluoromethyl)hexan-1-ol hydrochloride (93f). To a solution of compound 93e (146.5 mg, 0.480 mmol) in EtOH (1 mL) and concentrated HCl (0.3 mL) was added palladium hydroxide on carbon (67.4 mg) and the resulting mixture was stirred under H$_2$ atmosphere for 24 h. The reaction mixture was filtered through a pad of Celite and then the solids rinsed with EtOH (25 mL). The eluants were concentrated under reduced pressure, diluted with water (20 mL) and then extracted with EtOAc (20 mL×2). The organic extracts were combined and concentrated under reduced pressure to obtain of compound 93f as its HCl salt. LCMS-ESI$^+$ (m/z): [M+H]$^+$ calculated for $C_7H_{15}F_3NO$: 186.11; found: 185.95; $t_R$=0.51 min on LC/MS Method A.

Synthesis of (R)-2-((2-((2,4-dimethoxybenzyl)amino)pyrido[3,2-d]pyrimidin-4-yl)amino)-2-(trifluoromethyl)hexan-1-ol (93h). To a solution of compound 93f (123.84 mg, 0.480 mmol) and 2,4-dichloropyrido[3,2-d]pyrimidine (96.0 mg, 0.480 mmol) in THF (4 mL) was added N,N-diisopropylethylamine (0.251 mL, 1.439 mmol). The reaction mixture was stirred and heated to 80° C. for 18 h. The reaction mixture was allowed to cool and concentrated in vacuo. The resulting residue was subjected to silica gel chromatography eluting with 0-100% EtOAc in hexanes to afford compound 93g (109.9 mg, 66%). To a solution of compound 93g (109.9 mg, 0.315 mmol) in dioxane (3.5 mL) was added N,N-diisopropylethylamine (0.165 mL, 0.945 mmol) and 2,4-dimethoxybenzylamine (0.237 mL, 1.576 mmol). The mixture was refluxed at 110° C. for 20 h, allowed to cool to rt, diluted with EtOAc (30 mL), washed with water (30 mL×3) and brine (30 mL), dried over MgSO$_4$, filtered and concentrated in vacuo. The resulting residue was subjected to silica gel chromatography eluting with 0-100% EtOAc in hexanes. The collected fractions were concentrated in vacuo to a residue that was subjected to preparative HPLC purification (Gemini 10u C18 110A, AXIA; 10% aq. acetonitrile-80% aq. acetonitrile with 0.1% TFA, over 20 min. gradient) to afford compound 93h LCMS-ESI$^+$ (m/z): [M+H]$^+$ calculated for $C_{23}H_{29}F_3N_5O_3$: 480.22; found: 480.17; $t_R$=0.96 min on LC/MS Method A.

Synthesis of (R)-2-((2-aminopyrido[3,2-d]pyrimidin-4-yl)amino)-2-(trifluoromethyl)hexan-1-ol (93). Compound 93h (7.8 mg, 16.27 umol) was dissolved in TFA (1 mL) and stirred at rt for 1 h. The reaction mixture was then concentrated in vacuo and the residue was co-evaporated with methanol (5 mL×3). The residue was triturated with 50% aq. methanol and filtered through a Celite-membrane filter. The filtrate was subjected to preparative HPLC (Gemini 10u C18 110A, AXIA; 10% aq. acetonitrile-70% aq. acetonitrile with 0.1% TFA, over 20 min. gradient). The product fractions were combined, concentrated under reduced pressure, co-evaporated with methanol (10 mL×3), and dried under vacuum to provide compound 93 as its TFA salt. $^1$H NMR (400 MHz, Methanol-d4) δ 8.67 (dd, J=4.4, 1.4 Hz, 1H), 7.89 (dd, J=8.5, 1.4 Hz, 1H), 7.82 (dd, J=8.5, 4.4 Hz, 1H), 4.11 (d, J=12.2 Hz, 1H), 4.06-3.97 (m, 1H), 2.81 (ddd, J=13.8, 11.0, 4.4 Hz, 1H), 1.99-1.85 (m, 1H), 1.38 (m, 4H), 0.92 (t, J=7.0 Hz, 3H). $^{19}$F NMR (376 MHz, Methanol-d$_4$) δ −75.96 (s, 3F), −77.39 (s, 3F). LCMS-ESI$^+$ (m/z): [M+H]$^+$ calculated for $C_{14}H_{19}F_3N_5O$: 330.15; found: 330.16; $t_R$=0.76 min on LC/MS Method A.

Example 94
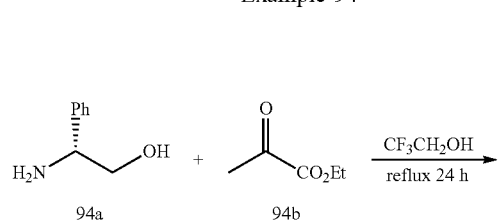
94a + 94b → (CF₃CH₂OH, reflux 24 h)
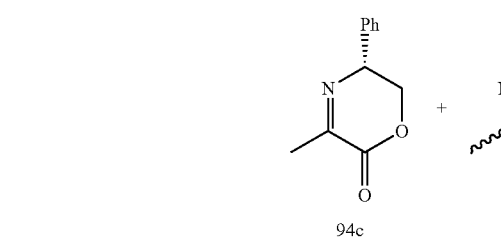
94c + 94d
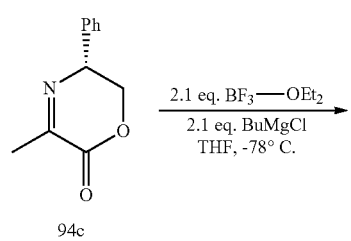
94c — 2.1 eq. BF₃—OEt₂, 2.1 eq. BuMgCl, THF, -78° C. →
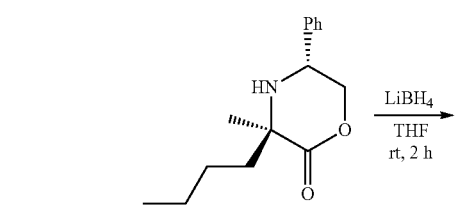
94e — LiBH₄, THF, rt, 2 h →
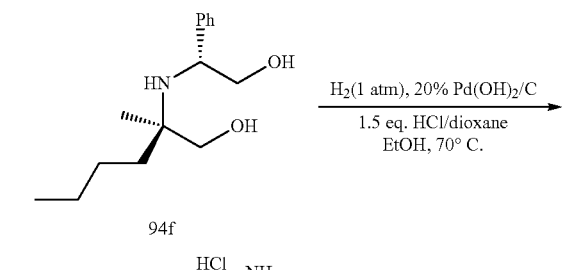
94f — H₂ (1 atm), 20% Pd(OH)₂/C, 1.5 eq. HCl/dioxane, EtOH, 70° C. →
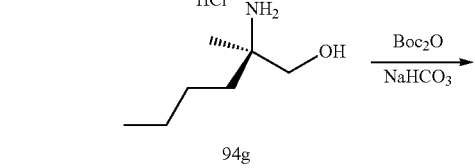
94g — Boc₂O, NaHCO₃ →
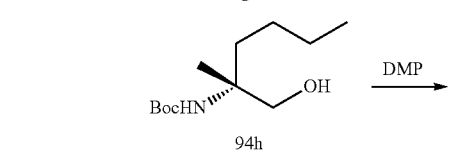
94h — DMP →
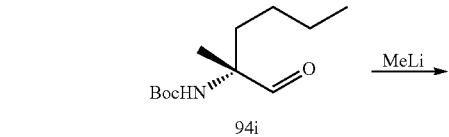
94i — MeLi →
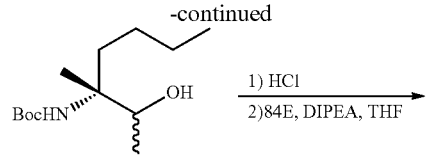
94j — 1) HCl  2) 84E, DIPEA, THF →
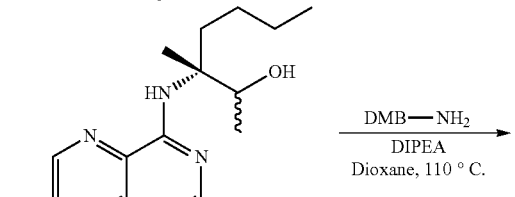
94k — DMB—NH₂, DIPEA, Dioxane, 110° C. →
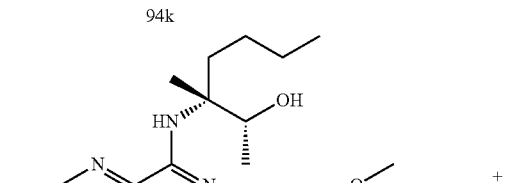
+
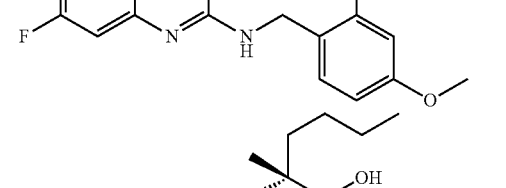
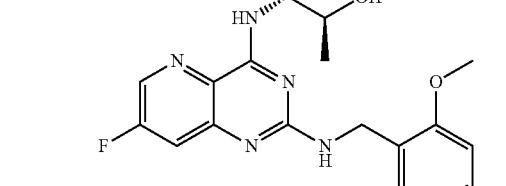
94m — TFA →
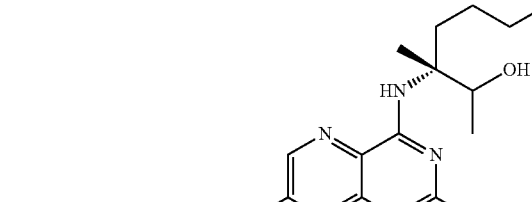
94
Synthesis of (R)-3-methyl-5-phenyl-5,6-dihydro-2H-1,4-oxazin-2-one (94c) and 3-methyl-5-phenyl-3,6-dihydro-2H-1,4-oxazin-2-one (94d). To a mixture of (R)-(−)-2-phenylglycinol 94a, (Sigma-Aldrich, 98%, 99% ee, 3.6296 g, 172.25 mmol) and molecular sieves (86.03 g) in 2,2,2-trifluoroethanol (500 mL) was added ethyl pyruvate 94b (19.2 mL, 172.29 mmol) and the resulting mixture heated to reflux temperature. After 24 h, the mixture was cooled to rt, filtered through a pad of Celite, and washed with EtOAc (50 mL). The orange filtrate and the EtOAc washes were separated into two flasks and each was concentrated under reduced pressure. Each of the resulting residues was subjected to silica gel chromatography eluting with 0-40% EtOAc in hexanes. Product fractions from the two chromatography's were combined, concentrated under reduced pressure, and dried in vacuo to provide compound 94c as well as the later eluting compound 94d.

Compound 94c: $^1$H NMR (400 MHz, Chloroform-d) δ 7.45-7.38 (m, 2H), 7.38-7.32 (m, 3H), 4.85 (ddd, J=10.9, 4.6, 2.4 Hz, 1H), 4.57 (dd, J=11.6, 4.5 Hz, 1H), 4.26 (dd, J=11.6, 10.9 Hz, 1H), 2.41 (d, J=2.4 Hz, 3H). LCMS-ESI$^+$ (m/z): [M+H]$^+$ calculated for $C_{11}H_{12}NO_2$: 190.09; found: 189.92; $t_R$=0.88 min on LC/MS Method A.

Compound 94d: $^1$H NMR (400 MHz, Chloroform-d) δ 7.81-7.71 (m, 2H), 7.55-7.41 (m, 3H), 5.47 (dd, J=16.0, 1.2 Hz, 1H), 5.25 (dd, J=16.0, 2.8 Hz, 1H), 4.31 (qdd, J=7.1, 3.0, 1.1 Hz, 1H), 1.72 (d, J=7.3 Hz, 3H). LCMS-ESI$^+$ (m/z): [M+H]$^+$ calculated for $C_{11}H_{12}NO_2$: 190.09; found: 189.94; $t_R$=0.83 min on LC/MS Method A.

Synthesis of (3R,5R)-3-butyl-3-methyl-5-phenylmorpholin-2-one (94e). A solution of compound 94c (14.84 g, 78.43 mmol) in THF (500 mL) was stirred at −78° C. bath under argon and boron trifluoride diethyl etherate (20.5 mL, 161.11 mmol) was added slowly over 30 min. The reaction mixture was allowed to stir at −78° C. for 1.5 h. 2M butylmagnesium chloride solution 2.0 M in THF (83.0 mL) was added slowly over ~30 min. and the reaction mixture was allowed to stir at −78° C. for 2h before addition of saturated ammonium chloride (300 mL) followed by warming to rt. The mixture was diluted with water (200 mL) and extracted with EtOAc (300 mL×3). The organic extracts were washed with water (500 mL×3), brine (300 mL), combined, dried (Na$_2$SO$_4$), and concentrated under reduced pressure. After the residue was dissolved in DCM (150 mL, heating), the insoluble material was removed by filtration. The filtrate was concentrated under reduced pressure to a small volume, and was subjected to silica gel chromatography eluting eluting with 0-20% EtOAc in hexanes to provide compound 94e. LCMS-ESI$^+$ (m/z): [M+H]$^+$ calculated for $C_{15}H_{22}NO_2$: 248.17; found: 248.02; $t_R$=1.07 min on LC/MS Method A.

Synthesis of (R)-2-(((R)-2-hydroxy-1-phenylethyl)amino)-2-methylhexan-1-ol (94f). To a stirred solution of compound 94e (14.01 g, 56.64 mmol) in THF (100 mL) at 0° C. was added 2.0 M LiBH$_4$ in THF (57 mL, 114 mmol). The solution was stirred at rt for 2 h, cooled with an ice bath and quenched with water (500 mL). The product was extracted with EtOAc (300 mL×3) and the extracts were washed with water (500 mL) and brine (100 mL). The combined extracts were dried (Na$_2$SO$_4$) and concentrated under reduced pressure to obtain 94f LCMS-ESI$^+$ (m/z): [M+H]$^+$ calculated for $C_{15}H_{26}NO_2$: 252.20; found: 252.05; $t_R$=0.68 min on LC/MS Method A.

Synthesis of (R)-2-amino-2-methylhexan-1-ol hydrochloride (94g). To a mixture of compound 94f (14.24 g, 56.65 mmol) and 20% Pd(OH)$_2$ on carbon (2.847 g) in EtOH (210 mL) was added 4 N HCl in dioxane (21.5 mL, 86.0 mmol) The resulting mixture was purged with H$_2$ gas (3 times) and then stirred under H$_2$ atmosphere at 70° C. for 8 h. The reaction mixture was allowed to cool and additional 20% Pd(OH)$_2$ on carbon (0.71 g) was added. The resulting mixture was purged with H$_2$ gas (3 times) and then stirred under H$_2$ atmosphere at 70° C. for 2 h. The reaction mixture was cooled and filtered through a Celite pad and the removed solids washed with EtOH (50 mL). The filtrate and EtOH washings were combined and concentrated under reduced pressure. The residue was co-evaporated with DCM (100 mL×3) and dried under vacuum to give compound 94g. The residue was triturated with DCM (50 mL) and toluene (50 mL) and then concentrated under reduced pressure. The residue was co-evaporated with toluene (50 mL×1) and dried under vacuum at 40° C. for 1 h, and rt overnight to obtain compound 94g as its HCl salt. LCMS-ESI$^+$ (m/z): [M+H]$^+$ calculated for $C_7H_{18}NO$: 132.14; found: 131.90; $t_R$=0.42 min on LC/MS Method A.

Synthesis of (R)-tert-butyl (1-hydroxy-2-methylhexan-2-yl)carbamate (94h). To a solution of 94g (3.1403 g, 16.01 mmol) in methanol (7 mL) and water (45 mL) was added sodium bicarbonate (4.05 g, 48.21 mmol) and di-tert-butyl dicarbonate (Boc$_2$O, 4.25 g, 19.47 mmol). The resulting mixture was stirred at rt for 3 h and then additional sodium bicarbonate (0.68 g, 8.095 mmol) and di-tert-butyl dicarbonate (1.752 g, 8.028 mmol) were added. The mixture was stirred for 48 h and then additional sodium bicarbonate (0.808 g, 9.618 mmol) and di-tert-butyl dicarbonate (1.92 g, 8.797 mmol) were added. The reaction mixture was stirred for 4 h, diluted with water (100 mL), and extracted with EtOAc (100 mL×2). The extracts were washed with water (100 mL), dried over MgSO$_4$, filtered and then concentrated under reduced pressure. The residue was subjected to silica gel chromatography eluting with 0-40% EtOAc in hexanes to obtain compound 94h LCMS-ESI$^+$ (m/z): [M+H]$^+$ calculated for $C_{12}H_{26}NO_3$: 232.19; found: 231.65; $t_R$=1.08 min on LC/MS Method A.

Synthesis of (R)-tert-butyl (2-methyl-1-oxohexan-2-yl)carbamate (94i). To a solution of compound 94h (446.7 mg, 1.931 mmol) in DCM (15 mL) was added Dess-Martin Periodinane (1230.6 mg, 2.901 mmol) and the resulting mixture was stirred for 3 h. The reaction mixture was filtered through a pad of Celite, and the filtrate was then washed with saturated aqueous Na$_2$S$_2$O$_3$ (30 mL) followed by water (30 mL×2). The aqueous fractions were back extracted with DCM (30 mL), and all the organic fractions were then combined, dried over MgSO$_4$, filtered and concentrated in vacuo. The resulting residue was subjected to silica gel chromatography eluting with 0-30% EtOAc in hexanes to obtain compound 94i. LCMS-ESI$^+$ (m/z): [M+H−C$_4$H$_8$]$^+$ calculated for $C_8H_{16}NO_3$: 174.11; found: 173.77; $t_R$=1.17 min on LC/MS Method A.

Synthesis of tert-butyl ((3R)-2-hydroxy-3-methylheptan-3-yl)carbamate (94j). To a solution of 94i (322.4 mg, 1.406 mmol) in diethyl ether (5 mL) in an ice-NaCl bath was added 1.6 M MeLi in diethyl ether (3.6 mL, 5.76 mmol) dropwise over 2 min. After 30 min, the reaction mixture was quenched with saturated aqueous ammonium chloride solution (20 mL). The two phases were separated and the aqueous fraction was extracted with DCM (30 mL). The organic fractions were washed with water (30 mL), combined, dried over MgSO$_4$, filtered and then concentrated in vacuo. The residue was then subjected to silica gel chromatography eluting with 0-40% EtOAc in hexanes to obtain compound 94j. LCMS-ESI$^+$ (m/z): [M+H]$^+$ calculated for $C_{13}H_{28}NO_3$: 246.21; found: 245.70; $t_R$=1.14 min. and $t_R$=1.16 min on LC/MS Method A.

Synthesis of (3R)-3-((2-chloro-7-fluoropyrido[3,2-d]pyrimidin-4-yl)amino)-3-methylheptan-2-ol (94k). Compound 94j (119.8 mg, 0.488 mmol) was dissolved in 4M HCl in dioxane (3 mL) and stirred at rt for 1 h. The reaction mixture was concentrated in vacuo and the residue was then treated with THF (10.5 mL) followed by 2,4-dichloro-7-fluoropyrido[3,2-d]pyrimidine 84E (110.9 mg, 0.508 mmol) and N,N-diisopropylethylamine (0.36 mL, 2.067 mmol). The mixture was heated in a 80° C. bath for 3 h. The reaction mixture was allowed to cool to rt, concentrated in vacuo and the residue subjected to silica gel chromatography eluting with 0-100% EtOAc in hexanes to obtain compound 94k as a mixture of two diastereomers (~2:3 ratio). $^1$H NMR (400 MHz, Chloroform-d) δ 8.55 (dd, J=2.6, 1.2 Hz, 1H), 7.66 (dd, J=8.8, 2.6 Hz, 1H), 7.35 (d, J=10.9 Hz, 1H), 5.29 (br, 1H), 3.97 (q, J=6.1 Hz, 0.4H), 3.91 (q, J=6.4 Hz, 0.6H), 2.09 (ddd, J=13.8, 12.3, 4.4 Hz, 0.6H), 2.03-1.88 (m, 1H), 1.67 (dt, J=14.2, 7.0 Hz, 0.4H), 1.51 (s, 1.2H), 1.43 (s, 1.8H), 1.49-1.136 (m, 4H), 1.22 (d, J=6.5 Hz, 1.8H), 1.20 (d, J=6.5 Hz, 1.2H), 0.99-0.91 (m, 1.2H), 0.88 (t, J=7.3 Hz, 1.8H). $^{19}$F NMR (376 MHz, Chloroform-d) δ −117.38 (t, J=8.9 Hz). LCMS-ESI$^+$ (m/z): [M+H]$^+$ calculated for C$_{15}$H$_{21}$ClFN$_4$O: 327.14; found: 327.11; $t_R$=1.23 min on LC/MS Method A.

Synthesis of (2R,3R)-3-((2-((2,4-dimethoxybenzyl)amino)-7-fluoropyrido[3,2-d]pyrimidin-4-yl)amino)-3-methylheptan-2-ol and (2S,3R)-3-((2-((2,4-dimethoxybenzyl)amino)-7-fluoropyrido[3,2-d]pyrimidin-4-yl)amino)-3-methylheptan-2-ol (94l and 94m). To a solution of compound 94k (128.5 mg, 0.416 mmol) in dioxane (5 mL) was added N,N-diisopropylethylamine (0.22 mL, 1.263 mmol) and 2,4-dimethoxybenzylamine (0.16 mL, 1.065 mmol) and the resulting mixture was refluxed in a 110° C. bath for 20 h. The reaction mixture was allowed to cool to rt, diluted with EtOAc (30 mL) and then washed with water (30 mL×2). The aqueous fractions were then back extracted with EtOAc (30 mL). The organic fractions were combined, dried over MgSO$_4$, and concentrated under reduced pressure. The residue was then subjected to silica gel chromatography eluting with 0-100% EtOAc in hexanes to obtain a mixture of compounds 94l and 94m. The compound mixture was further subjected to preparative chiral SFC (SFC IC-5 um-4.6×100 mm, 30% EtOH-ammonia, flow rate=3 mL/min) to obtain, compound 94l, eluting first, and compound 94m, eluting second.

Compound 94l: $^1$H NMR (400 MHz, Chloroform-d) δ 8.14 (d, J=2.5 Hz, 1H), 7.32 (s, 1H), 7.28 (d, J=8.3 Hz, 1H), 6.46 (d, J=2.4 Hz, 1H), 6.42 (dd, J=8.3, 2.4 Hz, 1H), 4.55 (d, J=5.7 Hz, 2H), 3.84 (s, 3H), 3.79 (s, 3H), 4.0-3.7 (m, 1H), 1.97 (s, 1H), 1.59 (s, 2H), 1.47 (s, 3H), 1.36 (d, J=5.2 Hz, 4H), 1.17 (d, J=6.4 Hz, 3H), 1.00-0.89 (m, 3H). $^{19}$F NMR (376 MHz, Chloroform-d) δ −121.41. LCMS-ESI$^+$ (m/z): [M+H]$^+$ calculated for C$_{24}$H$_{33}$FN$_5$O$_3$: 458.26; found: 458.17; $t_R$=1.19 min on LC/MS Method A.

Compound 94m: $^1$H NMR (400 MHz, Chloroform-d) δ 8.14 (d, J=2.6 Hz, 1H), 7.33 (s, 1H), 7.28 (d, J=8.3 Hz, 1H), 6.46 (d, J=2.3 Hz, 1H), 6.42 (dd, J=8.3, 2.4 Hz, 1H), 4.55 (d, J=5.8 Hz, 2H), 3.84 (d, J=1.1 Hz, 3H), 3.79 (s, 3H), 3.9-3.6 (m, 1H), 2.09 (d, J=14.1 Hz, 1H), 1.87 (s, 1H), 1.57 (s, 1H), 1.43 (m, 1H), 1.37 (s, 3H), 1.30 (m, 2H), 1.20 (d, J=6.4 Hz, 3H), 0.87 (t, J=7.2 Hz, 3H). $^{19}$F NMR (376 MHz, Chloroform-d) δ −121.40. LCMS-ESI$^+$ (m/z): [M+H]$^+$ calculated for C$_{24}$H$_{33}$FN$_5$O$_3$: 458.26; found: 458.16; $t_R$=1.22 min on LC/MS Method A.

Synthesis of (3R)-3-((2-amino-7-fluoropyrido[3,2-d]pyrimidin-4-yl)amino)-3-methylheptan-2-ol (94). Compound 94m (9.0 mg, 20.5 umol) was dissolved in TFA (1 mL) and stirred at rt for 1 h. The reaction mixture was carefully concentrated under reduced pressure to dryness, and the residue was then triturated with 50% aq. methanol, and filtered through a Celite-membrane filter. The filtrate was subjected to preparative HPLC (Gemini 10u C18 110A, AXIA; 10% aq. acetonitrile-70% aq. acetonitrile with 0.1% TFA, over 20 min. gradient). The product fractions were combined, concentrated under reduced pressure, co-evaporated with methanol (10 mL×3), and dried under vacuum to obtain compound 94 as its TFA salt. $^1$H NMR (400 MHz, Methanol-d4) δ 8.54 (d, J=2.4 Hz, 1H), 8.31 (s, 1H), 7.62 (dd, J=8.8, 2.5 Hz, 1H), 4.39-4.29 (m, 1H), 2.29 (dt, J=15.7, 6.7 Hz, 1H), 1.84 (dt, J=16.0, 6.9 Hz, 1H), 1.55 (s, 3H), 1.44-1.30 (m, 4H), 1.23 (d, J=6.5 Hz, 3H), 0.96-0.84 (m, 3H). $^{19}$F NMR (376 MHz, Methanol-d$_4$) δ −77.53 (s, 3F), −118.19 (dd, J=8.8, 4.0 Hz, 1F). LCMS-ESI$^+$ (m/z): [M+H]$^+$ calculated for C$_{15}$H$_{23}$FN$_5$O: 308.19; found: 308.12; $t_R$=1.46 min on LC/MS Method A.

Example 95

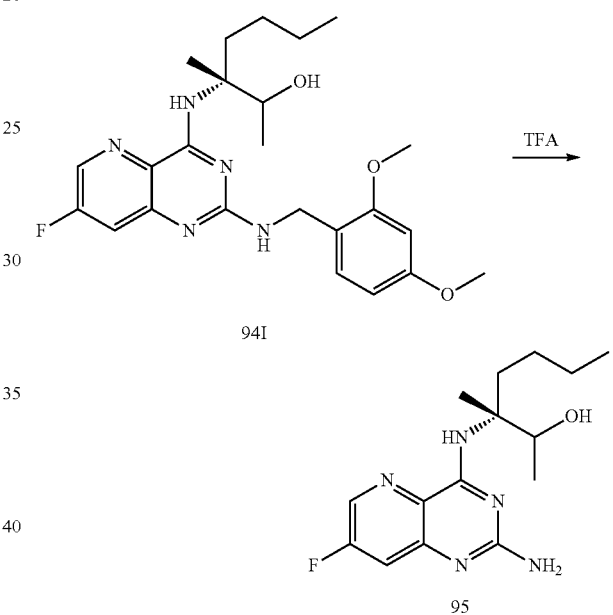

Synthesis of (2R,3R)-3-((2-amino-7-fluoropyrido[3,2-d]pyrimidin-4-yl)amino)-3-methylheptan-2-ol (95). Compound 94l (10.3 mg, 23.4 umol) was dissolved in TFA (1 mL) and stirred at rt for 1 h. After the reaction mixture was carefully concentrated to dryness in vacuo, the residue was triturated with 50% aq. methanol and filtered through Celite-membrane filter. The filtrate was subjected to preparative HPLC (Gemini 10u C18 110A, AXIA; 10% aq. acetonitrile-70% aq. acetonitrile with 0.1% TFA, over 20 min. gradient). The product fractions were combined, concentrated under reduced pressure, co-evaporated with methanol (10 mL×3), and dried under vacuum overnight to obtain compound 95 as its TFA salt. $^1$H NMR (400 MHz, Methanol-d$_4$) δ 8.53 (d, J=2.4 Hz, 1H), 8.41 (s, 1H), 7.62 (dd, J=8.7, 2.5 Hz, 1H), 4.24 (q, J=6.4 Hz, 1H), 2.14 (ddd, J=15.0, 11.3, 4.2 Hz, 1H), 2.04 (dq, J=14.3, 5.2 Hz, 1H), 1.48 (s, 3H), 1.39-1.24 (m, 4H), 1.22 (d, J=6.4 Hz, 3H), 0.89 (t, J=7.0 Hz, 3H). $^{19}$F NMR (376 MHz, Methanol-d$_4$) δ −77.52 (s, 3F), −118.31 (dd, J=8.7, 4.1 Hz, 1F). LCMS-ESI$^+$ (m/z): [M+H]$^+$ calculated for C$_{15}$H$_{23}$FN$_5$O: 308.19; found: 308.12; $t_R$=1.47 min on LC/MS Method A.

Example 96

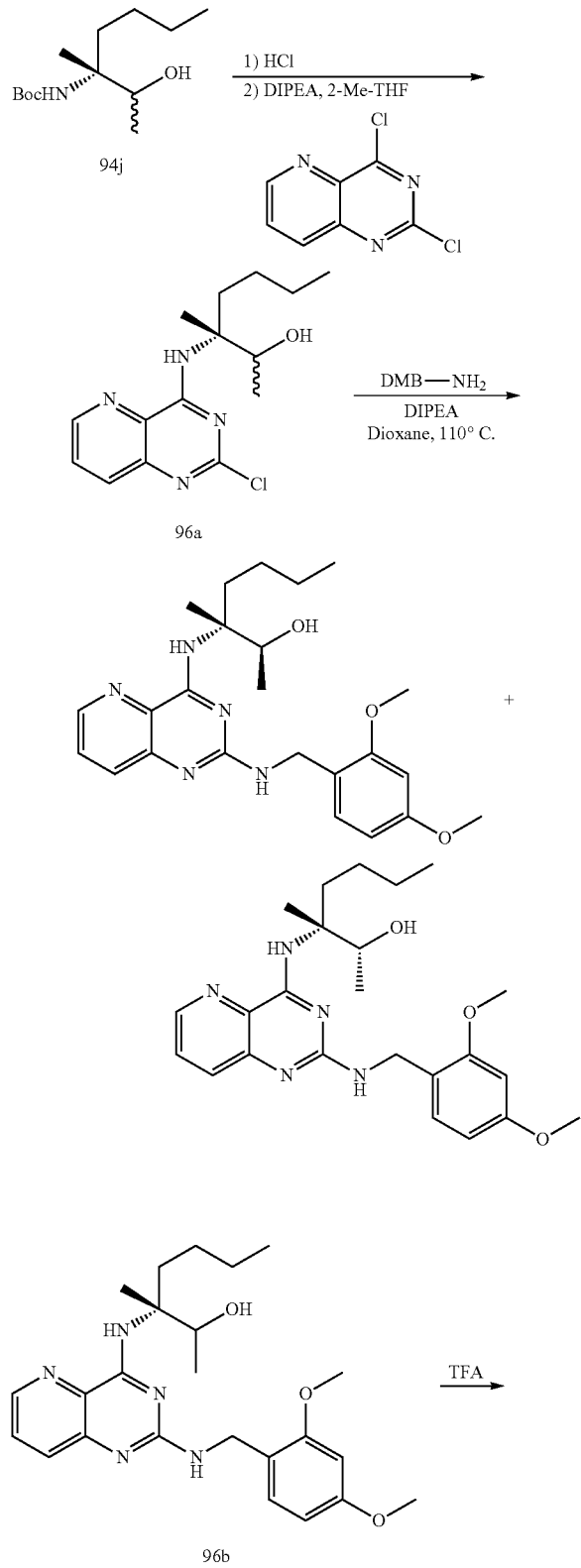

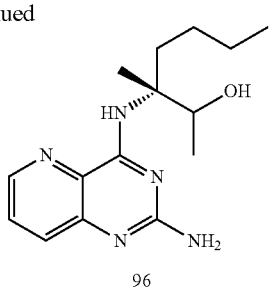

Synthesis of (3R)-3-((2-chloropyrido[3,2-d]pyrimidin-4-yl)amino)-3-methylheptan-2-ol (96a). Compound 94j (195.7 mg, 0.798 mmol) was dissolved in 4M HCl in dioxane (3 mL) and stirred at rt for 1 h. The reaction mixture was then concentrated in vacuo. The residue was treated with 2-methyltetrahydrofuran (5 mL), 2,4-dichloropyrido[3,2-d]pyrimidine (160 mg, 0.525 mmol) and N,N-diisopropylethylamine (0.57 mL, 3.272 mmol) and heated with an 80° C. bath for 3 h. The reaction mixture was cooled to rt, concentrated under reduced pressure and the residue was subjected to silica gel chromatography eluting with 0-100% EtOAc in hexanes to obtain compound 96a as a mixture of two diastereomers (~2:3 ratio). LCMS-ESI$^+$ (m/z): [M+H]$^+$ calculated for $C_{15}H_{22}ClN_4O$: 309.15; found: 309.08; TR=1.41 min on LC/MS Method A.

Synthesis of (2S,3R)-3-((2-((2,4-dimethoxybenzyl)amino)pyrido[3,2-d]pyrimidin-4-yl)amino)-3-methylheptan-2-ol and (2R,3R)-3-((2-((2,4-dimethoxybenzyl)amino)pyrido[3,2-d]pyrimidin-4-yl)amino)-3-methylheptan-2-ol (96b and 96c). To a solution of compound 96a (132.6 mg, 0.429 mmol) in dioxane (5 mL) was added N,N-diisopropylethylamine (0.23 mL, 1.320 mmol) and 2,4-dimethoxybenzylamine (0.16 mL, 1.065 mmol), and the resulting mixture refluxed at 110° C. for 20 h. The reaction mixture was diluted with EtOAc (30 mL) and washed with water (30 mL×2). The aqueous fractions were back extracted with EtOAc (50 mL). The organic fractions were combined, dried over MgSO$_4$, filtered and then concentrated under reduced pressure. The residue was subjected to silica gel chromatography eluting with 0-100% EtOAc in hexanes to obtain a mixture of compounds 96b and 96c. The mixture was further subjected to chiral SFC (SFC IC-5 um-4.6×100 mm, 40% EtOH-ammonia, flow rate=3 mL/min) to obtain compound 96b, eluting first, and compound 96c, eluting second.

Compound 96b: $^1$H NMR (400 MHz, Chloroform-d) δ 8.28 (dd, J=4.2, 1.5 Hz, 1H), 7.69 (d, J=8.4 Hz, 1H), 7.43 (dd, J=8.5, 4.3 Hz, 1H), 7.29 (d, J=8.2 Hz, 1H), 7.19 (s, 1H), 6.46 (d, J=2.4 Hz, 1H), 6.42 (dd, J=8.2, 2.4 Hz, 1H), 5.3 (br, 1H), 4.56 (d, J=5.7 Hz, 2H), 3.86 (m, 1H), 3.83 (s, 3H), 3.79 (s, 3H), 1.98 (m, 1H), 1.66-1.53 (m, 1H), 1.48 (s, 3H), 1.44-1.30 (m, 4H), 1.17 (d, J=6.4 Hz, 3H), 0.98-0.89 (m, 3H). LCMS-ESI$^+$ (m/z): [M+H]$^+$ calculated for $C_{24}H_{34}N_5O_3$: 440.27; found: 440.25; TR=0.99 min on LC/MS Method A.

Compound 96c: $^1$H NMR (400 MHz, Chloroform-d) δ 8.29 (dd, J=4.2, 1.5 Hz, 1H), 7.70 (d, J=8.4 Hz, 1H), 7.43 (dd, J=8.5, 4.2 Hz, 1H), 7.30 (d, J=8.2 Hz, 1H), 7.16 (s, 1H), 6.46 (d, J=2.3 Hz, 1H), 6.42 (dd, J=8.2, 2.4 Hz, 1H), 5.25 (s, 1H), 4.56 (d, J=5.7 Hz, 2H), 3.84 (s, 3H), 3.79 (s, 3H), 3.86-3.75 (m, 1H), 2.13 (t, J=13.0 Hz, 1H), 1.93-1.79 (m, 1H), 1.52-1.40 (m, 1H), 1.38 (s, 3H), 1.35-1.15 (m, 3H), 1.20 (d, J=6.4 Hz, 3H), 0.87 (t, J=7.2 Hz, 3H). LCMS-ESI$^+$ (m/z): [M+H]$^+$ calculated for $C_{24}H_{34}N_5O_3$: 440.27; found: 440.25; $t_R$=1.00 min on LC/MS Method A.

Synthesis of (3R)-3-((2-aminopyrido[3,2-d]pyrimidin-4-yl)amino)-3-methylheptan-2-ol (96). Compound 96b (8.7 mg, 19.79 umol) was dissolved in TFA (1 mL) and stirred at rt for 1 h. The reaction mixture was concentrated under reduced pressure to dryness and then co-evaporated with methanol (10 mL). The resulting residue was dissolved in methanol (1 mL) and concentrated ammonium hydroxide (0.1 mL). The reaction mixture was stirred for 10 min. and then concentrated under reduced pressure to dryness and co-evaporated with methanol (10 mL). The residue was triturated with 50% aq. MeOH (10 mL) and filtered through a Celite-membrane filter. The filtrate was subjected to preparative HPLC (Gemini 10u C18 110A, AXIA; 10% aq. acetonitrile-70% aq. acetonitrile with 0.1% TFA, over 20 min. gradient). The product fractions were combined, concentrated in vacuo, co-evaporated with methanol (10 mL×3), and dried under high-vacuum to provide compound 96 as its TFA salt. $^1$H NMR (400 MHz, Methanol-d4) δ 8.61 (dd, J=4.4, 1.5 Hz, 1H), 7.82 (dd, J=8.5, 1.5 Hz, 1H), 7.76 (dd, J=8.5, 4.4 Hz, 1H), 4.36 (q, J=6.5 Hz, 1H), 2.30 (dt, J=16.3, 6.8 Hz, 1H), 1.91-1.78 (m, 1H), 1.56 (s, 3H), 1.43-1.30 (m, 4H), 1.23 (d, J=6.5 Hz, 3H), 0.98-0.85 (m, 3H). LCMS-ESI$^+$ (m/z): [M+H]$^+$ calculated for $C_{15}H_{24}N_5O$: 290.20; found: 290.11; $t_R$=0.74 min on LC/MS Method A.

Example 97

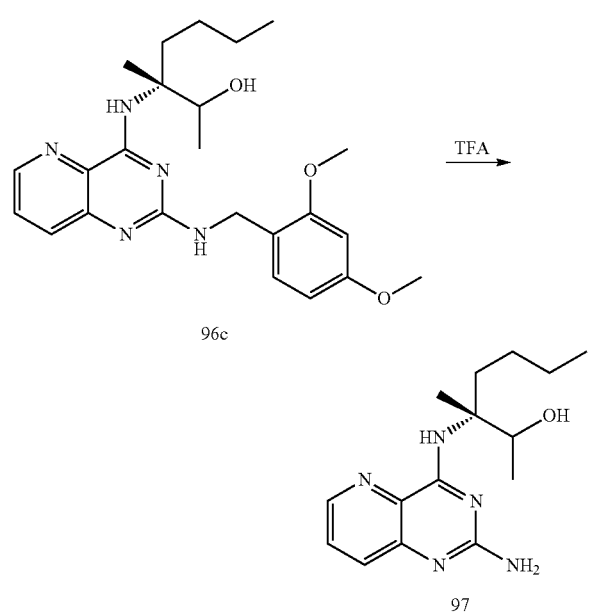

Synthesis of (3R)-3-((2-aminopyrido[3,2-d]pyrimidin-4-yl)amino)-3-methylheptan-2-ol (97). Compound 96c (9.0 mg, 20.5 umol) was dissolved in TFA (1 mL) and stirred at rt for 1 h. The reaction mixture was carefully concentrated under reduced pressure to dryness and co-evaporated with methanol (10 mL). The residue was dissolved in methanol (1 mL) and concentrated ammonium hydroxide (0.1 mL). The reaction mixture was stirred for 10 min. and then concentrated under reduced pressure to dryness and then co-evaporated with methanol (10 mL). The resulting residue was triturated with 50% aq. methanol and filtered through a Celite-membrane filter. The filtrate was then subjected to preparative HPLC (Gemini 10u C18 110A, AXIA; 10% aq. acetonitrile-70% aq. acetonitrile with 0.10% TFA, over 20 min. gradient). The product fractions were combined, concentrated under reduced pressure, co-evaporated with methanol (10 mL×3), and dried under high-vacuum to provide compound 97 as its TFA salt. $^1$H NMR (400 MHz, Methanol-d$_4$) δ 8.61 (dd, J=4.3, 1.3 Hz, 1H), 7.82 (dd, J=8.5, 1.4 Hz, 1H), 7.76 (dd, J=8.5, 4.3 Hz, 1H), 4.26 (q, J=6.4 Hz, 1H), 2.11 (dddd, J=24.9, 19.8, 12.8, 7.0 Hz, 2H), 1.49 (s, 3H), 1.40-1.24 (m, 4H), 1.22 (d, J=6.4 Hz, 3H), 0.89 (t, J=6.9 Hz, 3H). LCMS-ESI$^+$ (m/z): [M+H]$^+$ calculated for $C_{15}H_{24}N_5O$: 290.20; found: 290.10; $t_R$=0.74 min on LC/MS Method A.

Example 98

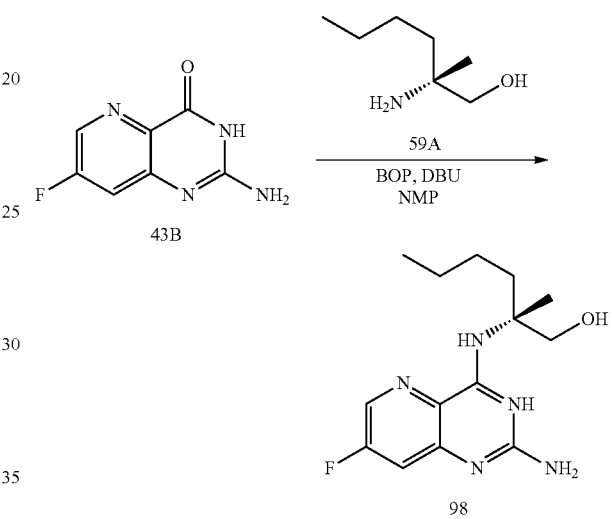

Synthesis of (R)-2-((2-amino-7-fluoropyrido[3,2-d]pyrimidin-4-yl)amino)-2-methylhexan-1-ol (98). Intermediate 43B (101 mg, 0.56 mmol) and (R)-a-Me-norleucinol 59A (109 mg, 0.83 mmol) were added to NMP (5.5 mL) followed by BOP reagent (0.36 g, 0.83 mmol) and DBU (0.25 mL, 1.67 mmol). The reaction mixture was stirred at rt for 16 h, and then diluted with EtOH (2 mL) and water (2 mL). The resulting mixture was subjected directly to HPLC purification (Gemini 10u C18 110A, AXIA; 10% aq. acetonitrile-80% aq. acetonitrile with 0.1% TFA, over 20 min. gradient) to provide, after collection of product fractions and removal of solvent in vacuo, compound 98 as a TFA salt. $^1$H NMR (400 MHz, Methanol-d4) δ 8.55 (d, J=2.4 Hz, 1H), 8.22 (s, 1H), 7.64 (dd, J=8.7, 2.5 Hz, 1H), 3.97 (d, J=11.2 Hz, 1H), 3.71 (d, J=11.2 Hz, 1H), 2.09 (m, 1H), 1.92 (m, 1H), 1.54 (s, 3H), 1.40-1.31 (m, 4H), 1.00-0.85 (m, 3H). $^{19}$F NMR (376 MHz, Methanol-d4) δ −77.68, −118.20 (d, J=8.8 Hz). LCMS-ESI$^+$ (m/z): [M+H]$^+$ calculated for $C_{14}H_{20}FN_5O$: 293.34; found: 294.1; $t_R$=0.68 min.

Example 99

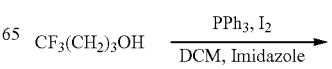

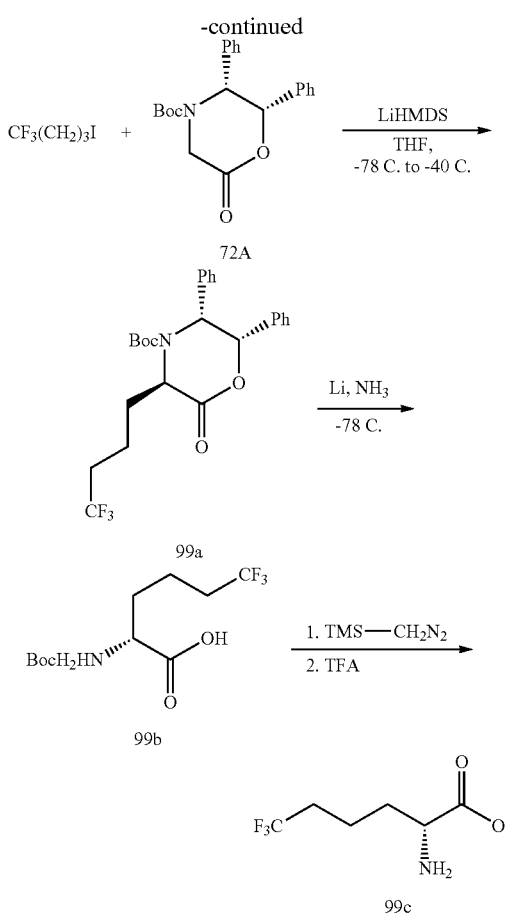

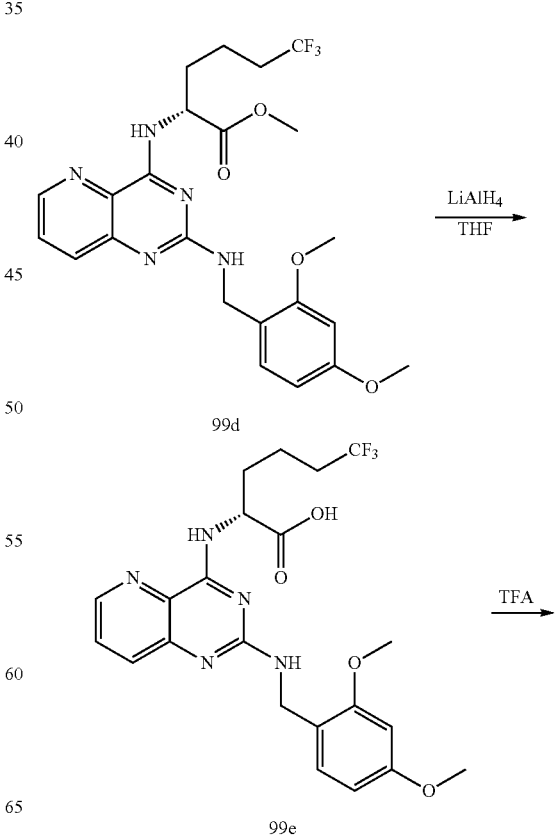

Synthesis of (R)-2-((tert-butoxycarbonyl)amino)-6,6,6-trifluorohexanoic acid (99b). Lithium (granular), (157.24 mg, 22.65 mmol) was cooled in a −40° C. bath. Ammonia gas was slowly condensed via a cold finger into the reaction for 15-20 minutes. After an additional 20 minutes(3R,5R,6S)-tert-butyl 2-oxo-5,6-diphenyl-3-(4,4,4-trifluorobutyl)morpholine-4-carboxylate, 99a (700 mg, 1.51 mmol) in THF (10 mL) and EtOH (0.5 mL) was added. The reaction was allowed to warm to rt, and the liquid ammonia allowed to evaporate with stirring overnight. The resulting residue was treated with THF (50 mL) and water (50 mL) and stirred until all the solids dissolved. A saturated aq. ammonium chloride (50 mL) solution was added followed by 1N NaOH to adjust the pH to basic. The reaction mixture was washed with diethyl ether (100 mL), and the aqueous layer was then pH adjusted with 1N HCl to ~ pH 4. The aq. layer was then extracted with EtOAc (3×50 mL). The combined organics were then washed with ammonium chloride (50 mL), water (50 mL), brine (50 mL), dried over sodium sulfate, filtered and concentrated under reduced pressure to provide 99b.

Synthesis of (R)-methyl 2-amino-6,6,6-trifluorohexanoate (99c). Compound 99b (230 mg, 0.81 mmol) was dissolved in DCM (10 mL) and MeOH (1 mL). A solution of 2M (Trimethylsilyl) Diazomethane, 2M solution in hexanes (0.6 mL, 1.2 mmol) was added dropwise. The reaction was allowed to stir for 20 minutes and then 2 drops of acetic acid were added. The reaction mixture was concentrated under reduced pressure and. the resulting residue treated with DCM (5 mL) and TFA (5 mL). The mixture was stirred for 90 minutes and then concentrated under reduced pressure. The residue was co-evaporated with DCM (20 mL×2) to provide 99c as its TFA salt.

Synthesis of (3R,5R,6S)-tert-butyl 2-oxo-5,6-diphenyl-3-(4,4,4-trifluorobutyl)morpholine-4-carboxylate (99a). Imidazole (1.75 g, 0.03 mol), and triphenylphosphine, 99+% (6.08 g, 0.02 mol) were stirred in DCM (100 mL) under argon and cooled to 0° C. for 10 minutes. Iodine (5.94 g, 0.02 mol) was added over 5 minutes and the reaction was stirred at 0° C. for 20 minutes. A solution of 4,4,4-trifluoro-1-butanol, 97% (2.48 mL, 0.02 mol) was slowly added. The reaction was stirred and allowed to warm to rt. After 16 h, pentane (200 mL) was added and the resulting solids filtered off. Solvent was partially removed under reduced pressure, and then additional cold pentane (50 mL) was added. The solids were filtered off and the eluent concentrated under reduced pressure to afford 1,1,1-trifluoro-4-iodobutane.

(2S,3R)-tert-butyl 6-oxo-2,3-diphenylmorpholine-4-carboxylate, 72A (1 g, 2.83 mmol) and 1,1,1-trifluoro-4-iodobutane (2.02 g, 8.49 mmol) were dissolved in THF (24 mL) and HMPA (2.5 mL), and the mixture was then cooled to −78° C. under argon. 1M lithium hexamethyldisilazide (1.0M THF in THF, 4.24 mL) was added and the reaction transferred to a −40° C. bath. The cold bath was recharged with dry ice and the reaction left to warm to ambient temperature with stirring overnight. The reaction was quenched with EtOAc (25 mL) and poured into a mixture of EtOAc (100 mL) and saturated aqueous solution of NH₄Cl (50 mL). The organic layer was separated and washed with water (100 mL), brine (100 mL), dried over Na₂SO₄, filtered and concentrated under reduced pressure. The residue was subjected to silica gel chromatography eluting with hexanes-EtOAc to provide (3R,5R,6S)-tert-butyl 2-oxo-5,6-diphenyl-3-(4,4,4-trifluorobutyl)morpholine-4-carboxylate 99a.

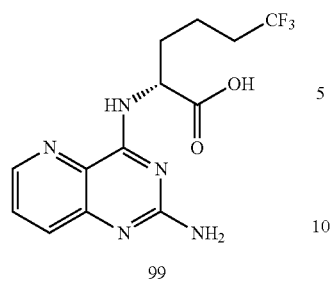

99

Synthesis of (R)-methyl 2-((2-((2,4-dimethoxybenzyl)amino)pyrido[3,2-d]pyrimidin-4-yl)amino)-6,6,6-trifluorohexanoate (99d). 99d was synthesized in a similar fashion to compound 63B, instead replacing 63A with (R)-methyl 2-amino-6,6,6-trifluorohexanoate TFA salt 99c (100 mg, 0.75 mmol), to obtain 99d. MS (m/z) 494.2 [M+H]$^+$; $t_R$=0.95 min.

Synthesis of (R)-2-((2-((2,4-dimethoxybenzyl)amino)pyrido[3,2-d]pyrimidin-4-yl)amino)-6,6,6-trifluorohexan-1-ol (99e). Compound 99d (100 mg, 0.2 mmol) was treated with THF (15 mL) and cooled to 0° C. under argon. To this solution was added 1M LiAlH$_4$ in THF (0.61 mL, 0.61 mmol) and the reaction mixture stirred at 0° C. Upon completion, the reaction was diluted in EtOAc/H$_2$O and extracted with EtOAc (50 mL×3). The combined organics were then washed with aq. ammonium chloride (50 mL), water (50 mL), brine (50 mL), dried over Na$_2$SO$_4$, filtered and concentrated under reduced pressure. The crude residue was subjected to silica gel chromatography eluting with hexanes-EtOAc to afford 99e. LCMS (m/z) 466.1 [M+H]$^+$. $t_R$ 1.14 min Synthesis of (R)-2-((2-aminopyrido[3,2-d]pyrimidin-4-yl)amino)-6,6,6-trifluorohexan-1-ol (99). Compound 99e (75 mg, 0.16 mmol) was dissolved in TFA (5 mL) and allowed to stir for 1 h. The TFA was removed under reduced pressure and MeOH (10 mL) was added. The mixture was stirred for 1 h and then filtered. The eluent was removed in vacuo and the residue was treated with MeOH (10 mL). The mixture was stirred for 16 h and then concentrated under reduced pressure. The residue was co-evaporated with MeOH (10 mL, ×3) and the resulting residue dried under high vacuum to afford compound 99 as its TFA salt. $^1$H NMR (400 MHz, Methanol-d4) δ 8.65 (dd, J=4.4, 1.4 Hz, 1H), 7.84 (dd, J=8.5, 1.4 Hz, 1H), 7.77 (dd, J=8.5, 4.4 Hz, 1H), 4.56 (ddt, J=10.9, 5.5, 3.1 Hz, 1H), 3.75 (d, J=5.3 Hz, 2H), 2.40-2.07 (m, 2H), 1.94-1.76 (m, 2H), 1.66 (dddd, J=19.0, 16.1, 8.7, 5.9 Hz, 2H). $^{19}$F NMR (376 MHz, Methanol-d$_4$) δ -68.49 (t, J=11.0 Hz), -77.91. LCMS-ESI$^+$ (m/z): [M+H]$^+$ calculated for C$_{13}$H$_{16}$F$_3$N$_5$O: 315.29; found: 316.2; $t_R$=0.82 min.

Example 100

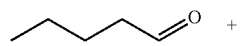 +

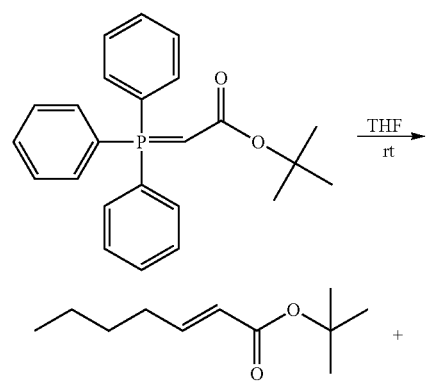

100a

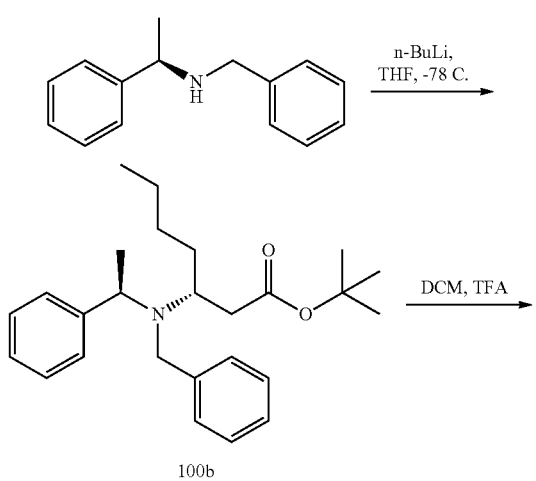

100b

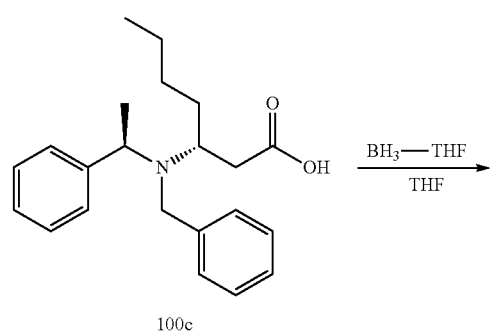

100c

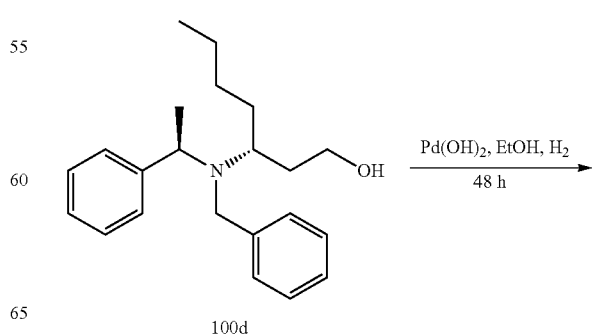

100d

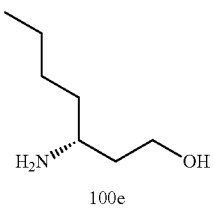

100e

Synthesis of (E)-tert-butyl hept-2-enoate (100a). To a solution of valeraldehyde (2.82 mL, 26.57 mmol) in THF (50 mL) was added (tert-butoxycarbonylmethylene)triphenylphosphorane (10 g, 26.57 mmol) and the reaction mixture stirred for 16 h at rt. The solvents were then removed under reduced pressure, and the residue slurried in diethyl ether and filtered. The filtrate was concentrated in vacuo and the residue subjected to silica gel chromatography eluting with hexanes-EtOAc to give 100a. $^1$H NMR (400 MHz, Methanol-d4) δ 6.85 (dt, J=15.5, 7.0 Hz, 1H), 5.73 (dt, J=15.6, 1.6 Hz, 1H), 2.26-2.11 (m, 2H), 1.52-1.25 (m, 13H), 0.93 (t, J=7.2 Hz, 3H).

Synthesis of (R)-tert-butyl 3-(benzyl((S)-1-phenylethyl)amino)heptanoate (100b). 2.5M Butyllithium (2.5M in Hexanes, 14.33 mL) was added to a stirred solution of (R)-(+)-N-benzyl-alpha-methylbenzylamine (7.99 mL, 38.2 mmol) in THF (100 mL) at −78° C. The reaction mixture was stirred for 30 minutes, and then 100a (4.4 g, 23.88 mmol) in THF (50 mL) was added slowly to the reaction mixture. The reaction mixture was then stirred at −78° C. for 2 h, quenched with sat. aq. NH$_4$Cl solution (100 mL) and allowed to warm to rt. EtOAc (200 mL) and water (100 mL) were added, and the organic layer separated. The aqueous layer was extracted with EtOAc (3×50 mL) and the combined organics were washed with brine (100 mL), dried over Na$_2$SO$_4$, filtered and concentrated in vacuo. The resulting residue was subjected to silica gel chromatography eluting with hexanes-EtOAc to provide 100b. $^1$H NMR (400 MHz, Methanol-d4) δ 7.41 (d, J=7.2 Hz, 2H), 7.36-7.10 (m, 8H), 3.87-3.73 (m, 2H), 3.50 (d, J=15.0 Hz, 1H), 3.24 (tt, J=9.4, 4.2 Hz, 1H), 2.04 (dd, J=14.4, 3.6 Hz, 1H), 1.89 (dd, J=14.4, 9.4 Hz, 1H), 1.57-1.43 (m, 3H), 1.38 (s, 8H), 1.33-1.12 (m, 7H), 0.87 (t, J=7.3 Hz, 3H).

Synthesis of (R)-3-(benzyl((S)-1-phenylethyl)amino)heptanoic acid (100c). (R)-tert-butyl 3-(benzyl((S)-1-phenylethyl)amino)heptanoate 100b (6.4 g, 16.18 mmol) was dissolved in DCM (40 mL) and treated with TFA (20 mL). The reaction mixture was allowed to stir at 40° C. for 24 h and then concentrated under reduced pressure to provide 100c. LCMS (m/z) 340.0 [M+H]$^+$. $t_R$=0.94 min Synthesis of (R)-3-(benzyl((S)-1-phenylethyl)amino)heptan-1-ol (100d). (R)-3-(benzyl((S)-1-phenylethyl)amino)heptanoic acid 100c (5.5 g, 16.2 mmol) was dissolved in THF (100 mL) under argon, and 1M borane-tetrahydrofuran in THF (64.81 mL, 64.81 mmol) was slowly added. The reaction was allowed to stir for several h at rt. MeOH was slowly added to quench the reaction and the mixture was allowed to stir for an additional 20 minutes. A ~2N HCl (aq) (14 mL) solution was added and the mixture concentrated under reduced pressure to afford a white solid. The solid material was suspended in DCM (100 mL) and filtered. The filter cake was rinsed with DCM (25 mL). The mother liquor was concentrated under reduced pressure to afford a light yellow oil which was subjected to silica gel chromatography eluting with DCM-MeOH to afford 100d. MS (m/z) 326.1 [M+H]$^+$; $t_R$=0.82 min Synthesis of (R)-3-aminoheptan-1-ol (100e). (R)-3-(benzyl((S)-1-phenylethyl)amino)heptan-1-ol 100d (0.78 g, 2.4 mmol) was treated with EtOH (25 mL) and 20% Pd(OH)$_2$/C (300 mg, 0.43 mmol). The reaction vessel was purged 3× with H$_2$ gas and then allowed to stir for 2 days under H$_2$. The reaction mixture was filtered and solvents were removed under reduced pressure to afford 100e. $^1$H NMR (400 MHz, Methanol-d4) δ 3.90-3.68 (m, 2H), 3.39-3.27 (m, 1H), 1.98-1.72 (m, 2H), 1.72-1.57 (m, 3H), 1.39 (h, J=4.5, 4.0 Hz, 4H), 1.03-0.86 (m, 3H).

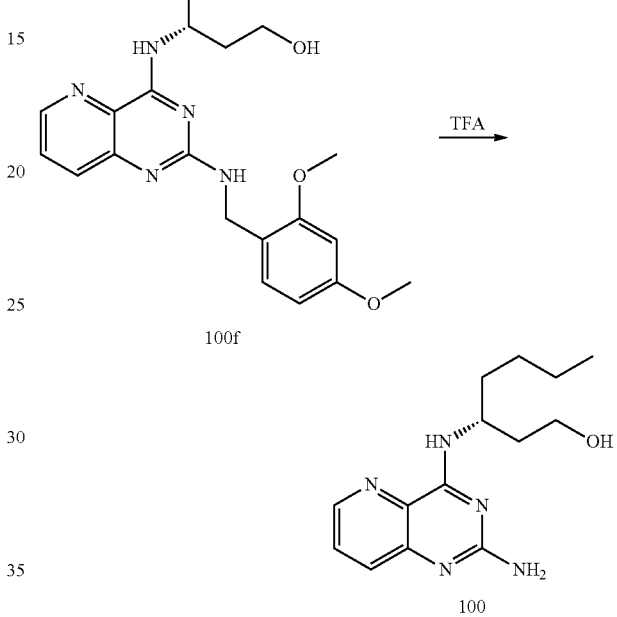

Synthesis of (R)-3-((2-aminopyrido[3,2-d]pyrimidin-4-yl)amino)heptan-1-ol (100). 2,4-dichloropyrido[3,2-d]pyrimidine (100 mg, 0.5 mmol) was reacted with 100e (65.6 mg, 0.5 mmol) followed by 2,4-dimethoxybenzylamine (150.21 μl, 1 mmol) as described for the synthesis of 59B from 59A, to prepare 100f. Compound 100f was then subjected to TFA (3 mL) for 1h as described in the preparation of compound 59 from 59B to afford, 100 as its TFA salt. MS (m/z) 276.1 [M+H]$^+$; $t_R$=0.64 min; $^1$H NMR (400 MHz, Methanol-d4) δ 8.63 (dd, J=4.4, 1.5 Hz, 1H), 7.82 (dd, J=8.5, 1.5 Hz, 1H), 7.76 (dd, J=8.5, 4.4 Hz, 1H), 4.64 (tt, J=7.9, 5.6 Hz, 1H), 3.72-3.59 (m, 2H), 1.99-1.83 (m, 2H), 1.81-1.66 (m, 2H), 1.46-1.29 (m, 4H), 0.97-0.82 (m, 3H). $^{19}$F NMR (376 MHz, Methanol-d4) δ −77.56.

Example 101

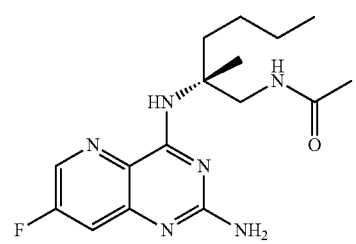

101

Synthesis of (R)—N-(2-((2-amino-7-fluoropyrido[3,2-d]pyrimidin-4-yl)amino)-2-methylhexyl)acetamide (101). Compound 101 was prepared following the procedure described in Example 84, using 2,4-dichloro-7-fluoropyrido[3,2-d]pyrimidine 84E (30 mg, 0.14 mmol) and reacting sequentially with (R)—N-(2-amino-2-methylhexyl)acetamide hydrochloride 61E (28.72 mg, 0.14 mmol) followed by 2,4-dimethoxybenzylamine (82.69 μl, 0.55 mmol). The resulting product was then subjected to TFA treatment as described in the preparation of 84 from 84G, to provide 101 as its TFA salt. MS (m/z) 335.2 [M+H]$^+$; $t_R$=0.64 min; $^1$H NMR (400 MHz, Methanol-d4) δ 8.54 (t, J=2.9 Hz, 2H), 7.62 (dd, J=8.8, 2.5 Hz, 1H), 3.99-3.86 (m, 1H), 3.51 (d, J=14.0 Hz, 1H), 2.26-2.05 (m, 1H), 1.95 (s, 4H), 1.54 (s, 3H), 1.45-1.27 (m, 4H), 0.99-0.80 (m, 3H); $^{19}$F NMR (376 MHz, Methanol-d4) δ −78.04, −118.27 (d, J=8.8 Hz).

Example 102

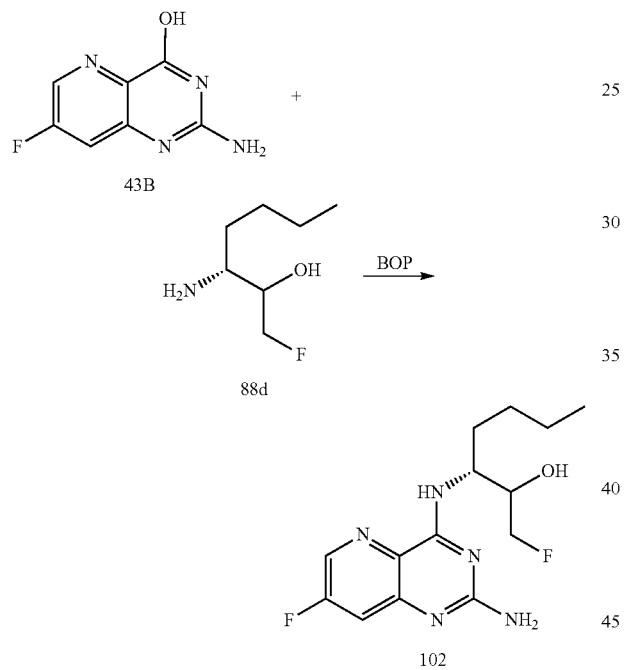

Synthesis of (3R)-3-((2-amino-7-fluoropyrido[3,2-d]pyrimidin-4-yl)amino)-1-fluoroheptan-2-ol (102). A solution of compound 43B (131.5 mg, 0.730 mmol), compound 88d (212.2 mg, 1.415 mmol), and BOP (392.7 mg, 0.888 mmol) in DMF (7 mL) was stirred at rt as DBU (0.33 mL, 2.209 mmol) was added. The reaction mixture was stirred at rt for 17.5 h, diluted with water (7 mL), and then the mixture was filtered. The filtrate was subjected to preparative HPLC (Gemini 10u C18 110A, AXIA; 10% aq. acetonitrile-70% aq. acetonitrile with 0.1% TFA, over 20 min. gradient) and the product fractions were combined, concentrated under reduced pressure to obtain the crude product. The crude product was re-subjected to preparative HPLC (Gemini 10u C18 110A, AXIA; 10% aq. acetonitrile-70% aq. acetonitrile with 0.1% TFA, over 20 min. gradient), and the combined product fractions concentrated under reduced pressure, co-evaporated with methanol (10 mL×4), and dried to obtain compound 102 as its TFA salt. $^1$H NMR (400 MHz, Methanol-d$_4$) δ 8.67 (d, J=9.6 Hz, OH), 8.55 (d, J=2.4 Hz, 1H), 7.65 (dd, J=8.8, 2.5 Hz, 1H), 4.63-4.54 (m, 1H), 4.51-4.39 (m, 1H), 4.39-4.26 (m, 1H), 4.03 (dddd, J=16.5, 6.0, 4.9, 3.2 Hz, 1H), 1.87-1.73 (m, 2H), 1.49-1.28 (m, 4H), 0.98-0.83 (m, 3H). $^{19}$F NMR (376 MHz, Methanol-d$_4$) δ −77.71, −117.85 (d, J=8.3 Hz), −231.37 (td, J=47.3, 16.5 Hz). LCMS-ESI$^+$ (m/z): [M+H]$^+$ calculated for $C_{14}H_{20}F_2N_5O$: 312.16; found: 312.16; $t_R$=0.70 min.

Example 103

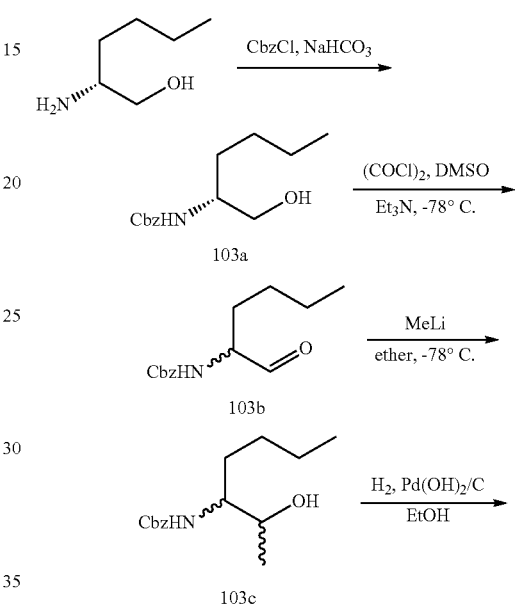

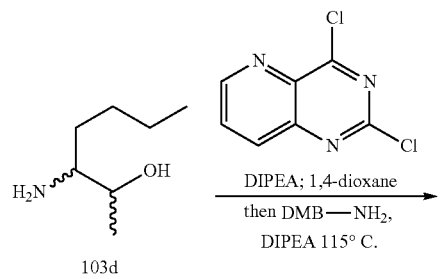

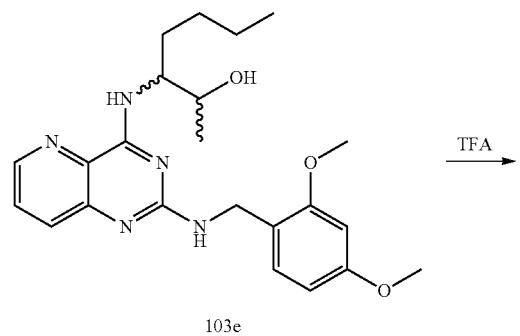

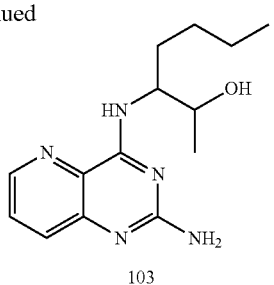

103

Synthesis of (R)-benzyl (1-hydroxyhexan-2-yl)carbamate (103a). A solution of (R)-2-aminohexan-1-ol (1.853 g, 15.81 mmol) and sodium bicarbonate (1961.6 mg, 31.63 mmol) in water (80 mL) was stirred at rt and benzyl chloroformate (2.7 mL, 95% purity, 18.98 mmol) was added. After stirring for 1 h at rt, the mixture was extracted with EtOAc (100 mL×1, 80 mL×2). The combined extracts were washed with brine, dried (Na$_2$SO$_4$), filtered and concentrated in vacuo. The residue was subjected to silica gel chromatography eluting with 0-100% EtOAc in hexanes to obtain 103a. $^1$H NMR (400 MHz, Methanol-d$_4$) δ 7.44-7.18 (m, 5H), 6.75 (d, J=8.7 Hz, OH), 5.07 (d, J=2.2 Hz, 2H), 3.57 (dt, J=11.1, 5.4 Hz, 1H), 3.48 (d, J=5.6 Hz, 2H), 1.58 (dq, J=14.0, 8.4, 6.4 Hz, 1H), 1.35 (dq, J=14.3, 7.4, 6.4 Hz, 5H), 0.91 (t, J=5.6 Hz, 3H). LCMS-ESI$^+$ (m/z): [M+H]$^+$ calculated for C$_{14}$H$_{22}$NO$_3$: 252.16; found: 251.80; t$_R$=0.90 min.

Synthesis of benzyl (1-oxohexan-2-yl)carbamate (103b). To a stirred solution of oxalyl chloride (0.125 mL, 1.432 mmol) in DCM (10 mL) cooled with an −78° C. bath was added DMSO (0.203 mL, 2.865 mmol) in DCM (2 mL) over 8 min. After 15 min, a solution of compound 103a (300 mg, 1.194 mmol) in DCM (4 mL) was added to the reaction mixture. The mixture was stirred at −78° C. for 30 min. and then triethylamine (0.832 mL, 5.968 mmol) was added with vigorous stirring. The resulting mixture was allowed to warm to rt, diluted with DCM (20 mL), washed with water (30 mL×3), brine (20 mL), dried (MgSO$_4$), filtered and concentrated under reduced pressure. The residue was subjected to silica gel chromatography eluting with 0-50% EtOAc in hexanes to obtain 103b. $^1$H NMR (400 MHz, Methanol-d$_4$) δ 9.41 (d, J=80.7 Hz, OH), 7.51-7.06 (m, 5H), 5.08 (d, J=2.1 Hz, 2H), 4.43 (d, J=3.9 Hz, 1H), 3.57 (dd, J=9.8, 5.1 Hz, 1H), 1.65 (dd, J=11.3, 6.7 Hz, 1H), 1.46-1.20 (m, 5H), 0.90 (t, J=6.3 Hz, 3H). LCMS-ESI$^+$ (m/z): [M+H]$^+$ calculated for C$_{14}$H$_{20}$NO$_3$: 250.14; found: 249.83; t$_R$=0.93 min.

Synthesis of benzyl (2-hydroxyheptan-3-yl)carbamate (103c). To a solution of compound 103b (277.0 mg, 1.111 mmol) dissolved in diethyl ether (10 mL) and cooled to −78° C. was added dropwise 1.57 M methyllithium in diethyl ether (1.557 mL, 2.444 mmol). After 10 min, saturated ammonium chloride (10 mL) was added to the reaction mixture and the resulting mixture was allowed to warm to rt for 45 min. The mixture was extracted with EtOAc (50 mL×3), the combined organic extracts were washed with brine, dried over MgSO$_4$, filtered and concentrated in vacuo. The residue was subjected to silica gel chromatography eluting with 0-70% EtOAc in hexanes to obtain compound 103c as a mixture of 4 diastereomers. $^1$H NMR (400 MHz, Methanol-d4) δ 7.44-7.19 (m, 5H), 5.08 (d, J=3.0 Hz, 2H), 3.83-3.57 (m, 1H), 3.54-3.40 (m, 1H), 1.76-1.41 (m, 2H), 1.43-1.24 (m, 6H), 1.12 (dd, J=9.4, 6.4 Hz, 3H), 0.90 (dd, J=7.9, 4.9 Hz, 3H). LCMS-ESI$^+$ (m/z): [M+H]$^+$ calculated for C$_{15}$H$_{24}$NO$_3$: 266.18; found: 265.81; t$_R$=0.93 min.

Synthesis of 3-aminoheptan-2-ol (103d). Compound 103c (59.6 mg, 0.225 mmol) and 20% Pd(OH)$_2$ on carbon (15.2 mg) were dissolved in EtOH (2 mL) and stirred under H$_2$ atmosphere. After 2 h, the reaction mixture was filtered through Celite pad and the removed solid was washed with EtOH (10 mL). The filtrate and washing were concentrated under reduced pressure and the crude compound, 103d, was used without further purification. LCMS-ESI$^+$ (m/z): [M+H]$^+$ calculated for C$_7$H$_{18}$NO: 132.14; found: 131.91; t$_R$=0.37 min.

Synthesis 3-((2-((2,4-dimethoxybenzyl)amino)pyrido[3,2-d]pyrimidin-4-yl)amino)heptan-2-ol (103e). To a solution of compound 103d (29.5 mg, 0.225 mmol) and 2,4-dichloropyrido[3,2-d]pyrimidine (37.4 mg, 0.187 mmol) in dioxane (2 mL) was added N,N-diisopropylethylamine (0.05 mL, 0.281 mmol). After 20 min, additional N,N-diisopropylethylamine (0.080 mL, 0.449 mmol) and 2,4-dimethoxybenzylamine (0.10 mL, 0.674 mmol) were added and the resulting mixture was heated at 115° C. bath for 7 h. The reaction mixture was allowed to cool to rt, diluted with water (50 mL), extracted with DCM (25 mL×2). The combined organic extracts were washed with water (25 mL×2), dried over MgSO$_4$, filtered and then concentrated in vacuo. The residue was subjected to silica gel chromatography eluting with 0-100% EtOAc in hexanes to obtain compound 103e. $^1$H NMR (400 MHz, Methanol-d$_4$) δ 8.31 (dt, J=4.3, 1.0 Hz, 0.85H), 8.05 (s, 0.15H), 7.63 (s, 1H), 7.48 (dd, J=8.5, 4.2 Hz, 1H), 7.18 (dd, J=8.3, 1.9 Hz, 1H), 6.52 (d, J=2.3 Hz, 1H), 6.48-6.38 (m, 1H), 4.64-4.47 (m, 2H), 4.35-4.21 (m, 1H), 4.00-3.87 (m, 1H), 3.83 (two s, 3H), 3.76 (two s, 3H), 3.35 (s, 1H), 1.90-1.52 (m, 2H), 1.33 (m, 4H), 1.16 (m, 3H), 0.97-0.78 (m, 3H). LCMS-ESI$^+$ (m/z): [M+H]$^+$ calculated for C$_{23}$H$_{34}$N$_5$O$_3$: 426.25; found: 426.17; t$_R$=1.00 min.

Synthesis of 3-((2-aminopyrido[3,2-d]pyrimidin-4-yl)amino)heptan-2-ol (103). Compound 103e (17.4 mg, 40.9 umol) was dissolved in TFA (1 mL) and stirred at rt for 1 h. The reaction mixture was concentrated under reduced pressure and co-evaporated with MeOH (10 mL). The resulting residue was dissolved in MeOH (1 mL) and concentrated ammonium hydroxide (0.1 mL). The mixture was stirred for 10 min. at rt and then concentrated under reduced pressure to dryness. The residue was dissolved in DMF-water (1:1, 5 mL) and filtered through a Celite/membrane filter. The filtrate was subjected to preparative HPLC (Gemini 10u C18 110A, AXIA; 10% aq. acetonitrile-70% aq. acetonitrile with 0.1% TFA, over 20 min. gradient). The product fractions were combined, concentrated under reduced pressure, co-evaporated with methanol (10 mL×3), and dried under high vacuum to obtain compound 103 as its TFA salt. $^1$H NMR (400 MHz, Methanol-d$_4$) δ 8.64 (dt, J=4.4, 1.2 Hz, 1H), 7.84 (dt, J=8.5, 1.4 Hz, 1H), 7.77 (ddd, J=8.5, 4.4, 1.5 Hz, 1H), 4.47-4.31 (m, 1H), 3.99 (tq, J=6.5, 3.5 Hz, 0.5H), 3.94 (dd, J=6.6, 5.5 Hz, 0.5H), 1.95-1.82 (m, 0.5H), 1.82-1.72 (m, 1H), 1.72-1.63 (m, 0.5H), 1.48-1.25 (m, 4H), 1.22 (d, J=6.4 Hz, 1.5H), 1.19 (d, J=6.4 Hz, 1.5H), 0.89 (two d, J=6.9, Hz each, 3H). LCMS-ESI$^+$ (m/z): [M+H]$^+$ calculated for C$_{14}$H$_{22}$N$_5$O: 276.18; found: 276.15; t$_R$=0.68 min.

Example 104

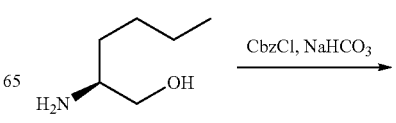

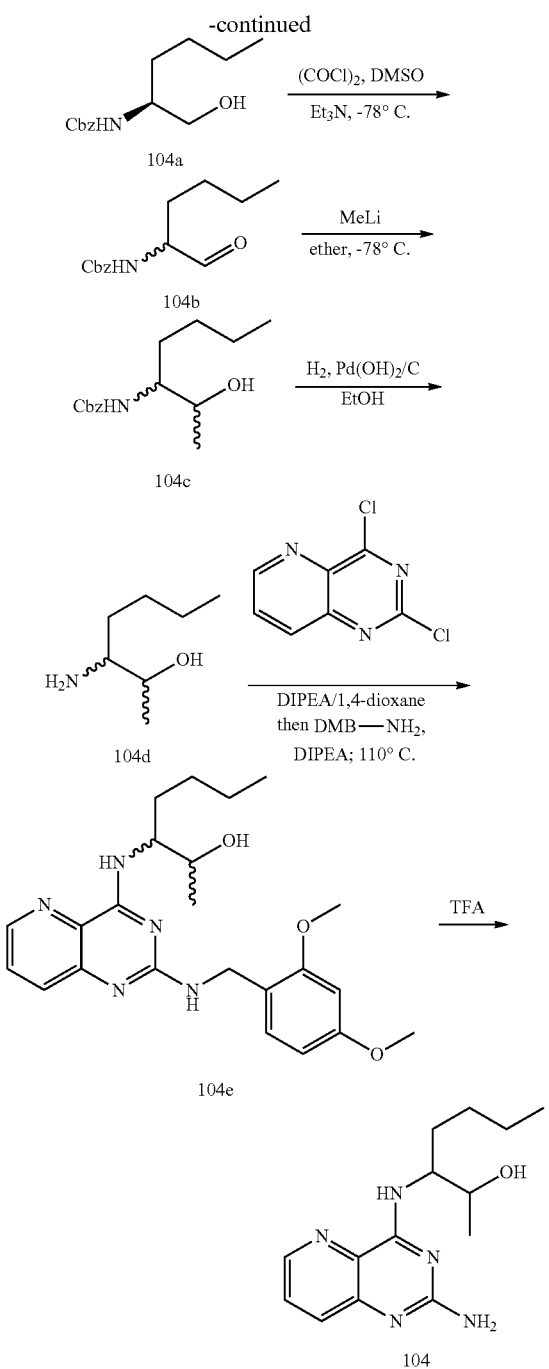

Synthesis of (S)-benzyl (1-hydroxyhexan-2-yl)carbamate (104a). To a mixture of (S)-2-aminohexan-1-ol (504.4 mg, 4.30 mmol) and sodium bicarbonate (533.9 mg, 8.61 mmol) in water (20 mL) was added benzyl chloroformate (0.74 mL, 95% purity, 5.17 mmol). The resulting mixture was vigorously stirred at rt overnight. The solid was dissolved with EtOAc (75 mL) and the mixture extracted with EtOAc (75 mL×2). The organic extracts were combined, dried over $Na_2SO_4$, filtered and concentrated in vacuo to obtain white solids. The solids were subjected to silica gel chromatography eluting with 0-100% EtOAc in hexanes to obtain compound 104a. $^1$H NMR (400 MHz, Methanol-$d_4$) δ 7.42-7.22 (m, 5H), 5.07 (d, J=2.1 Hz, 2H), 3.59 (d, J=8.0 Hz, 1H), 3.48 (d, J=5.6 Hz, 2H), 1.59 (d, J=10.8 Hz, 1H), 1.34 (td, J=15.4, 11.8, 7.3 Hz, 6H), 0.91 (t, J=6.0 Hz, 3H). LCMS-ESI$^+$ (m/z): [M+H]$^+$ calculated for $C_{14}H_{22}NO_3$: 252.16; found: 251.78; $t_R$=0.88 min.

Synthesis of benzyl (1-oxohexan-2-yl)carbamate (104b). To a stirred solution of oxalyl chloride (0.052 mL, 0.602 mmol) in DCM (1.5 mL) at −78° C. was added DMSO (0.086 mL, 1.205 mmol) in DCM (2 mL) over 8 min. After 15 min, a solution of compound 104a (108.1 mg, 0.430 mmol) in DCM (1.5 mL) was added to the reaction mixture. The mixture was stirred at −78° C. for 30 min. and then triethylamine (0.174 mL, 1.248 mmol) was added with vigorous stirring. The resulting mixture was allowed to warm to rt over 45 min. The mixture was diluted with DCM (30 mL), washed with water (30 mL×3), brine (25 mL), dried over $MgSO_4$, filtered and concentrated under reduced pressure to obtain the mixture 104b. LCMS-ESI$^+$ (m/z): [M+H]$^+$ calculated for $C_{14}H_{20}NO_3$: 250.14; found: 249.79; $t_R$=0.91 min.

Synthesis of benzyl (2-hydroxyheptan-3-yl)carbamate (104c). To a solution of compound 104b (107.3 mg, 0.430 mmol), dissolved in diethyl ether (4 mL) and cooled to −78° C. was added 1.57 M methyllithium in diethyl ether (0.685 mL, 1.076 mmol) dropwise. After 10 min, saturated aq. ammonium chloride (7 mL) was added to the reaction mixture and the resulting mixture was allowed to warm to rt for 45 min. The mixture was extracted with EtOAc (25 mL×2), and the combined organic extracts washed with brine, dried over $MgSO_4$, filtered and concentrated in vacuo. The residue was subjected to silica gel chromatography eluting with 0-70% EtOAc in hexanes to obtain compound 104c as a mixture of 4 diastereomers. $^1$H NMR (400 MHz, Methanol-$d_4$) δ 7.42-7.20 (m, 5H), 6.63 (dd, J=102.5, 9.6 Hz, 1H), 5.08 (d, J=3.3 Hz, 2H), 3.80-3.54 (m, 1H), 3.52-3.41 (m, 1H), 1.75-1.42 (m, 2H), 1.42-1.27 (m, 5H), 1.12 (dd, J=9.3, 6.4 Hz, 3H), 0.90 (d, J=3.5 Hz, 3H). LCMS-ESI$^+$ (m/z): [M+H]$^+$ calculated for $C_{15}H_{24}NO_3$: 266.18; found: 265.81; $t_R$=1.06 min.

Synthesis of 3-aminoheptan-2-ol (104d). Compound 104c (71.68 mg, 0.270 mmol) and 20% Pd(OH)$_2$ on carbon (19 mg) were dissolved in EtOH (2 mL) and stirred under H$_2$ atmosphere. After 2 h, the reaction mixture was filtered through Celite pad and the removed solid washed with EtOH (5 mL). The filtrate and washings were concentrated under reduced pressure to provide 104d that was used without further purification. LCMS-ESI$^+$ (m/z): [M+H]$^+$ calculated for $C_7H_{18}NO$: 132.14; found: 131.91; $t_R$=0.51 min.

Synthesis of 3-((2-((2,4-dimethoxybenzyl)amino)pyrido[3,2-d]pyrimidin-4-yl)amino)heptan-2-ol (104e). To a solution of compound 104d (35.45 mg, 0.270 mmol) and 2,4-dichloropyrido[3,2-d]pyrimidine (5.02 mg, 0.225 mmol) in dioxane (3 mL) was added N,N-diisopropylethylamine (0.06 mL, 0.338 mmol). After 20 min. additional N,N-diisopropylethylamine (0.096 mL, 0.540 mmol) and 2,4-dimethoxybenzylamine (0.120 mL, 0.811 mmol) were added and the resulting mixture was heated at 115° C. bath for 6 h. The reaction mixture was cooled to rt, diluted with water (30 mL), and extracted with DCM (20 mL×2). The organic extracts were combined, washed with water (30 mL×2), brine (25 mL), dried over $MgSO_4$, filtered and concentrated under reduced pressure. The residue was subjected to silica gel chromatography eluting with 0-100% EtOAc in hexanes to obtain compound 104e. $^1$H NMR (400 MHz, Methanol-d4) δ 8.31 (ddd, J=4.2, 1.5, 0.8 Hz, 1H), 7.63 (d, J=8.4 Hz, 1H), 7.48 (dd, J=8.5, 4.2 Hz, 1H), 7.25-7.08 (m, 1H), 6.60-6.37 (m, 2H), 4.84 (s, 3H), 4.54 (d, J=5.3 Hz, 2H), 4.35-4.22 (m, 1H), 3.83 (d, J=10.3 Hz, 3H), 3.79-3.73 (m, 3H), 1.88-1.52 (m, 2H), 1.46-1.28 (m, 4H), 1.23-1.12 (m, 3H), 0.86 (td, J=7.0, 2.2 Hz, 3H). LCMS-ESI⁺ (m/z): [M+H]⁺ calculated for $C_{23}H_{34}N_5O_3$: 426.25; found: 426.19; $t_R$=0.97 min.

Synthesis of 3-((2-aminopyrido[3,2-d]pyrimidin-4-yl)amino)heptan-2-ol (104). Compound 104e (27.3 mg, 64.2 umol) was dissolved in TFA (1 mL) and stirred at rt for 1 h. The reaction mixture was concentrated under reduced pressure and co-evaporated with MeOH (10 mL). The resulting residue was dissolved in MeOH (1 mL) and concentrated ammonium hydroxide (0.1 mL). The reaction mixture was stirred at rt, and then concentrated under reduced pressure to dryness. The residue was treated with DMF-water (1:1, 5 mL). The insoluble material was removed via filtration through a Celite/membrane filter, and the filtrate was subjected to preparative HPLC (Gemini 10u C18 110A, AXIA; 10% aq. acetonitrile-70% aq. acetonitrile with 0.1% TFA, over 20 min. gradient). The fractions were combined, concentrated under reduced pressure, co-evaporated with methanol (10 mL×3), and dried in vacuum overnight to obtain 104 as its TFA salt. ¹H NMR (400 MHz, Methanol-d4) δ 8.64 (dt, J=4.4, 1.2 Hz, 1H), 7.84 (dt, J=8.5, 1.4 Hz, 1H), 7.77 (ddd, J=8.5, 4.4, 1.5 Hz, 1H), 4.46-4.40 (m, 0.5H), 4.37 (m, 1H), 4.00 (m, 0.5H), 3.97-3.88 (m, 0.5H), 1.88 (m, 0.5H), 1.82-1.72 (m, 1H), 1.72-1.62 (m, 0.5H), 1.48-1.25 (m, 4H), 1.22 (d, J=6.4 Hz, 1.5H), 1.19 (d, J=6.4 Hz, 1.5H), 0.89 (two t, J=6.8 Hz each, 3H). LCMS-ESI⁺ (m/z): [M+H]⁺ calculated for $C_{14}H_{22}N_5O$: 276.18; found: 276.15; $t_R$=0.68 min.

Example 105

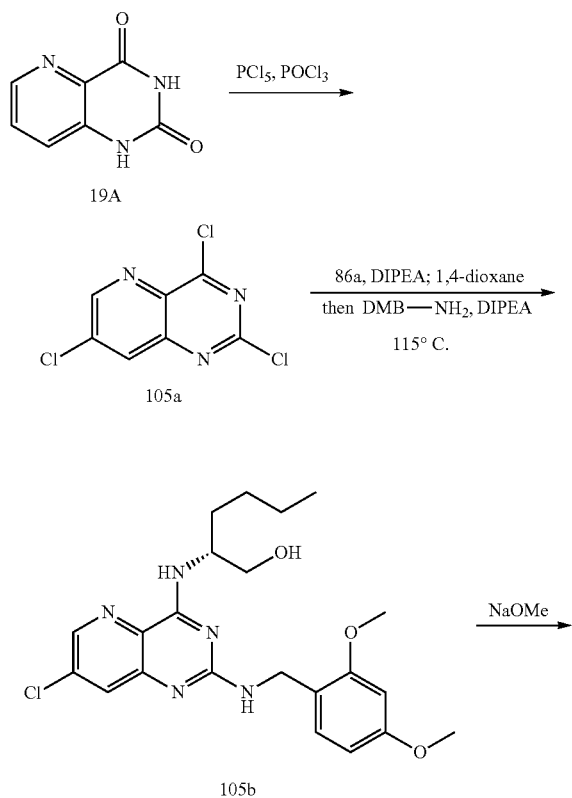

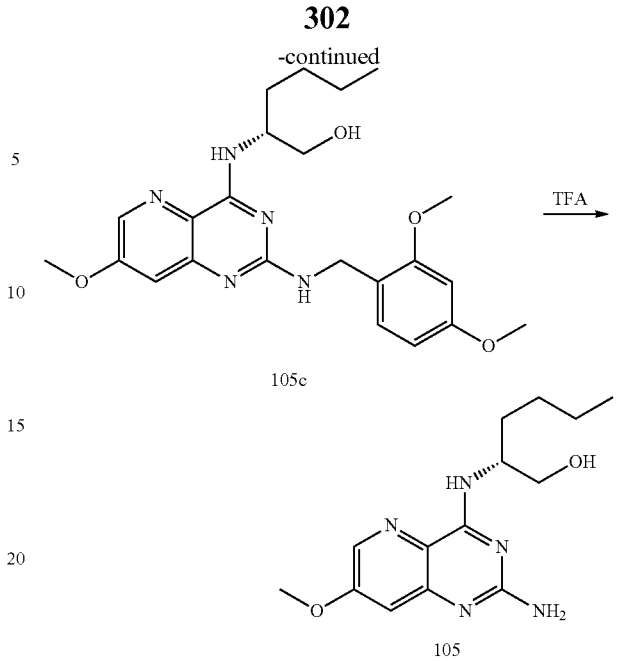

Synthesis of 2,4,7-trichloropyrido[3,2-d]pyrimidine (105a). A mixture of pyrido[3,2-d]pyrimidine-2,4(1H,3H)-dione 19A (supplied by Astatech, Inc., 2.00 g, 12.26 mmol), phosphorus pentachloride (15.32 g, 73.56 mmol) and phosphorus oxychloride (22.86 mL, 245.20 mmol) in a sealed, thick-walled reaction tube, was stirred at 160° C. for 5 h. The mixture was concentrated in vacuo and the residue was dissolved in DCM (100 mL). The organic solution was washed with water (100 mL), brine (100 mL), dried over MgSO₄, filtered and then concentrated in vacuo. The residue was subjected to silica gel chromatography eluting with 0-50% EtOAc in hexanes to obtain compound 105a. ¹H NMR (400 MHz, Chloroform-d) δ 9.02 (d, J=2.2 Hz, 21H), 8.29 (d, J=2.2 Hz, 21H). LCMS-ESI⁺ (m/z): $t_R$=0.86 min.

Synthesis of (R)-2-((7-chloro-2-((2,4-dimethoxybenzyl)amino)pyrido[3,2-d]pyrimidin-4-yl)amino)hexan-1-ol (105b). To a solution of compound 105a (336 mg, 1.066 mmol) and (R)-2-aminohexan-1-ol 86a (137.5 mg, 1.173 mmol) in dioxane (4 mL) was added N,N-diisopropylethylamine (0.23 mL, 1.292 mmol). The mixture was stirred for 40 min. and then additional N,N-diisopropylethylamine (0.38 mL, 2.132 mmol) and 2,4-dimethoxybenzylamine (0.473 mL, 3.198 mmol) were added. The resulting mixture was heated at 115° C. for 2 h. The reaction mixture was cooled to rt, diluted with water (30 mL) and extracted with DCM (30 mL). The organic extracts were washed with water (30 mL), brine (30 mL), dried over MgSO₄, filtered and concentrated in vacuo. The residue was subjected to silica gel chromatography eluting with 0-100% EtOAc in hexanes to obtain compound 105b. LCMS-ESI⁺ (m/z): [M+H]⁺ calculated for $C_{22}H_{29}ClN_5O_3$: 446.20; found: 446.23, $t_R$=0.80 min.

Synthesis of (R)-2-((2-((2,4-dimethoxybenzyl)amino)-7-methoxypyrido[3,2-d]pyrimidin-4-yl)amino)hexan-1-ol (105c). To a solution of compound 105b (50 mg, 0.113 mmol) in dioxane (2 mL) was added sodium methoxide (25 wt. %, 0.064 mL, 0.280 mmol) in a microwave vial. The resulting mixture was heated at 120° C. for 45 min. in a microwave reactor. The reaction mixture was concentrated in vacuo and the residue was dissolved in methanol (2 mL) and sodium methoxide (25 wt. %, 0.2 mL, 0.874 mmol). The resulting mixture was heated at 150° C. for 1 h in a microwave reactor. The reaction mixture was diluted with water (25 mL) and extracted with EtOAc (25 mL×2). The combined extracts were washed with saturated aqueous ammonium chloride (25 mL), dried over MgSO$_4$, filtered and concentrated under reduced pressure to obtain crude compound 105c. LCMS-ESI$^+$ (m/z): [M+H]$^+$ calculated for C$_{23}$H$_{32}$N$_5$O$_4$: 442.25; found: 442.23; t$_R$=0.82 min.

Synthesis of (R)-2-((2-amino-7-methoxypyrido[3,2-d]pyrimidin-4-yl)amino)hexan-1-ol (105). The compound 105c was dissolved in TFA (1 mL) and stirred at rt for 1 h. The reaction mixture was concentrated under reduced pressure and co-evaporated with MeOH (10 mL). The resulting residue was subjected to preparative HPLC (Gemini 10u C18 110A, AXIA; 5% aq. acetonitrile-50% aq. acetonitrile with 0.1% TFA, over 20 min. gradient). The product fractions were concentrated in vacuo, co-evaporated with methanol (10 mL×3), and dried under vacuum to obtain compound 105 as its TFA salt. $^1$H NMR (400 MHz, Methanol-d$_4$) δ 8.32 (d, J=2.5 Hz, 1H), 7.22 (d, J=2.6 Hz, 1H), 4.58-4.39 (m, 1H), 4.00 (s, 4H), 3.77-3.60 (m, 3H), 1.72 (dtd, J=14.7, 8.5, 8.0, 5.4 Hz, 2H), 1.51-1.22 (m, 5H), 1.00-0.80 (m, 4H). $^{19}$F NMR (376 MHz, Methanol-d$_4$) δ −77.51. LCMS-ESI$^+$ (m/z): [M+H]$^+$ calculated for C$_{14}$H$_{22}$N5O$_2$: 292.18; found: 292.19; t$_R$=0.45 min.

Example 106

(106a). To a solution of compound 105c (40 mg, 0.090 mmol) in EtOH (3 mL) was added sodium ethoxide (21 wt. %, 0.335 mL, 0.897 mmol) in a microwave vial. The resulting mixture was heated at 120° C. for 45 min. in a microwave reactor. The reaction mixture was concentrated in vacuo and the residue was then dissolved in water (25 mL) and EtOAc (25 mL). The organic layer was separated and washed with saturated aqueous ammonium chloride, dried over MgSO$_4$, filtered and then concentrated in vacuo to obtain crude compound 106a. LCMS-ESI$^+$ (m/z): [M+H]$^+$ calculated for C$_{24}$H$_{34}$N$_5$O$_4$: 456.26; found: 456.23; t$_R$=0.76 min.

Synthesis of (R)-2-((2-amino-7-ethoxypyrido[3,2-d]pyrimidin-4-yl)amino)hexan-1-ol (106). The compound 106a was dissolved in TFA (1 mL) and stirred at rt for 1 h. The reaction mixture was concentrated in vacuo and co-evaporated with MeOH (10 mL). The resulting residue was dissolved in MeOH (1 mL) and concentrated ammonium hydroxide (0.1 mL). The mixture was stirred at 50° C. for 10 min. and then concentrated under reduced pressure. The resulting residue was subjected to preparative HPLC (Gemini 10u C18 110A, AXIA; 5% aq. acetonitrile-50% aq. acetonitrile with 0.1% TFA, over 20 min. gradient). The product fractions were concentrated in vacuo, co-evaporated with methanol (10 mL×3), and then dried under high vacuum to obtain compound 106 as its TFA salt. $^1$H NMR (400 MHz, Methanol-d$_4$) δ 7.94 (d, J=2.6 Hz, 1H), 6.83 (d, J=2.6 Hz, 1H), 4.02 (q, J=7.0 Hz, 3H), 3.55 (d, J=4.9 Hz, 3H), 1.33 (t, J=7.0 Hz, 4H), 1.30-1.15 (m, 4H), 0.91-0.63 (m, 3H). $^{19}$F NMR (377 MHz, Methanol-d$_4$) δ −77.50. LCMS-ESI$^+$ (m/z): [M+H]$^+$ calculated for C$_{15}$H$_{24}$N$_5$O$_2$: 306.19; found: 306.20; t$_R$=0.51 min.

Example 107

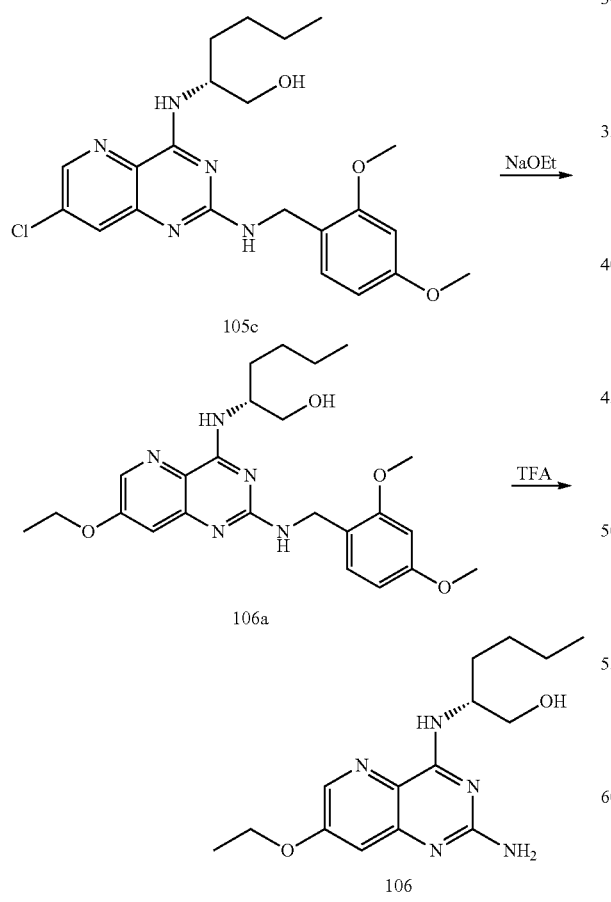

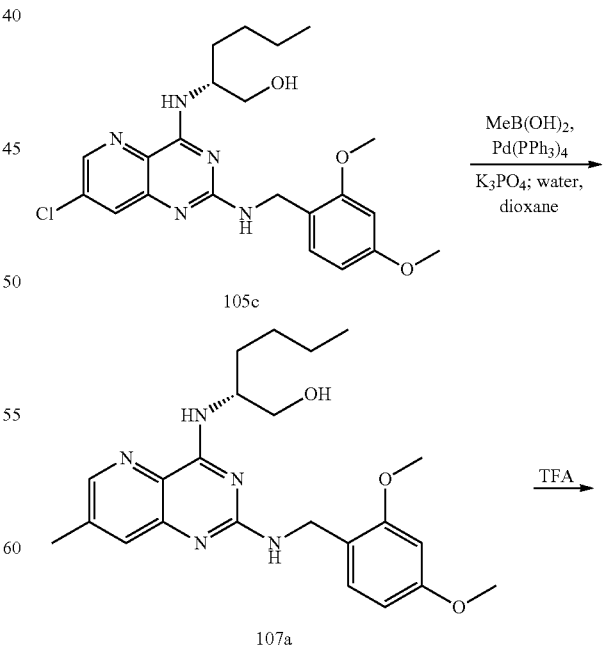

Synthesis of (R)-2-((2-((2,4-dimethoxybenzyl)amino)-7-ethoxypyrido[3,2-d]pyrimidin-4-yl)amino)hexan-1-ol

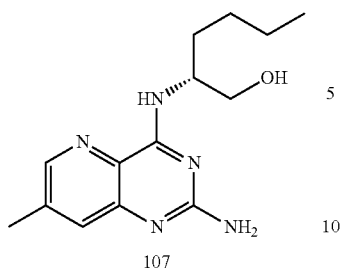

107

Synthesis of (R)-2-((2-((2,4-dimethoxybenzyl)amino)-7-methylpyrido[3,2-d]pyrimidin-4-yl)amino)hexan-1-ol (107a). A mixture of compound 105c (35 mg, 0.078 mmol), methylboronic acid (18.8 mg, 0.314 mmol), potassium phosphate tribasic (50.0 mg, 0.235 mmol), and palladium tetrakis (triphenylphosphine (18.14 mg, 0.016 mmol) in water (2 mL) and dioxane (2 mL) was stirred at 150° C. for 45 min. in a microwave reactor. The reaction mixture was diluted with water (25 mL) and extracted with EtOAc (25 mL). The organic layer was washed with water (25 mL), brine (25 mL), dried over MgSO₄, filtered and then concentrated under reduced pressure to obtain crude compound 107a. LCMS-ESI⁺ (m/z): [M+H]⁺ calculated for $C_{23}H_{32}N_5O_3$: 292.18; found: 426.22; $t_R$=0.70 min.

Synthesis of (R)-2-((2-amino-7-methylpyrido[3,2-d]pyrimidin-4-yl)amino)hexan-1-ol (107). The compound 107a was dissolved in TFA (1 mL) and stirred at rt for 1 h. The reaction mixture was concentrated in vacuo and the residue co-evaporated with MeOH (10 mL). The resulting residue was dissolved in MeOH (1 mL) and concentrated ammonium hydroxide (0.1 mL). The mixture was stirred for 10 min. at 50° C. and then concentrated under reduced pressure. The resulting residue was subjected to preparative HPLC (Gemini 10u C18 110A, AXIA; 5% aq. acetonitrile-50% aq. acetonitrile with 0.1% TFA, over 20 min. gradient). The product fractions were concentrated in vacuo, co-evaporated with methanol (10 mL×3), and dried under high-vacuum to obtain compound 107 as its TFA salt. ¹H NMR (400 MHz, Methanol-d₄) δ 8.53-8.46 (m, 1H), 7.62 (tt, J=1.9, 1.0 Hz, 1H), 4.51 (dtd, J=9.0, 5.5, 3.1 Hz, 1H), 3.72 (d, J=5.3 Hz, 2H), 2.51 (d, J=2.2 Hz, 3H), 1.83-1.62 (m, 2H), 1.49-1.29 (m, 4H), 0.98-0.86 (m, 3H). ¹⁹F NMR (376 MHz, Methanol-d4) δ -77.52. LCMS-ESI⁺ (m/z): [M+H]⁺ calculated for $C_{14}H_{22}N_5O$: 276.18; found: 276.16; $t_R$=0.50 min.

Example 108

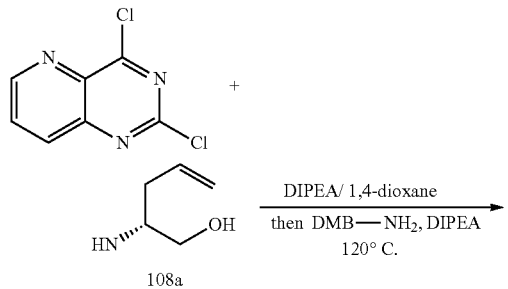

108a

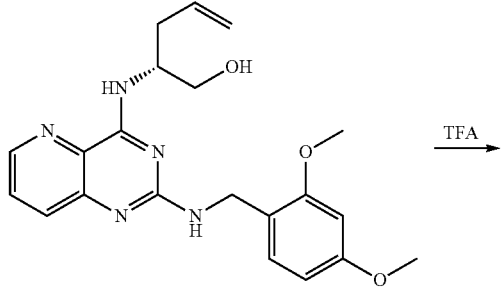

108b

Synthesis of (R)-2-((2-((2,4-dimethoxybenzyl)amino) pyrido[3,2-d]pyrimidin-4-yl)amino)pent-4-en-1-ol (108b). To a solution of 2,4-dichloropyrido[3,2-d]pyrimidine (50 mg, 0.250 mmol) and (R)-2-aminopent-4-en-1-ol hydrochloride 108a (26.6 mg, 0.280 mmol, Chiralix B.V., Netherland) in dioxane (2 mL) was added N,N-diisopropylethylamine (0.09 mL, 0.500 mmol). The mixture was stirred overnight and then additional N,N-diisopropylethylamine (0.09 mL, 0.500 mmol) and 2,4-dimethoxybenzylamine (0.403 mL, 2.727 mmol) were added. The resulting mixture was heated at 120° C. overnight. The reaction mixture was allowed to cool to rt, diluted with water (25 mL) and extracted with EtOAc (25 mL×3). The organic extracts were washed with water (25 mL), brine (25 mL), dried over MgSO), filtered and then concentrated in vacuo to obtain the crude compound 108b. LCMS-ESI⁺ (m/z): [M+H]⁺ calculated for $C_{21}H_{26}N_5O_3$: 396.20; found: 396.14, $t_R$=0.69 min.

Synthesis of (R)-2-((2-aminopyrido[3,2-d]pyrimidin-4-yl)amino)pent-4-en-1-ol (108). The compound 108b (99 mg) was dissolved in TFA (3 mL) and stirred at rt for 3 h. The reaction mixture was concentrated under reduced pressure and co-evaporated with MeOH (10 mL). The resulting residue was subjected to preparative HPLC (Gemini 10u C18 110A, AXIA; 5% aq. acetonitrile-50% aq. acetonitrile with 0.1% TFA, over 20 min. gradient). The product fractions were concentrated in vacuo, co-evaporated with methanol (10 mL×3), and dried under high vacuum to obtain compound 108 as its TFA salt. ¹H NMR (400 MHz, Methanol-d4) δ 8.64 (dd, J=4.3, 1.5 Hz, 1H), 7.89-7.65 (m, 2H), 6.02-5.70 (m, 1H), 5.24-5.10 (m, 1H), 5.11-4.99 (m, 1H), 4.63-4.45 (m, 1H), 3.76 (d, J=5.3 Hz, 2H), 2.68-2.35 (m, 2H). ¹⁹F NMR (376 MHz, Methanol-d₄) δ -77.49. LCMS-ESI⁺ (m/z): [M+H]⁺ calculated for $C_{12}H_{16}N_5O$: 246.14; found: 246.09, $t_R$=0.45 min.

Example 110

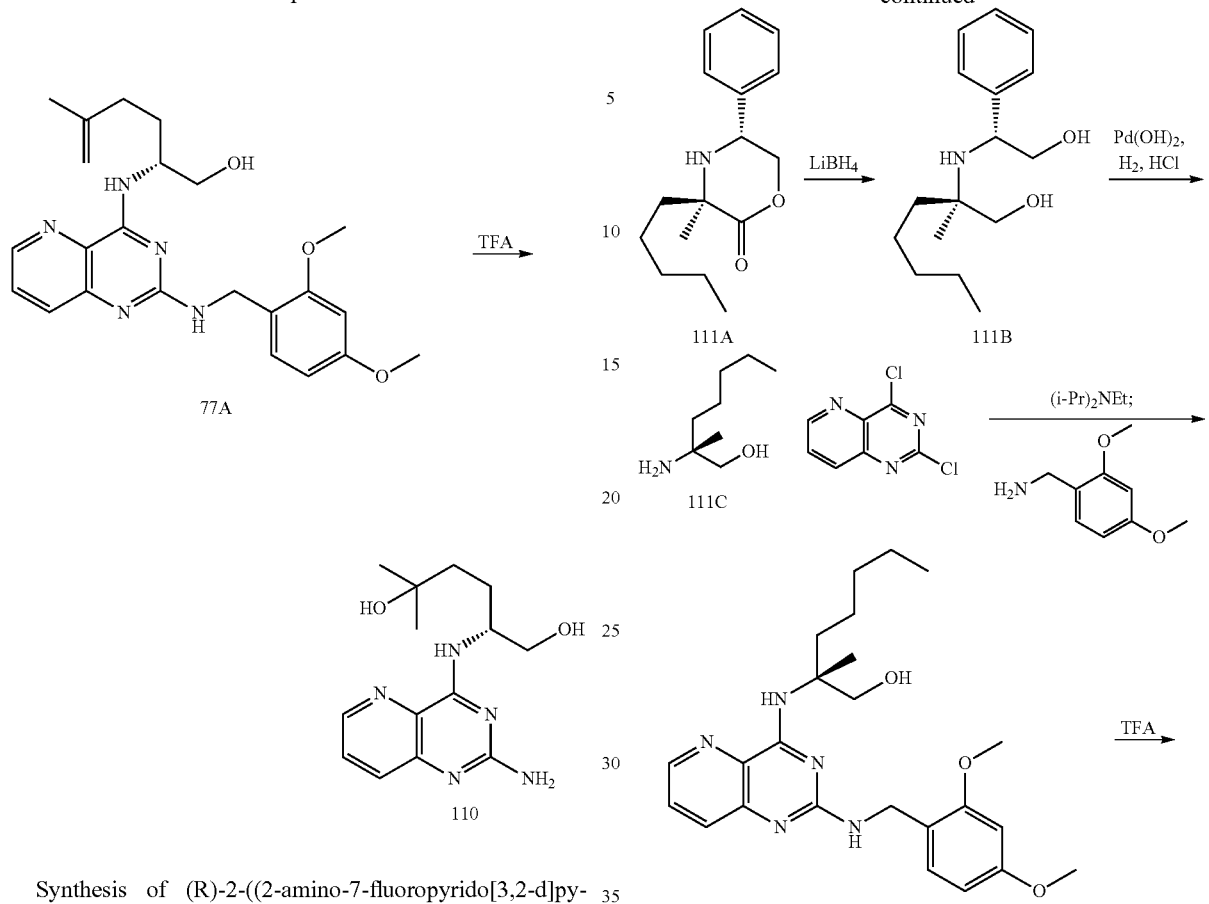

Synthesis of (R)-2-((2-amino-7-fluoropyrido[3,2-d]pyrimidin-4-yl)amino)-2-methylheptan-1-ol (110). To 77A (40 mg, 0.09 mmol) was added TFA (3 mL) and the mixture stirred for 2 h. The reaction mixture was concentrated under reduced pressure and the residue subjected to preparative HPLC (Synergi 4u Polar-RP 80A, Axia; 10% aq. acetonitrile-70% aq. acetonitrile with 0.1% TFA, over 20 min. gradient) to afford 110 as its TFA salt. LCMS (m/z): 292.12 [M+H]$^+$; $t_R$=0.50 min. on LC/MS Method A. $^1$H NMR (400 MHz, Methanol-d4) δ 8.63 (dd, J=4.4, 1.4 Hz, 1H), 7.87 (dd, J=8.5, 1.4 Hz, 1H), 7.76 (dd, J=8.5, 4.4 Hz, 1H), 4.61-4.34 (m, 1H), 3.76 (d, J=5.3 Hz, 2H), 1.96-1.70 (m, 2H), 1.64-1.51 (m, 2H), 1.19 (s, 6H). $^{19}$F NMR (377 MHz, Methanol-d4) δ −77.52.

Example 111

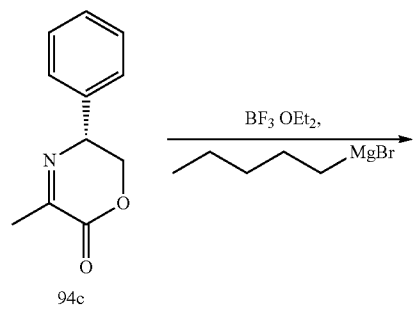

Synthesis of (3R,5R)-3-methyl-3-pentyl-5-phenylmorpholin-2-one (111A). To a solution of 94c (2 g, 10.57 mmol) in THF (50 ml) at −78° C. was added 2M boron trifluoride diethyl etherate in THF (2.76 ml, 22.39 mmol, 2.1 equiv.) over 10 minutes. After 90 minutes, 2M pentylmagnesium chloride solution in THF (11.19 ml, 22.38 mmol, 2.1 equiv.) was added slowly. The reaction was stirred for 2 h and then quenched with sat. NH$_4$Cl (200 mL). The mixture was allowed to warm to rt and then diluted with water (200 mL). The mixture was extracted with EtOAc (3×300 mL) and the combined extracts washed with water (3×500 mL), brine (300 mL), dried over NaSO$_4$, and concentrated under reduced pressure. The residue was subjected to silica gel chromatography eluting with hexanes-EtOAc to afford 111A. LCMS (m/z): 262.06 [M+H]$^+$; $t_R$=1.14 min. on LC/MS Method A.

Synthesis of (R)-2-(((R)-2-hydroxy-1-phenylethyl)amino)-2-methylheptan-1-ol (111B). To a solution of 111A (1.65 g, 6.31 mmol) in THF (100 ml) at 0° C. was added 2M lithium borohydride in THF (6.35 ml, 12.7 mmol, 2 equiv.). The reaction was warmed to rt and stirred overnight. The mixture was then quenched with water (100 mL) and extracted with EtOAc (3×300 mL). The combined organics were washed with water (500 mL), brine (100 mL), dried over $Na_2SO_4$, and concentrated under reduced pressure to afford 111B that was used without further purification. LCMS (m/z): 266.05 [M+H]$^+$; $t_R$=0.64 min. on LC/MS Method A.

Synthesis of (R)-2-amino-2-methylheptan-1-ol (111C). To a solution of 111B (1.66 g, 6.25 mmol) in EtOH (20 mL) was added Pd(OH)$_2$/C (20% wt %, 0.92 g) and 4M HCl in dioxane (2.37 ml, 9.50 mmol, 1.5 equiv.). The mixture was stirred under and atmosphere of H$_2$ at 70° C. overnight. The reaction was then filtered through Celite and concentrated to afford 111C that was used without further purification. LCMS (m/z): 145.95 [M+H]$^+$; $t_R$=0.57 min. on LC/MS Method A.

Synthesis of (R)-2-((2-((2,4-dimethoxybenzyl)amino)pyrido[3,2-d]pyrimidin-4-yl)amino)-2-methylheptan-1-ol (111D). To 2,4-dichloropyrido[3,2-d]pyrimidine (118.89 mg, 0.59 mmol) in dioxane (12 mL) was added 111C (135 mg, 0.74 mmol, 1.25 equiv.), and N,N-diisopropylethylamine (0.78 ml, 4.46 mmol, 7.5 equiv.). The reaction mixture was stirred at 80° C. overnight. 2,4-dimethoxybenzylamine (0.27 ml, 1.85 mmol, 3.1 equiv.) was added and the mixture was heated to 100° C. for 6 h. The reaction mixture was allowed to cool, diluted with EtOAc (50 mL), washed with water (50 mL), saturated NH$_4$Cl (50 mL), dried over MgSO$_4$, filtered, and concentrated under reduced pressure. The residue was subjected to silica gel chromatography eluting with hexanes-EtOAc to afford 111D. LCMS (m/z): 440.30 [M+H]$^+$; $t_R$=0.93 min. on LC/MS Method A.

Synthesis of (R)-2-((2-amino-7-fluoropyrido[3,2-d]pyrimidin-4-yl)amino)-2-methylheptan-1-ol (111). To 111D (155 mg, 0.35 mmol) was added TFA (3 mL). After 1 h, the reaction was concentrated under reduced pressure and the residue subjected to preparative HPLC (Synergi 4u Polar-RP 80A, Axia; 10% aq. acetonitrile-70% aq. acetonitrile with 0.1% TFA, over 20 min. gradient) to afford 111 as its TFA salt. LCMS (m/z): 290.15 [M+H]$^+$; $t_R$=0.72 min. on LC/MS Method A. $^1$H NMR (400 MHz, Methanol-d$_4$) δ 8.63 (dd, J=4.3, 1.5 Hz, 1H), 7.86-7.80 (m, 1H), 7.77 (dd, J=8.5, 4.3 Hz, 1H), 3.98 (d, J=11.2 Hz, 1H), 3.72 (d, J=11.2 Hz, 1H), 2.16-2.04 (m, 1H), 1.92 (tt, J=11.1, 4.9 Hz, 1H), 1.55 (s, 3H), 1.42-1.28 (m, 7H), 0.93-0.85 (m, 3H). $^{19}$F NMR (377 MHz, Methanol-d$_4$) δ -77.58.

Example 112

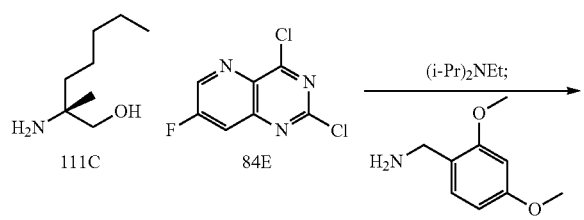

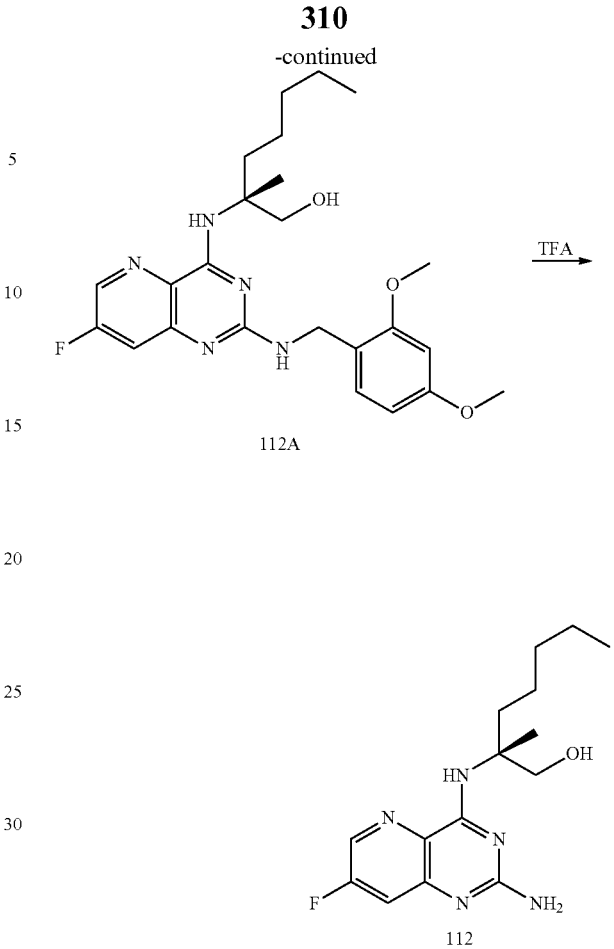

Synthesis of (R)-2-((2-((2,4-dimethoxybenzyl)amino)-7-fluoropyrido[3,2-d]pyrimidin-4-yl)amino)-2-methylheptan-1-ol (112A). To a solution of 84E (119.98 mg, 0.55 mmol) in dioxane (10 mL) was added 111C (125 mg, 0.69 mmol, 1.25 equiv.) and N,N-diisopropylethylamine (0.72 ml, 4.13 mmol, 6 equiv.). The mixture was stirred at 80° C. overnight. 2,4-dimethoxybenzylamine (0.2 ml, 1.38 mol, 2.5 equiv.) was added and the reaction heated to 100° C. for 6 h. The reaction mixture was allowed to cool, diluted with EtOAc (50 mL), washed with water (50 mL), sat. NH$_4$Cl (50 mL), dried over MgSO$_4$, filtered, and concentrated under reduced pressure. The residue was subjected to silica gel chromatography eluting with hexanes-EtOAc to afford 112A. LCMS (m/z): 458.26 [M+H]$^+$; $t_R$=1.00 min. on LC/MS Method A.

Synthesis of (R)-2-((2-amino-7-fluoropyrido[3,2-d]pyrimidin-4-yl)amino)-2-methylheptan-1-ol (112). To 112A (105 mg, 0.23 mmol) was added TFA (3 mL). After 1 h, the reaction mixture was concentrated under reduced pressure and subjected to preparative HPLC (Synergi 4u Polar-RP 80A, Axia; 10% aq. acetonitrile-70% aq. acetonitrile with 0.1% TFA, over 20 min. gradient) to afford 112 as its TFA salt. LCMS (m/z): 308.14 [M+H]$^+$; $t_R$=0.75 min. on LC/MS Method A. $^1$H NMR (400 MHz, Methanol-d$_4$) δ 8.54 (d, J=2.5 Hz, 1H), 8.22 (s, 1H), 7.62 (ddd, J=8.7, 2.4, 0.8 Hz, 1H), 3.96 (d, J=11.2 Hz, 1H), 3.70 (d, J=11.2 Hz, 1H), 2.13-2.02 (m, 1H), 1.91 (s, 1H), 1.53 (s, 3H), 1.41-1.28 (m, 7H), 0.93-0.84 (m, 3H). $^{19}$F NMR (377 MHz, Methanol-d$_4$) δ -77.56, -118.19 (dd, J=8.7, 4.2 Hz).

Example 113

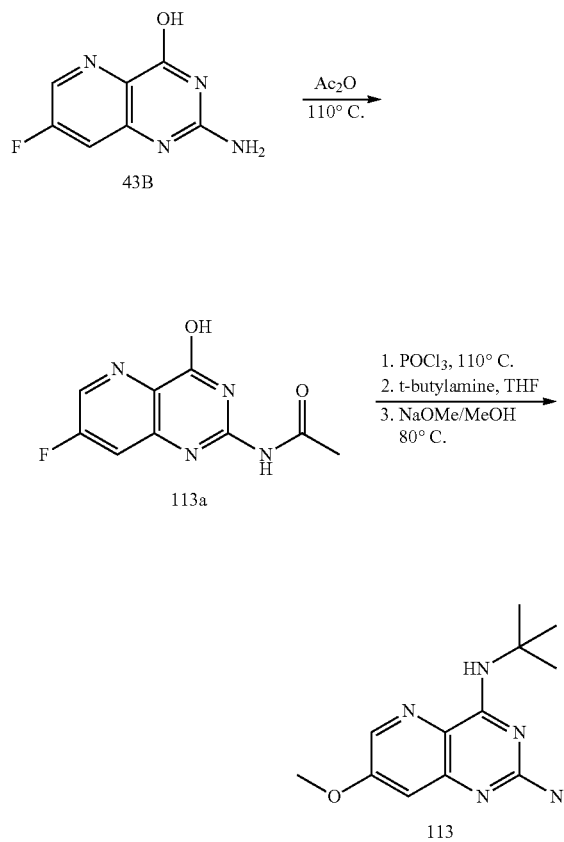

Synthesis of N-(7-fluoro-4-hydroxypyrido[3,2-d]pyrimidin-2-yl)acetamide (113a). Acetic anhydride was cooled to 0° C. under nitrogen and 2-amino-7-fluoropyrido[3,2-d]pyrimidin-4-ol 43B (200 mg, 1.11 mmol; Supplied by Medicilon, Shanghai) was added. The reaction mixture was then heated to 110° C. for 4 h. The mixture was cooled and concentrated under reduced pressure. The residue was triturated with DCM (20 mL), and the solids removed by filtration and air dried to provide of compound 113a as a solid. LCMS-ESI+ (m/z): [M+H]+ calculated for $C_9H_7FN_4O_2$: 223.06; found: 222.96; $t_R$=0.58 min.

Synthesis of $N^4$-(tert-butyl)-7-methoxypyrido[3,2-d]pyrimidine-2,4-diamine (113). 113a was suspended in POCl₃ (5 mL) and heated to 110° C. for 1 h. The reaction was then cooled and POCl₃ removed under reduced pressure. The residue was co-evaporated with toluene (15 mL) and then treated within THF (5 mL). tert-Butylamine (70 μL, 0.66 mmol) was added and the mixture stirred at rt for 15 minutes. 25% Sodium methoxide in methanol (100 μL, 0.45 mmol) was added and the reaction mixture heated in a sealed vessel at 80° C. The reaction mixture was allowed to cool to rt and was directly subjected to preparative HPLC (Synergi 4u Polar-RP 80A, Axia; 10% aq. acetonitrile-70% aq. acetonitrile with 0.1% TFA, over 20 min. gradient). The product fractions were concentrated in vacuo to afford 113 as its TFA salt. ¹H NMR (400 MHz, Methanol-d4) δ 8.30 (d, J=2.5 Hz, 1H), 8.04 (s, 1H), 7.18 (d, J=2.6 Hz, 1H), 3.99 (s, 3H), 1.61 (s, 9H). ¹⁹F NMR (376 MHz, Methanol-d4) δ −77.51. LCMS-ESI+ (m/z): [M+H]+ calculated for $C_{12}H_{17}N_5O$: 248.14; found: 248.09; $t_R$=0.81 min.

Example 114

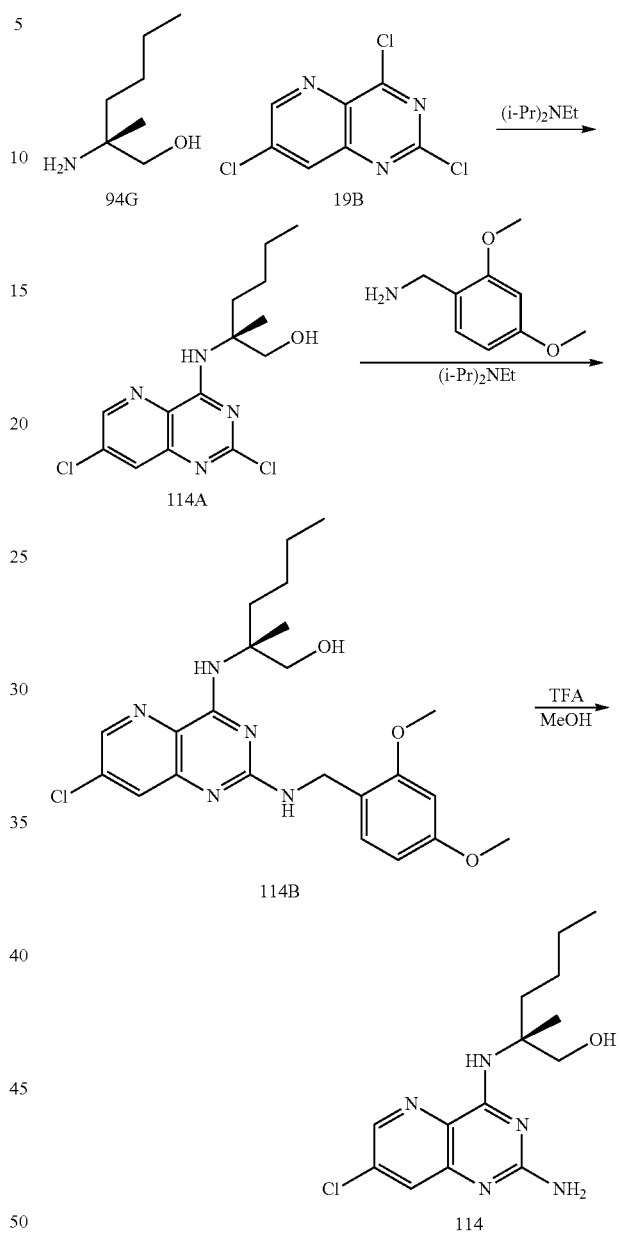

Synthesis of (R)-2-((2,7-dichloropyrido[3,2-d]pyrimidin-4-yl)amino)-2-methylhexan-1-ol (114A). To a solution of 94G (75 mg, 0.30 mmol) and 19B (51 mg, 0.30 mmol) in THF (5 mL) was added N,N-diisopropylethylamine (0.16 mL, 0.90 mmol). After stirring at 80° C. for 23 h, the reaction was cooled to ambient temperature, diluted with EtOAc (50 mL), washed with water (50 mL) and brine (50 mL), dried over Na₂SO₄, then filtered and concentrated in vacuo. The residue was subjected to silica gel chromatography eluting with hexanes-EtOAc (0-75%) to provide 114A. LCMS (m/z): 329.11 [M+H]+; $t_R$=1.27 min. on LC/MS Method A.

Synthesis of (R)-2-((7-chloro-2-((2,4-dimethoxybenzyl)amino)pyrido[3,2-d]pyrimidin-4-yl)amino)-2-methylhexan-1-ol (114B). To a solution of 114A in THF (5 mL) was added N,N-diisopropylethylamine (0.16 mL, 0.90 mmol) followed by 2,4-dimethoxybenzylamine (0.25 mL, 1.5 mmol). After stirring at 100° C. for 18 h, the reaction was cooled to ambient temperature, diluted with EtOAc (100 mL), washed with water (100 mL) and brine (100 mL), dried over $Na_2SO_4$, then filtered and concentrated in vacuo. The residue was subjected to silica gel chromatography eluting with hexanes-EtOAc (15-100%) to provide 114B. LCMS (m/z): 460.29 $[M+H]^+$; $t_R$=0.94 min. on LC/MS Method A.

Synthesis of (R)-2-((2-amino-7-chloropyrido[3,2-d]pyrimidin-4-yl)amino)-2-methylhexan-1-ol (114). To 114B (11 mg, 0.02 mmol) was added TFA (3 mL). After 4 h, the reaction mixture was concentrated in vacuo and coevaporated with MeOH (3×20 mL). The residue was suspended in MeOH (20 mL) and filtered. After stirring overnight, the solution was concentrated in vacuo to afford 114 as a TFA salt. LCMS (m/z): 310.12 $[M+H]^+$; $t_R$=0.98 min. on LC/MS Method A. $^1$H NMR (400 MHz, Methanol-$d_4$) δ 8.59 (d, J=2.1 Hz, 1H), 8.25 (s, 1H), 7.91 (d, J=2.1 Hz, 1H), 3.97 (d, J=11.3 Hz, 1H), 3.71 (d, J=11.2 Hz, 1H), 2.10 (ddd, J=13.9, 10.9, 5.0 Hz, 1H), 1.96-1.82 (m, 1H), 1.54 (s, 3H), 1.35 (qt, J=6.8, 2.8 Hz, 4H), 0.95-0.88 (m, 3H). $^{19}$F NMR (377 MHz, Methanol-$d_4$) δ -77.61.

EtOAc (50 mL), washed with water (50 mL) and brine (50 mL), dried over $Na_2SO_4$, then filtered and concentrated in vacuo. The residue was subjected to silica gel chromatography eluting with hexanes-EtOAc to provide 115A. LCMS (m/z): 313.08 $[M+H]^+$; $t_R$=1.19 min. on LC/MS Method A.

Synthesis of (R)-2-((2,7-bis((2,4-dimethoxybenzyl)amino)pyrido[3,2-d]pyrimidin-4-yl)amino)-2-methylhexan-1-ol (115B). To a solution of 115A in THF (5 mL) was added N,N-diisopropylethylamine (0.16 mL, 0.90 mmol) followed by 2,4-dimethoxybenzylamine (0.25 mL, 1.5 mmol). After stirring at 140° C. for 18 h, the reaction was cooled to ambient temperature, diluted with EtOAc (100 mL), washed with water (100 mL) and brine (100 mL), dried over $Na_2SO_4$, then filtered and concentrated in vacuo. The residue was subjected to silica gel chromatography eluting with hexanes-EtOAc (0-100%) to provide 115B. LCMS (m/z): 444.23 $[M+H]^+$; $t_R$=0.90 min. on LC/MS Method A.

Synthesis of (R)-2-((2,7-diaminopyrido[3,2-d]pyrimidin-4-yl)amino)-2-methylhexan-1-ol (115). To 115B (14 mg, 0.02 mmol) was added TFA (3 mL). After 4 h, the reaction mixture was concentrated in vacuo and coevaporated with MeOH (3×20 mL). The residue was suspended in MeOH (20 mL) and filtered. After stirring overnight, the solution was concentrated in vacuo to afford 115 as a bis-TFA salt. LCMS (m/z): 291.19 $[M+H]^+$; $t_R$=0.93 min. on LC/MS Method A.

Example 115

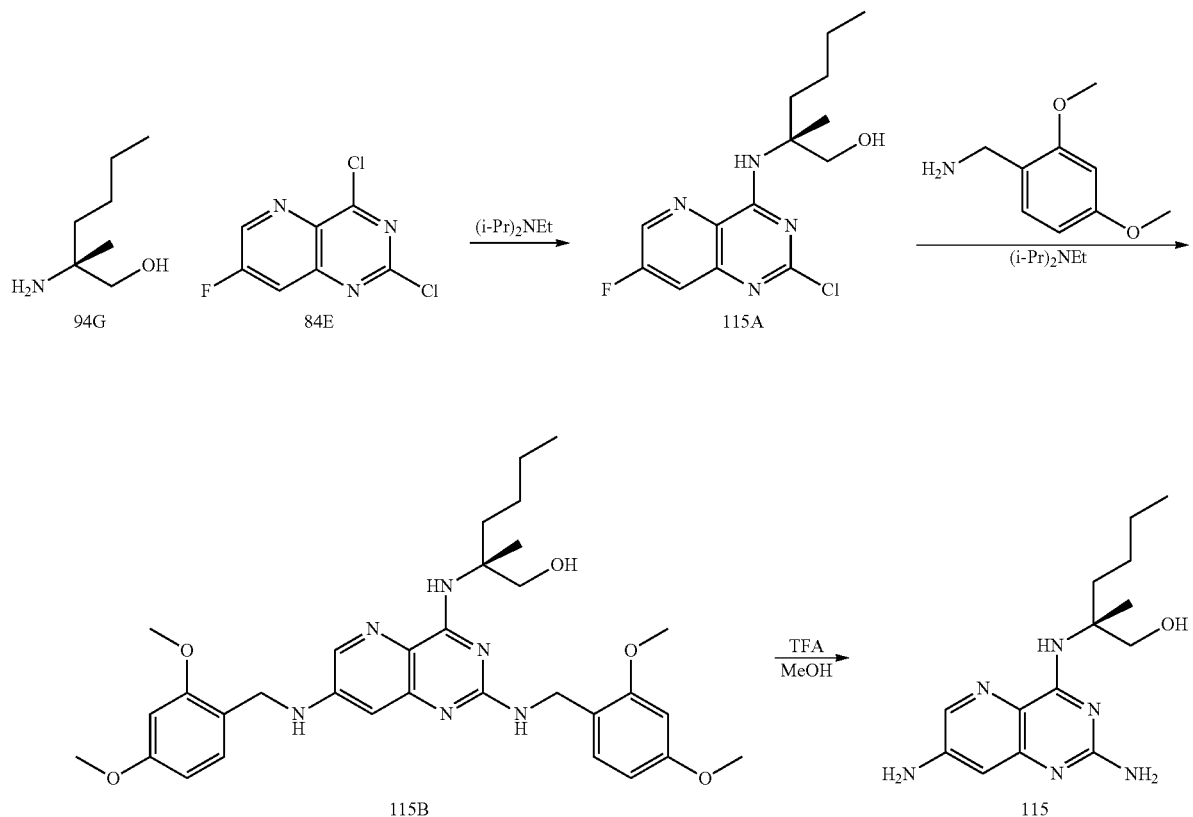

Synthesis of (R)-2-((2-chloro-7-fluoropyrido[3,2-d]pyrimidin-4-yl)amino)-2-methylhexan-1-ol (115A). To a solution of 94G (55 mg, 0.30 mmol) and 84E (65 mg, 0.30 mmol) in THF (5 mL) was added N,N-diisopropylethylamine (0.16 mL, 0.90 mmol). After stirring at 80° C. for 18 h, the reaction was cooled to ambient temperature, diluted with $^1$H NMR (400 MHz, Methanol-$d_4$) δ 8.02 (d, J=2.4 Hz, 1H), 6.69 (d, J=2.4 Hz, 1H), 3.94 (d, J=11.2 Hz, 1H), 3.69 (d, J=11.2 Hz, 1H), 2.06 (ddd, J=13.4, 11.0, 5.0 Hz, 1H), 1.91-1.79 (m, 1H), 1.49 (s, 3H), 1.35 (td, J=7.4, 4.2 Hz, 4H), 0.92 (t, J=7.0 Hz, 3H). $^{19}$F NMR (377 MHz, Methanol-$d_4$) δ -77.58.

Example 116

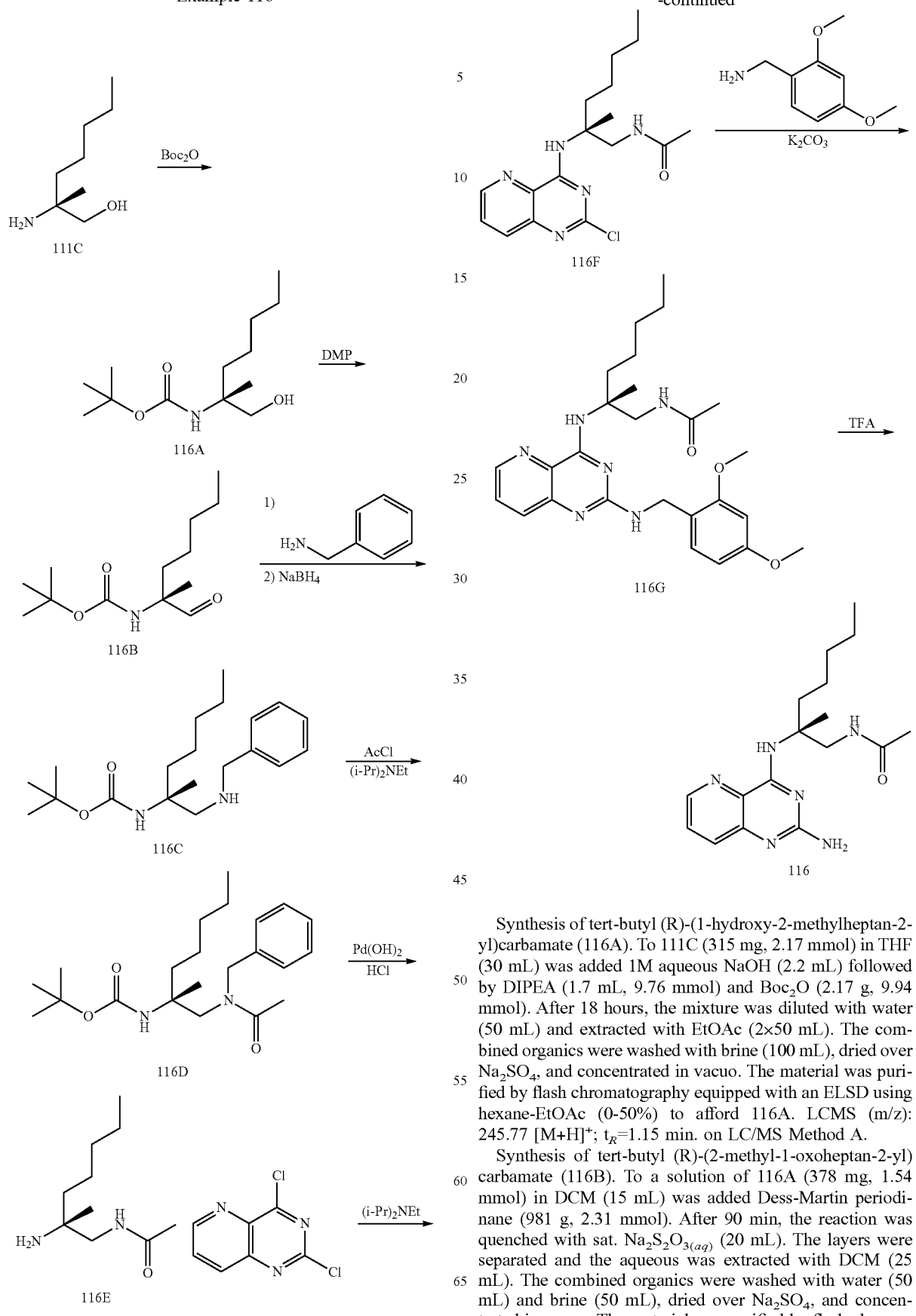

Synthesis of tert-butyl (R)-(1-hydroxy-2-methylheptan-2-yl)carbamate (116A). To 111C (315 mg, 2.17 mmol) in THF (30 mL) was added 1M aqueous NaOH (2.2 mL) followed by DIPEA (1.7 mL, 9.76 mmol) and Boc$_2$O (2.17 g, 9.94 mmol). After 18 hours, the mixture was diluted with water (50 mL) and extracted with EtOAc (2×50 mL). The combined organics were washed with brine (100 mL), dried over Na$_2$SO$_4$, and concentrated in vacuo. The material was purified by flash chromatography equipped with an ELSD using hexane-EtOAc (0-50%) to afford 116A. LCMS (m/z): 245.77 [M+H]$^+$; t$_R$=1.15 min. on LC/MS Method A.

Synthesis of tert-butyl (R)-(2-methyl-1-oxoheptan-2-yl)carbamate (116B). To a solution of 116A (378 mg, 1.54 mmol) in DCM (15 mL) was added Dess-Martin periodinane (981 g, 2.31 mmol). After 90 min, the reaction was quenched with sat. Na$_2$S$_2$O$_{3(aq)}$ (20 mL). The layers were separated and the aqueous was extracted with DCM (25 mL). The combined organics were washed with water (50 mL) and brine (50 mL), dried over Na$_2$SO$_4$, and concentrated in vacuo. The material was purified by flash chromatography equipped with an ELSD using hexane-EtOAc (0-50%) to afford 116B. LCMS (m/z): 143.95 [M+H]$^+$; $t_R$=1.23 min. on LC/MS Method A.

Synthesis of tert-butyl (R)-(1-(benzylamino)-2-methylheptan-2-yl)carbamate (116C). To a solution of 116B (351 mg, 1.44 mmol) in MeOH (6 mL) was added benzylamine (0.16 mL, 1.44 mmol). After 18 h, sodium borohydride (91 mg, 2.17 mmol) was added to the reaction. After 90 min, the mixture was concentrated in vacuo. The residue was diluted with EtOAc (25 mL), washed with 1 M NaOH$_{(aq)}$ (20 mL), dried over Na$_2$SO$_4$, and concentrated in vacuo to provide crude 116C that was used without further purification. LCMS (m/z): 335.02 [M+H]$^+$; $t_R$=0.95 min. on LC/MS Method A.

Synthesis of tert-butyl (R)-(1-(N-benzylacetamido)-2-methylheptan-2-yl)carbamate (116D). To a solution of 116C (519 mg, 1.55 mmol) in THF (15 mL) was added N,N-diisopropylethylamine (0.54 mL, 3.10 mmol) followed by acetyl chloride (0.17 mL, 2.33 mmol). After 60 min, the reaction was diluted with EtOAc (50 mL), washed with water (30 mL), sat. NaHCO$_{3(aq)}$ (30 mL), and brine (30 mL), dried over Na$_2$SO$_4$, and concentrated in vacuo. The material was purified by flash chromatography equipped with an ELSD using hexane-EtOAc (0-100%) to afford 116D. LCMS (m/z): 376.82 [M+H]$^+$; $t_R$=1.36 min. on LC/MS Method A.

Synthesis of (R)—N-(2-amino-2-methylheptyl)acetamide (116E). To a solution of 116D (584 mg, 1.55 mmol) in EtOH (15 mL) was added HCl solution (0.78 mL, 3.10 mmol, 4 M in 2,4-dioxane). The solution was then purged with Ar and Pd(OH)$_2$ (441 mg) were added. The mixture was purged with H$_2$ and heated to 75° C. After 18 h, the mixture was cooled to ambient temperature, purged with Ar, filtered, and concentrated in vacuo to provide crude 116E (288 mg) as an HCl salt. LCMS (m/z): 186.96 [M+H]$^+$; $t_R$=0.52 min. on LC/MS Method A.

Synthesis of (R)—N-(2-((2-chloropyrido[3,2-d]pyrimidin-4-yl)amino)-2-methylheptyl)acetamide (116F). To a solution of 116E (50 mg, 0.22 mmol) and 2,4-dichloropyrido [3,2-d]pyrimidine (45 mg, 0.22 mmol) in THF (3 mL) was added N,N-diisopropylethylamine (0.12 mL, 0.67 mmol). After stirring at 80° C. for 18 h, the reaction was cooled to ambient temperature, diluted with EtOAc (25 mL), washed with water (25 mL) and brine (25 mL), dried over Na$_2$SO$_4$, and concentrated in vacuo. The residue was subjected to silica gel chromatography eluting with hexanes-EtOAc (0-100%) to provide 116F. LCMS (m/z): 350.06 [M+H]$^+$; $t_R$=1.09 min. on LC/MS Method A Synthesis of (R)—N-(2-((2-((2,4-dimethoxybenzyl) amino)pyrido[3,2-d]pyrimidin-4-yl)amino)-2-methylheptyl)acetamide (116G). To a solution of 116F (58 mg, 0.17 mmol) in 2-MeTHF (3 mL) was added potassium carbonate (46 mg, 0.33 mmol) followed by 2,4-dimethoxybenzylamine (0.05 mL, 0.33 mmol). After stirring at 85° C. for 18 h, the reaction was cooled to ambient temperature, diluted with EtOAc (25 mL), washed with water (20 mL) and brine (20 mL), dried over Na$_2$SO$_4$, then filtered and concentrated in vacuo. The residue was subjected to silica gel chromatography eluting with hexanes-EtOAc (20-100%) to provide 116G. LCMS (m/z): 481.27 [M+H]$^+$; $t_R$=0.94 min. on LC/MS Method A.

Synthesis of (R)—N-(2-((2-aminopyrido[3,2-d]pyrimidin-4-yl)amino)-2-methylheptyl)acetamide (116). To 116G (53 mg, 0.11 mmol) was added TFA (3 mL). After 2 h, the reaction mixture was concentrated in vacuo and coevaporated with MeOH (3×20 mL). The residue was suspended in MeOH and filtered. The solution was concentrated in vacuo to afford 116 as a TFA salt. LCMS (m/z): 331.25 [M+H]$^+$; $t_R$=0.72 min. on LC/MS Method A. $^1$H NMR (400 MHz, Methanol-d$_4$) δ 8.63 (dd, J=4.4, 1.4 Hz, 1H), 7.85 (dd, J=8.5, 1.4 Hz, 1H), 7.76 (ddd, J=8.5, 4.4, 1.2 Hz, 1H), 3.95 (d, J=14.0 Hz, 1H), 3.56 (d, J=13.9 Hz, 1H), 2.22-2.12 (m, 1H), 1.95 (s, 3H), 1.94-1.85 (m, 1H), 1.54 (s, 3H), 1.41-1.30 (m, 6H), 0.88 (t, J=6.3 Hz, 3H). $^{19}$F NMR (377 MHz, Methanol-d$_4$) δ −77.86.

Example 117

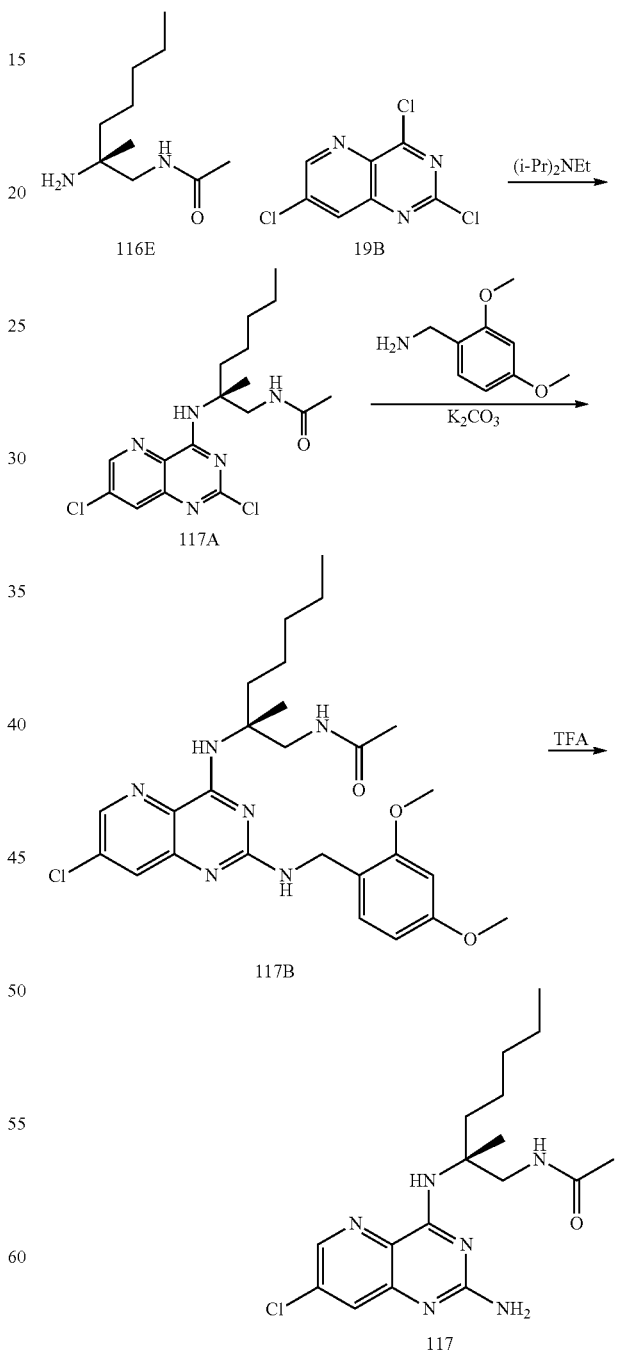

Synthesis of (R)—N-(2-((2,7-dichloropyrido[3,2-d]pyrimidin-4-yl)amino)-2-methylheptyl)acetamide (117A). To a solution of 116E (50 mg, 0.22 mmol) and 19B (53 mg, 0.22 mmol) in THF (3 mL) was added N,N-diisopropylethylamine (0.12 mL, 0.67 mmol). After stirring at 80° C. for 18 h, the reaction was cooled to ambient temperature, diluted with EtOAc (25 mL), washed with water (25 mL) and brine (25 mL), dried over $Na_2SO_4$, then filtered and concentrated in vacuo. The residue was subjected to silica gel chromatography eluting with hexanes-EtOAc (0-100%) to provide 117A. LCMS (m/z): 384.01 [M+H]$^+$; $t_R$=1.77 min. on LC/MS Method A.

Synthesis of (R)—N-(2-((7-chloro-2-((2,4-dimethoxybenzyl)amino)pyrido[3,2-d]pyrimidin-4-yl)amino)-2-methylheptyl)acetamide (117B). To a solution of 117A (33 mg, 0.09 mmol) in 2-MeTHF (3 mL) was added potassium carbonate (24 mg, 0.17 mmol) followed by 2,4-dimethoxybenzylamine (0.05 mL, 0.17 mmol). After stirring at 85° C. for 18 h, the reaction was cooled to ambient temperature, diluted with EtOAc (50 mL), washed with water (20 mL) and brine (20 mL), dried over $Na_2SO_4$, then filtered and concentrated in vacuo. The residue was subjected to silica gel chromatography eluting with hexanes-EtOAc (0-100%) then EtOAc-MeOH (0-25%) to provide 117B. LCMS (m/z): 515.26 [M+H]$^+$; $t_R$=1.06 min. on LC/MS Method A.

Synthesis of (R)—N-(2-((2-amino-7-chloropyrido[3,2-d]pyrimidin-4-yl)amino)-2-methylheptyl)acetamide (117). To 117B (38 mg, 0.07 mmol) was added TFA (3 mL). After 2 h, the reaction mixture was concentrated in vacuo and coevaporated with MeOH (3×20 mL). The residue was suspended in MeOH and filtered. The solution was concentrated in vacuo to afford 117 as a TFA salt. LCMS (m/z): 632.22 [M+H]$^+$; $t_R$=0.89 min. on LC/MS Method A. $^1$H NMR (400 MHz, Methanol-$d_4$) δ 8.59 (dd, J=3.5, 2.1 Hz, 1H), 7.92 (d, J=1.9 Hz, 1H), 3.93 (d, J=14.0 Hz, 1H), 3.51 (d, J=14.0 Hz, 1H), 2.21-2.10 (m, 1H), 1.96 (s, 3H), 1.95-1.87 (m, 1H), 1.54 (s, 3H), 1.35 (dd, J=17.6, 5.4 Hz, 6H), 0.88 (t, J=6.4 Hz, 3H). $^{19}$F NMR (377 MHz, Methanol-$d_4$) δ −77.80.

Example 118

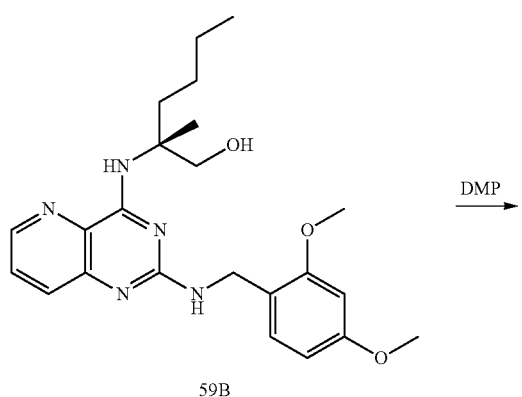

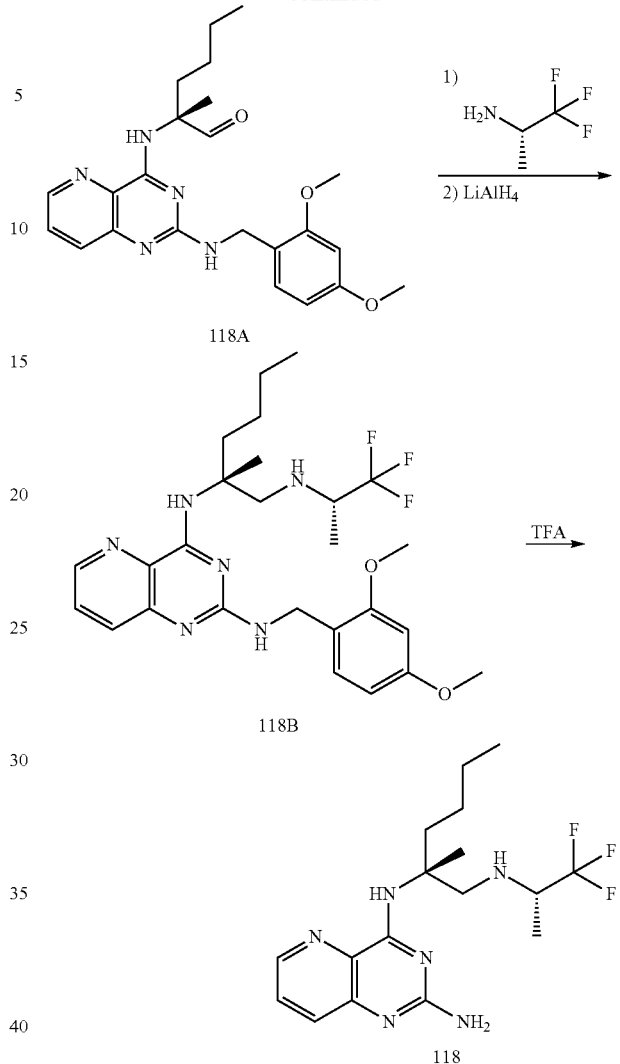

Synthesis of (R)-2-((2-((2,4-dimethoxybenzyl)amino)pyrido[3,2-d]pyrimidin-4-yl)amino)-2-methylhexanal (118A). To a solution of 59B (548 mg, 1.29 mmol) in DCM (24 mL) was added Dess-Martin periodinane (829 mg, 1.93 mmol). After 60 min, the reaction was quenched with sat. $Na_2S_2O_{3(aq)}$ (20 mL), the layers were separated, and the aqueous was extract with DCM (25 mL). The combined organics were washed with water (50 mL), sat. $NaHCO_{3(aq)}$ (50 mL), and brine (50 mL), dried over $Na_2SO_4$, and concentrated in vacuo. The material was purified by flash chromatography using hexane-EtOAc (25-100%) followed by EtOAc-MeOH (0-20%) to afford 118A. LCMS (m/z): 424.18 [M+H]$^+$; $t_R$=1.04 min. on LC/MS Method A.

Synthesis of $N^2$-(2,4-dimethoxybenzyl)-N—((R)-2-methyl-1-(((S)-1,1,1-trifluoropropan-2-yl)amino)hexan-2-yl)pyrido[3,2-d]pyrimidine-2,4-diamine (118B). To a solution of 118A (70 mg, 0.17 mmol) in MeOH (1 mL) was added (S)-1,1,1-trifluoro-2-propylamine (39 mg, 0.33 mmol, supplied by Oakwood Chemical). After 5 h, the reaction was concentrated in vacuo. The residue was diluted with THF (2 mL) and lithium aluminum hydride solution (0.82 mL, 0.82 mmol, 1 M in THF) was added. After 30 min, the reaction was quenched with water (20 mL) and extracted with EtOAc (2×20 mL). The combined organics were dried over $Na_2SO_4$ and concentrated in vacuo to afford crude 118B. LCMS (m/z): 521.24 [M+H]$^+$; $t_R$=1.26 min. on LC/MS Method A.

Synthesis of N$^4$—((R)-2-methyl-1-(((S)-1,1,1-trifluoropropan-2-yl)amino)hexan-2-yl)pyrido[3,2-d]pyrimidine-2,4-diamine (118). To 118B (66 mg, 0.13 mmol) was added TFA (3 mL). After 4 h, the reaction mixture was concentrated in vacuo. The residue was suspended in 50% EtOH$_{(aq)}$ (6 mL) and filtered. The solution was purified by preparative HPLC (Synergi 4u Polar-RP 80A, Axia; 20% aq. acetonitrile-60% aq. acetonitrile with 0.1% TFA, over 20 min. gradient) to afford 122 as a bis-TFA salt. LCMS (m/z): 371.10 [M+H]$^+$; $t_R$=1.14 min. on LC/MS Method A. $^1$H NMR (400 MHz, Methanol-d$_4$) δ 8.62 (dd, J=4.4, 1.4 Hz, 1H), 7.87 (dd, J=8.5, 1.4 Hz, 1H), 7.78 (dd, J=8.5, 4.4 Hz, 1H), 3.75 (hept, J=7.1 Hz, 1H), 3.64 (d, J=12.8 Hz, 1H), 3.28 (d, J=12.8 Hz, 1H), 2.17 (ddd, J=13.6, 11.4, 4.6 Hz, 1H), 1.95 (ddd, J=16.1, 12.3, 4.1 Hz, 1H), 1.61 (s, 3H), 1.42 (d, J=6.9 Hz, 3H), 1.40-1.26 (m, 4H), 0.92 (t, J=6.9 Hz, 3H). $^{19}$F NMR (376 MHz, Methanol-d$_4$) δ −76.47 (d, J=7.1 Hz), −77.87.

Unless otherwise stated, LC/MS retention times ($t_R$) reported above were measured using LC/MS Method A.

Method for LC/MS HPLC (Method A): HPLC LC/MS chromatograms were generated using a Thermo Scientific LCQ LC/MS system eluting with a Kinetex 2.6u C18 100 A, 5×30 mm HPLC column, using a 1.85 minute gradient elution from 2% aq. acetonitrile-98% aq. acetonitrile with 0.1% formic acid modifier.

Method for LC/MS HPLC (Method B): HPLC LC/MS chromatograms were generated using a Thermo Scientific LCQ LC/MS system eluting with a Kinetex 2.6u C18 100 A, 5×30 mm HPLC column, using a 2.85 minute gradient elution from 2% aq. acetonitrile-98% aq. acetonitrile with 0.1% formic acid modifier.

Biological Example 1—PBMC IFNα, IL12-p40 and TNFα Assays

Certain compounds disclosed herein we tested according to the procedure described below. Additionally, certain reference compounds were prepared and tested along with the compounds of the present disclosure. For example, the Compound X was prepared in a manner similar to that disclosed in PCT Application Publication No. WO2012/156498 (where the compound is identified as Compound 72). Compound Y was prepared in a manner similar to that disclosed in PCT Application Publication No. WO2015/014815 (where the compound is identified as Compound 6).

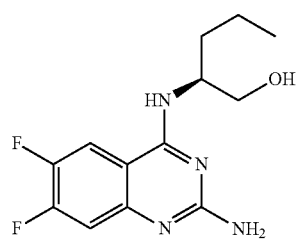

Cmpd. X

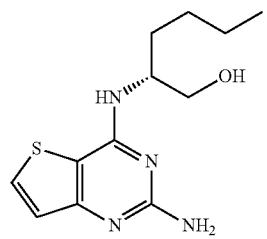

Cmpd. Y

Compounds were dissolved and stored in DMSO (Sigma-Aldrich, St. Louis, MO) at 10 mM concentration.

Cells and Reagents

Cryopreserved human PBMCs isolated from healthy donors were purchased from StemCell Technologies (Vancouver, Canada). Cell culture medium used was RPMI with L-Glutamine (Mediatech, Manassas, VA) supplemented with 10% fetal bovine serum (Hyclone, GE Healthcare, Logan, UT) and Penicillin-Streptomycin (Mediatech). Human TNFα, IL12p40, and IFNα2a 384-well Assay capture plates, standards, buffers and processing reagents were obtained from MesoScale Discovery Technologies (MSD; Rockville, MD).

Cryopreserved human PBMCs (1×10e8 cells/ml) were thawed at 37° C. and resuspended in 25 mL warm cell culture medium. The cells were pelleted at 200×g (Beckman Avanti J-E) for 5 min and resuspended in 20 mL of fresh culture media. Cells were counted using a Cellometer (Nexcelcom Bioscience), adjusted to 2×10e6 cells, and incubated for 2 hours in an incubator set at 37° C., 5% CO$_2$ to recover from cryopreservation. Compounds were serially diluted in DMSO at half-log steps to generate a 10-point dose range. Using a Bravo pipette equipped with a 384 well head (Agilent), 0.4 μL of compound was transferred to each well of a 384 well black, clear bottom plate (Greiner Bio-One, Germany) containing 30 μL of cell culture medium. Recovered PBMCs were then dispensed into the assay plate at 50 μL per well (100k cells/well) using the MicroFlow multichannel dispenser (Biotek). Final DMSO concentration was 0.5%. DMSO was used as the negative control. The plates were incubated for 24 hours at 37° C. PBMCs in the assay plate were pelleted by centrifugation (Beckman Avanti J-E) at 200×g for 5 min.

Using a Biomek FX 384 well pipetting station (Beckman), conditioned culture medium (CCM) from the assay plate was transferred to MSD capture plates customized for each cytokine. For IFNα and IL12-p40 detection, 25 μL and 20 μL of CCM were added directly to each capture plate, respectively. For TNFα detection, CCM was diluted 1:9 in fresh culture medium, and 20 μL of diluted CCM was used. Serially diluted calibration standards for each cytokine were used to generate standard curves and establish assay linearity. The plates were sealed and incubated overnight at 4° C. in a plate shaker (Titer Plate) set at 200 rpm. On the following day, antibodies specific for each cytokine were diluted 1:50 in MSD Diluent 100 antibody dilution buffer. Diluted antibodies were added to corresponding capture plates at 10 μL/well, and incubated at RT for 1-2 hrs in the shaker. The plates were washed with PBST buffer (3×, 60 μl/well) using a Biotek Multiflow plate washer. MSD Read Buffer diluted to 2× in deionized water and 35 μL/well was added via Biomek FX instrument. The plates were read immediately in a MSD6000 reader. Data were normalized to positive and negative controls in each assay plate. AC$_{50}$ values represent compound concentrations at half-maximal effect based on normalized percent activation and calculated by non-linear regression using Pipeline Pilot software (Accelrys, San Diego, CA).

Results of the cytokine profiling assay are reported in Table 1, Table 2, and Table 3 below.

TABLE 1

| Compound | TNFα $AC_{50}$ (μM) | IL12p40 $AC_{50}$ (μM) | IFNα $AC_{50}$ (μM) |
|---|---|---|---|
| 1B | 3.9 | 2 | 2.7 |
| 2B | 5.4 | 2.8 | 4.3 |
| 3B | 29.4 | 15.5 | 14.5 |
| 4B | 9.1 | 5.4 | 5.9 |
| 5B | >50 | >50 | 41 |
| 6B | >50 | >50 | >50 |
| 7 | >50 | >50 | 34 |
| 8 | 20.2 | 19.4 | >50 |
| 9 | 1.9 | 1.1 | 7.2 |
| 10 | 29.2 | 23.8 | >50 |
| 11 | 10.1 | 6 | 6.9 |
| 12 | >50 | >50 | >50 |
| 13 | >50 | >50 | >50 |
| 14 | 1.1 | 0.94 | 1.6 |
| 15 | 1.6 | 1.2 | >200 |
| 16 | >50 | >50 | >50 |
| 17 | >50 | >50 | >50 |
| 18F | 16.1 | 15.2 | 30.6 |
| 19E | 3.3 | 2.5 | 21.6 |
| 20 | 3.2 | 2.8 | 5.4 |
| 21 | 3.1 | 2.3 | 4.8 |
| 22 | >50 | >50 | 35.9 |
| 23C | 24.7 | 25.7 | >50 |
| 24D | 3.4 | 3.1 | 18.4 |
| 25E | 20 | 19.7 | 12.3 |
| 26E | 2.3 | 1.7 | 13.5 |
| 27C | 0.52 | 0.42 | 2 |
| 28 | 28.6 | 28.2 | 45 |
| 29 | 18.3 | 15.5 | 3.9 |
| 30B | 10.6 | 8.6 | >50 |
| 31 | 4.7 | 4.7 | 32.9 |
| 32 | >50 | >50 | >50 |
| 33 | 0.92 | 0.85 | 5.9 |
| 34 | 12.2 | 10.9 | >50 |
| 35 | 39.4 | 22.6 | >50 |
| 36 | 21.5 | 10.8 | >50 |
| 37 | >50 | >50 | >50 |
| 38C | >50 | >50 | >50 |
| 39C | >50 | 41.5 | >50 |
| 40C | 0.94 | 0.87 | 2.4 |
| 41 | 11 | 9.1 | 13 |
| 42B | 1.1 | 0.9 | 3.6 |
| 43C | 1.1 | 1 | 10.9 |
| 44 | 3 | 2.4 | >50 |
| 45 | 1.6 | 1.3 | 8.3 |
| 46C | 28.6 | 28.5 | >50 |
| 47B | 2.70 | 2.0 | >50 |
| 48 | 0.85 | 0.71 | 0.57 |

TABLE 2

| Compound | TNFα $AC_{50}$ (μM) | IL12p40 $AC_{50}$ (μM) | IFNα $AC_{50}$ (μM) |
|---|---|---|---|
| X | 1.2 | 0.97 | 7.1 |
| Y | 11.2 | 13.0 | >50 |

TABLE 3

| Compound | TNFα $AC_{50}$ (μM) | IL12p40 $AC_{50}$ (μM) | IFNα $AC_{50}$ (μM) |
|---|---|---|---|
| 49 | 22.4 | 18.1 | 41.6 |
| 50 | 26.9 | 23.1 | >50 |
| 51 | 0.37 | 0.33 | >200 |
| 52 | 3.2 | 3.6 | >50 |
| 53 | 0.26 | 0.28 | 3.9 |
| 54 | 34.0 | 42.5 | >50 |
| 55 | 23.9 | 21.5 | 28.8 |
| 56 | 3.6 | 3.4 | 1.9 |
| 57 | 11.0 | 9.7 | >50 |
| 58 | 3.9 | 3.8 | 4.1 |
| 59 | 0.18 | 0.17 | 15.0 |
| 60 | 2.6 | 2.3 | 7.9 |
| 61 | 0.02 | 0.02 | 42.1 |
| 62 | 1.0 | 0.91 | >50 |
| 63 | 0.41 | 0.43 | 22.4 |
| 64 | 3.1 | 3.2 | 37.9 |
| 65 | 0.11 | 0.09 | >50 |
| 66 | 0.04 | 0.03 | 1.6 |
| 67 | 6.3 | 3.9 | 23.0 |
| 68 | 11.1 | 14.2 | >50 |
| 69 | 31.0 | 30.8 | 34.8 |
| 70 | 3.3 | 2.7 | >50 |
| 71 | 2.6 | 2.7 | >50 |
| 72 | 7.2 | 7.0 | >50 |
| 73 | 1.3 | 1.3 | >50 |
| 74 | 9.1 | 9.6 | >50 |
| 75 | 4.0 | 3.3 | 20.3 |
| 76 | 36.9 | 31.8 | 36.9 |
| 77 | 43.6 | 43.6 | 43.6 |
| 78 | 16.0 | 14.2 | >50 |
| 79 | 9.1 | 11.5 | >50 |
| 80 | 2.7 | 2.4 | >50 |
| 81 | 7.6 | 7.8 | >50 |
| 82 | 16.6 | 14.3 | >50 |
| 83 | 1.7 | 1.8 | 43.1 |
| 84 | 3.0 | 3.9 | >50 |
| 85 | 0.86 | 0.80 | 4.0 |
| 86 | 2.9 | 2.4 | 37.4 |
| 87 | 5.0 | 4.5 | >50 |
| 88 | 0.4 | 0.37 | 35.6 |
| 89 | 2.2 | 1.7 | >50 |
| 90 | 0.86 | 0.62 | 7.8 |
| 91 | 2.0 | 1.9 | >50 |
| 92 | 4.3 | 4.7 | >50 |
| 93 | 0.44 | 0.40 | >50 |
| 94 | 1.0 | 0.7 | 2.2 |
| 95 | 0.15 | 0.15 | >50 |
| 96 | 1.1 | 1.0 | 2.8 |
| 97 | 0.14 | 0.13 | 26.0 |
| 98 | 0.24 | 0.23 | 134 |
| 99 | 3.4 | 3.6 | >50 |
| 100 | 3.8 | 3.5 | 4.6 |
| 101 | 0.10 | 0.11 | >50 |
| 102 | 0.81 | 0.76 | >50 |
| 103 | 3.3 | 2.6 | 10.3 |
| 104 | 2.1 | 1.9 | 4.2 |
| 105 | 3.5 | 3.4 | >50 |
| 106 | 13.8 | 10.2 | >50 |
| 107 | 2.8 | 1.8 | >50 |
| 108 | 38.7 | 22.0 | >50 |
| 110 | 32.6 | 32.6 | 32.6 |
| 111 | 0.61 | 0.47 | 19.8 |
| 112 | 0.36 | 0.33 | >50 |
| 113 | 12.5 | 13.6 | >50 |
| 114 | 0.34 | 0.20 | 34.1 |
| 115 | 0.024 | 0.027 | 9.0 |
| 116 | 0.036 | 0.11 | >50 |
| 117 | 0.37 | 0.33 | >50 |
| 118 | 9.3 | 9.1 | >50 |

In certain embodiments, certain compounds disclosed herein have an $AC_{50}$ for TNFα that is less than about 100 μM, less than about 50 μM, less than about 40 μM, less than about 30 μM, less than about 25 μM, less than about 20 μM, less than about 15 μM, less than about 10 μM, less than about 5 μM, less than about 4 μM, less than about 3 μM, less than about 2 μM, or less than about 1 μM. In certain embodiments, certain compounds disclosed herein have an $AC_{50}$ for TNFα that is greater than about 25 µM or greater than about 50 µM. In certain embodiments, certain compounds disclosed herein have an $AC_{50}$ for TNFα that is less than about 0.75 µM, less than about 0.5 µM, or less than about 0.25 µM. As is understood by those of skill in the art, the induction of TNFα is associated with agonism of TLR8.

In certain embodiments, certain compounds disclosed herein have an $AC_{50}$ for IL12p40 that is less than about 100 µM, less than about 50 µM, less than about 40 µM, less than about 30 µM, less than about 25 µM, less than about 20 µM, less than about 15 µM, less than about 10 µM, less than about 5 µM, less than about 4 µM, less than about 3 µM, less than about 2 µM, less than about 1 µM, or less than about 0.5 µM. In certain embodiments, certain compounds disclosed herein have an $AC_{50}$ for IL12p40 that is greater than about 25 µM or greater than about 50 µM. As is understood by those of skill in the art, the induction of IL12p40 is associated with agonism of TLR8.

In certain embodiments, certain compounds disclosed herein have an $AC_{50}$ for IFNα that is less than about 200 µM, less than about 100 µM, less than about 50 µM, less than about 40 µM, less than about 30 µM, less than about 25 µM, less than about 20 µM, less than about 15 µM, less than about 10 µM, less than about 5 µM, less than about 4 µM, less than about 3 µM, less than about 2 µM, or less than about 1 µM. In certain embodiments, certain compounds disclosed herein have an $AC_{50}$ for IFNα that is greater than about 25 µM, greater than about 50 µM, greater than about 100 µM, greater than about 150 µM, or greater than about 200 µM. As is understood by those of skill in the art, the induction of IFNα is associated with agonism of TLR7.

In certain embodiments, the compounds of the present disclosure are selective TLR8 agonists. Compounds that are selective TLR8 agonists produce a cytokine effect associated with TLR8 induction (e.g. TNFα and IL12p40) at a lower concentraction than that associated with TLR7 induction (e.g. IFNα). In certain embodiments, when analyzed in the cytokine profiling assay, the compounds induce IFNα at a concentration at least about 2 times higher than the concentration at which TNFα and/or IL12p40 are induced; in certain embodiments the compounds induce IFNα at a concentration at least about 4 times higher than the concentration at which TNFα and/or IL12p40 are induced; in certain embodiments the compounds induce IFNα at a concentration at least about 6 times higher than the concentration at which TNFα and/or IL12p40 are induced; in certain embodiments the compounds induce IFNα at a concentration at least about 8 times higher than the concentration at which TNFα and/or IL12p40 are induced; in certain embodiments the compounds induce IFNα at a concentration at least about 10 times higher than the concentration at which TNFα and/or IL12p40 are induced; in certain embodiments the compounds induce IFNα at a concentration at least about 20 times higher than the concentration at which TNFα and/or IL12p40 are induced; in certain embodiments the compounds induce IFNα at a concentration at least about 30 times higher than the concentration at which TNFα and/or IL12p40 are induced; in certain embodiments the compounds induce IFNα at a concentration at least about 40 times higher than the concentration at which TNFα and/or IL12p40 are induced; in certain embodiments the compounds induce IFNα at a concentration at least about 50 times higher than the concentration at which TNFα and/or IL12p40 are induced; in certain embodiments the compounds induce IFNα at a concentration at least about 75 times higher than the concentration at which TNFα and/or IL12p40 are induced; in certain embodiments the compounds induce IFNα at a concentration at least about 100 times higher than the concentration at which TNFα and/or IL12p40 are induced; in certain embodiments the compounds induce IFNα at a concentration at least about 125 times higher than the concentration at which TNFα and/or IL12p40 are induced; in certain embodiments the compounds induce IFNα at a concentration at least about 150 times higher than the concentration at which TNFα and/or IL12p40 are induced; in certain embodiments the compounds induce IFNα at a concentration at least about 175 times higher than the concentration at which TNFα and/or IL12p40 are induced; and in certain embodiments the compounds induce IFNα at a concentration at least about 200 times higher than the concentration at which TNFα and/or IL12p40 are induced.

As is understood by those of skill in the art, each compound of the present disclosure may have $AC_{50}$ values for each cytokine tested (e.g. TNFα, IL12p40, and IFNα) that include various combinations of the ranges disclosed above. As such, the present disclosure provides for such combinations. Further, the ability of any particular compound or group of compounds to selectively modulate a particular receptor can be extrapolated from the $AC_{50}$ data disclosed herein. One of skill in the art will necessarily appreciate the various selectivities of any particular compound or group of compounds.

Biological Example 2—Efficacy Study in WHV-Infected Woodchucks

The in vivo antiviral efficacy of a compound disclosed herein was evaluated in the woodchuck model of CHB. Woodchucks chronically infected with woodchuck hepatitis virus (WHV) (n=23) were stratified into a placebo group (n=11), a 1 mg/kg dose group (n=6), and a 3 mg/kg dose group (n=6) based on gender and baseline antiviral parameters. Animals with high gamma glutamyltransferase (GGT) levels (that correlate with an increased risk of hepatocellular carcinoma (HCC)) and/or with liver tumors observed at the pre-study biopsy screening were included in the placebo group. This stratification was performed so that adverse events (including death) associated with HCC would not confound safety assessment of the dosing groups receiving a compound disclosed herein. The plan for this ongoing study was as follows: animals were dosed PO once a week for 8 weeks with compound or vehicle, followed by a follow-up period of 24 weeks. The animals were monitored for safety and in-life parameters (blood chemistry/hematology/temperature), pharmacokinetics (serum PK), pharmacodynamics (whole blood MARCO mRNA and WHV-specific T cell responses) and antiviral efficacy (serum WHV DNA, woodchuck hepatitis surface antigen (WHsAg) and anti-sAg antibodies, and liver WHV cccDNA, DNA and mRNA).

Interim analysis of this ongoing study revealed that animals dosed with vehicle or 1 mg/kg for 8 weeks did not have any changes in serum WHV DNA or WHsAg levels. In contrast, there was a strong decline in both viral endpoints in 4/6 animals in the 3 mg/kg dose group. Serum WHV DNA and WHsAg levels for three of these animals did not revert at week 12, four weeks after cessation of treatment. Of note, three animals had detectable levels of anti-WHsAg starting at week 4 that were still increasing, stabilizing, or decreasing by week 12. These interim data show that a compound of the present disclosure has antiviral and anti-HBsAg activity as well as the ability to induce anti-HBsAg antibody in vivo in the woodchuck model of CHB.

Biological Example 3—Off Target Toxicity

To assess potential off-target toxicity of certain compounds disclosed herein, the in vitro cytotoxicity of those compounds was profiled using a panel of 5 cell lines with various tissue origins. Compound cytotoxicity was examined in hepatoma-derived Huh-7 and HepG2 cells, prostate carcinoma-derived PC-3 cells, lymphoma derived MT-4 cells and a normal diploid lung cell line MRC-5. HepG2 and PC-3 cells used were adapted to grow in glucose-free galactose-containing medium. These cells have a relatively higher sensitivity to inhibitors of mitochondrial oxidative phosphorylation compared to the same cells maintained in standard glucose-containing culture medium (Marroquin et al., Toxicol. Sci. 2007; 97 (2):539-47). Cell viability was determined by measuring intracellular ATP levels following five days of continuous incubation with test compounds.

Cell Cultures

The human hepatoma Huh-7 cell line was obtained from ReBLikon GmbH (Mainz, Germany) {20879}. The MT-4 cell line (HTLV-1 transformed, human T lymphoblastoid cells) was obtained from the NIH AIDS Reagent program (Bathesda, MD). The human hepatoblastoma cell line HepG2, human prostate carcinoma cell line PC-3, and normal fetal lung derived MRC-5 cells were obtained from the American Type Culture Collection (ATCC, Manassas, VA).

Huh-7 cells were maintained in Dulbecco's Modified Eagle Medium (DMEM) supplemented with 10% fetal bovine serum (FBS, Hyclone, Logan, UT), 1% non-essential amino acids (Gibco, Carlsbad, CA). PC-3 and HepG2 cells were adapted to grow in 0.2% galactose-containing, glucose-free Dulbecco's Modified Eagle Medium (DMEM) supplemented with 10% fetal bovine serum (FBS, Hyclone, Logan, UT), 1% non-essential amino acids (Gibco, Carlsbad, CA), 1% Pyruvate (Cellgro), 1% Glutamax (Invitrogen, Carlsbad, CA). Galactose-adapted cells were maintained in the same culture medium. MRC-5 cells were maintained in Eagle's Minimum Essential Medium (EMEM) supplemented with 10% fetal bovine serum (FBS, Hyclone, Logan, UT). MT-4 cells were maintained in RPMI-1640 supplemented with 10% fetal bovine serum (FBS, Hyclone, Logan, UT). All cell culture media were also supplemented with 100 Units/mL penicillin, 100 μg/mL streptomycin (Gibco).

Cytotoxicity Assays

Using a Biotek uFlow Workstation (Biotek, Winooski, VT), 1500 HepG2, 1500 PC-3, 500 Huh7 or 1500 MRC-5 cells in 90 μL of culture media were dispensed into each well of black polystyrene tissue culture-treated 384-well plates. Plated cells were incubated for 24 hours in an incubator at 37° C., 5% $CO_2$ and 90% humidity. Compound serial dilutions were performed in 100% DMSO in 384-well polypropylene (high recovery) plates on a Biomek FX Workstation (Beckman Coulter, Fullerton, CA). After 3-fold serial dilutions, 0.4 μL of compounds were transferred into 384-well plates containing cells using a Velocity 11 system equipped with a Bravo 384-well pipettor. The DMSO concentration in the final assay plates was 0.44% (v/v). Cells were incubated with compound(s) for five days at 37° C. Puromycin (44 μM final concentration) and DMSO (0.44%, v/v) were used as a positive and negative controls, respectively.

At the end of the incubation period the cytotoxicity assay was performed as follows: Media from 384-well cell culture plates were aspirated with a Biotek EL405 plate-washer (Biotek) and cells were washed with 100 μL PBS once. Twenty microliters of Cell Titer Glo (Promega, Madison, WI) was added to each well of the plates with a Biotek uFlow liquid dispenser. Plates were incubated for 15 minutes at room temperature before luminescence was measured with a Perkin Elmer Envision Plate Reader (Perkin Elmer, Waltham, MA).

For the MT-4 cytotoxicity assay, 0.4 μL of serially diluted compounds were added to 40 μl of cell maintenance media in 384-well black, solid bottom plate using a Biomek FX workstation (Beckman Coulter). Two thousand cells in 35 μL were added to each well using a Biotek uFlow Workstation (Biotek). Each assay plate contained 10 μM Puromycin (final concentration) and 0.5% DMSO in RPMI-1640 as positive and negative controls, respectively. Assay plates were incubated for five days at 37° C. in an incubator set at 5% CO2 and 90% humidity. After five days, 22 μL of Cell Titer Glo reagent (Promega) was added to the assay plates with a Biotek uFlow Workstation. Plates were subsequently placed on a Perkin Elmer Envision Plate Reader for five minutes before the luminescence signal was read.

Data Analysis $CC_{50}$ values were defined as the compound concentration that caused a 50% decrease in luminescence signal, and were calculated by non-linear regression using Pipeline Pilot software by applying a four parameter fit equation (Accelrys, San Diego, CA). Results are summarized in the table below. Individual CC50 values are listed as μM concentrations.

| Compound | CC50 GALHEPG2 CTG 5D | CC50 GALPC3 CTG 5D | CC50 HUH7 CTG 5D | CC50 MRC5 CTG 5D | CC50 (MT4) |
|---|---|---|---|---|---|
| 15 | 1.23 | 0.69. | 10.70 | 7.60 | 8.62 |
| 44 | 1.07 | 0.52 | 9.64 | 3.72 | 1.97 |
| 59 | 8.88 | 5.20 | 35.39 | 40.31 | 31.40 |
| 98 | 6.70 | 4.53 | 21.90 | 24.42 | 16.17 |
| 51 | 44.44 | 37.23 | 44.44 | 44.44 | 57.14 |
| 102 | 27.42 | 19.08 | 44.44 | 44.44 | 57.14 |
| 61 | 44.44 | 44.44 | 44.44 | 44.44 | 212.39 |
| 62 | 44.44 | 29.74 | 44.44 | 44.44 | 19.23 |
| 93 | 7.73 | 3.63 | 44.44 | 38.80 | 18.55 |
| 64 | 3.56 | 1.55 | 10.36 | 6.97 | 0.79 |
| 101 | 44.44 | 44.44 | 44.44 | 44.44 | 50.0 |
| 65 | 44.44 | 44.44 | 44.44 | 44.44 | 50.0 |
| 95 | 28.06 | 16.76 | 31.34 | 44.44 | 44.11 |
| 97 | 33.01 | 27.51 | 44.44 | 44.44 | 50.0 |
| X | 7.85 | 6.79 | 16.91 | 20.95 | 53.77 |
| Y | 0.19 | 0.18. | 2.31 | 0.95 | 1.42 |

As will be appreciated by one of skill in the art, a high ratio of $CC_{50}$ from the cytotoxicity assays to $AC_{50}$ (e.g. of TNFα and/or IL12p40) indicates potential good safety margins in vivo.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure.

We claim:

1. A compound, or a pharmaceutically acceptable salt thereof, of Formula (IVa)

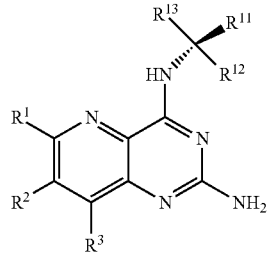

Formula (IVa)

$R^1$ is hydrogen;
$R^2$ is hydrogen, methyl, fluoro or chloro;
$R^3$ is hydrogen or methyl; and
the moiety

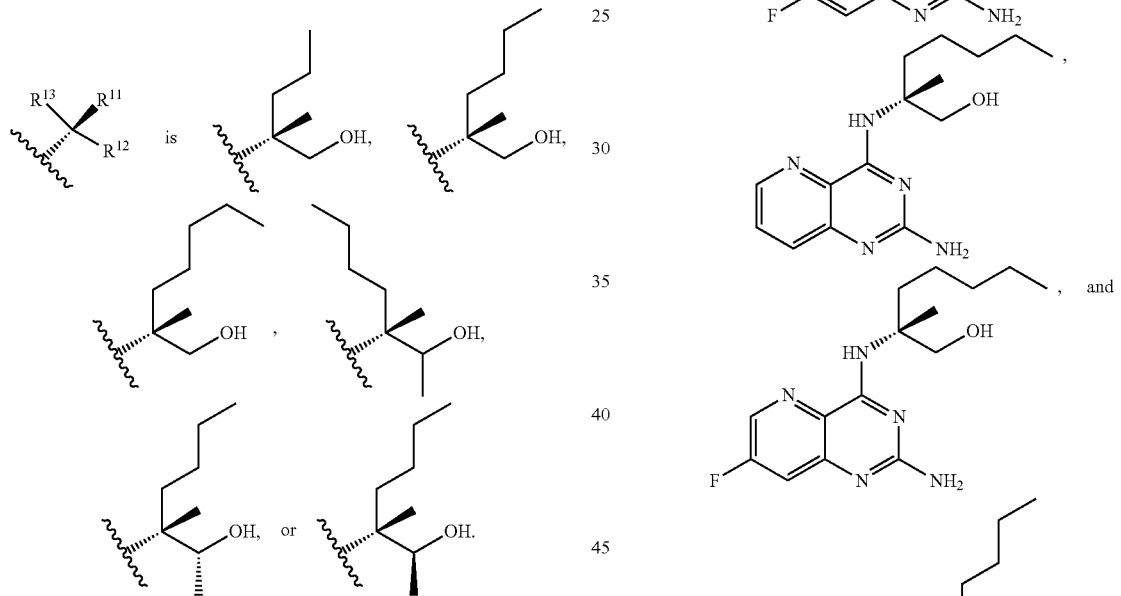

2. The compound of claim 1, or a pharmaceutically acceptable salt thereof, wherein:
$R^1$ is hydrogen;
$R^2$ is hydrogen or fluoro; and
$R^3$ is hydrogen or methyl.

3. The compound of claim 1, or a pharmaceutically acceptable salt thereof, wherein:
$R^1$ is hydrogen;
$R^2$ is hydrogen or fluoro; and
$R^3$ is hydrogen.

4. The compound of claim 1, selected from

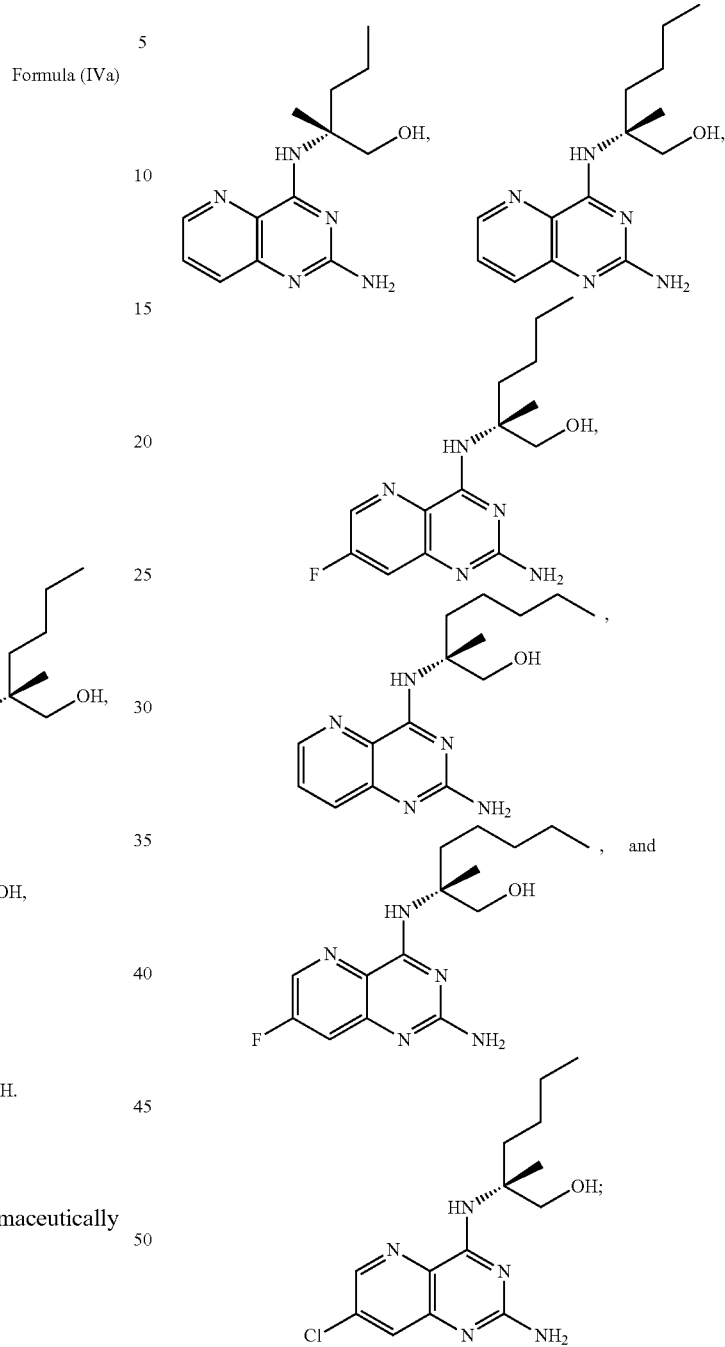

or a pharmaceutically acceptable salt thereof.

5. A pharmaceutical composition comprising a compound of claim 1, or a pharmaceutically acceptable salt thereof, and a pharmaceutically acceptable excipient.

* * * * *